United States Patent
Yang et al.

(10) Patent No.: US 12,162,820 B2
(45) Date of Patent: Dec. 10, 2024

(54) PERIPHERAL ALKYL AND ALKENYL CHAINS EXTENDED BENZENE DERIVATIVES AND PHARMACEUTICAL COMPOSITION INCLUDING THE SAME

(71) Applicant: TAIWANJ PHARMACEUTICALS CO., LTD., Zhubei (TW)

(72) Inventors: Syaulan S. Yang, Zhubei (TW); Yan-feng Jiang, Kaohsiung (TW); Meng-hsien Liu, Toufen (TW); Chia-hao Chang, New Taipei (TW); Hao Shiuan Liu, Taichung (TW); Ying-chu Shih, Zhubei (TW); Sheng Hung Liu, Zhubei (TW); Chiung Wen Wang, Zhubei (TW); Ting-ni Huang, Taipei (TW)

(73) Assignee: TAIWANJ PHARMACEUTICALS CO., LTD., Zhubei (TW)

( * ) Notice: Subject to any disclaimer, the term of this patent is extended or adjusted under 35 U.S.C. 154(b) by 552 days.

(21) Appl. No.: 17/442,296

(22) PCT Filed: Mar. 27, 2020

(86) PCT No.: PCT/US2020/025099
§ 371 (c)(1),
(2) Date: Sep. 23, 2021

(87) PCT Pub. No.: WO2020/205455
PCT Pub. Date: Oct. 8, 2020

(65) Prior Publication Data
US 2022/0153687 A1     May 19, 2022

Related U.S. Application Data
(60) Provisional application No. 62/825,977, filed on Mar. 29, 2019.

(51) Int. Cl.
| | |
|---|---|
| *C07D 209/14* | (2006.01) |
| *C07C 233/42* | (2006.01) |
| *C07C 235/38* | (2006.01) |
| *C07C 259/06* | (2006.01) |
| *C07C 311/20* | (2006.01) |
| *C07D 233/74* | (2006.01) |

(52) U.S. Cl.
CPC .......... *C07C 233/42* (2013.01); *C07C 235/38* (2013.01); *C07C 259/06* (2013.01); *C07C 311/20* (2013.01); *C07D 209/14* (2013.01); *C07D 233/74* (2013.01)

(58) Field of Classification Search
CPC ... C07C 233/42; C07C 235/38; C07C 259/06; C07D 209/14; C07D 233/74
See application file for complete search history.

(56) References Cited

U.S. PATENT DOCUMENTS

2002/0085282 A1    5/2002   Georges et al.

FOREIGN PATENT DOCUMENTS

| CN | 101979090 A | 2/2011 |
| WO | WO 2019/951222 A1 | 3/2019 |

OTHER PUBLICATIONS

Huang et al., "Arene CH-O Hydrogen Bonding: A Stereocontrolling Tool in Palladium-Catalyzed Arylation and Vinylation of Ketones**", Angew. Chem. Int. Ed., vol. 52, 2013, pp. 4906-4911.
Koch et al., "Hydroxy-Directed Hydroaluminations: A Stereoselective Approach to Cycloalkanols From β-Aryl Enones", Tetrahedron Letters, vol. 35, No. 8, 1994, pp. 1137-1140.
Pubchem-CID: 2732770 Create Date: Jul. 19, 2005, pp. 1-8, structure.
Yee et al., "Novel Tetralone-Derived Retinoic Acid Metabolism Blocking Agents: Synthesis and in Vitro Evaluation with Liver Microsomal and MCF-7 CYP26A1 Cell Assays", J. Med. Chem., vol. 48, 2005, pp. 7123-7131.
Yee et al., "Synthesis and CYP24 inhibitory activity of 2-substituted-3,4-dihydro-2H-naphthalen-1-one (tetralone) derivatives", Bioorganic & Medicinal Chemistry Letters, vol. 14, 2004 (available online Sep. 17, 2004), pp. 5651-5654.

*Primary Examiner* — D Margaret M Seaman
(74) *Attorney, Agent, or Firm* — Birch, Stewart, Kolasch & Birch, LLP

(57) ABSTRACT

The compounds represented by Formula (I), which are peripheral alkyl and alkenyl chains extended benzene derivatives, are useful as dual autotaxin (ATX)/histone deacetylase (HD AC) inhibitors. These compounds may be included in a pharmaceutical composition along with a pharmaceutically acceptable carrier, and be used in a therapeutically effective amount for prophylaxis or treatment of various diseases and disorders.

Formula (I)

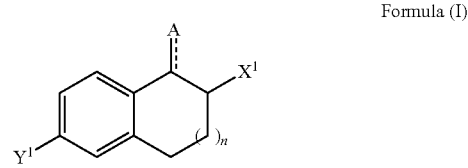

21 Claims, No Drawings

PERIPHERAL ALKYL AND ALKENYL CHAINS EXTENDED BENZENE DERIVATIVES AND PHARMACEUTICAL COMPOSITION INCLUDING THE SAME

CROSS-REFERENCE TO RELATED APPLICATION

This application is the National Phase of PCT International Application No. PCT/US2020/025099, filed on Mar. 27, 2020, which claims priority under 35 U.S.C. 119 (e) to U.S. Provisional Application No. 62/825,977, filed on Mar. 29, 2019, all of which are hereby expressly incorporated by reference into the present application.

BACKGROUND

Technical Field

The present disclosure relates to peripheral alkyl and alkenyl chains extended benzene derivatives and pharmaceutical compositions including the same. The peripheral alkyl and alkenyl chains extended benzene derivatives are useful as a dual autotaxin (ATX)/histone deacetylase (HDAC) inhibitor.

Description of Related Art

Histones form the core of nucleosomes, the DNA/protein complexes that are the subunits of eukaryotic chromatin. Histones' N-terminal "tails" are subject to a variety of posttranslational modifications, including phosphorylation, methylation, ubiquitination, ADP-ribosylation and acetylation. Histone deacetylases (HDACs) are responsible for removal of these acetyl groups, and play an important role in the regulation of gene expression. Human HDAC1 was the first protein to be linked to histone deacetylase activity. Aberrant expression of HDACs is observed in various human cancers. HDAC inhibitors could become useful as a therapeutic or prophylactic agent for diseases caused by abnormal gene expression such as inflammatory disorders, cancers or the like.

Autotaxin (ATX) is a secreted enzyme that in humans is encoded by the ENPP2 gene, and is known as ectonucleotide pyrophosphatase/phosphodiesterase family member 2 (NPP2 or ENPP2) or lysophospholipase D. Autotaxin has lysophospholipase D activity that converts lysophosphatidylcholine into lysophosphatidic acid (LPA). Autotaxin is a ~120 kDa secreted enzyme that is important in generating the lipid signaling molecule LPA. The ATX-LPA axis is involved in a range of pathophysiological functions, including, for example, embryonic development, chronic inflammatory disease, or cancer biology. In cancer biology, LPA signaling is being recognized as a central mediator of the progression of chronic inflammation in the establishment of a tumor microenvironment which promotes cancer growth. So far, there is no approved cancer therapy that target the ATX-LPA axis.

Previous studies have shown that HDAC inhibitors may potentially induce autotaxin expression. However, dual inhibitors of HDAC and autotaxin have rarely been reported. Therefore, development of dual inhibitors of HDAC and autotaxin is desired, as they have great potential in the prophylaxis and treatment of various diseases, disorders etc.

SUMMARY

In some embodiments of the present disclosure, a compound, which is a peripheral alkyl and alkenyl chains extended benzene derivative is described. The compound is represented by Formula (I), or its geometric isomers, enantiomers, diastereomers, racemates, pharmaceutically acceptable salts, prodrugs and solvates thereof:

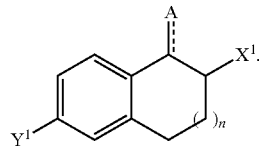

Formula (I)

In Formula (I), ==== is a single or double bond; n is an integer of 0 or 1; $X^1$ is hydrogen, $R^1$-$A^1$ or $R^2$-$A^1$, wherein $R^1$ is a single bond or a double bond, $R^2$ is independently selected from a group consisting of $C_1$-$C_{10}$ alkyl, $C_1$-$C_{10}$ alkenyl, and $C_1$-$C_{10}$ alkoxy, $A^1$ is an aryl optionally substituted with —$CF_3$; $Y^1$ is a hydrogen, a halogen, —OH, —$OCH_3$, —NHC(O)$R^2$C(O)NH$R^3$, —$R^2$C(O)NHR$^3$, —$R^2$C(O)NH$R^4$C(O)NHR$^3$, —C(O)NHR$^2$C(O)NHR$^3$, —OCH$_2$R$^5$C(O)NHR$^3$, —OCH$_2$R$^5$R$^2$C(O)NHR$^3$, —C(O)R$^6$C(O)R$^2$C(O)NHR$^3$, —R$^2$R$^5$C(O)NHR$^3$ or —R$^2$C(O)NHR$^3$, wherein $R^3$ is independently selected from a group consisting of OH, an aryl optionally substituted with at least one of a halogen, an alkyl, an alkoxy or —NH$_2$, and when $R^3$ is an aryl substituted with —NH$_2$, any hydrogen in the NH$_2$ may be optionally substituted with alkyl, $R^4$ is independently selected from a group consisting of $C_1$-$C_{10}$ alkyl, $C_1$-$C_{10}$ alkenyl, and $C_1$-$C_{10}$ alkoxy, $R^5$ is an aryl and $R^6$ is a heterocyclic alkyl; A is O, —OH, —OR$^2$A$^1$, —N—OH or —NZX$^2$, wherein Z is hydrogen or —CH$_3$, or Z forms a heterocyclic alkyl with the nitrogen, and the heterocyclic alkyl is substituted with $X^2$, $X^2$ is —C(O)-A$^1$, —C(O)R$^2$C(O)NHR$^3$, —R$^3$, —C(O)OR$^2$A$^1$, —SO$_2$R$^3$, —SO$_2$A$^1$, —C(O)A$^1$, —C(O)R$^3$, —R$^2$A$^1$, —R$^2$R$^3$, —R$^2$R$^7$, —C(O)R$^2$NR$^8$R$^4$C(O)NHR$^3$, —R$^2$C(O)NHA$^1$, wherein $R^7$ is a heterocyclic fused ring that may be optionally substituted with alkyl, and $R^8$ is —CH$_2$C(O)NHZ$^2$, and $Z^2$ is a fused ring.

The present disclosure further provides a pharmaceutical composition that includes a therapeutically effective amount of the compound of Formula (I) and a pharmaceutically acceptable carrier.

The compounds provided in the present disclosure may be used as dual HDAC/autotaxin inhibitors.

To make the aforementioned more comprehensible, several embodiments accompanied with drawings are described in detail as follows.

DESCRIPTION OF THE EMBODIMENTS

The compounds of the present disclosure are described in detail in the following embodiments.

In the present disclosure, when a range of values is listed, it is intended to encompass each value and sub-range within the range. For example, "$C_1$-$C_4$" is intended to encompass, $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$.

Unless otherwise indicated, the term "alkyl" means a straight chain, branched and/or cyclic hydrocarbon having from 1 to 20 (e.g., 1 to 10, 1 to 9, 1 to 8, 1 to 7, 1 to 6, 1 to 5, 1 to 4, 1 to 3, 1 to 2, or 1) carbon atoms. Alkyl moieties having from 1 to 4 carbons ($C_1$-$C_4$ alkyl) are referred to as "lower alkyl." Examples of alkyl groups include methyl, ethyl, propyl, isopropyl, n-butyl, t-butyl, isobutyl, 2-isopropyl-3-methyl butyl, pentyl, pentan-2-yl, hexyl, isohexyl, heptyl, heptan-2-yl, 4,4-dimethylpentyl, octyl, 2,2,4-trimethylpentyl, nonyl, decyl, undecyl and dodecyl. Unless otherwise specified, each instance of an alkyl group is independently optionally substituted, i.e., unsubstituted (an "unsubstituted alkyl") or substituted (a "substituted alkyl") with one or more substituents.

"Heterocyclic alkyl" refers to a radical of a 3- to 10-membered non-aromatic ring system having ring carbon atoms and 1 to 4 ring heteroatoms, wherein each heteroatom is independently selected from nitrogen, oxygen, sulfur, phosphorus, and silicon ("3-10 membered heterocyclic alkyl"). In heterocyclyl groups that contain one or more nitrogen atoms, the point of attachment can be a carbon or nitrogen atom, as valency permits. Unless otherwise specified, each instance of heterocyclic alkyl is independently optionally substituted, i.e., unsubstituted (an "unsubstituted heterocyclic alkyl") or substituted (a "substituted heterocyclic alkyl") with one or more substituents. In some embodiments, a heterocyclyl group is a 5-8 membered non-aromatic ring system having ring carbon atoms and 1-4 ring heteroatoms, wherein each heteroatom is independently selected from nitrogen, oxygen, and sulfur. In some embodiments, a heterocyclic alkyl group is a 5-6 membered nonaromatic ring system having ring carbon atoms and 1-4 ring heteroatoms, wherein each heteroatom is independently selected from nitrogen, oxygen, and sulfur. In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclic alkyl has one ring heteroatom selected from nitrogen, oxygen, and sulfur. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5 membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl.

Unless otherwise indicated, the term "aryl" means an aromatic ring or a partially aromatic ring system composed of carbon and hydrogen atoms. An aryl moiety may comprise multiple rings bound or fused together. Examples of aryl moieties include naphthyl, and phenyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is a substituted phenyl.

Unless otherwise indicated, the term "alkoxy" or "alkoxyl" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl), such as —OCH$_3$ and —OCH$_2$CH$_3$.

Unless otherwise indicated, the terms "halogen" and "halo" encompass fluoro-, chloro-, bromo-, and iodo-groups.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, —OH, —NH$_2$, —CHO, alkoxy, alkanoyloxy (e.g., —OAc), alkenyl, alkyl (e.g., methyl, ethyl, propyl, t-butyl), aryl, aryloxy, halo, or haloalkyl (e.g., —CCl$_3$, —CF$_3$, —C(CF$_3$)$_3$) etc.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6H$_2$O)).

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Unless otherwise indicated, "an effective amount" of a compound is an amount sufficient to provide a therapeutic or positive benefit in the treatment or management of a disease, environment or condition, or to delay or minimize one or more symptoms associated with the disease, environment or condition. An effective amount of a compound is an amount of therapeutic agent, alone or in combination with other therapies, which provides a therapeutic benefit in the treatment or management of the disease, environment or condition. The term "effective amount" can encompass an amount that improves overall therapy, reduces or avoids symptoms or causes of a disease, environment or condition, or enhances the therapeutic efficacy of another therapeutic agent.

Unless otherwise indicated, the terms "treat," "treating" and "treatment" contemplate an action that occurs while a subject (such as patient) is suffering from the specified disease or disorder, which reduces the severity of the disease or disorder, or one or more of its symptoms, or retards or slows the progression of the disease or disorder.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_1\text{-}C_4$ alkyl)-4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable carrier" refers to a carrier, whether diluent or excipient, that is compatible with the other ingredients of a formulation and not deleterious to the recipient thereof. Usable pharmaceutically acceptable carriers are disclosed in various references including Handbook of Pharmaceuticals Excipients edited by Raymond C Rowe, Paul J Sheskey, and Marian E Quinn. In an unlimited embodiment, said pharmaceutically acceptable carrier can be selected from the group consisting of inert diluents, dispersing and/or granulating agents, surface active agents and/or emulsifiers, disintegrating agents, binding agents, preservatives, buffering agents, lubricating agents, and/or oils. Said compositions optionally further comprise at least one of additional biologically active compounds or agents.

The terms "administration" or "administering" a composition are defined to include providing the compound or the pharmaceutical composition of the present disclosure to the subject in need of treatment or control. In an alternative embodiment, said administering is conducted through oral, intravenous, intramuscular, cutaneous, subcutaneous, intrathecal, transdermal, implantation, sublingual, buccal, rectal, vaginal, ocular, otic, nasal, inhalation, or nebulization route.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in the respective testing measurements. Accordingly, unless indicated to the contrary, the numerical parameters set forth in the present disclosure and attached claims are approximations that can vary as desired. At the very least, each numerical parameter should at least be constructed in light of the number of reported significant digits and by applying ordinary rounding techniques. The singular forms "a", "and", and "the" are used herein to include plural referents unless the context clearly dictates otherwise.

Novel Compounds

The present disclosure provides novel compounds of peripheral alkyl and alkenyl chains extended benzene derivatives. In some embodiments of the present disclosure, a compound represented by Formula (I), or its geometric isomers, enantiomers, diastereomers, racemates, pharmaceutically acceptable salts, prodrugs and solvates thereof is provided.

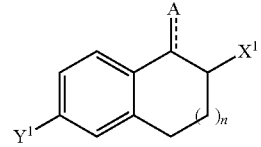

Formula (I)

In Formula (I), ==== is a single or double bond; n is an integer of 0 or 1; $X^1$ is hydrogen, $R^1\text{-}A^1$ or $R^2\text{-}A^1$, wherein $R^1$ is a single bond or a double bond, $R^2$ is independently selected from a group consisting of $C_1\text{-}C_{10}$ alkyl, $C_1\text{-}C_{10}$ alkenyl, and $C_1\text{-}C_{10}$ alkoxy, $A^1$ is an aryl optionally substituted with —$CF_3$; $Y^1$ is a hydrogen, a halogen, —OH, —$OCH_3$, —$NHC(O)R^2C(O)NHR^3$, —$R^2C(O)NHR^3$, —$R^2C(O)NHR^4C(O)NHR^3$, —$C(O)NHR^2C(O)NHR^3$, —$OCH_2R^5C(O)NHR^3$, —$OCH_2R^5R^2C(O)NHR^3$, —$C(O)R^6C(O)R^2C(O)NHR^3$, —$R^2R^5C(O)NHR^3$ or —$R^2C(O)NHR^3$, wherein $R^3$ is independently selected from a group consisting of OH, an aryl optionally substituted with at least one of a halogen, an alkyl, an alkoxy or —$NH_2$, and when $R^3$ is an aryl substituted with —$NH_2$, any hydrogen in the $NH_2$ may be optionally substituted with alkyl, $R^4$ is independently selected from a group consisting of $C_1$-$C_{10}$ alkyl, $C_1$-$C_{10}$ alkenyl, and $C_1$-$C_{10}$ alkoxy, $R^5$ is an aryl and $R^6$ is a heterocyclic alkyl; A is O, —OH, —$OR^2A^1$, —N—OH or —$NZX^2$, wherein Z is hydrogen or —$CH_3$, or Z forms a heterocyclic alkyl with the nitrogen, and the heterocyclic alkyl is substituted with $X^2$, $X^2$ is —C(O)-$A^1$, —C(O)$R^2$C(O)$NHR^3$, —$R^3$, —C(O)$OR^2A^1$, —$SO_2R^3$, —$SO_2A^1$, —C(O)$A^1$, —C(O)$R^3$, —$R^2A^1$, —$R^2R^3$, —$R^2R^7$, —C(O)$R^2NR^8R^4$C(O)$NHR^3$, —$R^2$C(O)$NHA^1$, wherein $R^7$ is a heterocyclic fused ring that may be optionally substituted with alkyl, and $R^8$ is —$CH_2$C(O)$NHZ^2$, and $Z^2$ is a fused ring.

In some embodiments of the present disclosure, in Formula (I), at least one of $Y^1$ and A includes a peptide bond (—C(O)—NH—; —NH—C(O)—) in its structure. In other words, the compound of Formula (I) at least include a peptide bond in the side chain. Taking $Y^1$ for example, —NHC(O)$R^2$C(O)$NHR^3$, —$R^2$C(O)$NHR^3$, —$R^2$C(O)$NHR^4$C(O)$NHR^3$, —C(O)$NHR^2$C(O)$NHR^3$, —$OCH_2R^5$C(O)$NHR^3$, —$OCH_2R^5R^2$C(O)$NHR^3$, —C(O)$R^6$C(O)$R^2$C(O)$NHR^3$, —$R^2R^5$C(O)$NHR^3$ or —$R^2$C(O)$NHR^3$ are all examples of substituents that includes peptide bonds in its structure.

In some embodiments, the compound of Formula (I) may be further represented by Formula (I-1), or its geometric isomers, enantiomers, diastereomers, racemates, pharmaceutically acceptable salts, prodrugs and solvates thereof.

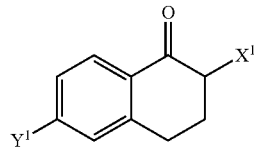

Formula (I-1)

In Formula (I-1), $X^1$ is hydrogen, or $R^1$-$A^1$, and $R^1$ is a single bond or a double bond, $A^1$ is an aryl optionally substituted with —$CF_3$ groups; $Y^1$ is —NHC(O)$R^2$C(O)$NHR^3$, —$R^2$C(O)$NHR^3$, —$R^2$C(O)$NHR^4$C(O)$NHR^3$, —C(O)$NHR^2$C(O)$NHR^3$, —$OCH_2R^5$C(O)$NHR^3$, —$OCH_2R^5R^2$C(O)$NHR^3$, —C(O)$R^6$C(O)$R^2$C(O)$NHR^3$, wherein $R^2$ and $R^4$ are independently selected from a group consisting of $C_1$-$C_{10}$ alkyl, $C_1$-$C_{10}$ alkenyl, and $C_1$-$C_{10}$ alkoxy, $R^3$ is independently selected from a group consisting of —OH, an aryl optionally substituted with at least one of a halogen, an alkyl, an alkoxy or —$NH_2$, and when $R^3$ is an aryl substituted with —$NH_2$, any hydrogen in the $NH_2$ may be optionally substituted with alkyl, $R^5$ is an aryl and $R^6$ is a heterocyclic alkyl.

In some embodiments, the compound of Formula (I-1) is selected from the group consisting of the compounds delineated in Table A or its geometric isomers, enantiomers, diastereomers, racemates, pharmaceutically acceptable salts, prodrugs and solvates thereof.

TABLE A

| (No.) | Structure |
|---|---|
| 1 | ![structure 1] |
| 4 | ![structure 4] |
| 5 | ![structure 5] |
| 6 | ![structure 6] |

TABLE A-continued
| (No.) | Structure |
|---|---|
| 7 | 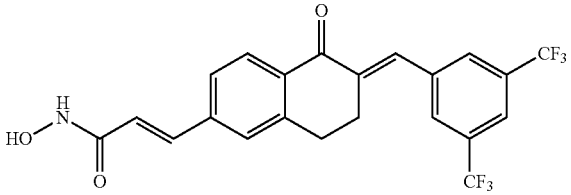 [SMILES: O=C(/C=C/c1ccc2c(c1)CC/C(=C\c1cc(C(F)(F)F)cc(C(F)(F)F)c1)C2=O)NO] |
| 8 | 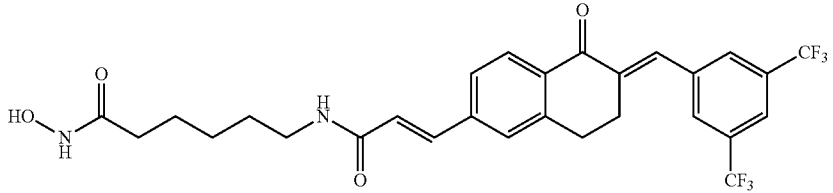 [SMILES: O=C(/C=C/c1ccc2c(c1)CC/C(=C\c1cc(C(F)(F)F)cc(C(F)(F)F)c1)C2=O)NCCCCCC(=O)NO] |
| 9 | 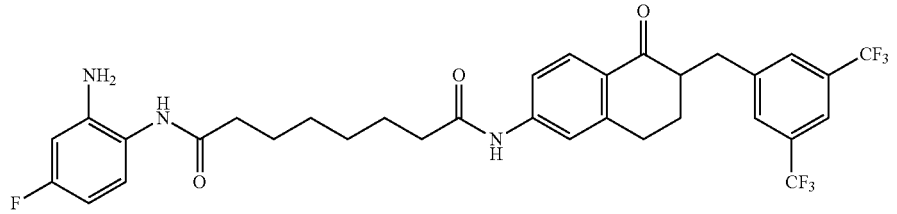 [SMILES: Nc1cc(F)ccc1NC(=O)CCCCCCC(=O)Nc1ccc2c(c1)CCC(Cc1cc(C(F)(F)F)cc(C(F)(F)F)c1)C2=O] |
| 10 | 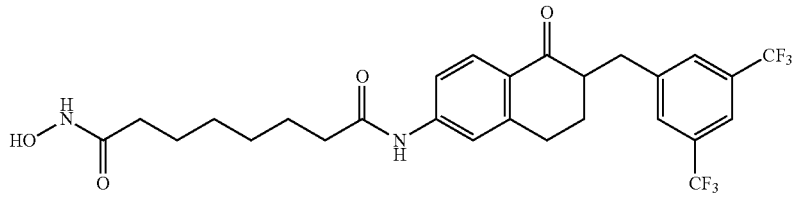 [SMILES: O=C(CCCCCCC(=O)Nc1ccc2c(c1)CCC(Cc1cc(C(F)(F)F)cc(C(F)(F)F)c1)C2=O)NO] |
| 11 | 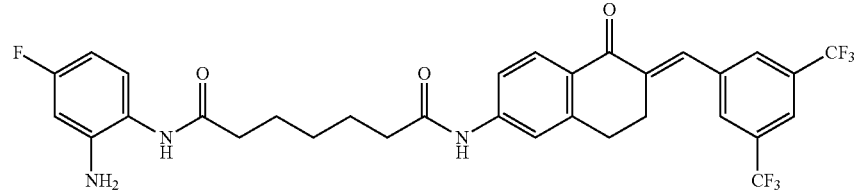 [SMILES: Nc1cc(F)ccc1NC(=O)CCCCCC(=O)Nc1ccc2c(c1)CC/C(=C\c1cc(C(F)(F)F)cc(C(F)(F)F)c1)C2=O] |
| 12 | 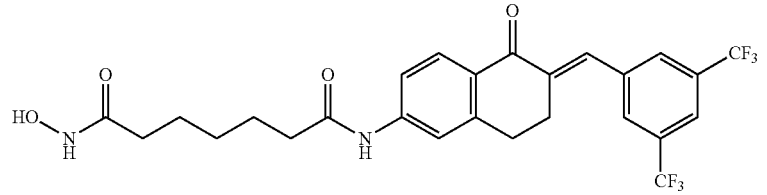 [SMILES: O=C(CCCCCC(=O)Nc1ccc2c(c1)CC/C(=C\c1cc(C(F)(F)F)cc(C(F)(F)F)c1)C2=O)NO] |
| 13 | 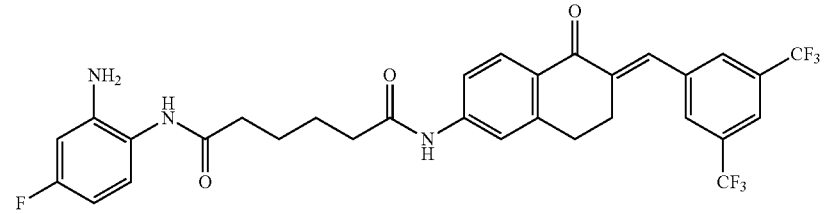 [SMILES: Nc1cc(F)ccc1NC(=O)CCCCC(=O)Nc1ccc2c(c1)CC/C(=C\c1cc(C(F)(F)F)cc(C(F)(F)F)c1)C2=O] |

TABLE A-continued
| (No.) | Structure |
|---|---|
| 14 | 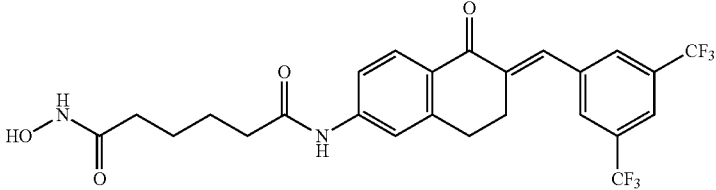 [SMILES: O=C(CCCCC(=O)Nc1ccc2c(c1)CC/C(=C\c1cc(C(F)(F)F)cc(C(F)(F)F)c1)C2=O)NO] |
| 66 | 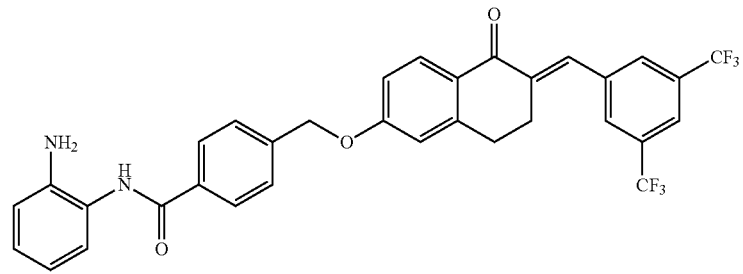 [SMILES: Nc1ccccc1NC(=O)c1ccc(COc2ccc3c(c2)CC/C(=C\c2cc(C(F)(F)F)cc(C(F)(F)F)c2)C3=O)cc1] |
| 67 | 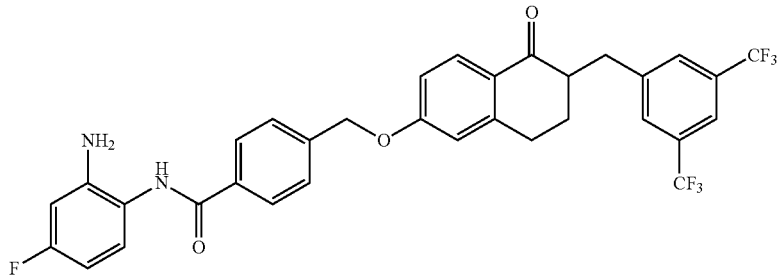 [SMILES: Nc1cc(F)ccc1NC(=O)c1ccc(COc2ccc3c(c2)CCC(Cc2cc(C(F)(F)F)cc(C(F)(F)F)c2)C3=O)cc1] |
| 68 | 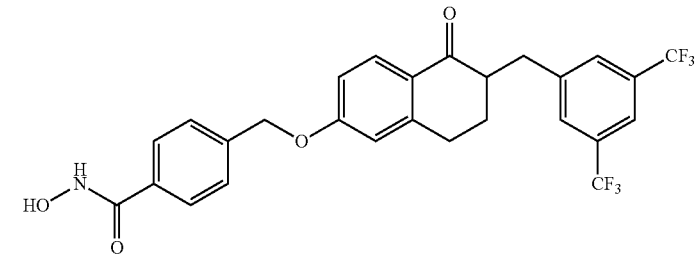 [SMILES: O=C(NO)c1ccc(COc2ccc3c(c2)CCC(Cc2cc(C(F)(F)F)cc(C(F)(F)F)c2)C3=O)cc1] |
| 69 | 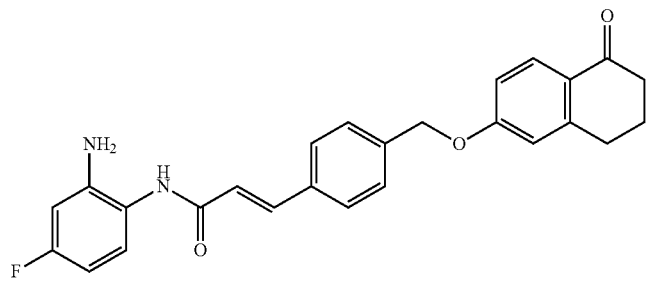 [SMILES: Nc1cc(F)ccc1NC(=O)/C=C/c1ccc(COc2ccc3c(c2)CCCC3=O)cc1] |
| 70 | 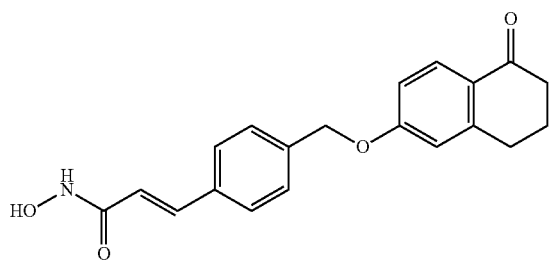 [SMILES: O=C(/C=C/c1ccc(COc2ccc3c(c2)CCCC3=O)cc1)NO] |

TABLE A-continued

| (No.) | Structure |
|---|---|
| 71 | 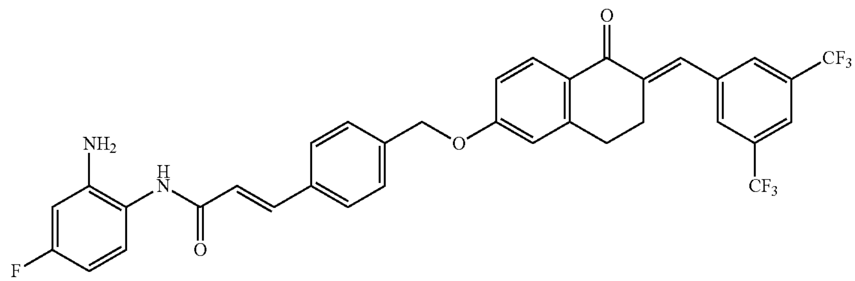 [SMILES: Nc1cc(F)ccc1NC(=O)/C=C/c1ccc(COc2ccc3c(c2)CC/C(=C\c2cc(C(F)(F)F)cc(C(F)(F)F)c2)C3=O)cc1] |
| 72 | 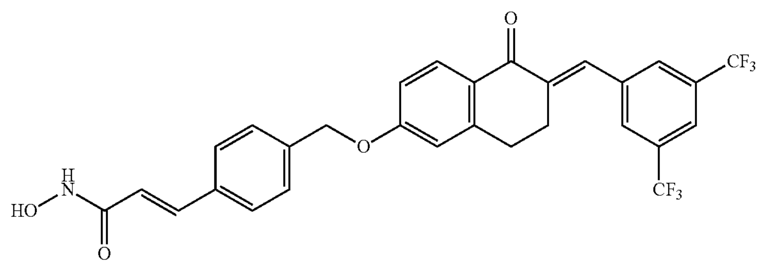 [SMILES: O=C(/C=C/c1ccc(COc2ccc3c(c2)CC/C(=C\c2cc(C(F)(F)F)cc(C(F)(F)F)c2)C3=O)cc1)NO] |
| 73 | 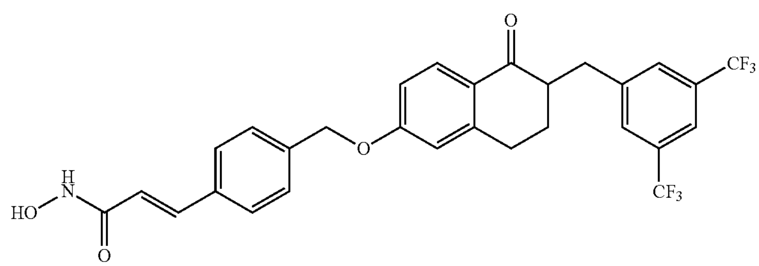 [SMILES: O=C(/C=C/c1ccc(COc2ccc3c(c2)CCC(Cc2cc(C(F)(F)F)cc(C(F)(F)F)c2)C3=O)cc1)NO] |
| 74 | 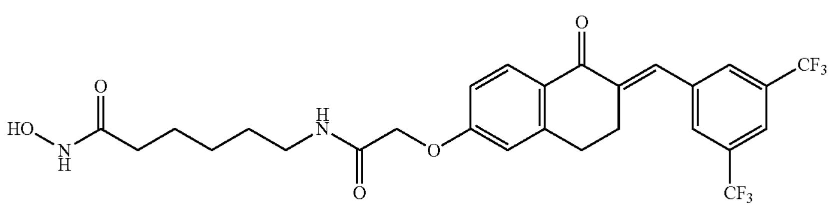 [SMILES: O=C(CCCCCNC(=O)COc1ccc2c(c1)CC/C(=C\c1cc(C(F)(F)F)cc(C(F)(F)F)c1)C2=O)NO] |
| 75 | 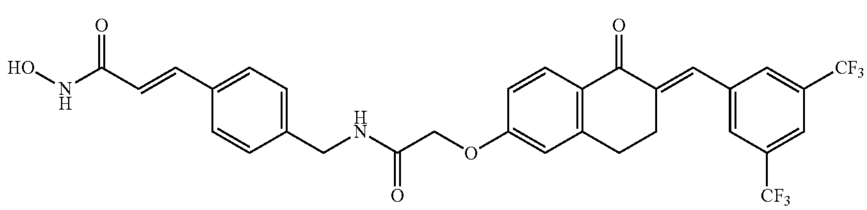 [SMILES: O=C(/C=C/c1ccc(CNC(=O)COc2ccc3c(c2)CC/C(=C\c2cc(C(F)(F)F)cc(C(F)(F)F)c2)C3=O)cc1)NO] |
| 78 | 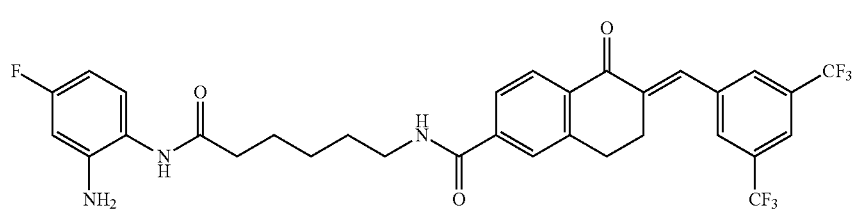 [SMILES: Nc1cc(F)ccc1NC(=O)CCCCCNC(=O)c1ccc2c(c1)CC/C(=C\c1cc(C(F)(F)F)cc(C(F)(F)F)c1)C2=O] |

TABLE A-continued

| (No.) | Structure |
|---|---|
| 79 | 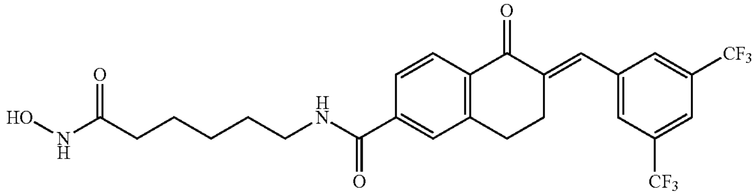 [SMILES: O=C(CCCCCNC(=O)c1ccc2c(c1)CC/C(=C\c1cc(C(F)(F)F)cc(C(F)(F)F)c1)C2=O)NO] |
| 80 | 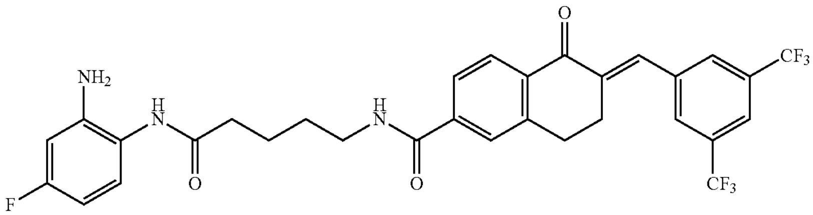 [SMILES: Nc1cc(F)ccc1NC(=O)CCCCNC(=O)c1ccc2c(c1)CC/C(=C\c1cc(C(F)(F)F)cc(C(F)(F)F)c1)C2=O] |
| 81 | 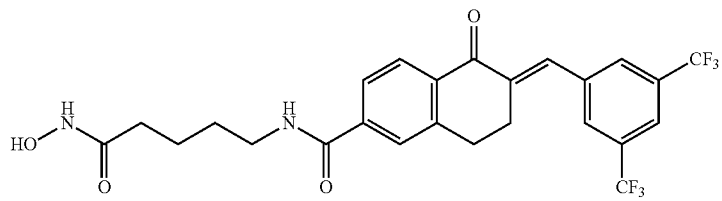 [SMILES: O=C(CCCCNC(=O)c1ccc2c(c1)CC/C(=C\c1cc(C(F)(F)F)cc(C(F)(F)F)c1)C2=O)NO] |
| 82 | 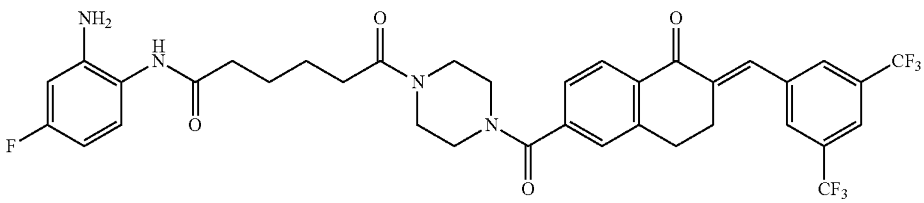 [SMILES: Nc1cc(F)ccc1NC(=O)CCCCC(=O)N1CCN(C(=O)c2ccc3c(c2)CC/C(=C\c2cc(C(F)(F)F)cc(C(F)(F)F)c2)C3=O)CC1] |
| 83 | 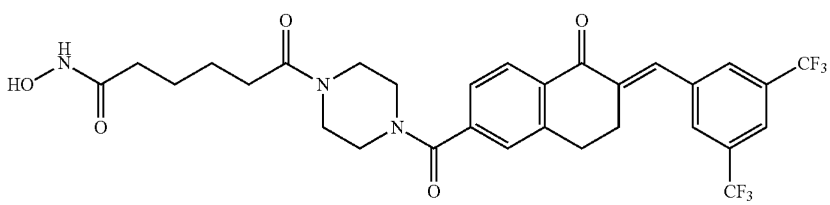 [SMILES: O=C(CCCCC(=O)N1CCN(C(=O)c2ccc3c(c2)CC/C(=C\c2cc(C(F)(F)F)cc(C(F)(F)F)c2)C3=O)CC1)NO] |

In some embodiments, the compound of Formula (I) may be further represented by Formula (I-2), or its geometric isomers, enantiomers, diastereomers, racemates, pharmaceutically acceptable salts, prodrugs and solvates thereof.

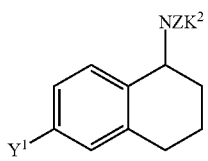

Formula (I-2)

In Formula (I-2), Z is hydrogen, $X^2$ is —C(O)-$A^1$, —C(O)$R^2$C(O)NH$R^3$, —$R^2R^7$, $Y^1$ is a halogen, —OH, —OCH$_3$ or —$R^2$C(O)NH$R^3$, wherein $R^2$ is independently selected from a group consisting of $C_1$-$C_{10}$ alkyl, $C_1$-$C_{10}$ alkenyl, and $C_1$-$C_{10}$ alkoxy, $A^1$ is an aryl optionally substituted with —CF$_3$, $R^3$ is independently selected from a group consisting of OH, an aryl optionally substituted with at least one of a halogen, an alkyl, an alkoxy or —NH$_2$, and when $R^3$ is an aryl substituted with —NH$_2$, any hydrogen in the NH$_2$ may be optionally substituted with alkyl, $R^7$ is a heterocyclic fused ring that may be optionally substituted with alkyl.

In some embodiments, the compound of Formula (I-2) is selected from the group consisting of the compounds delineated in Table B or its geometric isomers, enantiomers, diastereomers, racemates, pharmaceutically acceptable salts, prodrugs and solvates thereof.

TABLE B
| (No.) | Structure |
|---|---|
| 23 | 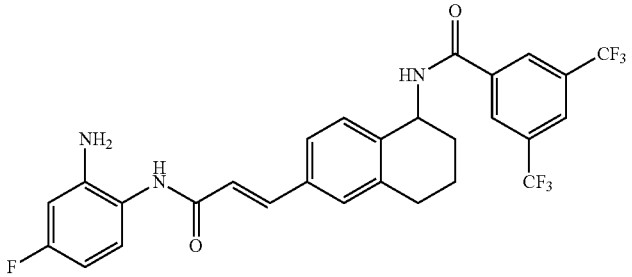 [SMILES: Nc1cc(F)ccc1NC(=O)/C=C/c1ccc2c(c1)CCCC2NC(=O)c1cc(C(F)(F)F)cc(C(F)(F)F)c1] |
| 24 | 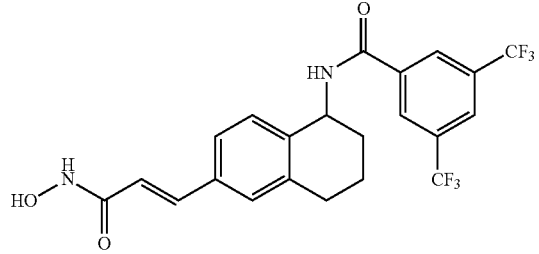 [SMILES: O=C(/C=C/c1ccc2c(c1)CCCC2NC(=O)c1cc(C(F)(F)F)cc(C(F)(F)F)c1)NO] |
| 46 | 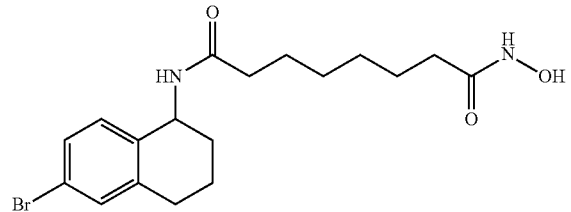 [SMILES: O=C(CCCCCCC(=O)NC1CCCc2cc(Br)ccc21)NO] |
| 47 | 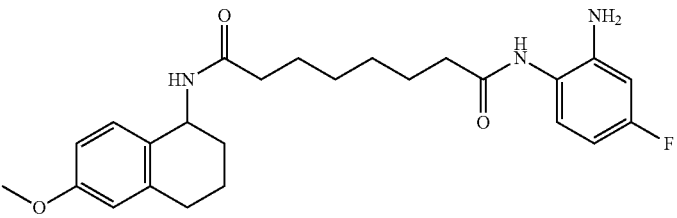 [SMILES: COc1ccc2c(c1)CCCC2NC(=O)CCCCCCC(=O)Nc1ccc(F)cc1N] |
| 48 | 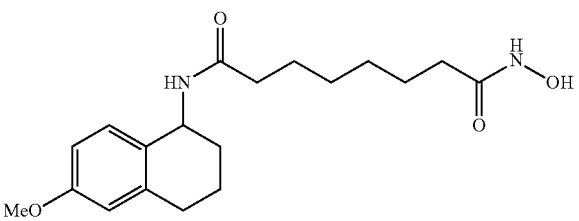 [SMILES: COc1ccc2c(c1)CCCC2NC(=O)CCCCCCC(=O)NO] |
| 61 | 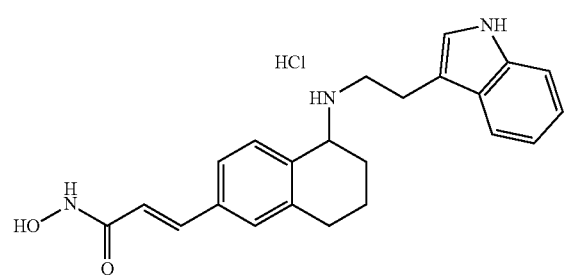 [SMILES: O=C(/C=C/c1ccc2c(c1)CCCC2NCCc1c[nH]c2ccccc12)NO ; Cl] |

TABLE B-continued

| (No.) | Structure |
|---|---|
| 62 | (structure: 2-amino-4-fluorophenyl cinnamamide linked to tetrahydronaphthalene bearing 2-methylindolyl-ethylamine, 2HCl salt) |
| 63 | (structure: N-hydroxy cinnamamide linked to tetrahydronaphthalene bearing 2-methylindolyl-ethylamine, HCl salt) |

In some embodiments, the compound of Formula (I) may be further represented by Formula (I-3), or its geometric isomers, enantiomers, diastereomers, racemates, pharmaceutically acceptable salts, prodrugs and solvates thereof.

Formula (I-3)

(structure showing indane core with NZK² substituent and Y¹ substituent)

In Formula (I-3), Z is hydrogen or —CH₃, or Z forms a heterocyclic alkyl with the nitrogen, wherein the heterocyclic alkyl is substituted with X², X² is —R³, —C(O)OR²A¹, —SO₂R³, —SO₂A¹, —C(O)A¹, —C(O)R³, —R²A¹, —R²R³, —R²R⁷, —C(O)R²C(O)NHR³, —C(O)R²NR⁸R⁴C(O)NHR³, —R²C(O)NHA¹, Y¹ is hydrogen, halogen, —OCH₃, —R²C(O)NHR³, —R²C(O)NHR⁴C(O)NHR³, wherein R² is independently selected from a group consisting of C₁-C₁₀ alkyl, C₁-C₁₀ alkenyl, and C₁-C₁₀ alkoxy, A¹ is an aryl optionally substituted with —CF₃, R³ is independently selected from a group consisting of —OH, an aryl optionally substituted with at least one of a halogen, an alkyl, an alkoxy or —NH₂, and when R³ is an aryl substituted with —NH₂, any hydrogen in the NH₂ may be optionally substituted with alkyl, R⁷ is a heterocyclic fused ring that may be optionally substituted with alkyl, and R⁸ is —CH₂C(O)NHZ², and Z² is a fused ring.

In some embodiments, the compound of Formula (I-3) is selected from the group consisting of the compounds delineated in Table C or its geometric isomers, enantiomers, diastereomers, racemates, pharmaceutically acceptable salts, prodrugs and solvates thereof.

TABLE C

| (No.) | Structure |
|---|---|
| 15 | (structure: indane bearing N-hydroxy acrylamide and carbamate linked to 3,5-bis(trifluoromethyl)benzyl) |

TABLE C-continued

| (No.) | Structure |
|---|---|
| 16 | 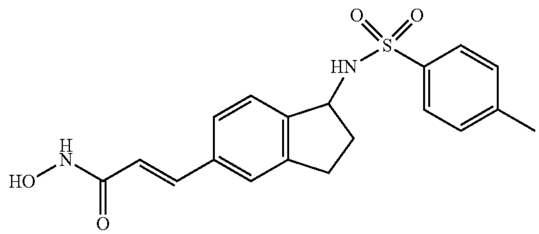 [SMILES: Cc1ccc(S(=O)(=O)NC2CCc3cc(/C=C/C(=O)NO)ccc32)cc1] |
| 17 | 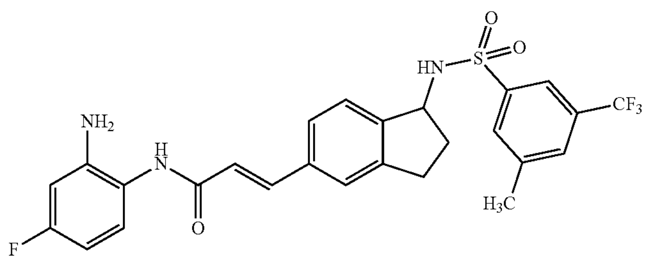 [SMILES: Cc1cc(C(F)(F)F)cc(S(=O)(=O)NC2CCc3cc(/C=C/C(=O)Nc4ccc(F)cc4N)ccc32)c1] |
| 18 | 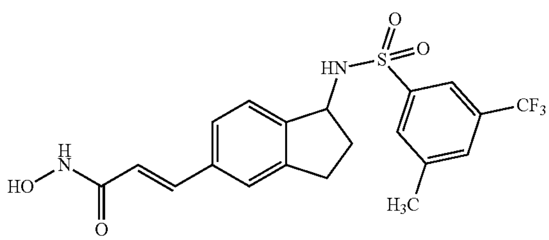 [SMILES: Cc1cc(C(F)(F)F)cc(S(=O)(=O)NC2CCc3cc(/C=C/C(=O)NO)ccc32)c1] |
| 19 | 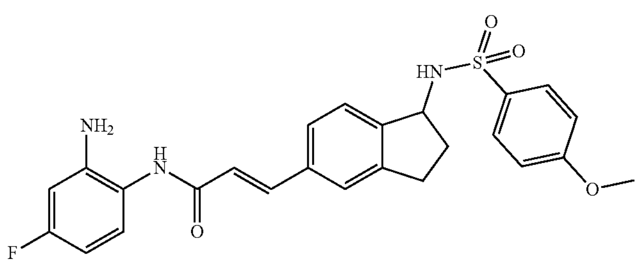 [SMILES: COc1ccc(S(=O)(=O)NC2CCc3cc(/C=C/C(=O)Nc4ccc(F)cc4N)ccc32)cc1] |
| 20 | 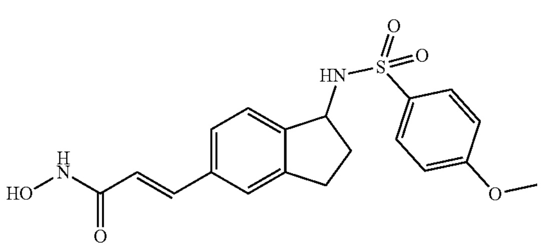 [SMILES: COc1ccc(S(=O)(=O)NC2CCc3cc(/C=C/C(=O)NO)ccc32)cc1] |
| 21 | 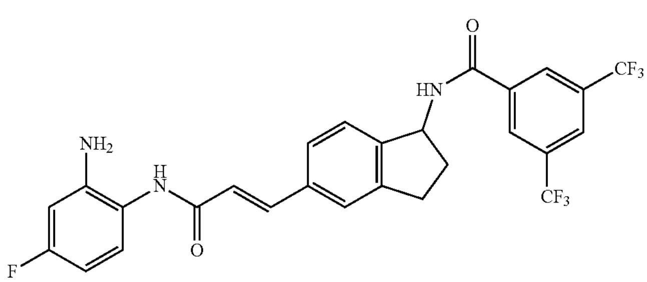 [SMILES: Nc1cc(F)ccc1NC(=O)/C=C/c1ccc2c(c1)CCC2NC(=O)c1cc(C(F)(F)F)cc(C(F)(F)F)c1] |

TABLE C-continued

| (No.) | Structure |
|---|---|
| 22 | 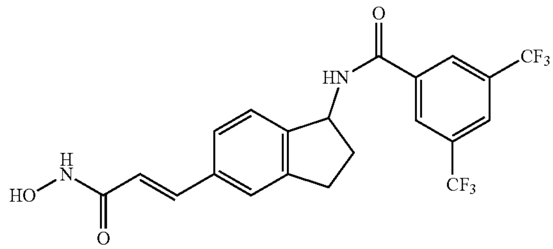 [SMILES: O=C(/C=C/c1ccc2c(c1)CCC2NC(=O)c1cc(C(F)(F)F)cc(C(F)(F)F)c1)NO] |
| 25 | 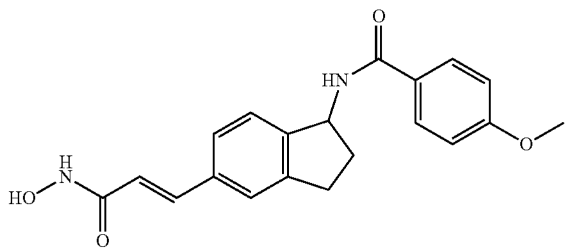 [SMILES: COc1ccc(C(=O)NC2CCc3cc(/C=C/C(=O)NO)ccc32)cc1] |
| 26 | 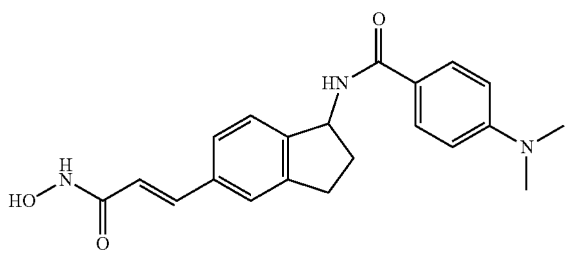 [SMILES: CN(C)c1ccc(C(=O)NC2CCc3cc(/C=C/C(=O)NO)ccc32)cc1] |
| 27 | 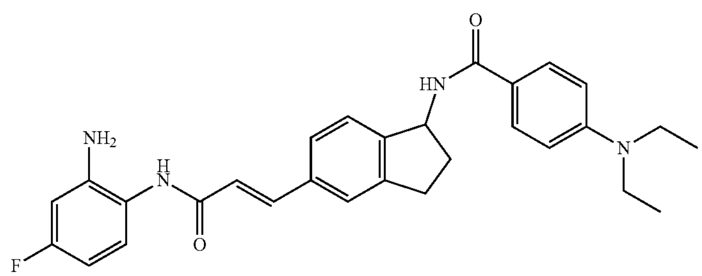 [SMILES: CCN(CC)c1ccc(C(=O)NC2CCc3cc(/C=C/C(=O)Nc4ccc(F)cc4N)ccc32)cc1] |
| 28 | 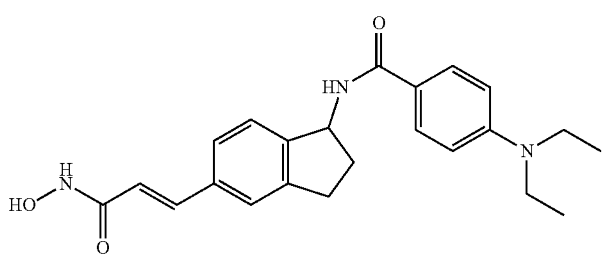 [SMILES: CCN(CC)c1ccc(C(=O)NC2CCc3cc(/C=C/C(=O)NO)ccc32)cc1] |
| 29 | 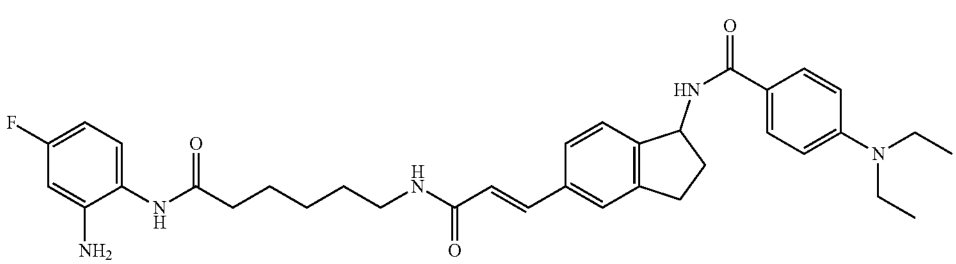 [SMILES: CCN(CC)c1ccc(C(=O)NC2CCc3cc(/C=C/C(=O)NCCCCCC(=O)Nc4ccc(F)cc4N)ccc32)cc1] |

TABLE C-continued

| (No.) | Structure |
|---|---|
| 30 | 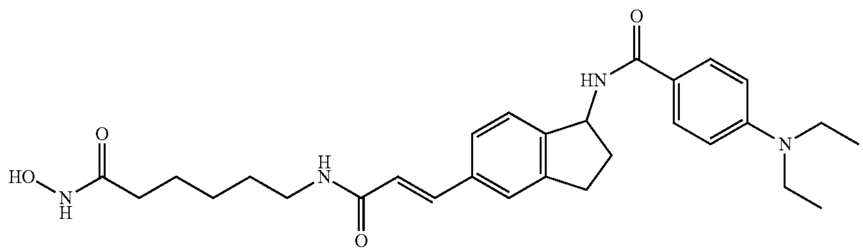 [SMILES: CCN(CC)c1ccc(C(=O)NC2CCc3cc(/C=C/C(=O)NCCCCCC(=O)NO)ccc32)cc1] |
| 31 | 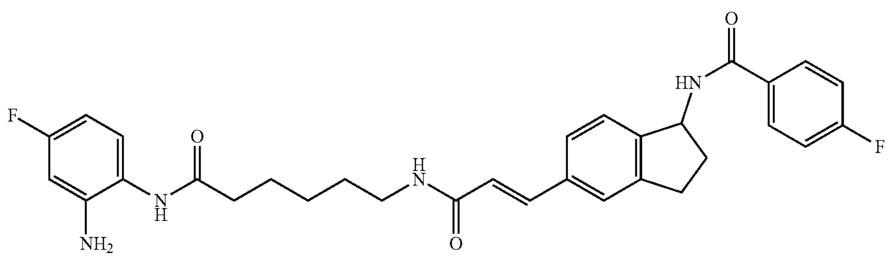 [SMILES: Nc1cc(F)ccc1NC(=O)CCCCCNC(=O)/C=C/c1ccc2c(c1)CCC2NC(=O)c1ccc(F)cc1] |
| 32 | 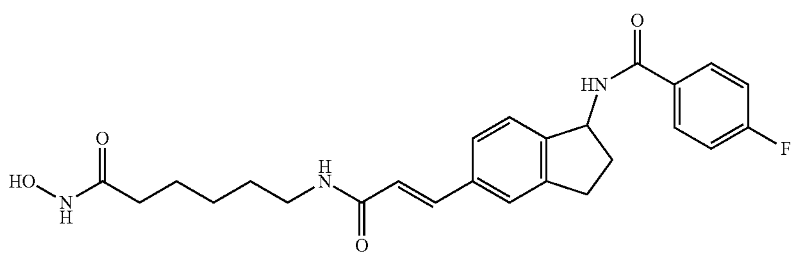 [SMILES: O=C(/C=C/c1ccc2c(c1)CCC2NC(=O)c1ccc(F)cc1)NCCCCCC(=O)NO] |
| 33 | 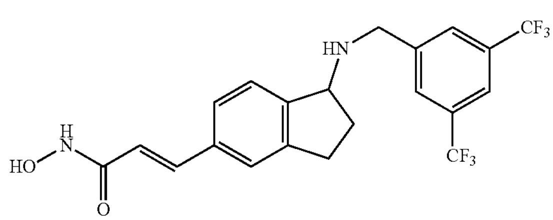 [SMILES: O=C(/C=C/c1ccc2c(c1)CCC2NCc1cc(C(F)(F)F)cc(C(F)(F)F)c1)NO] |
| 37 | 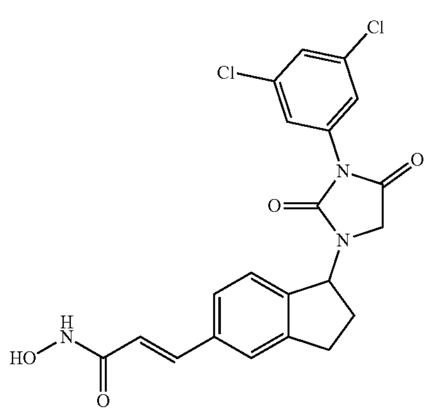 [SMILES: O=C(/C=C/c1ccc2c(c1)CCC2N1CC(=O)N(c2cc(Cl)cc(Cl)c2)C1=O)NO] |

TABLE C-continued
| (No.) | Structure |
|---|---|
| 38 | 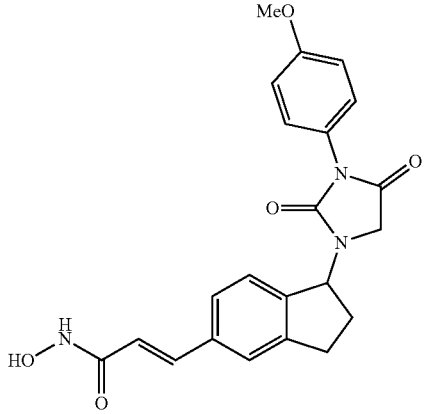 [SMILES: COc1ccc(N2C(=O)CN(C3CCc4cc(/C=C/C(=O)NO)ccc43)C2=O)cc1] |
| 39 | 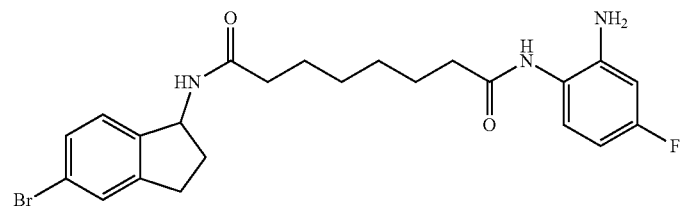 [SMILES: Nc1cc(F)ccc1NC(=O)CCCCCCC(=O)NC1CCc2cc(Br)ccc21] |
| 40 | 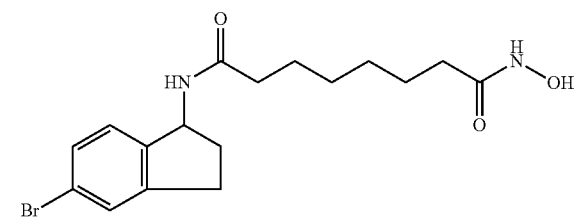 [SMILES: O=C(CCCCCCC(=O)NC1CCc2cc(Br)ccc21)NO] |
| 41 | 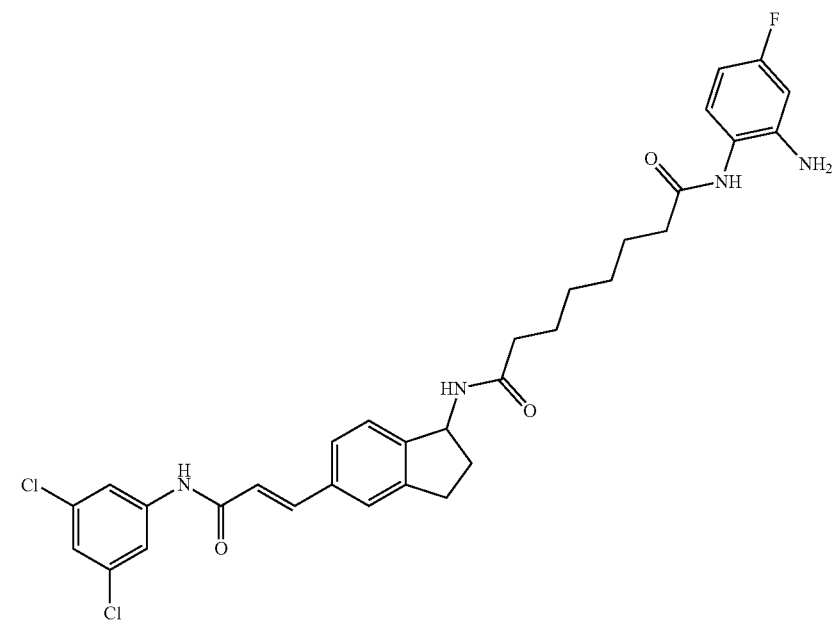 [SMILES: Nc1cc(F)ccc1NC(=O)CCCCCCC(=O)NC1CCc2cc(/C=C/C(=O)Nc3cc(Cl)cc(Cl)c3)ccc21] |

TABLE C-continued

| (No.) | Structure |
|---|---|
| 42 | 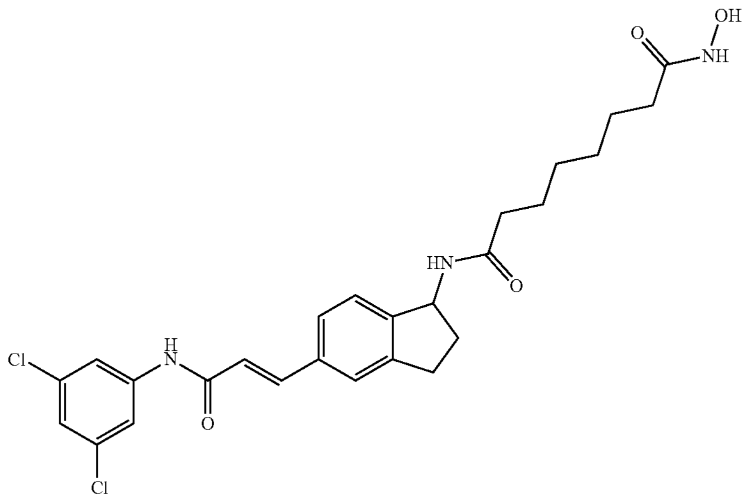 [SMILES: O=C(/C=C/c1ccc2c(c1)CCC2NC(=O)CCCCCCC(=O)NO)Nc1cc(Cl)cc(Cl)c1] |
| 43 | 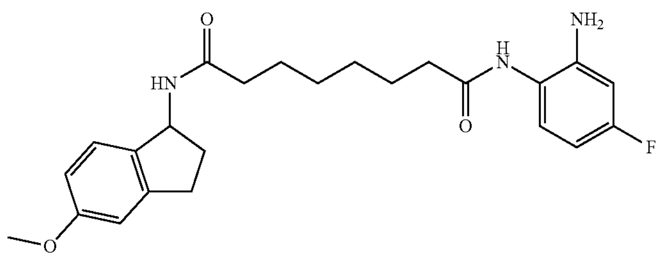 [SMILES: COc1ccc2c(c1)CCC2NC(=O)CCCCCCC(=O)Nc1ccc(F)cc1N] |
| 44 | 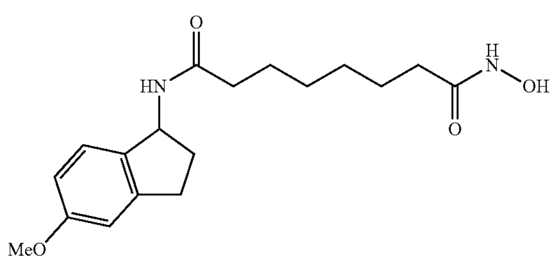 [SMILES: COc1ccc2c(c1)CCC2NC(=O)CCCCCCC(=O)NO] |
| 45 | 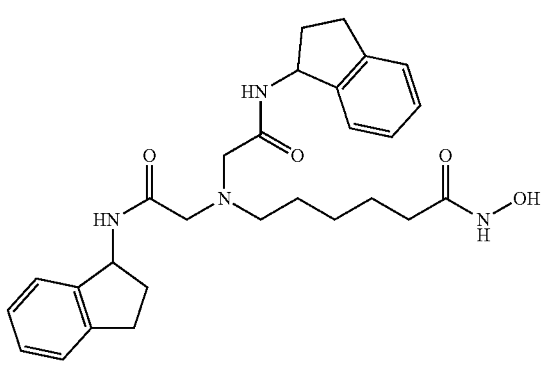 [SMILES: O=C(CCCCCN(CC(=O)NC1CCc2ccccc21)CC(=O)NC1CCc2ccccc21)NO] |

TABLE C-continued
| (No.) | Structure |
|---|---|
| 49 | 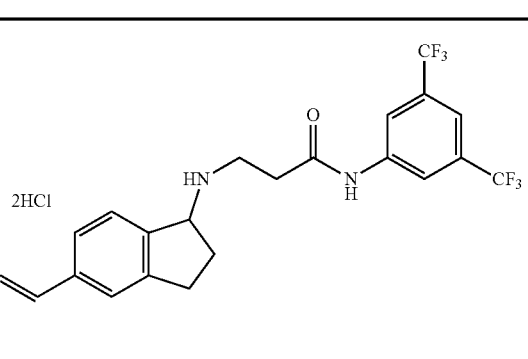 |
| 50 | 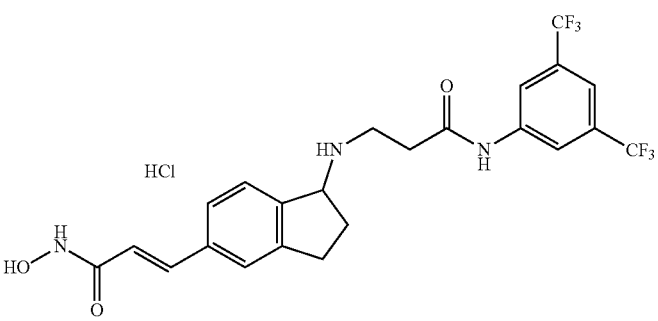 [SMILES: O=C(/C=C/c1ccc2c(c1)CCC2NCCC(=O)Nc1cc(C(F)(F)F)cc(C(F)(F)F)c1)NO ; Cl] |
| 51 | 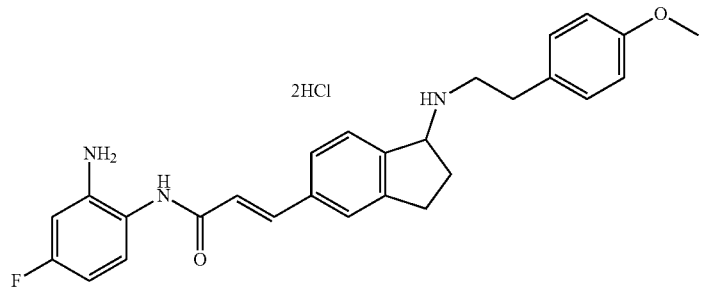 [SMILES: COc1ccc(CCNC2CCc3cc(/C=C/C(=O)Nc4ccc(F)cc4N)ccc32)cc1] |
| 52 | 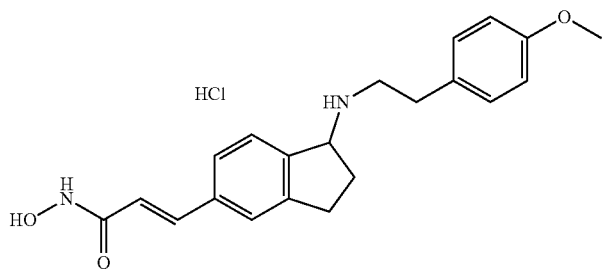 [SMILES: COc1ccc(CCNC2CCc3cc(/C=C/C(=O)NO)ccc32)cc1 ; Cl] |
| 53 | 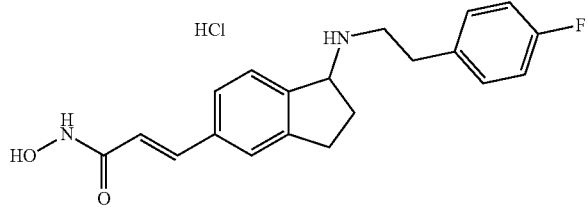 [SMILES: O=C(/C=C/c1ccc2c(c1)CCC2NCCc1ccc(F)cc1)NO ; Cl] |

TABLE C-continued
| (No.) | Structure |
|---|---|
| 54 | 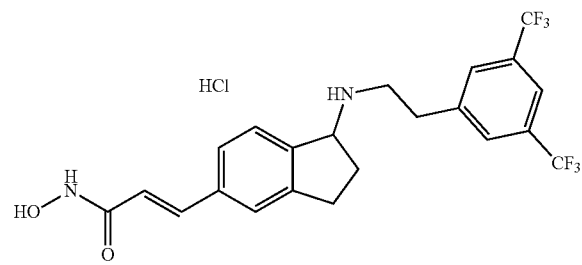 [SMILES: O=C(/C=C/c1ccc2c(c1)CCC2NCCc1cc(C(F)(F)F)cc(C(F)(F)F)c1)NO ; Cl] |
| 55 | 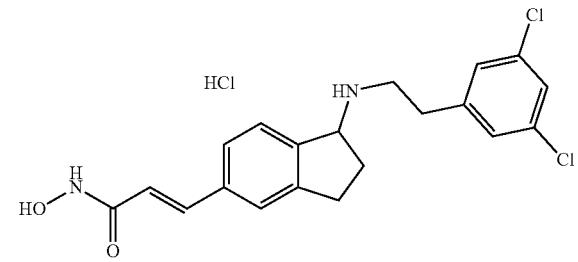 [SMILES: O=C(/C=C/c1ccc2c(c1)CCC2NCCc1cc(Cl)cc(Cl)c1)NO ; Cl] |
| 56 | 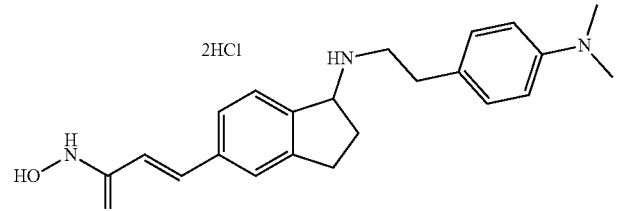 |
| 57 | 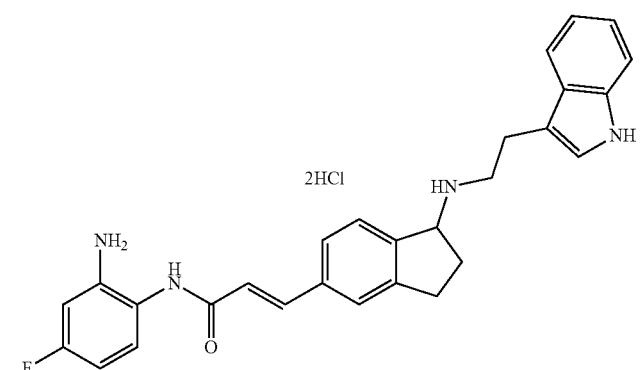 |
| 58 | 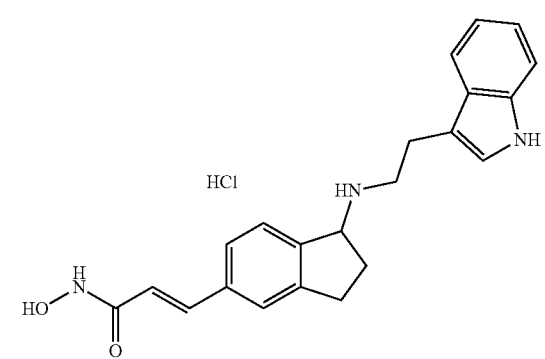 [SMILES: O=C(/C=C/c1ccc2c(c1)CCC2NCCc1c[nH]c2ccccc12)NO ; Cl] |

TABLE C-continued

| (No.) | Structure |
|---|---|
| 59 | 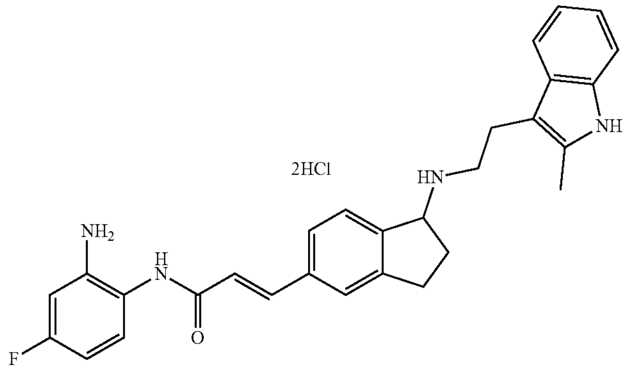 [SMILES: Cc1[nH]c2ccccc2c1CCNC1CCc2cc(/C=C/C(=O)Nc3ccc(F)cc3N)ccc21 ; "2HCl"] |
| 60 | 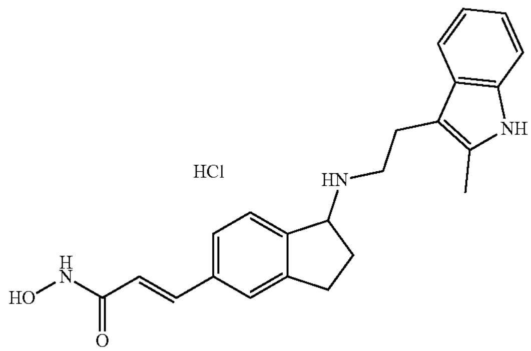 [SMILES: Cc1[nH]c2ccccc2c1CCNC1CCc2cc(/C=C/C(=O)NO)ccc21 ; Cl] |
| 64 | 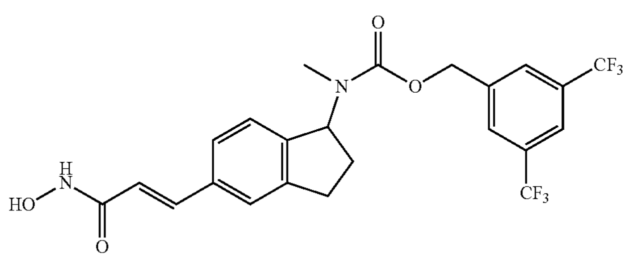 [SMILES: CN(C(=O)OCc1cc(C(F)(F)F)cc(C(F)(F)F)c1)C1CCc2cc(/C=C/C(=O)NO)ccc21] |
| 65 | 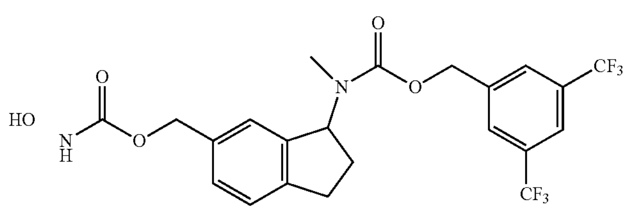 |

In some embodiments, the compound of Formula (I) may be further represented by Formula (I-4), or its geometric isomers, enantiomers, diastereomers, racemates, pharmaceutically acceptable salts, prodrugs and solvates thereof.

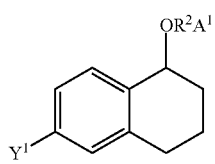

Formula (I-4)

In Formula (I-4), $Y^1$ is —$R^2C(O)NHR^3$, and $R^2$ is independently selected from a group consisting of $C_1$-$C_{10}$ alkyl, $C_1$-$C_{10}$ alkenyl, and $C_1$-$C_{10}$ alkoxy, $A^1$ is an aryl optionally substituted with —$CF_3$, and $R^3$ is independently selected from a group consisting of —OH, an aryl optionally substituted with at least one of a halogen, an alkyl, an alkoxy or —$NH_2$, and when $R^3$ is an aryl substituted with —$NH_2$, any hydrogen in the $NH_2$ may be optionally substituted with alkyl.

In some embodiments, the compound of Formula (I-4) is selected from the group consisting of the compounds delineated in Table D or its geometric isomers, enantiomers, diastereomers, racemates, pharmaceutically acceptable salts, prodrugs and solvates thereof.

TABLE D

| (No.) | Structure |
|---|---|
| 35 | (structure) |
| 36 | (structure) |

In some embodiments, the compound of Formula (I) may be further represented by Formula (I-5), or its geometric isomers, enantiomers, diastereomers, racemates, pharmaceutically acceptable salts, prodrugs and solvates thereof.

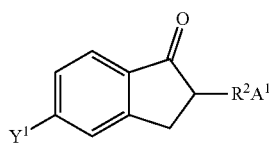

Formula (I-5)

In Formula (I-5), $Y^1$ is $R^2R^5C(O)NHR^3$, $R^2$ is independently selected from a group consisting of $C_1$-$C_{10}$ alkyl, $C_1$-$C_{10}$ alkenyl, and $C_1$-$C_{10}$ alkoxy, $A^1$ is an aryl optionally substituted with —$CF_3$, $R^3$ is independently selected from a group consisting of —OH, an aryl optionally substituted with at least one of a halogen, an alkyl, an alkoxy or —$NH_2$, and when $R^3$ is an aryl substituted with —$NH_2$, any hydrogen in the $NH_2$ may be optionally substituted with alkyl, and $R^5$ is an aryl.

In some embodiments, the compound of Formula (I-5) is selected from the group consisting of the compounds delineated in Table E or its geometric isomers, enantiomers, diastereomers, racemates, pharmaceutically acceptable salts, prodrugs and solvates thereof.

TABLE E

| (No.) | Structure |
|---|---|
| 76 | (structure) |
| 77 | (structure) |

In some embodiments, the compound of Formula (I) is selected from the group consisting of the compounds delineated in Table F or its geometric isomers, enantiomers, diastereomers, racemates, pharmaceutically acceptable salts, prodrugs and solvates thereof.

TABLE F

| (No.) | Structure |
|---|---|
| 2 | (structure) |
| 3 | (structure) |
| 34 | (structure) |

It will be appreciated that certain compounds of the above Formula (I), Formula (I-1), Formula (I-2), Formula (I-3), Formula (I-4) and Formula (I-5) of the present disclosure can possess an asymmetric carbon atom(s) and are thus capable of existing as enantiomers. Unless otherwise specified, the present disclosure includes such enantiomers, including racemates. The separate enantiomers may be synthesized from chiral starting materials, or the racemates can be resolved by procedures that are well known in the art of chemistry such as chiral chromatography, fractional crystallization of diastereometric salts and the like.

Active compounds of the present disclosure further comprise the use of the compounds according to any one of Formula (I), Formula (I-1), Formula (I-2), Formula (I-3), Formula (I-4) and Formula (I-5) of the present disclosure, for the prophylaxis and treatment of various diseases, disorders and/or conditions.

In another aspect, the present disclosure further provides a pharmaceutical composition comprising a therapeutically effective amount of the peripheral alkyl and alkenyl chains extended benzene derivative of Formula (I) or any one of Formula (I-1), Formula (I-2), Formula (I-3), Formula (I-4) and Formula (I-5), and a pharmaceutically acceptable carrier.

The compounds of the present disclosure are useful as pharmaceutically active agents and may be utilized in bulk form. More preferably, these compounds are formulated into pharmaceutical formulations for administration. Any of a number of suitable pharmaceutical formulations may be utilized as a vehicle for the administration of the compounds of the present disclosure.

The compounds of the present disclosure may be formulated for administration for the treatment of a variety of conditions. In the manufacture of a pharmaceutical composition according to the present disclosure, the compounds of the present disclosure and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation. One or more of each of the active compounds may be incorporated in the formulations of the present disclosure, which may be prepared by any of the well-known techniques of pharmacy consisting essentially of admixing the components, optionally including one or more accessory ingredients.

The present disclosure encompasses pharmaceutical compositions for the prophylaxis or the treatment of an inflammatory diseases, disorders and/or conditions. The pharmaceutical composition comprises a therapeutically effective amount of a compound according to Formula (I) or any one of Formula (I-1), Formula (I-2), Formula (I-3), Formula (I-4) and Formula (I-5) of the present disclosure (includes but not limited to Compounds delineated in Tables A~F).

In one aspect of the present disclosure, the compounds according to Formula (I) or any one of Formula (I-1), Formula (I-2), Formula (I-3), Formula (I-4) and Formula (I-5), are dual autotaxin/HDAC inhibitors. In some embodiments, the compounds according to the Formula (I) or any one of Formula (I-1), Formula (I-2), Formula (I-3), Formula (I-4) and Formula (I-5) of the present disclosure can inhibit the activity of autotaxin in a cell. In some embodiments, the compounds according to the Formula (I) or any one of Formula (I-1), Formula (I-2), Formula (I-3), Formula (I-4) and Formula (I-5) of the present disclosure can inhibit the activity of HDAC in a cell.

EXAMPLES

Example I: Synthesis of Compounds 1-83

To prove that the compounds of the present disclosure may be appropriately synthesized and utilized, the synthesis of the Compounds 1-83 delineated in Tables AF are described in detail below.

Synthesis of Compounds 1~3

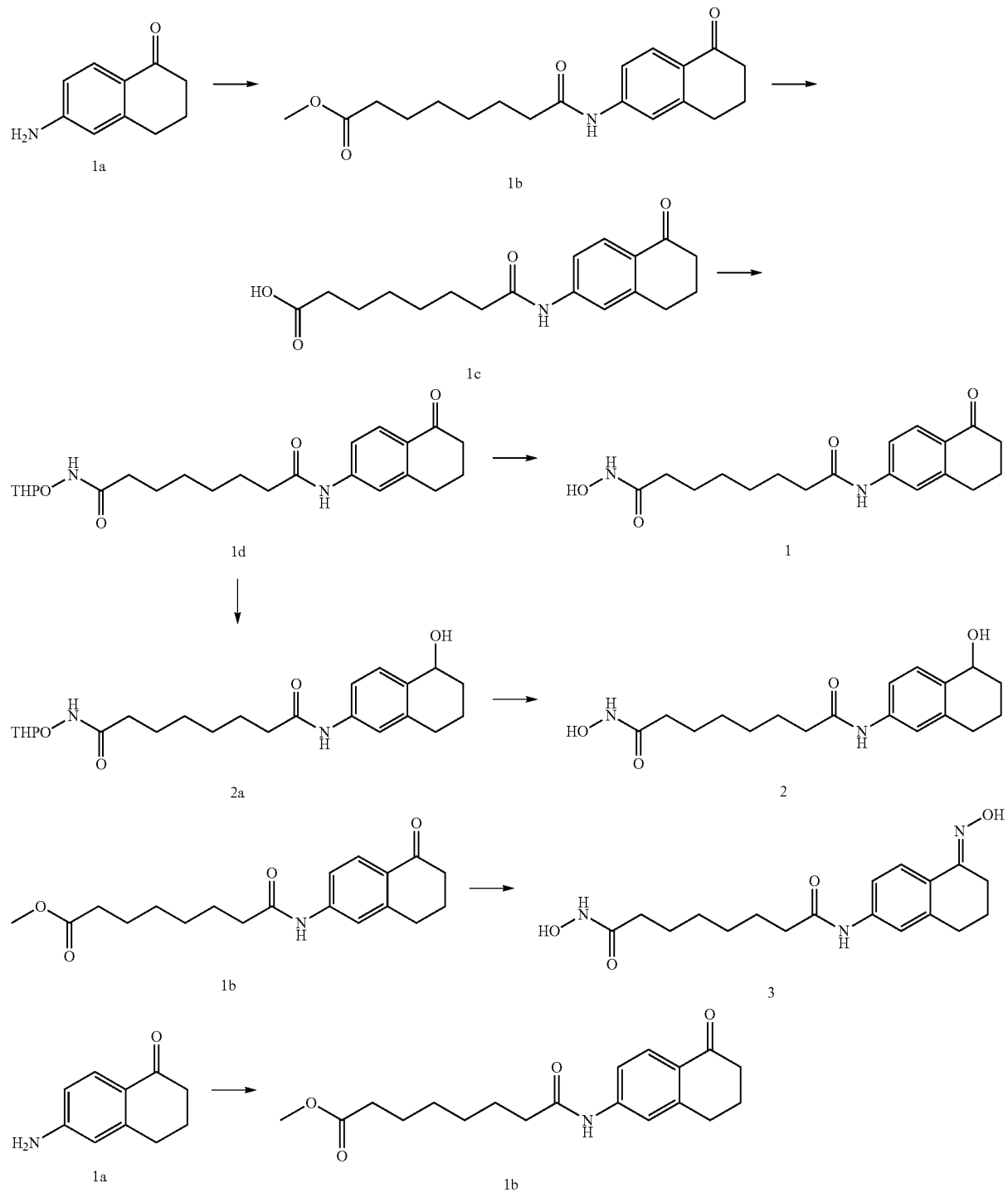

Scheme 01

To a solution of Compound 1a (6-Amino-1-tetralone) (0.50 g, 3.10 mmol), suberic acid monomethyl ester (0.70 g, 3.72 mmol) and hydroxybenzotriazole (HOBt; 0.21 g, 1.55 mmol) in dichloromethane (DCM; 50 mL) was added N,N-diisopropylethylamine (DIPEA; 1.20 g, 9.31 mmol) and 1-ethyl-3-(3-dimethylaminopropyl)carbodiimide (EDCI; 0.82 g, 4.65 mmol) at 0° C. After addition, the reaction mixture was slowly warmed to room temperature (RT) and stirred for overnight.

After reaction was completed, the solvent was removed under reduced pressure. The residual was diluted with EtOAc and washed with Sat. (saturated) $NH_4Cl$ and Sat.

NaHCO₃. The combined organic layers were washed with brine and dried over MgSO₄ and concentrated in vacuo to afford Compound 1b (methyl 8-oxo-8-((5-oxo-5,6,7,8-tetrahydronaphthalen-2-yl)amino)octanoate) (0.44 g, 1.33 mmol, yield 43%). The product (Compound 1b) was used in next step without further purification.

over MgSO₄ and concentrated in vacuo. The crude product was purified via flash column chromatography on a silica gel column using 10:1 DCM-MeOH as the eluent to give Compound 1d (N¹-(5-oxo-5,6,7,8-tetrahydronaphthalen-2-yl)-N⁸-((tetrahydro-2H-pyran-2-yl)oxy)octanediamide) (0.06 g, 0.14 mmol, yield 45%).

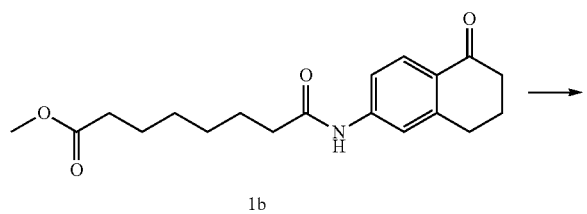

1b

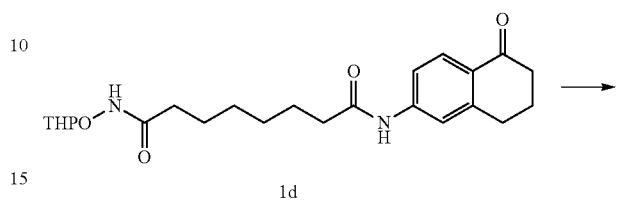

1d

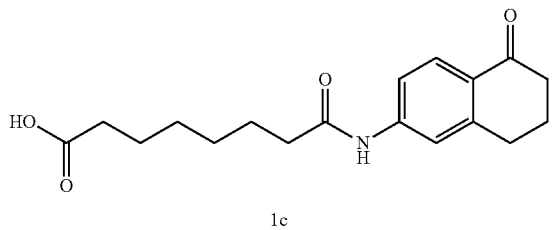

1c

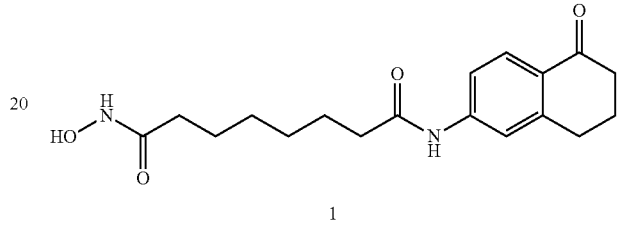

1

To a solution of Compound 1b (0.44 g, 1.33 mmol) in MeOH (20 mL) was added 2N NaOH (2 mL, 4.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 50% MeOH/water to give Compound 1c (8-oxo-8-((5-oxo-5,6,7,8-tetrahydronaphthalen-2-yl)amino)octanoic acid) (0.36 g, 1.13 mmol, yield 85%). The product (Compound 1c) was used in next step without further purification.

To a solution of Compound 1d (0.06 g, 0.14 mmol) in MeOH (10 mL) was added 1N HCl (0.5 mL) and stirred for 3 hrs.

After reaction was completed, the solvent was removed under reduced pressure. The precipitated solid was washed with water and ether to produce Compound 1 (N¹-hydroxy-N⁸-(5-oxo-5,6,7,8-tetrahydronaphthalen-2-yl)octanediamide) (0.02 g, 0.05 mmol, yield 39%).

Compound 1, ¹H-NMR (400 MHz, CD₃OD): δ 7.91-7.89 (d, 1H), 7.64 (s, 1H), 7.46-7.45 (d, 1H), 2.96-2.94 (m, 2H), 2.62-2.59 (m, 2H), 2.41-2.38 (m, 2H), 2.12-2.08 (m, 4H), 1.70-1.62 (m, 4H), 1.40-1.39 (m, 4H). ESI-MS m/z calcd for C₁₈H₂₄N₂O₄ 332.17, found 355 [M+Na]⁺.

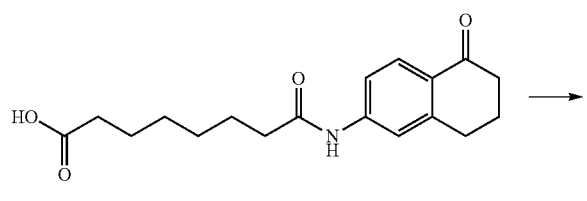

1c

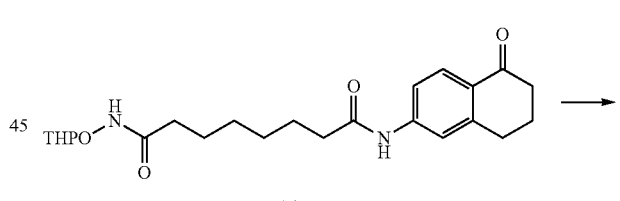

1d

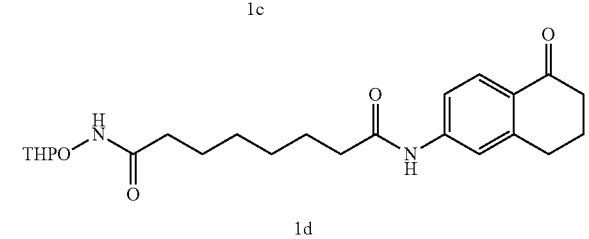

1d

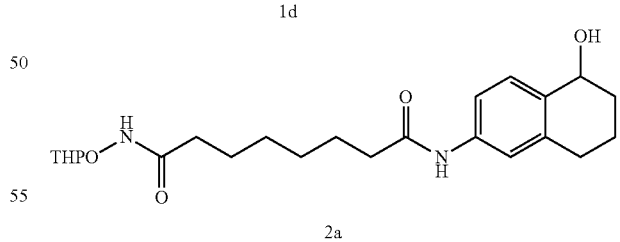

2a

To a solution of Compound 1c (0.1 g, 0.32 mmol) and O-(Tetrahydro-2H-pyran-2-yl)hydroxylamine (0.06, 0.47 mmol) in dimethylformamide (DMF; 10 mL) was added EDCI (0.09 g, 0.47 mmol) at 0° C. After addition, the reaction mixture was slowly warmed to RT and stirred for overnight.

After reaction was completed, the reaction mixture was diluted with EtOAc and washed with Sat. NH₄Cl. The combined organic layers were washed with brine and dried To a solution of Compound 1d (0.21 g, 0.52 mmol) in MeOH (10 mL) was added NaBH₄ (0.02 g, 0.52 mmol) at 0° C. and stirred at the same temperature for 30 min.

After reaction was completed, the reaction mixture was quenched with Sat. NH₄Cl. The solvent was removed under reduced pressure. The residual was diluted with EtOAc and washed with Sat. NH₄Cl. The combined organic layers were washed with brine and dried over MgSO₄ and concentrated in vacuo to obtain Compound 2a (N¹-(5-hydroxy-5,6,7,8- tetrahydronaphthalen-2-yl)-N⁸-((tetrahydro-2H-pyran-2-yl)oxy)octanediamide) (0.08 g, 0.21 mmol, yield 40%). The crude product (Compound 2a) was used in the next step without further purification.

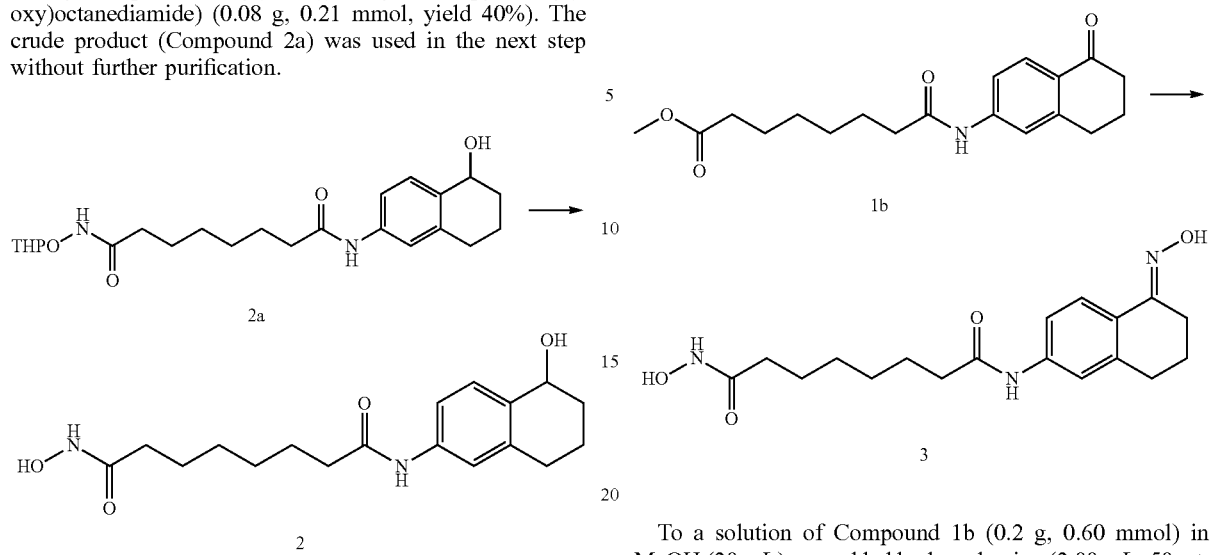

To a solution of Compound 2a (0.08 g, 0.21 mmol) in MeOH (10 mL) was added 1N HCl (0.5 mL) and stirred for 2 hours.

After reaction was completed, the solvent was removed under reduced pressure. The crude product was purified via flash column chromatography on a silica gel column using 10:1 DCM-MeOH as the eluent to give Compound 2 ($N^1$-hydroxy-$N^8$-(5-hydroxy-5,6,7,8-tetrahydronaphthalen-2-yl)octanediamide) (0.005 g, 0.015 mmol, yield 7%).

Compound 2, $^1$H-NMR (400 MHz, CD$_3$OD): δ 7.31-7.29 (d, 2H), 6.94-6.93 (d, 1H), 6.43-6.41 (d, 1H), 5.98-5.94 (m, 1H), 2.76-2.73 (m, 2H), 2.37-2.34 (m, 2H), 2.30-2.26 (m, 2H), 2.11-2.08 (m, 2H), 1.71-1.62 (m, 5H), 1.40-1.39 (m, 5H). ESI-MS m/z calcd for $C_{18}H_{26}N_2O_4$ 334.19, found 335 [M+H]⁺.

To a solution of Compound 1b (0.2 g, 0.60 mmol) in MeOH (20 mL) was added hydroxylamine (2.00 mL, 50 wt. % in H$_2$O) and 2N NaOH (0.60 mL, 1.20 mmol). After addition, the reaction mixture was stirred for overnight.

After reaction was completed, the solvent was removed under reduced pressure. The residual was acidified with 1N HCl. The precipitated solid was collected by filtration to give compound 3 ((E)-N1-hydroxy-N8-(5-(hydroxyimino)-5,6,7,8-tetrahydronaphthalen-2-yl)octanediamide) (0.03 g, 0.09 mmol, yield 14%).

Compound 3, $^1$H-NMR (500 MHz, CD$_3$OD): δ 7.83-7.81 (d, 1H), 7.44 (s, 1H), 7.32-7.30 (d, 1H), 2.75-2.73 (m, 4H), 2.38-2.35 (t, 2H), 2.11-2.08 (t, 2H), 1.84-1.82 (m, 2H), 1.70-1.63 (m, 4H), 1.40 (br, 4H). ESI-MS m/z calcd for $C_{18}H_{25}N_3O_4$ 347.18, found 348 [M+H]⁺.

Synthesis of Compounds 4~5

Scheme 02

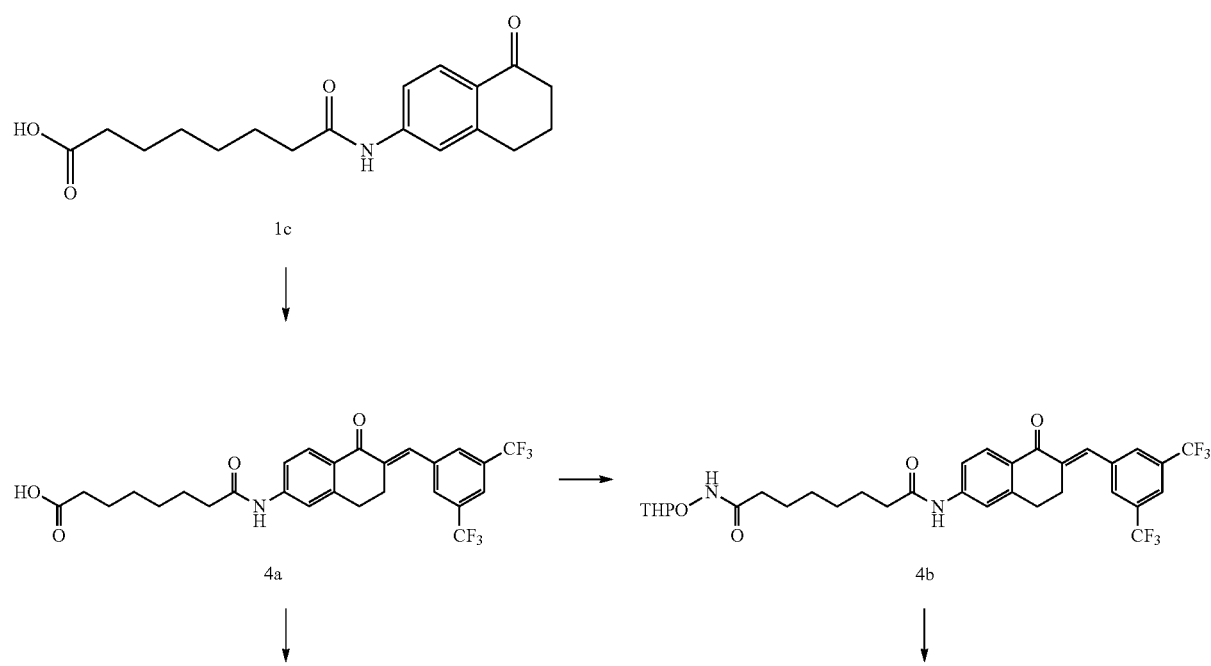

-continued

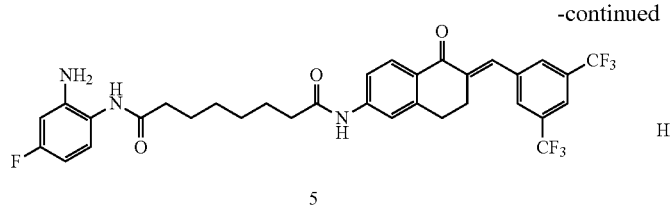

5

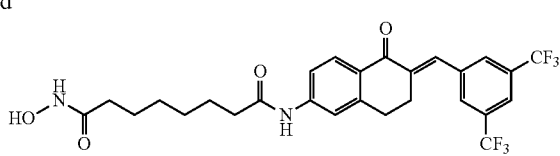

4

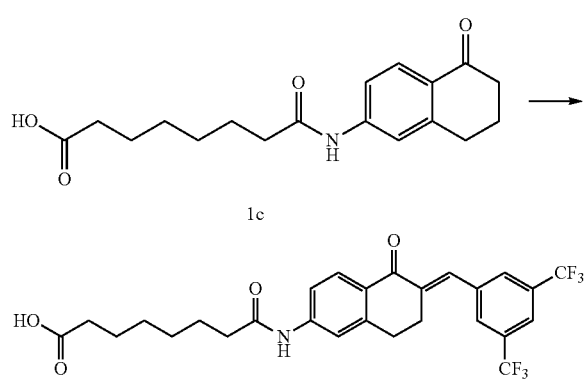

1c

To a solution of Compound 1c (0.1 g, 0.32 mmol) and 3,5-Bis(trifluoromethyl)benzaldehyde (0.09 g, 0.38 mmol) in MeOH (10 mL) was added 2N NaOH (1 mL, 2.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 50% MeOH/water to get Compound 4a ((E)-8-((6-(3,5-bis(trifluoromethyl)benzylidene)-5-oxo-5,6,7,8-tetrahydronaphthalen-2-yl)amino)-8-oxooctanoic acid) (0.13 g, 0.24 mmol, yield 75%).

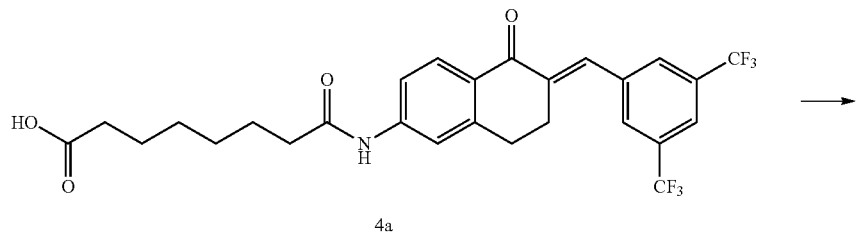

4a

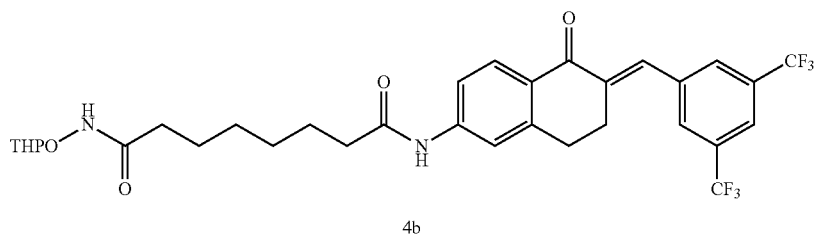

4b

To a solution of Compound 4a (0.13 g, 0.24 mmol) and O-(Tetrahydro-2H-pyran-2-yl)hydroxylamine (0.04, 0.36 mmol) in DMF (10 mL) was added EDCI (0.07 g, 0.36 mmol) at 0° C. After addition, the reaction mixture was slowly warmed to RT and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 10:1 DCM-MeOH as the eluent to give Compound 4b ((E)-N$^1$-(6-(3,5-bis(trifluoromethyebenzylidene)-5-oxo-5,6,7,8-tetrahydronaphthalen-2-yl)-N$^8$-((tetrahydro-2H-pyran-2-yl)oxy)octanediamide) (0.10 g, 0.16 mmol, yield 67%).

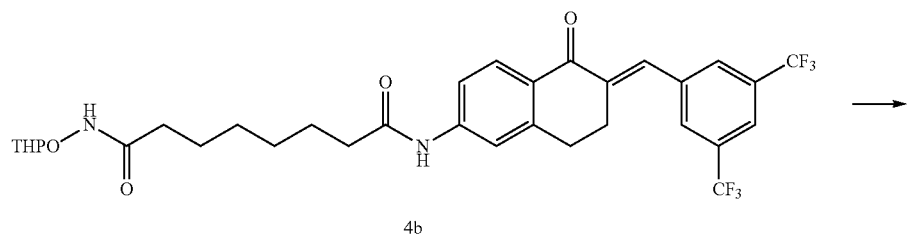

4b

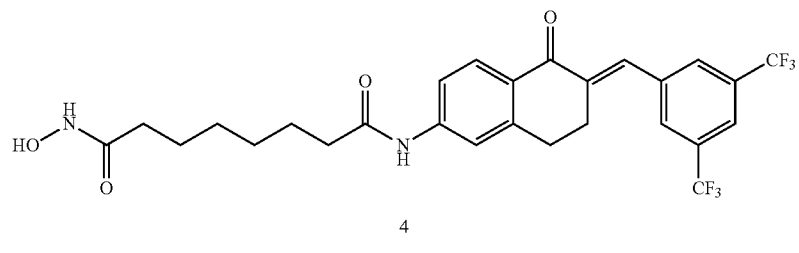

4

To a solution of Compound 4b (0.10 g, 0.16 mmol) in MeOH (10 mL) was added 1N HCl (0.5 mL) and stirred for 2 hrs.

After reaction was completed, the solvent was removed under reduced pressure. The precipitated solid was washed with water and ether to yield Compound 4 ((E)-N$^1$-(6-(3,5-bis(trifluoromethyebenzylidene)-5-oxo-5,6,7,8-tetrahydronaphthalen-2-yl)-N$^8$-hydroxyoctanediamide) (0.08 g, 0.14 mmol, yield 89%).

Compound 4, $^1$H-NMR (400 MHz, CD$_3$OD): δ 7.31-7.29 (d, 2H), 6.94-6.93 (d, 1H), 6.43-6.41 (d, 1H), 5.98-5.94 (m, 1H), 2.76-2.73 (m, 2H), 2.37-2.34 (m, 2H), 2.30-2.26 (m, 2H), 2.11-2.08 (m, 2H), 1.71-1.62 (m, 5H), 1.40-1.39 (m, 5H). ESI-MS m/z calcd for C$_{27}$H$_{26}$F$_6$N$_2$O$_4$ 556.18, found 557 [M+H]$^+$.

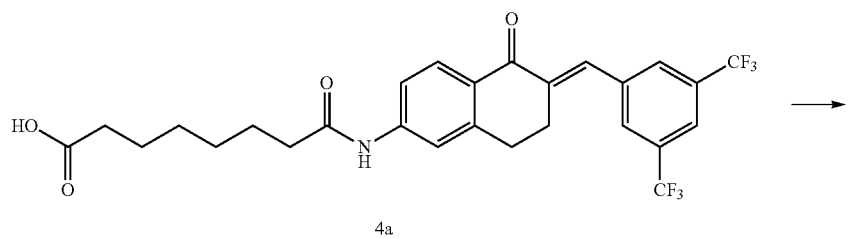

4a

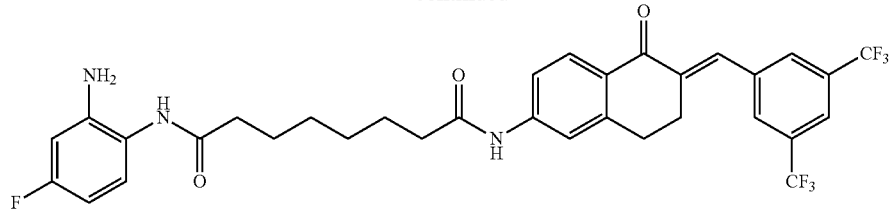

To a solution of Compound 4a (0.2 g, 0.37 mmol), 4-fluoro-1,2-phenylenediamine (0.06 g, 0.44 mmol) and 4-dimethylaminopyridine (DMAP; 0.05 g, 0.37 mmol) in THF (20 mL) was added NMM (0.06 g, 0.56 mmol) and EDCI (0.11 g, 0.55 mmol) at 0° C. After addition, the reaction mixture was warmed to room temperature and stirred for overnight.

After reaction was completed, the reaction mixture was diluted with EtOAc and washed with Sat. $NH_4Cl$. The combined organic layers were washed with brine and dried over $MgSO_4$ and concentrated in vacuo. The crude product was purified via flash column chromatography on a silica gel column using 2:1 EtOAc-Hexane as the eluent to give compound 5 ((E)-N1-(2-amino-4-fluorophenyl)-N8-(6-(3,5-bis(trifluoromethyl)benzylidene)-5-oxo-5,6,7,8-tetrahydronaphthalen-2-yl)octanediamide) (0.09 g, 0.14 mmol, yield 39%).

Compound 5, $^1$H-NMR (500 MHz, $d_6$-DMSO): δ 10.25 (s, 1H), 9.01 (s, 1H), 8.18 (s, 2H), 8.12 (s, 1H), 7.95-7.93 (d, 1H), 7.77 (s, 1H), 7.69 (s, 1H), 7.58-7.56 (d, 1H), 7.10-7.07 (dd, 1H), 6.49-6.46 (dd, 1H), 6.30-6.27 (td, 1H), 5.12 (s, 2H), 3.04-2.90 (m, 4H), 2.38-2.35 (t, 2H), 2.31-2.28 (t, 2H), 1.60 (br, 4H), 1.34 (br, 4H). ESI-MS m/z calcd for $C_{33}H_{30}F_7N_3O_3$ 649.22, found 650 [M+1-1]$^+$.

Synthesis of Compounds 6~7

Scheme 03

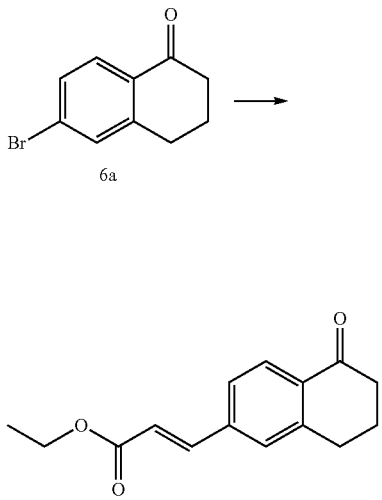

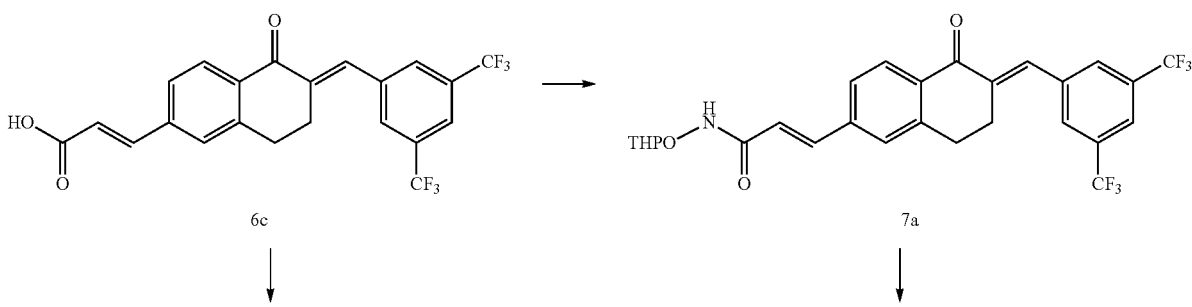

-continued

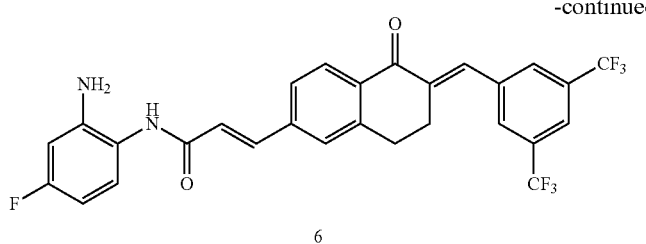

6

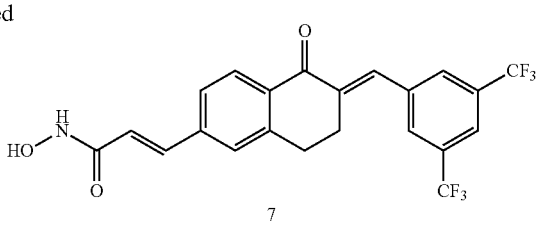

7

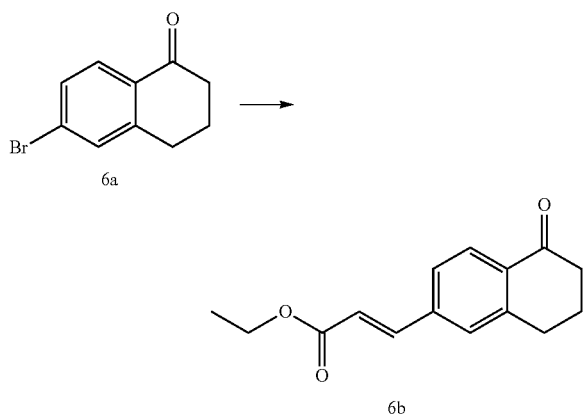

To a solution of compound 6a (6-bromo-3,4-dihydronaphthalen-1(2H)-one) (220 mg, 1.0 eq) in DMF (0.1 M) was added ethyl acrylate (1.3 eq) at rt, followed Et₃N (0.05 M), PPh₃ (0.4 eq). The mixture was stirred at RT for 5 min then degas with nitrogen, followed added Pd(OAc)₂ (0.05 eq). The reaction was stirred at 100° C. for overnight.

After cooling to RT, removed the solvent in vacuo and purified with column chromatography to afford the compound 6b (ethyl (E)-3-(5-oxo-5,6,7,8-tetrahydronaphthalen-2-yl)acrylate) (179 mg, yield 75%).

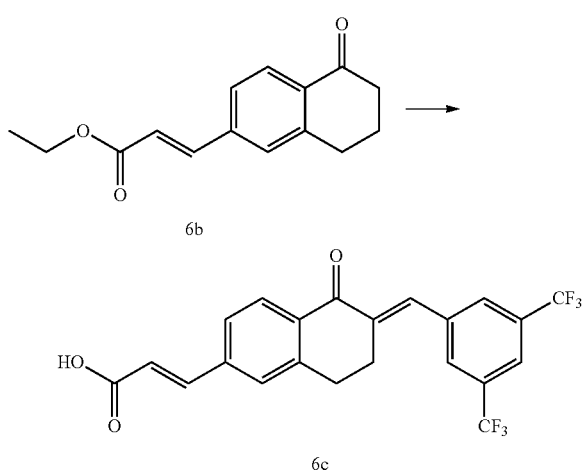

To a solution of compound 6b (ethyl (E)-3-(5-oxo-5,6,7,8-tetrahydronaphthalen-2-yl)acrylate) (280 mg, 1 eq) in MeOH (10 mL) was added 3,5-bis(trifluoromethyl)benzaldehyde (333 mg, 1 eq), NaOH aqueous solution (1.0 M, 2.2 mL) at RT.

The mixture was stirred at RT for overnight, then removed the solvent in vacuo followed quench with HCl aqueous solution (1.0 M) to pH=3. The mixture was extracted with EtOAc, then take the organic layer washed with brine. The combined organic layer was dried over anhydrous MgSO₄. Remove the solvent to afford the compound 6c ((E)-3-(6-((E)-3,5-bis(trifluoromethyl)benzylidene)-5-oxo-5,6,7,8-tetrahydronaphthalen-2-yl)acrylic acid) (414 mg, yield 82%).

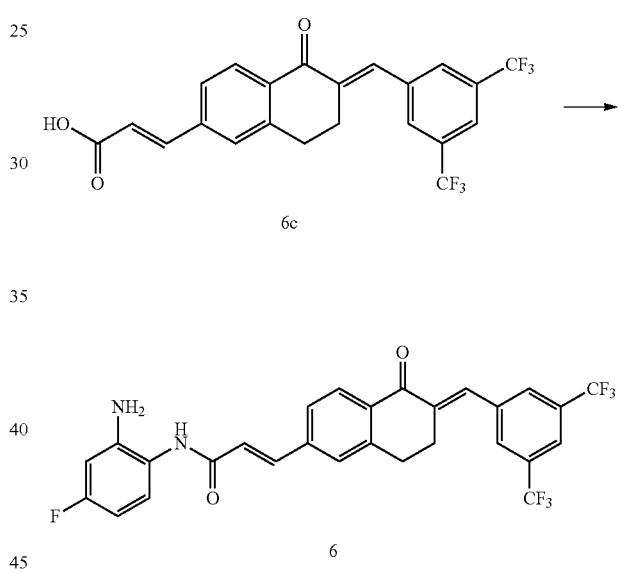

To a solution of compound 6c ((E)-3-(6-((E)-3,5-bis(trifluoromethyl)benzylidene)-5-oxo-5,6,7,8-tetrahydronaphthalen-2-yl)acrylic acid) (140 mg, 1 eq) in tetrahydrofuran (THF; 0.1 M) at 0° C. under nitrogen was added EDC hydrochloride (91 mg, 1.5 eq), followed N-methylmorpholine (NMM; 48 mg, 1.5 eq), HOBT (19 mg, 0.4 eq) and 4-Fluoro-1,2-phenylenediamine (48 mg, 1.2 eq). The mixture was allowed to warm to RT and stirred for overnight.

After removing the solvent, the crude product was purified by column chromatography to afford the compound 6 ((E)-N-(2-amino-4-fluorophenyl)-3-(6-((E)-3,5-bis(trifluoromethyl)benzylidene)-5-oxo-5,6,7,8-tetrahydronaphthalen-2-yl)acrylamide) (5 mg, yield 3%).

Compound 6, ¹H-NMR (500 MHz, CD₃OD): δ 8.12-8.10 (d, 1H), 8.05 (s, 2H), 7.99 (s, 1H), 7.87 (s, 1H), 7.71-7.65 (m, 2H), 7.58 (s, 1H), 7.19 (m, 1H), 6.98-6.95 (d, 1H), 6.59-6.56 (dd, 1H), 6.43-6.40 (td, 1H), 3.13-3.06 (m, 4H). ESI-MS m/z calcd for $C_{28}H_{19}F_7N_2O_2$ 548.13, found 549 [M+H]⁺.

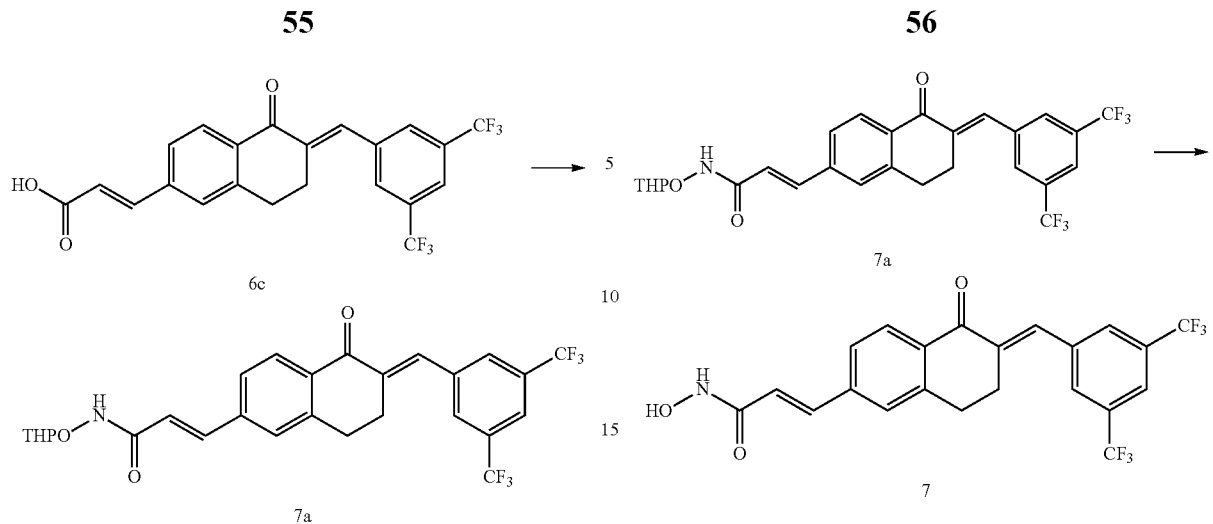

To a solution of compound 6c ((E)-3-(6-((E)-3,5-bis(trifluoromethyl)benzylidene)-5-oxo-5,6,7,8-tetrahydronaphthalen-2-yl)acrylic acid) (300 mg, 1.0 eq) in THF at 0° C. under nitrogen was added EDC hydrochloride (156 mg, 1.2 eq), followed NMM (83 mg, 1.2 eq), HOBT (42 mg, 0.4 eq) and O-(Tetrahydro-2H-pyran-2-yl)hydroxylamine (120 mg, 1.5 eq). The mixture was allowed to warm to RT and stirred for overnight.

After removing the solvent, the crude product was purified by column chromatography to afford compound 7a ((E)-3-(6-((E)-3,5-bis(trifluoromethyl)benzylidene)-5-oxo-5,6,7,8-tetrahydronaphthalen-2-yl)-N-((tetrahydro-2H-pyran-2-yl)oxy)acrylamide) (300 mg, yield 82%).

To a solution of compound 7a ((E)-3-(6-((E)-3,5-bis(trifluoromethyl)benzylidene)-5-oxo-5,6,7,8-tetrahydronaphthalen-2-yl)-N-((tetrahydro-2H-pyran-2-yl)oxy)acrylamide) (200 mg, 1.0 eq) in MeOH (3.8 mL) at RT was added HCl aqueous solution (1.0 M, 1 mL).

The reaction was stirred at RT for 2 hours, then the solid was filtered out to afford the compound 7 ((E)-3-(6-((E)-3,5-bis(trifluoromethyl)benzylidene)-5-oxo-5,6,7,8-tetrahydronaphthalen-2-yl)-N-hydroxyacrylamide) (20 mg, yield 8%).

Compound 7, $^1$H-NMR (500 MHz, $d_6$-DMSO): δ 8.19 (s, 2H), 8.13 (s, 1H), 8.01-7.99 (d, 1H), 7.82 (s, 1H), 7.62-7.60 (d, 1H), 7.58 (s, 1H), 7.51-7.48 (d, 1H), 6.63-6.60 (d, 1H), 3.07-2.98 (m, 4H). ESI-MS m/z calcd for $C_{22}H_{15}F_6NO_3$ 455.10, found 456 $[M+H]^+$.

Synthesis of Compound 8

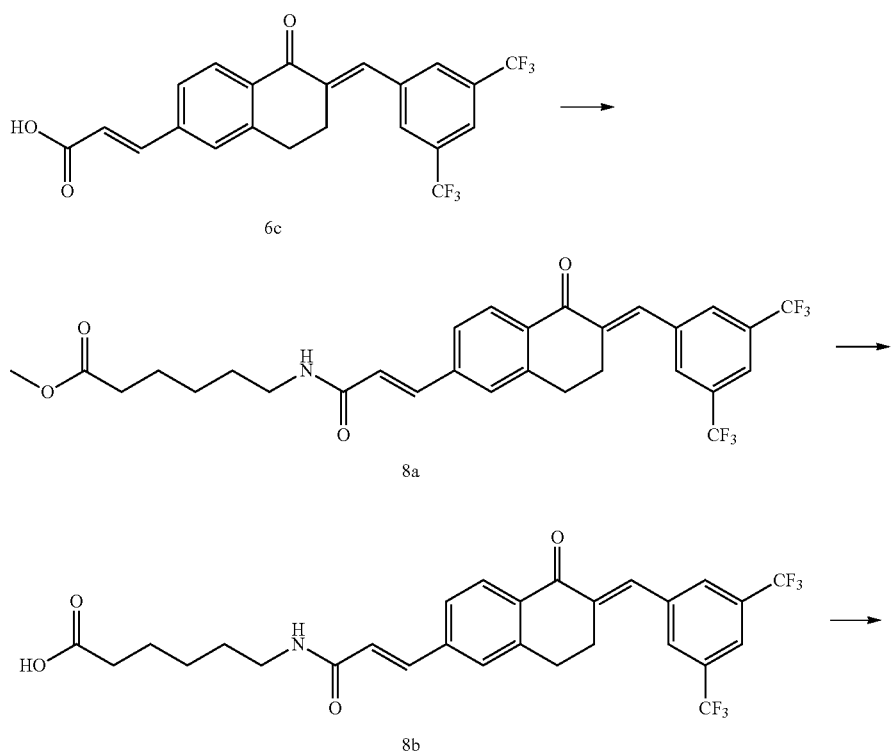

Scheme 04

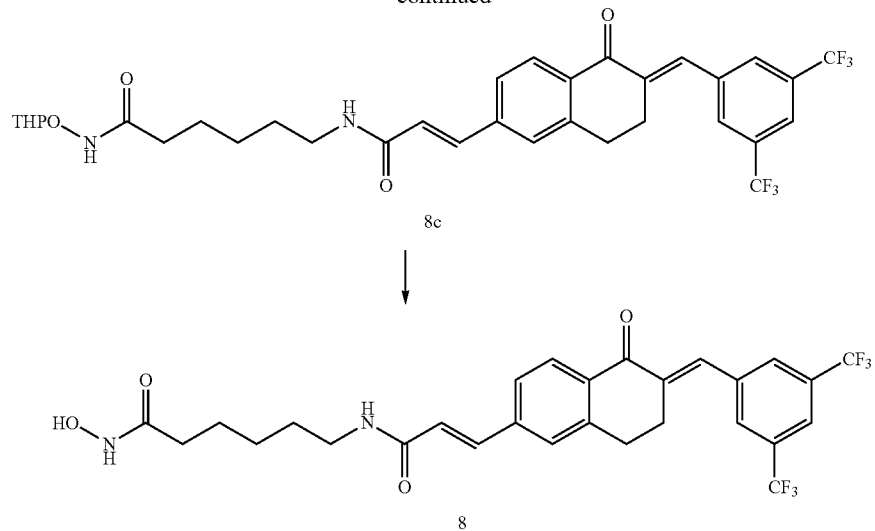

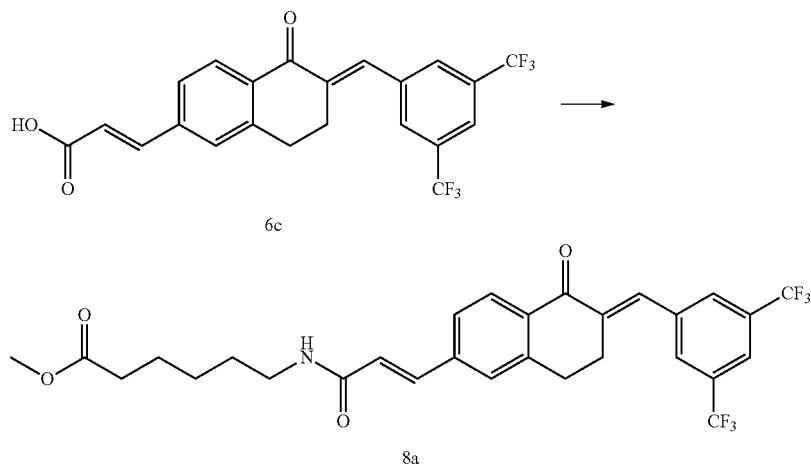

To a solution of compound 6c ((E)-3-(6-((E)-3,5-bis(trifluoromethyl)benzylidene)-5-oxo-5,6,7,8-tetrahydronaphthalen-2-yl)acrylic acid) (300 mg, 1.0 eq) in THF at 0° C. under nitrogen was added EDC hydrochloride (156 mg, 1.2 eq), followed NMM (82 mg, 1.2 eq), HOBT (42 mg, 0.4 eq) and methyl 6-aminohexanoate (162 mg, 1.5 eq). The mixture was allowed to warm to RT and stirred for overnight.

After removing the solvent, the crude product was purified by column chromatography to afford the product 8a (methyl 6-((E)-3-(6-((E)-3,5-bis(trifluoromethyl)benzylidene)-5-oxo-5,6,7,8-tetrahydronaphthalen-2-yl)acrylamido)hexanoate) (367 mg, yield 95%).

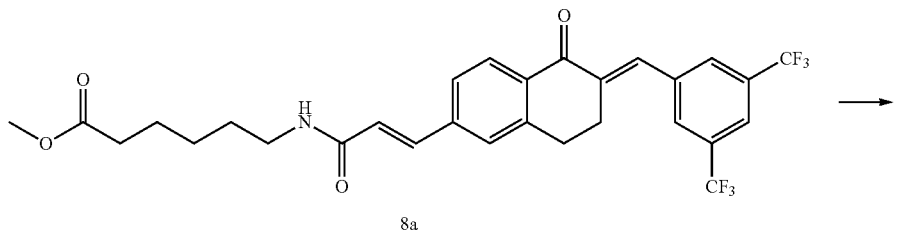

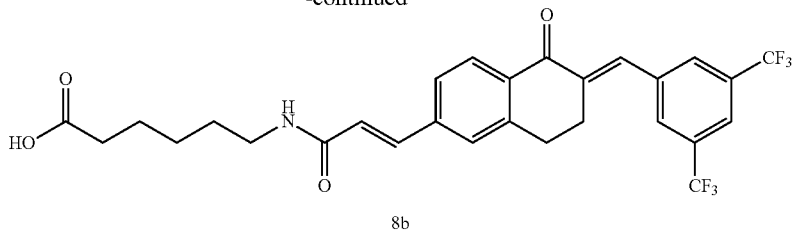

8b

To a solution of compound 8a (methyl 6-((E)-3-(6-((E)-3,5-bis(trifluoromethyl)benzylidene)-5-oxo-5,6,7,8-tetrahydronaphthalen-2-yl)acrylamido)hexanoate) (367 mg, 0.65 mmol) in MeOH (50 mL) was added 2N NaOH (1 mL) and stirred for overnight.

After reaction was completed, the solvent was removed under reduced pressure. The residual was diluted with ice-cold water and acidified with 1N HCl. The precipitated solid was collected by filtration and washed with 30% MeOH/water to get compound 8b (6-((E)-3-(6-((E)-3,5-bis(trifluoromethyl)benzylidene)-5-oxo-5,6,7,8-tetrahydronaphthalen-2-yl) acrylamido)hexanoic acid) (288 mg, 0.52 mmol, yield 80%).

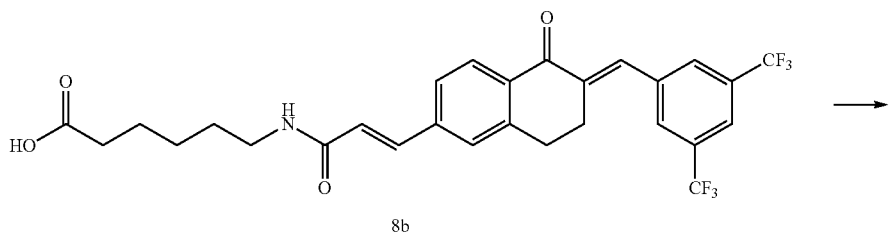

8b

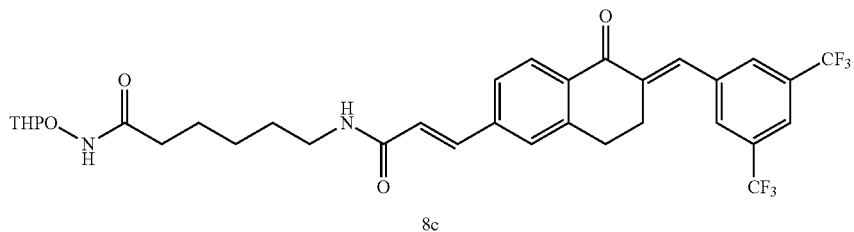

8c

To a solution of compound 8b (6-((E)-3-(6-((E)-3,5-bis(trifluoromethyl)benzylidene)-5-oxo-5,6,7,8-tetrahydronaphthalen-2-yl) acrylamido)hexanoic acid) (230 mg, 1.0 eq) in THF (0.1 M) at 0° C. under nitrogen was added EDC hydrochloride (99 mg, 1.2 eq), followed NMM (52 mg, 1.2 eq), HOBT (26 mg, 0.4 eq) and O-(Tetrahydro-2H-pyran-2-yl)hydroxylamine (75 mg, 1.5 eq). The mixture was allowed to warm to RT and stirred for overnight.

After removing the solvent, the crude product was purified by column chromatography to afford the product 8c (6-((E)-3-(6-((E)-3,5-bis(trifluoromethyl)benzylidene)-5-oxo-5,6,7,8-tetrahydronaphthalen-2-yl) acrylamido)-N-((tetrahydro-2H-pyran-2-yl)oxy)hexanamide) (130 mg, yield 48%).

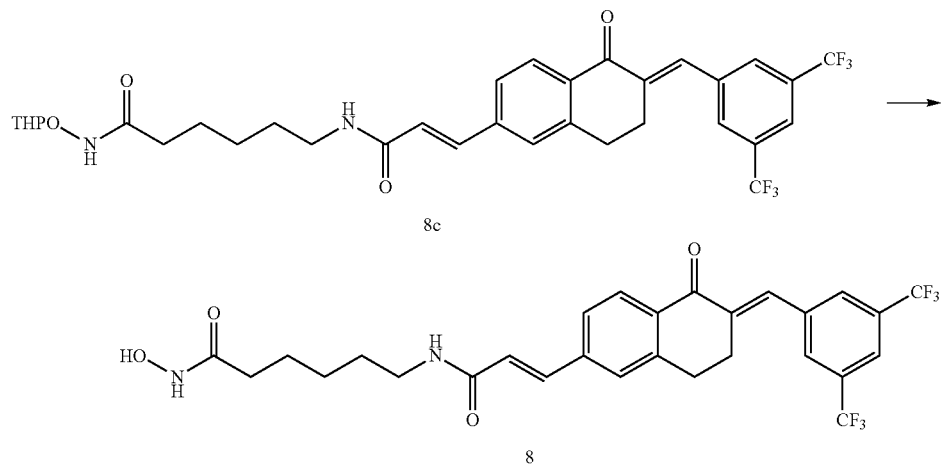

To a solution of compound 8c (6-((E)-3-(6-((E)-3,5-bis(trifluoromethyl)benzylidene)-5-oxo-5,6,7,8-tetrahydronaphthalen-2-yl) acrylamido)-N-((tetrahydro-2H-pyran-2-yl)oxy)hexanamide) (130 mg, 1.0 eq) in HCl aqueous solution (1.0 M, 0.6 mL).

The reaction was stirred at RT for 2 hours, then the solid was filtered out to afford the product 8 (6-((E)-3-(6-((E)-3,5-bis(trifluoromethyl)benzylidene)-5-oxo-5,6,7,8-tetrahydronaphthalen-2-yl) acrylamido)-N-hydroxyhexanamide) (30 mg, yield 26%).

Compound 8, $^1$H-NMR (500 MHz, $d_6$-DMSO): δ 10.34 (s, 1H), 10.16 (s, 1H), 8.20 (s, 2H), 8.14 (s, 1H), 8.02-8.00 (d, 1H), 7.83 (s, 1H), 7.61-7.60 (d, 1H), 7.56 (s, 1H), 7.46-7.43 (d, 1H), 6.79-6.76 (d, 1H), 3.17-3.16 (m, 2H), 3.08-3.07 (m, 1H), 3.00-2.99 (m, 1H), 1.96-1.93 (t, 2H), 1.52-1.44 (m, 4H), 1.28-1.27 (m, 2H). ESI-MS m/z calcd for $C_{28}H_{26}F_6N_2O_4$ 568.18, found 569 [M+1-1]$^+$.

Synthesis of Compounds 9~10

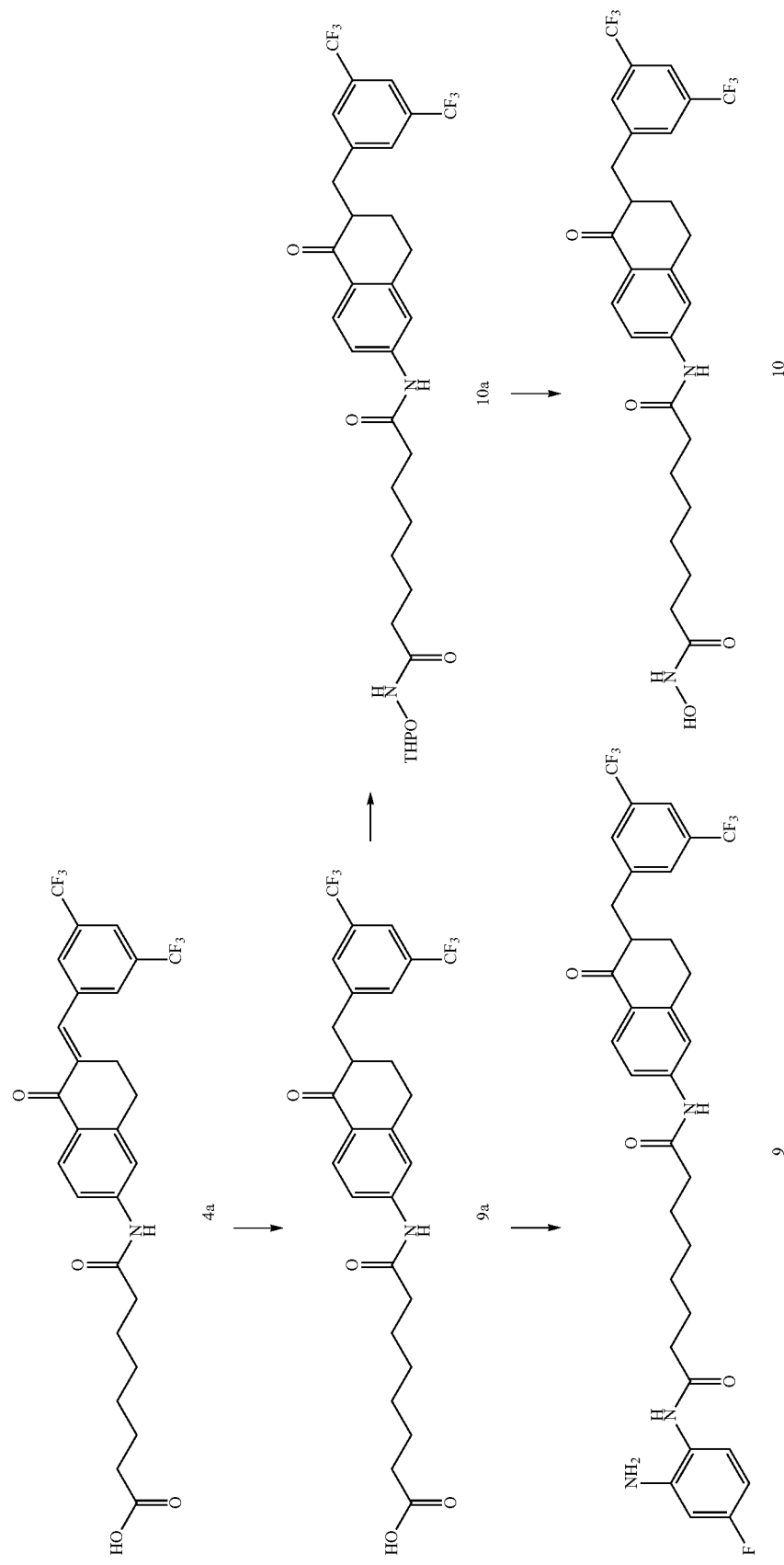

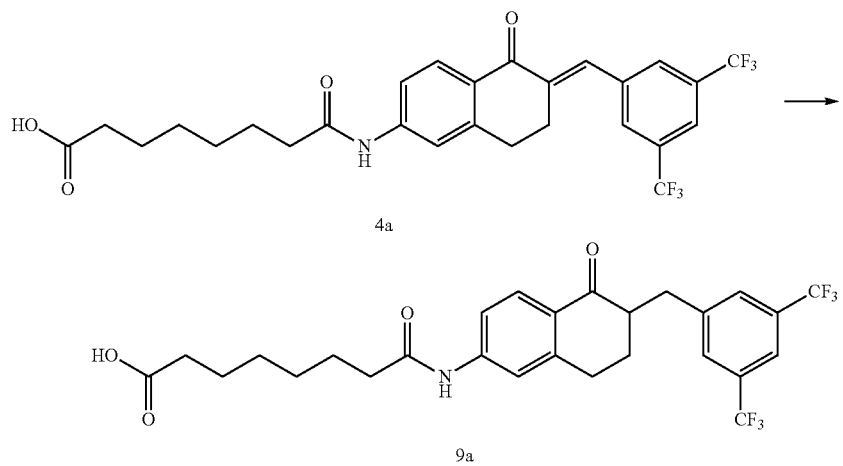

To a solution of Compound 4a ((E)-8-((6-(3,5-bis(trifluoromethyl)benzylidene)-5-oxo-5,6,7,8-tetrahydronaphthalen-2-yl)amino)-8-oxooctanoic acid) (0.20 g, 0.37 mmol) in MeOH (50 mL) was added Pd/C (0.1 g). After addition, the reaction mixture was stirred under $H_2$ for 30 mins.

After reaction was completed, the solvent was removed under reduced pressure. Pd/C was filed off through a pad of celite and washed with EtOAc. The filtrate was concentrated in vacuo to afford compound 9a (8-((6-(3,5-bis(trifluoromethyl)benzyl)-5-oxo-5,6,7,8-tetrahydronaphthalen-2-yl)amino)-8-oxooctanoic acid) (0.17 g, 0.31 mmol, yield 83%).

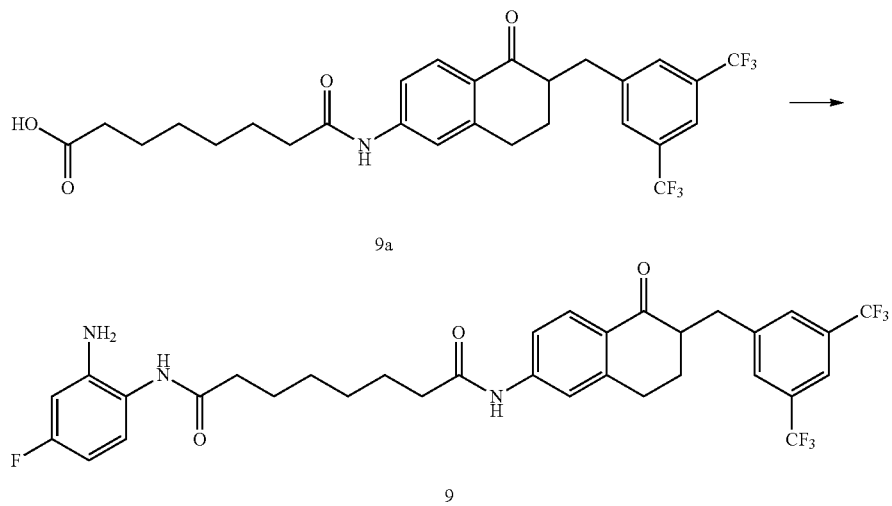

To a solution of compound 9a (8-((6-(3,5-bis(trifluoromethyl)benzyl)-5-oxo-5,6,7,8-tetrahydronaphthalen-2-yl)amino)-8-oxooctanoic acid) (0.47 g, 0.86 mmol), 4-fluoro-1,2-phenylenediamine (0.12 g, 0.95 mmol) in DCM (30 mL) was added NMM (0.18 g, 0.1.73 mmol) and HATU (0.39 g, 1.04 mmol) at 0° C. After addition, the reaction mixture was slowly warmed to room temperature and stirred for 3 hours.

After reaction was completed, the solvent was removed under reduced pressure. The residual was diluted with Sat. $NH_4Cl$. The precipitated solid was collected by filtration. The crude product was washed with 30% EtOAc/Hex to give compound 9 (N1-(2-amino-4-fluorophenyl)-N8-(6-(3,5-bis(trifluoromethyl)benzyl)-5-oxo-5,6,7,8-tetrahydronaphthalen-2-yl)octanediamide) (0.18 g, 0.28 mmol, yield 32%).

Compound 9, ¹H-NMR (500 MHz, CD₃OD): δ 7.93-7.91 (d, 1H), 7.89 (s, 2H), 7.80 (s, 1H), 7.62 (s, 1H), 7.46-7.44 (d, 1H), 7.02-6.99 (dd, 1H), 6.54-6.51 (dd, 1H), 6.37-6.33 (td, 1H), 3.51-3.48 (dd, 1H), 3.01-2.89 (m, 4H), 2.42-2.39 (t, 4H), 2.10-2.07 (m, 1H), 1.82-1.78 (m, 1H), 1.74-1.72 (t, 4H), 1.46-1.45 (t, 4H). ESI-MS m/z calcd for C₃₃H₃₂F₇N₃O₃ 651.23, found 652 [M+1-1]⁺.

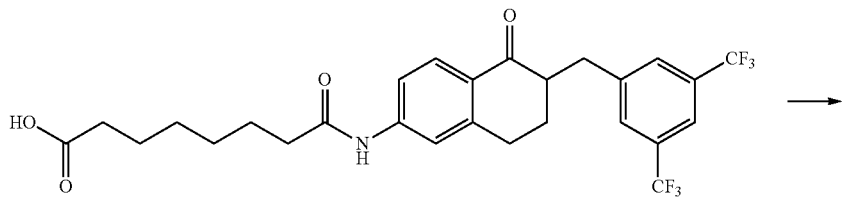

9a

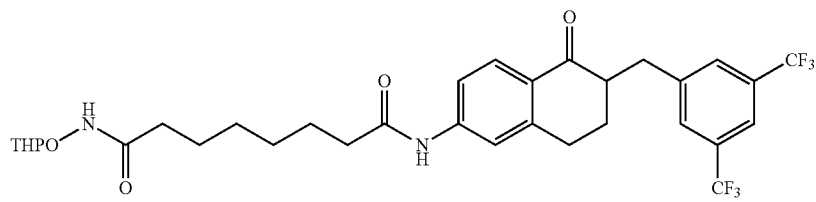

10a

To a solution of compound 9a (8-((6-(3,5-bis(trifluoromethyl)benzyl)-5-oxo-5,6,7,8-tetrahydronaphthalen-2-yl)amino)-8-oxooctanoic acid) (0.17 g, 0.31 mmol), O-(Tetrahydro-2H-pyran-2-yl)hydroxylamine (0.04, 0.31 mmol) and DMAP (0.04 g, 0.31 mmol) in DCM (10 mL) was added NMM (0.03 g, 0.31 mmol) and EDCI (0.06 g, 0.31 mmol) at 0° C. After addition, the reaction mixture was slowly warmed to RT and stirred for overnight.

After reaction was completed, the reaction mixture was diluted with EtOAc and washed with Sat. NH₄Cl. The combined organic layers were washed with brine and dried over MgSO₄ and concentrated in vacuo. The crude product was purified via flash column chromatography on a silica gel column using 10:1 DCM-MeOH as the eluent to give compound 10a (N1-(6-(3,5-bis(trifluoromethyl)benzyl)-5-oxo-5,6,7,8-tetrahydronaphthalen-2-yl)-N8-((tetrahydro-2H-pyran-2-yl)oxy)octanediamide) (0.12 g, 0.19 mmol, yield 62%).

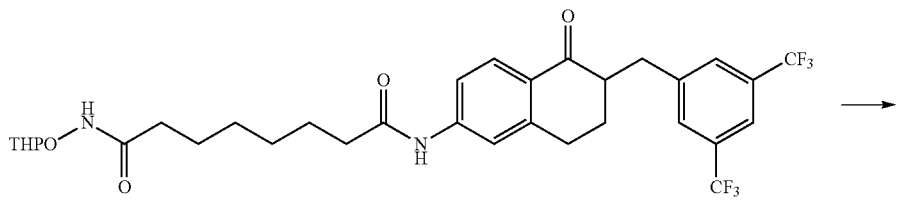

10a

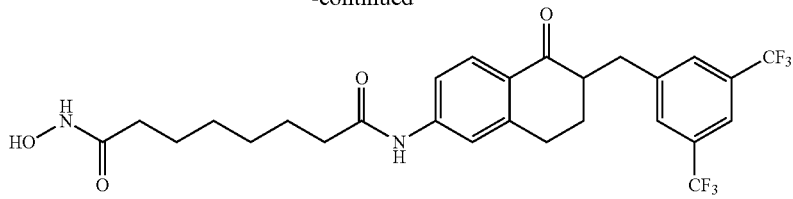

To a solution of compound 10a (N1-(6-(3,5-bis(trifluoromethyl)benzyl)-5-oxo-5,6,7,8-tetrahydronaphthalen-2-yl)-N8-((tetrahydro-2H-pyran-2-yl)oxy)octanediamide) (0.12 g, 0.19 mmol) in DCM (10 mL) was added 2N HCl (excess, in diethyl ether) and stirred for 3 hours.

After reaction was completed, the solvent was removed under reduced pressure. The precipitated solid was washed with water and ether to yield compound 10 (N1-(6-(3,5-bis(trifluoromethyl)benzyl)-5-oxo-5,6,7,8-tetrahydronaphthalen-2-yl)-N8-hydroxyoctanediamide) (0.08 g, 0.01 mmol, yield 8%).

Compound 10, $^1$H-NMR (500 MHz, CD$_3$OD): δ 7.94-7.92 (d, 1H), 7.89 (s, 2H), 7.80 (s, 1H), 7.62 (s, 1H), 7.46-7.44 (dd, 1H), 3.52-3.48 (dd, 1H), 3.02-2.90 (m, 4H), 2.40-2.37 (t, 2H), 2.10-2.07 (t, 2H), 1.85-1.79 (m, 1H), 1.71-1.60 (m, 5H), 1.39-1.38 (m, 4H). ESI-MS m/z calcd for C$_{27}$H$_{28}$F$_6$N$_2$O$_4$ 558.20, found 559 [M+H]$^+$.

Synthesis of Compounds 11~12

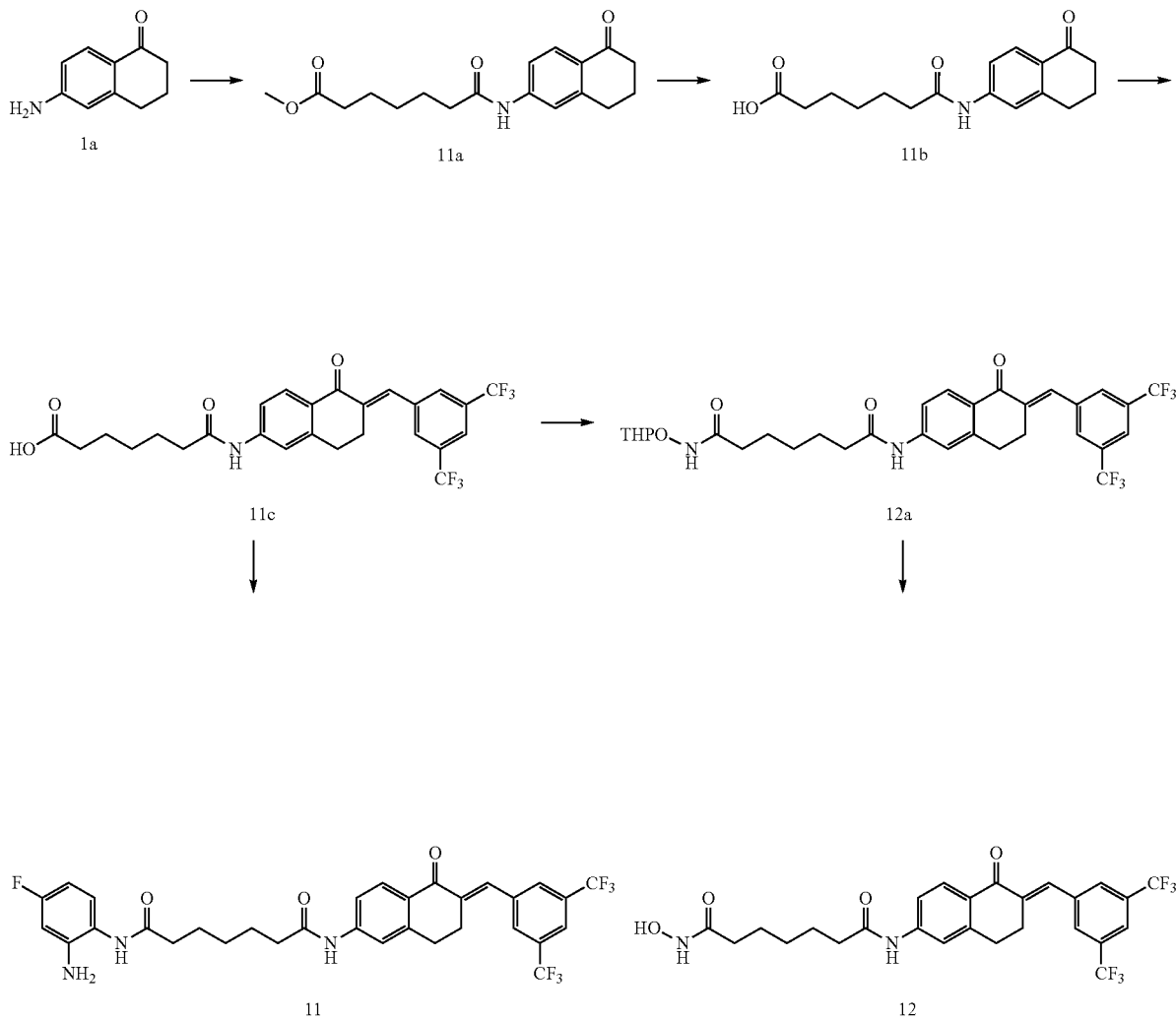

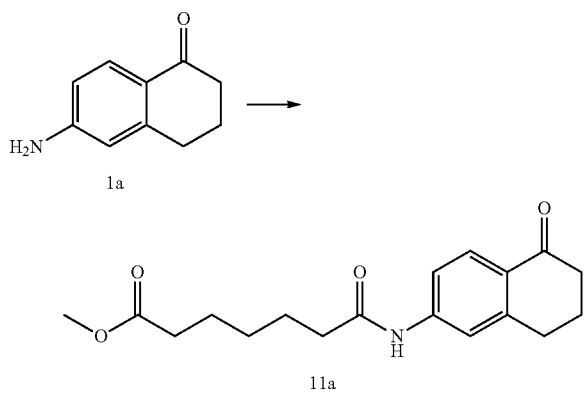

To a solution of Compound 1a (6-Amino-1-tetralone) (0.50 g, 3.10 mmol), 7-methoxy-7-oxoheptanoic acid (0.81 g, 4.65 mmol) and HOBt (0.21 g, 1.55 mmol) in DCM (50 mL) was added DIPEA (1.20 g, 9.31 mmol) and EDCI (0.89 g, 4.65 mmol) at 0° C. After addition, the reaction mixture was slowly warmed to RT and stirred for overnight.

After reaction was completed, the solvent was removed under reduced pressure. The residual was diluted with EtOAc and washed with Sat. $NH_4Cl$ and Sat. $NaHCO_3$. The combined organic layers were washed with brine and dried over $MgSO_4$ and concentrated in vacuo to afford Compound 11a (methyl 7-oxo-7-((5-oxo-5,6,7,8-tetrahydronaphthalen-2-yl)amino)heptanoate) (0.88 g, 2.76 mmol, yield 89%). The product was used in next step without further purification.

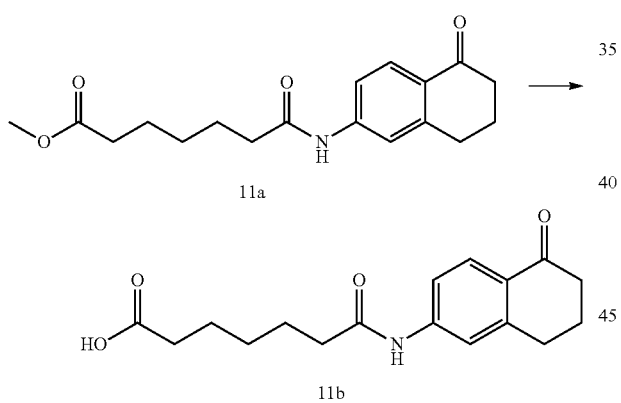

To a solution of compound 11a (methyl 7-oxo-7-((5-oxo-5,6,7,8-tetrahydronaphthalen-2-yl)amino)heptanoate) (0.88 g, 2.76 mmol) in MeOH (50 mL) was added 2N NaOH (2 mL, 4.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 30% MeOH/water to give Compound 11b (7-oxo-7-((5-oxo-5,6,7,8-tetrahydronaphthalen-2-yl)amino)heptanoic acid) (0.78 g, 2.57 mmol, yield 93%). The product was used in next step without further purification.

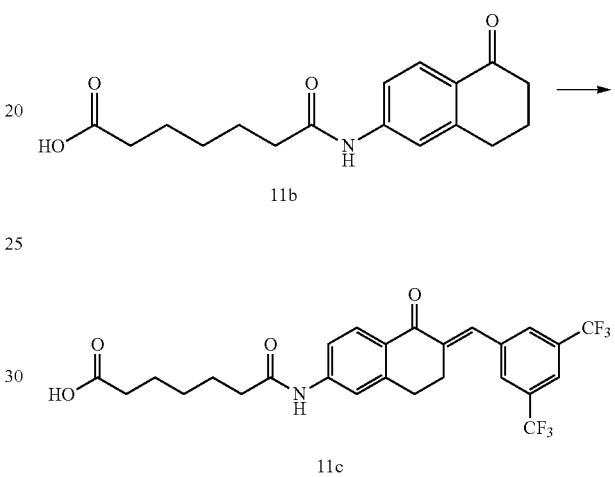

To a solution of Compound 11b (7-oxo-7-((5-oxo-5,6,7,8-tetrahydronaphthalen-2-yl)amino)heptanoic acid) (0.67 g, 2.22 mmol) and 3,5-Bis(trifluoromethyl)benzaldehyde (0.65, 2.67 mmol) in MeOH (50 mL) was added 2N NaOH (3.30 mL, 6.67 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 30% MeOH/water to get Compound 11c ((E)-7-((6-(3,5-bis(trifluoromethyl)benzylidene)-5-oxo-5,6,7,8-tetrahydronaphthalen-2-yl)amino)-7-oxoheptanoic acid) (1.14 g, 2.16 mmol, yield 97%).

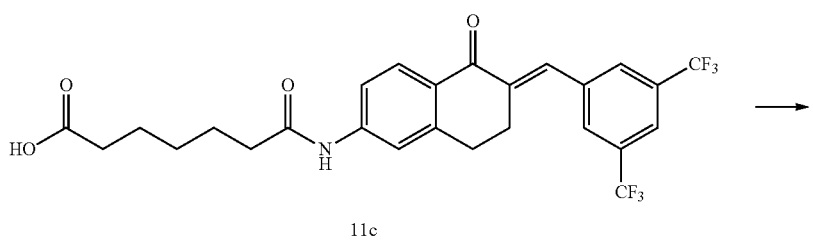

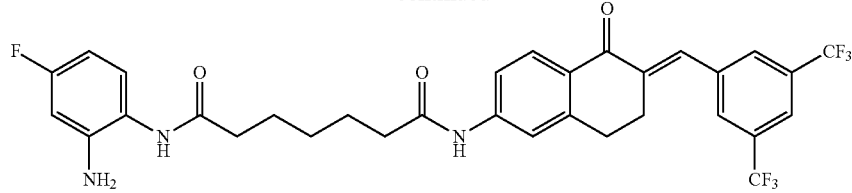

11

To a solution of Compound 11c ((E)-7-((6-(3,5-bis(trifluoromethyl)benzylidene)-5-oxo-5,6,7,8-tetrahydronaphthalen-2-yl)amino)-7-oxoheptanoic acid) (0.66 g, 1.24 mmol), 4-fluoro-1,2-phenylenediamine (0.19 g, 1.49 mmol) and DMAP (0.08 g, 0.62 mmol) in THF (50 mL) was added NMM (0.19 g, 1.87 mmol) and EDCI (0.36 g, 1.87 mmol) at 0° C. After addition, the reaction mixture was warmed to room temperature and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 2:1 EtOAc-Hexane as the eluent to give Compound 11 ((E)-N1-(2-amino-4-fluorophenyl)-N7-(6-(3,5-bis(trifluoromethyl)benzylidene)-5-oxo-5,6,7,8-tetrahydronaphthalen-2-yl)heptanediamide) (0.04 g, 0.07 mmol, yield 6%).

Compound 11, $^1$H-NMR (500 MHz, CD$_3$OD): δ 8.02-8.00 (m, 3H), 7.97 (s, 1H), 7.81 (s, 1H), 7.67 (s, 1H), 7.54-7.52 (d, 1H), 7.01-6.98 (dd, 1H), 6.53-6.51 (dd, 1H), 6.35-6.31 (td, 1H), 3.08-2.95 (m, 4H), 2.46-2.41 (q, 4H), 1.79-1.76 (t, 4H), 1.53-1.48 (m, 2H). ESI-MS m/z calcd for C$_{32}$H$_{28}$F$_7$N$_3$O$_3$ 635.20, found 636 [M+H]$^+$.

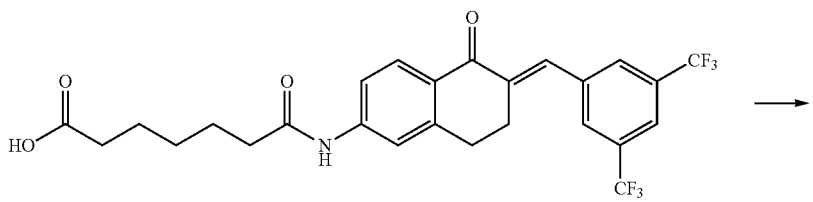

11c

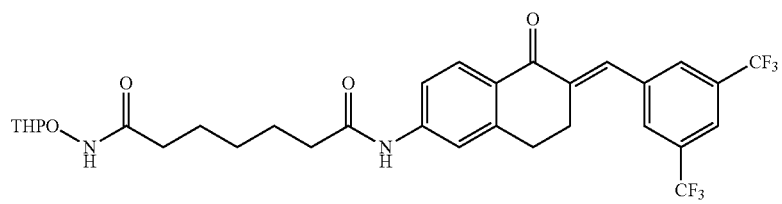

12a

To a solution of Compound 11c ((E)-7-((6-(3,5-bis(trifluoromethyl)benzylidene)-5-oxo-5,6,7,8-tetrahydronaphthalen-2-yl)amino)-7-oxoheptanoic acid) (0.49 g, 0.92 mmol), O-(Tetrahydro-2H-pyran-2-yl)hydroxylamine (0.04, 0.36 mmol), and DMAP (0.06 g, 0.47 mmol) in DCM (20 mL) was added EDCI (0.27 g, 1.38 mmol) at 0° C. After addition, the reaction mixture was slowly warmed to RT and stirred for overnight.

After reaction was completed, the reaction mixture was diluted with EtOAc and washed with Sat. $NH_4Cl$. The combined organic layers were washed with brine and dried over $MgSO_4$ and concentrated in vacuo. The crude product was purified via flash column chromatography on a silica gel column using 10:1 DCM-MeOH as the eluent to give Compound 12a ((E)-N1-(6-(3,5-bis(trifluoromethyl)benzylidene)-5-oxo-5,6,7,8-tetrahydronaphthalen-2-yl)-N7-((tetrahydro-2H-pyran-2-yl)oxy)heptanediamide) (0.22 g, 0.35 mmol, yield 38%).

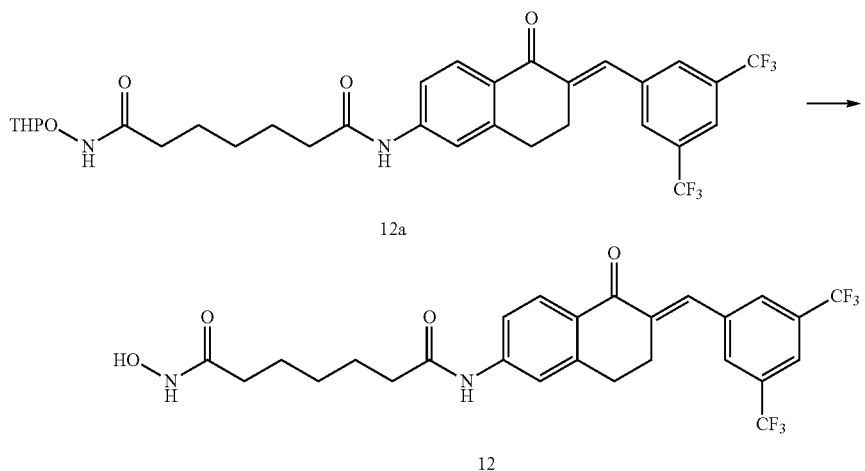

To a solution of Compound 12a ((E)-N1-(6-(3,5-bis(trifluoromethyl)benzylidene)-5-oxo-5,6,7,8-tetrahydronaphthalen-2-yl)-N7-((tetrahydro-2H-pyran-2-yl)oxy)heptanediamide) (0.22 g, 0.35 mmol) in MeOH (10 mL) was added 1N HCl (0.5 mL) and stirred for 2 hours.

After reaction was completed, the solvent was removed under reduced pressure. The precipitated solid was washed with water and ether to yield Compound 12 ((E)-N1-(6-(3,5-bis(trifluoromethyl)benzylidene)-5-oxo-5,6,7,8-tetrahydronaphthalen-2-yl)-N7-hydroxyheptanediamide) (0.08 g, 0.14 mmol, yield 43%).

Compound 12, $^1$H-NMR (500 MHz, $CD_3OD$): δ 8.03-8.01 (m, 3H), 7.97 (s, 1H), 7.82 (s, 1H), 7.69 (s, 1H), 7.55-7.53 (d, 1H), 3.09-2.98 (m, 4H), 2.43-2.41 (t, 2H), 2.13-2.10 (t, 2H), 1.74-1.66 (m, 4H), 1.43-1.40 (m, 2H). ESI-MS m/z calcd for $C_{26}H_{24}F_6N_2O_4$ 542.16, found 565 $[M+Na]^+$.

Synthesis of Compounds 13~14

Scheme 07

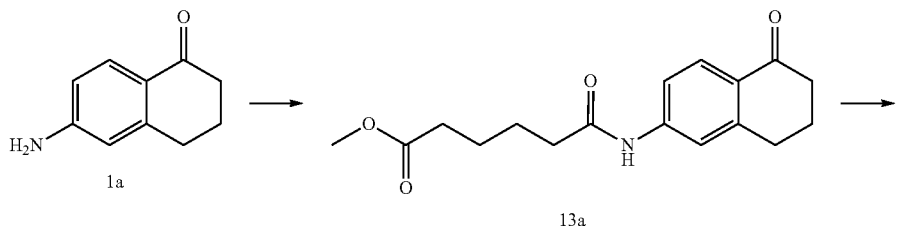

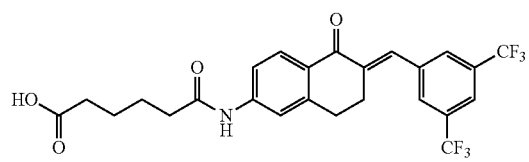

13b

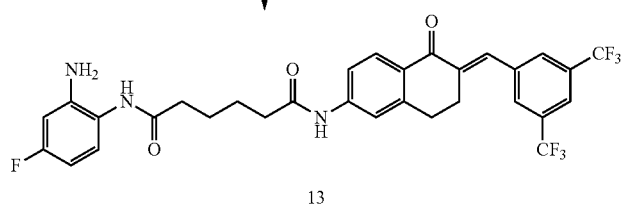

13

-continued

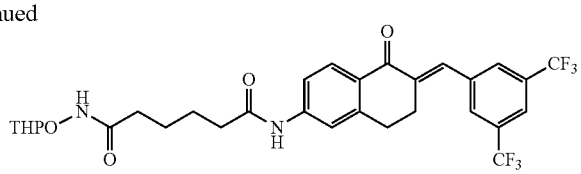

14a

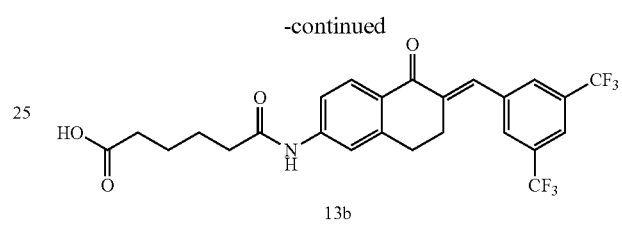

14

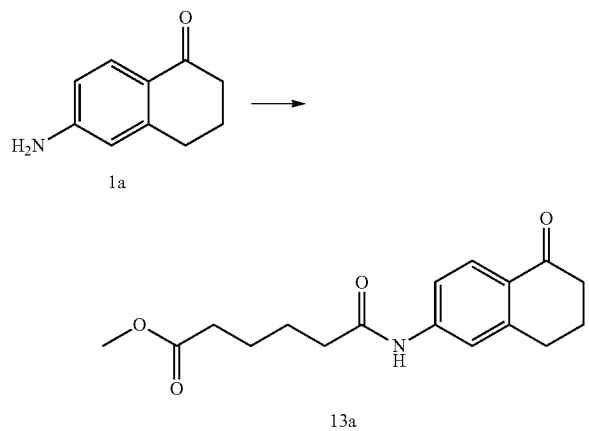

1a

13a

To a solution of Compound 1a (6-Amino-1-tetralone) (1.00 g, 6.20 mmol), monomethyl adipate (1.29 g, 8.07 mmol) and DMAP (0.99 g, 8.07 mmol) in DCM (100 mL) was added DIPEA (2.41 g, 18.61 mmol) and EDCI (1.78 g, 9.31 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl and Sat. NaHCO₃. The combined organic layers were washed with brine and dried over MgSO₄ and concentrated in vacuo to afford Compound 13a (methyl 6-oxo-6-((5-oxo-5,6,7,8-tetrahydronaphthalen-2-yl)amino)hexanoate) (1.48 g, 4.87 mmol, yield 78%). The product was used in next step without further purification.

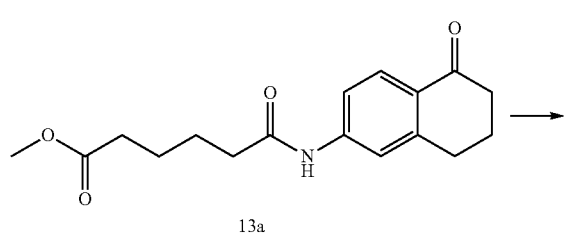

13a

-continued

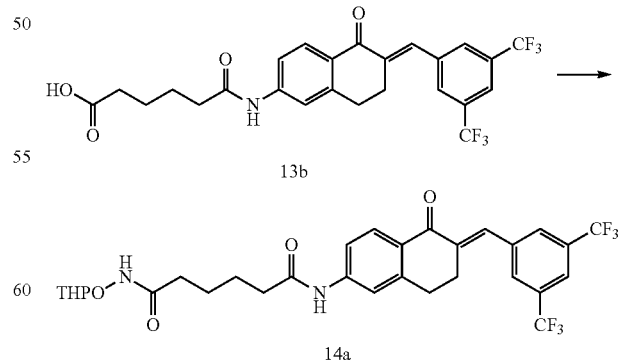

13b

14a

To a solution of Compound 13a (methyl 6-oxo-6-((5-oxo-5,6,7,8-tetrahydronaphthalen-2-yl)amino)hexanoate) (1.12 g, 3.69 mmol) in MeOH (50 mL) was added 2N NaOH (4 mL, 8.00 mmol). After addition, the reaction mixture was stirred for overnight.

After the methyl ester was hydrolyzed, the reaction mixture was added 3,5-Bis(trifluoromethyl)benzaldehyde (1.07, 4.43 mmol) and stirred for further 6 hours. After the reaction was completed, the solvent was removed under reduced pressure. The residual was diluted with ice-cold water and acidified with 1N HCl. The precipitated solid was collected by filtration and washed with 30% MeOH/water to give Compound 13b ((E)-6-((6-(3,5-bis(trifluoromethyl)benzylidene)-5-oxo-5,6,7,8-tetrahydronaphthalen-2-yl)amino)-6-oxohexanoic acid) (1.41 g, 2.75 mmol, yield 74%). The product was used in next step without further purification.

To a solution of Compound 13b (E)-6-((6-(3,5-bis(trifluoromethyl)benzylidene)-5-oxo-5,6,7,8-tetrahydronaphthalen-2-yl)amino)-6-oxohexanoic acid (0.20 g, 0.39 mmol), O-(Tetrahydro-2H-pyran-2-yl)hydroxylamine (0.06, 0.51 mmol), and DMAP (0.02 g, 0.20 mmol) in DCM (20 mL) was added NMM (0.06 g, 0.59 mmol) and EDCI (0.11 g, 0.59 mmol) at 0° C. After addition, the reaction mixture was slowly warmed to RT and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 10:1 DCM-MeOH as the eluent to give Compound 14a ((E)-N1-(6-(3,5-bis(trifluoromethyl)benzylidene)-5-oxo-5,6,7,8-tetrahydronaphthalen-2-yl)-N6-((tetrahydro-2H-pyran-2-yl)oxy)adipamide) (0.10 g, 0.16 mmol, yield 41%).

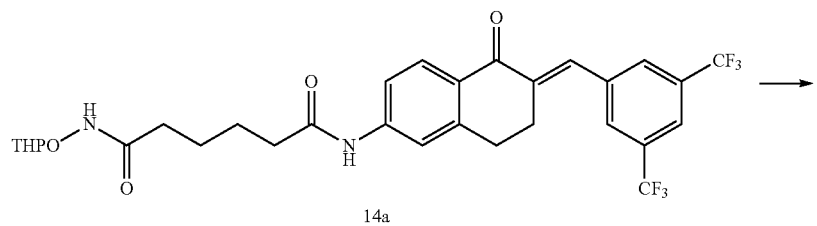

14a

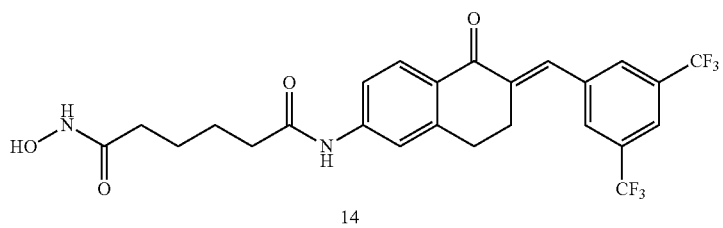

14

To a solution of Compound 14a ((E)-N1-(6-(3,5-bis(trifluoromethyl)benzylidene)-5-oxo-5,6,7,8-tetrahydronaphthalen-2-yl)-N6-((tetrahydro-2H-pyran-2-yl)oxy)adipamide) (0.10 g, 0.16 mmol) in DCM (10 mL) was added 2N HCl (excess, in diethyl ether) and stirred for 3 hrs.

After reaction was completed, the solvent was removed under reduced pressure. The precipitated solid was washed with water and ether to yield Compound 14 ((E)-N1-(6-(3,5-bis(trifluoromethyl)benzylidene)-5-oxo-5,6,7,8-tetrahydronaphthalen-2-yl)-N6-hydroxyadipamide) (0.04 g, 0.07 mmol, yield 45%).

Compound 14, $^1$H-NMR (500 MHz, CD$_3$OD): δ 8.02-8.00 (m, 3H), 7.97 (s, 1H), 7.81 (s, 1H), 7.67 (s, 1H), 7.55-7.53 (d, 1H), 3.08-3.07 (t, 2H), 2.98-2.96 (t, 2H), 2.44-2.41 (t, 2H), 2.16-2.15 (t, 2H), 1.70 (s, 4H). ESI-MS m/z calcd for C$_{25}$H$_{22}$F$_6$N$_2$O$_4$ 528.15, found 529 [M+H]$^+$.

13b

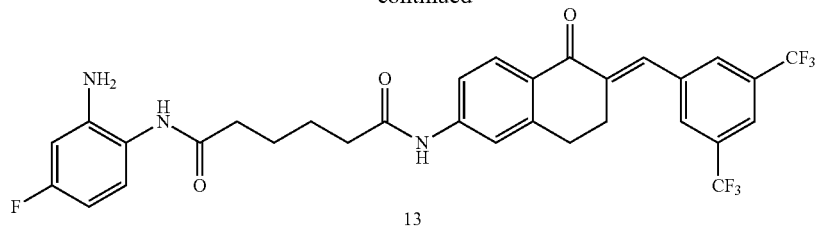

13

To a solution of Compound 13b ((E)-6-((6-(3,5-bis(trifluoromethyl)benzylidene)-5-oxo-5,6,7,8-tetrahydronaphthalen-2-yl)amino)-6-oxohexanoic acid) (0.20 g, 0.39 mmol), 4-fluoro-1,2-phenylenediamine (0.05 g, 0.39 mmol) and DMAP (0.05 g, 0.39 mmol) in THF (50 mL) was added NMM (0.04 g, 0.39 mmol) and EDCI (0.10 g, 0.51 mmol) at 0° C. After addition, the reaction mixture was warmed to room temperature and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 2:1 EtOAc-Hexane as the eluent to give Compound 13 ((E)-N1-(2-amino-4-fluorophenyl)-N6-(6-(3,5-bis(trifluoromethyl)benzylidene)-5-oxo-5,6,7,8-tetrahydronaphthalen-2-yl)adipamide) (0.11 g, 0.18 mmol, yield 47%).

Compound 13, $^1$H-NMR (500 MHz, CD$_3$OD): δ 8.03-8.01 (m, 3H), 7.97 (s, 1H), 7.82 (s, 1H), 7.69 (s, 1H), 7.56-7.54 (dd, 1H), 7.04-7.01 (m, 1H), 6.54-6.52 (dd, 1H), 6.38-6.34 (td, 1H), 3.10-3.08 (t, 2H), 2.99-2.97 (t, 2H), 2.49-2.45 (m, 4H), 1.81-1.79 (t, 4H). ESI-MS m/z calcd for C$_{31}$H$_{26}$F$_7$N$_3$O$_3$ 621.19, found 622 [M+1-1]$^+$.

Synthesis of Compound 15

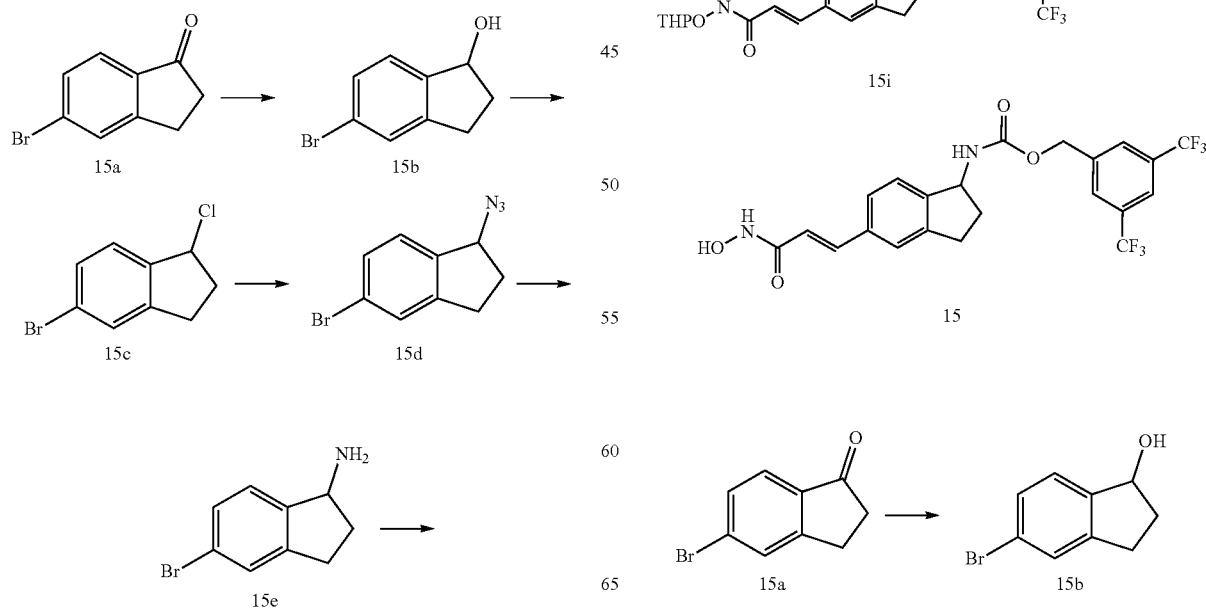

Scheme 08

To a solution of Compound 15a (5-Bromo-1-indanone) (5.00 g, 23.69 mmol) in THF/water (25 mL, 4:1) was added NaBH$_4$ (0.90 g, 23.69 mmol) at 0° C. After addition, the reaction mixture was slowly warmed to RT and stirred for 2 hrs.

After reaction was completed, the reaction mixture was quenched with Sat. NH$_4$Cl. The solvent was removed under reduced pressure. The residual was diluted with EtOAc and washed with Sat. NH$_4$Cl. The combined organic layers were washed with brine and dried over MgSO$_4$ and concentrated in vacuo to obtain Compound 15b (5-bromo-2,3-dihydro-1H-inden-1-ol) (4.99 g, 23.42, yield 99%). The crude product (Compound 15b) was used in the next step without further purification.

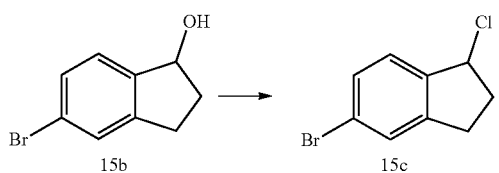 [SMILES: OC1CCc2cc(Br)ccc21 ; ClC1CCc2cc(Br)ccc21]

To a solution of Compound 15b (1.00 g, 4.69 mmol) in DCM (50 mL) was added SOCl$_2$ (2 mL) at 0° C. After addition, the reaction mixture was slowly warmed to RT and stirred for overnight.

After reaction was completed, the solvent was removed under reduced pressure. The residual was diluted with EtOAc and washed with brine. The combined organic layers were washed with brine and dried over MgSO$_4$ and concentrated in vacuo to get Compound 15c (5-bromo-1-chloro-2,3-dihydro-1H-indene) (1.03 g, 4.45 mmol, yield 95%). The crude product (Compound 15c) was used in the next step without further purification.

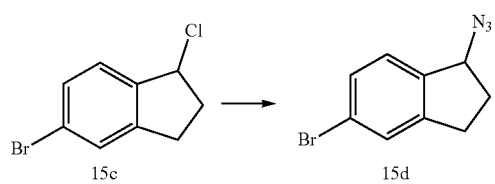 [SMILES: ClC1CCc2cc(Br)ccc21 ; [N-]=[N+]=NC1CCc2cc(Br)ccc21]

To a solution of Compound 15c (1.03 g, 4.45 mmol) in DMF (40 mL) was added NaN$_3$ (0.58 g, 8.92 mmol) at 0° C. After addition, the reaction mixture was slowly warmed to RT and stirred for overnight.

After reaction was completed, the reaction mixture was diluted with EtOAc and washed with water and brine. The combined organic layers were washed with brine and dried over MgSO$_4$ and concentrated in vacuo to produce Compound 15d (1-azido-5-bromo-2,3-dihydro-1H-indene) (1.02 g, 4.28 mmol, yield 96%). The crude product (Compound 15d) was used in the next step without further purification.

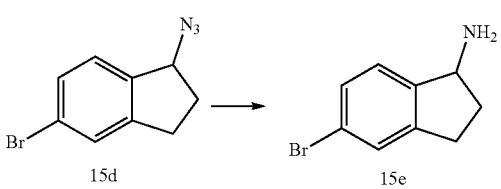 [SMILES: [N-]=[N+]=NC1CCc2cc(Br)ccc21 ; NC1CCc2cc(Br)ccc21]

To a solution of Compound 15d (1.02 g, 4.28 mmol) in MeOH (50 mL) was added Pd/C (0.1 g). After addition, the reaction mixture was stirred under H$_2$ for overnight.

After reaction was completed, the solvent was removed under reduced pressure. Pd/C was filed off through a pad of celite and washed with EtOAc. The filtrate was concentrated in vacuo to afford Compound 15e (5-bromo-2,3-dihydro-1H-inden-1-amine) (0.88 g, 4.15 mmol, yield 97%)

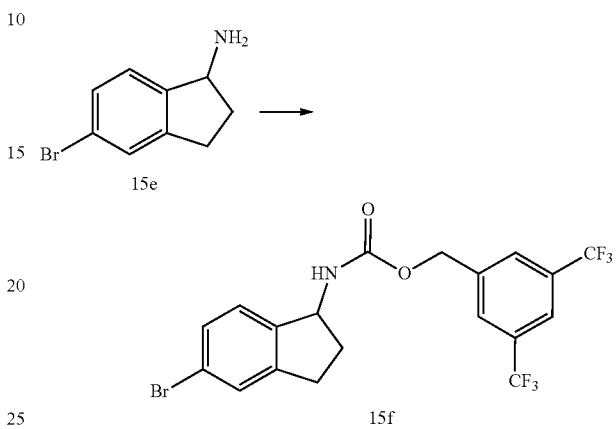

To a solution of 3,5-bis(trifluoromethyl)benzyl alcohol (0.13 g, 0.75 mmol) in DCM (10 mL) was added DIPEA (0.10 g, 0.75 mmol) and triphosgene (0.07 g, 0.25 mmol) at 0° C. The reaction mixture was stirred at the same temperature for 30 min. After the 3,5-bis(trifluoromethyl)benzyl alcohol was consumed, a solution of Compound 15e (0.13 g, 0.62 mmol) and DIPEA (0.10 g, 0.75 mmol) in DCM (10 mL) was added into the reaction mixture. Then the reaction mixture was slowly warmed to RT and stirred for overnight.

After reaction was completed, the solvent was removed under reduced pressure. The residual was diluted with Sat. NH$_4$Cl and extracted with EtOAc. The combined organic layers were dried over MgSO$_4$ and concentrated in vacuo. The crude product was purified via flash column chromatography on a silica gel column using 10:1 DCM-MeOH as the eluent to give Compound 15f (3,5-bis(trifluoromethyl)benzyl (5-bromo-2,3-dihydro-1H-inden-1-yl)carbamate) (0.22 g, 0.46 mmol, yield 61%).

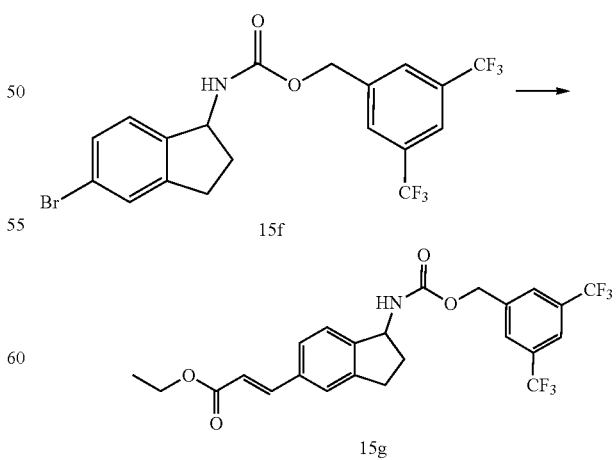

To a solution of Compound 15f (0.22 g, 0.46 mmol) in DMF (5 mL) and triethylamine (3 mL) was added PPh$_3$ (0.05 g, 0.18 mmol), ethyl acrylate (0.06 g, 0.60 mmol) and Pd(OAc)$_2$ (5.2 mg, 0.02 mmol). The mixture was degassed with Ar for 15 min, then heated to 90° C. for overnight.

After reaction was completed, the solvent was removed under reduced pressure, then the residual was filtered through celite and washed with EtOAc. After concentration in vacuo, the crude product was purified via flash column chromatography on a silica gel column using 5:1 hexane-EtOAc as the eluent to give Compound 15g (ethyl (E)-3-(1-((((3,5-bis(trifluoromethyl)benzyl)oxy)carbonyl)amino)-2,3-dihydro-1H-inden-5-yl)acrylate) (0.14 g, 0.29 mmol, 63%).

mmol) at 0° C. After addition, the reaction mixture was slowly warmed to RT and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 10:1 DCM-MeOH as the eluent to give Compound 15i (3,5-bis(trifluoromethyl)benzyl (E)-(5-(3-oxo-3-(((tetrahydro-2H-pyran-2-yl)oxy)amino)prop-1-en-1-yl)-2,3-dihydro-1H-inden-1-yl)carbamate) (0.13 g, 0.23 mmol, yield 81%).

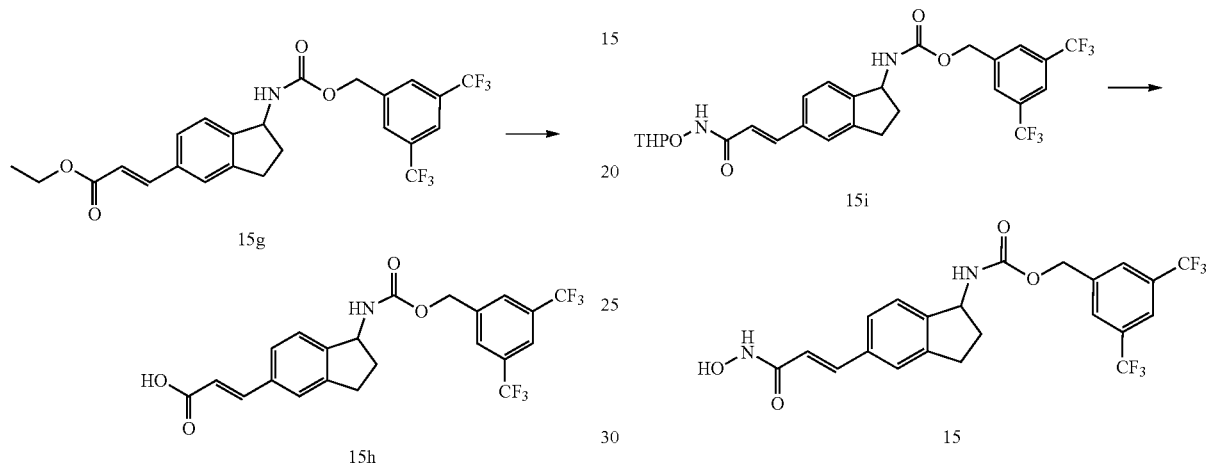

To a solution of Compound 15g (0.14 g, 0.29 mmol) in MeOH (30 mL) was added 2N NaOH (1 mL) and stirred at RT for overnight.

After reaction was completed, the solvent was removed under reduced pressure. The residual was diluted with ice-cold water and acidified with 1N HCl. The precipitated solid was collected by filtration and washed with water and diethyl ether to obtain Compound 15h ((E)-3-(1-((((3,5-bis(trifluoromethyl)benzyl)oxy)carbonyl)amino)-2,3-dihydro-1H-inden-5-yl)acrylic acid) (0.13 g, 0.28 mmol, yield 96%). The crude product (Compound 15h) was used in the next step without further purification.

To a solution of Compound 15i (0.13 g, 0.23 mmol) in MeOH (10 mL) was added 1N HCl (0.5 mL) and stirred for 2 hrs.

After reaction was completed, the solvent was removed under reduced pressure. The precipitated solid was washed with water and ether to produce Compound 15 (3,5-bis(trifluoromethyl)benzyl (E)-(5-(3-(hydroxyamino)-3-oxo-prop-1-en-1-yl)-2,3-dihydro-1H-inden-1-yl)carbamate) (0.08 g, 0.17 mmol, yield 75%).

Compound 15, $^1$H-NMR (400 MHz, d$_6$-DMSO): δ 8.09-8.08 (m, 3H), 7.92-7.90 (d, 1H), 7.44-7.36 (m, 3H), 7.21-7.20 (d, 1H), 6.44-6.41 (d, 1H), 5.31-5.24 (q, 2H), 5.07-5.04 (q, 1H), 2.95-2.91 (m, 1H), 2.82-2.78 (m, 1H), 2.42-2.38 (m, 1H), 1.86-1.82 (m, 1H). ESI-MS m/z calcd for C$_{22}$H$_{18}$F$_6$N$_2$O$_4$ 488.12, found 489 [M+H]$^+$ Synthesis of Compound 16

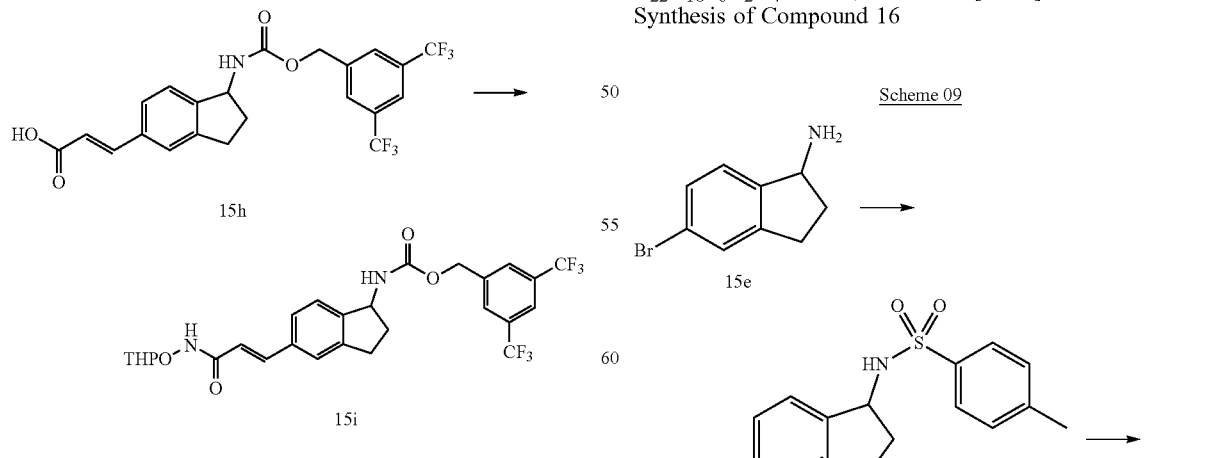

Scheme 09

-continued

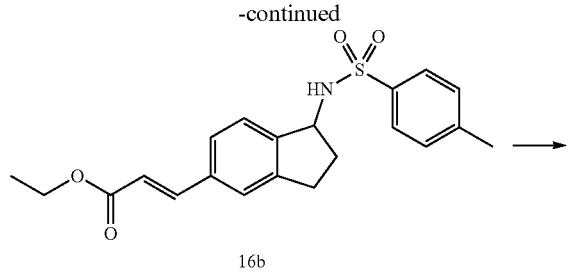
16b

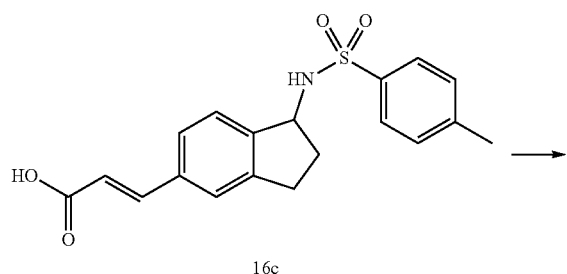
16c

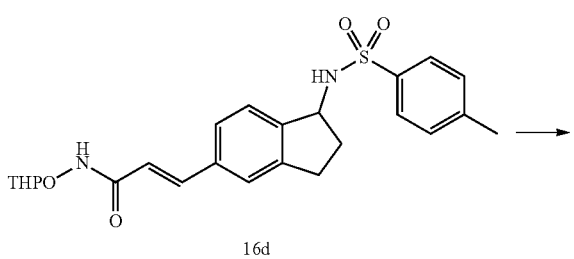
16d

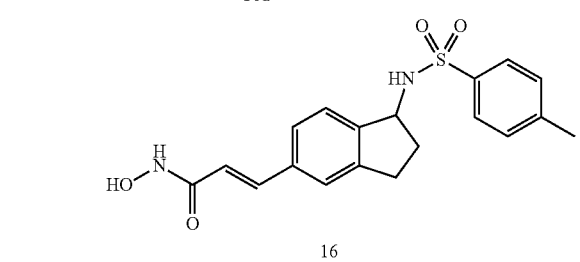
16

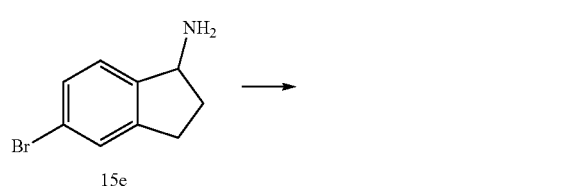
15e

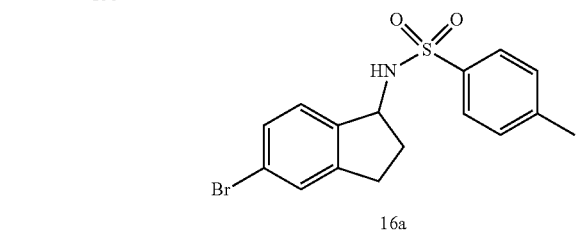
16a

To a solution of Compound 15e (5-bromo-2,3-dihydro-1H-inden-1-amine) (0.20 g, 0.94 mmol) in DCM (20 mL) was added TEA (0.14 g, 1.41 mmol) and 4-methylbenzenesulfonyl chloride (0.20 g, 1.04 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl and Sat. NaHCO$_3$. The organic phase was dried with MgSO$_4$ and concentrated under reduced pressure. The crude product was purified by silica gel column chromatography using ethyl acetate/hexane=1/4 as elution to afford Compound 16a (N-(5-bromo-2,3-dihydro-1H-inden-1-yl)-4-methylbenzenesulfonamide) (0.28 g, 0.78 mmol, yield 83%).

To a solution of Compound 16a (N-(5-bromo-2,3-dihydro-1H-inden-1-yl)-4-methylbenzenesulfonamide) (0.28 g, 0.78 mmol), triphenylphosphine (0.08 g, 0.31 mmol), ethyl acrylate (0.10 g, 1.01 mmol) in DMF/TEA (20 mL, 1:1) was added Pd(OAc)$_2$ (0.01 g, 0.04 mmol). After addition, the reaction mixture was heated to 100° C. and stirred for overnight.

The reaction was monitored by thin layer chromatography (TLC). After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/3 as elution to yield the desired product Compound 16b (ethyl (E)-3-(1-((4-methylphenyl)sulfonamido)-2,3-dihydro-1H-inden-5-yl)acrylate) (0.20 g, 0.54 mmol, yield 69%).

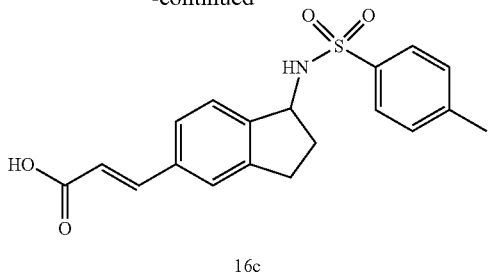

16c

To a solution of Compound 16b (ethyl (E)-3-(1-((4-methylphenyl)sulfonamido)-2,3-dihydro-1H-inden-5-yl)acrylate) (0.20 g, 0.54 mmol) in MeOH (10 mL) was added 2N NaOH$_{(aq)}$ (0.53 mL, 1.05 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 16c ((E)-3-(1-((4-methylphenyl)sulfonamido)-2,3-dihydro-1H-inden-5-yl)acrylic acid) (0.19 g, 0.53 mmol, yield 98%).

16c

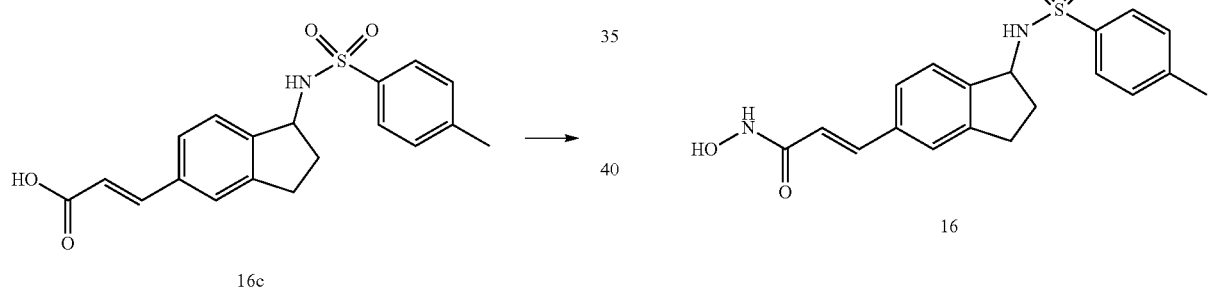

16d

To a solution of Compound 16c ((E)-3-(1-((4-methylphenyl)sulfonamido)-2,3-dihydro-1H-inden-5-yl)acrylic acid) (0.19 g, 0.53 mmol), O-(Tetrahydro-2H-pyran-2-yl)hydroxylamine (0.08 g, 0.69 mmol) and DMAP (0.03 g, 0.27 mmol) in DCM (20 mL) was added NMM (0.08 g, 0.80 mmol) and EDCI (0.15 g, 0.80 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=3/1 as elution to yield the desired product Compound 16d ((E)-3-(1-((4-methylphenyl)sulfonamido)-2,3-dihydro-1H-inden-5-yl)-N-((tetrahydro-2H-pyran-2-yl)oxy)acrylamide) (0.16 g, 0.34 mmol, yield 64%).

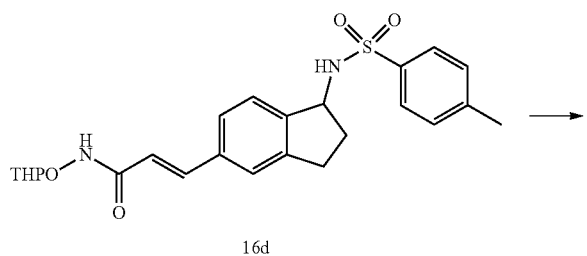

16d

16

To a solution of Compound 16d ((E)-3-(1-((4-methylphenyl)sulfonamido)-2,3-dihydro-1H-inden-5-yl)-N-((tetrahydro-2H-pyran-2-yl)oxy)acrylamide) (0.16 g, 0.34 mmol) in CH$_2$Cl$_2$ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 16 ((E)-N-hydroxy-3-(1-((4-methylphenyl)sulfonamido)-2,3-dihydro-1H-inden-5-yl)acrylamide) (0.13 g, 0.34 mmol, yield 99%).

Compound 16, $^1$H-NMR (500 MHz, CD$_3$OD): δ 7.83-7.81 (d, 2H), 7.54-7.51 (d, 1H), 7.42-7.40 (d, 2H), 7.37 (s, 1H), 7.34-7.33 (d, 1H), 7.12-7.10 (d, 1H), 6.43-6.40 (d, 1H), 4.77-4.74 (t, 1H), 2.91-2.86 (m, 1H), 2.75-2.69 (m, 1H), 2.46 (s, 3H), 2.21-2.15 (m, 1H), 1.74-1.66 (m, 1H). ESI-MS m/z calcd for C$_{19}$H$_{20}$N$_2$O$_4$S 372.11, found 373 [M+H]$^+$.

Synthesis of Compounds 17~18
Scheme 10
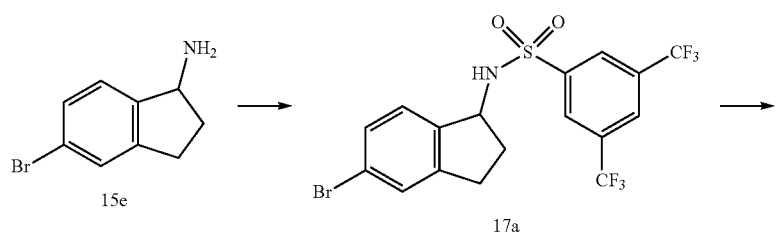
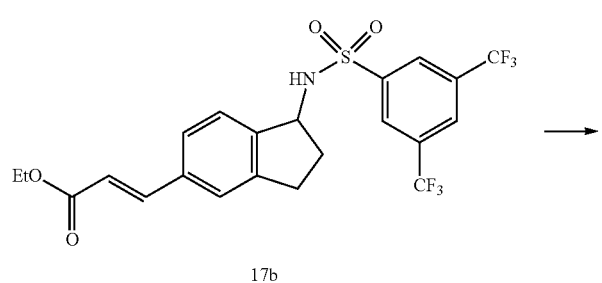
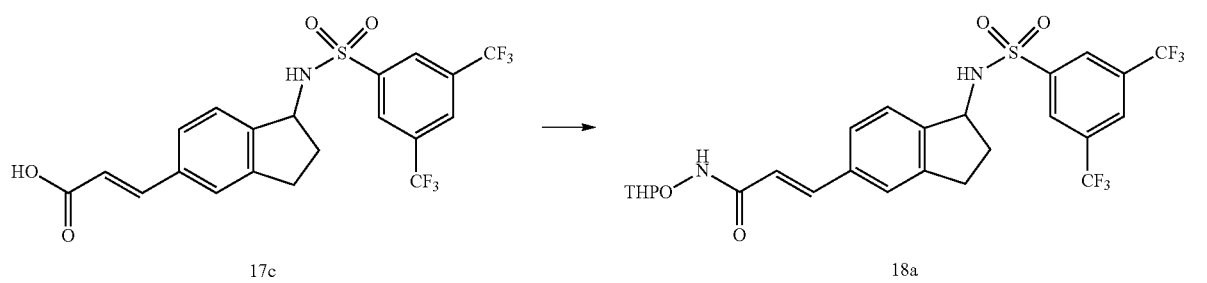
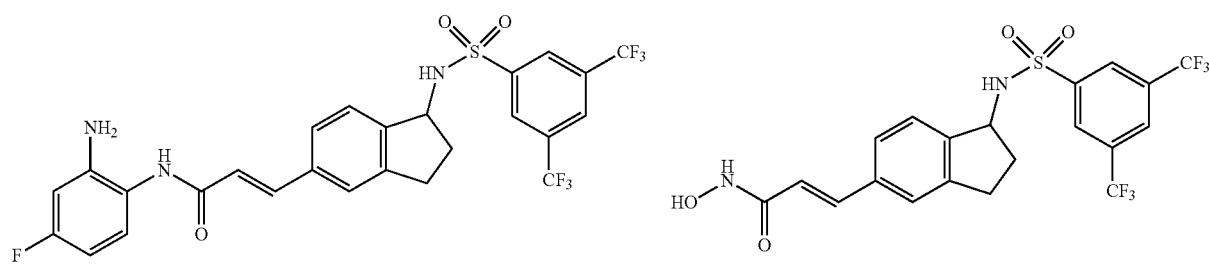

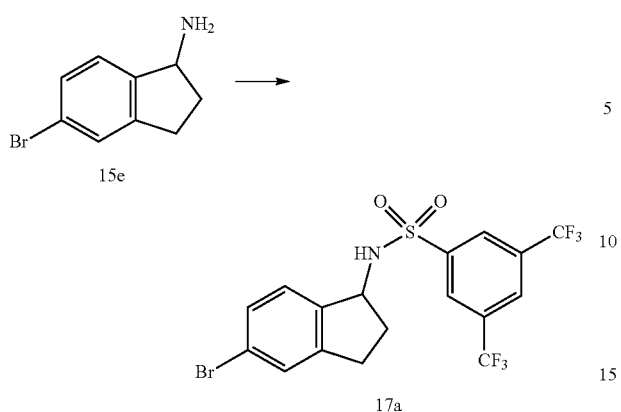

15e

17a

To a solution of Compound 15e (5-bromo-2,3-dihydro-1H-inden-1-amine) (0.5 g, 2.36 mmol) in THF (50 mL) at 0° C. was added TEA (0.66 mL, 4.72 mmol) followed by 3,5-bis(trifluoromethyl)benzenesulfonyl chloride (0.88 g, 2.83 mmol). The reaction mixture was stirred at 0° C. for 30 min, then was allowed to warm to RT over 12 hours.

The mixture was quenched with H$_2$O and extracted with EtOAc. The combined organics were washed with NH$_4$Cl$_{(aq)}$, brine, dried over MgSO$_4$ and concentrated. The resulting material was purified by silica gel column chromatography (EtOAc./Hexane=1:8) to provide the product Compound 17a (N-(5-bromo-2,3-dihydro-1H-inden-1-yl)-3,5-bis(trifluoromethyl)benzenesulfonamide) (580.0 mg, yield 50%).

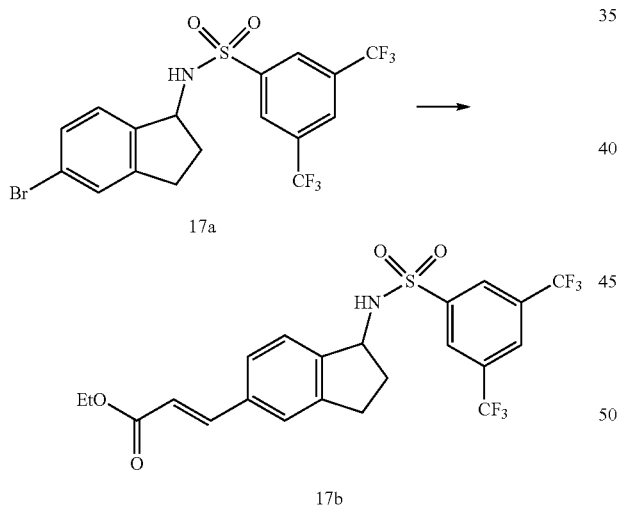

17a

17b

A solution of Compound 17a (N-(5-bromo-2,3-dihydro-1H-inden-1-yl)-3,5-bis(trifluoromethyl)benzenesulfonamide) (0.3 g, 0.61 mmol), the ethyl acrylate (0.13 mL, 1.23 mmol), triphenylphosphine (62.9 mg, 0.24 mmol), TEA (0.09 mL, 0.61 mmol), and DMF (12 mL) was degassed by bubbling argon for 3 mins. Pd(OAc)$_2$ (13.6 mg, 0.06 mmol) was added, and vacuum/argon was applied three times. The reaction mixture was stirred under argon at 100° C. for 48 hours.

The mixture was extracted with EtOAc and NH$_4$Cl (aq.). The organic layers were dried over MgSO$_4$ and concentrated in vacuo and purified by flash chromatography (EtOAc:

Hex.=1:4) to provide the yellow solid product Compound 17b (ethyl (E)-3-(1-((3,5-bis(trifluoromethyl)phenyl)sulfonamido)-2,3-dihydro-1H-inden-5-yl)acrylate) (138.4 mg, yield 45%).

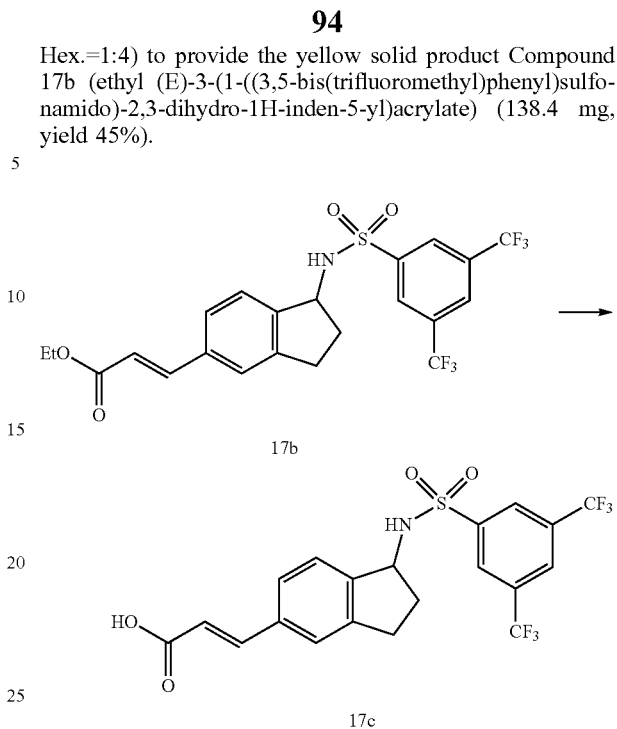

17b

17c

To a solution of Compound 17b (ethyl (E)-3-(1-((3,5-bis(trifluoromethyl)phenyl)sulfonamido)-2,3-dihydro-1H-inden-5-yl)acrylate) (138.4 mg, 0.27 mmol) in MeOH (50 mL) was added 2N NaOH solution (0.25 mL) at RT and stirred for overnight.

The reaction mixture was concentrated to remove the organic solvent. The residue was diluted with water and acidified to pH=4 with 2N HCl$_{(aq)}$. The resulting yellow precipitate was filtered, washed with H$_2$O and ether, then dried in vacuo to provide the product as a solid product Compound 17c ((E)-3-(1-((3,5-bis(trifluoromethyl)phenyl)sulfonamido)-2,3-dihydro-1H-inden-5-yl)acrylic acid) (70.0 mg, yield 53%).

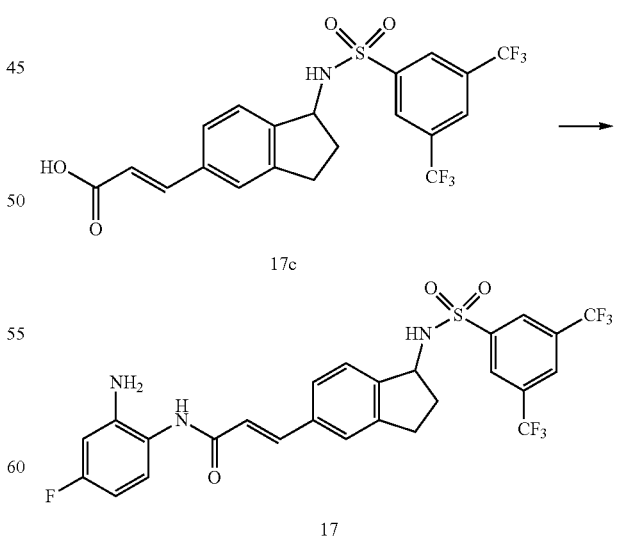

17c

17

To a stirred solution of 4-Fluoro-1,2-phenylenediamine (9.5 mg, 0.075 mmol) and DMAP (11.6 mg, 0.1 mmol) in DCM (2 mL) was added Compound 17c (bis(trifluoromethyl)phenyl)sulfonamido)-2,3-dihydro-1H-inden-5-yl) acrylic acid) (30.0 mg. 0.06 mmol) in one portion, followed by the addition of EDCI (14.4 mg, 0.075 mmol) in one portion at RT. The resulting mixture was stirred at RT overnight.

After which time it was washed successively with NaHCO$_3$(aq.) and brine. The organic layer was dried over MgSO$_4$ and concentrated in vacuo to give the crude material. The resulting residue was purified by silica gel column chromatography (EtOAc:Hex.=1:1) and washed with ether to provide the solid product Compound 17 ((E)-N-(2-amino-4-fluorophenyl)-3-(1-((3,5-bis(trifluoromethyl)phenyl)sulfonamido)-2,3-dihydro-1H-inden-5-yl)acrylamide) (8.5 mg, yield 24%).

Compound 17, $^1$H-NMR (500 MHz, CD$_3$OD): δ 8.46 (s, 2H), 8.30 (s, 1H), 7.64-7.60 (d, 1H), 7.46 (s, 1H), 7.41-7.39 (d, 1H), 7.15-7.14 (d, 2H), 6.80-6.77 (d, 1H), 6.58-6.56 (d, 1H), 6.42-6.39 (t, 1H), 4.57 (s, 1H), 4.95-4.92 (t, 1H), 2.98-2.94 (m, 1H), 2.83-2.77 (m, 1H), 2.26-2.45 (m, 1H), 1.79-1.75 (m, 1H). ESI-MS m/z calcd for C$_{26}$H$_{20}$F$_7$N$_3$O$_3$S 587.11, found 588.4[M+H]$^+$.

portion, followed by the addition of EDCI (54.1 mg, 0.28 mmol) in one portion at RT. The resulting mixture was stirred at RT overnight.

After which time it was washed successively with NaHCO$_3$(aq.) and brine. The organic layer was dried over MgSO$_4$ and concentrated in vacuo to give the crude material. The resulting residue was purified by silica gel column chromatography (EA:Hex.=1:1) to provide the product Compound 18a ((E)-3-(1-((3,5-bis(trifluoromethyl)phenyesulfonamido)-2,3-dihydro-1H-inden-5-yl)-N-((tetrahydro-2H-pyran-2-yl)oxy)acrylamide) (120.0 mg, yield 86%).

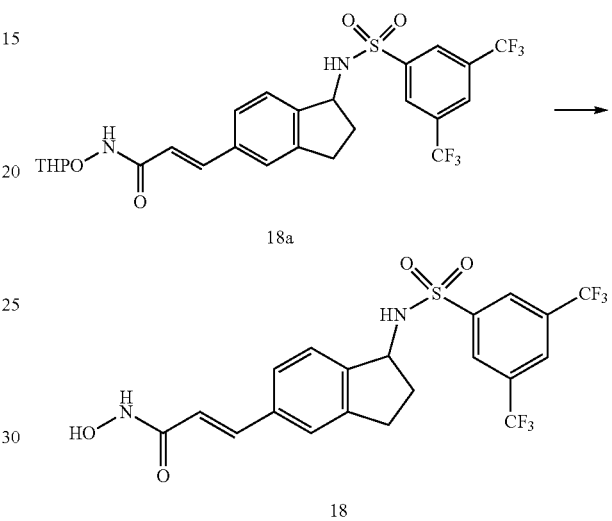

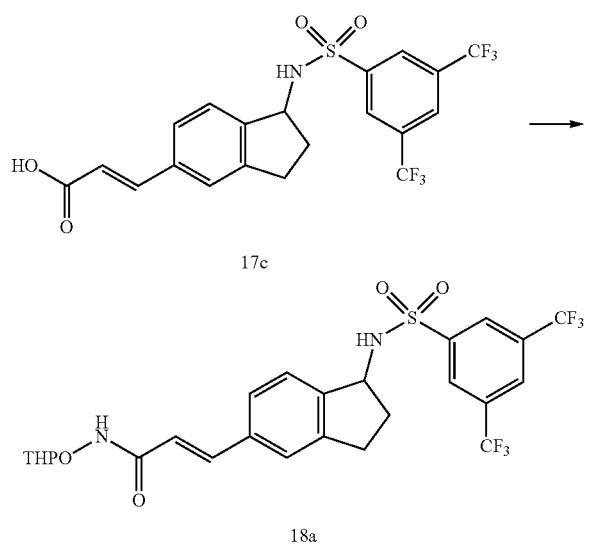

To a stirred solution of O-(Tetrahydro-2H-pyran-2-yl) hydroxylamine (33.1 mg, 0.28 mmol) and DMAP (43.1 mg, 0.35 mmol) in DCM (5 mL) was added Compound 17c (bis(trifluoromethyl)phenyesulfonamido)-2,3-dihydro-1H-inden-5-yl)acrylic acid) (112.5 mg, 0.24 mmol) in one To a solution of Compound 18a ((E)-3-(1-((3,5-bis(trifluoromethyl)phenyesulfonamido)-2,3-dihydro-1H-inden-5-yl)-N-((tetrahydro-2H-pyran-2-yl)oxy)acrylamide) (110.0 mg, 0.19 mmol) in MeOH (5 mL) was added 1N HCl$_{(aq.)}$ (1.5 mL) at 0° C. The mixture was stirred at RT for 3 hours.

The mixture was concentrated in vacuo and the resulting white solids were filtered, rinsed with H$_2$O and air dried to provide the product Compound 18 ((E)-3-(1-((3,5-bis(trifluoromethyl)phenyesulfonamido)-2,3-dihydro-1H-inden-5-yl)-N-hydroxy acrylamide) (53.4 mg, yield 57%).

Compound 18, $^1$H-NMR (500 MHz, CD$_3$OD): δ 8.44 (s, 2H), 8.29 (s, 1H), 7.54-7.51 (d, 1H), 7.40 (s, 1H), 7.34-7.32 (d, 1H), 7.12-7.11 (d, 1H), 6.44-6.40 (d, 1H), 4.93-4.85 (t, 1H), 2.97-2.93 (m, 1H), 2.82-2.77 (m, 1H), 2.27-2.17 (m, 1H), 1.79-1.74 (m, 1H). ESI-MS m/z calcd for C$_{20}$H$_{16}$F$_6$N$_2$O$_4$S 494.07, found 495.2 [M+H]$^+$.

Synthesis of Compounds 19~20

Scheme 11

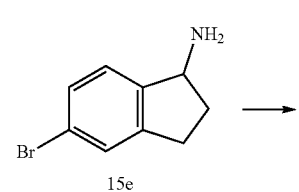

-continued

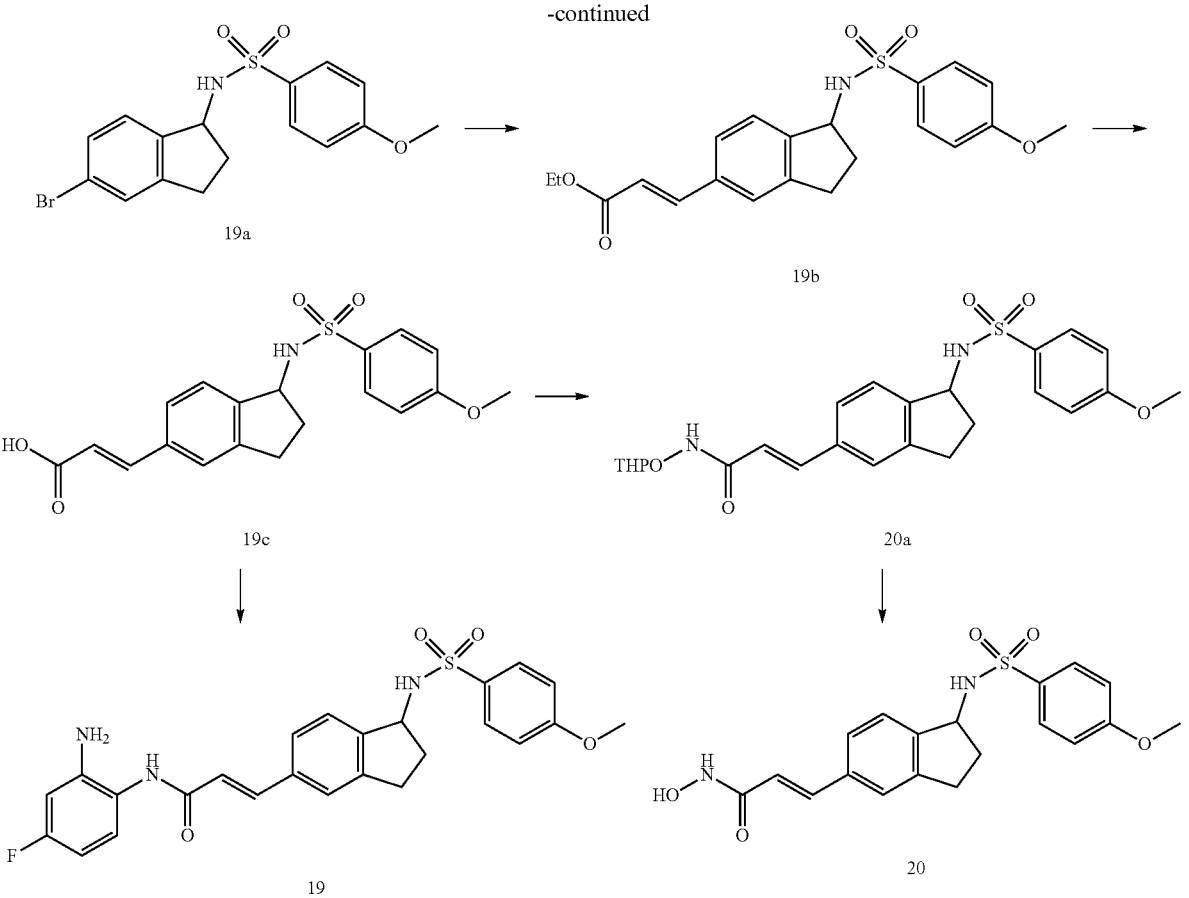

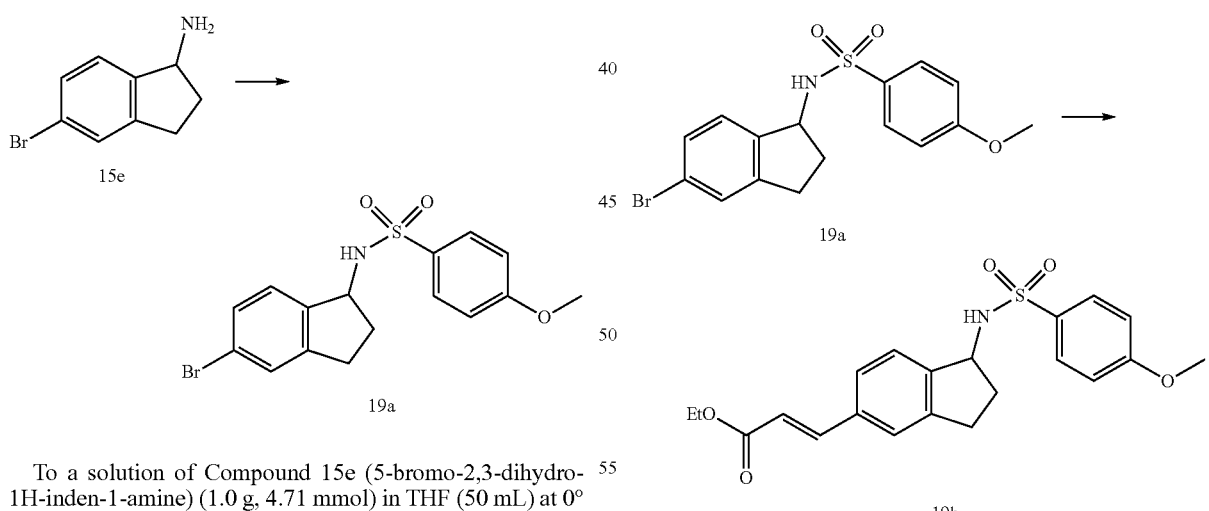

To a solution of Compound 15e (5-bromo-2,3-dihydro-1H-inden-1-amine) (1.0 g, 4.71 mmol) in THF (50 mL) at 0° C. was added TEA (1.3 mL, 9.44 mmol) followed by 3,5-4-Methoxybenzenesulfonyl chloride (0.97 g, 4.71 mmol). The reaction mixture was stirred at 0° C. for 30 mins, then was allowed to warm to RT over 12 hours.

The mixture was quenched with $H_2O$ and extracted with EtOAc. The combined organics were washed with $NH_4Cl_{(aq)}$, brine, dried over $MgSO_4$, and concentrated. The resulting material was purified by silica gel column chromatography (EtOAc./Hexane=1:4) to provide the product Compound 19a (N-(5-bromo-2,3-dihydro-1H-inden-1-yl)-4-methoxybenzenesulfonamide) (1.0 g, yield 56%).

A solution of Compound 19a (N-(5-bromo-2,3-dihydro-1H-inden-1-yl)-4-methoxybenzenesulfonamide) (0.6 g, 1.57 mmol), ethyl acrylate (0.34 mL, 3.15 mmol), triphenylphosphine (164.7 mg, 0.63 mmol) in TEA (0.22 mL, 1.57 mmol) and DMF (20 mL) was degassed by bubbling argon for 3 mins. $Pd(OAc)_2$ (35.2 mg, 0.157 mmol) was added, and vacuum/argon was applied three times. The reaction mixture was stirred under argon at 100° C. for 24 hours.

The mixture was extracted with EtOAc and NH₄Cl (aq.). The organic layers were dried over MgSO₄ and concentrated in vacuo and purified by flash chromatography (EtOAc./Hexane=1:4) to provide yellow solid product Compound 19b (ethyl (E)-3-(1-((4-methoxyphenyl)sulfonamido)-2,3-dihydro-1H-inden-5-yl)acrylate) (280.0 mg, yield 45%).

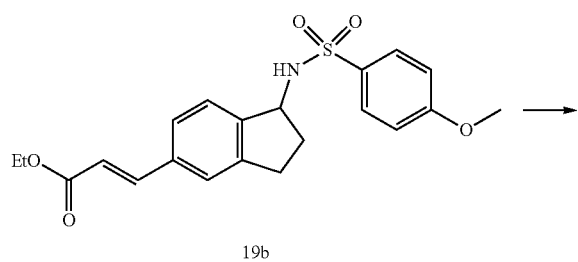

19b

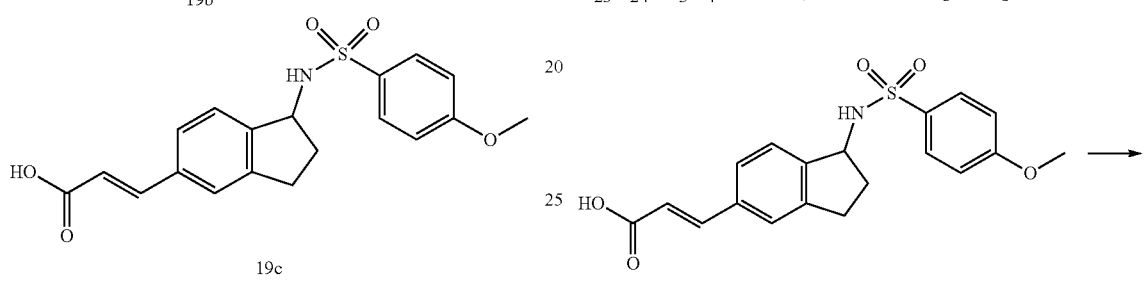

19c

To a solution of Compound 19b (ethyl (E)-3-(1-((4-methoxyphenyl)sulfonamido)-2,3-dihydro-1H-inden-5-yl)acrylate) (280.0 mg, 0.7 mmol) in MeOH (14 mL) was added 2N NaOH solution (1.0 mL) at RT and the mixture was stirred at 60° C. for 2 hours.

After Compound 19b was full conversion, the mixture was concentrated to remove the organic solvent. The residue was diluted with water and acidified to pH=4 with 2N HCl$_{(aq)}$. The resulting precipitate was filtered, washed with H₂O and ether, then dried in vacuo to provide product as a solid product Compound 19c ((E)-3-(1-((4-methoxyphenyl)sulfonamido)-2,3-dihydro-1H-inden-5-yl)acrylic acid) (230.0 mg, yield 62%).

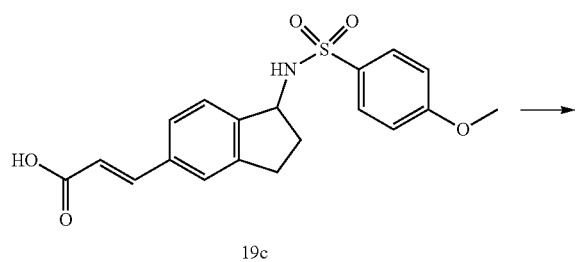

19c

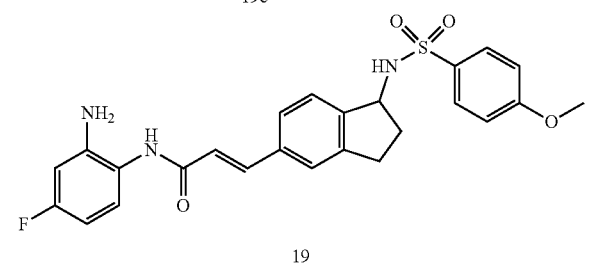

19

To a stirred solution of 4-fluoro-1,2-phenylenediamine (40.4 mg, 0.32 mmol) and DMAP (50.1 mg, 0.41 mmol) in DCM (6 mL) was added Compound 19c ((E)-3-(1-((4-methoxyphenyl)sulfonamido)-2,3-dihydro-1H-inden-5-yl)acrylic acid) (100.0 mg, 0.27 mmol) in one portion, followed by the addition of EDCI (61.3 mg, 0.32 mmol) in one portion at RT. The resulting mixture was stirred at RT for overnight.

After washing with brine, the organic layer was dried over MgSO₄ and concentrated in vacuo to give the crude material. The resulting residue was washed with ether to provide the product Compound 19 ((E)-N-(2-amino-4-fluorophenyl)-3-(1-((4-methoxyphenyl)sulfonamido)-2,3-dihydro-1H-inden-5-yl)acrylamide) (75.2 mg, yield 58%).

Compound 19, ¹H-NMR (500 MHz, CD₃OD): δ 7.88-7.86 (d, 2H), 7.63-7.60 (d, 1H), 7.43 (s, 1H), 7.41-7.39 (d, 1H), 7.16-7.14 (d, 2H), 7.11-7.10 (d, 2H), 6.79-6.76 (d, 1H), 6.57-6.55 (d, 1H), 6.40 (s, 1H), 4.85-4.74 (t, 1H), 3.90 (s, 3H), 2.89-2.88 (m, 1H), 2.75-2.74 (m, 1H), 2.20-2.18 (m, 1H), 1.72-1.71 (m, 1H). ESI-MS m/z calcd for C₂₅H₂₄FN₃O₄S 481.15, found 482.2 [M+H]⁺.

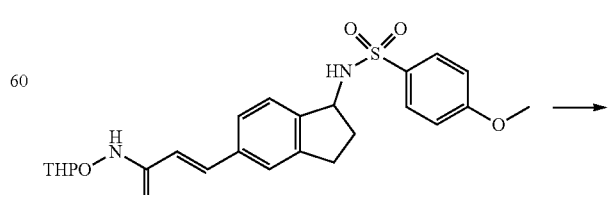

20a

To a stirred solution of O-(Tetrahydro-2H-pyran-2-yl)hydroxylamine (37.5 mg, 0.32 mmol) and DMAP (50.1 mg, 0.41 mol) in DCM (6 mL) was added Compound 19c ((E)-3-(1-((4-methoxyphenyl)sulfonamido)-2,3-dihydro-1H-inden-5-yl)acrylic acid) (100.0 mg, 0.27 mmol) in one portion, followed by the addition of EDCI (61.3 mg, 0.32 mmol) in one portion at RT. The resulting mixture was stirred at RT for overnight.

After which time it was washed successively with NaHCO₃(aq.) and brine. The organic layer was dried over MgSO₄ and concentrated in vacuo to give the crude material. The resulting residue was purified by silica gel column chromatography (EA:Hex.=1:1) to provide the product Compound 20a ((E)-3-(1-((4-methoxyphenyl)sulfonamido)-2,3-dihydro-1H-inden-5-yl)-N-((tetrahydro-2H-pyran-2-yl)oxy)acrylamide) (47.0 mg, yield 37%).

20a

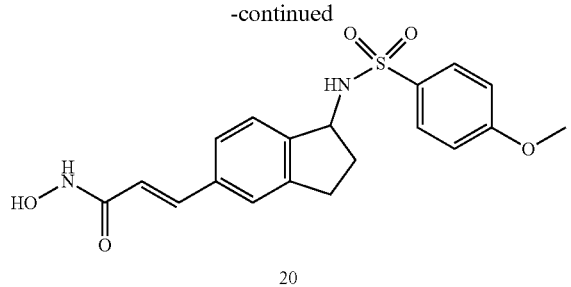

To a solution of Compound 20a ((E)-3-(1-((4-methoxy-phenyl)sulfonamido)-2,3-dihydro-1H-inden-5-yl)-N-((tetra-hydro-2H-pyran-2-yl)oxy)acrylamide) (47.0 mg, 0.1 mmol) in MeOH (5 mL) was added 1N HCl$_{(aq.)}$ (0.3 mL) at 0° C. The mixture was stirred at RT for 2 hours.

The mixture was concentrated in vacuo and the resulting white solids were filtered, rinsed with H$_2$O and dried in vacuo to provide the product Compound 20 ((E)-N-hydroxy-3-(1-((4-methoxyphenyl)sulfonamido)-2,3-dihydro-1H-inden-5-yl)acrylamide) (3.0 mg, yield 8%).

Compound 20, $^1$H-NMR (500 MHz, CD$_3$OD): δ 7.88-7.86 (d, 2H), 7.55-7.51 (d, 1H), 7.37 (s, 1H), 7.35-7.33 (d, 1H), 7.13-7.09 (m, 3H), 6.43-6.40 (d, 1H), 4.76-4.73 (t, 3H), 3.90 (d, 3H), 2.92-2.87 (m, 1H), 2.75-2.69 (m, 1H), 2.22-2.16 (m, 1H), 1.74-1.69 (m, 1H). ESI-MS m/z calcd for C$_{19}$H$_{20}$N$_2$O$_5$S 388.11, found 389.2 [M+H]$^+$.

Synthesis of Compounds 21~22

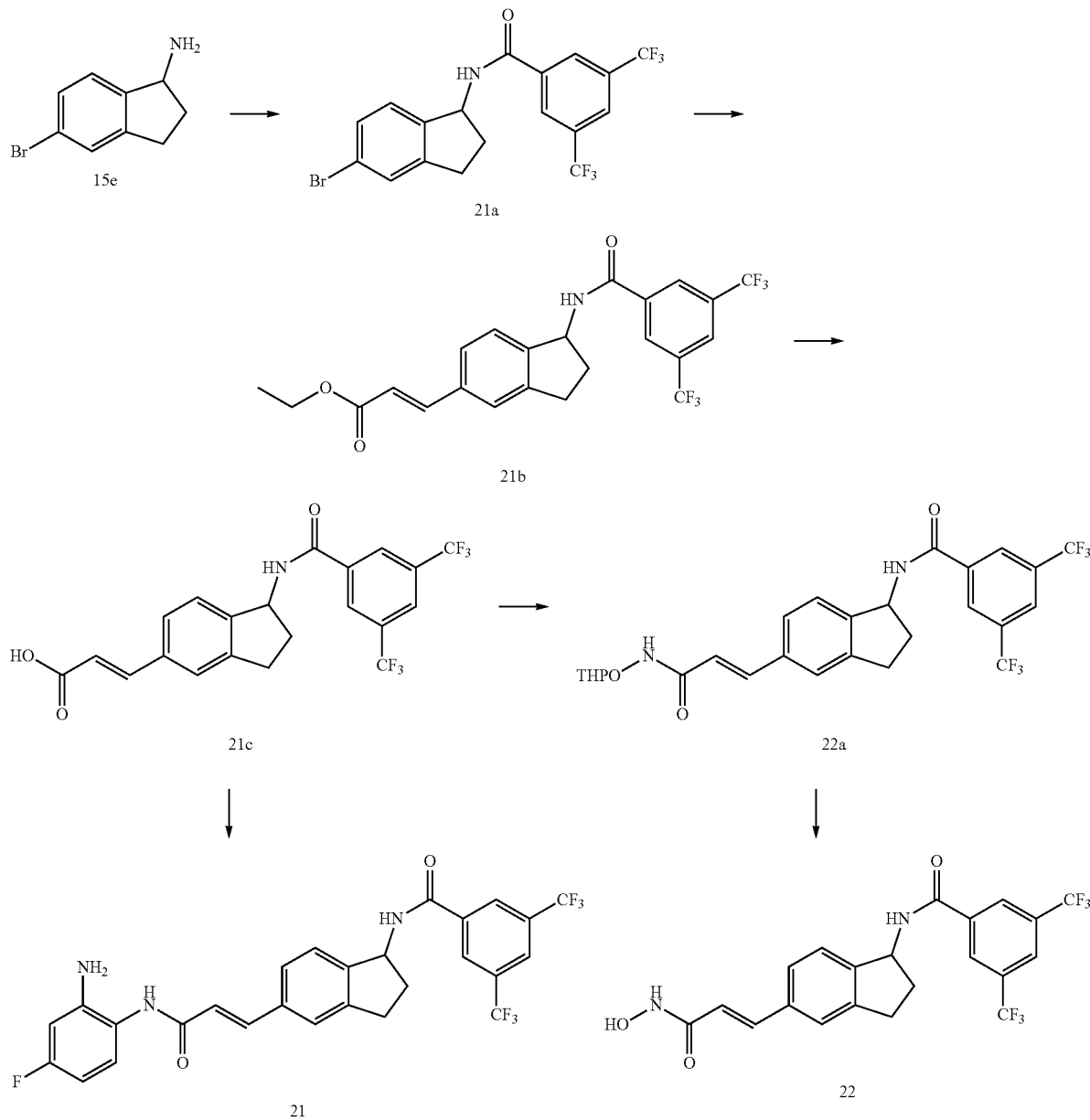

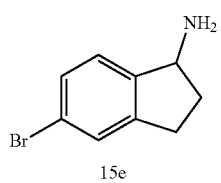

15e

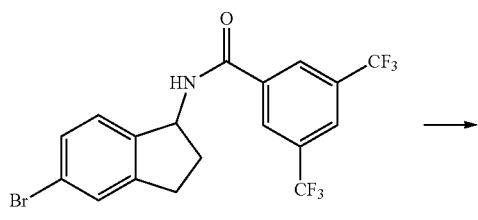

21a

To a solution of Compound 15e (5-bromo-2,3-dihydro-1H-inden-1-amine) (0.30 g, 1.41 mmol) in DCM (20 mL) was added DIPEA (0.27 g, 2.12 mmol) and 3,5-Bis(trifluoromethyl)benzoyl chloride (0.43 g, 1.56 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl and Sat. NaHCO$_3$. The organic phase was dried with MgSO$_4$ and concentrated under reduced pressure. The crude product was purified by silica gel column chromatography using ethyl acetate/hexane=1/5 as elution to afford Compound 21a (N-(5-bromo-2,3-dihydro-1H-inden-1-yl)-3,5-bis(trifluoromethyl)benzamide) (0.32 g, 0.72 mmol, yield 51%).

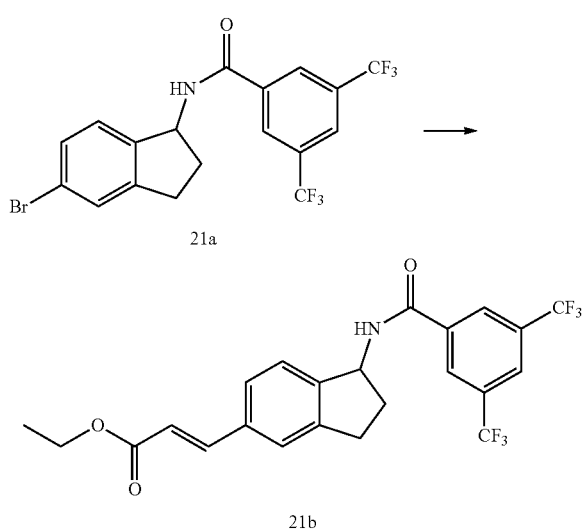

21a

21b

To a solution of Compound 21a (N-(5-bromo-2,3-dihydro-1H-inden-1-yl)-3,5-bis(trifluoromethyl)benzamide) (0.32 g, 0.72 mmol), triphenylphosphine (0.08 g, 0.29 mmol), ethyl acrylate (0.09 g, 0.93 mmol) in DMF/TEA (20 mL, 1:1) was added Pd(OAc)$_2$ (0.01 g, 0.03 mmol). After addition, the reaction mixture was heated to 100° C. and stirred for overnight.

The reaction was monitored by TLC. After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/4 as elution to yield the desired product Compound 21b (ethyl (E)-3-(1-(3,5-bis(trifluoromethyl)benzamido)-2,3-dihydro-1H-inden-5-yl)acrylate) (0.24 g, 0.50 mmol, yield 70%).

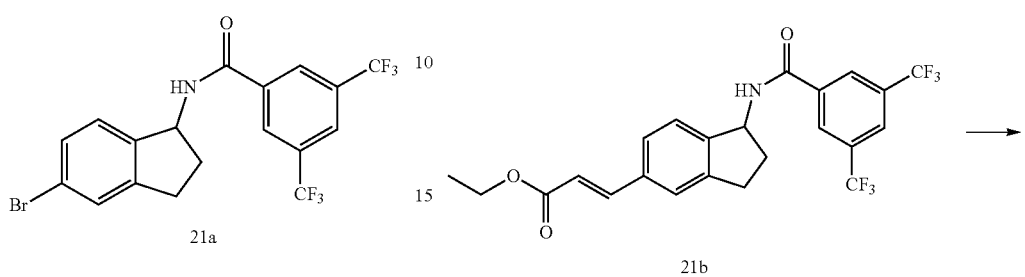

21b

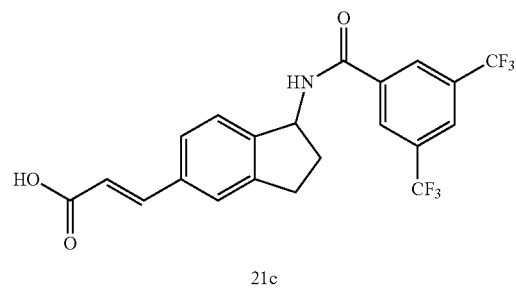

21c

To a solution of Compound 21b (ethyl (E)-3-(1-(3,5-bis(trifluoromethyl)benzamido)-2,3-dihydro-1H-inden-5-yl)acrylate) (0.24 g, 0.50 mmol) in MeOH (50 mL) was added 2N NaOH$_{(aq)}$ (0.50 mL, 1.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 21c ((E)-3-(1-(3,5-bis(trifluoromethyl)benzamido)-2,3-dihydro-1H-inden-5-yl)acrylic acid) (0.18 g, 0.41 mmol, yield 82%).

21c

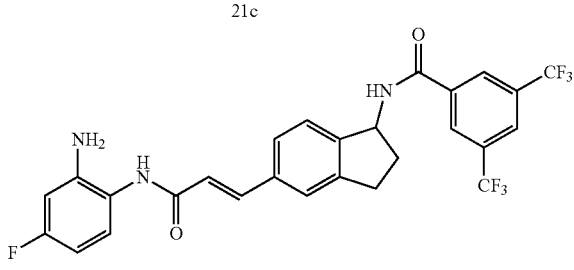

21

To a solution of Compound 21c ((E)-3-(1-(3,5-bis(trifluoromethyl)benzamido)-2,3-dihydro-1H-inden-5-yl)acrylic acid) (0.16 g, 0.35 mmol), 4-fluoro-1,2-phenylenediamine (0.05 g, 0.42 mmol) and DMAP (0.04 g, 0.35 mmol) in THF (50 mL) was added NMM (0.04 g, 0.35 mmol) and EDCI (0.10 g, 0.53 mmol) at 0° C. After addition, the reaction mixture was warmed to room temperature and stirred for overnight.

After reaction was completed, the reaction mixture was diluted with EtOAc and washed with Sat. NH₄Cl. The combined organic layers were washed with brine and dried over MgSO₄ and concentrated in vacuo. The crude product was purified via flash column chromatography on a silica gel column using 1:1 EtOAc-Hexane as the eluent to give Compound 21 ((E)-N-(5-(3-((2-amino-4-fluorophenyl)amino)-3-oxoprop-1-en-1-yl)-2,3-dihydro-1H-inden-1-yl)-3,5-bis(trifluoromethyl)benzamide) (0.18 g, 0.33 mmol, yield 93%).

Compound 21, ¹H-NMR (500 MHz, d₆-DMSO): δ 9.33-9.30 (m, 2H), 8.59 (s, 2H), 8.33 (s, 1H), 7.56-7.54 (m, 2H), 7.49-7.47 (d, 1H), 7.37-7.35 (d, 1H), 7.29-7.26 (t, 1H), 6.87-6.84 (d, 1H), 6.53-6.51 (d, 1H), 6.37-6.33 (t, 1H), 5.63-5.60 (q, 1H), 5.25 (s, 2H), 3.12-3.04 (m, 1H), 2.96-2.91 (m, 1H), 2.56-2.50 (m, 1H), 2.07-2.02 (m, 1H). ESI-MS m/z calcd for C₂₇H₂₀F₇N₃O₂ 551.14, found 552 [M+H]⁺.

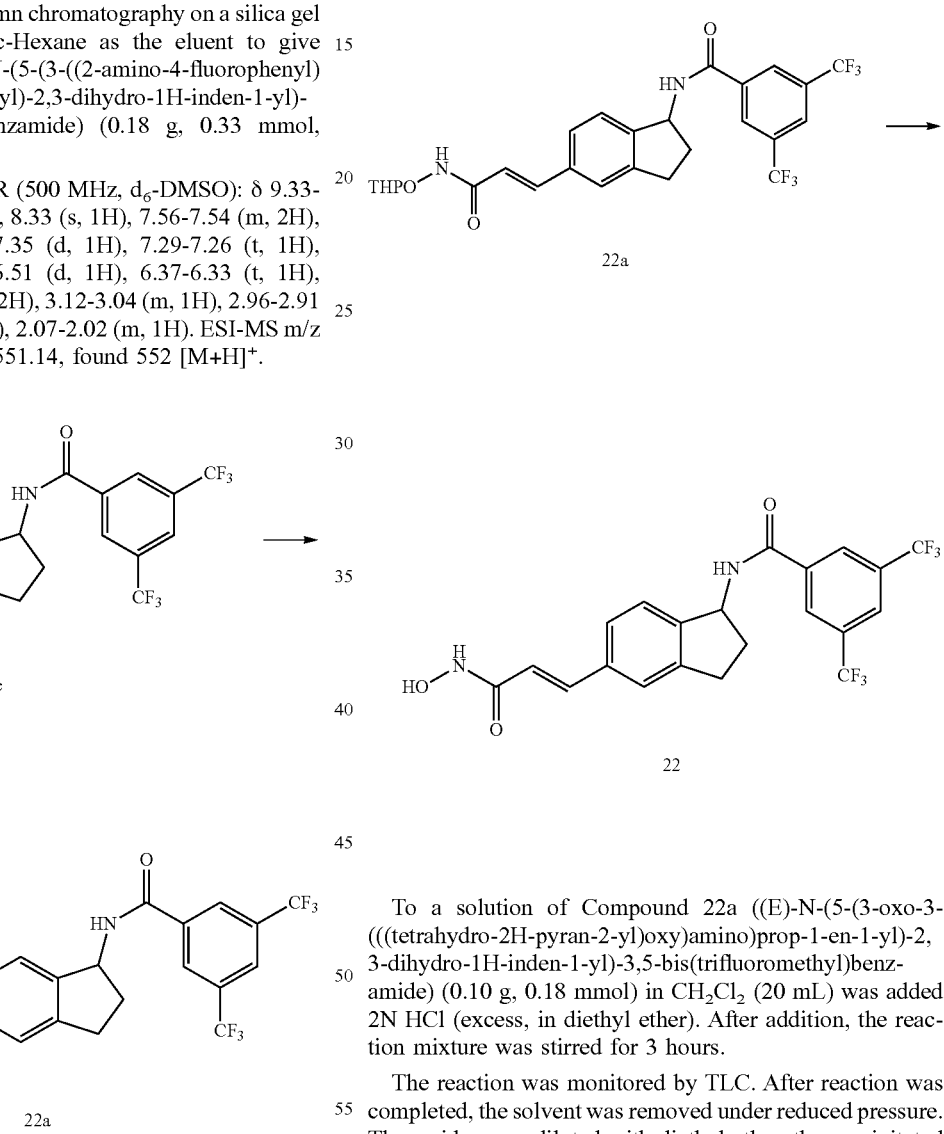

To a solution of Compound 21c ((E)-3-(1-(3,5-bis(trifluoromethyl)benzamido)-2,3-dihydro-1H-inden-5-yl)acrylic acid) (0.10 g, 0.23 mmol), O-(Tetrahydro-2H-pyran-2-yl)hydroxylamine (0.04 g, 0.34 mmol) and DMAP (0.01 g, 0.11 mmol) in DCM (20 mL) was added NMM (0.05 g, 0.46 mmol) and EDCI (0.07 g, 0.34 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl. The combined organic layers were washed with brine and dried over MgSO₄ and concentrated in vacuo. The crude product was purified by silica gel column chromatography using ethyl acetate/hexane=2/1 as elution to yield the desired product Compound 22a ((E)-N-(5-(3-oxo-3-(((tetrahydro-2H-pyran-2-yl)oxy)amino)prop-1-en-1-yl)-2,3-dihydro-1H-inden-1-yl)-3,5-bis(trifluoromethyl)benzamide) (0.10 g, 0.18 mmol, yield 77%).

To a solution of Compound 22a ((E)-N-(5-(3-oxo-3-(((tetrahydro-2H-pyran-2-yl)oxy)amino)prop-1-en-1-yl)-2,3-dihydro-1H-inden-1-yl)-3,5-bis(trifluoromethyl)benzamide) (0.10 g, 0.18 mmol) in CH₂Cl₂ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 22 ((E)-N-(5-(3-(hydroxyamino)-3-oxoprop-1-en-1-yl)-2,3-dihydro-1H-inden-1-yl)-3,5-bis(trifluoro methyl)benzamide) (0.06 g, 0.13 mmol, yield 72%).

Compound 22, ¹H-NMR (500 MHz, CD₃OD): δ 8.49 (s, 2H), 8.16 (s, 1H), 7.60-7.56 (d, 1H), 7.49 (s, 1H), 7.44-7.42 (d, 1H), 7.37-7.35 (d, 1H), 6.47-6.44 (d, 1H), 5.69-5.66 (t, 1H), 3.13-3.09 (m, 1H), 2.99-2.94 (m, 1H), 2.66-2.62 (m, 1H), 2.11-2.07 (m, 1H). ESI-MS m/z calcd for C₂₁H₁₆F₆N₂O₃ 458.11, found 459 [M+H]⁺.

Synthesis of Compounds 23~24
Scheme 13
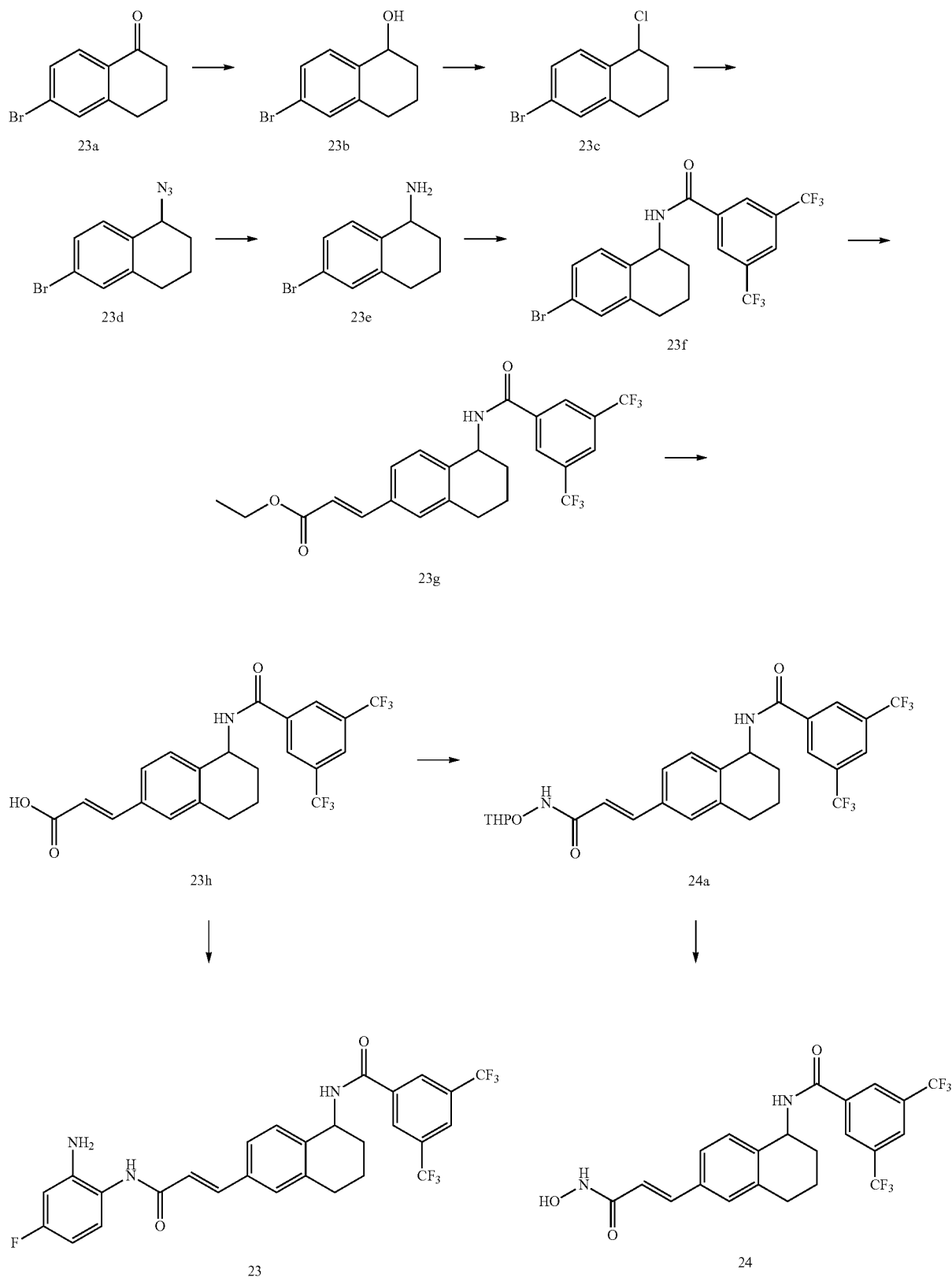

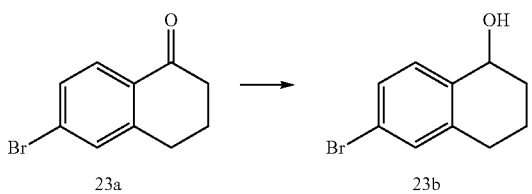 [SMILES: O=C1CCCc2cc(Br)ccc21 ; OC1CCCc2cc(Br)ccc21]

To a solution of Compound 23a (6-bromo-3,4-dihydronaphthalen-1(2H)-one) (1.0 g, 4.44 mmol) in the co-solvent of THF:H$_2$O=4:1 (22 mL) was added NaBH$_4$ (0.34 g, 8.9 mmol) at RT and stirred for 2 hours.

The mixture was extracted with DCM and NH$_4$Cl (aq.). The organic layer was dried over MgSO$_4$ and concentrated to provide the product Compound 23b (6-bromo-1,2,3,4-tetrahydronaphthalen-1-ol) (950.0 mg, yield 95%) without further purification to go on next step.

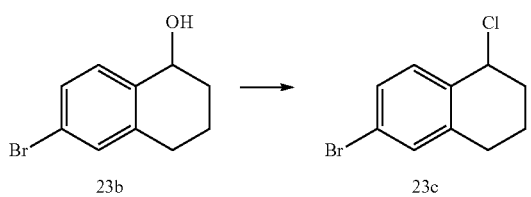 [SMILES: OC1CCCc2cc(Br)ccc21 ; ClC1CCCc2cc(Br)ccc21]

To the solution of Compound 23b (6-bromo-1,2,3,4-tetrahydronaphthalen-1-ol) (1.0 g, 4.44 mmol) in the solvent of DCM (22.0 mL) was added SOCl$_2$ (0.6 mL, 8.88 mmol) at RT and stirred for 3 hours.

The mixture was concentrated to provide the product Compound 23c (6-bromo-1-chloro-1,2,3,4-tetrahydronaphthalene) (1.0 g, yield 94%) without further purification to go on the next step.

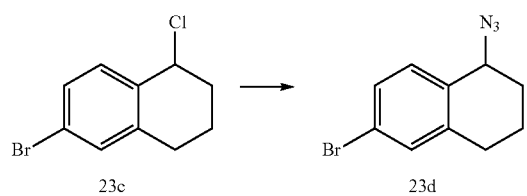 [SMILES: ClC1CCCc2cc(Br)ccc21 ; [N-]=[N+]=NC1CCCc2cc(Br)ccc21]

To a solution of Compound 23c (6-bromo-1-chloro-1,2,3,4-tetrahydronaphthalene) (1.0 g, 4.17 mmol) in the solvent of DMF (14.0 mL) was added NaN$_3$ (578.0 mg, 8.88 mmol) at RT and stirred for overnight.

The mixture was concentrated to provide the product Compound 23d (6-bromo-1-chloro-1,2,3,4-tetrahydronaphthalene) (1.0 g, yield 96%) without further purification to go on next step.

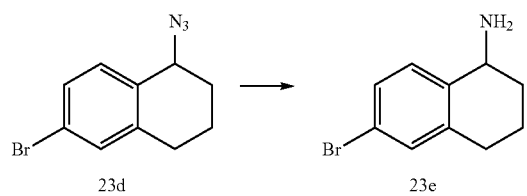 [SMILES: [N-]=[N+]=NC1CCCc2cc(Br)ccc21 ; NC1CCCc2cc(Br)ccc21]

A mixture of Compound 23d (6-bromo-1-chloro-1,2,3,4-tetrahydronaphthalene) (0.3 g, 1.2 mmol) and 10% Pd/C (28.0 mg) in MeOH (7.0 mL) was stirred under an atmosphere of H$_2$ (1 atm) at RT for 2 hours.

The mixture was filtered through celite and the filtrate was concentrated. The residue was purified by silica gel flash chromatography to provide the product Compound 23e (6-bromo-1,2,3,4-tetrahydronaphthalen-1-amine) (200.1 mg, yield 74%) without further purification to go on next step.

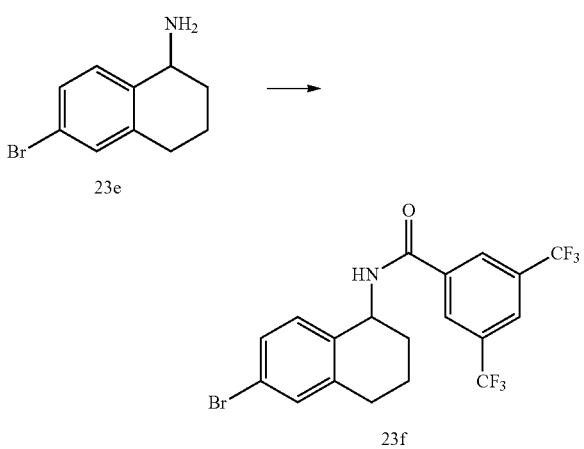

To a solution of Compound 23e (6-bromo-1,2,3,4-tetrahydronaphthalen-1-amine) (265 mg, 1.0 eq) in THF (10 mL) was added Et$_3$N (111 mg, 1.1 eq) at 0° C., followed 3,5-bis(trifluoromethyl)benzoyl chloride (303 mg, 1.1 eq). The mixture was stirred at 0° C. for 1 hour.

Extraction with EtOAc, then take the organic layer washed with brine. The combined organic layer was dried over anhydrous MgSO$_4$. After removing the solvent, the crude product was purified by column chromatography to afford the product Compound 23f (N-(6-bromo-1,2,3,4-tetrahydronaphthalen-1-yl)-3,5-bis(trifluoromethyl)benzamide) (300 mg, yield 55%).

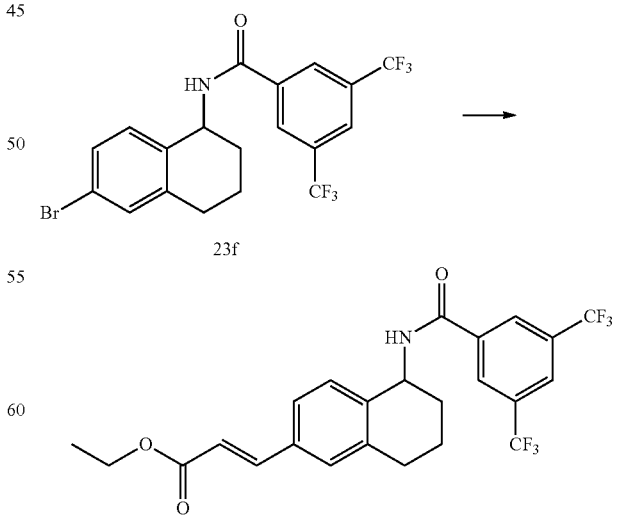

To a solution of Compound 23f (N-(6-bromo-1,2,3,4-tetrahydronaphthalen-1-yl)-3,5-bis(trifluoromethyl)benzamide) (300 mg, 1.0 eq) in DMF (6.4 mL) was added ethyl acrylate (84 mg, 1.3 eq) at rt, followed Et$_3$N (1.2 mL), PPh$_3$ (63 mg, 0.4 eq). The mixture was stirred at rt for 5 min then degas with nitrogen, followed added Pd(OAc)$_2$ (8 mg, 0.05 eq). The reaction was stirred at 100° C. for overnight.

After cooling to RT, quench with NH$_4$Cl and extracted with EtOAc, then take the organic layer washed with brine. The combined organic layer was dried over anhydrous MgSO$_4$. After removing the solvent in vacuo and purified with column chromatography to afford the product Compound 23g (ethyl (E)-3-(5-(3,5-bis(trifluoromethyl)benzamido)-5,6,7,8-tetrahydronaphthalen-2-yl)acrylate) (180 mg, yield 58%).

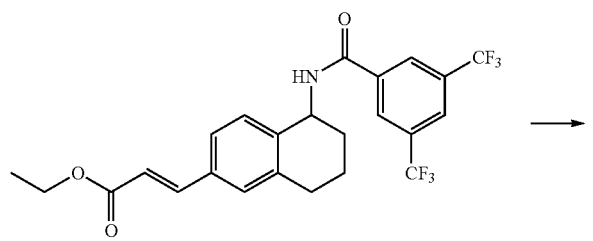

23g

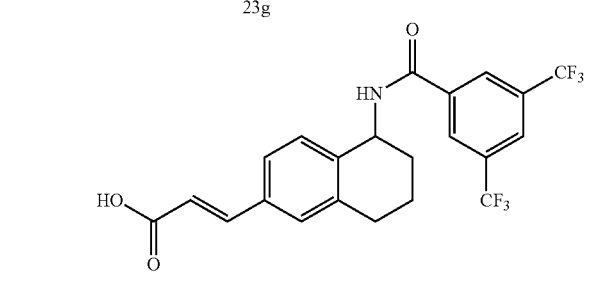

23h

To a solution of Compound 23g (ethyl (E)-3-(5-(3,5-bis(trifluoromethyl)benzamido)-5,6,7,8-tetrahydronaphthalen-2-yl)acrylate) (180 mg, 1 eq) in MeOH (3.7 mL) was added NaOH aqueous solution (1.0 M, 1.7 mL) at RT.

The mixture was stirred at RT for overnight, then removed the solvent in vacuo followed quench with HCl aqueous solution (1.0 M) to pH=3. The mixture was extracted with EtOAc, then take the organic layer washed with brine. The combined organic layer was dried over anhydrous MgSO$_4$. Remove the solvent to afford Compound 23h ((E)-3-(5-(3,5-bis(trifluoromethyl)benzamido)-5,6,7,8-tetrahydronaphthalen-2-yl)acrylic acid) (132 mg, yield 78%).

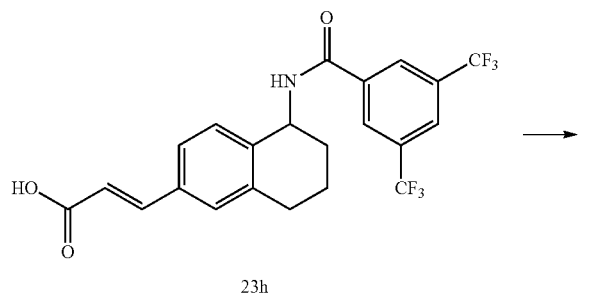

23h

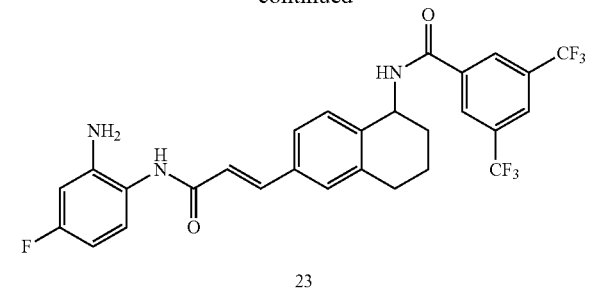

23

To a solution of Compound 23h ((E)-3-(5-(3,5-bis(trifluoromethyl)benzamido)-5,6,7,8-tetrahydronaphthalen-2-yl)acrylic acid) (200 mg, 1 eq) in THF (4.3 mL, 0.1 M) at 0° C. under nitrogen was added EDC hydrochloride (124 mg, 1.5 eq), followed NMM (65 mg, 1.5 eq), HOBT (26 mg, 0.4 eq) and 4-Fluoro-1,2-phenylenediamine (65 mg, 1.2 eq). The mixture was allowed to warm to RT and stirred for overnight.

After removing the solvent, the crude product was purified by column chromatography to afford Compound 23 ((E)-N-(6-(3 #2-amino-4-fluorophenyl)amino)-3-oxoprop-1-en-1-yl)-1,2,3,4-tetrahydronaphthalen-1-yl)-3,5-bis(trifluoromethyl)benzamide) (24 mg, 10%).

Compound 23, $^1$H-NMR (500 MHz, d$_6$-DMSO): δ 9.34-9.31 (m, 2H), 8.59 (s, 2H), 8.33 (s, 1H), 7.51-7.48 (d, 1H), 7.43-7.40 (m, 2H), 7.31-7.27 (m, 2H), 6.86-6.83 (d, 1H), 6.53-6.51 (d, 1H), 6.36-6.33 (t, 1H), 5.29-5.26 (m, 3H), 2.84-2.81 (m, 2H), 2.08-1.91 (m, 2H), 1.87-1.80 (m, 2H). ESI-MS m/z calcd for C$_{28}$H$_{22}$F$_7$N$_3$O$_2$ 565.16, found 566 [M+H]$^+$.

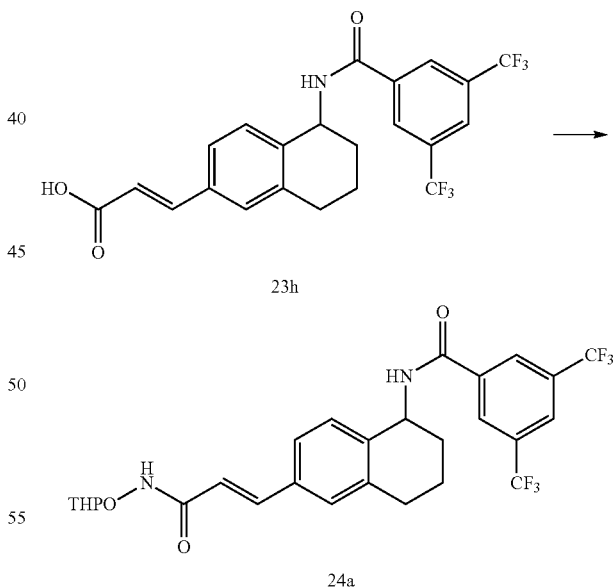

23h

24a

To a solution of Compound 23h ((E)-3-(5-(3,5-bis(trifluoromethyl)benzamido)-5,6,7,8-tetrahydronaphthalen-2-yl)acrylic acid) (30 mg, 1.0 eq) in THF (6.5 mL, 0.1 M) at 0° C. under nitrogen was added EDC hydrochloride (15 mg, 1.2 eq), followed NMM (8 mg, 1.2 eq), HOBT (4 mg, 0.4 eq) and O-(Tetrahydro-2H-pyran-2-yl)hydroxylamine (12 mg, 1.5 eq). The mixture was allowed to warm to RT and stirred for overnight.

After removing the solvent, the crude product was purified by column chromatography to afford Compound 24a ((E)-N-(6-(3-oxo-3-(((tetrahydro-2H-pyran-2-yl)oxy)amino)prop-1-en-1-yl)-1,2,3,4-tetrahydronaphthalen-1-yl)-3,5-bis(trifluoromethyl)benzamide) (19 mg, yield 52%).

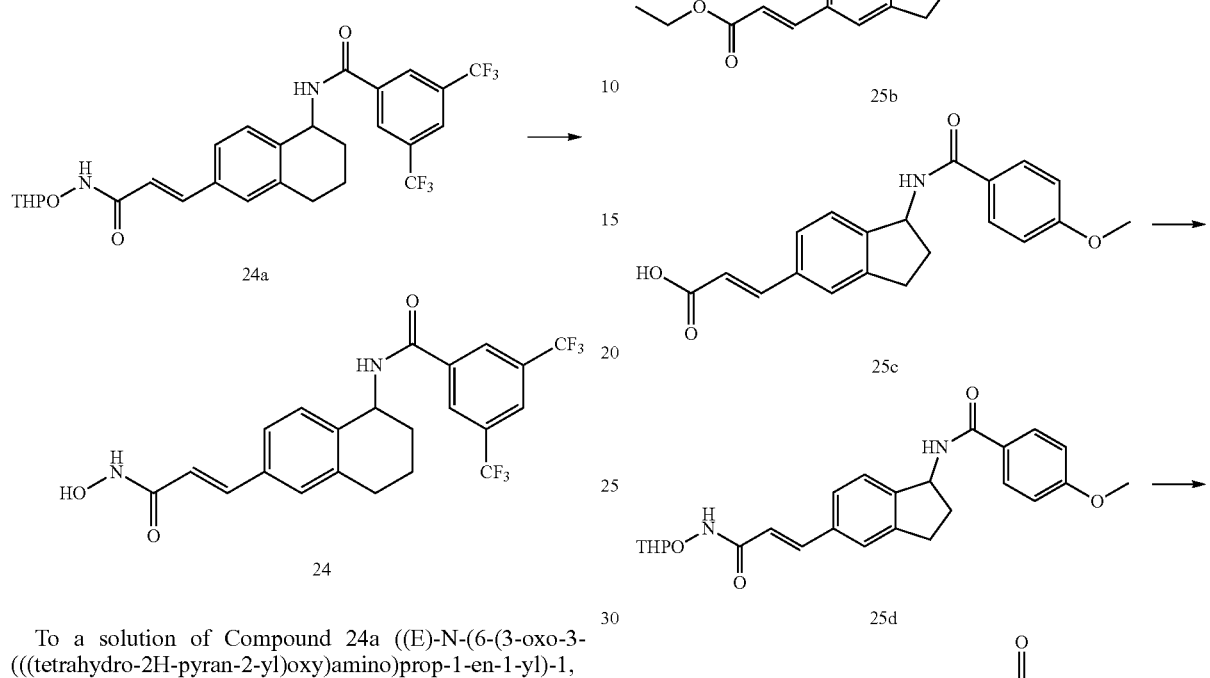

To a solution of Compound 24a ((E)-N-(6-(3-oxo-3-(((tetrahydro-2H-pyran-2-yl)oxy)amino)prop-1-en-1-yl)-1,2,3,4-tetrahydronaphthalen-1-yl)-3,5-bis(trifluoromethyl)benzamide) (100 mg, 1.0 eq) in MeOH (10 mL, 0.1 M) was added HCl aqueous solution (1.0 M, 1 mL).

The reaction was stirred at RT for 2 hours, then the solid was filtered out and washed with Et$_2$O to afford Compound 24 ((E)-N-(6-(3-(hydroxyamino)-3-oxoprop-1-en-1-yl)-1,2,3,4-tetrahydronaphthalen-1-yl)-3,5-bis(trifluoromethyl)benzamide) (43 mg, yield 51%).

Compound 24, $^1$H-NMR (500 MHz, d$_6$-DMSO): δ 9.31-9.29 (d, 1H), 9.02 (s, 1H,), 8.58 (s, 2H), 8.32 (s, 1H), 7.42-7.34 (m, 3H), 7.27-7.25 (d, 1H), 6.45-6.41 (d, 1H), 5.27-5.26 (m, 1H), 2.84-2.77 (m, 2H), 2.02-1.96 (m, 2H), 1.86-1.82 (m, 2H). ESI-MS m/z calcd for C$_{22}$H$_{18}$F$_6$N$_2$O$_3$ 472.12, found 473 [M+H]$^+$.

Synthesis of Compound 25

Scheme 14

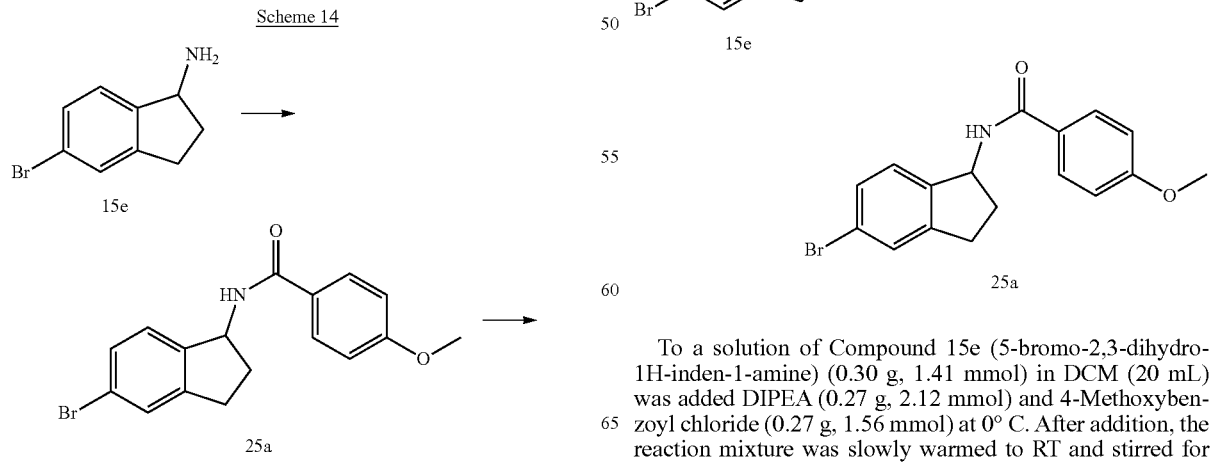

To a solution of Compound 15e (5-bromo-2,3-dihydro-1H-inden-1-amine) (0.30 g, 1.41 mmol) in DCM (20 mL) was added DIPEA (0.27 g, 2.12 mmol) and 4-Methoxybenzoyl chloride (0.27 g, 1.56 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl and Sat. NaHCO₃. The organic phase was dried with MgSO₄ and concentrated under reduced pressure. The crude product was purified by silica gel column chromatography using ethyl acetate/hexane=1/4 as elution to afford Compound 25a (N-(5-bromo-2,3-dihydro-1H-inden-1-yl)-4-methoxybenzamide) (0.26 g, 0.76 mmol, yield 54%).

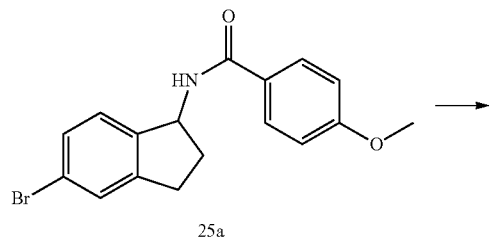

25a

To a solution of Compound 25a (N-(5-bromo-2,3-dihydro-1H-inden-1-yl)-4-methoxybenzamide) (0.26 g, 0.76 mmol), triphenylphosphine (0.08 g, 0.30 mmol), ethyl acrylate (0.10 g, 0.99 mmol) in DMF/TEA (20 mL, 1:1) was added Pd(OAc)₂ (0.01 g, 0.04 mmol). After addition, the reaction mixture was heated to 100° C. and stirred for overnight.

The reaction was monitored by TLC. After reaction was completed, the reaction mixture was diluted with sat. NH₄Cl₍aq₎ and extracted with EtOAc. The organic phase was dried with MgSO₄ and concentrated under reduced pressure. The crude product was purified by silica gel column chromatography using ethyl acetate/hexane=1/4 as elution to yield the desired product Compound 25b (ethyl (E)-3-(1-(4-methoxybenzamido)-2,3-dihydro-1H-inden-5-yl)acrylate) (0.15 g, 0.40 mmol, yield 53%).

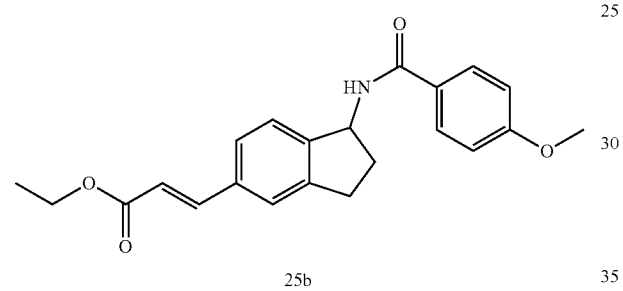

25b

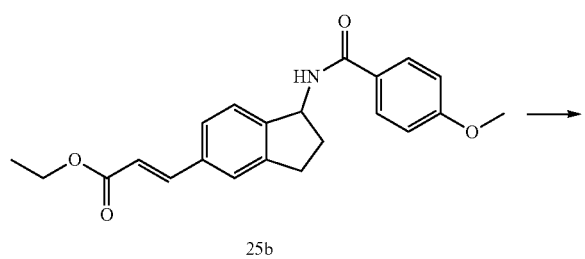

25b

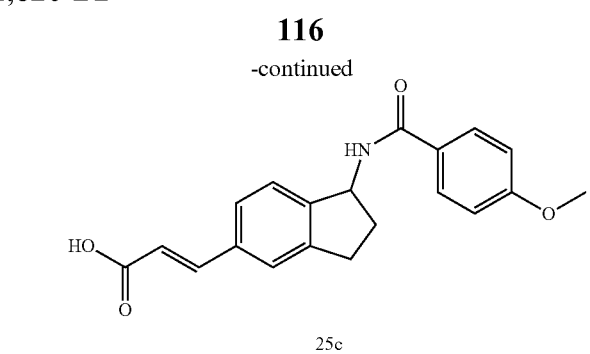

25c

To a solution of Compound 25b (ethyl (E)-3-(1-(4-methoxybenzamido)-2,3-dihydro-1H-inden-5-yl)acrylate) (0.15 g, 0.40 mmol) in MeOH (50 mL) was added 2N NaOH₍aq₎ (0.50 mL, 1.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 25c ((E)-3-(1-(4-methoxybenzamido)-2,3-dihydro-1H-inden-5-yl)acrylic acid) (0.12 g, 0.35 mmol, yield 86%).

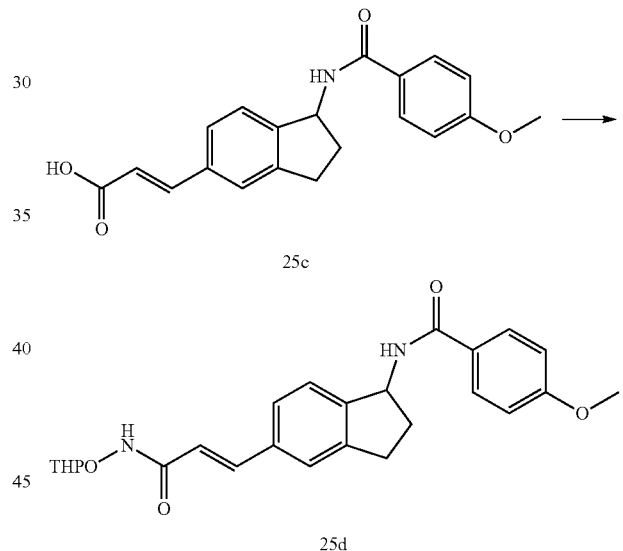

25c

25d

To a solution of Compound 25c ((E)-3-(1-(4-methoxybenzamido)-2,3-dihydro-1H-inden-5-yl)acrylic acid) (0.12 g, 0.35 mmol), O-(Tetrahydro-2H-pyran-2-yl)hydroxylamine (0.05 g, 0.41 mmol) and DMAP (0.02 g, 0.17 mmol) in DCM (20 mL) was added NMM (0.05 g, 0.52 mmol) and EDCI (0.10 g, 0.52 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl. The combined organic layers were washed with brine and dried over MgSO₄ and concentrated in vacuo. The crude product was purified by silica gel column chromatography using ethyl acetate/hexane=2/1 as elution to yield the desired product Compound 25d ((E)-4-methoxy-N-(5-(3-oxo-3-(((tetrahydro-2H-pyran-2-yl)oxy)amino)prop-1-en-1-yl)-2,3-dihydro-1H-inden-1-yl)benzamide) (0.13 g, 0.30 mmol, yield 86%).

117

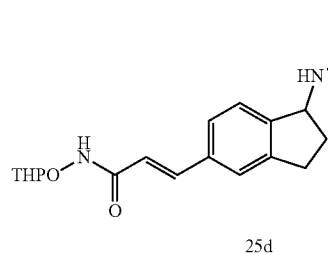

25d

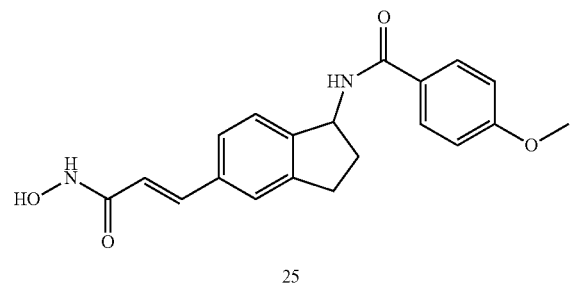

25

To a solution of Compound 25d ((E)-4-methoxy-N-(5-(3-oxo-3-(((tetrahydro-2H-pyran-2-yl)oxy)amino)prop-1-en-1-yl)-2,3-dihydro-1H-inden-1-yl)benzamide) (0.13 g, 0.30 mmol) in $CH_2Cl_2$ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 25 ((E)-N-(5-(3-(hydroxyamino)-3-oxoprop-1-en-1-yl)-2,3-dihydro-1H-inden-1-yl)-4-methoxybenz amide) (0.07 g, 0.21 mmol, yield 69%).

Compound 25, $^1$H-NMR (500 MHz, $CD_3OD$): δ 7.86-7.84 (d, 2H), 7.59-7.56 (d, 1H), 7.47 (s, 1H), 7.42-7.40 (d, 1H), 7.31-7.30 (d, 1H), 6.99-6.98 (d, 2H), 6.46-6.43 (d, 1H), 5.66-5.62 (t, 1H), 3.85 (s, 3H), 3.10-3.06 (m, 1H), 2.97-2.90 (m, 1H), 2.64-2.58 (m, 1H), 2.07-2.02 (m, 1H). ESI-MS m/z calcd for $C_{20}H_{20}N_2O_4$ 352.14, found 353 $[M+H]^+$.

Synthesis of Compound 26

Scheme 15

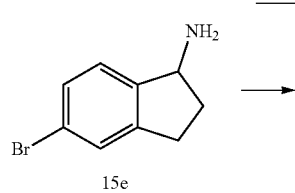

15e

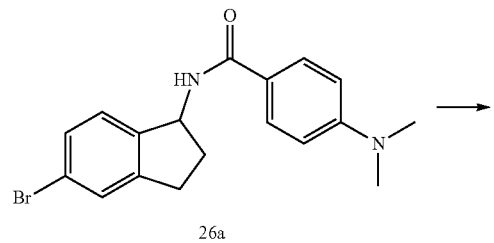

26a

118

-continued

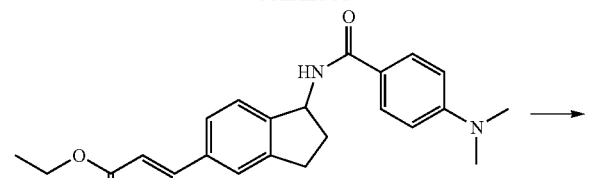

26b

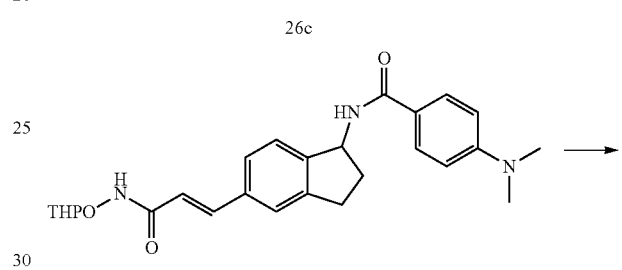

26c

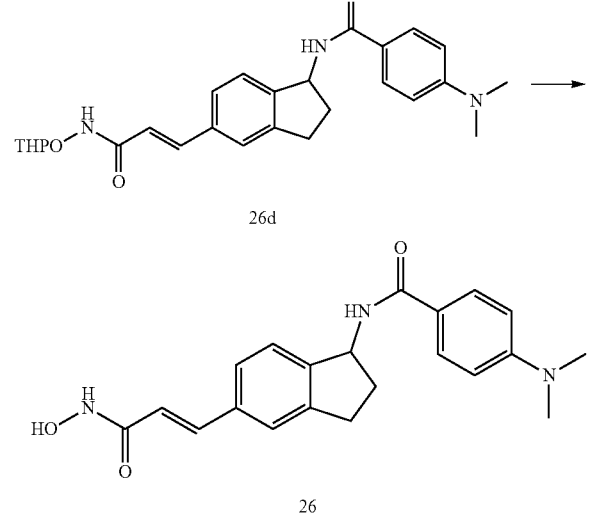

26d

26

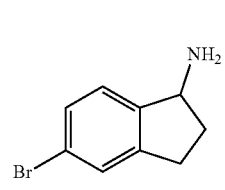

15e

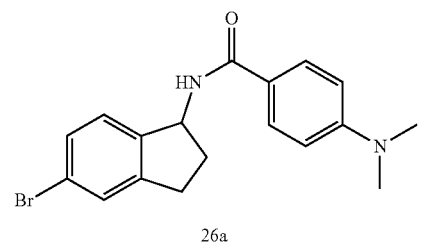

26a

To a solution of Compound 15e (5-bromo-2,3-dihydro-1H-inden-1-amine) (0.40 g, 1.89 mmol), 4-(Dimethylamino)benzoic acid (0.31 g, 1.89 mmol) and DMAP (0.12 g, 0.95 mmol) in DMF (30 mL) was added NMM (0.23 g, 2.26 mmol) and EDCI (0.43 g, 2.26 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl and Sat. NaHCO$_3$. The organic phase was dried with MgSO$_4$ and concentrated under reduced pressure. The crude product was purified by silica gel column chromatography using ethyl acetate/hexane=1/4 as elution to afford Compound 26a (N-(5-bromo-2,3-dihydro-1H-inden-1-yl)-4-(dimethylamino)benzamide) (0.50 g, 1.38 mmol, yield 73%).

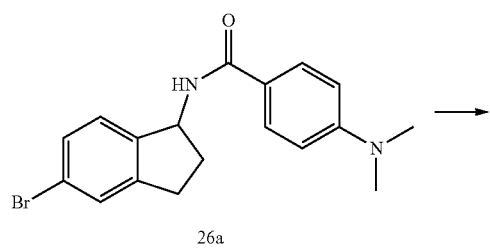

26a

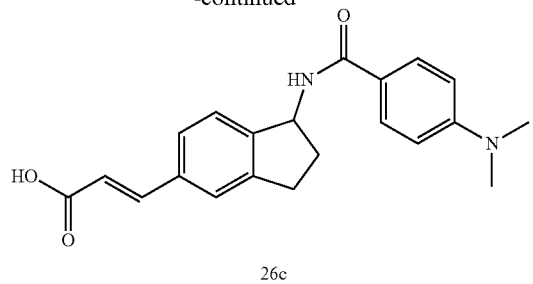

26c

To a solution of Compound 26b (ethyl (E)-3-(1-(4-(dimethylamino)benzamido)-2,3-dihydro-1H-inden-5-yl)acrylate) (0.12 g, 0.31 mmol) in MeOH (50 mL) was added 2N NaOH$_{(aq)}$ (0.50 mL, 1.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 26c ((E)-3-(1-(4-(dimethylamino)benzamido)-2,3-dihydro-1H-inden-5-yl)acrylic acid) (0.07 g, 0.20 mmol, yield 67%).

26b

To a solution of Compound 26a (N-(5-bromo-2,3-dihydro-1H-inden-1-yl)-4-(dimethylamino)benzamide) (0.50 g, 1.38 mmol), triphenylphosphine (0.14 g, 0.55 mmol), ethyl acrylate (0.18 g, 1.79 mmol) in DMF/TEA (20 mL, 1:1) was added Pd(OAc)$_2$ (0.02 g, 0.07 mmol). After addition, the reaction mixture was heated to 100° C. and stirred for overnight.

The reaction was monitored by TLC. After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/4 as elution to yield the desired product Compound 26b (ethyl (E)-3-(1-(4-(dimethylamino)benzamido)-2,3-dihydro-1H-inden-5-yl)acrylate) (0.12 g, 0.31 mmol, yield 22%).

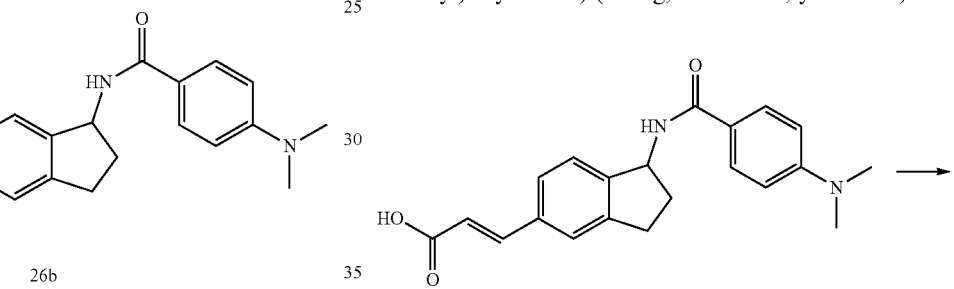

26c

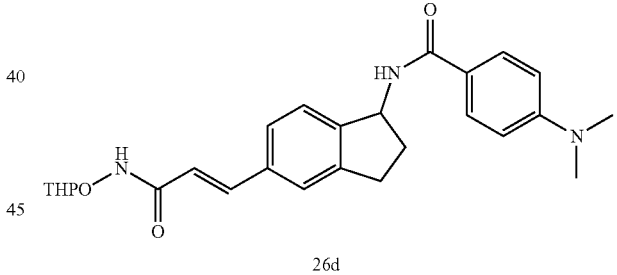

26d

To a solution of Compound 26c ((E)-3-(1-(4-(dimethylamino)benzamido)-2,3-dihydro-1H-inden-5-yl)acrylic acid) (0.07 g, 0.20 mmol), O-(Tetrahydro-2H-pyran-2-yl)hydroxylamine (0.04 g, 0.31 mmol) and DMAP (0.01 g, 0.10 mmol) in DCM (20 mL) was added NMM (0.03 g, 0.31 mmol) and EDCI (0.06 g, 0.31 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=2/1 as elution to yield the desired product Compound 26d ((E)-4-(dimethylamino)-N-(5-(3-oxo-3-(((tetrahydro-2H-pyran-2-yl)oxy)amino)prop-1-en-1-yl)-2,3-dihydro-1H-inden-1-yl)benzamide) (0.05 g, 0.11 mmol, yield 53%).

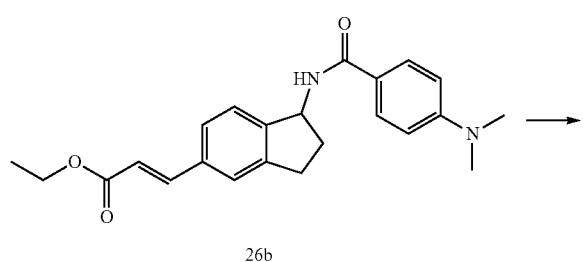

26b

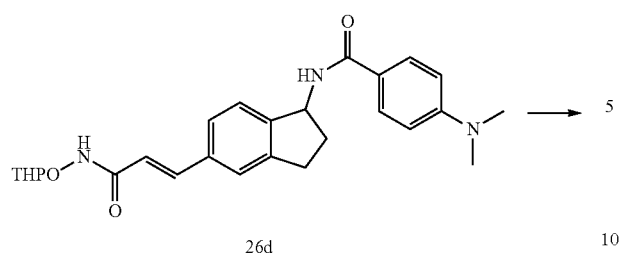

26d

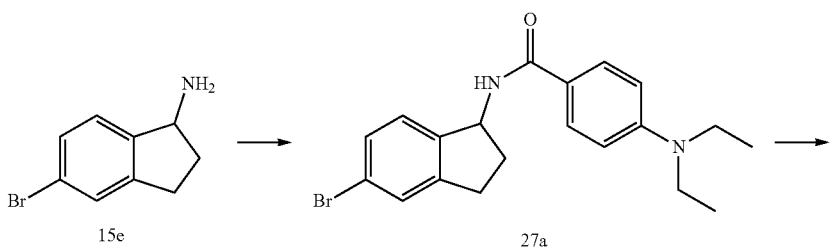

26

To a solution of Compound 26d ((E)-4-(dimethylamino)-N-(5-(3-oxo-3-(((tetrahydro-2H-pyran-2-yl)oxy)amino)prop-1-en-1-yl)-2,3-dihydro-1H-inden-1-yl)benzamide) (0.05 g, 0.11 mmol) in $CH_2Cl_2$ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 26 ((E)-4-(dimethylamino)-N-(5-(3-(hydroxyamino)-3-oxo-prop-1-en-1-yl)-2,3-dihydro-1H-inden-1-yl)benzamide) (0.03 g, 0.08 mmol, yield 74%).

Compound 26, $^1$H-NMR (500 MHz, $CD_3OD$): δ 8.00-7.98 (d, 2H), 7.59-7.56 (d, 1H), 7.48 (s, 1H), 7.43-7.40 (m, 3H), 7.32-7.30 (d, 1H), 6.47-6.44 (d, 1H), 5.67-5.64 (t, 1H), 3.24 (s, 6H), 3.12-3.07 (m, 1H), 2.98-2.92 (m, 1H), 2.63-2.60 (m, 1H), 2.08-2.03 (m, 1H). ESI-MS m/z calcd for $C_{21}H_{23}N_3O_3$ 365.17, found 366 $[M+H]^+$.

Synthesis of Compounds 27~28

Scheme 16

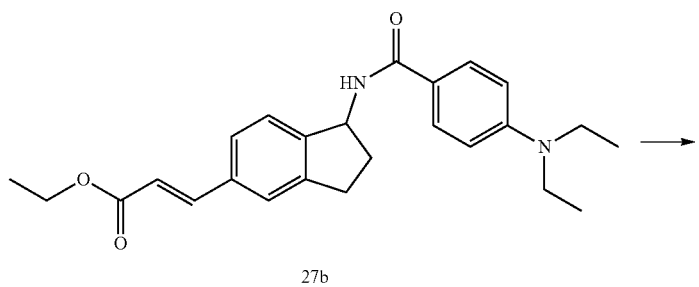

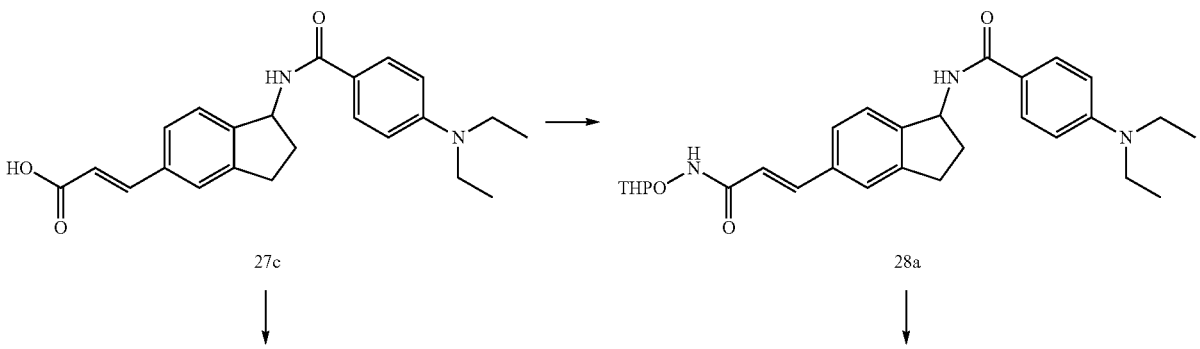

-continued

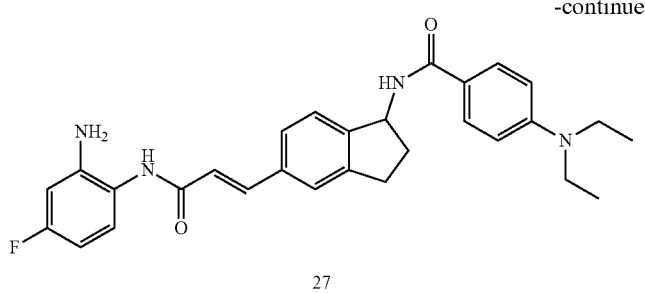
27

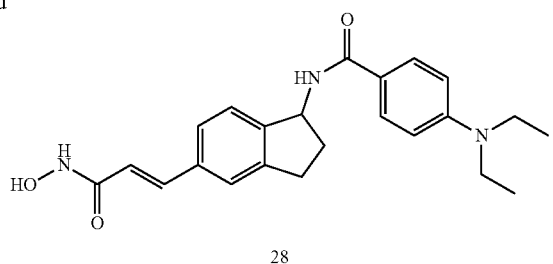
28

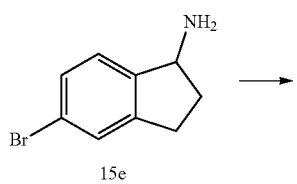
15e

-continued

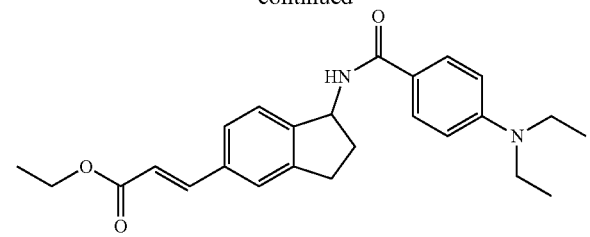
27b

To a solution of Compound 27a (N-(5-bromo-2,3-dihydro-1H-inden-1-yl)-4-(diethylamino)benzamide) (0.60 g, 1.56 mmol), triphenylphosphine (0.6 g, 0.62 mmol), ethyl acrylate (0.23 g, 2.34 mmol) in DMF/TEA (30 mL, 1:1) was added Pd(OAc)$_2$ (0.02 g, 0.08 mmol). After addition, the reaction mixture was heated to 100° C. and stirred for overnight.

The reaction was monitored by TLC. After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/4 as elution to yield the desired product Compound 27b (ethyl (E)-3-(1-(4-(diethylamino)benzamido)-2,3-dihydro-1H-inden-5-yl)acrylate) (0.59 g, 1.45 mmol, yield 93%).

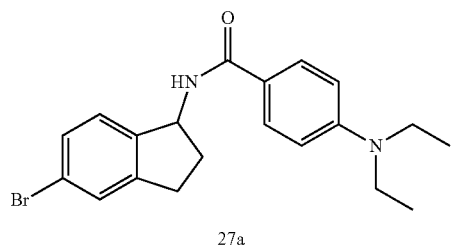
27a

To a solution of Compound 15e (5-bromo-2,3-dihydro-1H-inden-1-amine) (0.50 g, 2.36 mmol), 4-(Diethylamino)benzoic acid (0.46 g, 2.36 mmol) and DMAP (0.29 g, 0.2.36 mmol) in DCM (30 mL) was added NMM (0.48 g, 4.71 mmol) and EDCI (0.54 g, 2.83 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl and Sat. NaHCO$_3$. The organic phase was dried with MgSO$_4$ and concentrated under reduced pressure. The crude product was purified by silica gel column chromatography using ethyl acetate/hexane=1/4 as elution to afford Compound 27a (N-(5-bromo-2,3-dihydro-1H-inden-1-yl)-4-(diethylamino)benzamide) (0.60 g, 1.56 mmol, yield 66%).

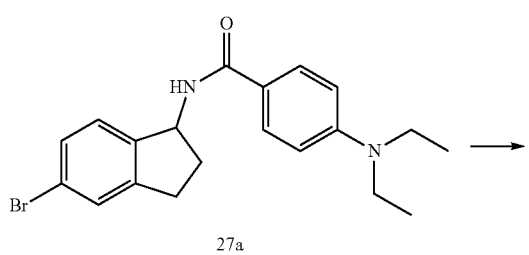
27a

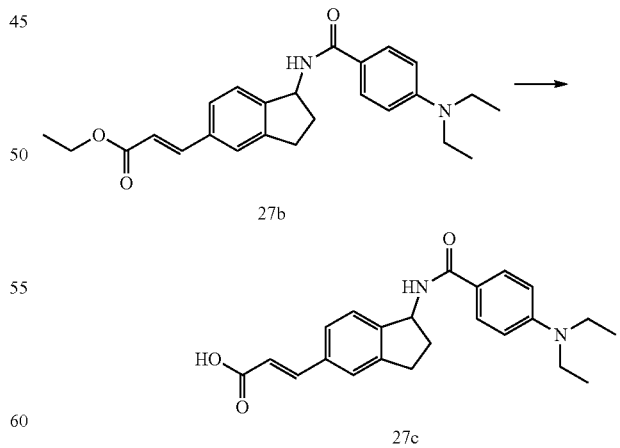
27b

27c

To a solution of Compound 27b (ethyl (E)-3-(1-(4-(diethylamino)benzamido)-2,3-dihydro-1H-inden-5-yl)acrylate) (0.59 g, 1.45 mmol) in MeOH (50 mL) was added 2N NaOH$_{(aq)}$ (1.50 mL, 3.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 27c ((E)-3-(1-(4-(diethylamino)benzamido)-2,3-dihydro-1H-inden-5-yl)acrylic acid) (0.50 g, 1.32 mmol, yield 91%).

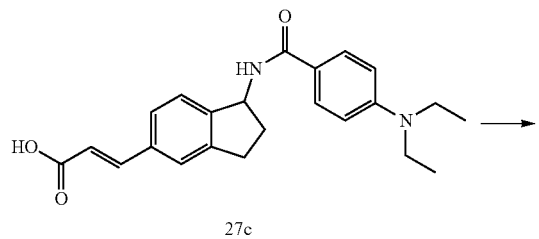

27c

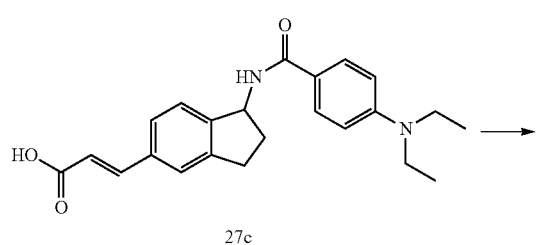

27

To a solution of Compound 27c ((E)-3-(1-(4-(diethylamino)benzamido)-2,3-dihydro-1H-inden-5-yl)acrylic acid) (0.10 g, 0.26 mmol), 4-fluoro-1,2-phenylenediamine (0.03 g, 0.26 mmol) and DMAP (0.03 g, 0.26 mmol) in THF (30 mL) was added NMM (0.03 g, 0.26 mmol) and EDCI (0.06 g, 0.32 mmol) at 0 t. After addition, the reaction mixture was warmed to room temperature and stirred for overnight.

After reaction was completed, the reaction mixture was diluted with EtOAc and washed with Sat. NH₄Cl. The combined organic layers were washed with brine and dried over MgSO₄ and concentrated in vacuo. The crude product was purified via flash column chromatography on a silica gel column using 1:1 EtOAc-Hexane as the eluent to give Compound 27 ((E)-N-(5-(3 #2-amino-4-fluorophenyl)amino)-3-oxoprop-1-en-1-yl)-2,3-dihydro-1H-inden-1-yl)-4-(diethylamino)benzamide) (0.02 g, 0.04 mmol, yield 16%).

Compound 27, $^1$H-NMR (500 MHz, d$_6$-DMSO): δ 7.75-7.74 (d, 2H), 7.68-7.65 (d, 1H), 7.52 (s, 1H), 7.48-7.46 (d, 1H), 7.33-7.31 (d, 1H), 7.16-7.14 (dd, 1H), 6.82-6.79 (d, 1H), 6.71-6.69 (d, 2H), 6.58-6.56 (dd, 1H), 6.43-6.39 (td, 1H), 5.67-5.64 (t, 1H), 3.46-3.42 (q, 4H), 3.11-3.06 (m, 1H), 2.97-2.93 (m, 1H), 2.62-2.59 (m, 1H), 2.07-2.03 (m, 1H), 1.20-1.17 (t, 6H). ESI-MS m/z calcd for C$_{29}$H$_{31}$FN$_4$O$_2$ 486.24, found 487 [M+H]$^+$.

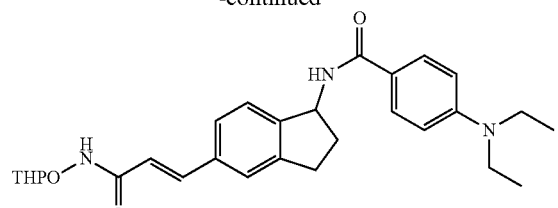

28a

To a solution of Compound 27c ((E)-3-(1-(4-(diethylamino)benzamido)-2,3-dihydro-1H-inden-5-yl)acrylic acid) (0.10 g, 0.26 mmol), O-(Tetrahydro-2H-pyran-2-yl)hydroxylamine (0.04 g, 0.34 mmol) and DMAP (0.02 g, 0.13 mmol) in DCM (20 mL) was added NMM (0.04 g, 0.40 mmol) and EDCI (0.08 g, 0.40 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl. The combined organic layers were washed with brine and dried over MgSO₄ and concentrated in vacuo. The crude product was purified by silica gel column chromatography using ethyl acetate/hexane=2/1 as elution to yield the desired product Compound 28a ((E)-4-(diethylamino)-N-(5-(3-oxo-3-(((tetrahydro-2H-pyran-2-yl)oxy)amino)prop-1-en-1-yl)-2,3-dihydro-1H-inden-1-yl)benzamide) (0.11 g, 0.23 mmol, yield 89%).

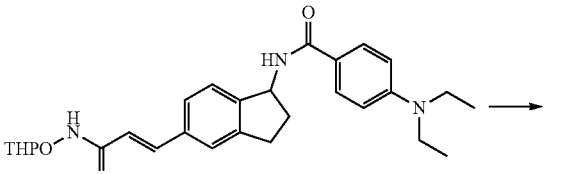

28a

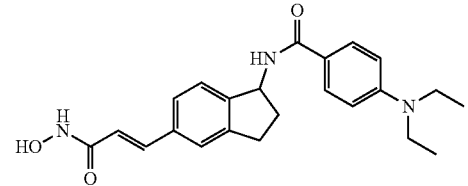

28

To a solution of Compound 28a ((E)-4-(diethylamino)-N-(5-(3-oxo-3-(((tetrahydro-2H-pyran-2-yl)oxy)amino)prop-1-en-1-yl)-2,3-dihydro-1H-inden-1-yl)benzamide) (0.11 g, 0.23 mmol) in CH₂Cl₂ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 28 ((E)-4-(diethylamino)-N-(5-(3-(hydroxyamino)-3-oxoprop-1-en-1-yl)-2,3-dihydro-1H-inden-1-yl)benzamide) (0.08 g, 0.21 mmol, yield 91%).

Compound 28, $^1$H-NMR (500 MHz, CD$_3$OD): δ 7.97 (s, 1H), 7.59-7.56 (d, 1H), 7.48 (s, 1H), 7.42-7.40 (d, 1H), 7.32-7.31 (d, 1H), 6.47-6.44 (d, 1H), 5.67-5.64 (t, 1H), 3.61 (s, 4H), 3.11-3.07 (m, 1H), 2.98-2.91 (m, 1H), 2.65-2.60 (m, 1H), 2.09-2.01 (m, 1H), 1.18-1.15 (t, 6H). ESI-MS m/z calcd for C$_{23}$H$_{27}$N$_3$O$_3$ 393.21, found 394 [M+H]$^+$.

Synthesis of Compounds 29~30
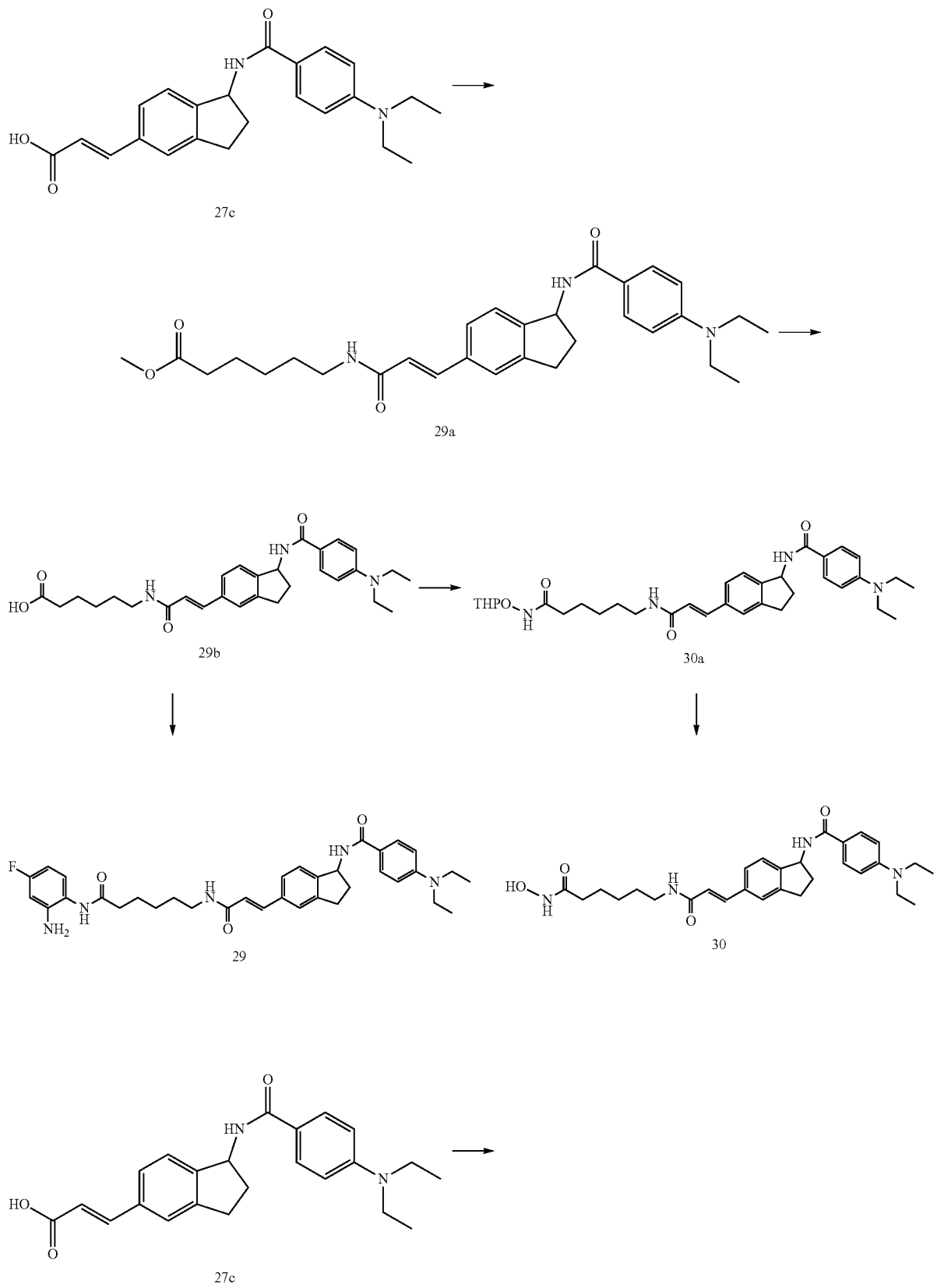

-continued

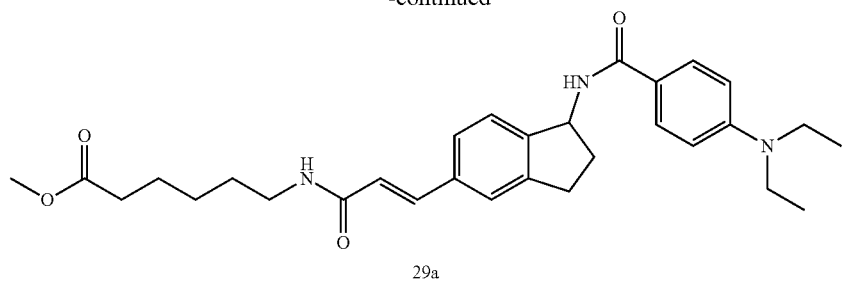
29a

To a solution of Compound 27c ((E)-3-(1-(4-(diethylamino)benzamido)-2,3-dihydro-1H-inden-5-yl)acrylic acid) (0.36 g, 0.96 mmol), methyl 6-aminohexanoate hydrogen chloride (0.19 g, 1.05 mmol) and DMAP (0.12 g, 0.96 mmol) in DCM (20 mL) was added DIPEA (0.15 g, 1.43 mmol) and EDCI (0.24 g, 1.24 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=1/1 as elution to yield the desired product Compound 29a (methyl (E)-6-(3-(1-(4-(diethylamino)benzamido)-2,3-dihydro-1H-inden-5-yl)acrylamido)hexanoate) (0.45 g, 0.90 mmol, yield 94%).

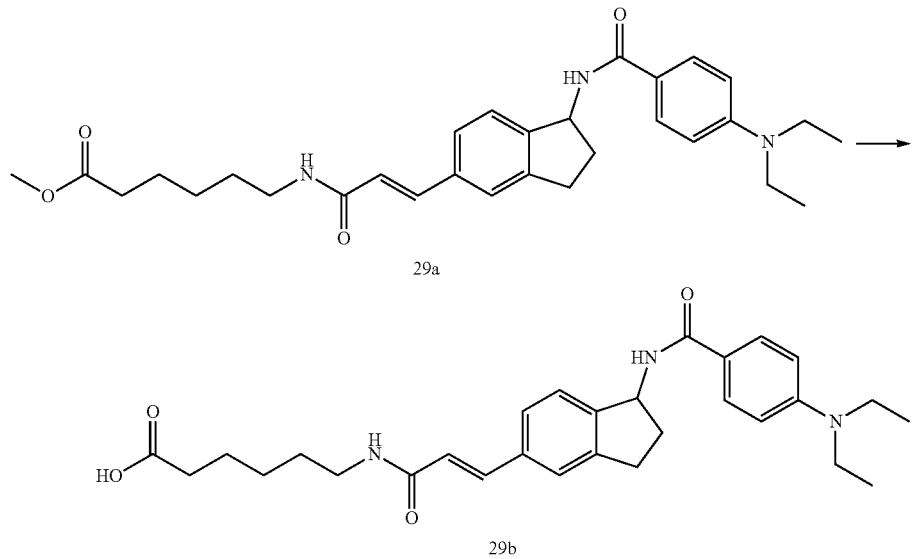

To a solution of Compound 29a (methyl (E)-6-(3-(1-(4-(diethylamino)benzamido)-2,3-dihydro-1H-inden-5-yl) acrylamido)hexanoate) (0.45 g, 0.90 mmol) in MeOH (50 mL) was added 2N NaOH$_{(aq)}$ (1.50 mL, 3.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 29b ((E)-6-(3-(1-(4-(diethylamino)benzamido)-2,3-dihydro-1H-inden-5-yl)acrylamido)hexanoic acid) (0.35 g, 0.72 mmol, yield 80%).

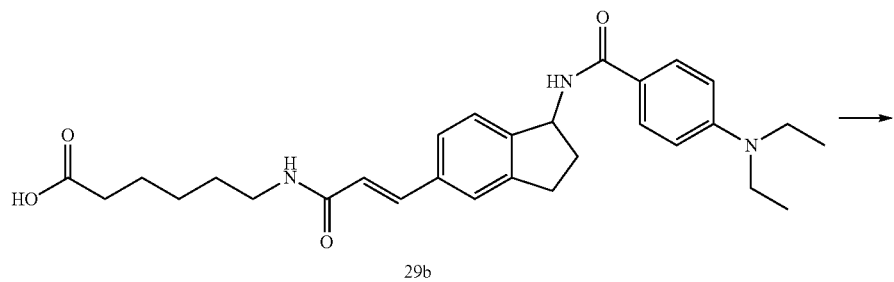

29b

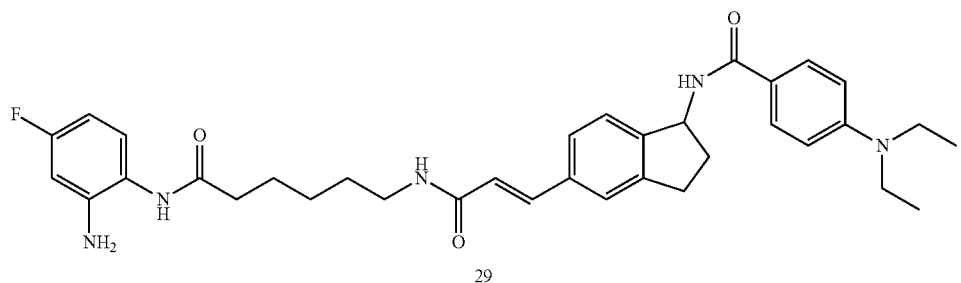

29

To a solution of Compound 29b ((E)-6-(3-(1-(4-(diethyl-amino)benzamido)-2,3-dihydro-1H-inden-5-yl)acrylamido)hexanoic acid) (0.10 g, 0.20 mmol), 4-fluoro-1,2-phenylenediamine (0.03 g, 0.20 mmol) and DMAP (0.03 g, 0.20 mmol) in THF (30 mL) was added NMM (0.02 g, 0.20 mmol) and EDCI (0.05 g, 0.26 mmol) at 0° C. After addition, the reaction mixture was warmed to room temperature and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 1:1 EtOAc-Hexane as the eluent to give Compound 29 ((E)-N-(5-(3-((6-((2-amino-4-fluorophenyl)amino)-6-oxohexyl)amino)-3-oxoprop-1-en-1-yl)-2,3-dihydro-1H-inden-1-yl)-4-(diethylamino)benzamide) (0.09 g, 0.15 mmol, yield 76%).

Compound 29, $^1$H-NMR (500 MHz, CD$_3$OD): δ 7.75-7.73 (d, 2H), 7.54-7.50 (d, 1H), 7.46 (s, 1H), 7.41-7.39 (d, 1H), 7.30-7.28 (d, 1H), 7.03-7.00 (dd, 1H), 6.71-6.69 (d, 2H), 6.61-6.57 (d, 1H), 6.54-6.51 (dd, 1H), 6.36-6.32 (td, 1H), 5.65-5.62 (t, 1H), 3.46-3.42 (q, 4H), 3.35-3.32 (t, 2H), 3.08-3.05 (m, 1H), 2.94-2.88 (m, 1H), 2.61-2.58 (m, 1H), 2.45-2.42 (t, 2H), 2.06-2.02 (m, 1H), 1.78-1.73 (m, 2H), 1.67-1.61 (m, 2H), 1.51-1.46 (m, 2H), 1.19-1.17 (t, 6H). ESI-MS m/z calcd for C$_{35}$H$_{42}$FN$_5$O$_3$ 599.33, found 600 [M+H]$^+$.

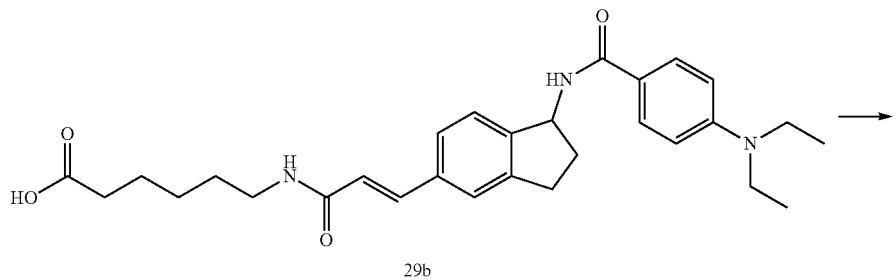

29b

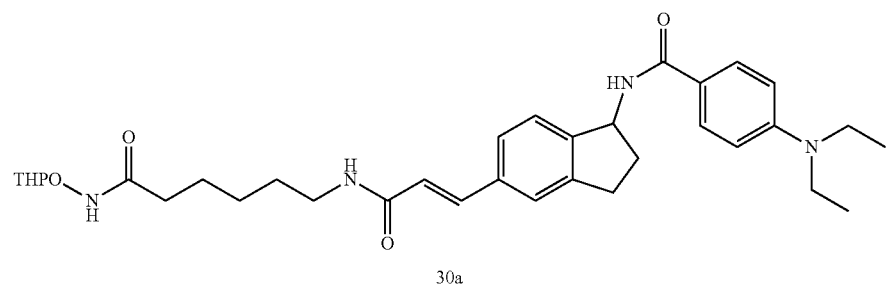

30a

To a solution of Compound 29b ((E)-6-(3-(1-(4-(diethylamino)benzamido)-2,3-dihydro-1H-inden-5-yl)acrylamido)hexanoic acid) (0.10 g, 0.20 mmol), O-(Tetrahydro-2H-pyran-2-yl)hydroxylamine (0.03 g, 0.26 mmol) and DMAP (0.01 g, 0.10 mmol) in DCM (20 mL) was added NMM (0.03 g, 0.30 mmol) and EDCI (0.06 g, 0.30 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=2/1 as elution to yield the desired product Compound 30a ((E)-4-(diethylamino)-N-(5-(3-oxo-3-((6-oxo-6-(((tetrahydro-2H-pyran-2-yl)oxy)amino)hexyl)amino)prop-1-en-1-yl)-2,3-dihydro-1H-inden-1-yl)benzamide) (0.10 g, 0.20 mmol, yield 98%).

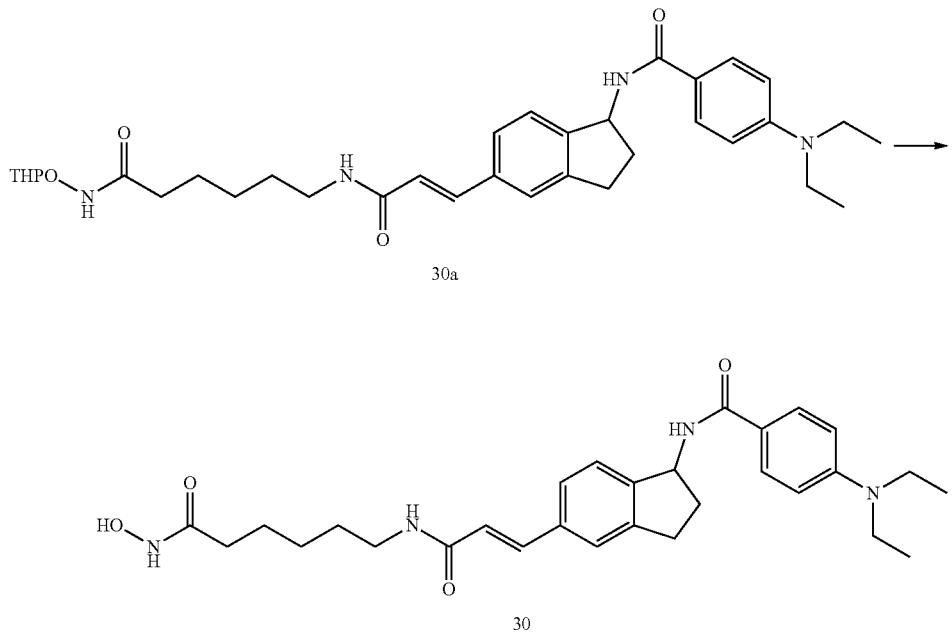

To a solution of Compound 30a ((E)-4-(diethylamino)-N-(5-(3-oxo-3-((6-oxo-6-(((tetrahydro-2H-pyran-2-yl)oxy)amino)hexyl)amino)prop-1-en-1-yl)-2,3-dihydro-1H-inden-1-yl)benzamide) (0.10 g, 0.20 mmol) in CH$_2$Cl$_2$ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 30 ((E)-4-(diethylamino)-N-(5-(3-((6-(hydroxyamino)-6-oxohexyl)amino)-3-oxoprop-1-en-1-yl)-2,3-dihydro-1H-inden-1-yl)benzamide) (0.09 g, 0.18 mmol, yield 90%).

Compound 30, $^1$H-NMR (500 MHz, CD$_3$OD): δ 7.75-7.73 (d, 2H), 7.53-7.50 (d, 1H), 7.46 (s, 1H), 7.41-7.40 (d, 1H), 7.30-7.28 (d, 1H), 6.70 (d, 2H), 6.59-6.55 (d, 1H), 5.65-5.62 (t, 1H), 3.49-3.41 (q, 4H), 3.31-3.28 (m, 2H) 3.10-3.04 (m, 1H), 2.95-2.89 (m, 1H), 2.62-2.57 (m, 1H), 2.12-2.09 (t, 2H), 2.07-2.01 (m, 1H), 1.69-1.56 (m, 4H), 1.42-1.38 (m, 2H), 1.19-1.17 (t, 6H). ESI-MS m/z calcd for C$_{29}$H$_{38}$N$_4$O$_4$ 506.29, found 507 [M+H]$^+$.

Synthesis of Compounds 31~32
Scheme 18
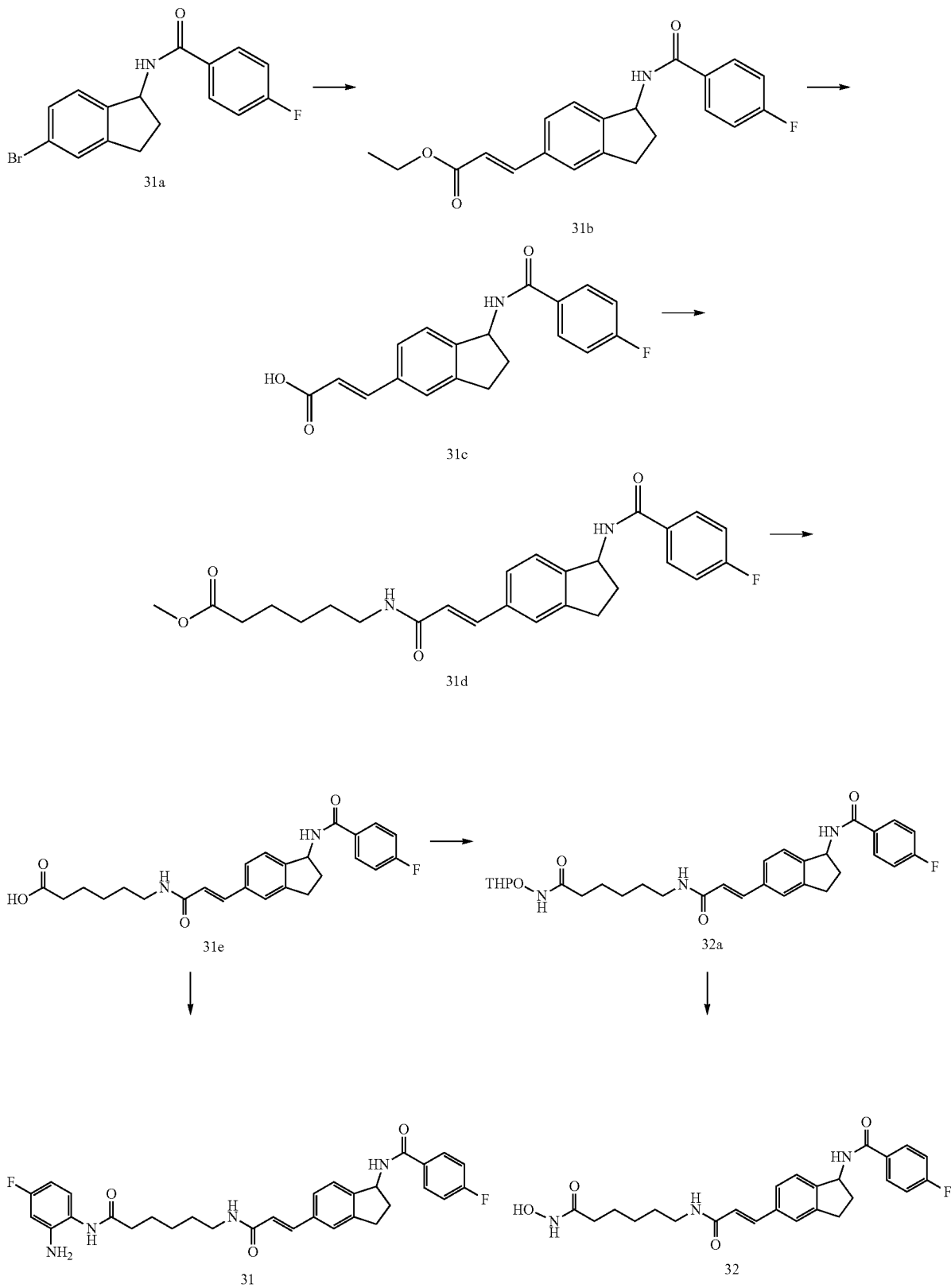

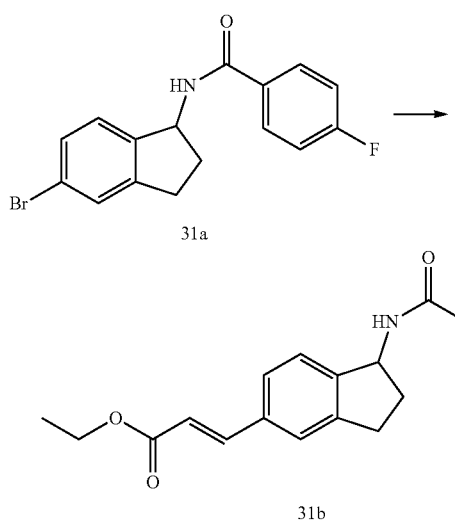

31a

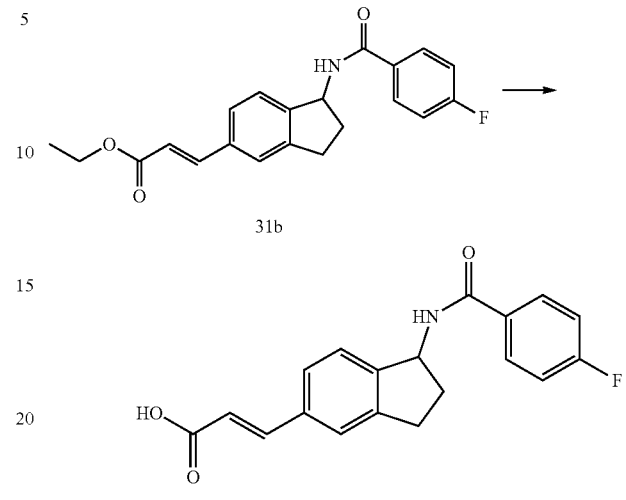

31b fluorobenzamido)-2,3-dihydro-1H-inden-5-yl)acrylate) (0.25 g, 0.71 mmol, yield 41%).

31b

To a solution of Compound 31a (N-(5-bromo-2,3-dihydro-1H-inden-1-yl)-4-fluorobenzamide) (0.58 g, 1.73 mmol), triphenylphosphine (0.18 g, 0.69 mmol), ethyl acrylate (0.26 g, 2.60 mmol) in DMF/TEA (30 mL, 1:1) was added Pd(OAc)$_2$ (0.02 g, 0.09 mmol). After addition, the reaction mixture was heated to 100° C. and stirred for overnight.

The reaction was monitored by TLC. After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/4 as elution to yield the desired product Compound 31b (ethyl (E)-3-(1-(4-

31c

To a solution of Compound 31b (ethyl (E)-3-(1-(4-fluorobenzamido)-2,3-dihydro-1H-inden-5-yl)acrylate) (0.25 g, 0.71 mmol) in MeOH (50 mL) was added 2N NaOH$_{(aq)}$ (1.00 mL, 2.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 31c ((E)-3-(1-(4-fluorobenzamido)-2,3-dihydro-1H-inden-5-yl) acrylic acid) (0.22 g, 0.69 mmol, yield 97%).

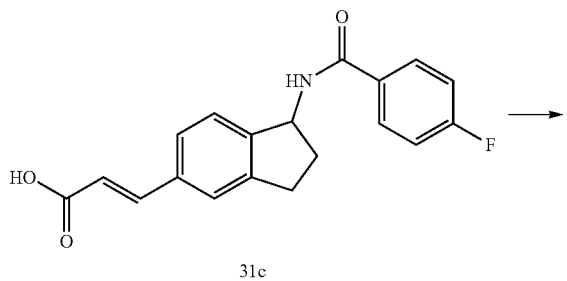

31c

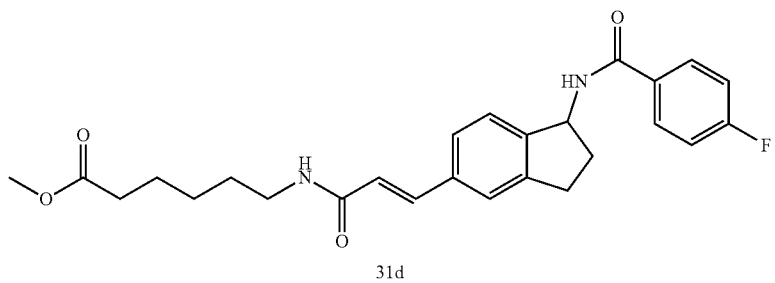

31d

To a solution of Compound 31c ((E)-3-(1-(4-fluorobenzamido)-2,3-dihydro-1H-inden-5-yl)acrylic acid) (0.28 g, 0.87 mmol), methyl 6-aminohexanoate hydrogen chloride (0.16 g, 0.87 mmol) and DMAP (0.05 g, 0.44 mmol) in DCM (20 mL) was added DIPEA (0.34 g, 2.62 mmol) and EDCI (0.20 g, 1.05 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=1/1 as elution to yield the desired product Compound 31d (methyl (E)-6-(3-(1-(4-fluorobenzamido)-2,3-dihydro-1H-inden-5-yl)acrylamido)hexanoate) (0.35 g, 0.78 mmol, yield 90%).

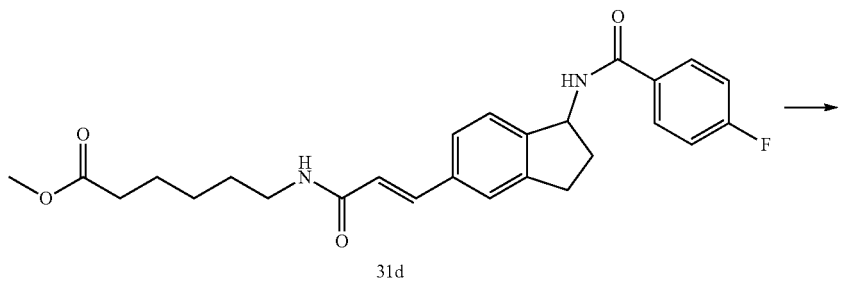

31d

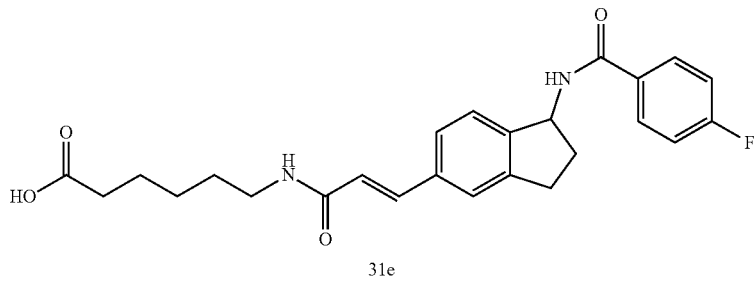

31e

To a solution of Compound 31d (methyl (E)-6-(3-(1-(4-fluorobenzamido)-2,3-dihydro-1H-inden-5-yl)acrylamido)hexanoate) (0.35 g, 0.78 mmol) in MeOH (50 mL) was added 2N NaOH$_{(aq)}$ (1.00 mL, 2.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 31e ((E)-6-(3-(1-(4-fluorobenzamido)-2,3-dihydro-1H-inden-5-yl)acrylamido)hexanoic acid) (0.24 g, 0.56 mmol, yield 71%).

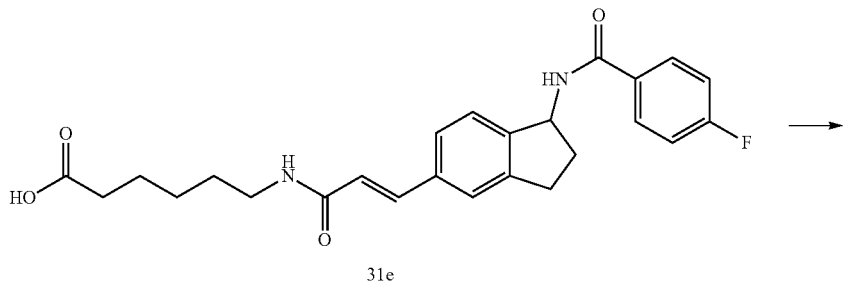

31e

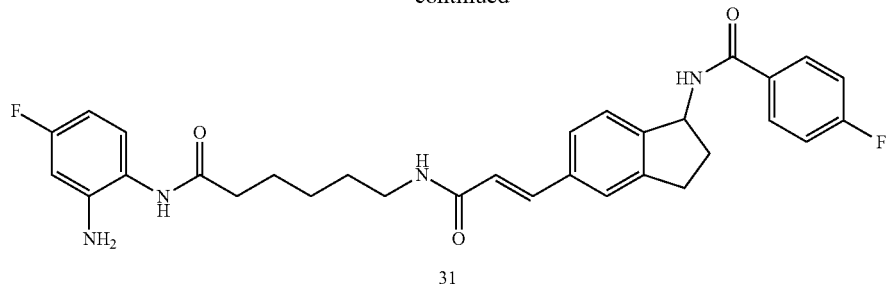

31

To a solution of Compound 31e ((E)-6-(3-(1-(4-fluorobenzamido)-2,3-dihydro-1H-inden-5-yl)acrylamido)hexanoic acid) (0.11 g, 0.25 mmol), 4-fluoro-1,2-phenylenediamine (0.03 g, 0.25 mmol) and DMAP (0.03 g, 0.25 mmol) in THF (30 mL) was added NMM (0.03 g, 0.25 mmol) and EDCI (0.06 g, 0.29 mmol) at 0° C. After addition, the reaction mixture was warmed to room temperature and stirred for overnight.

After reaction was completed, the reaction mixture was diluted with EtOAc and washed with Sat. NH₄Cl. The combined organic layers were washed with brine and dried over MgSO₄ and concentrated in vacuo. The crude product was purified via flash column chromatography on a silica gel column using 1:1 EtOAc-Hexane as the eluent to give Compound 31 ((E)-N-(5-(3-((6-((2-amino-4-fluorophenyl)amino)-6-oxohexyl)amino)-3-oxoprop-1-en-1-yl)-2,3-dihydro-1H-inden-1-yl)-4-fluorobenzamide) (0.03 g, 0.05 mmol, yield 21%).

Compound 31, $^1$H-NMR (500 MHz, CD$_3$OD): δ 7.94-7.91 (t, 2H), 7.54-7.51 (d, 1H), 7.46 (s, 1H), 7.42-7.30 (dd, 2H), 7.21-7.17 (t, 2H), 7.03-7.00 (m, 1H), 6.59-6.56 (d, 1H), 6.53-6.51 (m, 1H), 6.36-6.32 (m, 1H), 5.66-5.63 (t, 1H), 3.11-3.06 (m, 1H), 2.97-2.93 (m, 1H), 2.62-2.59 (m, 1H), 2.44-2.41 (t, 2H), 2.07-2.03 (m, 1H), 1.78-1.75 (m, 2H), 1.65-1.62 (m, 2H), 1.49-1.47 (m, 2H), 1.30 (br, 2H). ESI-MS m/z calcd for C$_{31}$H$_{32}$F$_2$N$_4$O$_3$ 546.24, found 547 [M+H]⁺.

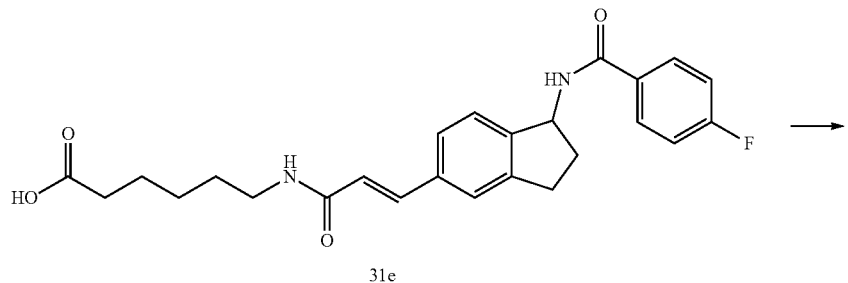

31e

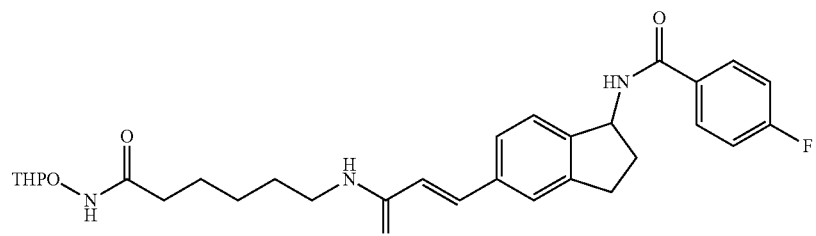

32a

To a solution of Compound 31e ((E)-6-(3-(1-(4-fluorobenzamido)-2,3-dihydro-1H-inden-5-yl)acrylamido)hexanoic acid) (0.14 g, 0.31 mmol), O-(Tetrahydro-2H-pyran-2-yl)hydroxylamine (0.05 g, 0.40 mmol) and DMAP (0.02 g, 0.16 mmol) in DCM (20 mL) was added NMM (0.05 g, 0.47 mmol) and EDCI (0.09 g, 0.47 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=2/1 as elution to yield the desired product Compound 32a ((E)-4-fluoro-N-(5-(3-oxo-3-((6-oxo-6-(((tetrahydro-2H-pyran-2-yl)oxy)amino)hexyl)amino)prop-1-en-1-yl)-2,3-dihydro-1H-inden-1-yl)benzamide) (0.12 g, 0.22 mmol, yield 72%).

To a solution of Compound 32a ((E)-4-fluoro-N-(5-(3-oxo-3-((6-oxo-6-(((tetrahydro-2H-pyran-2-yl)oxy)amino)hexyl)amino)prop-1-en-1-yl)-2,3-dihydro-1H-inden-1-yl)benzamide) (0.12 g, 0.22 mmol) in CH$_2$Cl$_2$ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 32 ((E)-4-fluoro-N-(5-(3-((6-(hydroxyamino)-6-oxohexyl)amino)-3-oxoprop-1-en-1-yl)-2,3-dihydro-1H-inden-1-yl)benzamide) (0.07 g, 0.16 mmol, yield 75%).

Compound 32, $^1$H-NMR (500 MHz, CD$_3$OD): δ 7.94-7.91 (t, 2H), 7.54-7.51 (d, 1H), 7.47 (s, 1H), 7.42-7.30 (dd, 2H), 7.21-7.17 (t, 2H), 6.59-6.56 (d, 1H), 5.66-5.63 (t, 1H), 3.11-3.06 (m, 1H), 2.96-2.93 (m, 1H), 2.62-2.61 (m, 1H), 2.12-2.04 (m, 3H), 1.67-1.59 (m, 4H), 1.41-1.38 (m, 2H), 1.30 (br, 2H). ESI-MS m/z calcd for C$_{25}$H$_{28}$FN$_3$O$_4$ 453.21, found 545 [M+1-1]$^+$.

Synthesis of Compound 33

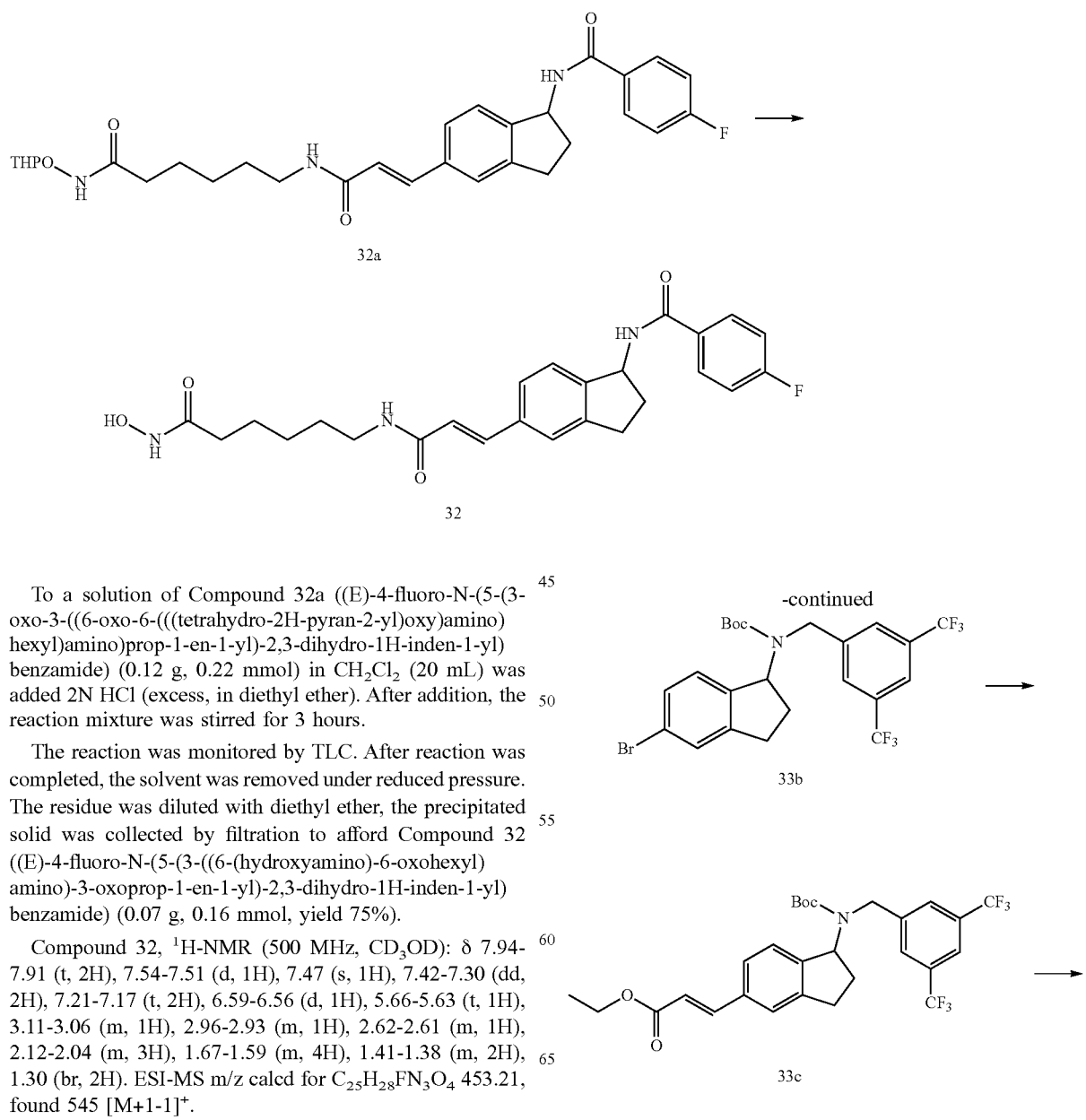

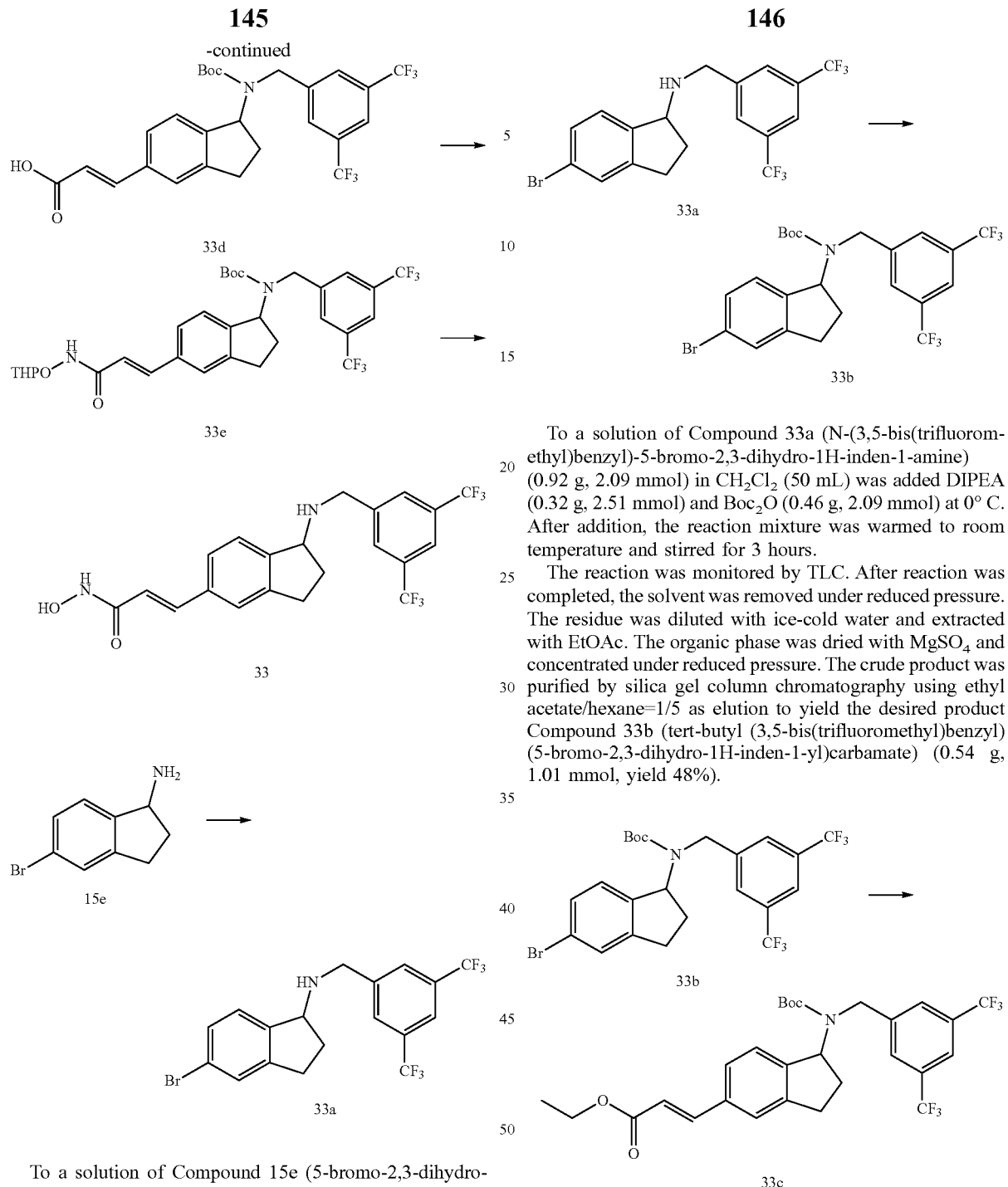

To a solution of Compound 15e (5-bromo-2,3-dihydro-1H-inden-1-amine) (0.5 g, 2.36 mmol) in MeOH (50 mL) was added 3,5-bis(trifluoromethyl)benzaldehyde (0.69 g, 2.83 mmol) and stirred for overnight. To the reaction mixture was added NaBH₃CN (0.13g, 2.13 mmol) and stirred for overnight.

The reaction was monitored by TLC. After reaction was completed, the solvent was removed under reduced pressure. The residue was diluted with sat. NaHCO₃$_{(aq)}$ and extracted with EtOAc. The organic phase was dried with MgSO₄ and concentrated under reduced pressure. The crude product Compound 33a (N-(3,5-bis(trifluoromethyl)benzyl)-5-bromo-2,3-dihydro-1H-inden-1-amine) (0.92g, 2.09 mmol, yield 89%) was used in the next step without further purification.

To a solution of Compound 33a (N-(3,5-bis(trifluoromethyl)benzyl)-5-bromo-2,3-dihydro-1H-inden-1-amine) (0.92 g, 2.09 mmol) in CH₂Cl₂ (50 mL) was added DIPEA (0.32 g, 2.51 mmol) and Boc₂O (0.46 g, 2.09 mmol) at 0° C. After addition, the reaction mixture was warmed to room temperature and stirred for 3 hours.

The reaction was monitored by TLC. After reaction was completed, the solvent was removed under reduced pressure. The residue was diluted with ice-cold water and extracted with EtOAc. The organic phase was dried with MgSO₄ and concentrated under reduced pressure. The crude product was purified by silica gel column chromatography using ethyl acetate/hexane=1/5 as elution to yield the desired product Compound 33b (tert-butyl (3,5-bis(trifluoromethyl)benzyl)(5-bromo-2,3-dihydro-1H-inden-1-yl)carbamate) (0.54 g, 1.01 mmol, yield 48%).

To a solution of Compound 33b (tert-butyl (3,5-bis(trifluoromethyl)benzyl)(5-bromo-2,3-dihydro-1H-inden-1-yl) carbamate) (0.54 g, 1.00 mmol), triphenylphosphine (0.11 g, 0.40 mmol), ethyl acrylate (0.15 g, 1.51 mmol) in DMF/TEA (20 mL, 1:1) was added Pd(OAc)₂ (0.01 g, 0.05 mmol). After addition, the reaction mixture was heated to 100° C. and stirred for overnight.

The reaction was monitored by TLC. After reaction was completed, the reaction mixture was diluted with sat. NH₄Cl$_{(aq)}$ and extracted with EtOAc. The organic phase was dried with MgSO₄ and concentrated under reduced pressure. The crude product was purified by silica gel column chromatography using ethyl acetate/hexane=1/5 as elution to yield the desired product Compound 33c (ethyl (E)-3-(1-((3,5-bis(trifluoromethyl)benzyl)(tert-butoxycarbonyl) amino)-2,3-dihydro-1H-inden-5-yl)acrylate) (0.34 g, 0.61 mmol, yield 61%).

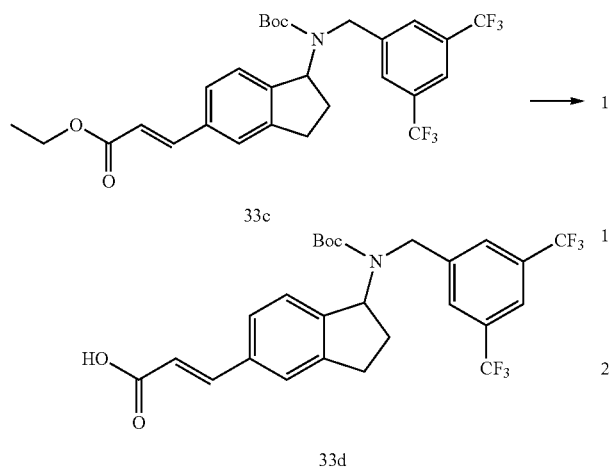

To a solution of Compound 33c (ethyl (E)-3-(1-((3,5-bis (trifluoromethyl)benzyl)(tert-butoxycarbonyl)amino)-2,3-dihydro-1H-inden-5-yl)acrylate) (0.10 g, 0.18 mmol) in MeOH (10 mL) was added 2N NaOH$_{(aq)}$ (0.2 mL, 0.40 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 33d ((E)-3-(1-((3,5-bis(trifluoromethyl)benzyl)(tert-butoxycarbonyl) amino)-2,3-dihydro-1H-inden-5-yl)acrylic acid) (0.07 g, 0.14 mmol, yield 78%).

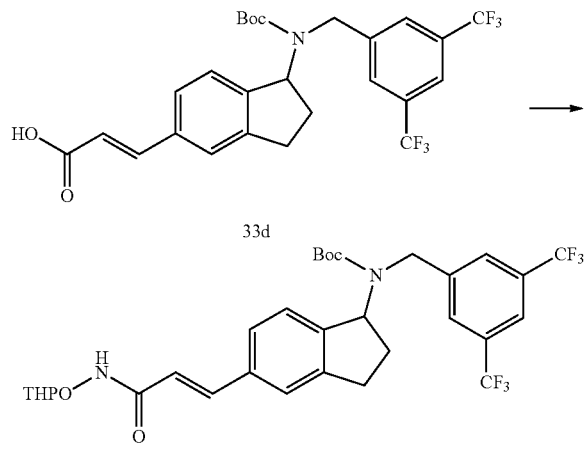

To a solution of Compound 33d ((E)-3-(1-((3,5-bis(trifluoromethyl)benzyl)(tert-butoxycarbonyl)amino)-2,3-dihydro-1H-inden-5-yl)acrylic acid) (0.07 g, 0.14 mmol), NH$_2$OTHP (0.03 g, 0.21 mmol) and DMAP (0.01 g, 0.09 mmol) in CH$_2$Cl$_2$ (20 mL) was added NMM (0.02 g, 0.21 mmol) and EDC (0.04 g, 0.21 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=1/1 as elution to yield the desired product Compound 33e (tert-butyl (E)-(3,5-bis(trifluoromethyl)benzyl)(5-(3-oxo-3-(((tetrahydro-2H-pyran-2-yl)oxy)amino) prop-1-en-1-yl)-2,3-dihydro-1H-inden-1-yl)carbamate) (0.07 mg, 0.11 mmol, yield 80%).

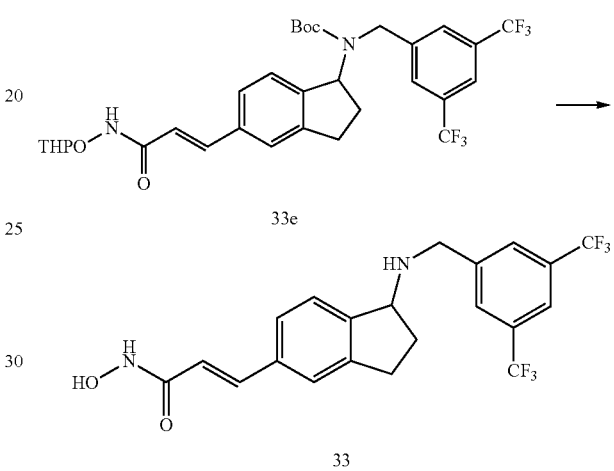

To a solution of Compound 33e (tert-butyl (E)-(3,5-bis (trifluoromethyl)benzyl)(5-(3-oxo-3-(((tetrahydro-2H-pyran-2-yl)oxy)amino)prop-1-en-1-yl)-2,3-dihydro-1H-inden-1-yl)carbamate) (0.07 mg, 0.11 mmol) in CH$_2$Cl$_2$ (20 mL) was added 4N HCl (excess, in 1,4-dioxane). After addition, the reaction mixture was stirred for 2 hours.

The reaction was monitored by TLC. After reaction was completed, the solvent was removed under reduced pressure. The residue was diluted with diethyl ether, the precipitated solid was collected by filtration to afford the desired product Compound 33 ((E)-3-(1-((3,5-bis(trifluoromethyl)benzyl) amino)-2,3-dihydro-1H-inden-5-yl)-N-hydroxyacrylamide) (0.04 g, 0.09 mmol, yield 83%).

Compound 33, $^1$H-NMR (500 MHz, d$_6$-DMSO): δ 10.19-8.13 (s, 1H), 9.70 (s, 1H), 8.37 (s, 2H), 8.17 (s, 1H), 7.77-7.76 (d, 1H), 7.55-7.46 (m, 3H), 6.52-6.49 (d, 1H), 4.89 (s, 1H), 4.47-4.44 (m, 2H), 3.22-3.16 (m, 1H), 2.96-2.93 (m, 1H), 2.56-2.36 (m, 2H). ESI-MS m/z calcd for C$_{21}$H$_{18}$F$_6$N$_2$O$_2$ 444.13, found 445 [M+H]$^+$.

Synthesis of Compound 34

Scheme 20

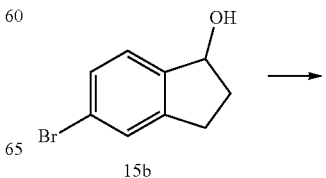

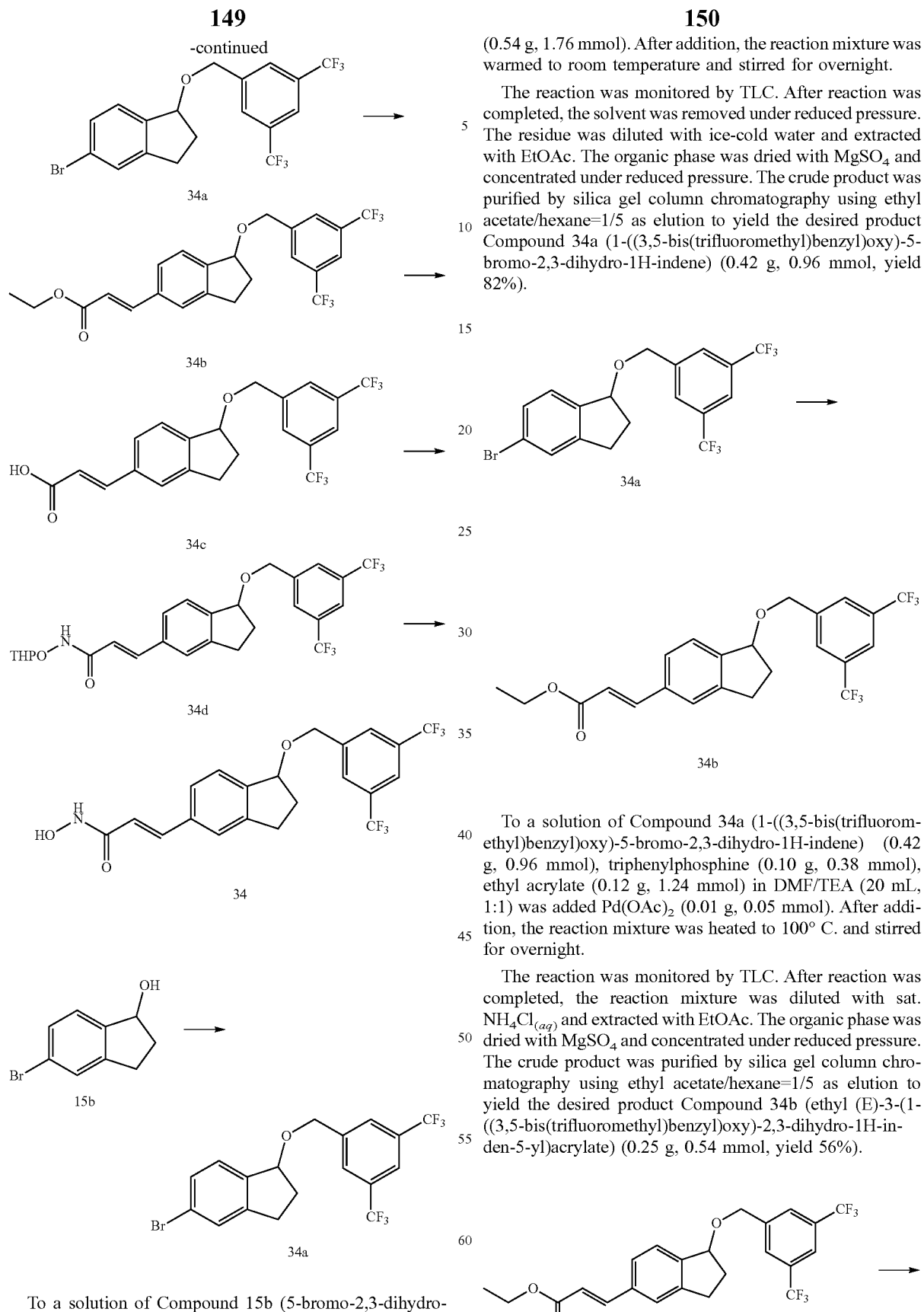

To a solution of Compound 15b (5-bromo-2,3-dihydro-1H-inden-1-ol) (0.25 g, 1.17 mmol) in THF/DMF (25 mL, 4:1) was added NaH (0.08 g) at 0° C. and stirred at the same temperature for 30 mins. And then, the reaction mixture was added 1-(bromomethyl)-3,5-bis(trifluoromethyl)benzene (0.54 g, 1.76 mmol). After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with $MgSO_4$ and concentrated under reduced pressure. The crude product was purified by silica gel column chromatography using ethyl acetate/hexane=1/5 as elution to yield the desired product Compound 34a (1-((3,5-bis(trifluoromethyl)benzyl)oxy)-5-bromo-2,3-dihydro-1H-indene) (0.42 g, 0.96 mmol, yield 82%).

To a solution of Compound 34a (1-((3,5-bis(trifluoromethyl)benzyl)oxy)-5-bromo-2,3-dihydro-1H-indene) (0.42 g, 0.96 mmol), triphenylphosphine (0.10 g, 0.38 mmol), ethyl acrylate (0.12 g, 1.24 mmol) in DMF/TEA (20 mL, 1:1) was added $Pd(OAc)_2$ (0.01 g, 0.05 mmol). After addition, the reaction mixture was heated to 100° C. and stirred for overnight.

The reaction was monitored by TLC. After reaction was completed, the reaction mixture was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/hexane=1/5 as elution to yield the desired product Compound 34b (ethyl (E)-3-(1-((3,5-bis(trifluoromethyl)benzyl)oxy)-2,3-dihydro-1H-inden-5-yl)acrylate) (0.25 g, 0.54 mmol, yield 56%).

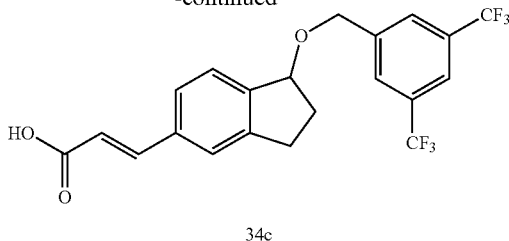

34c

To a solution of Compound 34b (ethyl (E)-3-(1-((3,5-bis(trifluoromethyl)benzyl)oxy)-2,3-dihydro-1H-inden-5-yl)acrylate) (0.25 g, 0.54 mmol) in MeOH (30 mL) was added 2N NaOH$_{(aq)}$ (0.50 mL, 1.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 34c ((E)-3-(1-((3,5-bis(trifluoromethyl)benzyl)oxy)-2,3-dihydro-1H-inden-5-yl)acrylic acid) (0.18 g, 0.42 mmol, yield 77%).

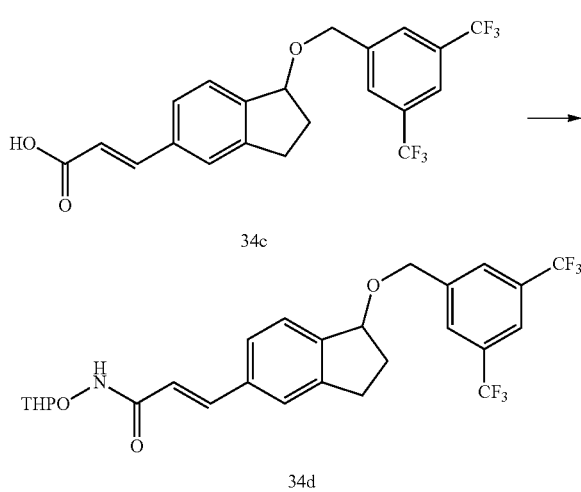

34c

34d

To a solution of Compound 34c ((E)-3-(1-((3,5-bis(trifluoromethyl)benzyl)oxy)-2,3-dihydro-1H-inden-5-yl)acrylic acid) (0.18 g, 0.42 mmol), NH$_2$OTHP (0.07 g, 0.62 mmol) and DMAP (0.03 g, 0.21 mmol) in CH$_2$Cl$_2$ (30 mL) was added NMM (0.06 g, 0.62 mmol) and EDC (0.12 g, 0.62 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=1/1 as elution to yield the desired product Compound 34d ((E)-3-(1-((3,5-bis(trifluoromethyl)benzyl)oxy)-2,3-dihydro-1H-inden-5-yl)-N-((tetrahydro-2H-pyran-2-yl)oxy)acrylamide) (0.19 mg, 0.37 mmol, yield 87%).

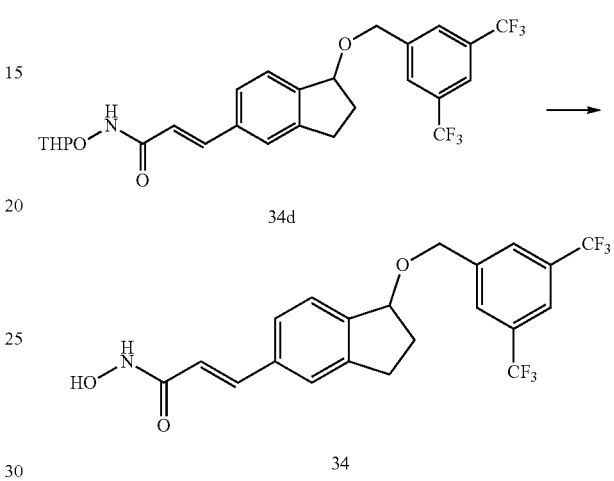

34d

34

To a solution of Compound 34d ((E)-3-(1-((3,5-bis(trifluoromethyl)benzyl)oxy)-2,3-dihydro-1H-inden-5-yl)-N-((tetrahydro-2H-pyran-2-yl)oxy)acrylamide) (0.19 mg, 0.37 mmol) in CH$_2$Cl$_2$ (30 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford the desired product Compound 34 ((E)-3-(1-((3,5-bis(trifluoromethyl)benzyl)oxy)-2,3-dihydro-1H-inden-5-yl)-N-hydroxyacrylamide) (0.11 g, 0.25 mmol, yield 67%).

Compound 34, $^1$H-NMR (500 MHz, CD$_3$OD): δ 7.94 (s, 2H), 7.86 (s, 1H), 7.60-7.57 (d, 1H), 7.49 (s, 1H), 7.46-7.41 (q, 2H), 6.48-6.45 (d, 1H), 5.12-5.10 (t, 1H), 4.85-4.78 (q, 2H), 3.15-3.09 (m, 1H), 2.91-2.85 (m, 1H), 2.47-2.43 (m, 1H), 2.23-2.17 (m, 1H). ESI-MS m/z calcd for C$_{21}$H$_{17}$F$_6$NO$_3$ 445.11, found 446 [M+H]$^+$.

Synthesis of Compounds 35~36

Scheme 21

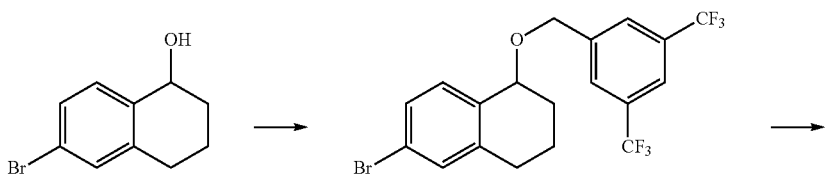

23b

35a

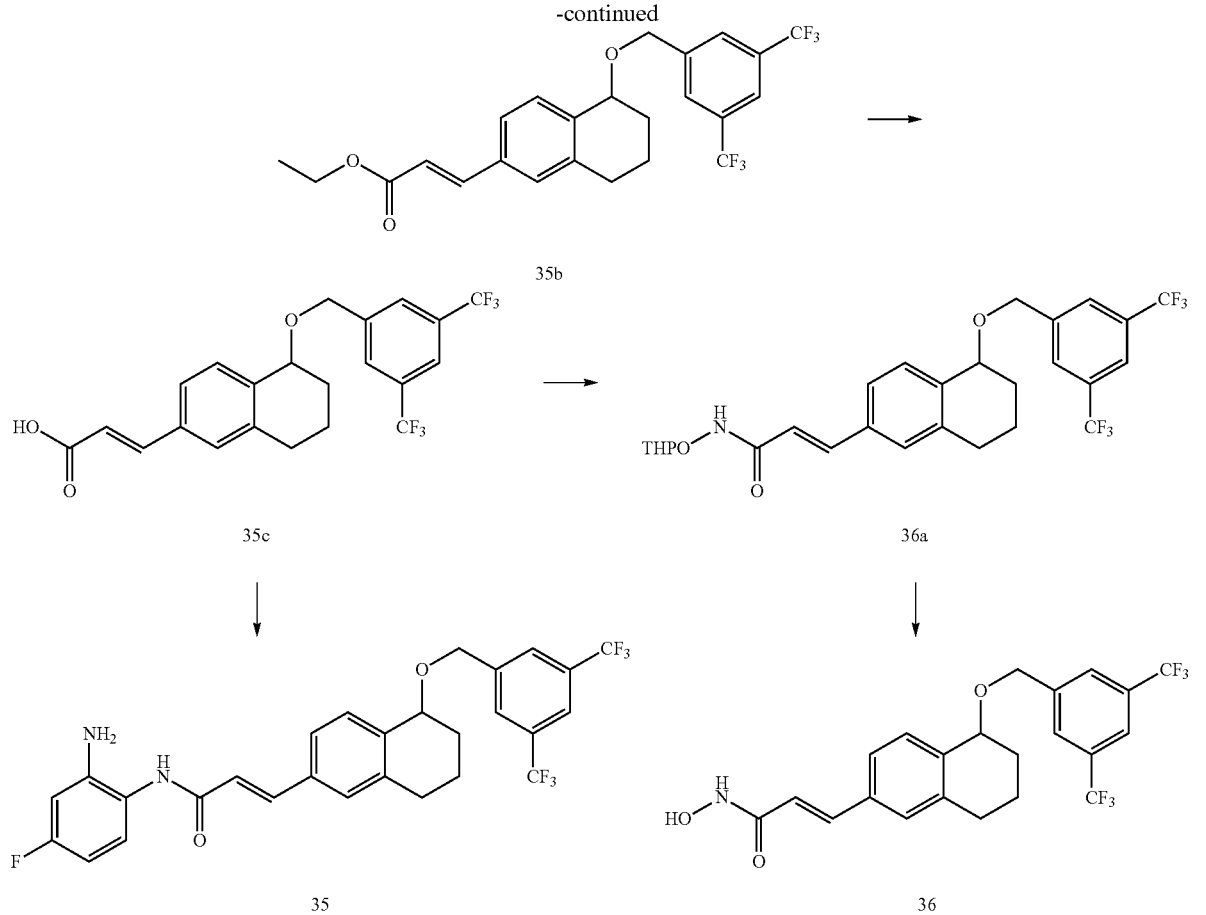

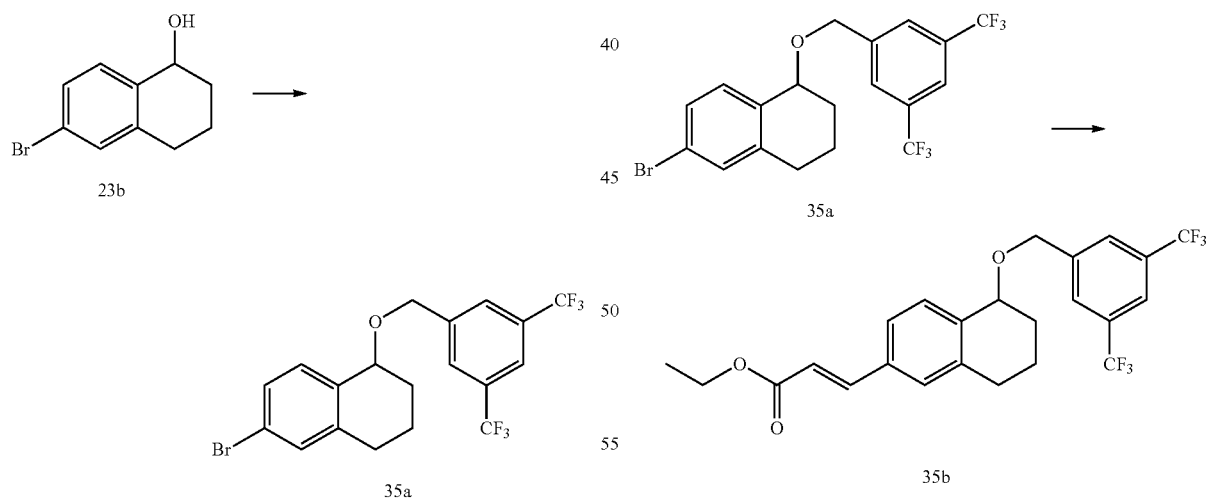

To a solution of Compound 23b (6-bromo-1,2,3,4-tetrahydronaphthalen-1-ol) (590 mg, 1.0 eq) in THF (25 mL) and Et₃N (289 mg, 1.1 eq) at RT, followed 1-(bromomethyl)-3,5-bis(trifluoromethyl)benzene (957 mg, 1.2 eq). The mixture was stirred for overnight.

After removing the solvent to afford the product Compound 35a (1-((3,5-bis(trifluoromethyl)benzyl)oxy)-6-bromo-1,2,3,4-tetrahydronaphthalene) (300 mg, yield 28%).

To a solution of Compound 35a (1-((3,5-bis(trifluoromethyl)benzyl)oxy)-6-bromo-1,2,3,4-tetrahydronaphthalene) (300 mg, 1.0 eq) in DMF (6.6 mL) was added ethyl acrylate (86 mg, 1.3 eq) at rt, followed Et₃N (1.3 mL), PPh₃ (69 mg, 0.4 eq). The mixture was stirred at rt for 5 min then degas with nitrogen, followed added Pd(OAc)₂ (8 mg, 0.05 eq). The reaction was stirred at 100° C. for overnight.

After cooling to RT, quench with NH₄Cl and extracted with EtOAc, then take the organic layer washed with brine.

The combined organic layer was dried over anhydrous MgSO₄. After removing the solvent in vacuo and purified with column chromatography to afford the product Compound 35b (ethyl (E)-3-(5-((3,5-bis(trifluoromethyl)benzyl)oxy)-5,6,7,8-tetrahydronaphthalen-2-yl)acrylate) (200 mg, yield 64%).

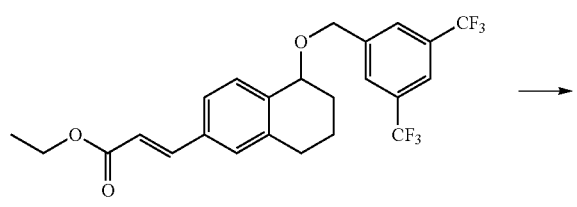

35b

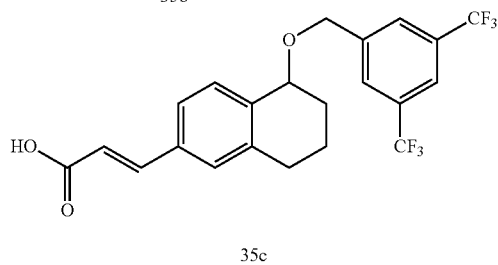

35c

To a solution of Compound 35b (ethyl (E)-3-(5-((3,5-bis(trifluoromethyl)benzyl)oxy)-5,6,7,8-tetrahydronaphthalen-2-yl)acrylate) (200 mg, 1 eq) in MeOH (10.5 mL) was added NaOH aqueous solution (1.0 M, 1.5 mL) at RT.

The mixture was stirred at RT for overnight, then removed the solvent in vacuo followed quench with HCl aqueous solution (1.0 M) to pH=3. The mixture was extracted with EtOAc, then take the organic layer washed with brine. The combined organic layer was dried over anhydrous MgSO₄. Remove the solvent to afford the product Compound 35c ((E)-3-(5-((3,5-bis(trifluoromethyl)benzyl)oxy)-5,6,7,8-tetrahydronaphthalen-2-yl)acrylic acid) (149 mg, yield 79%).

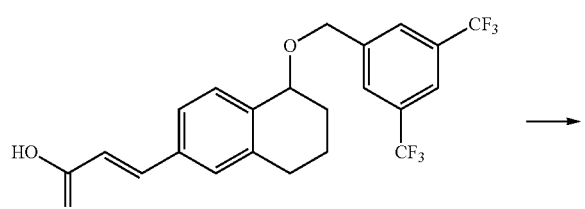

35c

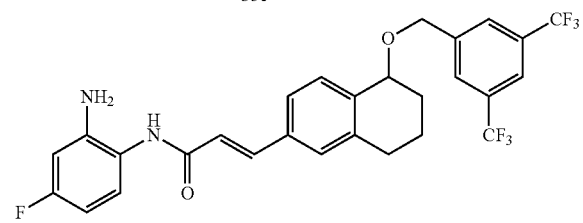

35

To a solution of Compound 35c ((E)-3-(5-((3,5-bis(trifluoromethyl)benzyl)oxy)-5,6,7,8-tetrahydronaphthalen-2-yl) acrylic acid) (200 mg, 1 eq) in THF (4.3 mL, 0.1 M) at 0° C. under nitrogen was added EDC hydrochloride (124 mg, 1.5 eq), followed NMM (65 mg, 1.5 eq), HOBT (26 mg, 0.4 eq) and 4-Fluoro-1,2-phenylenediamine (65 mg, 1.2 eq). The mixture was allowed to warm to RT and stirred for overnight.

After removing the solvent, the crude product was purified by column chromatography to afford the product Compound 35 ((E)-N-(2-amino-4-fluorophenyl)-3-(5-((3,5-bis(trifluoromethyl)benzyl)oxy)-5,6,7,8-tetrahydronaphthalen-2-yl)acrylamide) (10 mg, yield 4%).

Compound 35, ¹H-NMR (500 MHz, CDCl₃): δ 7.83 (s, 2H), 7.80 (s, 1H), 7.73-7.70 (d, 1H), 7.39-7.38 (d, 2H), 7.31 (s, 1H), 7.16-7.11 (m, 2H), 6.60-6.52 (m, 3H), 4.82-4.69 (dd, 2H), 4.60 (s, 1H), 4.04 (s, 2H), 2.92-2.76 (m, 2H), 2.10-2.00 (m, 3H), 1.85-1.82 (m, 1H). ESI-MS m/z calcd for $C_{28}H_{23}F_7N_2O_2$ 552.16, found 553 [M+H]⁺.

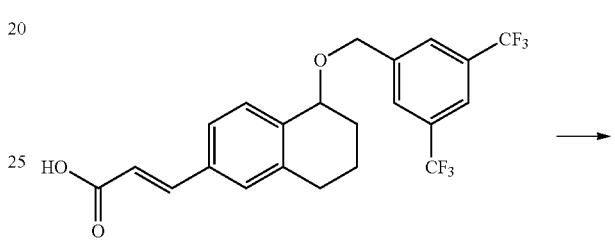

35c

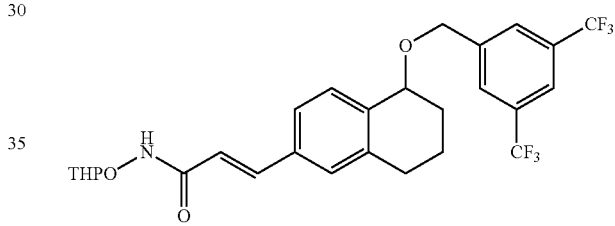

36a

To a solution of Compound 35c ((E)-3-(5-((3,5-bis(trifluoromethyl)benzyl)oxy)-5,6,7,8-tetrahydronaphthalen-2-yl) acrylic acid) (300 mg, 1.0 eq) in THF (6.4 mL, 0.1 M) at 0° C. under nitrogen was added EDC hydrochloride (149 mg, 1.2 eq), followed NMM (79 mg, 1.2 eq), HOBT (40 mg, 0.4 eq) and O-(Tetrahydro-2H-pyran-2-yl)hydroxylamine (114 mg, 1.5 eq). The mixture was allowed to warm to RT and stirred for overnight.

After removing the solvent, the crude product was purified by column chromatography to afford the product Compound 36a ((E)-3-(5-((3,5-bis(trifluoromethyl)benzyl)oxy)-5,6,7,8-tetrahydronaphthalen-2-yl)-N-((tetrahydro-2H-pyran-2-yl)oxy)acrylamide) (300 mg, yield 82%).

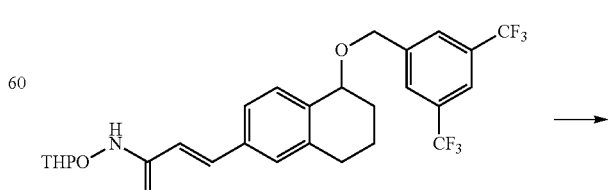

36a

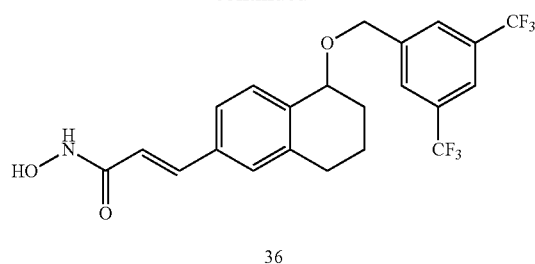

36

To a solution of Compound 36a ((E)-3-(5-((3,5-bis(trifluoromethyl)benzyl)oxy)-5,6,7,8-tetrahydronaphthalen-2-yl)-N-((tetrahydro-2H-pyran-2-yl)oxy)acrylamide) (300 mg, 1.0 eq) in MeOH (5.5 mL, 0.1 M) was added HCl aqueous solution (1.0 M, 59.6 mL).

The reaction was stirred at RT for 2 hours, then the solid was filtered out and washed with Et$_2$O to afford the product Compound 36 ((E)-3-(5-((3,5-bis(trifluoromethyl)benzyl)oxy)-5,6,7,8-tetrahydronaphthalen-2-yl)-N-hydroxy acrylamide) (13 mg, yield 5%).

Compound 36, $^1$H-NMR (500 MHz, CD$_3$OD): δ 7.95 (s, 2H), 7.86 (s, 1H), 7.55-7.52 (d, 1H), 7.38 (s, 2H), 7.31 (s, 1H), 6.46-6.43 (d, 1H), 4.89-4.77 (dd, 2H), 4.64-4.63 (t, 1H), 2.90-2.73 (m, 2H), 2.15-1.97 (m, 3H), 1.82-1.79 (m, 1H). ESI-MS m/z calcd for C$_{22}$H$_{19}$F$_6$NO$_3$ 459.13, found 460 [M+H]$^+$.

Synthesis of Compound 37

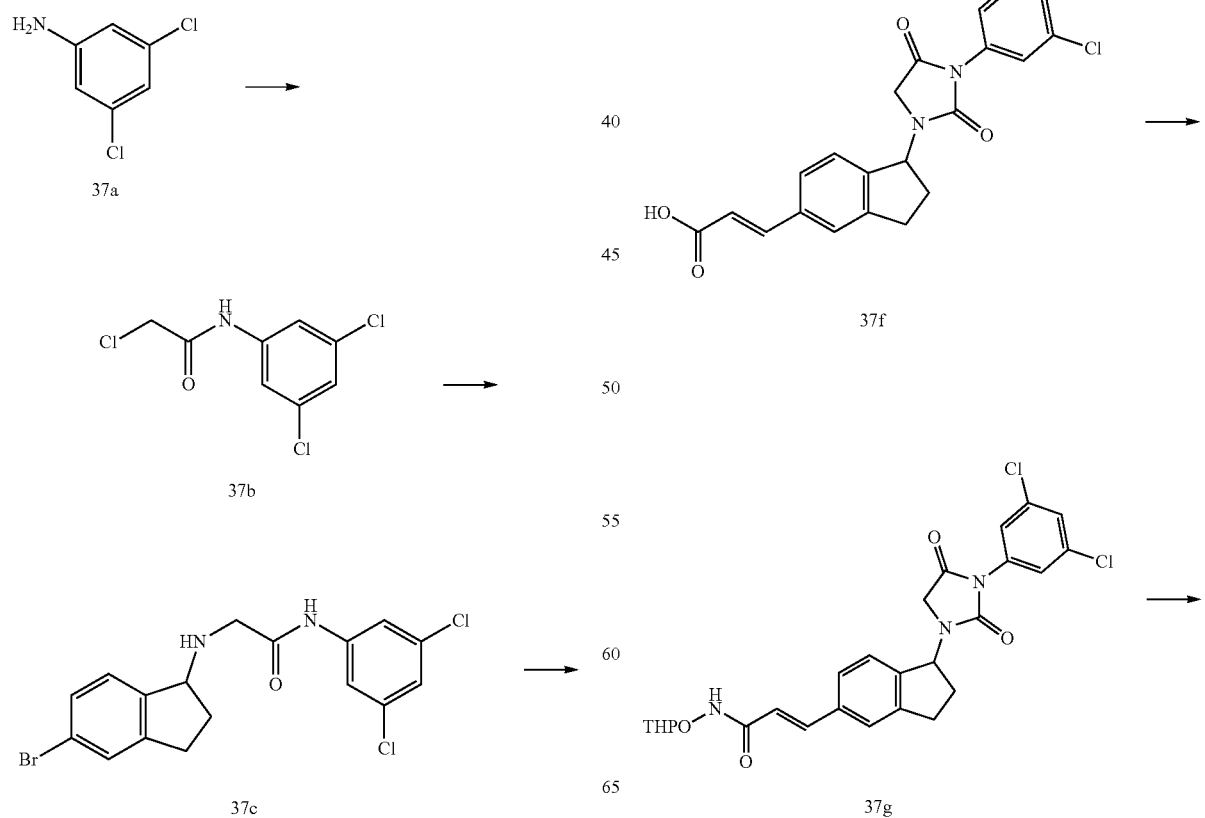

-continued

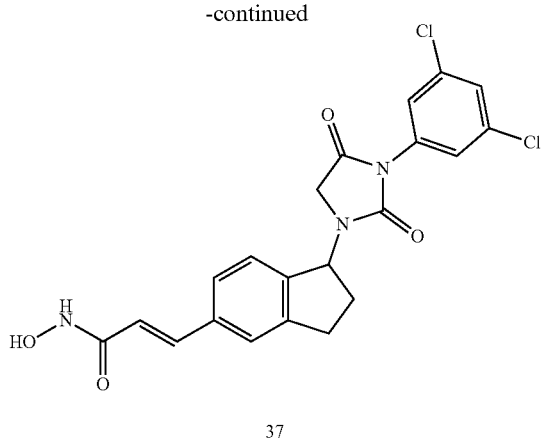

37

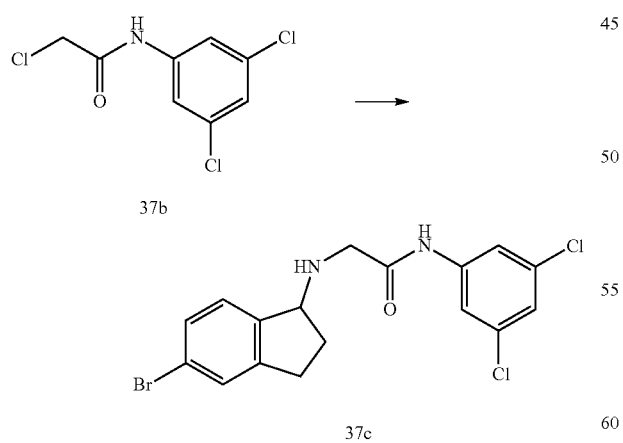

To a stirred solution of Compound 37a (3,5-dichloroaniline) (812 mg, 5.00 mmol) in DCM (5 mL) was added Et₃N (562 mg, 5.50 mmol) followed by a solution of chloroacetyl chloride (621 mg, 5.50 mmol) in DCM (3 mL) at RT. The reaction mixture was stirred at RT for 5 hours.

The reaction mixture was diluted with DCM (20 mL) and washed with NaHCO₃ (sat.), 1N HCl (aq) and brine. The combined organic layer dried over anhydrous MgSO₄, and the solvent was removed under reduced pressure without further purification to afford the product Compound 37b (2-chloro-N-(3,5-dichlorophenyl)acetamide) (1193 mg, 99%).

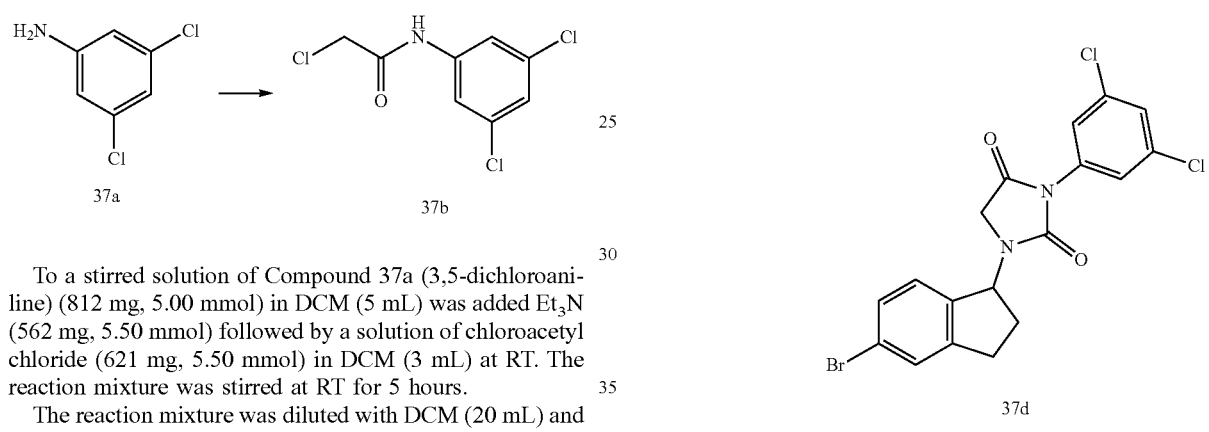

To a solution of Compound 37b (2-chloro-N-(3,5-dichlorophenyl)acetamide) (239 mg, 1.00 mmol) in acetonitrile (ACN; 5 mL) was added Compound 15e (5-bromo-2,3-dihydro-1H-inden-1-amine) (212 mg, 1.00 mmol), followed potassium iodide (166 mg, 1.00 mmol) and DIPEA (133 mg, 1.00 mmol) at rt. The mixture was stirred at RT for 5 mins then warm to 90° C. under nitrogen for 19 hours.

After cooling to RT, removed the solvent in vacuo, then purified with column chromatography (EtOAc:n-hexane=1:4) to afford the product Compound 37c (2-((5-bromo-2,3-dihydro-1H-inden-1-yl)amino)-N-(3,5-dichlorophenyl)acetamide) (317 mg, 76%).

To a solution of Compound 37c (2-((5-bromo-2,3-dihydro-1H-inden-1-yl)amino)-N-(3,5-dichlorophenyl)acetamide) (317 mg, 0.77 mmol) in DCM (10 mL) was added Boc₂O (427 mg, 1.91 mmol) at RT, followed Et₃N (212 mg, 1.91 mmol) and DMAP (20 mg, 0.16 mmol). The mixture was stirred at RT for 1 hour.

Then removed the solvent in vacuo and purified with column chromatography (EtOAc:n-hexane=1:5) to afford the product Compound 37d (1-(5-bromo-2,3-dihydro-1H-inden-1-yl)-3-(3,5-dichlorophenyl)imidazolidine-2,4-dione) (264 mg, 78%).

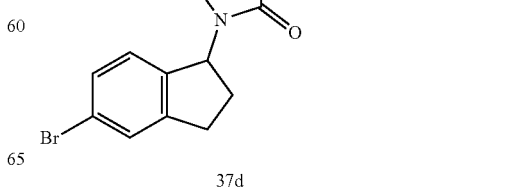

37d

-continued

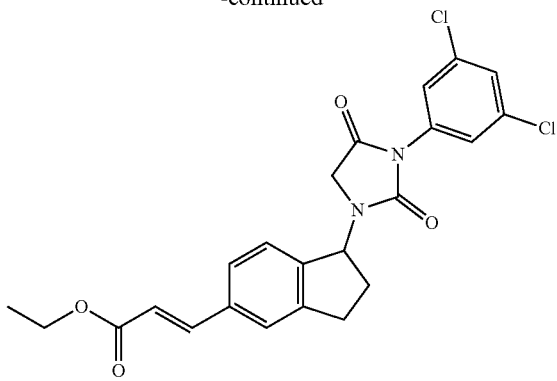

37e

To a solution of Compound 37d (1-(5-bromo-2,3-dihydro-1H-inden-1-yl)-3-(3,5-dichlorophenyl)imidazolidine-2,4-dione) (248 mg, 0.56 mmol) in ACN (8 mL) was added ethyl acrylate (1.5 mL, 14.1 mmol) at RT in pressure tube, followed Et₃N (8 mL) and PPh₃ (222 mg, 0.85 mmol). The mixture was stirred at RT for 5 mins then degas with nitrogen, followed added Pd(OAc)₂ (76 mg, 0.34 mmol) and seal the tube. The reaction was stirred at 100° C. for 12 hours.

After cooling to RT, removed the solvent in vacuo and purified with column chromatography (EtOAc:n-hexane=1:2) to afford the product Compound 37e (ethyl (E)-3-(1-(3-(3,5-dichlorophenyl)-2,4-dioxoimidazolidin-1-yl)-2,3-dihydro-1H-inden-5-yl)acrylate) (207 mg, 80%).

37e

37f

To a solution of Compound 37e (ethyl (E)-3-(1-(3-(3,5-dichlorophenyl)-2,4-dioxoimidazolidin-1-yl)-2,3-dihydro-1H-inden-5-yl)acrylate) (200 mg, 0.44 mmol) in MeOH (90 mL) was added NaOH aqueous solution (2.0 M, 10 mL) at rt. The mixture was stirred at RT for 1 hour.

The solvent was removed in vacuo, and then quenched with HCl aqueous solution (1.0 M) to pH=3. The mixture was extracted with EtOAc, then take the organic layer washed with brine. The combined organic layer was dried over anhydrous MgSO₄. After remove the solvent, the crude product was taken the next step. Compound 37f ((E)-3-(1-(3-(3,5-dichlorophenyl)-2,4-dioxoimidazolidin-1-yl)-2,3-dihydro-1H-inden-5-yl)acrylic acid) (188 mg, 99%).

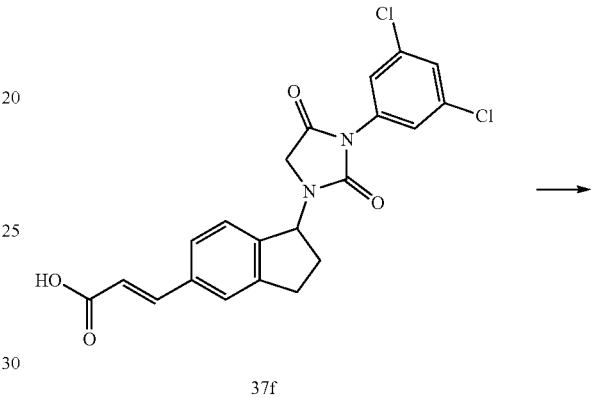

37f

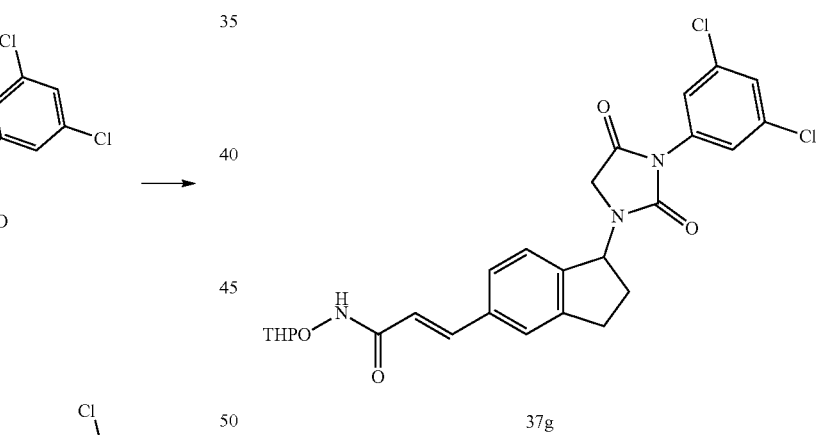

37g

To a solution of Compound 37f ((E)-3-(1-(3-(3,5-dichlorophenyl)-2,4-dioxoimidazolidin-1-yl)-2,3-dihydro-1H-inden-5-yl)acrylic acid) (202 mg, 0.47 mmol) in DCM (10 mL) at 0° C. under nitrogen was added EDC hydrochloride (104 mg, 0.52 mmol), followed DMAP (66 mg, 0.52 mmol) and O-(Tetrahydro-2H-pyran-2-yl)hydroxylamine (62 mg, 0.52 mmol). The mixture was allowed to warm to RT and stirred for 3 hours.

After removing the solvent, the crude product was purified by column chromatography (EtOAc:n-hexane=2:1) to afford the solid Compound 37g ((E)-3-(1-(3-(3,5-dichlorophenyl)-2,4-dioxoimidazolidin-1-yl)-2,3-dihydro-1H-inden-5-yl)-N-((tetrahydro-2H-pyran-2-yl)oxy)acrylamide) (52 mg, 21%).

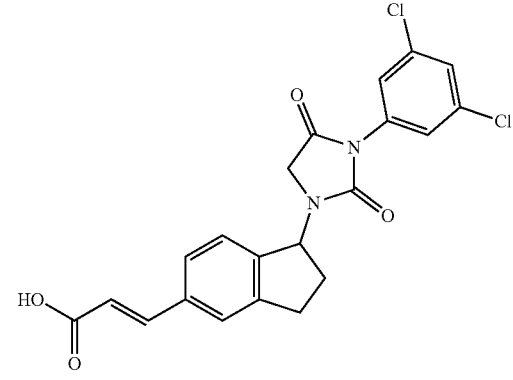

37f

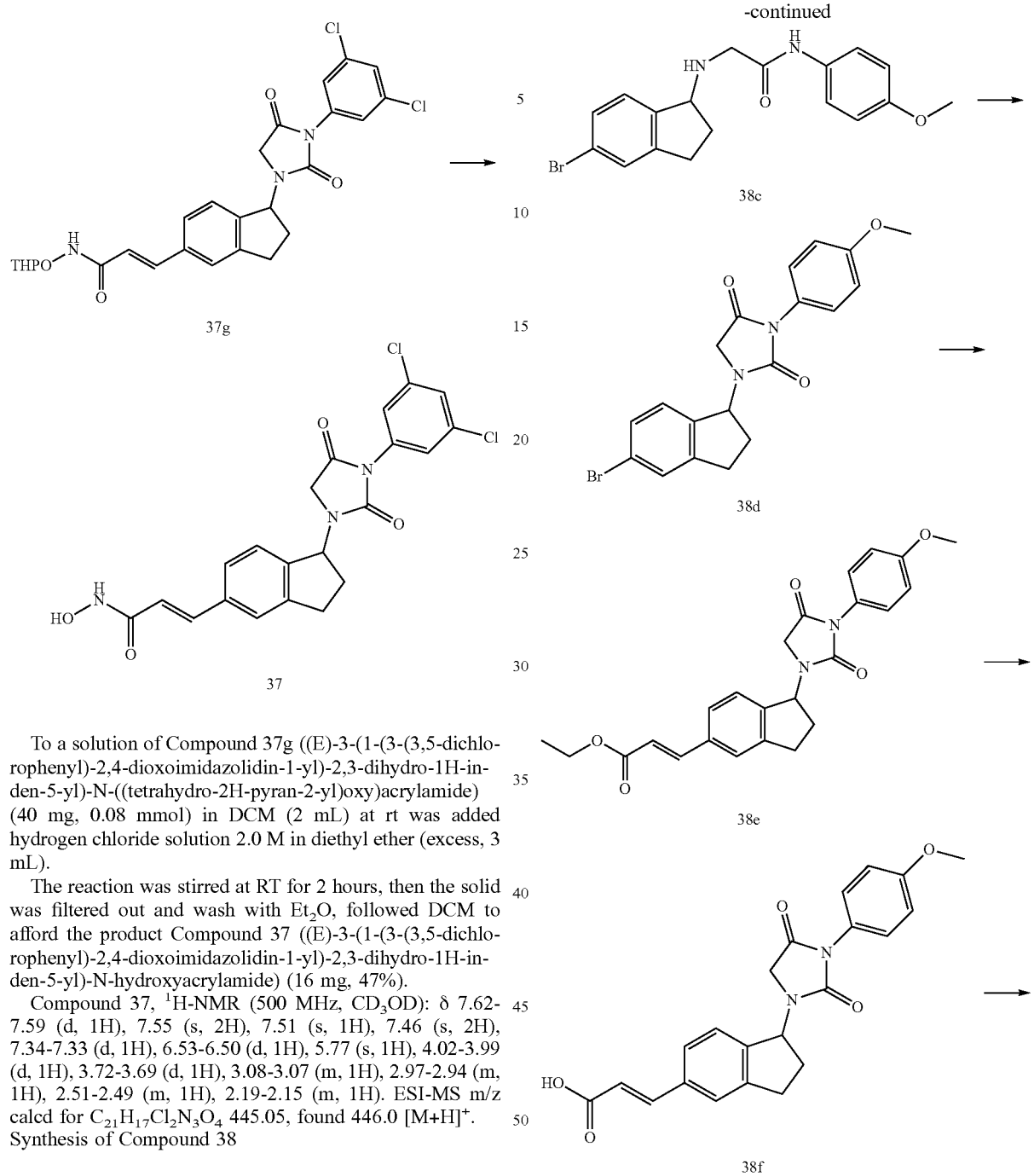

To a solution of Compound 37g ((E)-3-(1-(3-(3,5-dichlorophenyl)-2,4-dioxoimidazolidin-1-yl)-2,3-dihydro-1H-inden-5-yl)-N-((tetrahydro-2H-pyran-2-yl)oxy)acrylamide) (40 mg, 0.08 mmol) in DCM (2 mL) at rt was added hydrogen chloride solution 2.0 M in diethyl ether (excess, 3 mL).

The reaction was stirred at RT for 2 hours, then the solid was filtered out and wash with Et₂O, followed DCM to afford the product Compound 37 ((E)-3-(1-(3-(3,5-dichlorophenyl)-2,4-dioxoimidazolidin-1-yl)-2,3-dihydro-1H-inden-5-yl)-N-hydroxyacrylamide) (16 mg, 47%).

Compound 37, $^1$H-NMR (500 MHz, CD$_3$OD): δ 7.62-7.59 (d, 1H), 7.55 (s, 2H), 7.51 (s, 1H), 7.46 (s, 2H), 7.34-7.33 (d, 1H), 6.53-6.50 (d, 1H), 5.77 (s, 1H), 4.02-3.99 (d, 1H), 3.72-3.69 (d, 1H), 3.08-3.07 (m, 1H), 2.97-2.94 (m, 1H), 2.51-2.49 (m, 1H), 2.19-2.15 (m, 1H). ESI-MS m/z calcd for C$_{21}$H$_{17}$Cl$_2$N$_3$O$_4$ 445.05, found 446.0 [M+H]$^+$.

Synthesis of Compound 38

Scheme 23

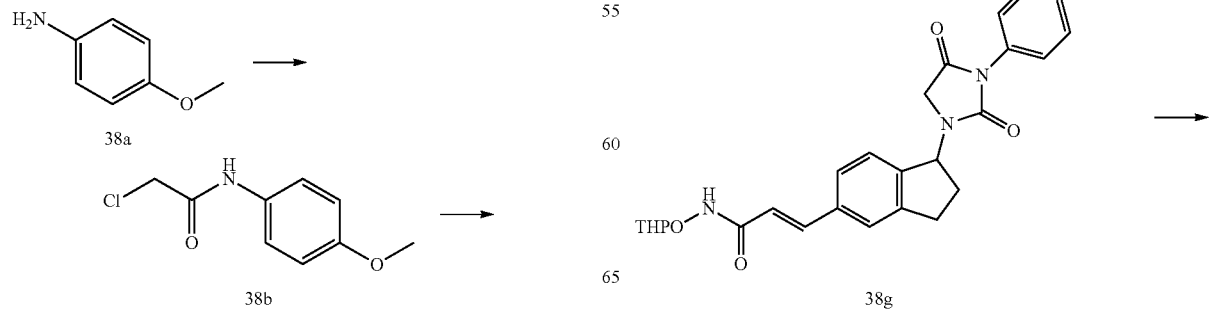

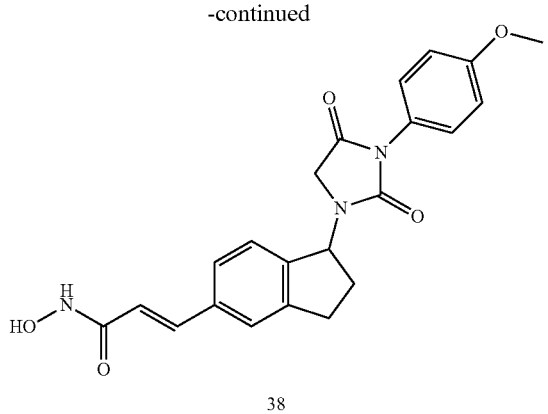

38

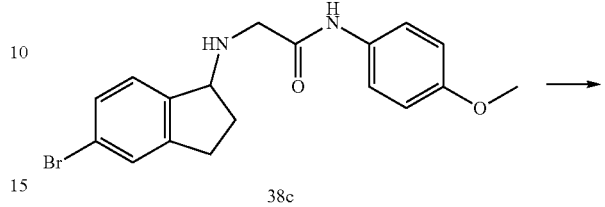

38a

After cooling to RT, removed the solvent in vacuo, then purified with column chromatography (EtOAc:n-hexane=1:4) to afford Compound 38c (2-((5-bromo-2,3-dihydro-1H-inden-1-yl)amino)-N-(4-methoxyphenyl)acetamide) (307 mg, 82%).

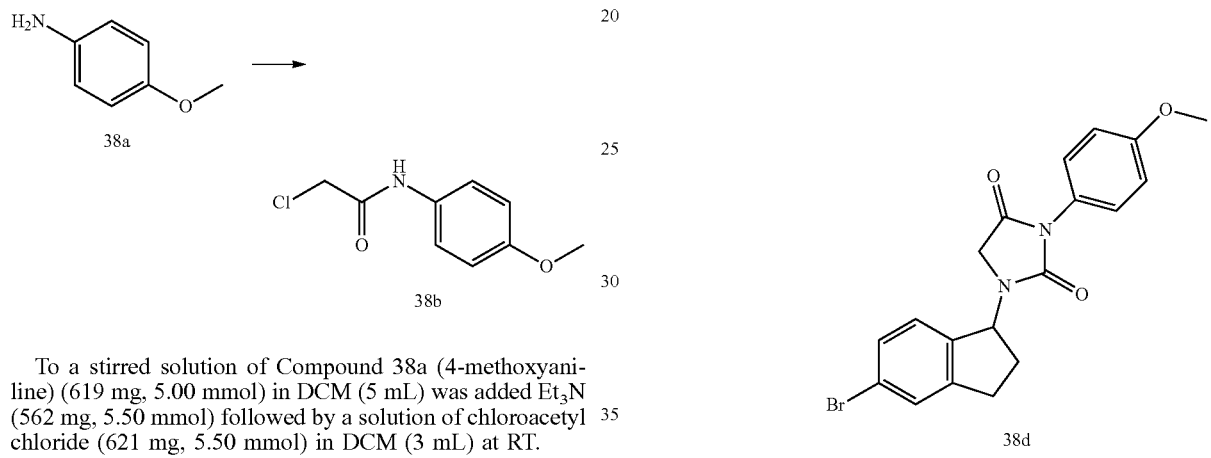

38c

38d

To a stirred solution of Compound 38a (4-methoxyaniline) (619 mg, 5.00 mmol) in DCM (5 mL) was added Et₃N (562 mg, 5.50 mmol) followed by a solution of chloroacetyl chloride (621 mg, 5.50 mmol) in DCM (3 mL) at RT.

The reaction mixture was stirred at RT for 5 hours, then diluted with DCM (20 mL) and washed with NaHCO₃ (sat.), 1N HCl (aq.) and brine. The combined organic layer dried over anhydrous MgSO₄, and the solvent was removed under reduced pressure without further purification to afford the product Compound 38b (2-chloro-N-(4-methoxyphenyl)acetamide) (1193 mg, 99%).

To a solution of Compound 38c (2-((5-bromo-2,3-dihydro-1H-inden-1-yl)amino)-N-(4-methoxyphenyl)acetamide) (300 mg, 0.80 mmol) in DCM (10 mL) was added Boc₂O (433 mg, 2.00 mmol) at RT, followed Et₃N (202 mg, 2.00 mmol) and DMAP (14 mg, 0.11 mmol).

The mixture was stirred at RT for 1 hour, then removed the solvent in vacuo and purified with column chromatography (EtOAc:n-hexane=1:4) to afford Compound 38d (1-(5-bromo-2,3-dihydro-1H-inden-1-yl)-3-(4-methoxyphenyl)imidazolidine-2,4-dione) (276 mg, 86%).

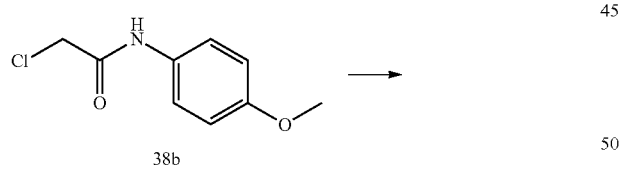

38b

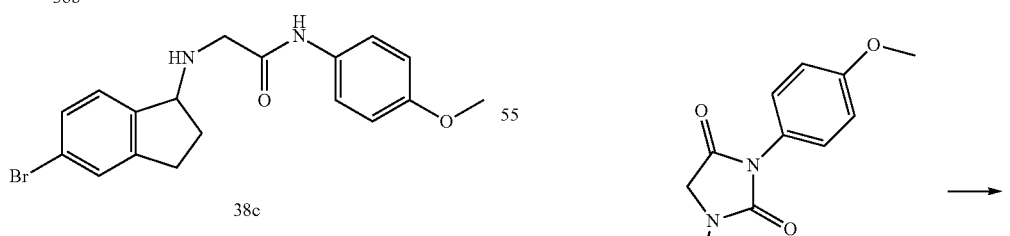

38c

38d

To a solution of Compound 38b (2-chloro-N-(4-methoxyphenyl)acetamide) (200 mg, 1.00 mmol) in ACN (5 mL) was added Compound 15e (5-bromo-2,3-dihydro-1H-inden-1-amine) (212 mg, 1.00 mmol), followed potassium iodide (166 mg, 1.00 mmol) and DIPEA (136 mg, 1.00 mmol) at RT. The mixture was stirred at RT for 5 mins then warm to 90° C. under nitrogen for 19 hours.

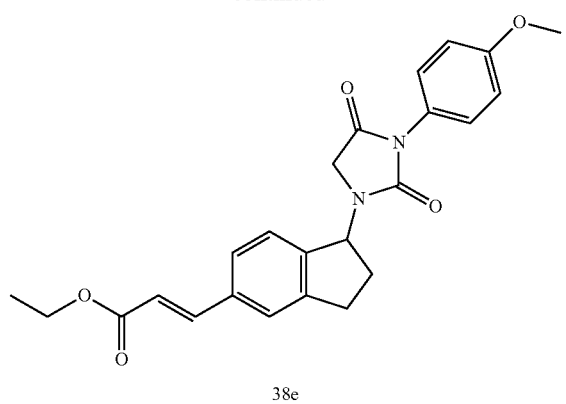

38e

To a solution of Compound 38d (1-(5-bromo-2,3-dihydro-1H-inden-1-yl)-3-(4-methoxyphenyl)imidazolidine-2,4-dione) (265 mg, 0.66 mmol) in ACN (9 mL) was added ethyl acrylate (1.8 mL, 16.52 mmol) at rt in pressure tube, followed Et₃N (9 mL), PPh₃ (259 mg, 0.99 mmol). The mixture was stirred at RT for 5 mins then degas with nitrogen, followed added Pd(OAc)₂ (89 mg, 0.40 mmol) and seal the tube. The reaction was stirred at 100° C. for 12 hours.

After cooling to RT, removed the solvent in vacuo and purified with column chromatography (EtOAc:n-hexane=1:2) to afford Compound 38e (ethyl (E)-3-(1-(3-(4-methoxyphenyl)-2,4-dioxoimidazolidin-1-yl)-2,3-dihydro-1H-inden-5-yl)acrylate) (232 mg, 83%).

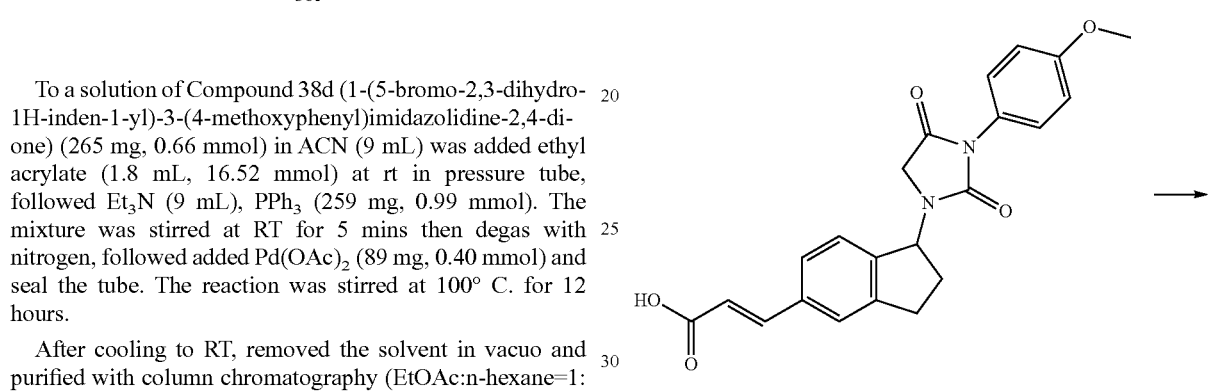

38e

38f

To a solution of Compound 38e (ethyl (E)-3-(1-(3-(4-methoxyphenyl)-2,4-dioxoimidazolidin-1-yl)-2,3-dihydro-1H-inden-5-yl)acrylate) (224 mg, 0.53 mmol) in MeOH (100 mL) was added NaOH aqueous solution (2.0 M, 10 mL) at RT.

The mixture was stirred at RT for 1 hour, then removed the solvent in vacuo then quench with HCl aqueous solution (1.0 M) to pH=3. The mixture was extracted with EtOAc, then take the organic layer washed with brine. The combined organic layer was dried over anhydrous MgSO₄. After remove the solvent, the crude product was taken the next step. Compound 38f ((E)-3-(1-(3-(4-methoxyphenyl)-2,4-dioxoimidazolidin-1-yl)-2,3-dihydro-1H-inden-5-yl)acrylic acid) (195 mg, 93%).

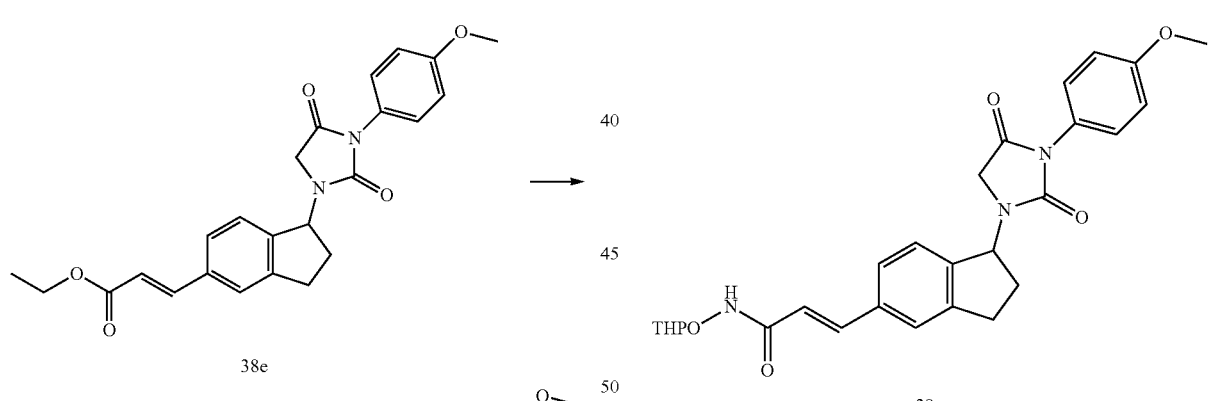

38f

38g

To a solution of Compound 38f ((E)-3-(1-(3-(4-methoxyphenyl)-2,4-dioxoimidazolidin-1-yl)-2,3-dihydro-1H-inden-5-yl)acrylic acid) (120 mg, 0.31 mmol) in DMF (10 mL) at 0° C. under nitrogen was added EDC hydrochloride (65 mg, 0.34 mmol), followed DMAP (47 mg, 0.34 mmol) and O-(Tetrahydro-2H-pyran-2-yl)hydroxylamine (40 mg, 0.34 mmol). The mixture was allowed to warm to RT and stirred for 12 hours.

After removing the solvent, the crude product was purified by column chromatography (EtOAc:n-hexane=2:1) to afford the solid Compound 38g ((E)-3-(1-(3-(4-methoxyphenyl)-2,4-dioxoimidazolidin-1-yl)-2,3-dihydro-1H-inden-5-yl)-N-((tetrahydro-2H-pyran-2-yl)oxy)acrylamide) (123 mg, 82%).

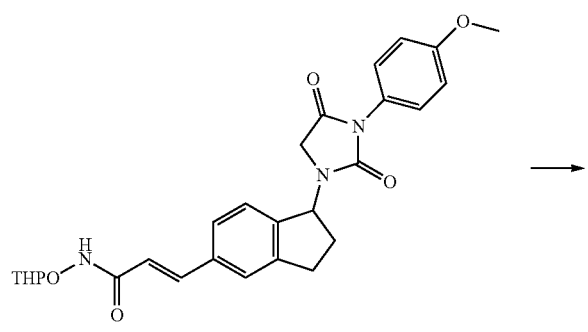

38g

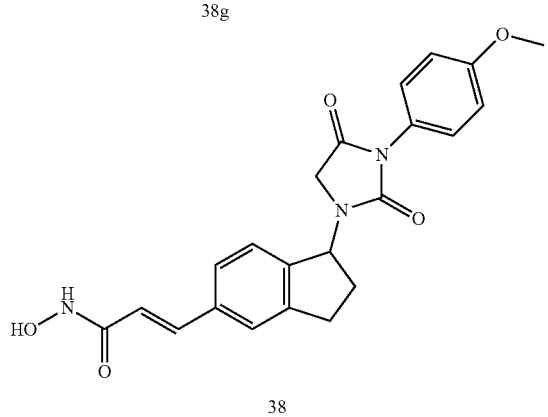

38

To a solution of Compound 38g ((E)-3-(1-(3-(4-methoxyphenyl)-2,4-dioxoimidazolidin-1-yl)-2,3-dihydro-1H-inden-5-yl)-N-((tetrahydro-2H-pyran-2-yl)oxy)acrylamide) (113 mg, 0.23 mmol) in DCM (20 mL) at RT was added hydrogen chloride solution 2.0 M in diethyl ether (excess, 2 mL).

The reaction was stirred at RT for 2 hours, then the solid was filtered out to afford the product Compound 38 (E)-N-hydroxy-3-(1-(3-(4-methoxyphenyl)-2,4-dioxoimidazolidin-1-yl)-2,3-dihydro-1H-inden-5-yl)acrylamide (60 mg, 64%).

Compound 38, $^1$H-NMR (500 MHz, CD$_3$OD): δ 7.73-7.70 (d, 1H), 7.55 (s, 1H), 7.50-7.49 (d, 1H), 7.34-7.30 (m, 3H), 7.01-6.99 (d, 2H), 6.59-6.56 (d, 1H), 5.77-5.74 (t, 1H), 4.02-3.98 (d, 1H), 3.81 (s, 3H), 3.70-3.66 (d, 1H), 3.09-3.05 (m, 1H), 2.96-2.91 (m, 1H), 2.51-2.47 (m, 1H), 2.19-2.15 (m, 1H). ESI-MS m/z calcd for C$_{22}$H$_{21}$N$_3$O$_5$ 407.14, found 408.1 [M+1-1]$^+$.

Synthesis of Compounds 39~40

Scheme 24

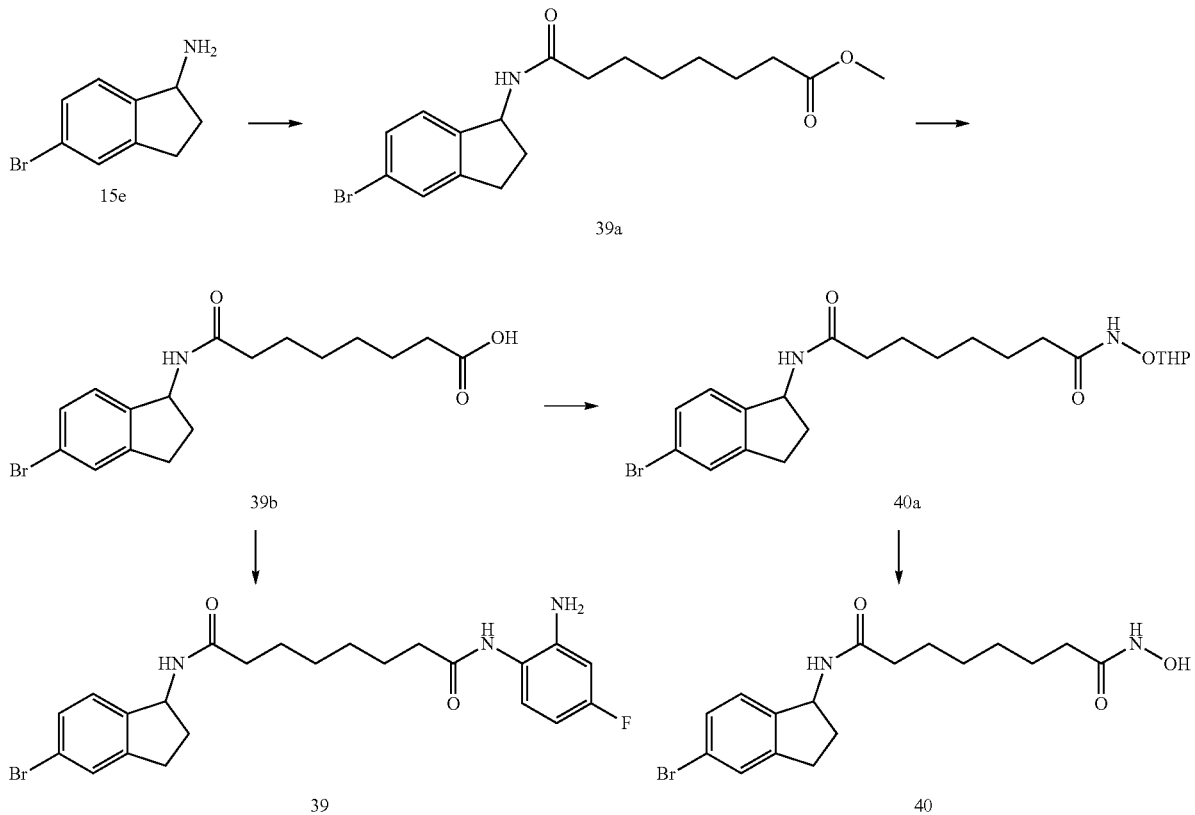

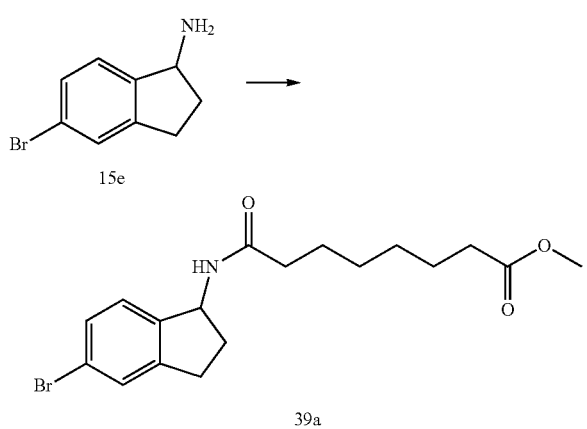

To a solution of Compound 15e (5-bromo-2,3-dihydro-1H-inden-1-amine) (0.43 g, 2.03 mmol), suberic acid monomethyl ester (0.46 g, 2.44 mmol) and DMAP (0.12 g, 0.93 mmol) in DCM (30 mL) was added DIPEA (0.39 g, 3.05 mmol) and EDCI (0.58 g, 3.05 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl and Sat. NaHCO$_3$. The organic phase was dried with MgSO$_4$ and concentrated under reduced pressure. The crude product was purified by silica gel column chromatography using ethyl acetate/hexane=2/1 as elution to afford Compound 39a (methyl 8-((5-bromo-2,3-dihydro-1H-inden-1-yl)amino)-8-oxooctanoate) (0.77 g, 2.02 mmol, yield 99%).

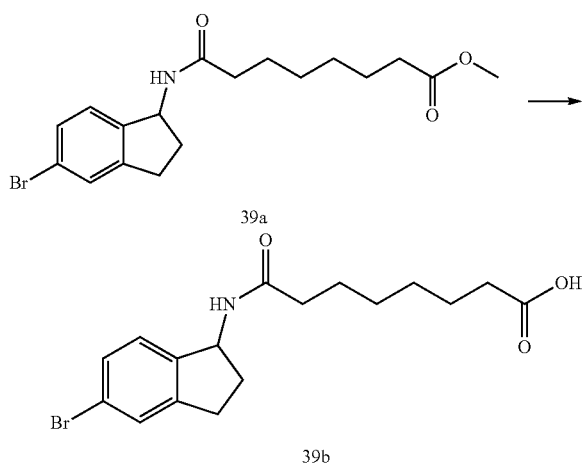

To a solution of Compound 39a (methyl 8-((5-bromo-2,3-dihydro-1H-inden-1-yl)amino)-8-oxooctanoate) (0.77 g, 2.02 mmol) in MeOH (50 mL) was added 2N NaOH (3 mL, 6.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 10% MeOH/water to give Compound 39b (8-((5-bromo-2,3-dihydro-1H-inden-1-yl)amino)-8-oxooctanoic acid) (0.61 g, 1.67 mmol, yield 82%). The product Compound 39b was used in next step without further purification.

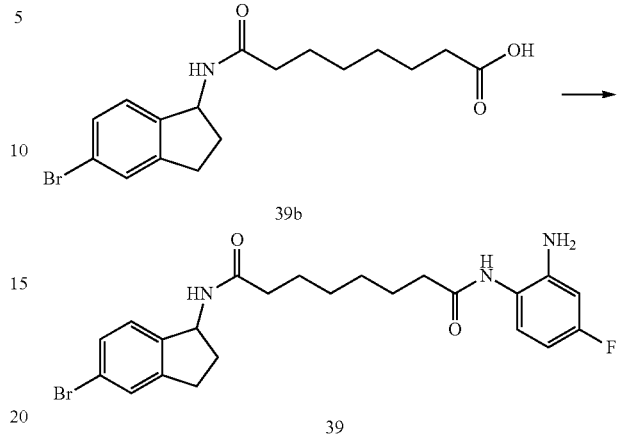

To a solution of Compound 39b (8-((5-bromo-2,3-dihydro-1H-inden-1-yl)amino)-8-oxooctanoic acid) (100 mg, 1 eq) in THF (2.7 mL, 0.1 M) at 0° C. under nitrogen was added EDC hydrochloride (78 mg, 1.5 eq), followed NMM (41 mg, 1.5 eq), HOBT (8 mg, 0.2 eq) and 4-Fluoro-1,2-phenylenediamine (41 mg, 1.2 eq).

The mixture was allowed to warm to RT and stirred overnight, then quench with NH$_4$Cl and extracted with EtOAc, then take the organic layer washed with brine. The combined organic layer was dried over anhydrous MgSO$_4$. After removing the solvent in vacuo and washed with DCM, Et$_2$O to afford the product Compound 39 (N$^1$-(2-amino-4-fluorophenyl)-N8-(5-bromo-2,3-dihydro-1H-inden-1-yl)octanediamide) (52 mg, yield 40%).

Compound 39, $^1$H-NMR (500 MHz, d$_6$-DMSO): δ 9.00 (s, 1H), 8.17-8.15 (d, 1H), 7.44 (s, 1H), 7.36-7.35 (d, 1H), 7.11-7.09 (m, 2H), 6.49-6.46 (dd, 1H), 6.31-6.27 (td, 1H), 5.23-5.19 (q, 1H), 5.11 (s, 2H), 2.92-2.78 (m, 2H), 2.36-2.34 (m, 1H), 2.30-2.27 (t, 2H), 2.13-2.10 (t, 2H), 1.79-1.75 (m, 1H), 1.58-1.55 (m, 4H), 1.32-1.30 (m, 4H). ESI-MS m/z calcd for C$_{23}$H$_{27}$BrFN$_3$O$_2$ 475.13, found 476 [M+H]$^+$.

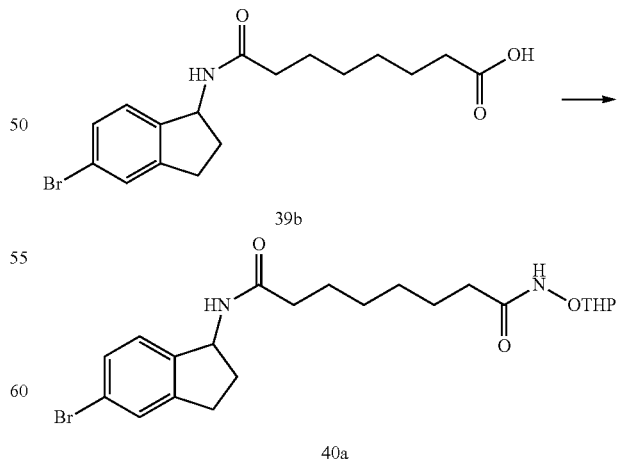

To a solution of Compound 39b (8-((5-bromo-2,3-dihydro-1H-inden-1-yl)amino)-8-oxooctanoic acid) (0.30 g, 0.82 mmol), O-(Tetrahydro-2H-pyran-2-yl)hydroxylamine (0.14 g, 1.22 mmol) and DMAP (0.05 g, 0.41 mmol) in DMF (20 mL) was added NMM (0.25 g, 2.46 mmol) and EDCI (0.23 g, 1.22 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo. The crude product was purified by silica gel column chromatography using ethyl acetate/hexane=2/1 as elution to yield the desired product Compound 40a (N1-(5-bromo-2,3-dihydro-1H-inden-1-yl)-N8-((tetrahydro-2H-pyran-2-yl)oxy)octanediamide) (0.19 g, 0.40 mmol, yield 49%).

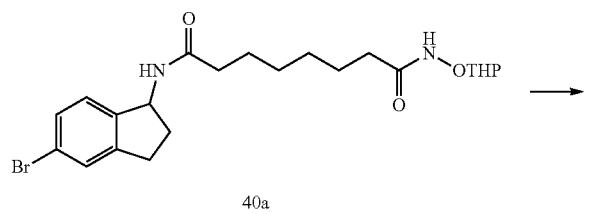

40a

-continued

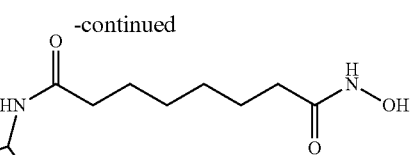

40

To a solution of Compound 40a (N1-(5-bromo-2,3-dihydro-1H-inden-1-yl)-N8-((tetrahydro-2H-pyran-2-yl)oxy)octanediamide) (0.19 g, 0.40 mmol) in CH$_2$Cl$_2$ (20 mL) was added 2N HCl (excess, in diethyl ether). After addition, the reaction mixture was stirred for 3 hours.

The reaction was monitored by TLC. After reaction was completed, the solvent was removed under reduced pressure. The residue was diluted with diethyl ether, the precipitated solid was collected by filtration to afford Compound 40 (N1-(5-bromo-2,3-dihydro-1H-inden-1-yl)-N8-hydroxyoctanediamide) (0.04 g, 0.11 mmol, yield 28%).

Compound 40, $^1$H-NMR (500 MHz, CD$_3$OD): δ 7.40 (s, 1H), 7.34-7.33 (d, 1H), 7.14-7.12 (d, 1H), 5.33-5.31 (1, 1H), 3.02-2.97 (m, 1H), 2.90-2.83 (m, 1H), 2.50-2.48 (m, 1H), 2.30-2.22 (m, 3H), 2.10-2.07 (t, 1H), 1.88-1.84 (m, 1H), 1.66-1.62 (m, 4H), 1.37 (br, 4H). ESI-MS m/z calcd for C$_{17}$H$_{23}$BrN$_2$O$_3$ 383.09, found 406 [M+Na]$^+$.

Synthesis of Compounds 41~42

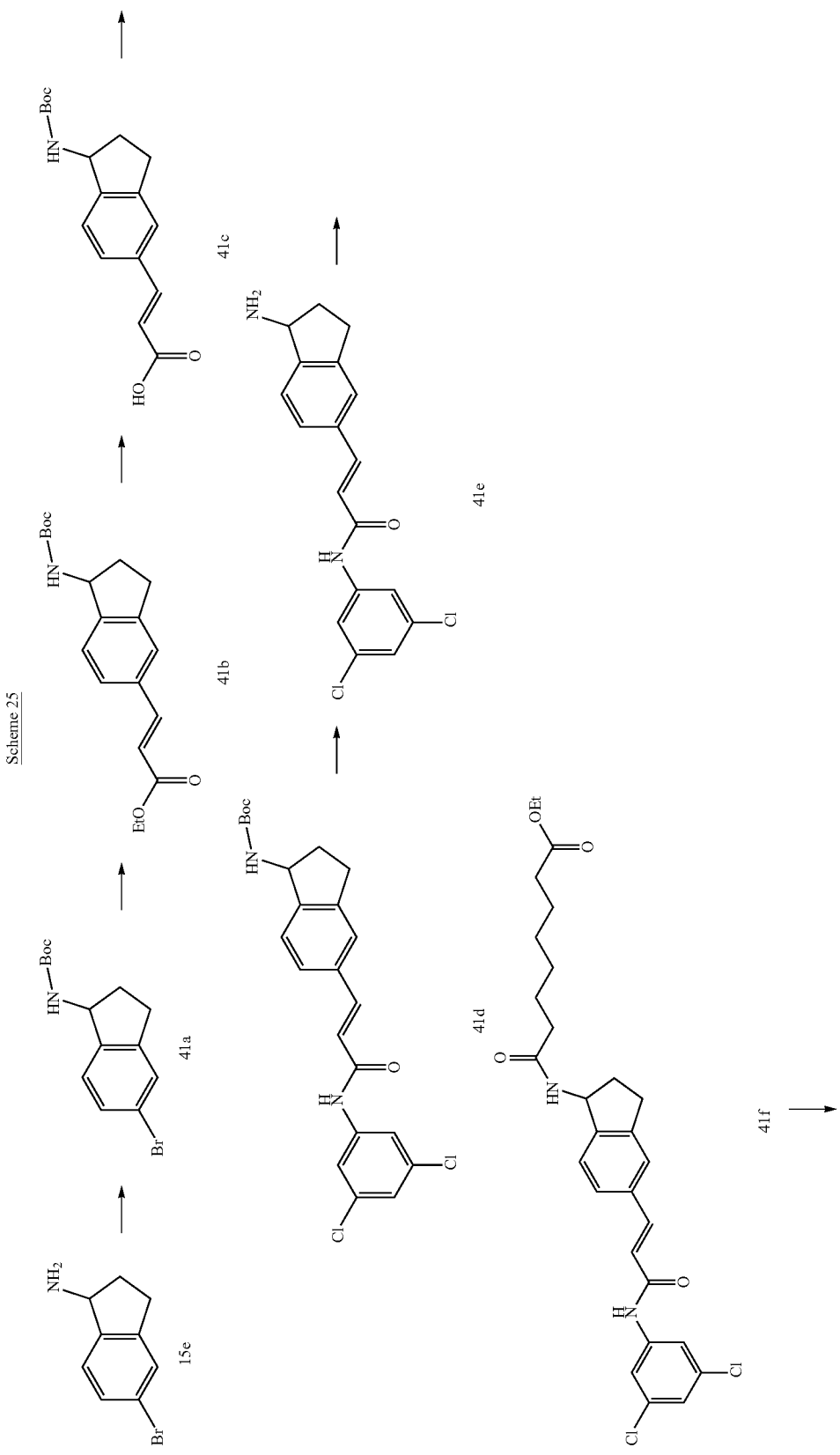
Scheme 25

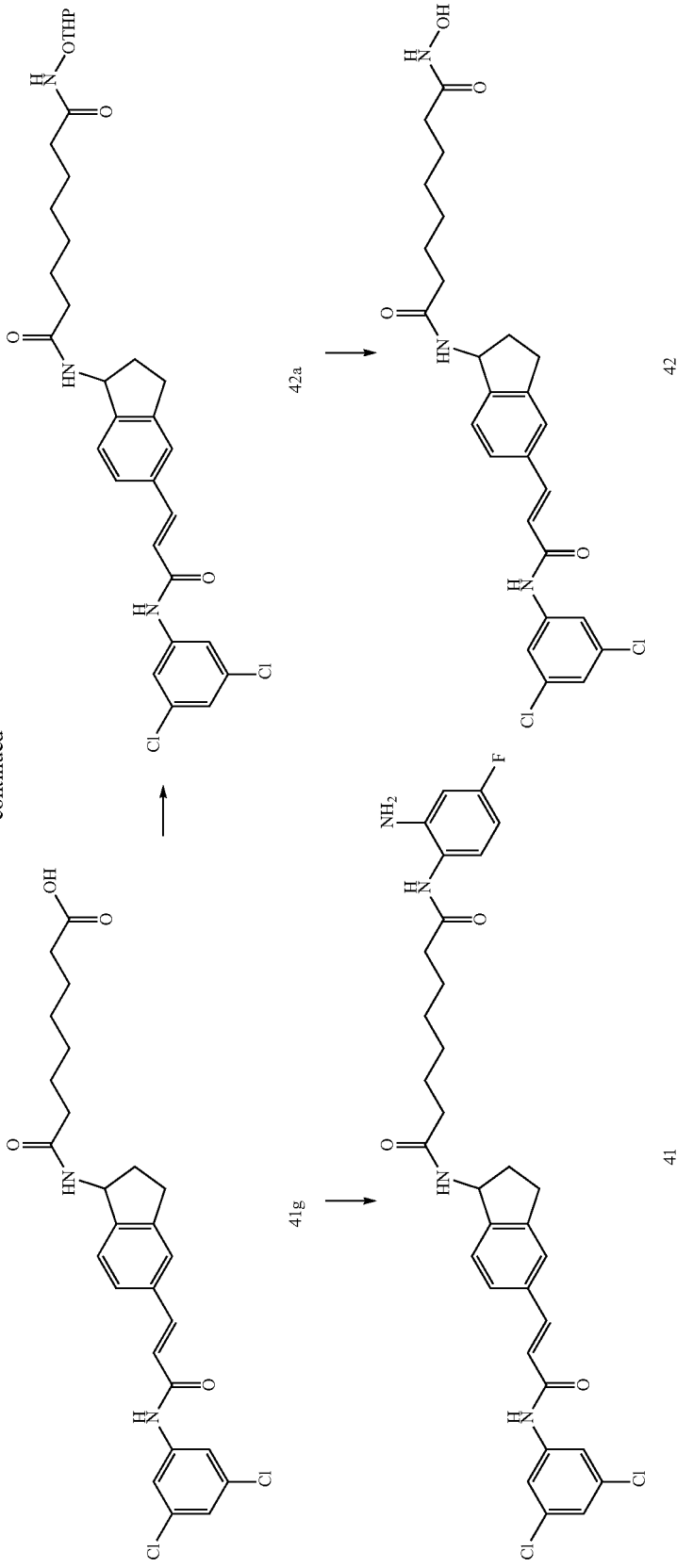

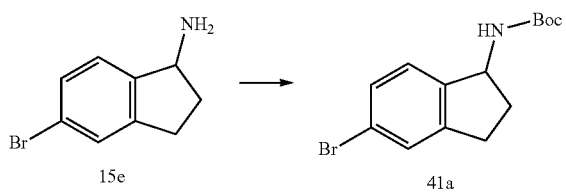 [SMILES: NC1CCc2cc(Br)ccc21 ; CC(C)(C)OC(=O)NC1CCc2cc(Br)ccc21]

A solution of Compound 15e (5-bromo-2,3-dihydro-1H-inden-1-amine) (1.0 g, 4.71 mmol), (Boc)₂O (1.24 g, 5.7 mmol) and DMAP (635.4 mg, 5.2 mmol) in THF (30 mL) was stirred at RT for 48 hours.

The mixture was extracted with EtOAc and NH₄Cl (aq.). The organic layer was dried over MgSO₄ and concentrated in vacuo and purified by flash chromatography (EtOAc./Hexane=1:5) to provide product Compound 41a (tert-butyl (5-bromo-2,3-dihydro-1H-inden-1-yl)carbamate) (1.0 g, yield 68%).

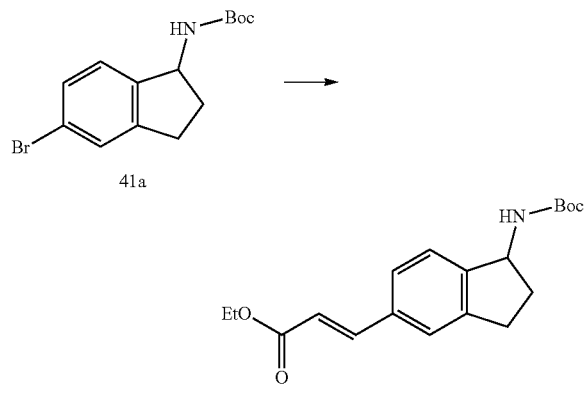

A solution of Compound 41a (tert-butyl (5-bromo-2,3-dihydro-1H-inden-1-yl)carbamate) (1.0 g, 3.2 mmol), ethyl acrylate (0.7 mL, 6.4 mmol), triphenylphosphine (0.34 g, 1.28 mmol) in TEA (0.45 mL, 3.2 mmol) and DMF (20 mL) was degassed by bubbling argon for 3 mins. Pd(OAc)₂ (70.8 mg, 0.32 mmol) was added, and vacuum/argon was applied three times. The reaction mixture was stirred under argon at 100° C. for 24 hours.

The mixture was extracted with EtOAc and NH₄Cl (aq.). The organic layer was dried over MgSO₄ and concentrated in vacuo and purified by flash chromatography (EtOAc:Hex.=1:4) to provide colorless oil product Compound 41b (ethyl (E)-3-(1-((tert-butoxycarbonyl)amino)-2,3-dihydro-1H-inden-5-yl)acrylate) (0.35 g, yield 33%).

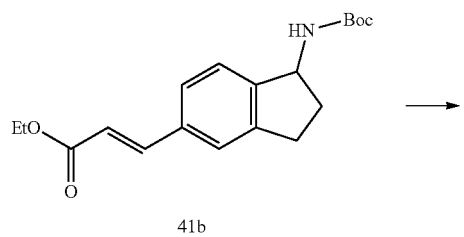

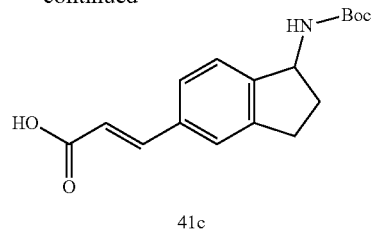

To a solution of Compound 41b (ethyl (E)-3-(1-((tert-butoxycarbonyl)amino)-2,3-dihydro-1H-inden-5-yl)acrylate) (0.35 g, 1.06 mmol) in MeOH (10 mL) was added 2N NaOH solution (0.65 mL) at RT and stirred for overnight.

The reaction mixture was concentrated to remove the organic solvent. The residue was diluted with water and acidified to pH=4 with 2N HCl$_{(aq.)}$. The resulting white precipitate was filtered, washed with H₂O and ether, then dried in vacuo to provide the product as a solid product Compound 41c ((E)-3-(1-((tert-butoxycarbonyl)amino)-2,3-dihydro-1H-inden-5-yl)acrylic acid) (193.0 mg, yield 60%).

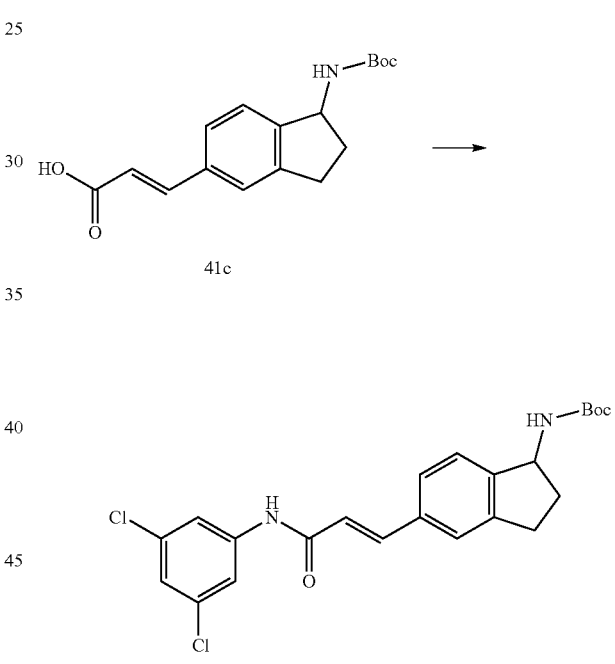

To a stirred solution of 3,5-Dichloroaniline (194.4 mg, 1.2 mmol) and DMAP (183.3 mg, 1.5 mmol) in DCM (10 mL) was added Compound 41c ((E)-3-(1-((tert-butoxycarbonyl) amino)-2,3-dihydro-1H-inden-5-yl)acrylic acid) (300.0 mg, 1.0 mmol) in one portion, followed by the addition of EDCI (230.0 mg, 1.2 mmol) in one portion at RT. The resulting mixture was stirred at RT for overnight.

After which time it was washed successively with NaHCO₃(aq.) and brine. The organic layer was dried over MgSO₄ and concentrated in vacuo to give the crude material. The resulting residue was purified by silica gel column chromatography (EtOAc:Hex.=1:4) to provide the product Compound 41d (tert-butyl (E)-(5-(3-((3,5-dichlorophenyl) amino)-3-oxoprop-1-en-1-yl)-2,3-dihydro-1H-inden-1-yl) carbamate) (227.5 mg, yield 51%).

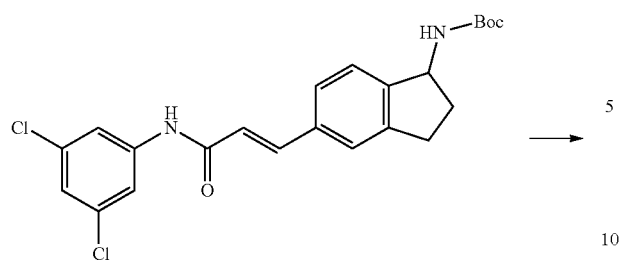
41d
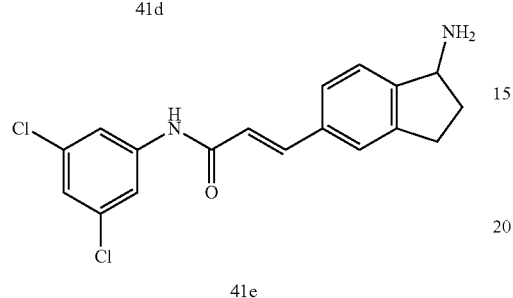
41e
To a solution of Compound 41d (tert-butyl (E)-(5-(3-((3,5-dichlorophenyl)amino)-3-oxoprop-1-en-1-yl)-2,3-dihydro-1H-inden-1-yl)carbamate) (50.0 mg, 0.1 mmol) in MeOH (5 mL) was added 2N HCl$_{(aq.)}$ (0.8 mL) at 0° C. The mixture was stirred at RT for 2 hours.
The mixture was concentrated in vacuo to provide the product Compound 41e ((E)-3-(1-amino-2,3-dihydro-1H-inden-5-yl)-N-(3,5-dichlorophenyl)acrylamide) (37.5 mg, yield 98%).
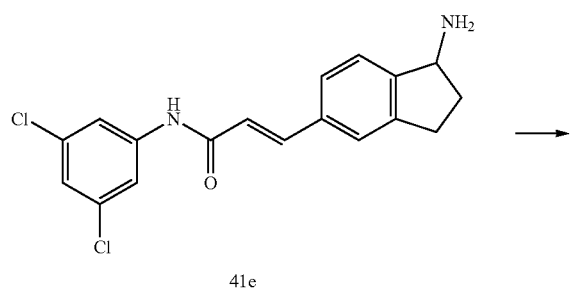
41e
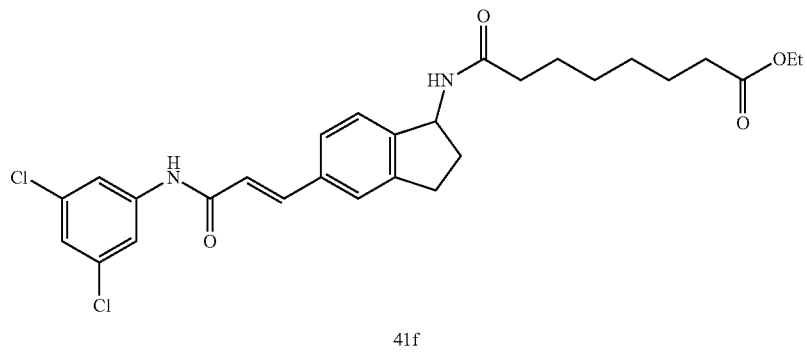
41f To a stirred solution of suberic acid monomethyl ester (115.4 mg, 0.61 mmol) and DMAP (93.5 mg, 0.77 mmol) in DCM (10 mL) was added EDCI (117.5 mg, 0.61 mmol) in one portion, followed by addition of Compound 41e ((E)-3-(1-amino-2,3-dihydro-1H-inden-5-yl)-N-(3,5-dichlorophenyl)acrylamide) (177.5 mg, 0.51 mmol) in one portion at RT. The resulting mixture was stirred at RT overnight.

After which time it was washed successively with $NH_4Cl$ (aq.) and brine. The organic layer was dried over $MgSO_4$ and concentrated in vacuo to give the crude material. The resulting residue was purified by silica gel column chromatography (EtOAc:Hex.=1:3) to provide the product Compound 41f (methyl (E)-8-((5-(3-((3,5-dichlorophenyl)amino)-3-oxoprop-1-en-1-yl)-2,3-dihydro-1H-inden-1-yl)amino)-8-oxooctanoate) (232.0 mg, yield 88%).

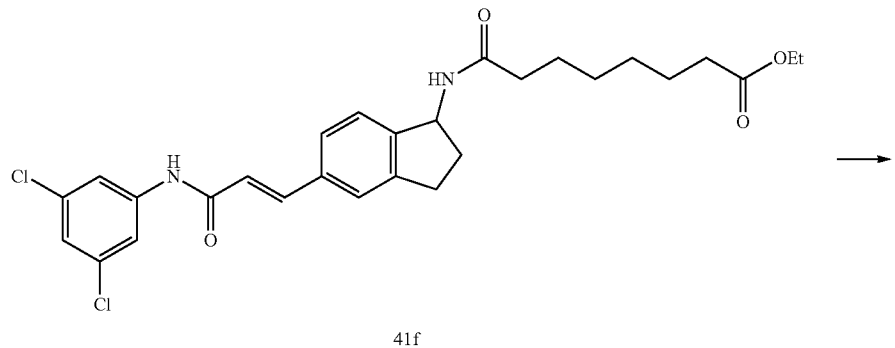

41f

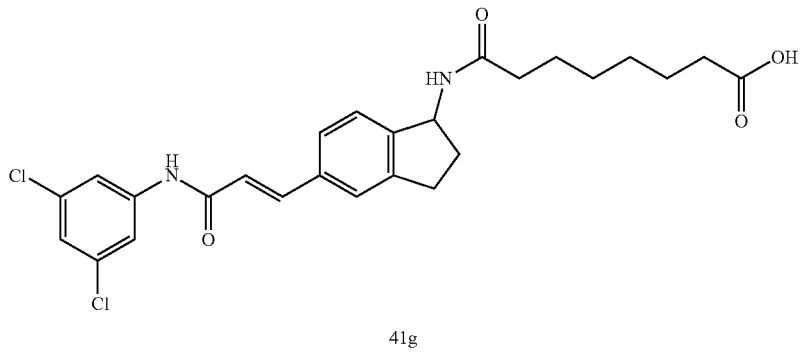

41g

To a solution of Compound 41f (methyl (E)-8-((5-(3-((3,5-dichlorophenyl)amino)-3-oxoprop-1-en-1-yl)-2,3-dihydro-1H-inden-1-yl)amino)-8-oxooctanoate) (232.0 mg, 0.45 mmol) in MeOH (5 mL) was added 2N NaOH solution (0.5 mL) at RT and stirred for overnight.

The reaction mixture was concentrated to remove the organic solvent. The residue was diluted with water and acidified to pH=4 with 2N $HCl_{(aq.)}$. The resulting white precipitate was filtered, washed with $H_2O$ and ether, then dried in vacuo to provide the product as a solid product Compound 41g ((E)-8-((5-(3-((3,5-dichlorophenyl)amino)-3-oxoprop-1-en-1-yl)-2,3-dihydro-1H-inden-1-yl)amino)-8-oxooctanoic acid) (133.4 mg, yield 59%).

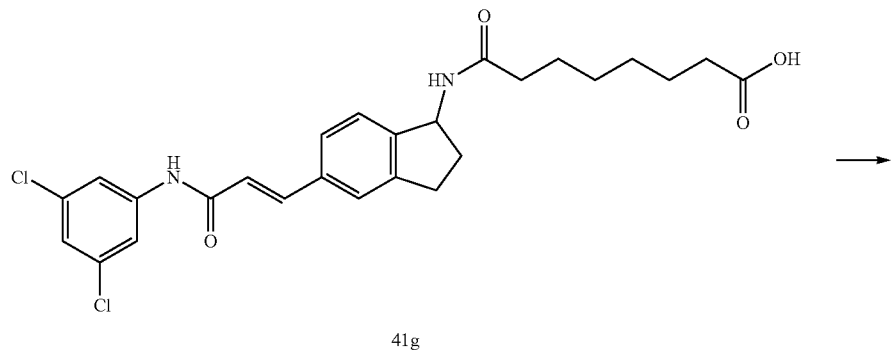

41g

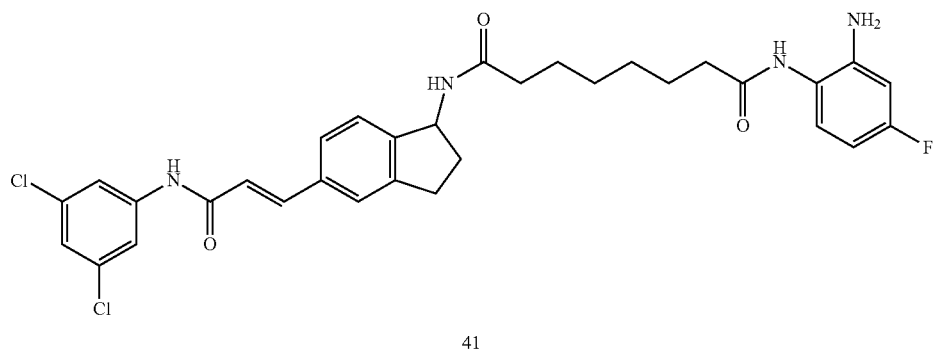

41

To a stirred solution of 4-Fluoro-1,2-phenylenediamine (15.1 mg, 0.12 mmol) and DMAP (73.3 mg, 0.6 mmol) in DCM (3 mL) was added Compound 41g ((E)-N$^1$-(5-(3-((3,5-dichlorophenyl)amino)-3-oxoprop-1-en-1-yl)-2,3-dihydro-1H-inden-1-yl)-N$^8$-hydroxyoctanediamide) (60.0 mg, 0.12 mmol) in one portion, followed by addition of EDCI (27.6 mg, 0.14 mmol) in one portion at RT. The resulting mixture was stirred at RT overnight.

After which time it was washed successively with NH$_4$Cl (aq.) and brine. The organic layer was dried over MgSO$_4$ and concentrated in vacuo to give the crude material. The resulting residue was purified by recrystallization (DCM: Ether=1:1) to provide the solid product Compound 41 ((E)-N$^1$-(2-amino-4-fluorophenyl)-N$^8$-(5-(3 #3,5-dichlorophenyl)amino)-3-oxoprop-1-en-1-yl)-2,3-dihydro-1H-inden-1-yl)octanediamide) (3.3 mg, yield: 5%).

Compound 41, $^1$H-NMR (500 MHz, CD$_3$OD): δ 7.71 (s, 2H), 7.67 (s, 1H), 7.50 (s, 1H), 7.47-7.46 (d, 1H), 7.29-7.28 (d, 1H), 7.16 (s, 1H), 7.03-7.00 (m, 1H), 6.73-6.70 (d, 1H), 6.54-6.51 (d, 1H), 6.38-6.34 (t, 1H), 5.49-5.39 (t, 1H), 3.06-3.01 (m, 1H), 2.93-2.87 (m, 1H), 2.54-2.52 (m, 1H), 2.42-2.39 (t, 2H), 2.27-2.25 (t, 2H), 1.91-1.87 (m, 1H), 1.74-1.71 (m, 4H), 1.45 (s, 4H). ESI-MS m/z calcd for C$_{32}$H$_{33}$Cl$_2$FN$_4$O$_3$ 610.19, found 633.2[M+Na]$^+$.

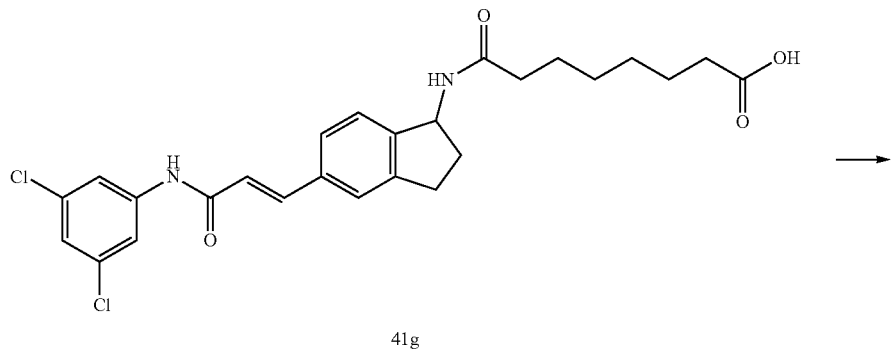

41g

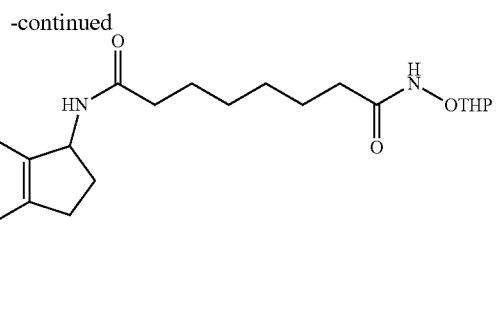

42a

To a stirred solution of O-(Tetrahydro-2H-pyran-2-yl)hydroxylamine (17.2 mg, 0.15 mmol) and DMAP (53.9 mg, 0.44 mmol) in DCM (5 mL) was added Compound 41g ((E)-8-((5-(3-((3,5-dichlorophenyl)amino)-3-oxoprop-1-en-1-yl)-2,3-dihydro-1H-inden-1-yl)amino)-8-oxooctanoic acid) (74.0 mg, 0.15 mmol) in one portion, followed by addition of EDCI (28.2 mg, 0.22 mmol) in one portion at RT. The resulting mixture was stirred at RT overnight.

After which time it was washed successively with NH$_4$Cl (aq.) and brine. The organic layer was dried over MgSO$_4$ and concentrated in vacuo to give the crude material. The resulting residue was purified by silica gel column chromatography (EtOAc:Hex.=1:2) to provide the product Compound 42a (E)-N$^1$-(5-(3-((3,5-dichlorophenyl)amino)-3-oxoprop-1-en-1-yl)-2,3-dihydro-1H-inden-1-yl)-N$^8$-((tetrahydro-2H-pyran-2-yl)oxy)octanediamide (76.0 mg, yield 84%).

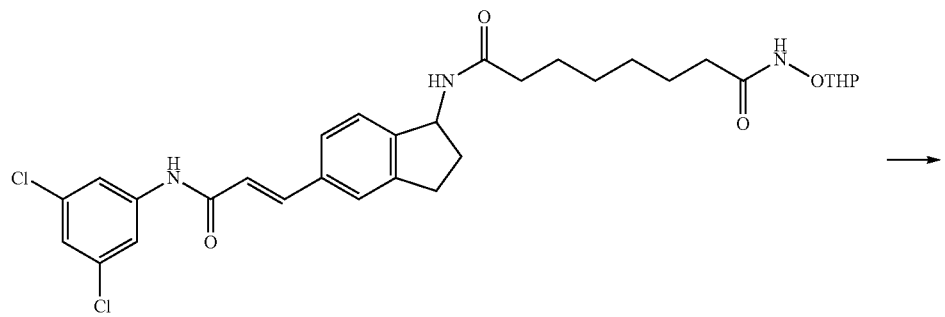

42a

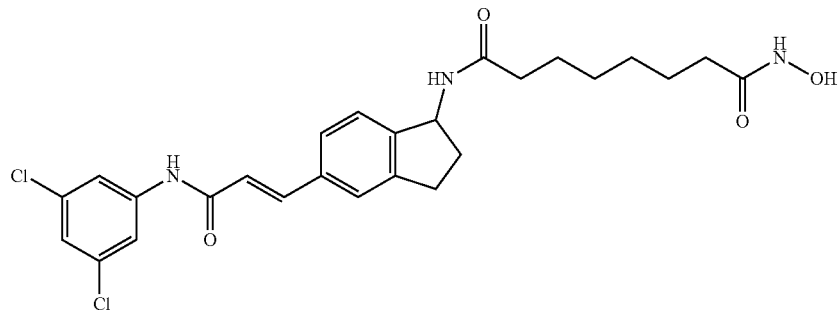

42

A solution of Compound 42a ((E)-N$^1$-(5-(3-((3,5-dichlorophenyl)amino)-3-oxoprop-1-en-1-yl)-2,3-dihydro-1H-inden-1-yl)-N$^8$-((tetrahydro-2H-pyran-2-yl)oxy)octanediamide) (76.0 mg, 0.13 mmol) in DCM (10 mL) was added 2N HCl in ether (2.0 mL) at 0° C. The mixture was stirred at RT for 5 hours.

The mixture was concentrated and washed with DCM to provide the product Compound 42 ((E)-N$^1$-(5-(3-((3,5-dichlorophenyl)amino)-3-oxoprop-1-en-1-yl)-2,3-dihydro-1H-inden-1-yl)-N$^8$-hydroxyoctanediamide) (26.7 mg, yield 40%).

Compound 42, $^1$H-NMR (500 MHz, DMSO): δ 10.51 (s, 1H), 10.33 (s, 1H), 8.65 (s, 1H), 8.19-8.17 (d, 1H), 7.76 (s, 2H), 7.66-7.63 (d, 1H), 7.60-7.47 (m, 2H), 7.27 (s, 1H), 7.23-7.22 (d, 1H), 6.75-6.71 (d, 1H), 5.30-5.29 (m, 1H), 2.94-2.93 (m, 1H), 2.84-2.83 (m, 1H), 2.39-2.36 (m, 2H), 2.19-2.12 (m, 2H), 1.94-1.92 (m, 2H), 1.54-1.48 (m, 4H), 1.26-1.24 (m, 4H). ESI-MS m/z calcd for C$_{26}$H$_{29}$Cl$_2$N$_3$O$_4$ 517.15, found 518.2 [M+H]$^+$.

Synthesis of Compounds 43~44

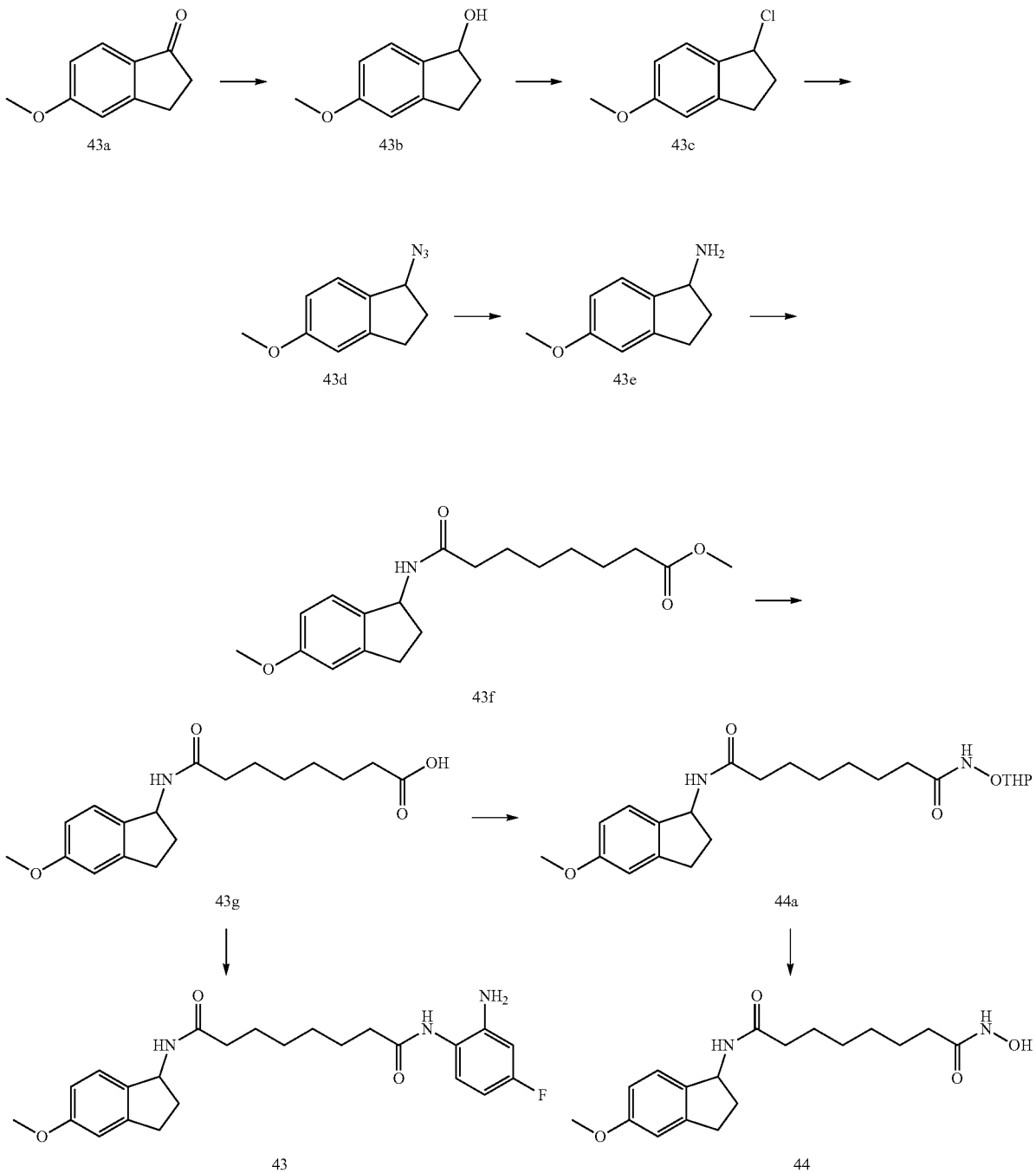

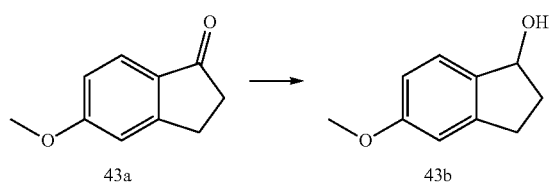

To a solution of Compound 43a (5-methoxy-2,3-dihydro-1H-inden-1-one) (1.50 g, 9.25 mmol) in THF/water (25 mL, 4:1) was added NaBH₄ (0.35 g, 9.25 mmol) at 0° C. After addition, the reaction mixture was slowly warmed to RT and stirred for 2 hrs.

After reaction was completed, the reaction mixture was quenched with Sat. NH₄Cl. The solvent was removed under reduced pressure. The residue was diluted with EtOAc and washed with sat. NH₄Cl. The organic phase was dried with MgSO₄ and concentrated under reduced pressure to obtain the desired product Compound 43b (5-methoxy-2,3-dihydro-1H-inden-1-ol) (1.44 g, 8.81 mmol, yield 95%). The crude product was used in the next step without further purification.

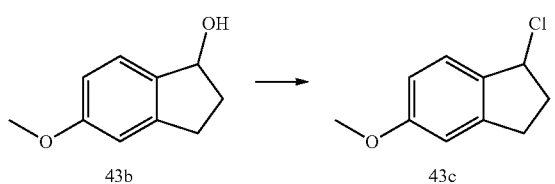

To a solution of Compound 43b (5-methoxy-2,3-dihydro-1H-inden-1-ol) (1.06 g, 6.43 mmol) in DCM (50 mL) was added SOCl₂ (2 mL) at 0° C. After addition, the reaction mixture was slowly warmed to RT and stirred for overnight.

After reaction was completed, the solvent was removed under reduced pressure. The residual was diluted with EtOAc and washed with brine. The combined organic layers were washed with brine and dried over MgSO₄ and concentrated in vacuo to get Compound 43c (1-chloro-5-methoxy-2,3-dihydro-1H-indene) (1.05 g, 5.75 mmol, yield 89%). The crude product Compound 43c was used in the next step without further purification.

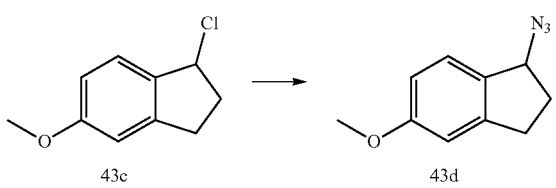

To a solution of Compound 43c (1-chloro-5-methoxy-2,3-dihydro-1H-indene) (1.05 g, 5.75 mmol) in DMF (40 mL) was added NaN₃ (0.75 g, 11.50 mmol) at 0° C. After addition, the reaction mixture was slowly warmed to RT and stirred for overnight.

After reaction was completed, the reaction mixture was diluted with EtOAc and washed with water and brine. The combined organic layers were washed with brine and dried over MgSO₄ and concentrated in vacuo to obtain Compound 43d (1-azido-5-methoxy-2,3-dihydro-1H-indene) (1.01 g, 5.34 mmol, yield 93%). The crude product Compound 43d was used in the next step without further purification.

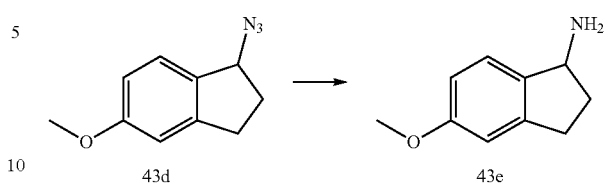

To a solution of Compound 43d (1-azido-5-methoxy-2,3-dihydro-1H-indene) (0.33 g, 1.74 mmol) in MeOH (50 mL) was added Pd/C (0.07 g). After addition, the reaction mixture was stirred under H₂ for 3 hours.

After reaction was completed, the solvent was removed under reduced pressure. Pd/C was filed off through a pad of celite and washed with EtOAc. The filtrate was concentrated in vacuo to afford Compound 43e (5-methoxy-2,3-dihydro-1H-inden-1-amine) (0.25 g, 1.53 mmol, yield 88%).

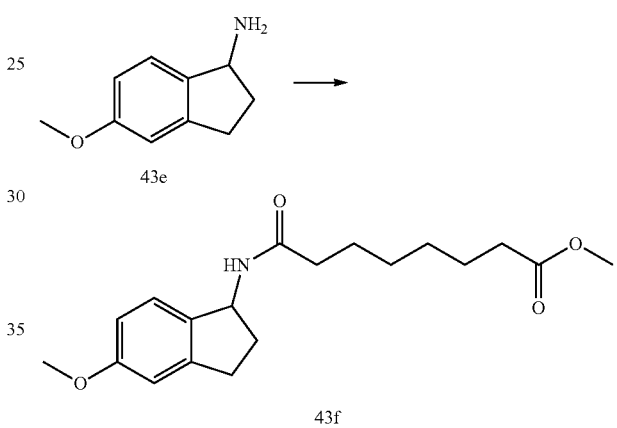

To a solution of Compound 43e (5-methoxy-2,3-dihydro-1H-inden-1-amine) (0.31 g, 1.87 mmol), suberic acid monomethyl ester (0.46 g, 2.44 mmol) and DMAP (0.12 g, 0.93 mmol) in DCM (30 mL) was added DIPEA (0.73 g, 5.63 mmol) and EDCI (0.54 g, 2.81 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl and Sat. NaHCO₃. The organic phase was dried with MgSO₄ and concentrated under reduced pressure. The crude product was purified by silica gel column chromatography using ethyl acetate/hexane=2/1 as elution to afford Compound 43f (methyl 8-((5-methoxy-2,3-dihydro-1H-inden-1-yl)amino)-8-oxooctanoate) (0.62 g, 1.86 mmol, yield 99%).

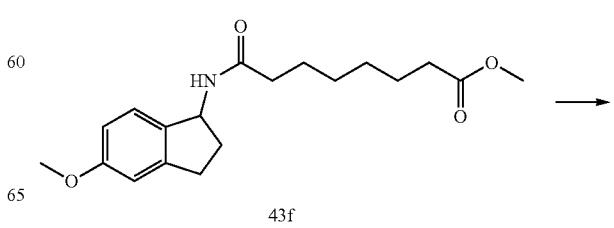

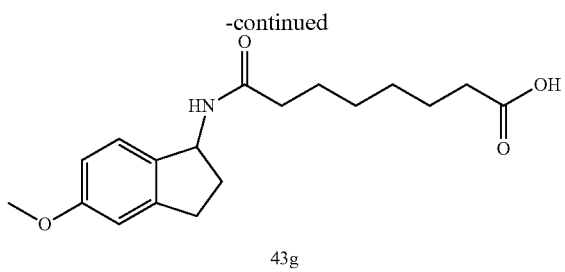

43g

To a solution of Compound 43f (methyl 8-((5-methoxy-2,3-dihydro-1H-inden-1-yl)amino)-8-oxooctanoate) (0.62 g, 1.86 mmol) in MeOH (50 mL) was added 2N NaOH (2 mL, 4.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 10% MeOH/water to give Compound 43g (8-((5-methoxy-2,3-dihydro-1H-inden-1-yl)amino)-8-oxooctanoic acid) (0.55 g, 1.72 mmol, yield 93%). The product Compound 43g was used in next step without further purification.

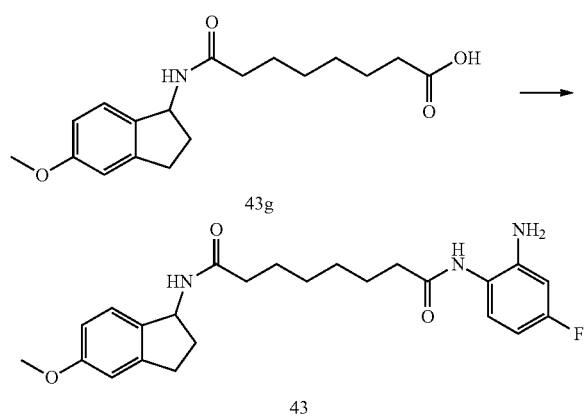

43g

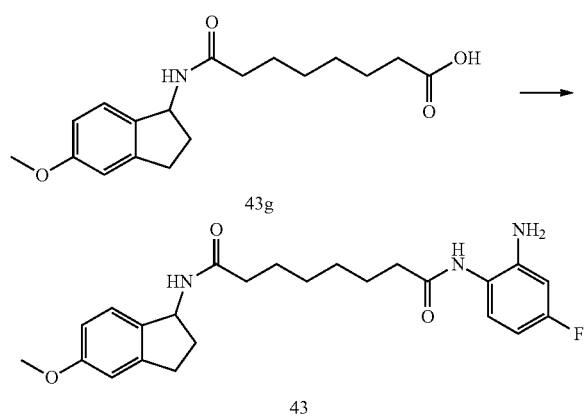

43

To a solution of Compound 43g (8-((5-methoxy-2,3-dihydro-1H-inden-1-yl)amino)-8-oxooctanoic acid) (0.17 g, 0.52 mmol), 4-fluoro-1,2-phenylenediamine (0.08 g, 0.63 mmol) and DMAP (0.03 g, 0.26 mmol) in THF (20 mL) was added NMM (0.08 g, 0.78 mmol) and EDCI (0.15 g, 0.78 mmol) at 0° C. After addition, the reaction mixture was slowly warmed to RT and stirred for overnight.

After reaction was completed, the solvent was removed under reduced pressure. The residual was diluted the reaction mixture was diluted with EtOAc and washed with Sat. NH$_4$Cl. The combined organic layers were washed with brine and dried over MgSO$_4$ and concentrated in vacuo. The crude product was washed with diethyl ether to give Compound 43 (N1-(2-amino-4-fluorophenyl)-N8-(5-methoxy-2,3-dihydro-1H-inden-1-yl)octanediamide) (0.06 g, 0.14 mmol, yield 28%).

Compound 43, $^1$H-NMR (500 MHz, CD$_3$OD): δ 7.13-7.11 (d, 1H), 7.03-7.00 (t, 1H), 6.79 (s, 1H), 6.75-6.74 (d, 1H), 6.54-6.51 (m, 1H), 6.39-6.35 (m, 1H), 5.32-5.29 (t, 1H), 3.76 (s, 3H), 3.00-2.94 (m, 1H), 2.85-2.78 (m, 1H), 2.51-2.39 (m, 4H), 2.25-2.22 (t, 2H), 1.88-1.80 (m, 1H), 1.74-1.67 (m, 5H), 1.48-1.43 (m, 2H). ESI-MS m/z calcd for C$_{24}$H$_{30}$FN$_3$O$_3$ 427.23, found 450 [M+Na]$^+$.

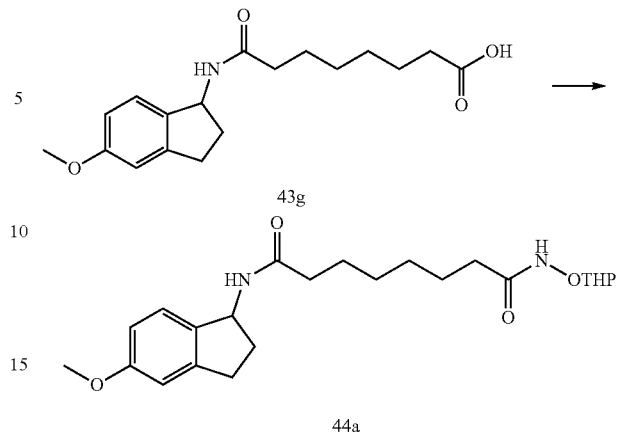

43g

44a

To a solution of Compound 43g (8-((5-methoxy-2,3-dihydro-1H-inden-1-yl)amino)-8-oxooctanoic acid) (105 mg, 0.33 mmol) in DCM (3 mL) at 0° C. under nitrogen was added EDC hydrochloride (69 mg, 0.36 mmol), followed DMAP (44 mg, 0.36 mmol) and O-(Tetrahydro-2H-pyran-2-yl)hydroxylamine (43 mg, 0.36 mmol). The mixture was allowed to warm to RT and stirred for 5 hours.

The reaction mixture was diluted with ether and extracted with NaHCO$_3$ (sat.), followed NH$_4$Cl (sat.) and brine. The combined organic layer was dried over anhydrous MgSO$_4$. After removed the solvent, the crude product was purified by column chromatography (EA:n-hexane=2:1) to afford the product Compound 44a (N$^1$-(5-methoxy-2,3-dihydro-1H-inden-1-yl)-N$^8$-((tetrahydro-2H-pyran-2-yl)oxy)octanediamide) (130 mg, 95%).

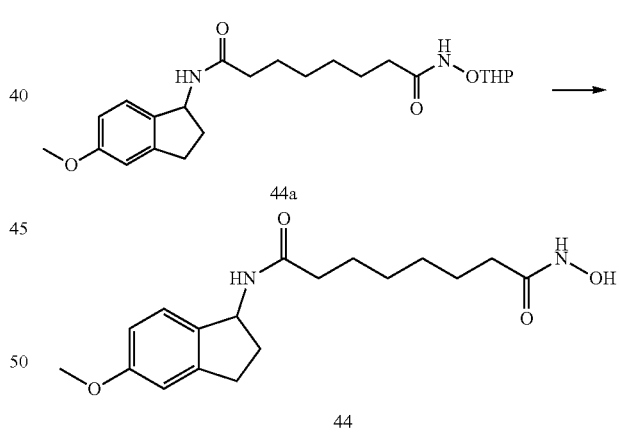

44a

44

To a solution of Compound 44a (N$^1$-(6-methoxy-1,2,3,4-tetrahydronaphthalen-1-yl)-N$^8$-((tetrahydro-2H-pyran-2-yl)oxy)octanediamide) (36 mg, 0.09 mmol) in DCM (1 mL) at RT was added hydrogen chloride solution 2.0 M in diethyl ether (excess, 1 mL). The reaction was stirred at RT for 4 hours.

Thereafter, the solid was filtered out to afford the product Compound 44 (N$^1$-hydroxy-N$^8$-(6-methoxy-1,2,3,4-tetrahydronaphthalen-1-yl)octanediamide) (22 mg, 53%).

Compound 44, $^1$H-NMR (500 MHz, CD$_3$OD): δ 7.12-7.11 (d, 1H), 6.79 (s, 1H), 6.76-6.74 (d, 1H), 5.31-5.28 (t, 1H), 3.76 (s, 3H), 3.00-2.95 (m, 1H), 2.85-2.80 (m, 1H), 2.23-2.20 (t, 2H), 2.10-2.07 (t, 2H), 2.04-2.03 (m, 1H), 1.86-1.82 (m, 1H), 1.65-1.62 (m, 4H), 1.40-1.36 (m, 4H). ESI-MS m/z calcd for $C_{18}H_{26}N_2O_4$ 334.18, found 357.1 $[M+Na]^+$.

Synthesis of Compound 45

Scheme 27

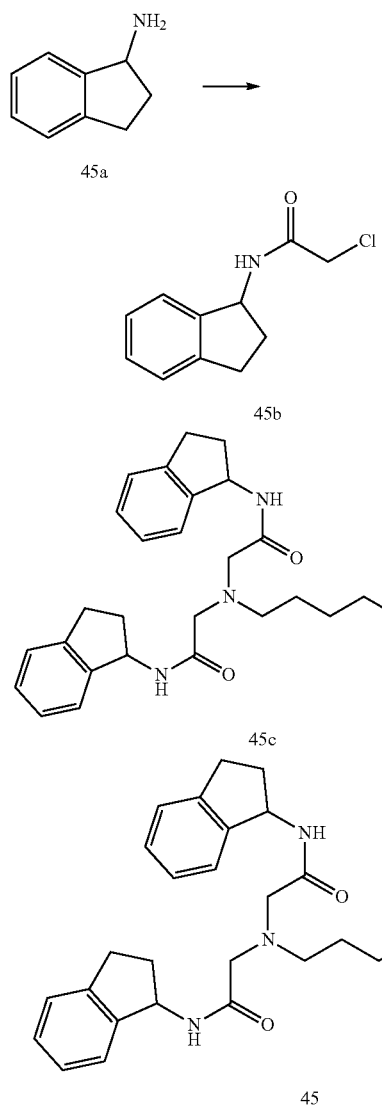

4.50 mmol) at 0° C. After addition, the reaction mixture was slowly warmed to RT and stirred for 1 hour.

After reaction was completed, the solvent was removed under reduced pressure. The residual was diluted with EtOAc and washed with Sat. $NH_4Cl$ and Sat. $NaHCO_3$. The organic phase was dried with $MgSO_4$ and concentrated under reduced pressure. The crude product was purified by silica gel column chromatography using ethyl acetate/hexane=1/4 as elution to afford Compound 45b (2-chloro-N-(2,3-dihydro-1H-inden-1-yl)acetamide) (0.47 g, 2.56 mmol, yield 50%).

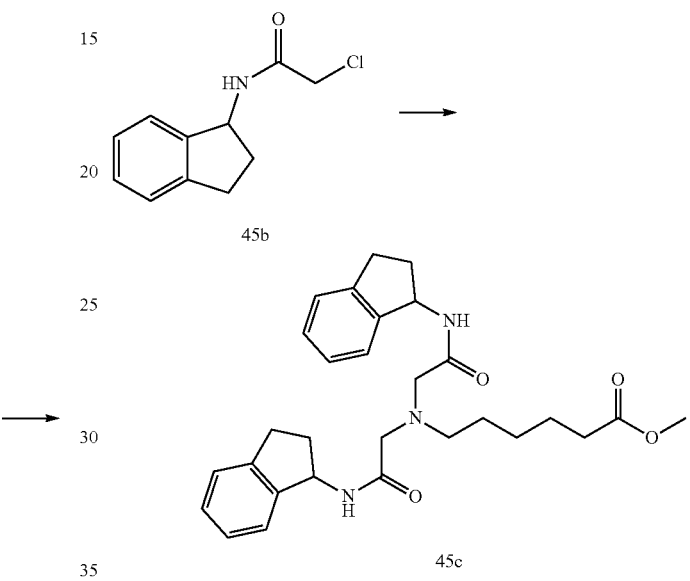

To a solution of Compound 45b (2-chloro-N-(2,3-dihydro-1H-inden-1-yl)acetamide) (0.47 g, 2.56 mmol) and methyl 6-aminohexanoate hydrogen chloride (0.30 g, 1.65 mmol) in acetone (50 mL) was added $K_2CO_3$ (0.71 g, 5.12 mmol). After addition, the reaction mixture was refluxed for overnight.

After reaction was completed, the solvent was removed under reduced pressure. The residual was diluted with EtOAc and washed with Sat. $NH_4Cl$ and Sat. $NaHCO_3$. The organic phase was dried with $MgSO_4$ and concentrated under reduced pressure. The crude product was purified by silica gel column chromatography using ethyl acetate/hexane=2/1 as elution to afford Compound 45c (methyl 6-(bis(2-((2,3-dihydro-1H-inden-1-yl)amino)-2-oxoethyl)amino)hexanoate) (0.08 g, 0.16 mmol, yield 10%).

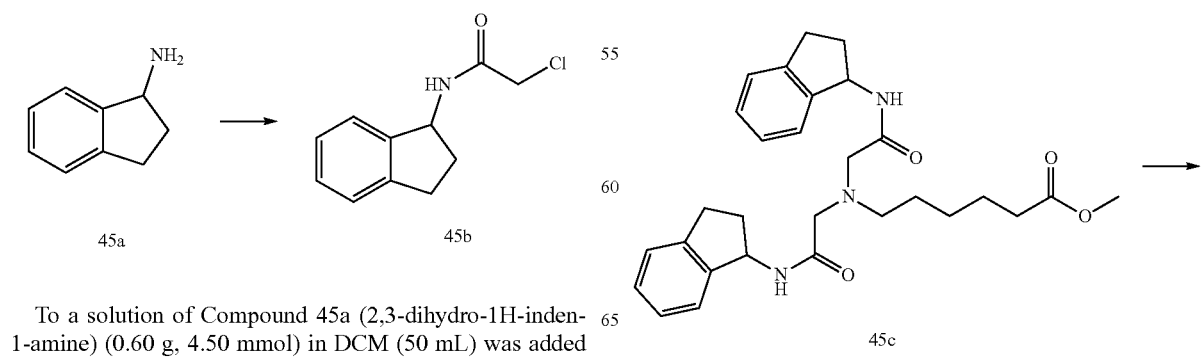

To a solution of Compound 45a (2,3-dihydro-1H-inden-1-amine) (0.60 g, 4.50 mmol) in DCM (50 mL) was added TEA (0.46 g, 4.50 mmol) and chloroacetyl chloride (0.51 g,

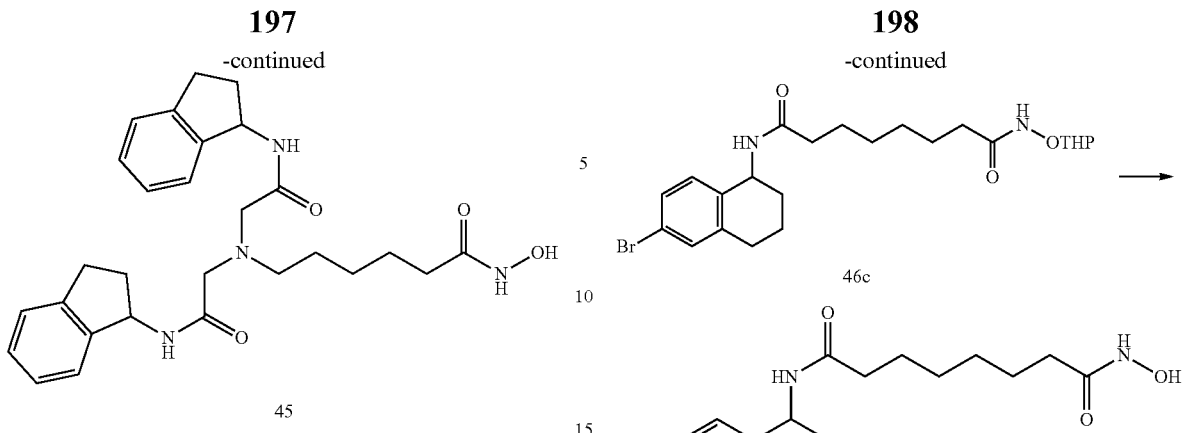

To a solution of Compound 45c (methyl 6-(bis(2-((2,3-dihydro-1H-inden-1-yl)amino)-2-oxoethyl)amino)hexanoate) (0.08 g, 0.16 mmol) in MeOH (10 mL) was added hydroxylamine (2.00 mL, 50 wt. % in H₂O) and 2N NaOH (0.16 mL, 0.32 mmol). After addition, the reaction mixture was stirred for overnight.

After reaction was completed, the solvent was removed under reduced pressure. The residual was diluted with ice-cold water and acidified with 1N HCl. The precipitated solid was collected by filtration to get product Compound 45 (2,2'-((6-(hydroxyamino)-6-oxohexyl)azanediyl)bis(N-(2,3-dihydro-1H-inden-1-yl)acetamide)) (0.05 g, 0.10 mmol, yield 61%).

Compound 45, ¹H-NMR (500 MHz, CD₃OD): δ 7.23-7.17 (m, 8H), 5.42-5.39 (t, 2H), 3.27 (s, 4H), 3.01-2.99 (m, 2H), 2.89-2.85 (m, 2H), 2.59-2.56 (t, 2H), 2.49-2.46 (m, 2H), 2.05-2.02 (t, 2H), 1.90-1.85 (m, 2H), 1.59-1.56 (m, 2H), 1.50-1.44 (m, 2H), 1.30-1.29 (m, 2H). ESI-MS m/z calcd for C₂₈H₃₆N₄O₄ 492.27, found 493 [M+H]⁺.

Synthesis of Compound 46

To a stirred solution of suberic acid monomethyl ester (396.0 mg, 2.1 mmol) and HOBt (227.0 mL, 1.68 mmol) in THF (14 mL) was added EDCI (322.0 mg, 1.68 mmol) in one portion, followed by addition of a solution of Compound 23e (6-bromo-1,2,3,4-tetrahydronaphthalen-1-amine) (317.0 mg, 1.4 mmol) in THF (14 mL) in one portion at RT and stirred for 12 hours.

The resulting residue was purified by silica gel column chromatography (EtOAc:Hex.=1:4) to provide the product Compound 46a (methyl 8-((6-bromo-1,2,3,4-tetrahydronaphthalen-1-yl)amino)-8-oxooctanoate) (109.0 mg, yield 20%).

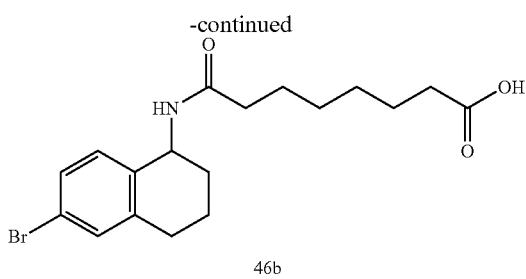

46b

To a solution of Compound 46a (tert-butyl (E)-(6-(3-((2-amino-4-fluorophenyl)amino)-3-oxoprop-1-en-1-yl)-1,2,3,4-tetrahydronaphthalen-1-yl)(2-(2-methyl-1H-indol-3-yl)ethyl)carbamate) (109 mg, 0.28 mmol) in MeOH (3 mL) was added 2N NaOH (0.4 mL) and stirred at RT for 3 hours.

The reaction mixture was concentrated to remove the organic solvent. The residue was diluted with water and acidified to pH=4 with 1N HCl$_{(aq)}$. The mixture was extracted with EtOAc and brine. The organic layer was dried over MgSO$_4$ and concentrated in vacuo to obtain the product Compound 46b (8-((6-bromo-1,2,3,4-tetrahydronaphthalen-1-yl)amino)-8-oxooctanoic acid) (105.0 mg, yield 96%).

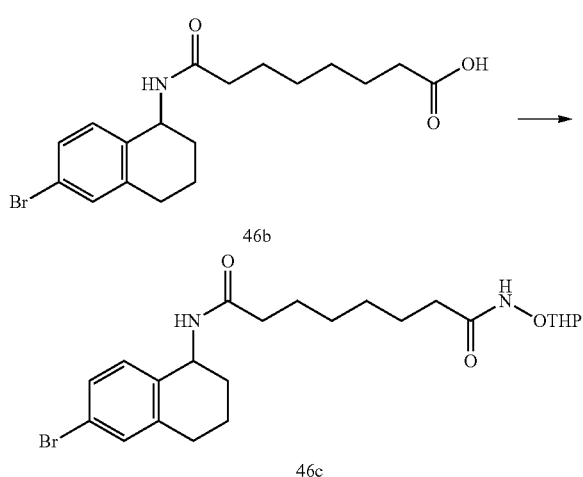

To a stirred solution of Compound 46b (8-((6-bromo-1,2,3,4-tetrahydronaphthalen-1-yl)amino)-8-oxooctanoic acid) (105.0 mg, 0.27 mmol) and HOBt (45.0 mg, 0.33 mmol) in DCM (3 mL) was added O-(Tetrahydro-2H-pyran-2-yl)hydroxylamine (48.0 mg, 0.41 mmol) in one portion, followed by a solution of EDCI (63.0 mg, 0.33 mmol) in DCM (1 mL) was added dropwise to the mixture in one portion at 0° C. The resulting mixture was stirred at RT for overnight.

After which time the mixture dilute with DCM and washed with NaHCO$_3$ and brine. The organic layer was dried over MgSO$_4$ and concentrated in vacuo to give the crude material.

The resulting residue was purified by silica gel column chromatography (EtOAc:Hexane=3:1) to provide the white solid product Compound 46c (N$^1$-(6-bromo-1,2,3,4-tetrahydronaphthalen-1-yl)-N$^8$-((tetrahydro-2H-pyran-2-yl)oxy)octanediamide) (20.0 mg, yield 15%).

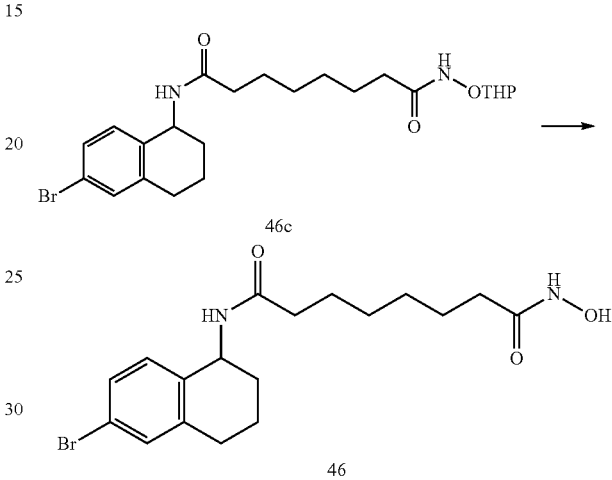

A solution of Compound 46c ((E)-4-(((6-(3,5-bis(trifluoromethyl)benzylidene)-5-oxo-5,6,7,8-tetrahydronaphthalen-2-yl)oxy)methyl)-N-((tetrahydro-2H-pyran-2-yl)oxy)benzamide) (20.0 mg, 0.04 mmol) in DCM (0.4 mL) was added 1N HCl$_{(aq)}$ (0.05 mL) at 0° C. and stirred for 3 hours.

The resulting crude was washed with ether to provide the product Compound 46 (N1-(6-bromo-1,2,3,4-tetrahydronaphthalen-1-yl)-N8-hydroxyoctanediamide) (5.0 mg, yield 31%).

Compound 46, $^1$H-NMR (500 MHz, CD$_3$OD): 7.15-7.09 (m, 3H), 5.07 (s, 1H), 2.81-2.77 (m, 2H), 2.23 (s, 2H), 2.11-2.09 (m, 2H), 1.98-1.92 (m, 2H), 1.80 (s, 2H), 1.66-1.63 (m, 4H), 1.37 (s, 4H). ESI-MS m/z calcd for C$_{18}$H$_{25}$BrN$_2$O$_3$ 396.11, found 397 [M+H]$^+$.

Synthesis of Compounds 47~48

Scheme 29

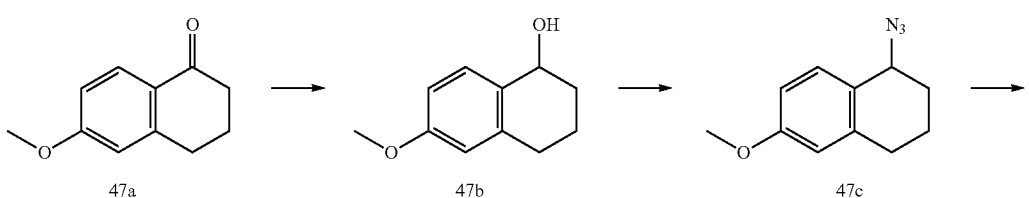

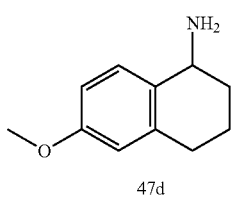

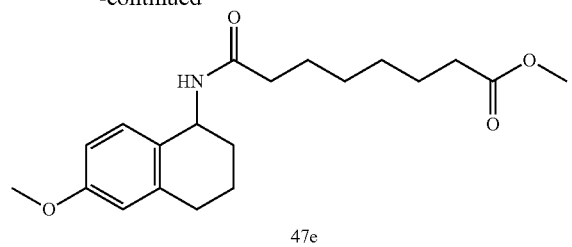

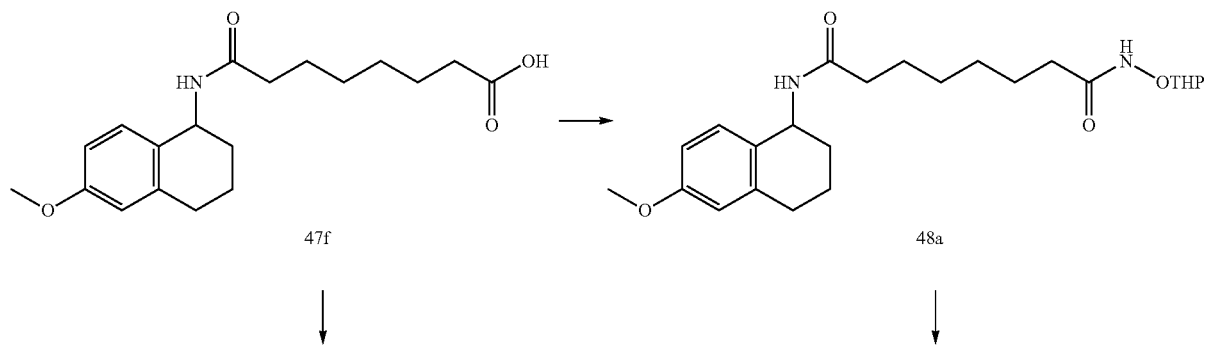

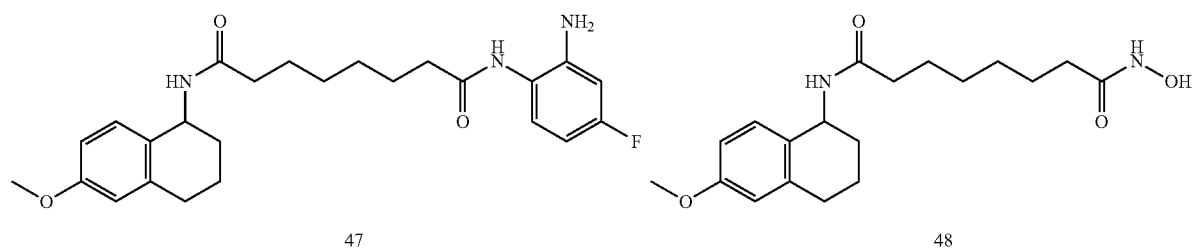

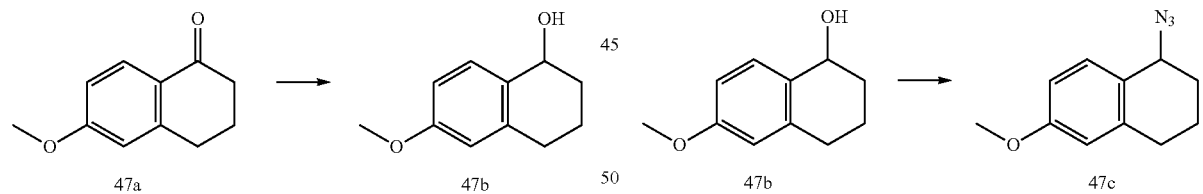

To a solution of Compound 47a (6-methoxy-3,4-dihydronaphthalen-1(2H)-one) (3.00 g, 17.02 mmol) in THF/water (25 mL, 4:1) was added NaBH$_4$ (0.97 g, 25.54 mmol) at 0° C. After addition, the reaction mixture was slowly warmed to RT and stirred for 2 hrs.

After reaction was completed, the reaction mixture was quenched with Sat. NH$_4$Cl. The solvent was removed under reduced pressure. The residue was diluted with EtOAc and washed with sat. NH$_4$Cl. The organic phase was dried with MgSO$_4$ and concentrated under reduced pressure to obtain the desired product Compound 47b (6-methoxy-1,2,3,4-tetrahydronaphthalen-1-ol) (2.97 g, 16.68 mmol, yield 98%). The crude product was used in the next step without further purification.

To a solution of Compound 47b (6-methoxy-1,2,3,4-tetrahydronaphthalen-1-ol) (0.22 g, 1.21 mmol) and 1,8-Diazabicyclo[5.4.0]undec-7-ene (0.28 g, 1.82 mmol) in THF (20 mL) was added Diphenyl phosphoryl azide (0.43 g, 1.58 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl and Sat. NaHCO$_3$. The organic phase was dried with MgSO$_4$ and concentrated under reduced pressure. The crude product was purified by silica gel column chromatography using ethyl acetate/hexane=1/5 as elution to afford Compound 47c (1-azido-6-methoxy-1,2,3,4-tetrahydronaphthalene) (0.14 g, 0.66 mmol, yield 55%).

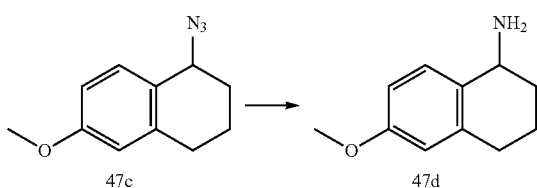

To a solution of Compound 47c (1-azido-6-methoxy-1,2,3,4-tetrahydronaphthalene) (0.14 g, 0.66 mmol) in MeOH (50 mL) was added Pd/C (0.03 g). After addition, the reaction mixture was stirred under H₂ for 3 hours.

After reaction was completed, the solvent was removed under reduced pressure. Pd/C was filed off through a pad of celite and washed with EtOAc. The filtrate was concentrated in vacuo to afford Compound 47d (6-methoxy-1,2,3,4-tetrahydronaphthalen-1-amine) (0.11 g, 0.59 mmol, yield 90%).

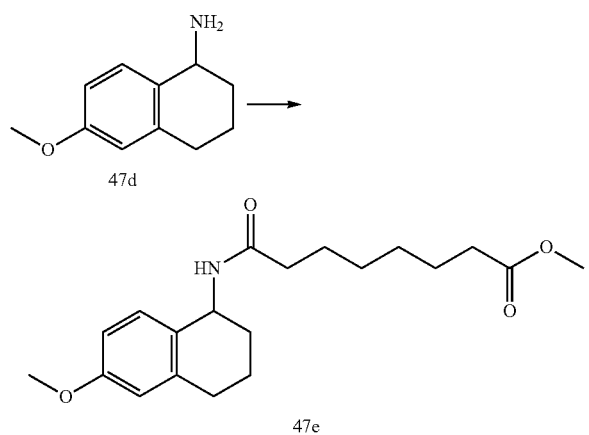

To a solution of Compound 47d (6-methoxy-1,2,3,4-tetrahydronaphthalen-1-amine) (0.48 g, 2.70 mmol), suberic acid monomethyl ester (0.66 g, 3.51 mmol) and DMAP (0.17 g, 1.35 mmol) in DCM (50 mL) was added DIPEA (1.05 g, 8.10 mmol) and EDCI (0.78 g, 4.05 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl and Sat. NaHCO₃. The organic phase was dried with MgSO₄ and concentrated under reduced pressure. The crude product was purified by silica gel column chromatography using ethyl acetate/hexane=2/1 as elution to afford Compound 47e (methyl 8-((6-methoxy-1,2,3,4-tetrahydronaphthalen-1-yl)amino)-8-oxooctanoate) (0.93 g, 2.67 mmol, yield 99%).

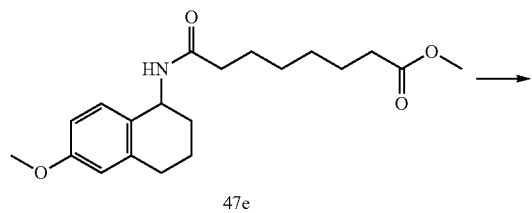

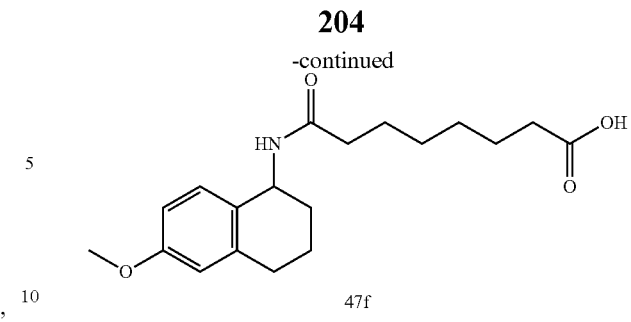

To a solution of Compound 47e (methyl 8-((6-methoxy-1,2,3,4-tetrahydronaphthalen-1-yl)amino)-8-oxooctanoate) (0.93 g, 2.67 mmol) in MeOH (50 mL) was added 2N NaOH (2.50 mL, 5.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 10% MeOH/water to give Compound 47f (8-((6-methoxy-1,2,3,4-tetrahydronaphthalen-1-yl)amino)-8-oxooctanoic acid) (0.85 g, 2.56 mmol, yield 96%). The product Compound 47f was used in next step without further purification.

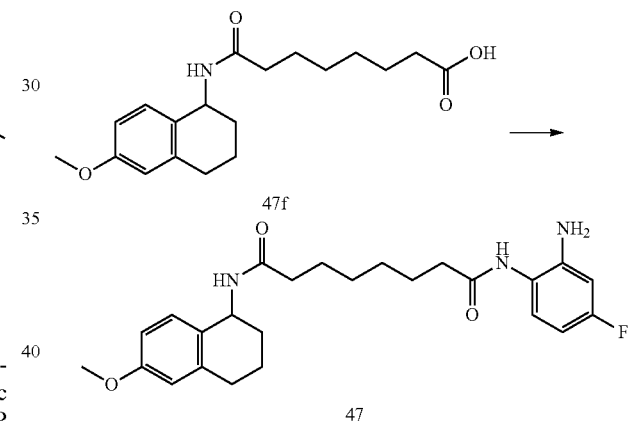

To a solution of Compound 47f (8-((6-methoxy-1,2,3,4-tetrahydronaphthalen-1-yl)amino)-8-oxooctanoic acid) (0.10 g, 0.30 mmol), 4-fluoro-1,2-phenylenediamine (0.05 g, 0.36 mmol) and DMAP (0.02 g, 0.15 mmol) in THF (20 mL) was added NMM (0.05 g, 0.45 mmol) and EDCI (0.09 g, 0.45 mmol) at 0° C. After addition, the reaction mixture was slowly warmed to RT and stirred for overnight.

After reaction was completed, the solvent was removed under reduced pressure. The residual was diluted the reaction mixture was diluted with EtOAc and washed with Sat. NH₄Cl. The combined organic layers were washed with brine and dried over MgSO₄ and concentrated in vacuo. The crude product was washed with diethyl ether to give Compound 47 (N1-(2-amino-4-fluorophenyl)-N8-(6-methoxy-1,2,3,4-tetrahydronaphthalen-1-yl)octanediamide) (0.06 g, 0.14 mmol, yield 48%).

Compound 47, $^1$H-NMR (500 MHz, CD$_3$OD): δ 7.09-7.07 (d, 1H), 7.03-7.00 (t, 1H), 6.73-6.70 (dd, 1H), 6.63 (s, 1H), 6.54-6.51 (dd, 1H), 6.39-6.35 (td, 1H), 5.01 (t, 1H), 3.74 (s, 3H), 2.81-2.70 (m, 2H), 2.42-2.39 (t, 2H), 2.24-2.21 (t, 2H), 1.97-1.89 (m, 2H), 1.78-1.67 (m, 6H), 1.48-1.43 (m, 4H). ESI-MS m/z calcd for $C_{25}H_{32}FN_3O_3$ 441.24, found 464 [M+Na]$^+$.

205 206

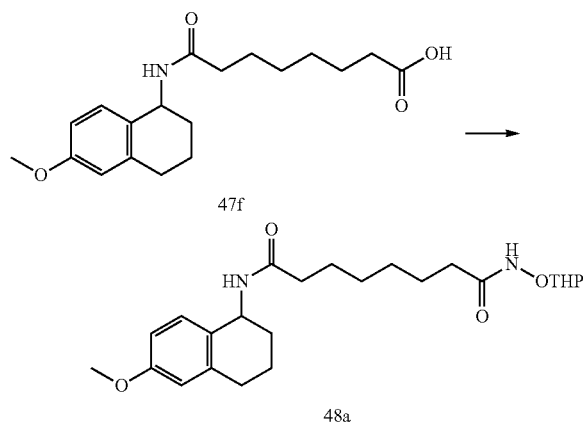

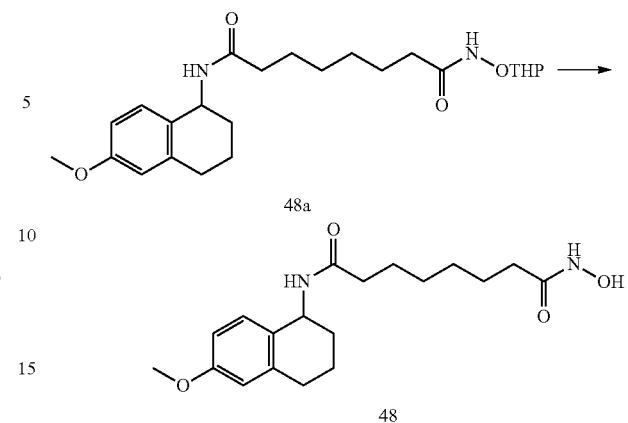

To a solution of Compound 47f (8-((6-methoxy-1,2,3,4-tetrahydronaphthalen-1-yl)amino)-8-oxooctanoic acid) (110 mg, 0.33 mmol) in DCM (3 mL) at 0° C. under nitrogen was added EDC hydrochloride (69 mg, 0.36 mmol), followed DMAP (44 mg, 0.36 mmol) and O-(Tetrahydro-2H-pyran-2-yl)hydroxylamine (43 mg, 0.36 mmol). The mixture was allowed to warm to RT and stirred for 4 hours.

The reaction mixture was diluted with ether and extracted with $NaHCO_3$ (sat.), followed $NH_4Cl$ (sat.) and brine. The combined organic layer was dried over anhydrous $MgSO_4$. After removed the solvent, the crude product was purified by column chromatography (EtOAc:n-hexane=2:1) to afford the product Compound 48a ($N^1$-(6-methoxy-1,2,3,4-tetrahydronaphthalen-1-yl)-$N^8$-((tetrahydro-2H-pyran-2-yl)oxy) octanediamide) (138 mg, 96%).

To a solution of Compound 48a ($N^1$-(6-methoxy-1,2,3,4-tetrahydronaphthalen-1-yl)-$N^8$-((tetrahydro-2H-pyran-2-yl)oxy)octanediamide) (44 mg, 0.10 mmol) in DCM (1 mL) at RT was added hydrogen chloride solution 2.0 M in diethyl ether (excess, 1 mL). The reaction was stirred at RT for 3 hours.

Thereafter, the solid was filtered out to afford the product Compound 48 ($N^1$-hydroxy-$N^8$-(6-methoxy-1,2,3,4-tetrahydronaphthalen-1-yl)octanediamide) (24 mg, 68%).

Compound 48, $^1$H-NMR (500 MHz, $CD_3OD$): δ 7.08-7.06 (d, 1H), 6.73-6.71 (d, 1H), 6.63 (s, 1H), 5.00 (s, 1H), 3.74 (s, 3H), 2.81-2.70 (dd, 2H), 2.22-2.19 (t, 2H), 2.10-2.07 (t, 2H), 1.96-1.89 (m, 2H), 1.78-1.77 (m, 2H), 1.65-1.62 (m, 4H), 1.36 (s, 4H). ESI-MS m/z calcd for $C_{19}H_{28}N_2O_4$ 348.20, found 371.2 $[M+Na]^+$.

Synthesis of Compounds 49~50

Scheme 30

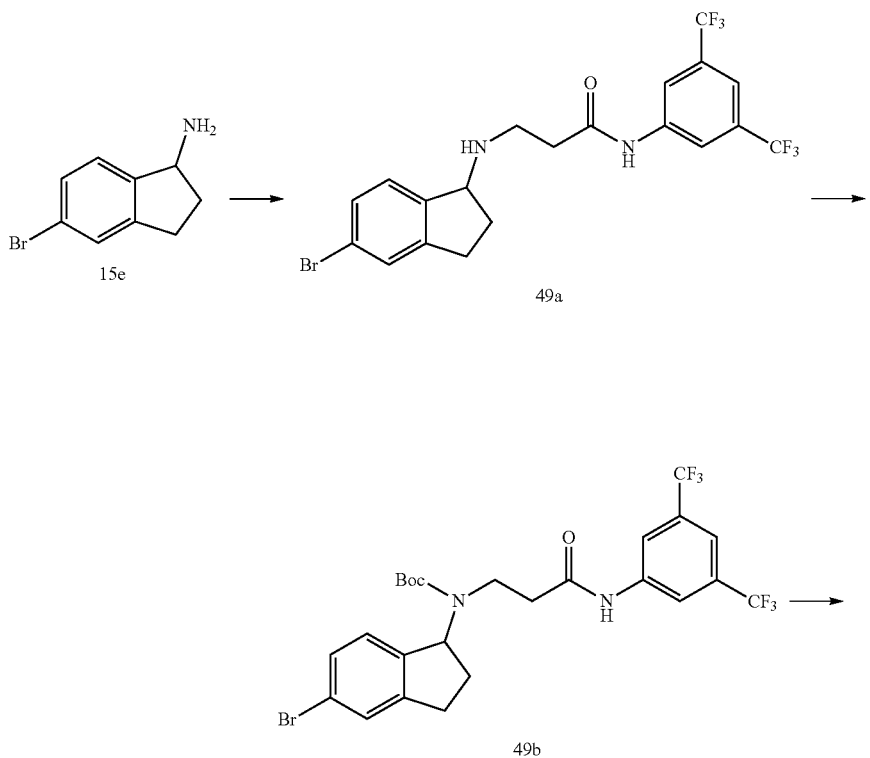

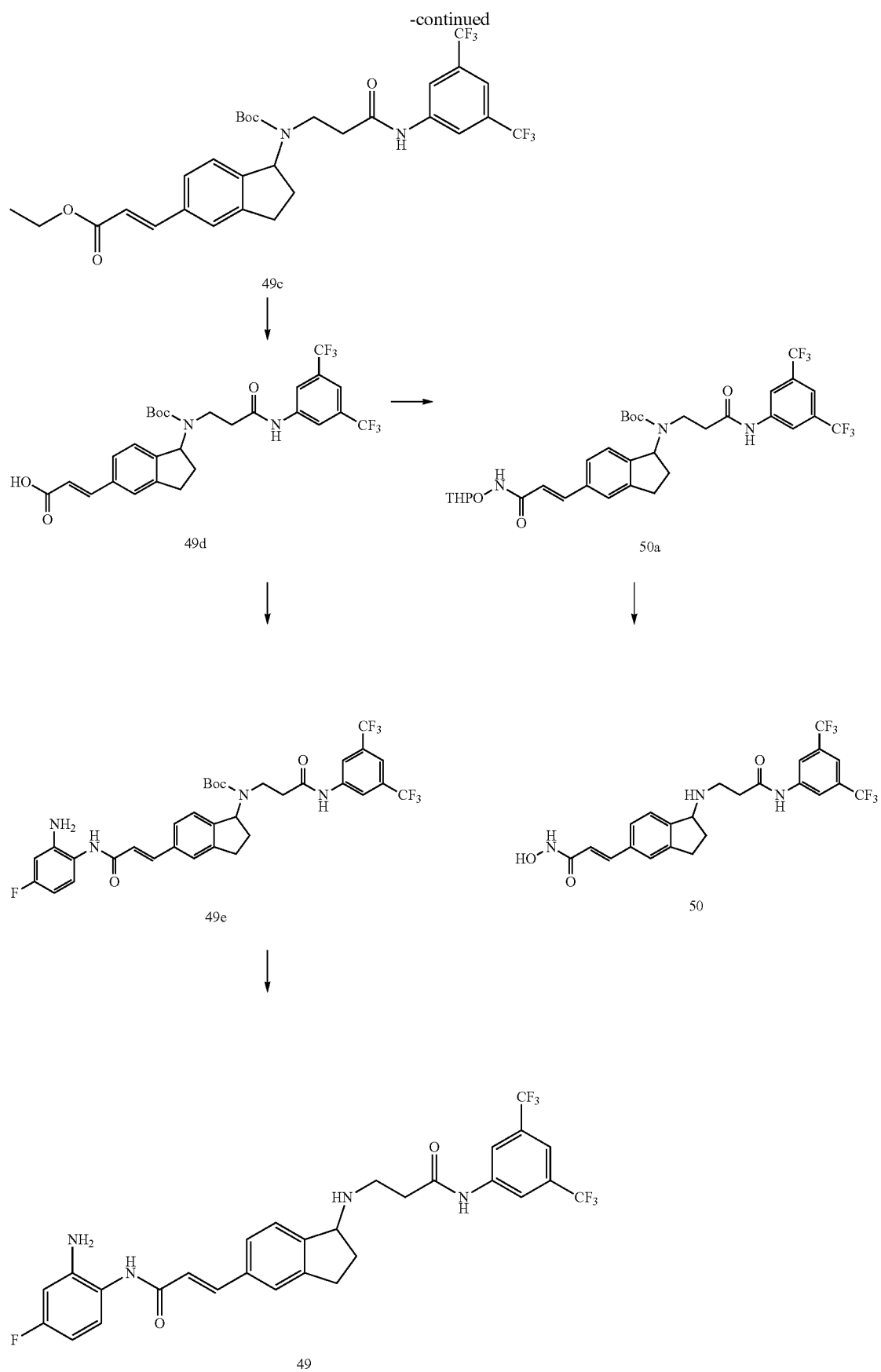

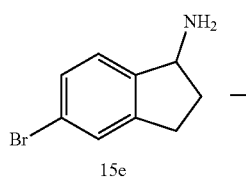

15e

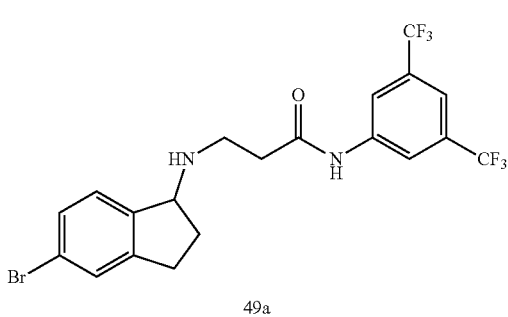

49a

To a solution of Compound 15e (5-bromo-2,3-dihydro-1H-inden-1-amine) (0.20 g, 0.94 mmol) and N-(3,5-bis(trifluoromethyl)phenyl)acrylamide (0.22 g, 0.79 mmol) in THF (20 mL) was added K$_2$CO$_3$ (0.22 g, 1.57 mmol). After addition, the reaction mixture was refluxed for overnight.

The reaction was monitored by TLC. After reaction was completed, the solvent was removed under reduced pressure. The residue was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/3 as elution to yield the desired product Compound 49a (N-(3,5-bis(trifluoromethyl)phenyl)-3-((5-bromo-2,3-dihydro-1H-inden-1-yl)amino)propenamide) (0.41 g, 0.83 mmol, yield 89%).

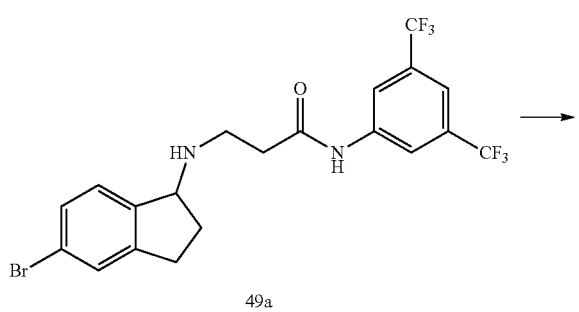

49a

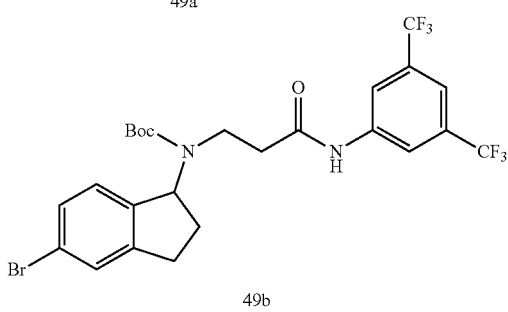

49b

To a solution of Compound 49a (N-(3,5-bis(trifluoromethyl)phenyl)-3-((5-bromo-2,3-dihydro-1H-inden-1-yl)amino)propenamide) (0.57 g, 1.16 mmol) in THF (20 mL) was added DIPEA (0.23 g, 1.74 mmol) and Boc$_2$O (0.38 g, 1.74 mmol) at 0° C. After addition, the reaction mixture was warmed to room temperature and stirred for 3 hours.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=1/5 as elution to yield the desired product Compound 49b (tert-butyl (3-((3,5-bis(trifluoromethyl)phenyl)amino)-3-oxopropyl)(5-bromo-2,3-dihydro-1H-inden-1-yl)carbamate) (0.55 g, 0.93 mmol, yield 80%).

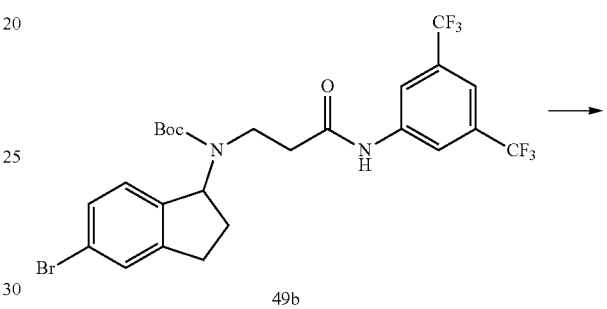

49b

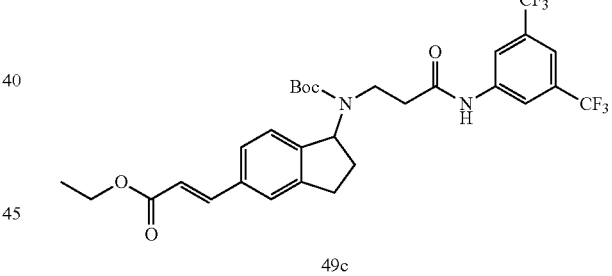

49c

To a solution of Compound 49b (tert-butyl (3-((3,5-bis(trifluoromethyl)phenyl)amino)-3-oxopropyl)(5-bromo-2,3-dihydro-1H-inden-1-yl)carbamate) (0.55 g, 0.93 mmol), triphenylphosphine (0.10 g, 0.37 mmol), ethyl acrylate (0.14 g, 1.40 mmol) in DMF/TEA (20 mL, 1:1) was added Pd(OAc)$_2$ (0.01 g, 0.05 mmol). After addition, the reaction mixture was heated to 100° C. and stirred for overnight.

The reaction was monitored by TLC. After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/5 as elution to yield the desired product Compound 49c (ethyl (E)-3-(1-((3-((3,5-bis(trifluoromethyl)phenyl)amino)-3-oxopropyl)(tert-butoxycarbonyl)amino)-2,3-dihydro-1H-inden-5-yl)acrylate) (0.30 g, 0.48 mmol, yield 52%).

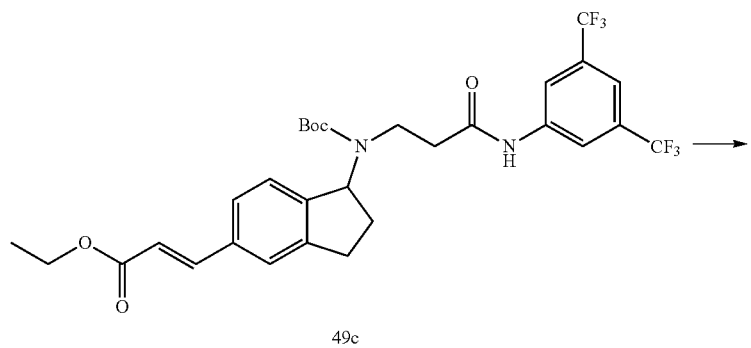

49c

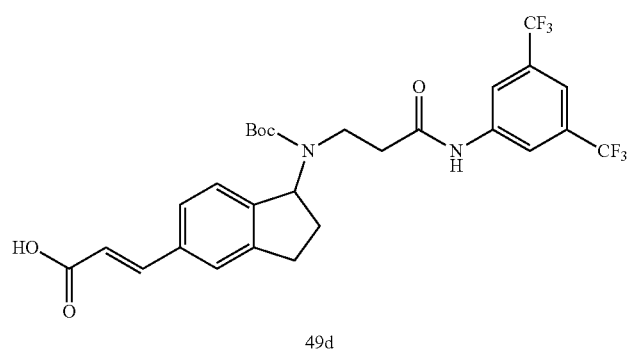

49d

To a solution of Compound 49c (ethyl (E)-3-(1-((3-((3, 5-bis(trifluoromethyl)phenyl)amino)-3-oxopropyl)(tert-butoxycarbonyl)amino)-2,3-dihydro-1H-inden-5-yl)acrylate) (0.30 g, 0.48 mmol) in MeOH (10 mL) was added 2N NaOH$_{(aq)}$ (0.5 mL, 1.00 mmol). After addition, the reaction mixture was heated to 50° C. and stirred for 4 hours.

The reaction was monitored by TLC. After reaction was completed, the solvent was removed under reduced pressure. The residue was diluted with ice-cold water and acidified with 1N HCl. The precipitated solid was collected by filtration to afford the desired product Compound 49d ((E)-3-(1-((3-((3,5-bis(trifluoromethyl)phenyl)amino)-3-oxopropyl)(tert-butoxycarbonyl)amino)-2,3-dihydro-1H-inden-5-yl)acrylic acid) (0.22 g, 0.38 mmol, yield 78%).

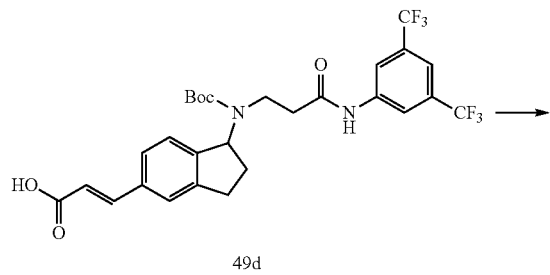

49d

-continued

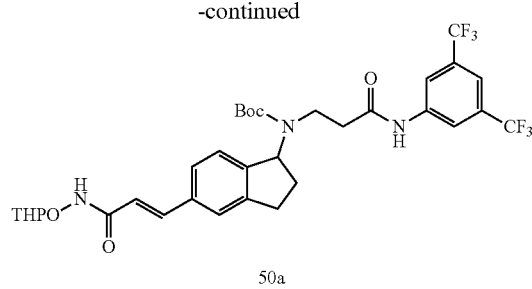

50a

To a solution of Compound 49d ((E)-3-(1-((3-((3,5-bis(trifluoromethyl)phenyl)amino)-3-oxopropyl)(tert-butoxycarbonyl)amino)-2,3-dihydro-1H-inden-5-yl)acrylic acid) (0.10 g, 0.17 mmol), NH$_2$OTHP (0.02 g, 0.19 mmol) and DMAP (0.01 g, 0.09 mmol) in CH$_2$Cl$_2$ (20 mL) was added NMM (0.03 g, 0.26 mmol) and EDC (0.04 g, 0.22 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=1/1 as elution to yield the desired product Compound 50a (tert-butyl (E)-(3-((3,5-bis(trifluoromethyl) phenyl)amino)-3-oxopropyl)(5-(3-oxo-3-(((tetrahydro-2H-pyran-2-yl)oxy)amino)prop-1-en-1-yl)-2,3-dihydro-1H-inden-1-yl)carbamate) (0.08 g, 0.12 mmol, yield 71%).

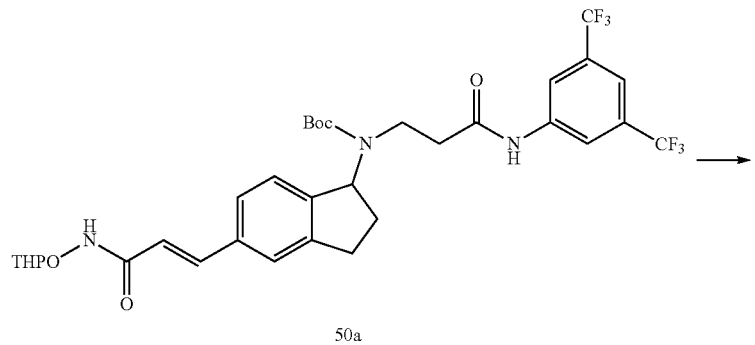

50a

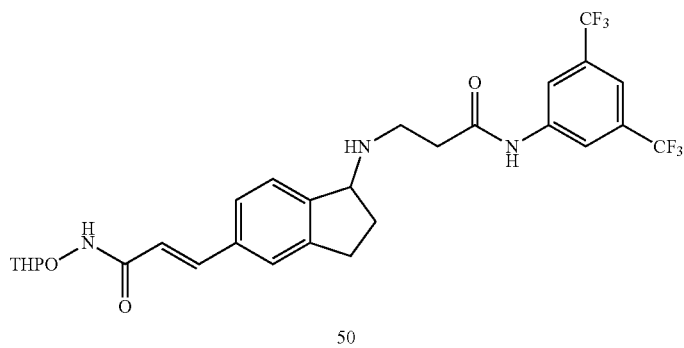

50

To a solution of Compound 50a (tert-butyl (E)-(3-((3,5-bis(trifluoromethyl)phenyl)amino)-3-oxopropyl)(5-(3-oxo-3-(((tetrahydro-2H-pyran-2-yl)oxy)amino)prop-1-en-1-yl)-2,3-dihydro-1H-inden-1-yl)carbamate) (0.08 mg, 0.12 mmol) in $CH_2Cl_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 50 ((E)-3-(1-((3-((3,5-bis(trifluoromethyl)phenyl)amino)-3-oxopropyl)amino)-2,3-dihydro-1H-inden-5-yl)-N-hydroxyacrylamide) (0.06 g, 0.11 mmol, yield 95%).

Compound 50, $^1$H-NMR (500 MHz, $CD_3OD$): δ 8.23 (s, 2H), 7.67-7.54 (m, 5H), 6.54-6.51 (d, 1H), 4.93-4.91 (m, 1H), 3.47-3.45 (t, 2H), 3.26-3.22 (m, 1H), 3.10-3.04 (m, 1H), 2.96-2.94 (t, 2H), 2.69-2.65 (m, 1H), 2.41-2.36 (m, 1H). ESI-MS m/z calcd for $C_{23}H_{21}F_6N_3O_3$ 501.15, found 502 [M+1-1]$^+$.

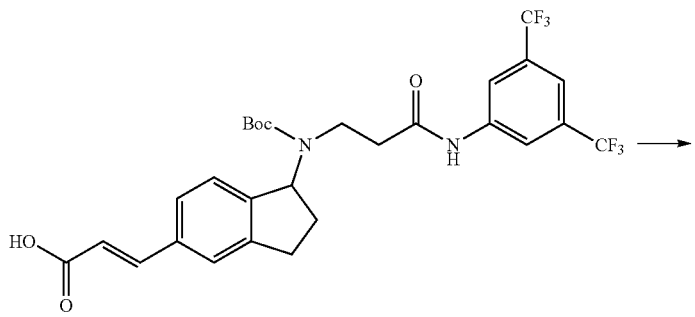

49d

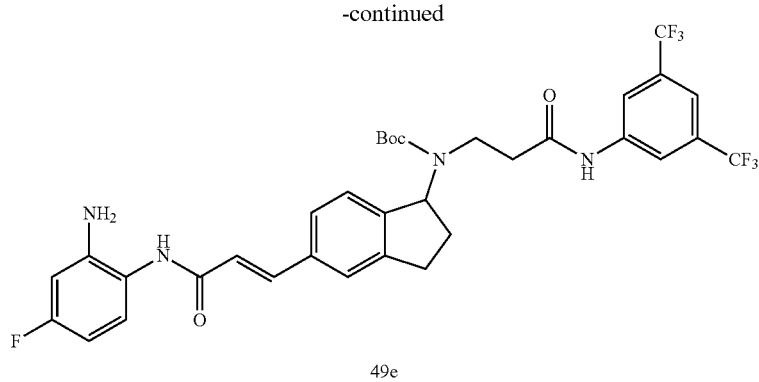

49e

To a solution of Compound 49d ((E)-3-(1-(((3-((3,5-bis(trifluoromethyl)phenyl)amino)-3-oxopropyl)(tert-butoxycarbonyl)amino)-2,3-dihydro-1H-inden-5-yl)acrylic acid) (0.12 g, 0.21 mmol), 4-fluoro-1,2-phenylenediamine (0.03 g, 0.23 mmol) in $CH_2Cl_2$ (20 mL) was added NMM (0.04 g, 0.42 mmol) and HATU (0.10 g, 0.25 mmol) at 0° C. After addition, the reaction mixture was warmed to room temperature and stirred for 4 hours.

The reaction was monitored by TLC. After reaction was completed, the solvent was removed under reduced pressure. The residue was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/hexane=1/1 as elution to yield the desired product Compound 49e (tert-butyl (E)-(5-(3-((2-amino-4-fluorophenyl)amino)-3-oxoprop-1-en-1-yl)-2,3-dihydro-1H-inden-1-yl)(3-((3,5-bis(trifluoromethyl)phenyl)amino)-3-oxopropyl)carbamate) (0.11 mg, 0.16 mmol, yield 78%).

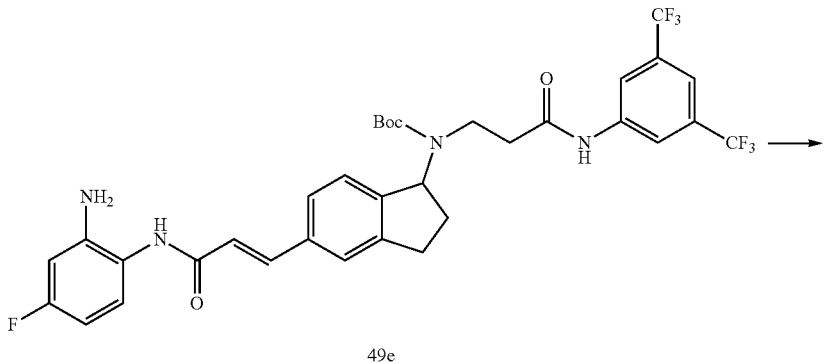

49e

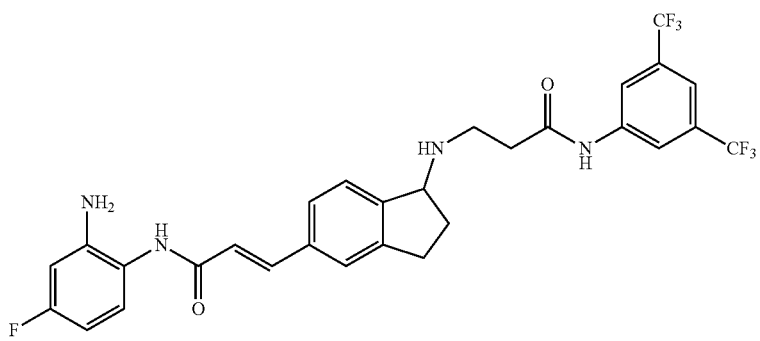

49

To a solution of Compound 49e (tert-butyl (E)-(5-(3-((2-amino-4-fluorophenyl)amino)-3-oxoprop-1-en-1-yl)-2,3-dihydro-1H-inden-1-yl)(3-((3,5-bis(trifluoromethyl)phenyl)amino)-3-oxopropyl)carbamate) (0.11 mg, 0.16 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 49 ((E)-N-(2-amino-4-fluorophenyl)-3-(1-((3-((3,5-bis(trifluoromethyl)phenyl)amino)-3-oxopropyl)amino)-2,3-dihydro-1H-inden-5-yl)acrylamide) (0.10 g, 0.15 mmol, yield 96%).

Compound 49, $^1$H-NMR (500 MHz, CD$_3$OD): δ 8.23 (s, 2H), 7.83-7.80 (d, 1H), 7.73-7.64 (m, 4H), 7.40-7.37 (m, 1H), 7.17-7.15 (d, 2H), 6.95-6.91 (d, 1H), 4.96-4.94 (m, 1H), 3.48-3.46 (t, 2H), 3.28-3.24 (t, 1H), 3.12-3.06 (m, 1H), 2.99-2.96 (t, 2H), 2.17-2.66 (m, 1H), 2.44-2.38 (m, 1H). ESI-MS m/z calcd for C$_{29}$H$_{25}$F$_7$N$_4$O$_2$ 594.19, found 595 [M+H]$^+$.

Synthesis of Compounds 51~52

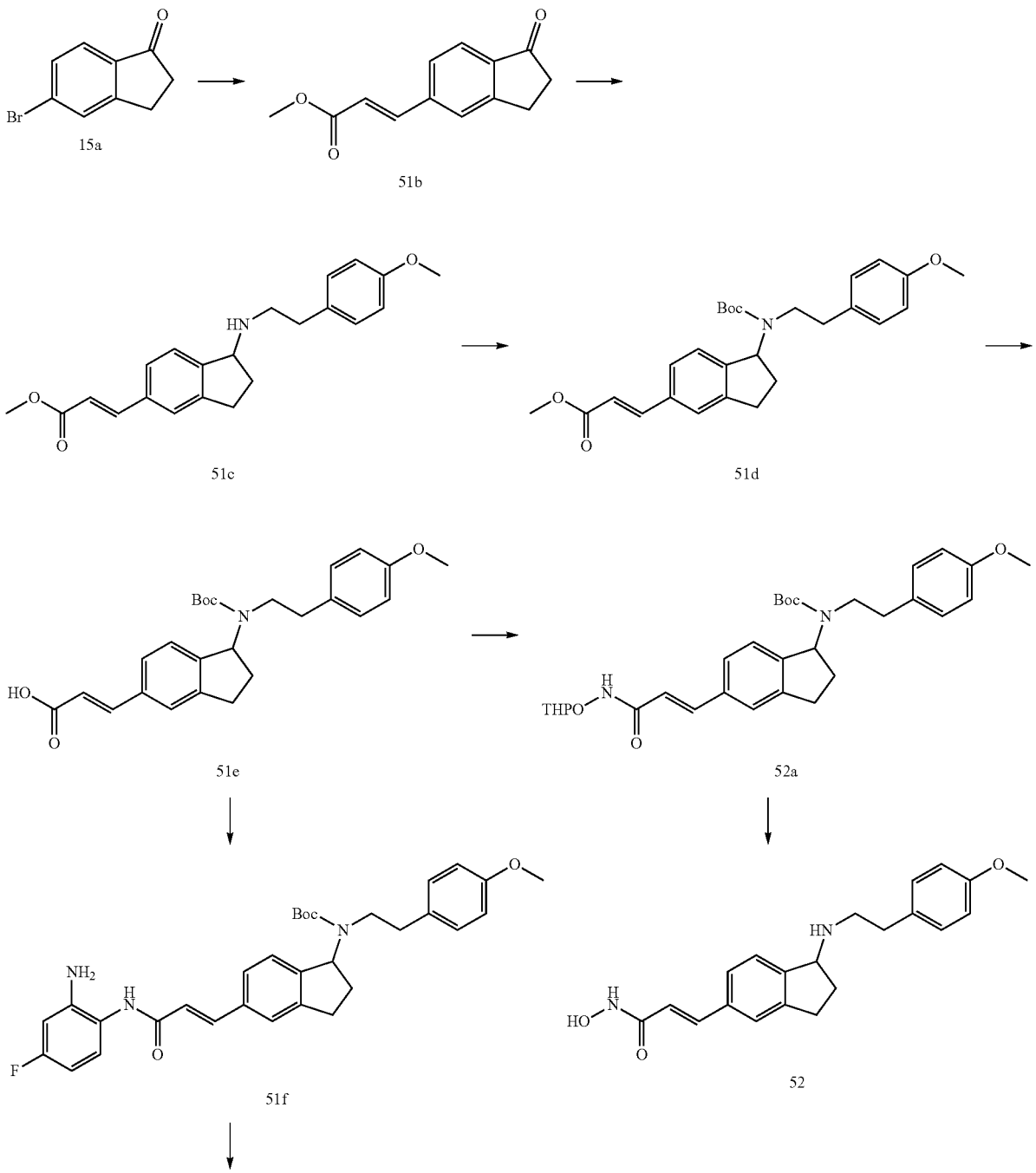

Scheme 31

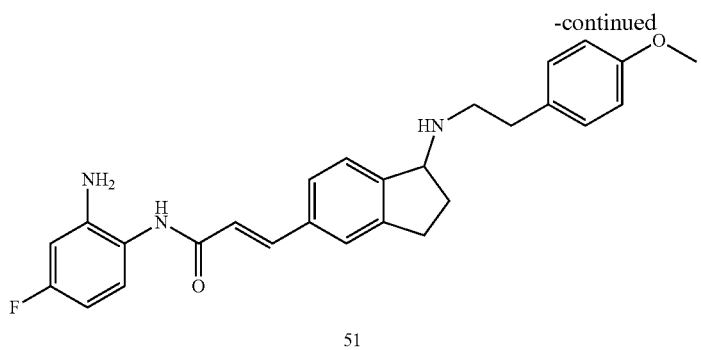

51

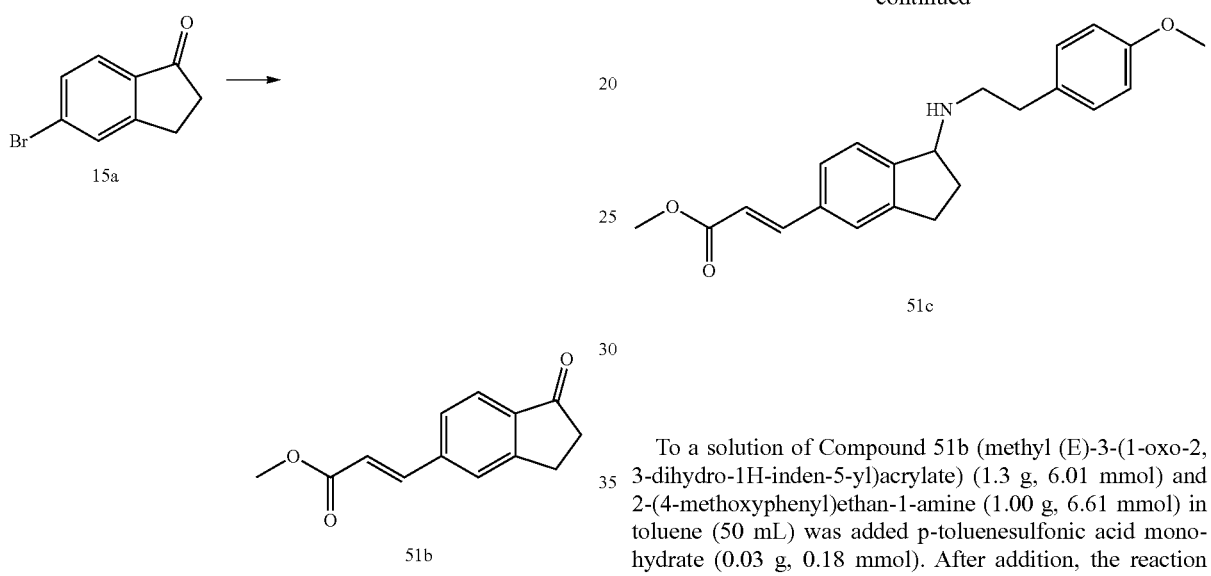

To a solution of Compound 15a (5-Bromo-1-indanone) (1.50 g, 7.11 mmol), triphenylphosphine (2.80 g, 10.66 mmol), methyl acrylate (1.53 g, 17.77 mmol) in ACN/TEA (100 mL, 1:1) was added Pd(OAc)$_2$ (0.96 g, 4.27 mmol). After addition, the reaction mixture was heated to 100° C. and stirred for overnight.

The reaction was monitored by TLC. After reaction was completed, the solvent was removed under reduced pressure. The residual was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/4 as elution to yield the desired product Compound 51b (methyl (E)-3-(1-oxo-2,3-dihydro-1H-inden-5-yl)acrylate) (1.17 g, 5.40 mmol, yield 76%).

To a solution of Compound 51b (methyl (E)-3-(1-oxo-2,3-dihydro-1H-inden-5-yl)acrylate) (1.3 g, 6.01 mmol) and 2-(4-methoxyphenyl)ethan-1-amine (1.00 g, 6.61 mmol) in toluene (50 mL) was added p-toluenesulfonic acid monohydrate (0.03 g, 0.18 mmol). After addition, the reaction mixture was heated to 130° C. and stirred for 3 hours. And then, the solvent was removed under reduced pressure. The residual was dissolved in DCM (100 mL) and added NaBH(OAc)$_3$ (1.27 g, 6.01 mmol). After addition, the reaction mixture was stirred for overnight.

The reaction was monitored by TLC. After reaction was completed, the solvent was removed under reduced pressure. The residual was diluted with sat. NaHCO$_{3(aq)}$ and extracted with DCM. The organic phase was dried with MgSO$_4$ and concentrated under reduced pressure to obtain Compound 51c (methyl (E)-3-(1-((4-methoxyphenethyl)amino)-2,3-dihydro-1H-inden-5-yl)acrylate) (1.50 g, 4.27 mmol, yield 71%). The crude product was used in the next step without further purification.

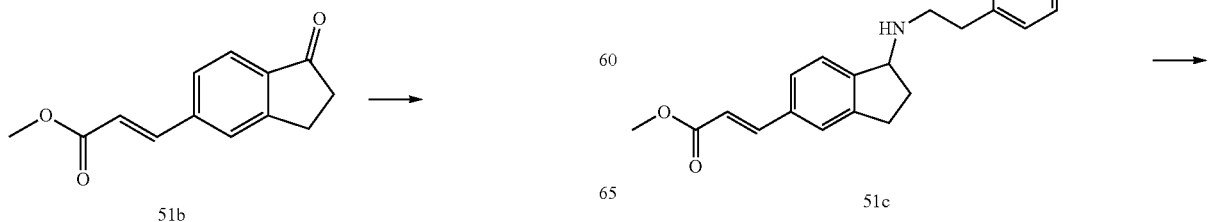

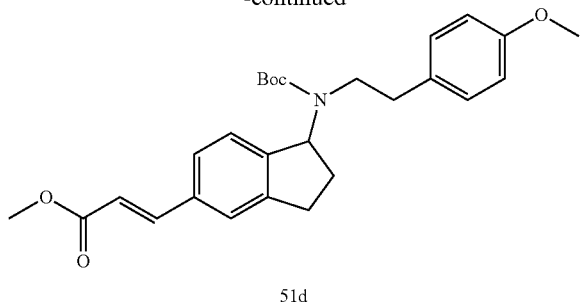

51d

To a solution of Compound 51c (methyl (E)-3-(1-((4-methoxyphenethyl)amino)-2,3-dihydro-1H-inden-5-yl)acrylate) (1.50 g, 4.27 mmol) in THF (100 mL) was added TEA (0.91 g, 9.02 mmol) and (Boc)₂O (1.31 g, 6.01 mmol) at 0° C. After addition, the reaction mixture was warmed to room temperature and stirred for 6 hours.

The reaction was monitored by TLC. After reaction was completed, the solvent was removed under reduced pressure. The residue was diluted with ice-cold water and extracted with EtOAc. The organic phase was dried with MgSO₄ and concentrated under reduced pressure. The crude product was purified by silica gel column chromatography using ethyl acetate/hexane=1/5 as elution to yield the desired product 51d (methyl (E)-3-(1-((tert-butoxycarbonyl)(4-methoxyphenethyl)amino)-2,3-dihydro-1H-inden-5-yl)acrylate) (0.65 g, 1.44 mmol, yield 34%).

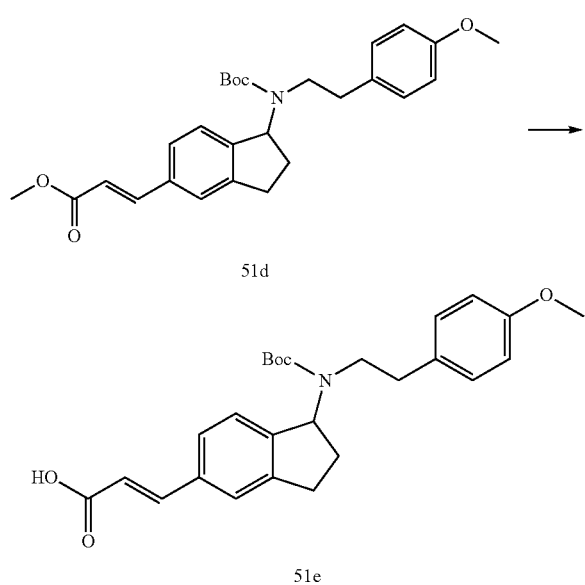

51d

51e

To a solution of Compound 51d (methyl (E)-3-(1-((tert-butoxycarbonyl)(4-methoxyphenethyl)amino)-2,3-dihydro-1H-inden-5-yl)acrylate) (0.65 g, 1.44 mmol) in MeOH (30 mL) was added 2N NaOH$_{(aq)}$ (1.5 mL, 3.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 51e ((E)-3-(1-((tert-butoxy carbonyl)(4-methoxyphenethyl)amino)-2,3-dihydro-1H-inden-5-yl)acrylic acid) (0.57 g, 1.29 mmol, yield 90%).

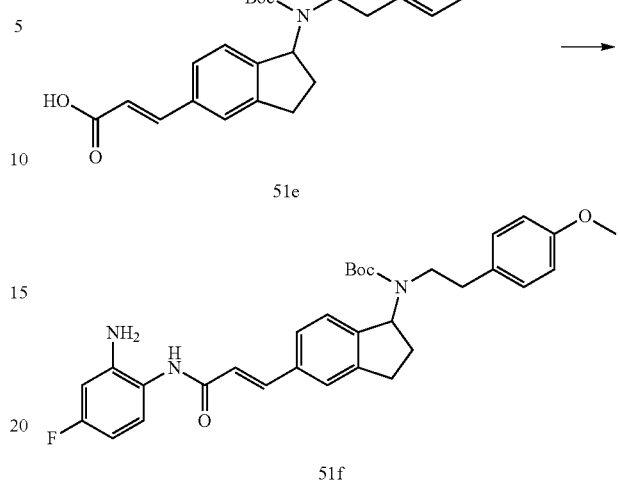

51e

51f

To a solution of Compound 51e ((E)-3-(1-((tert-butoxy carbonyl)(4-methoxyphenethyl)amino)-2,3-dihydro-1H-inden-5-yl)acrylic acid (0.36 g, 0.82 mmol), 4-fluoro-1,2-phenylenediamine (0.11 g, 0.91 mmol) and DMAP (0.10 g, 0.82 mmol) in THF (30 mL) was added NMM (0.08 g, 0.82 mmol) and EDCI (0.21 g, 1.07 mmol) at 0° C. After addition, the reaction mixture was warmed to room temperature and stirred for 6 hours.

The reaction was monitored by TLC. After reaction was completed, the solvent was removed under reduced pressure. The residue was diluted with sat. NH₄Cl$_{(aq)}$ and extracted with EtOAc. The organic phase was dried with MgSO₄ and concentrated under reduced pressure. The crude product was purified by silica gel column chromatography using ethyl acetate/hexane=1/1 as elution to yield the desired product Compound 51f (tert-butyl (E)-(5-(3-((2-amino-4-fluorophenyl)amino)-3-oxoprop-1-en-1-yl)-2,3-dihydro-1H-inden-1-yl)(4-methoxyphenethyl)carbamate) (0.28 mg, 0.52 mmol, yield 63%).

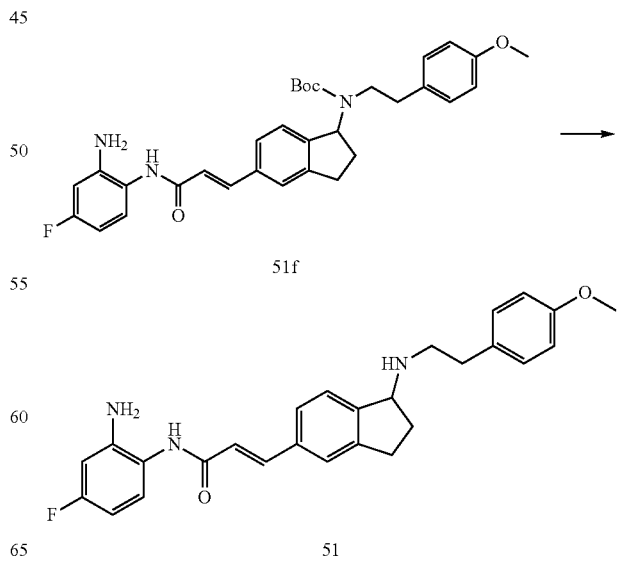

51f

51

To a solution of Compound 51f (tert-butyl (E)-(5-(3-((2-amino-4-fluorophenyl)amino)-3-oxoprop-1-en-1-yl)-2,3-dihydro-1H-inden-1-yl)(4-methoxyphenethyl)carbamate) (0.28 mg, 0.52 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 51 ((E)-N-(2-amino-4-fluorophenyl)-3-(1-((4-methoxyphenethyl)amino)-2,3-dihydro-1H-inden-5-yl)acrylamide) (0.22 g, 0.50 mmol, yield 96%).

Compound 51, $^1$H-NMR (500 MHz, CD$_3$OD): δ 7.82 (d, 1H), 7.69-7.62 (m, 3H), 7.41-7.39 (m, 1H), 7.23-7.18 (m, 4H), 6.95-6.91 (m, 3H), 3.78 (s, 3H), 3.28-3.24 (m, 4H), 3.06-2.96 (m, 3H), 2.65-2.63 (m, 1H), 2.31-2.30 (m, 1H). ESI-MS m/z calcd for C$_{27}$H$_{28}$FN$_3$O$_2$ 445.22, found 446 [M+H]$^+$.

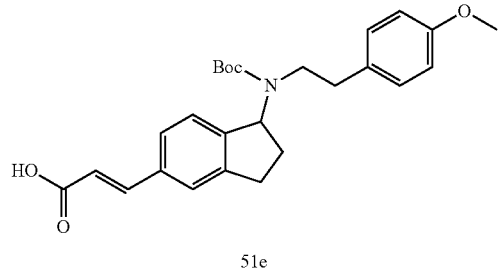

51e

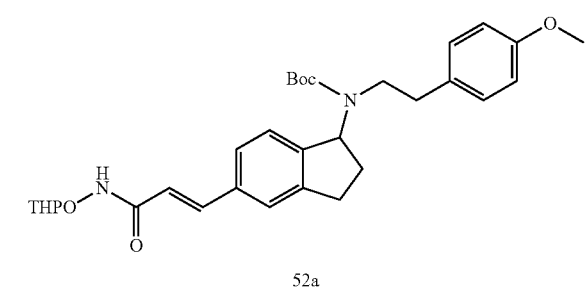

52a

To a solution of Compound 51e ((E)-3-(1-((tert-butoxycarbonyl)(4-methoxyphenethyl)amino)-2,3-dihydro-1H-inden-5-yl)acrylic acid) (0.21 g, 0.48 mmol), NH$_2$OTHP (0.07 g, 0.61 mmol) and DMAP (0.03 g, 0.24 mmol) in CH$_2$Cl$_2$ (20 mL) was added NMM (0.07 g, 0.71 mmol) and EDCI (0.14 g, 0.71 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=1/1 as elution to yield the desired product 52a (tert-butyl (E)-(4-methoxyphenethyl)(5-(3-oxo-3-(((tetrahydro-2H-pyran-2-yl)oxy)amino)prop-1-en-1-yl)-2,3-dihydro-1H-inden-1-yl)carbamate) (0.20 g, 0.37 mmol, yield 78%).

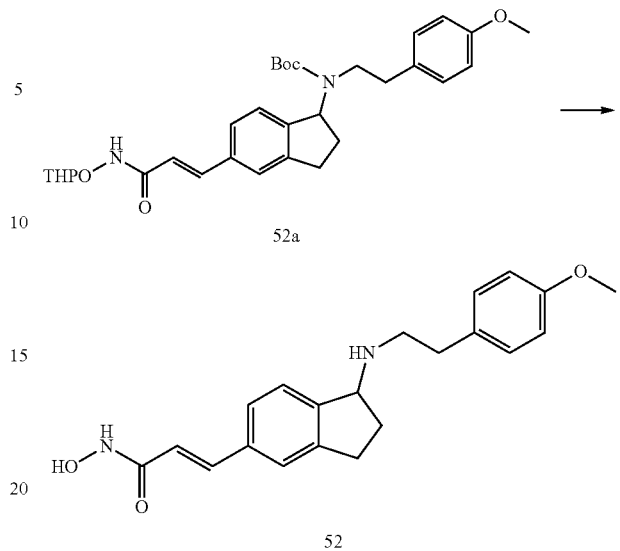

To a solution of Compound 52a (tert-butyl (E)-(4-methoxyphenethyl)(5-(3-oxo-3-(((tetrahydro-2H-pyran-2-yl)oxy)amino)prop-1-en-1-yl)-2,3-dihydro-1H-inden-1-yl)carbamate) (0.20 g, 0.37 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 52 ((E)-N-hydroxy-3-(1-((4-methoxyphenethyl)amino)-2,3-dihydro-1H-inden-5-yl)acrylamide) (0.09 g, 0.26 mmol, yield 69%).

Compound 52, $^1$H-NMR (500 MHz, CD$_3$OD): δ 7.61-7.58 (m, 3H), 7.54-7.52 (d, 1H), 7.21-7.20 (d, 2H), 6.92-6.90 (d, 2H), 6.53-6.50 (d, 1H), 4.83 (m, 1H), 3.78 (s, 3H), 3.29-3.27 (d, 2H), 3.25-3.19 (m, 1H), 3.06-2.93 (m, 3H), 2.64-2.60 (m, 1H), 2.31-2.26 (m, 1H). ESI-MS m/z calcd for C$_{21}$H$_{24}$N$_2$O$_3$ 352.18, found 353 [M+H]$^+$.

Synthesis of Compound 53

Scheme 32

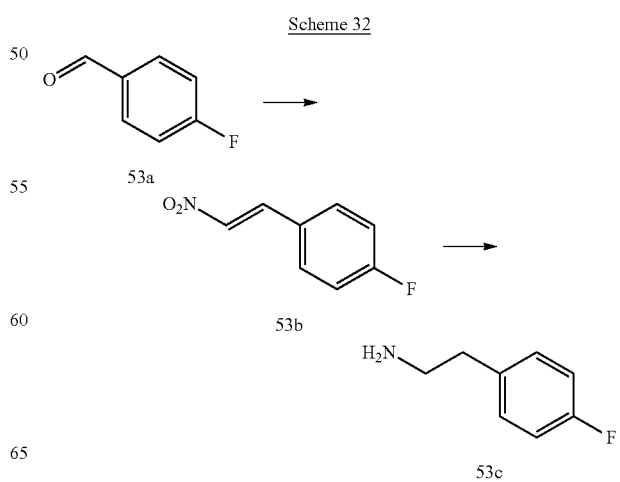

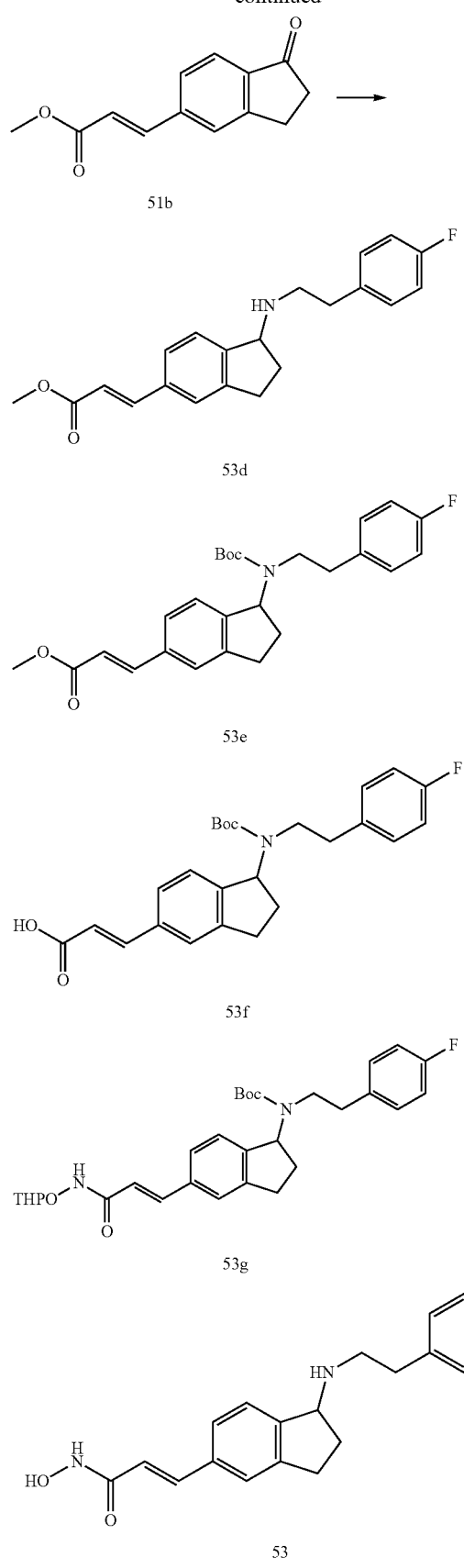

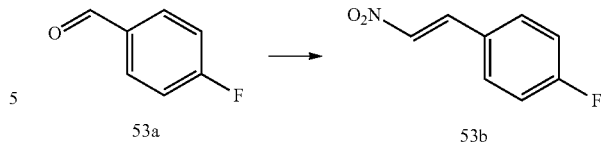

To a solution of Compound 53a (4-fluorobenzaldehyde) (1488 mg, 12 mmol) was added nitromethane (12 mL), NH₄OAc (185 mg, 2.4 mmol), and acetic acid (4.8 mL) at rt in pressure tube then sealed. The reaction mixture was stirred at 120° C. for 4 hours.

After cooling to RT, the solvent was removed in vacuo. Purification by column chromatography (EtOAc:n-hexane=1:50) to afford the product Compound 53b ((E)-1-fluoro-4-(2-nitrovinyl)benzene) (1572 mg, 78%).

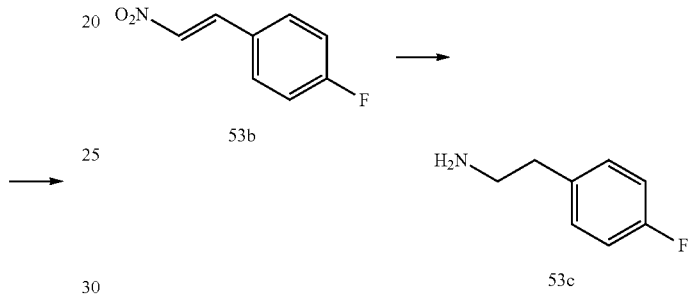

To a solution of Compound 53b ((E)-1-fluoro-4-(2-nitrovinyl)benzene) (990 mg, 6.00 mmol) in MeOH (450 mL) at RT was added hydrogen chloride solution 2.0 M in diethyl ether (54 mL, 108 mmol), the mixture was stirred at 0° C. for 0.5 h. Palladium on carbon (732 mg) was added to the mixture and degas with hydrogen three times. The reaction was stirred with hydrogen balloon at 0° C. for 5 hours and return to RT for additional 13 hours.

The reaction was filtered with celite and removed the solvent in vacuo. The crude product was washed with Et₂O (10 mL) three times to afford the product Compound 53c (2-(4-fluorophenyl)ethan-1-amine HCl salt) (940 mg, 89%).

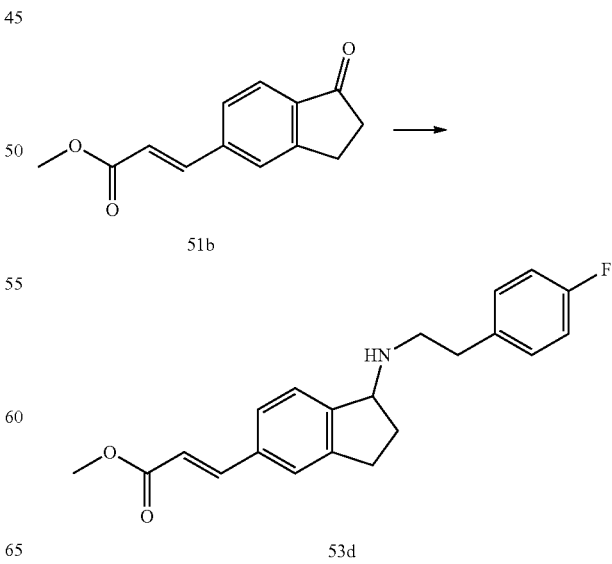

To a solution of Compound 51b (methyl (E)-3-(1-oxo-2,3-dihydro-1H-inden-5-yl)acrylate) (432 mg, 2.00 mmol) in toluene (16 mL) was added p-toluene sulfonic acid monohydrate (28 mg, 0.06 mmol) at RT in pressure tube. Neutralization of Compound 53c (2-(4-fluorophenyl)ethan-1-amine HCl salt) (385 mg, 2.20 mmol) to free amine with NaOH aqueous solution, then remove solvent in vacuo and add to the pressure tube. The tube was sealed and stirred at 130° C. for 3 hours. After cooling to RT, removed solvent in vacuo and dissolved the intermediate in DCM (20 mL). Sodium triacetoxyborohydride (424 mg, 2.00 mmol) was added. The mixture was stirred at RT under nitrogen for 18 hours.

After removing the solvent, purified with column chromatography (EtOAc:n-hexane=2:1) to afford the product Compound 53d (methyl (E)-3-(1-((4-fluorophenethyl)amino)-2,3-dihydro-1H-inden-5-yl)acrylate) (313 mg, 46%).

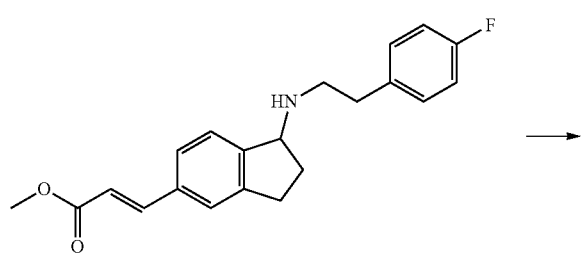

53d

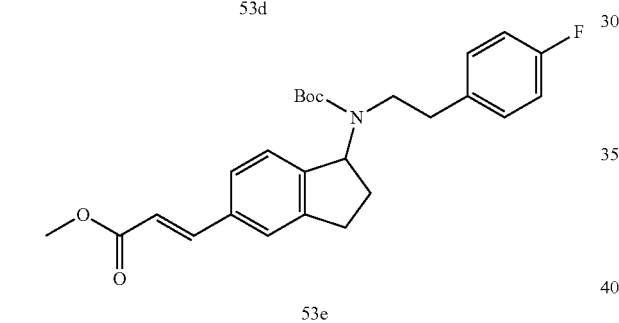

53e

To a solution of Compound 53d (methyl (E)-3-(1-((4-fluorophenethyl)amino)-2,3-dihydro-1H-inden-5-yl)acrylate) (303 mg, 0.89 mmol) in DCM (16 mL) was added Boc$_2$O (430 mg, 1.97 mmol) at RT, followed Et$_3$N (214 mg, 1.97 mmol) and DMAP (36 mg, 0.09 mmol).

The mixture was stirred at RT for 4 hours, then removed the solvent in vacuo and purified with column chromatography (EtOAc:n-hexane=1:10) to afford the product Compound 53e (methyl (E)-3-(1-((tert-butoxycarbonyl)(4-fluorophenethyl)amino)-2,3-dihydro-1H-inden-5-yl)acrylate) (133 mg, 34%).

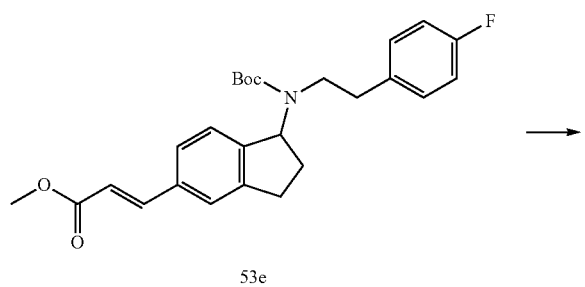

53e

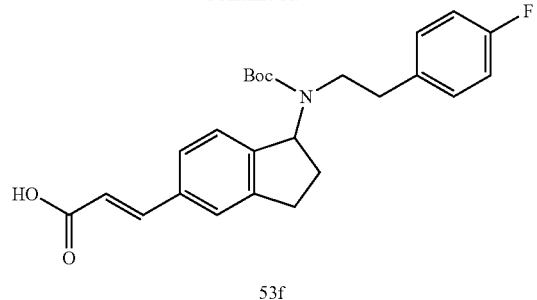

53f

To a solution of Compound 53e (methyl (E)-3-(1-((tert-butoxycarbonyl)(4-fluorophenethyl)amino)-2,3-dihydro-1H-inden-5-yl)acrylate) (124 mg, 0.30 mmol) in MeOH (100 mL) was added NaOH aqueous solution (2.0 M, 10 mL) at RT.

The mixture was stirred at RT for 3 hours, then removed the solvent in vacuo then quench with HCl aqueous solution (1.0 M) to pH=3. The mixture was extracted with EtOAc, then take the organic layer washed with brine. The combined organic layer was dried over anhydrous MgSO$_4$. After remove the solvent, the crude product was taken the next step. Compound 53f ((E)-3-(1-((tert-butoxy carbonyl)(4-fluorophenethyl)amino)-2,3-dihydro-1H-inden-5-yl)acrylic acid) (101 mg, 84%).

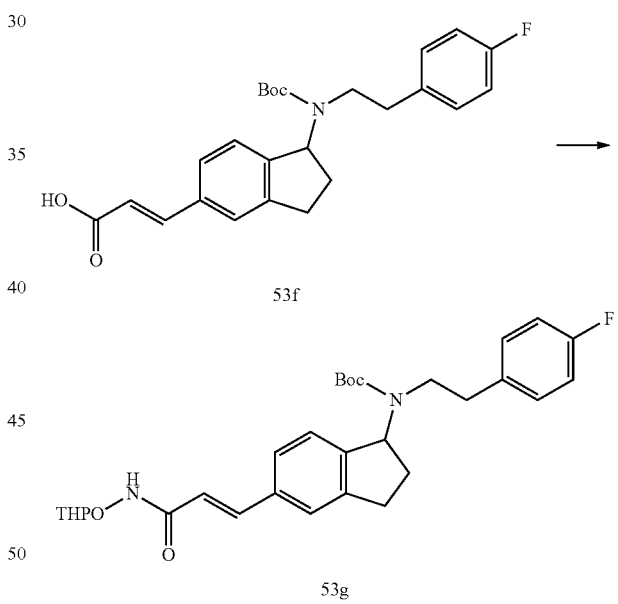

To a solution of Compound 53f ((E)-3-(1-((tert-butoxy carbonyl)(4-fluorophenethyl)amino)-2,3-dihydro-1H-inden-5-yl)acrylic acid) (101 mg, 0.24 mmol) in DMF (16 mL) at 0° C. under nitrogen was added EDC hydrochloride (54 mg, 0.26 mmol), followed DMAP (47 mg, 0.26 mmol) and O-(Tetrahydro-2H-pyran-2-yl)hydroxylamine (31 mg, 0.26 mmol). The mixture was allowed to warm to RT and stirred for 12 hours.

After removing the solvent, the crude product was purified by column chromatography (EtOAc:n-hexane=2:1) to afford the solid Compound 53g (tert-butyl (E)-(4-fluorophenethyl)(5-(3-oxo-3-(((tetrahydro-2H-pyran-2-yl)oxy)amino)prop-1-en-1-yl)-2,3-dihydro-1H-inden-1-yl)carbamate) (70 mg, 56%).

229

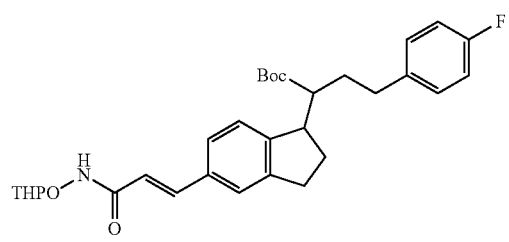

53g

↓

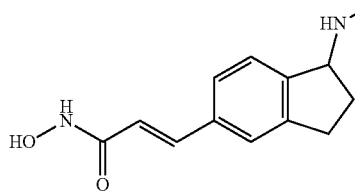

53

To a solution of Compound 53g (tert-butyl (E)-(4-fluorophenethyl)(5-(3-oxo-3-(((tetrahydro-2H-pyran-2-yl)oxy)amino)prop-1-en-1-yl)-2,3-dihydro-1H-inden-1-yl)carbamate) (70 mg, 0.13 mmol) in DCM (10 mL) at RT was added hydrogen chloride solution 2.0 M in diethyl ether (excess, 2 mL).

The reaction was stirred at RT for 90 mins, then the solid was filtered out, washed with DCM, Et$_2$O to afford the product Compound 53 ((E)-3-(14(4-fluorophenethyl)amino)-2,3-dihydro-1H-inden-5-yl)-N-hydroxyacrylamide) (17 mg, 34%).

Compound 53, $^1$H-NMR (500 MHz, CD$_3$OD): δ 7.67-7.65 (d, 1H), 7.59-7.57 (m, 2H), 7.53-7.51 (d, 1H), 7.34-7.31 (t, 2H), 7.09-7.05 (t, 2H), 6.55-6.52 (d, 1H), 4.87-4.86 (m, 1H), 3.34-3.31 (m, 2H), 3.26-3.20 (m, 1H), 3.11-3.01 (m, 3H), 2.65-2.58 (m, 1H), 2.34-2.30 (m, 1H). ESI-MS m/z calcd for C$_{20}$H$_{21}$FN$_2$O$_2$ 340.15 (free acid), found 341.1 [M+H]$^+$.

Synthesis of Compound 54

Scheme 33

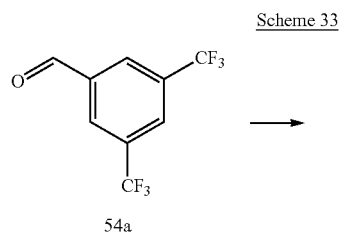

54a

↓

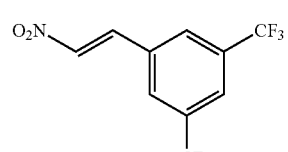

54b

↓

230

-continued

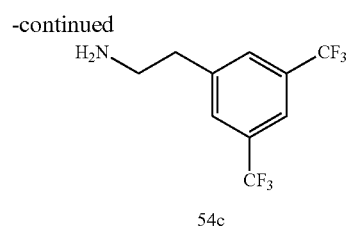

54c

↓

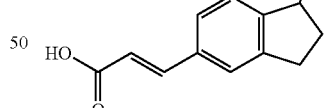

51b

↓

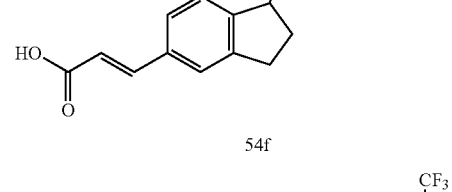

54d

↓

54e

↓

54f

↓

54g

↓

-continued

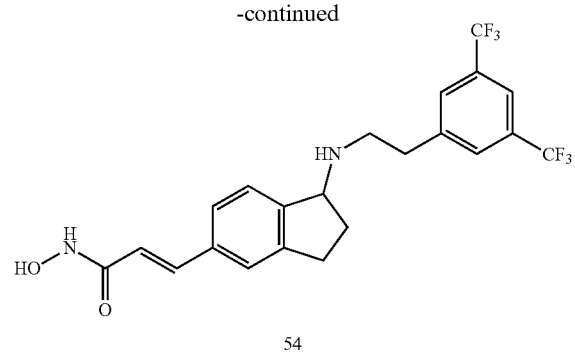

54

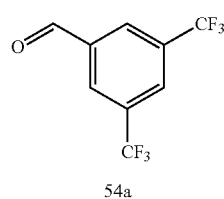

54a

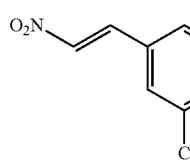

54b

To a solution of Compound 54a (3,5-bis(trifluoromethyl) benzaldehyde) (1945 mg, 8 mmol) was added nitromethane (8 mL), NH₄OAc (135 mg, 1.6 mmol), and acetic acid (3.2 mL) at RT in pressure tube then sealed. The reaction mixture was stirred at 120° C. for 3 hours.

After cooling to RT, the solvent was removed in vacuo. Purification by column chromatography (EtOAc:n-hexane=1:50) to afford the product Compound 54b ((E)-1-(2-nitrovinyl)-3,5-bis(trifluoromethyl)benzene) (1430 mg, 62%).

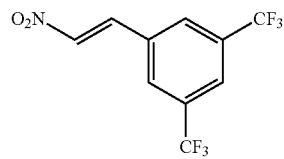

54b

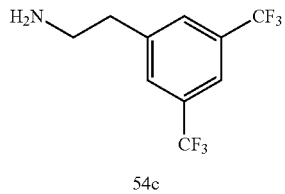

54c

To a solution of Compound 54b ((E)-1-(2-nitrovinyl)-3,5-bis(trifluoromethyl)benzene) (1140 mg, 4.00 mmol) in MeOH (360 mL) at rt was added hydrogen chloride solution 2.0 M in diethyl ether (40 mL, 80 mmol), the mixture was stirred at 0° C. for 0.5 hour. Palladium on carbon (1140 mg) was added to the mixture and degas with hydrogen three times. The reaction was stirred with hydrogen balloon at 0° C. for 5 hours and return to RT for additional 11 hours.

The reaction was filtered with celite and removed the solvent in vacuo. The crude product was washed with Et₂O (15 mL) three times to afford the product Compound 54c (2-(3,5-bis(trifluoromethyl)phenyl)ethan-1-amine HCl salt) (957 mg, 82%).

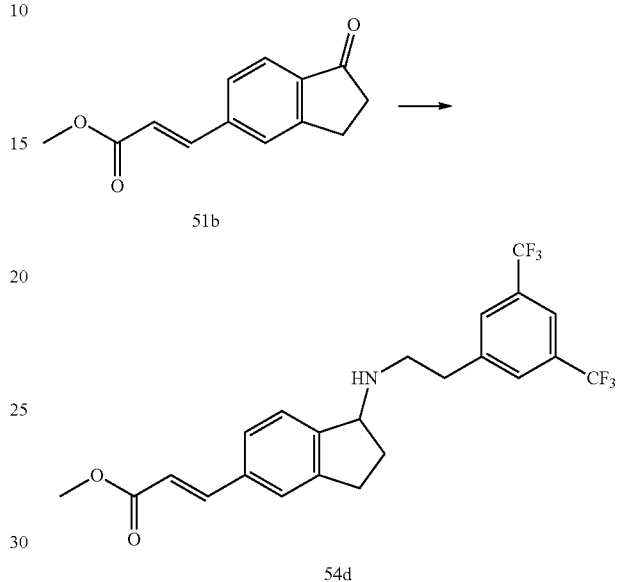

51b

54d

To a solution of Compound 51b (methyl (E)-3-(1-oxo-2,3-dihydro-1H-inden-5-yl)acrylate) (432 mg, 2.00 mmol) in toluene (16 mL) was added p-toluene sulfonic acid monohydrate (15 mg, 0.06 mmol) at rt in pressure tube. Neutralization of Compound 54c (2-(3,5-bis(trifluoromethyl)phenyl)ethan-1-amine HCl salt) (645 mg, 2.20 mmol) to free amine with NaOH aqueous solution, then remove solvent in vacuo and added to the pressure tube. The tube was sealed and stirred at 130° C. for 4 hours.

After cooling to RT, removed solvent in vacuo and dissolved the intermediate in DCM (20 mL). Sodium triacetoxyborohydride (435 mg, 2.00 mmol) was added. The mixture was stirred at RT under nitrogen for 14 hours. After removing the solvent, purified with column chromatography (EtOAc:n-hexane=2:1) to afford the product Compound 54d (methyl (E)-3-(1-(((3,5-bis(trifluoromethyl)phenethyl)amino)-2,3-dihydro-1H-inden-5-yl)acrylate) (415 mg, 45%).

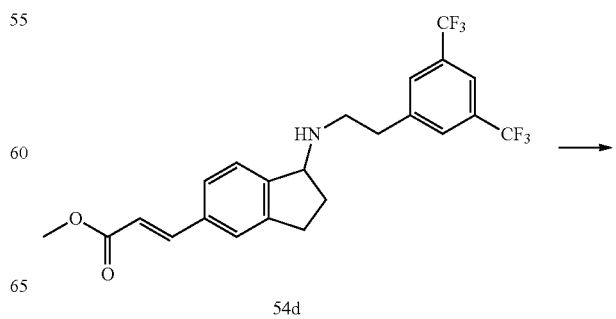

54d

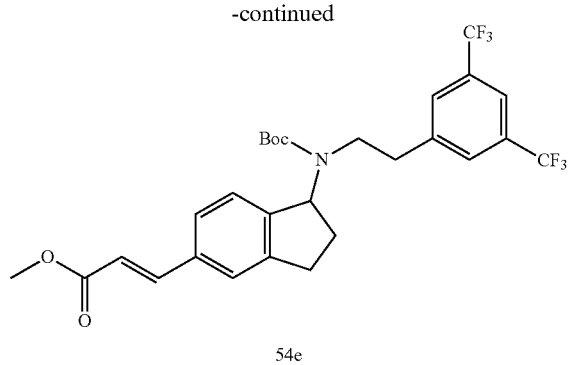

54e

To a solution of Compound 54d (methyl (E)-3-(1-((3,5-bis(trifluoromethyl)phenethyl)amino)-2,3-dihydro-1H-inden-5-yl)acrylate) (405 mg, 0.89 mmol) in DCM (10 mL) was added Boc$_2$O (391 mg, 1.77 mmol) at RT, followed by Et$_3$N (179 mg, 1.77 mmol) and DMAP (26 mg, 0.18 mmol).

The mixture was stirred at RT for 2 hours, then removed the solvent in vacuo and purified with column chromatography (EtOAc:n-hexane=1:10) to afford the product Compound 54e (methyl (E)-3-(1-((3,5-bis(trifluoromethyl)phenethyl)(tert-butoxycarbonyl)amino)-2,3-dihydro-1H-inden-5-yl)acrylate) (192 mg, 39%).

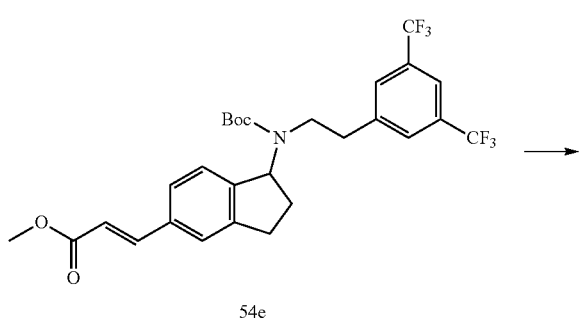

54e

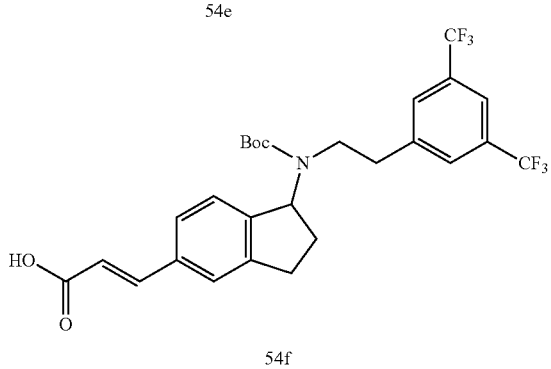

54f

To a solution of Compound 54e (methyl (E)-3-(1-((3,5-bis(trifluoromethyl)phenethyl)(tert-butoxycarbonyl)amino)-2,3-dihydro-1H-inden-5-yl)acrylate) (180 mg, 0.32 mmol) in MeOH (100 mL) was added NaOH aqueous solution (2.0 M, 20 mL) at RT.

The mixture was stirred at RT for 4 hours, then removed the solvent in vacuo then quench with HCl aqueous solution (1.0 M) to pH=4. The mixture was extracted with EtOAc, then take the organic layer washed with brine. The combined organic layer was dried over anhydrous MgSO$_4$. After remove the solvent, the crude product was taken the next step. Compound 54f ((E)-3-(1-((3,5-bis(trifluoromethyl) phenethyl)(tert-butoxycarbonyl)amino)-2,3-dihydro-1H-inden-5-yl)acrylic acid) (176 mg, 99%).

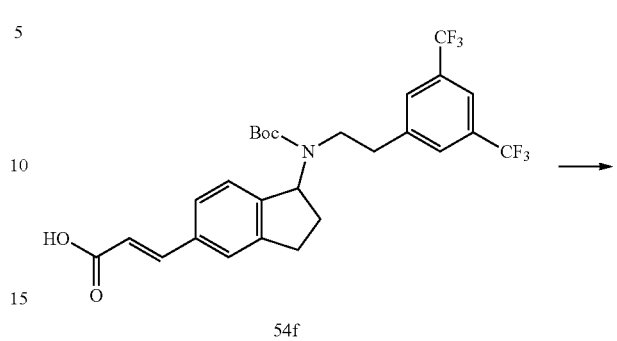

54f

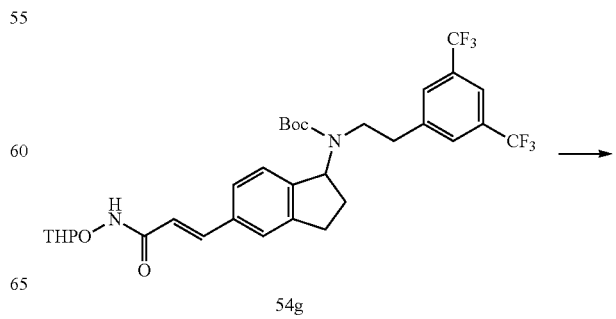

54g

To a solution of Compound 54f ((E)-3-(1-((3,5-bis(trifluoromethyl)phenethyl)(tert-butoxycarbonyl)amino)-2,3-dihydro-1H-inden-5-yl)acrylic acid) (176 mg, 0.32 mmol) in DMF (30 mL) at 0° C. under nitrogen was added EDC hydrochloride (69 mg, 0.36 mmol), followed DMAP (44 mg, 0.36 mmol) and O-(Tetrahydro-2H-pyran-2-yl)hydroxylamine (46 mg, 0.36 mmol). The mixture was allowed to warm to RT and stirred for 12 hours.

After removing the solvent, the crude product was purified by column chromatography (EtOAc:n-hexane=1:1) to afford the solid Compound 54g (tert-butyl (E)-(3,5-bis(trifluoromethyl)phenethyl)(5-(3-oxo-3-(((tetrahydro-2H-pyran-2-yl)oxy)amino)prop-1-en-1-yl)-2,3-dihydro-1H-inden-1-yl)carbamate) (111 mg, 53%).

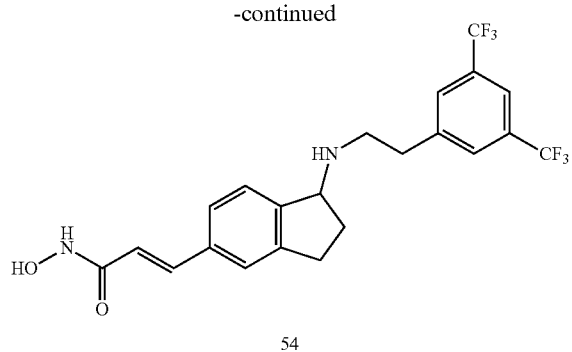

54

To a solution of Compound 54g (tert-butyl (E)-(3,5-bis(trifluoromethyl)phenethyl)(5-(3-oxo-3-(((tetrahydro-2H-pyran-2-yl)oxy)amino)prop-1-en-1-yl)-2,3-dihydro-1H-inden-1-yl)carbamate) (100 mg, 0.16 mmol) in DCM (15 mL) at RT was added hydrogen chloride solution 2.0 M in diethyl ether (excess, 2 mL).

The reaction was stirred at RT for 5 hours, then the solid was filtered out, and washed with DCM, Et$_2$O to afford the product Compound 54 ((E)-3-(1-((3,5-bis(trifluoromethyl)phenethyl)amino)-2,3-dihydro-1H-inden-5-yl)-N-hydroxyacrylamide) (25 mg, 32%).

Compound 54, $^1$H-NMR (500 MHz, CD$_3$OD): δ 7.98 (s, 2H), 7.91 (s, 1H), 7.67-7.66 (d, 1H), 7.57-7.51 (m, 3H), 6.53-6.50 (d, 1H), 3.45-3.44 (m, 2H), 3.27-3.22 (m, 3H), 3.04-3.02 (m, 1H), 2.65-2.61 (m, 1H), 2.34-2.34 (brs, 1H). ESI-MS m/z calcd for C$_{22}$H$_{20}$F$_6$N$_2$O$_2$ 458.14 (free acid), found 459.1 [M+H]$^+$.

Synthesis of Compound 55

Scheme 34

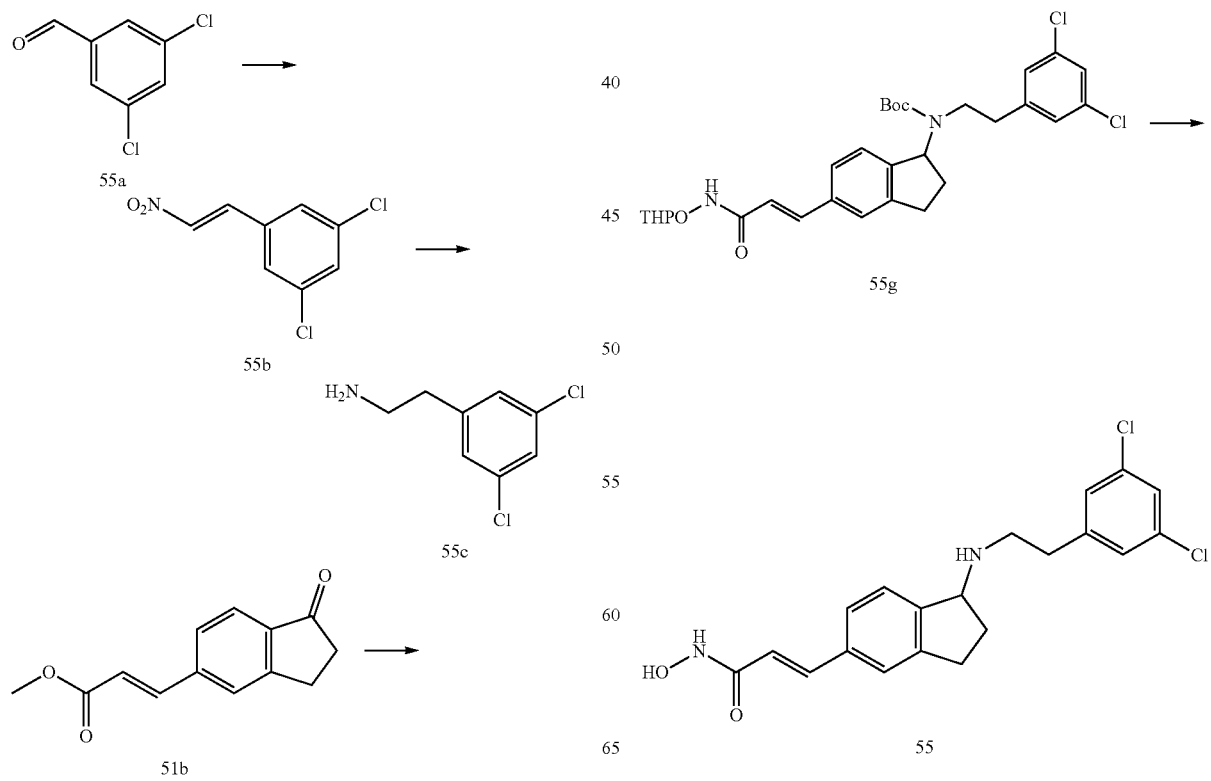

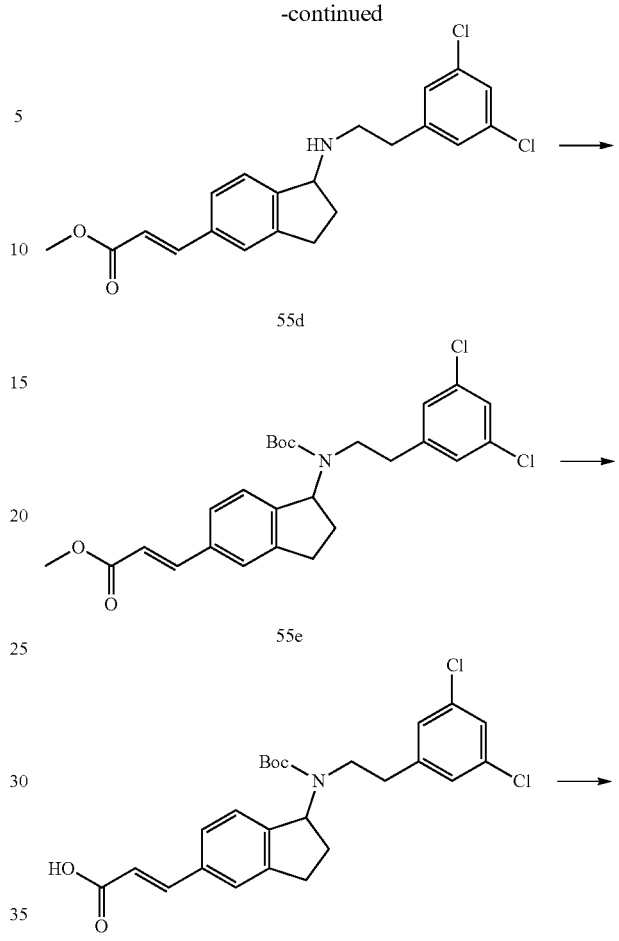

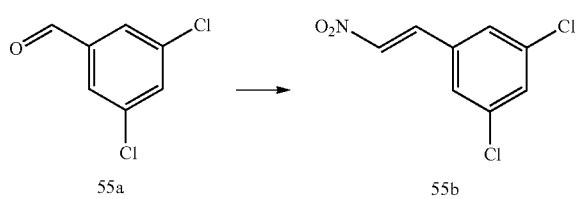 [SMILES: O=Cc1cc(Cl)cc(Cl)c1 ; O=[N+]([O-])/C=C/c1cc(Cl)cc(Cl)c1]

To a solution of Compound 55a (3,5-dichlorobenzaldehyde) (2100 mg, 12 mmol) was added nitromethane (12 mL), NH₄OAc (185 mg, 2.4 mmol), and acetic acid (4.8 mL) at RT in pressure tube then sealed. The reaction mixture was stirred at 120° C. for 4 hours.

After cooling to RT, the solvent was removed in vacuo. Purification by column chromatography (EtOAc:n-hexane=1:50) to afford the product Compound 55b ((E)-1,3-dichloro-5-(2-nitrovinyl)benzene) (1423 mg, 54%).

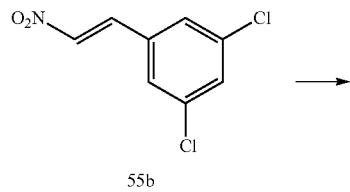

To a solution of Compound 55b ((E)-1,3-dichloro-5-(2-nitrovinyl)benzene) (720 mg, 3.3 mmol) in MeOH (300 mL) at RT was added hydrogen chloride solution 2.0 M in diethyl ether (30 mL, 60 mmol), the mixture was stirred at 0° C. for 0.5 hour. Palladium on carbon (1440 mg) was added to the mixture and degas with hydrogen three times. The reaction was stirred with hydrogen balloon at 0° C. for 5 hours and return to RT for additional 4 hours.

The reaction was filtered with celite and removed the solvent in vacuo. The crude product was washed with Et₂O (10 mL) three times to afford the product Compound 55c (2-(3,5-dichlorophenyl)ethan-1-amine HCl salt) (605 mg, 81%).

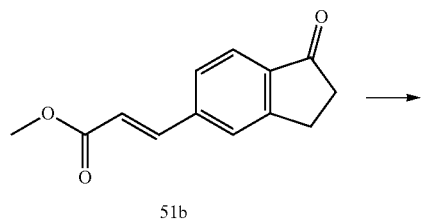

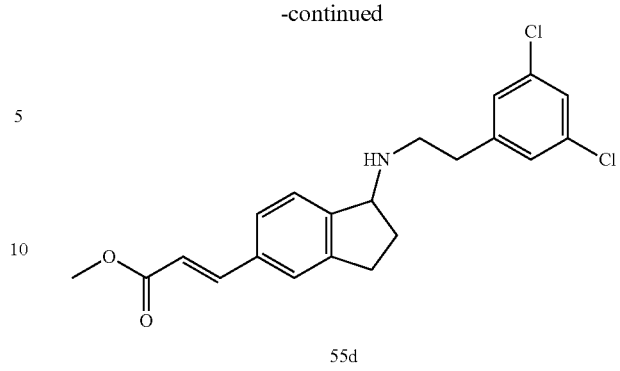

To a solution of Compound 51b (methyl (E)-3-(1-oxo-2,3-dihydro-1H-inden-5-yl)acrylate) (432 mg, 2.00 mmol) in toluene (15 mL) was added p-toluene sulfonic acid monohydrate (16 mg, 0.06 mmol) at RT in pressure tube. Neutralization of Compound 55c (2-(3,5-dichlorophenyl)ethan-1-amine HCl salt) (513 mg, 2.20 mmol) to free amine with NaOH aqueous solution, then remove solvent in vacuo and added to the pressure tube. The tube was sealed and stirred at 125° C. for 4 hours. After cooling to RT, removed solvent in vacuo and dissolved the intermediate in DCM (20 mL). Sodium triacetoxyborohydride (435 mg, 2.00 mmol) was added. The mixture was stirred at RT under nitrogen for 20 hours.

After removing the solvent, purified with column chromatography (EtOAc:n-hexane=2:1) to afford the product Compound 55d (methyl (E)-3-(1-((3,5-dichlorophenethyl)amino)-2,3-dihydro-1H-inden-5-yl)acrylate) (396 mg, 51%).

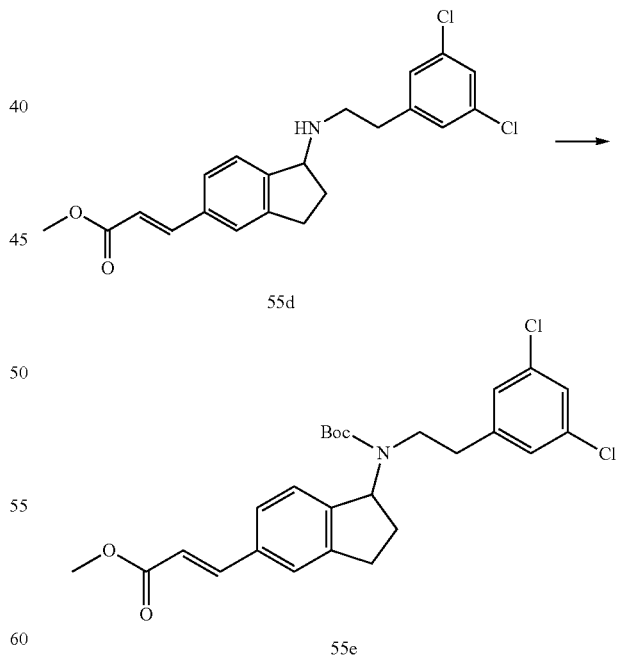

To a solution of Compound 55d (methyl (E)-3-(1-((3,5-dichlorophenethyl)amino)-2,3-dihydro-1H-inden-5-yl)acrylate) (396 mg, 1.02 mmol) in DCM (10 mL) was added Boc₂O (443 mg, 2.03 mmol) at RT, followed Et₃N (230 mg, 2.03 mmol), DMAP (23 mg, 0.10 mmol).

The mixture was stirred at RT for 2 hours, then removed the solvent in vacuo and purified with column chromatography (EtOAc:n-hexane=1:10) to afford the product Compound 55e (methyl (E)-3-(1-((tert-butoxycarbonyl)(3,5-dichlorophenethyl)amino)-2,3-dihydro-1H-inden-5-yl)acrylate) (207 mg, 42%).

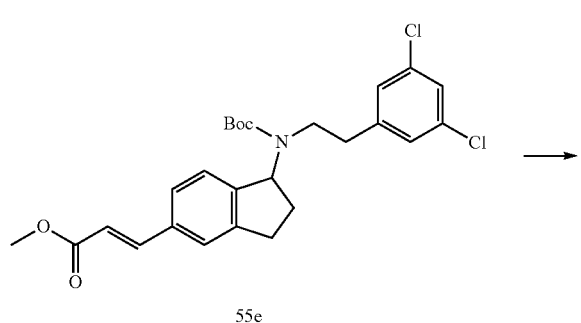

55e

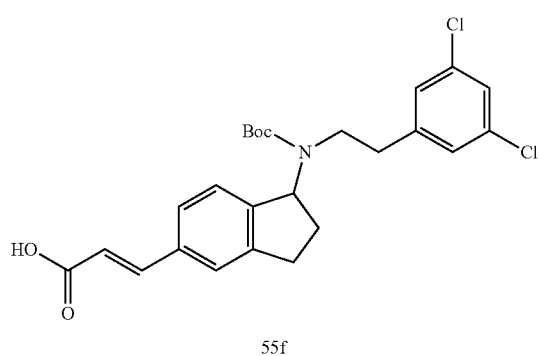

55f

To a solution of Compound 55e (methyl (E)-3-(1-((tert-butoxycarbonyl)(3,5-dichlorophenethyl)amino)-2,3-dihydro-1H-inden-5-yl)acrylate) (207 mg, 0.42 mmol) in MeOH (50 mL) was added NaOH aqueous solution (2.0 M, 20 mL) at RT.

The mixture was stirred at rt for 90 mins, then removed the solvent in vacuo then quench with HCl aqueous solution (1.0 M) to pH=4. The mixture was extracted with EtOAc, then take the organic layer washed with brine. The combined organic layer was dried over anhydrous MgSO₄. After remove the solvent, the crude product was taken the next step. Compound 55f ((E)-3-(1-((tert-butoxy carbonyl)(3,5-dichlorophenethyl)amino)-2,3-dihydro-1H-inden-5-yl)acrylic acid) (174 mg, 87%).

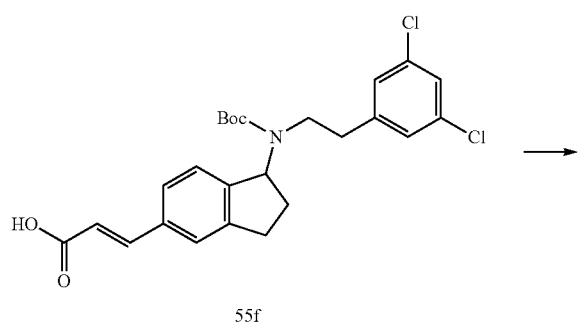

55f

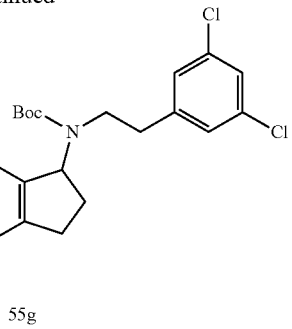

55g

To a solution of Compound 55f ((E)-3-(1-((tert-butoxy carbonyl)(3,5-dichlorophenethyl)amino)-2,3-dihydro-1H-inden-5-yl)acrylic acid) (174 mg, 0.37 mmol) in DMF (30 mL) at 0° C. under nitrogen was added EDC hydrochloride (86 mg, 0.40 mmol), followed DMAP (51 mg, 0.40 mmol) and O-(Tetrahydro-2H-pyran-2-yl)hydroxylamine (50 mg, 0.40 mmol). The mixture was allowed to warm to RT and stirred for 9 hours.

After removing the solvent, the crude product was purified by column chromatography (EtOAc:n-hexane=1:1) to afford the solid Compound 55g (tert-butyl (E)-(3,5-dichlorophenethyl)(5-(3-oxo-3-(((tetrahydro-2H-pyran-2-yl)oxy)amino)prop-1-en-1-yl)-2,3-dihydro-1H-inden-1-yl)carbamate) (117 mg, 54%).

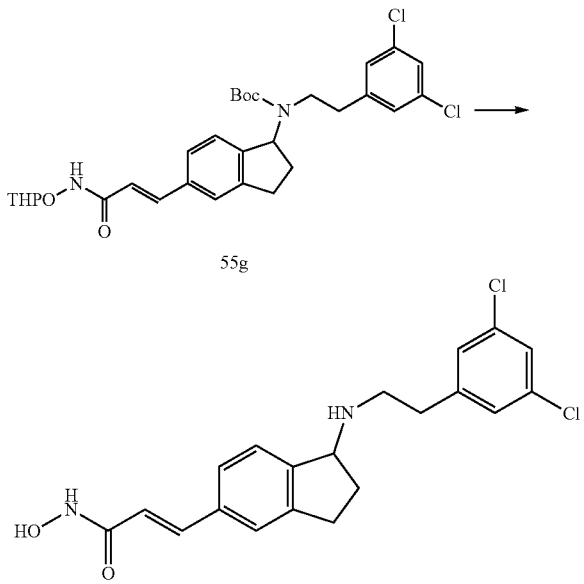

To a solution of Compound 55g (tert-butyl (E)-(3,5-dichlorophenethyl)(5-(3-oxo-3-(((tetrahydro-2H-pyran-2-yl)oxy)amino)prop-1-en-1-yl)-2,3-dihydro-1H-inden-1-yl)carbamate) (104 mg, 0.18 mmol) in DCM (5 mL) at RT was added hydrogen chloride solution 2.0 M in diethyl ether (excess, 2 mL).

The reaction was stirred at RT for 5 hours, then the solid was filtered out, and washed with DCM, Et₂O to afford the product Compound 55 ((E)-3-(1-((3,5-dichlorophenethyl)amino)-2,3-dihydro-1H-inden-5-yl)-N-hydroxyacrylamide) (40 mg, 52%).

Compound 55, ¹H-NMR (500 MHz, CD₃OD): δ 7.68-7.66 (d, 1H), 7.60-7.57 (m, 2H), 7.54-7.52 (m, 1H), 7.37-7.37 (d, 1H), 7.34-7.34 (d, 2H), 6.55-5.52 (d, 1H), 4.87-4.85 (m, 1H), 3.38-3.34 (m, 2H), 3.27-3.20 (m, 1H), 3.12-3.00 (m, 3H), 2.66-2.58 (m, 1H), 2.35-2.29 (m, 1H). ESI-MS m/z calcd for $C_{20}H_{20}Cl_2N_2O_2$ 390.09 (free acid), found 391.0 $[M+H]^+$.

Synthesis of Compound 56

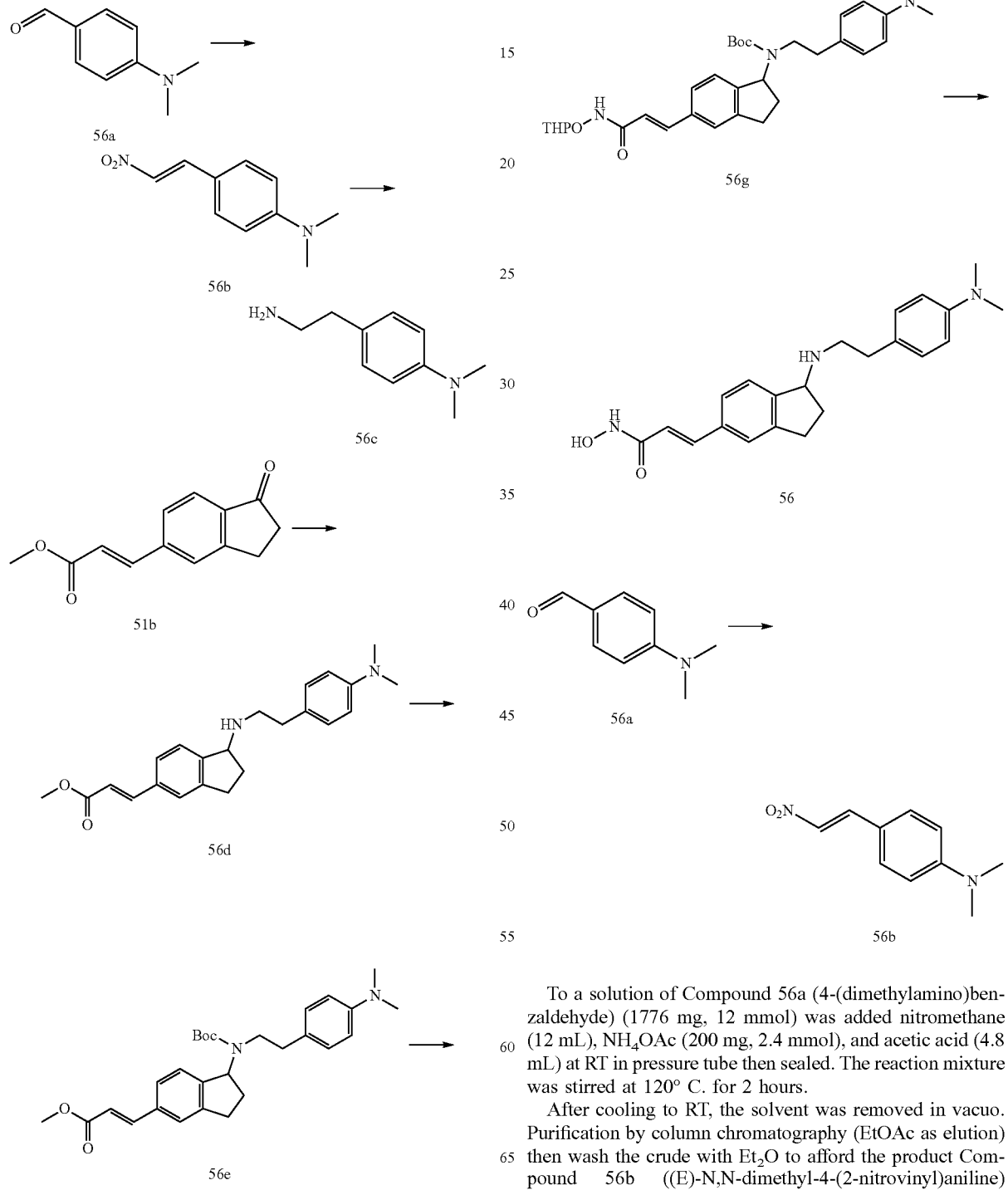

To a solution of Compound 56a (4-(dimethylamino)benzaldehyde) (1776 mg, 12 mmol) was added nitromethane (12 mL), NH₄OAc (200 mg, 2.4 mmol), and acetic acid (4.8 mL) at RT in pressure tube then sealed. The reaction mixture was stirred at 120° C. for 2 hours.

After cooling to RT, the solvent was removed in vacuo. Purification by column chromatography (EtOAc as elution) then wash the crude with Et₂O to afford the product Compound 56b ((E)-N,N-dimethyl-4-(2-nitrovinyl)aniline) (1242 mg, 54%).

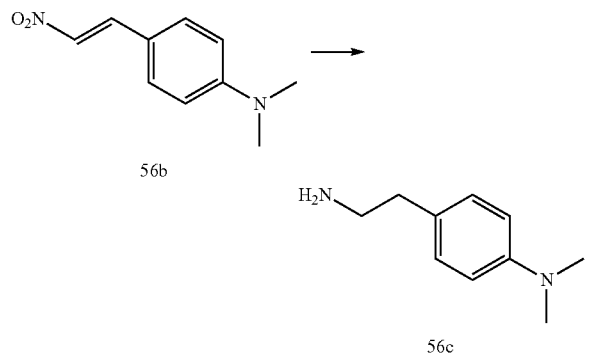

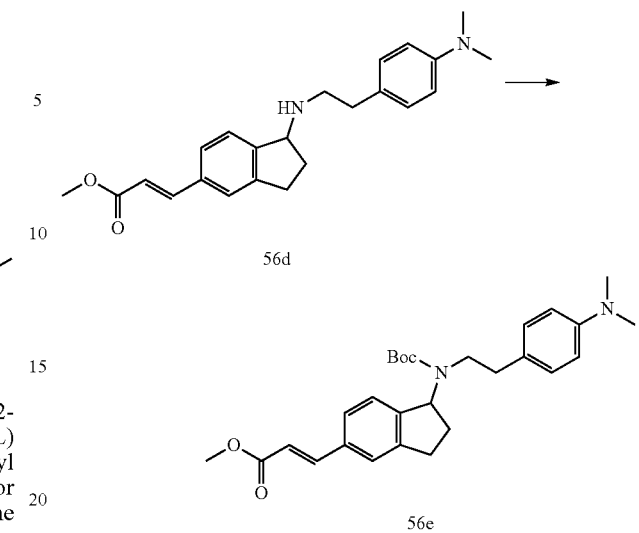

To a solution of Compound 56b ((E)-N,N-dimethyl-4-(2-nitrovinyl)aniline) (672 mg, 3.5 mmol) in MeOH (320 mL) at RT was added hydrogen chloride solution 2.0 M in diethyl ether (35 mL, 70 mmol), the mixture was stirred at 0° C. for 0.5 hour. Palladium on carbon (700 mg) was added to the mixture and degas with hydrogen three times. The reaction was stirred with hydrogen balloon at 0° C. for 5 hours and return to RT for additional 7 hours.

The reaction was filtered with celite and removed the solvent in vacuo. The crude product was afforded Compound 56c (4-(2-aminoethyl)-N,N-dimethylaniline HCl salt) (829 mg, 99%).

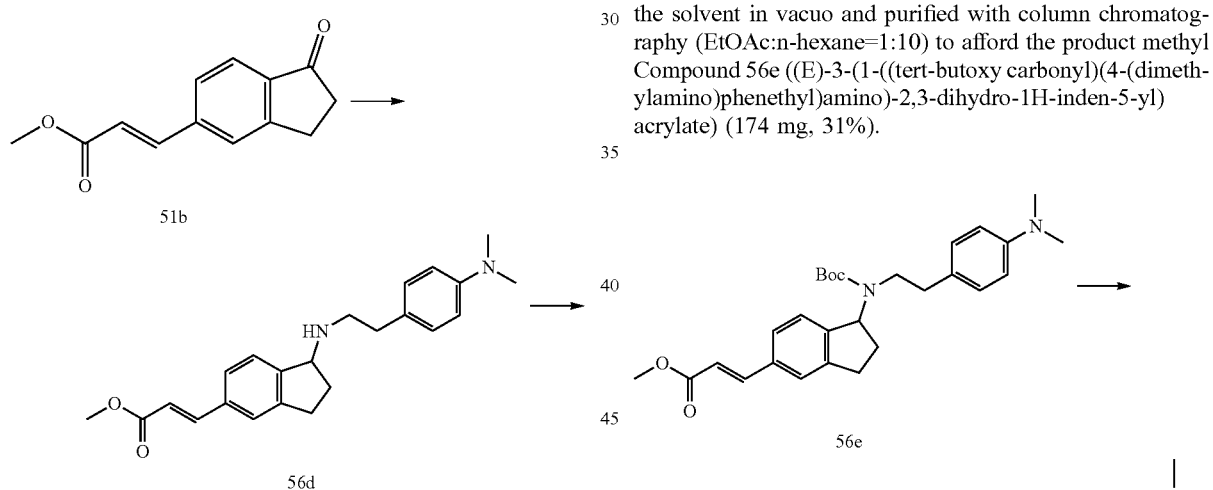

To a solution of Compound 51b (methyl (E)-3-(1-oxo-2,3-dihydro-1H-inden-5-yl)acrylate) (432 mg, 2.00 mmol) in toluene (15 mL) was added p-toluene sulfonic acid monohydrate (18 mg, 0.06 mmol) at RT in pressure tube. Neutralization of Compound 56c (4-(2-aminoethyl)-N,N-dimethylaniline HCl salt) (829 mg, 3.50 mmol) to free amine with NaOH aqueous solution, then remove solvent in vacuo and added to the pressure tube. The tube was sealed and stirred at 130° C. for 3 hours. After cooling to rt, removed solvent in vacuo and dissolved the intermediate in DCM (20 mL). Sodium triacetoxyborohydride (524 mg, 2.00 mmol) was added. The mixture was stirred at RT under nitrogen for 21 hours.

After removing the solvent, purified with column chromatography (EtOAc:n-hexane=5:1) to afford the product Compound 56d (methyl (E)-3-(1-((4-(dimethylamino)phenethyl)amino)-2,3-dihydro-1H-inden-5-yl)acrylate) (444 mg, 61%).

To a solution of Compound 56d (methyl (E)-3-(1-((4-(dimethylamino)phenethyl)amino)-2,3-dihydro-1H-inden-5-yl)acrylate) (444 mg, 1.22 mmol) in DCM (10 mL) was added Boc$_2$O (563 mg, 2.44 mmol) at RT, followed Et$_3$N (268 mg, 2.44 mmol), DMAP (23 mg, 0.12 mmol).

The mixture was stirred at RT for 3 hours, then removed the solvent in vacuo and purified with column chromatography (EtOAc:n-hexane=1:10) to afford the product methyl Compound 56e ((E)-3-(1-((tert-butoxy carbonyl)(4-(dimethylamino)phenethyl)amino)-2,3-dihydro-1H-inden-5-yl)acrylate) (174 mg, 31%).

To a solution of Compound 56e (methyl (E)-3-(1-((tert-butoxycarbonyl)(4-(dimethylamino)phenethyl)amino)-2,3-dihydro-1H-inden-5-yl) acrylate) (164 mg, 0.35 mmol) in MeOH (100 mL) was added NaOH aqueous solution (2.0 M, 20 mL) at RT.

The mixture was stirred at RT for 15 hours, then removed the solvent in vacuo followed quench with HCl aqueous solution (1.0 M) to pH=4. The mixture was extracted with EtOAc, then take the organic layer washed with brine. The combined organic layer was dried over anhydrous MgSO₄. After remove the solvent, the crude product was taken the next step. Compound 56f ((E)-3-(1-((tert-butoxy carbonyl)(4-(dimethylamino)phenethyl)amino)-2,3-dihydro-1H-inden-5-yl) acrylic acid) (159 mg, 99%).

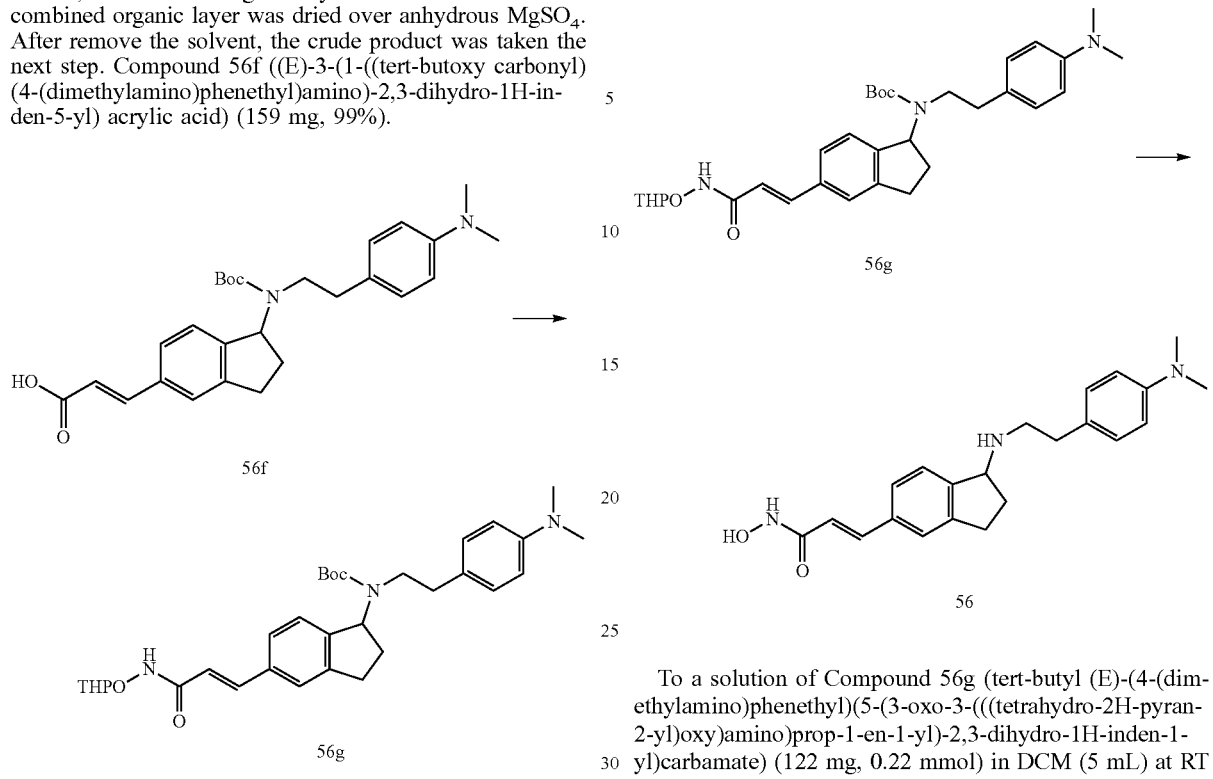

To a solution of Compound 56f ((E)-3-(1-((tert-butoxy carbonyl)(4-(dimethylamino)phenethyl)amino)-2,3-dihydro-1H-inden-5-yl) acrylic acid) (164 mg, 0.36 mmol) in DMF (30 mL) at 0° C. under nitrogen was added EDC hydrochloride (83 mg, 0.40 mmol), followed DMAP (59 mg, 0.48 mmol) and O-(Tetrahydro-2H-pyran-2-yl)hydroxylamine (68 mg, 0.58 mmol). The mixture was allowed to warm to RT and stirred for 22 hours.

After removing the solvent, the crude product was purified by column chromatography (EtOAc:n-hexane=1:1) to afford the solid Compound 56g (tert-butyl (E)-(4-(dimethylamino)phenethyl)(5-(3-oxo-3-(((tetrahydro-2H-pyran-2-yl)oxy)amino)prop-1-en-1-yl)-2,3-dihydro-1H-inden-1-yl)carbamate) (137 mg, 69%).

To a solution of Compound 56g (tert-butyl (E)-(4-(dimethylamino)phenethyl)(5-(3-oxo-3-(((tetrahydro-2H-pyran-2-yl)oxy)amino)prop-1-en-1-yl)-2,3-dihydro-1H-inden-1-yl)carbamate) (122 mg, 0.22 mmol) in DCM (5 mL) at RT was added hydrogen chloride solution 2.0 M in diethyl ether (excess, 2 mL).

The reaction was stirred at RT for 6 hours, then the solid was filtered out, and washed with DCM, Et₂O to afford the product Compound 56 ((E)-3-(1-((4-(dimethylamino)phenethyl)amino)-2,3-dihydro-1H-inden-5-yl)-N-hydroxyacrylamide) (70 mg, 72%).

Compound 56, ¹H-NMR (500 MHz, CD₃OD): δ 7.71-7.69 (m, 3H), 7.60-7.51 (m, 5H), 6.55-6.52 (d, 1H), 3.38-3.35 (m, 2H), 3.30 (s, 6H), 3.28-3.15 (m, 3H), 3.05-3.00 (m, 1H), 2.64-2.60 (m, 1H), 2.37-2.32 (m, 1H). ESI-MS m/z calcd for $C_{22}H_{27}N_3O_2$ 365.21 (free acid), found 366.0 [M+H]⁺.

Synthesis of Compounds 57~58

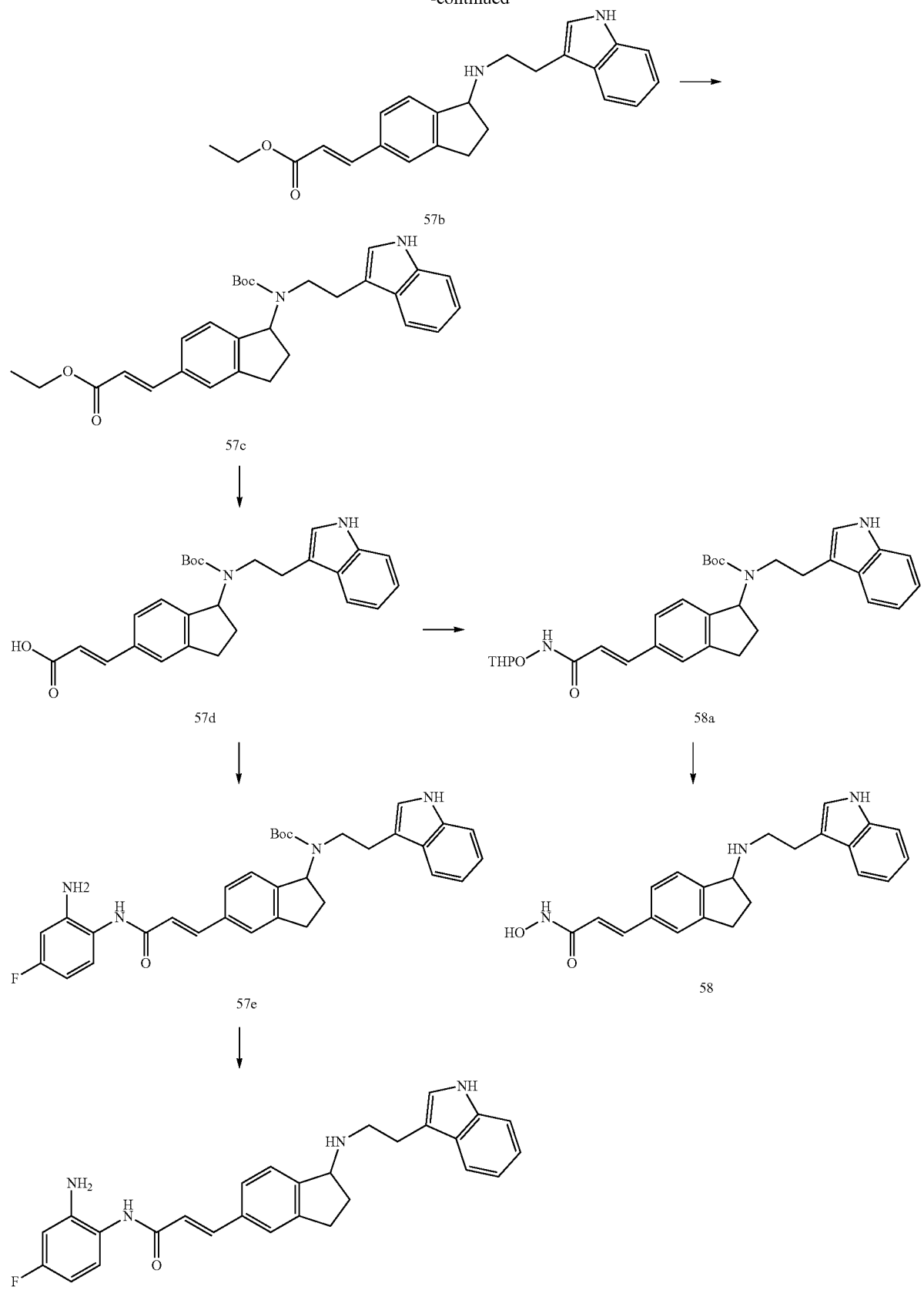

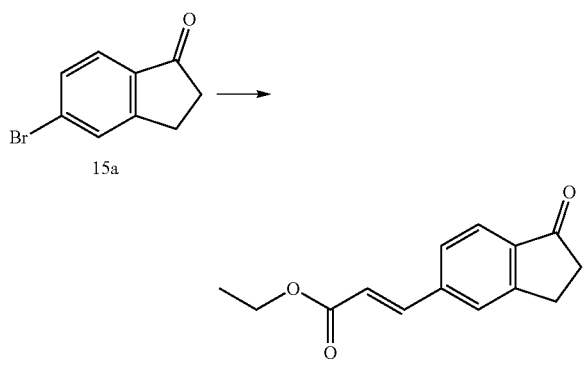

A solution of Compound 15a (5-bromo-2,3-dihydro-1H-inden-1-one) (1.0 g, 4.74 mmol), ethyl acrylate (1.1 mL, 9.48 mmol) and triphenylphosphine (0.5 g, 0.40 mmol) in TEA (0.7 mL, 4.74 mmol) and DMF (8 mL) was degassed by bubbling argon for 3 min. Pd(OAc)$_2$ (0.1 g, 0.47 mmol) was added, and vacuum/argon was applied three times. The reaction mixture was stirred under argon at 100° C. for 12 hours.

The mixture was extracted with EtOAc and NH$_4$Cl (aq.). The organic layer was dried over MgSO$_4$ and concentrated in vacuo and purified by flash chromatography (EtOAc:Hex.=1:4) to provide the yellow solid product Compound 57a (ethyl (E)-3-(1-oxo-2,3-dihydro-1H-inden-5-yl)acrylate) (640.0 mg, yield 59%).

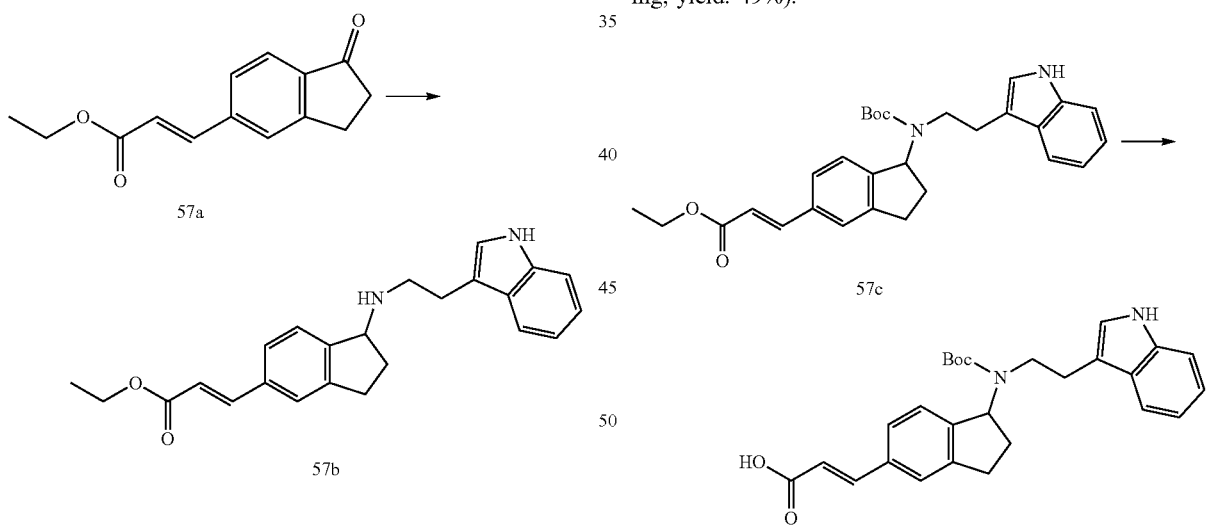

A mixture of Compound 57a (ethyl (E)-3-(1-oxo-2,3-dihydro-1H-inden-5-yl)acrylate) (100.0 mg, 0.434 mmol), tryptamine (76.9 mg, 0.48 mmol) and p-Toluenesulfonic acid (2.5 mg, 0.01 mmol) in toluene (5 mL) were stirred at 160° C. for 4 hours. The mixture was diluted with DCM when the temperature at RT, followed by addition of NaB(OAc)$_3$ (92.0 mg, 0.43 mmol) and stirred at RT for overnight.

The mixture was concentrated and purified by silica gel column chromatography (EtOAc:Hex.=2:1) to provide the product Compound 57b (ethyl (E)-3-(1-((2-(1H-indol-3-yl)ethyl)amino)-2,3-dihydro-1H-inden-5-yl)acrylate) (66.0 mg, Yield 41%).

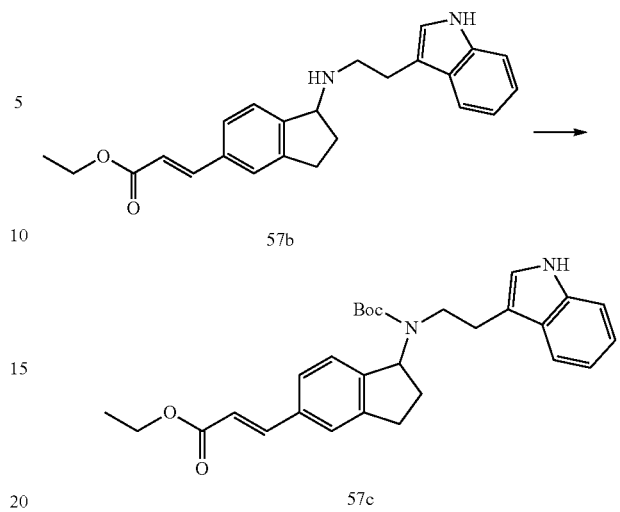

A mixture of Compound 57b (ethyl (E)-3-(1-((2-(1H-indol-3-yl)ethyl)amino)-2,3-dihydro-1H-inden-5-yl)acrylate) (0.1 g, 0.27 mmol), (Boc)$_2$O (116.5 mg, 0.53 mmol) and DMAP (97.8 mg, 0.8 mmol) in THF (10 mL) was stirred at 50° C. for 2 hours.

The mixture was extracted with EtOAc and NH$_4$Cl (aq.). The organic layer was dried over MgSO$_4$ and concentrated in vacuo and purified by flash chromatography (EtOAc./Hexane=1:2) to provide the black oil product Compound 57c (ethyl (E)-3-(1-((2-(1H-indol-3-yl)ethyl)(tert-butoxycarbonyl)amino)-2,3-dihydro-1H-inden-5-yl)acrylate) (63.2 mg, yield: 49%).

To a solution of Compound 57c (ethyl (E)-3-(1-((2-(1H-indol-3-yl)ethyl)(tert-butoxycarbonyl)amino)-2,3-dihydro-1H-inden-5-yl)acrylate) (300.0 mg, 0.63 mmol) in MeOH (3 mL) was added 2N NaOH solution (2.5 mL) at 50° C. and stirred for 3 hours.

The reaction mixture was concentrated to remove the organic solvent. The residue was diluted with water and acidified to pH=6 with 2N HCl$_{(aq.)}$. and extracted with DCM. The organic layer was dried over MgSO$_4$ and concentrated in vacuo to give the product Compound 57d ((E)-3-(1-((2-(1H-indol-3-yl)ethyl)(tert-butoxycarbonyl) amino)-2,3-dihydro-1H-inden-5-yl)acrylic acid) (280.0 mg, yield 67%).

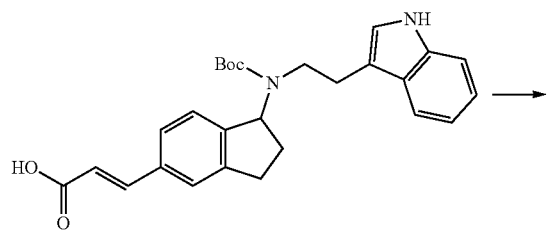

57d

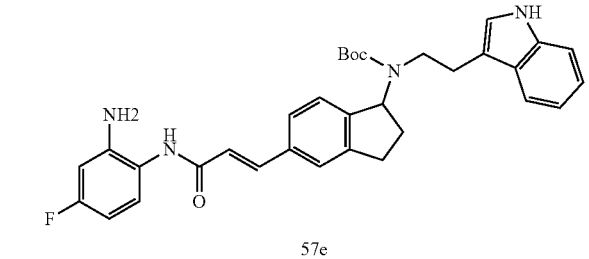

57e

To a stirred solution of 4-Fluoro-1,2-phenylenediamine (34.0 mg, 0.27 mmol) and NMM (0.05 mL, 0.44 mmol) in DCM (5 mL) was added Compound 57d ((E)-3-(1-((2-(1H-indol-3-yl)ethyl)(tert-butoxycarbonyl)amino)-2,3-dihydro-1H-inden-5-yl)acrylic acid) (100.0 mg, 0.22 mmol) in one portion, followed by addition of HATU (92.0 mg, 0.24 mmol) in one portion at RT. The resulting mixture was stirred at RT for overnight.

The resulting residue was purified by flash chromatography (EtOAc. only) to provide the product Compound 57e (tert-butyl (E)-(2-(1H-indol-3-yl)ethyl)(5-(34(2-amino-4-fluorophenyl)amino)-3-oxoprop-1-en-1-yl)-2,3-di hydro-1H-inden-1-yl)carbamate) (30.0 mg, yield 25%).

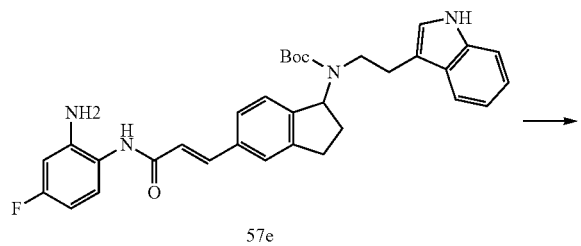

57e

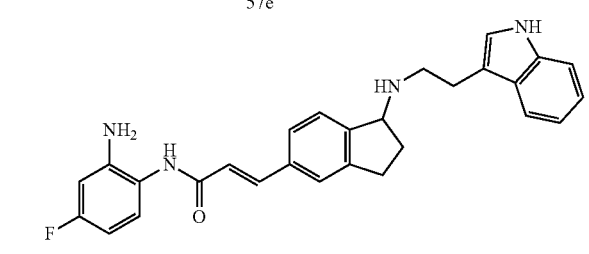

57

Compound 57e (Tert-butyl (E)-(2-(1H-indol-3-yl)ethyl) (5-(3-((2-amino-4-fluorophenyl)amino)-3-oxoprop-1-en-1-yl)-2,3-di hydro-1H-inden-1-yl)carbamate) (68.0 mg, 0.12 mmol) was added 2N HCl (3.0 mL, in diethyl ether) at 0° C. The mixture was stirred at RT for 12 hours.

The mixture was concentrated and washed with ether to provide the red product Compound 57 ((E)-3-(1-((2-(1H-indol-3-yl)ethyl)amino)-2,3-dihydro-1H-inden-5-yl)-N-(2-amino-4-fluorophen yl)acrylamide) (44.0 mg, yield 80%).

Compound 57, $^1$H-NMR (500 MHz, $d_6$-DMSO): δ 10.96 (s, 1H), 9.64 (s, 1H), 9.35 (s, 1H), 7.82 (s, 1H), 7.70-7.67 (m, 1H), 7.58-7.55 (m, 3H), 7.37-7.36 (m, 2H), 7.32 (s, 1H), 7.19-7.18 (m, 1H), 7.10-6.98 (m, 2H), 6.64-6.61 (m, 1H), 6.46-6.45 (m, 1H), 4.84 (s, 1H), 3.29 (s, 1H), 3.21-3.15 (m, 4H), 2.94-2.91 (m, 1H), 2.49 (s, 1H), 2.26 (s, 1H). ESI-MS m/z calcd for $C_{28}H_{27}FN_4O$ 454.22 (free acid), found 455.2 [M+H]$^+$.

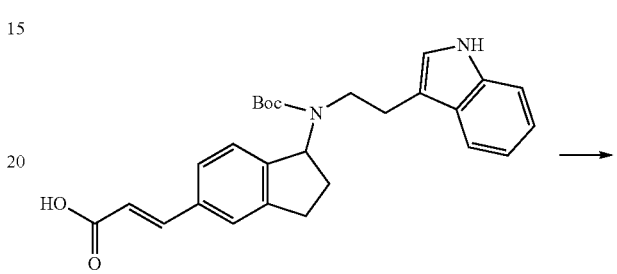

57d

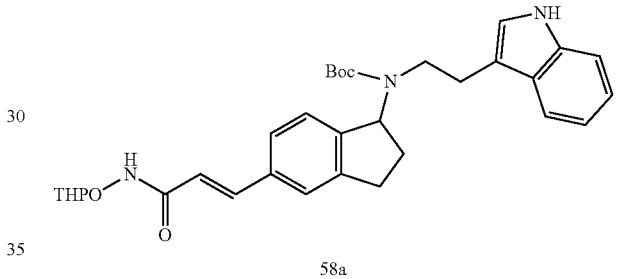

58a

To a stirred solution of O-(Tetrahydro-2H-pyran-2-yl) hydroxylamine (31.25 mg, 0.27 mmol) and DMAP (59.1 mg, 0.48 mmol) in DCM (15 mL) was added Compound 57d ((E)-3-(1-((2-(1H-indol-3-yl)ethyl)(tert-butoxycarbonyl) amino)-2,3-dihydro-1H-inden-5-yl)acrylic acid) (100.0 mg, 0.22 mmol) in one portion, followed by addition of EDCI (51.7 mg, 0.27 mmol) in one portion at RT and stirred for 12 hours.

The mixture was washed with NH$_4$Cl(aq.) and brine. The organic layer was dried over MgSO$_4$ and concentrated in vacuo to give the crude material. The resulting residue was purified by silica gel column chromatography (EtOAc: Hex.=1:1) to provide the product Compound 58a (tert-butyl (E)-(2-(1H-indol-3-yl)ethyl)(5-(3-oxo-3-(((tetrahydro-2H-pyran-2-yl)oxy)amino)prop-1-en-1-yl)-2,3-dihydro-1H-inden-1-yl)carbamate) (67.0 mg, yield 56%).

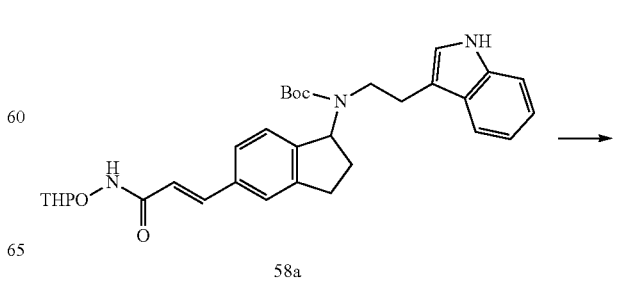

58a

-continued

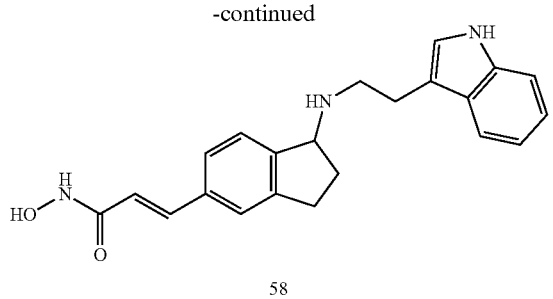

58

Compound 58a (Tert-butyl (E)-(2-(1H-indol-3-yl)ethyl) (5-(3-oxo-3-(((tetrahydro-2H-pyran-2-yl)oxy)amino)prop-1-en-1-yl)-2,3-dihydro-1H-inden-1-yl)carbamate) (66.0 mg, 0.12 mmol) was added 2N HCl (2.0 mL, in diethyl ether) at 0° C. The mixture was stirred at RT for 12 hours.

The mixture was concentrated and washed with ether to provide the product Compound 58 ((E)-3-(1-((2-(1H-indol-3-yl)ethyl)amino)-2,3-dihydro-1H-inden-5-yl)-N-hydroxyacrylamide) (17.0 mg, yield 31%).

Compound 58, $^1$H-NMR (500 MHz, $d_6$-DMSO): δ 10.96 (s, 1H), 10.78 (s, 1H), 9.48 (s, 1H), 9.33 (s, 1H), 7.78-7.76 (d, 1H), 7.73-7.67 (d, 1H), 7.59-7.45 (m, 3H), 7.37-7.36 (d, 1H), 7.26 (s, 1H), 7.11-7.00 (d, 2H), 6.52-6.49 (d, 1H), 4.82 (s, 1H), 3.32-3.11 (m, 4H), 2.91-2.90 (m, 2H), 2.36-2.24 (m, 2H). ESI-MS m/z calcd for $C_{22}H_{23}N_3O_2$ 361.18 (free acid), found 362.1 [M+H]$^+$.

Synthesis of Compounds 59~60

Scheme 37

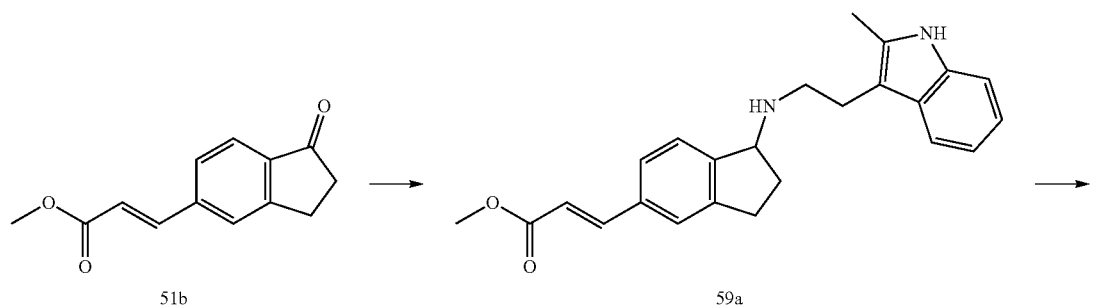

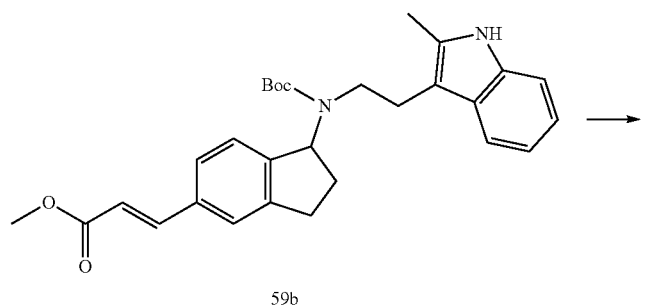

59b

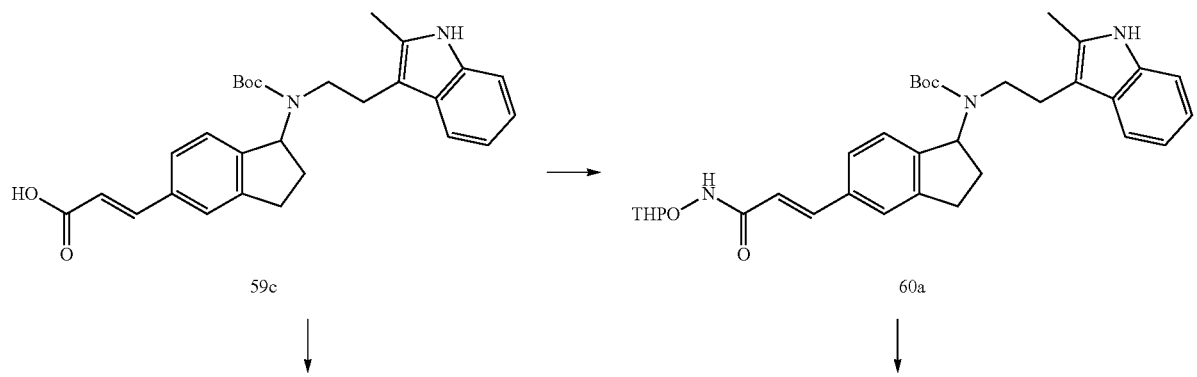

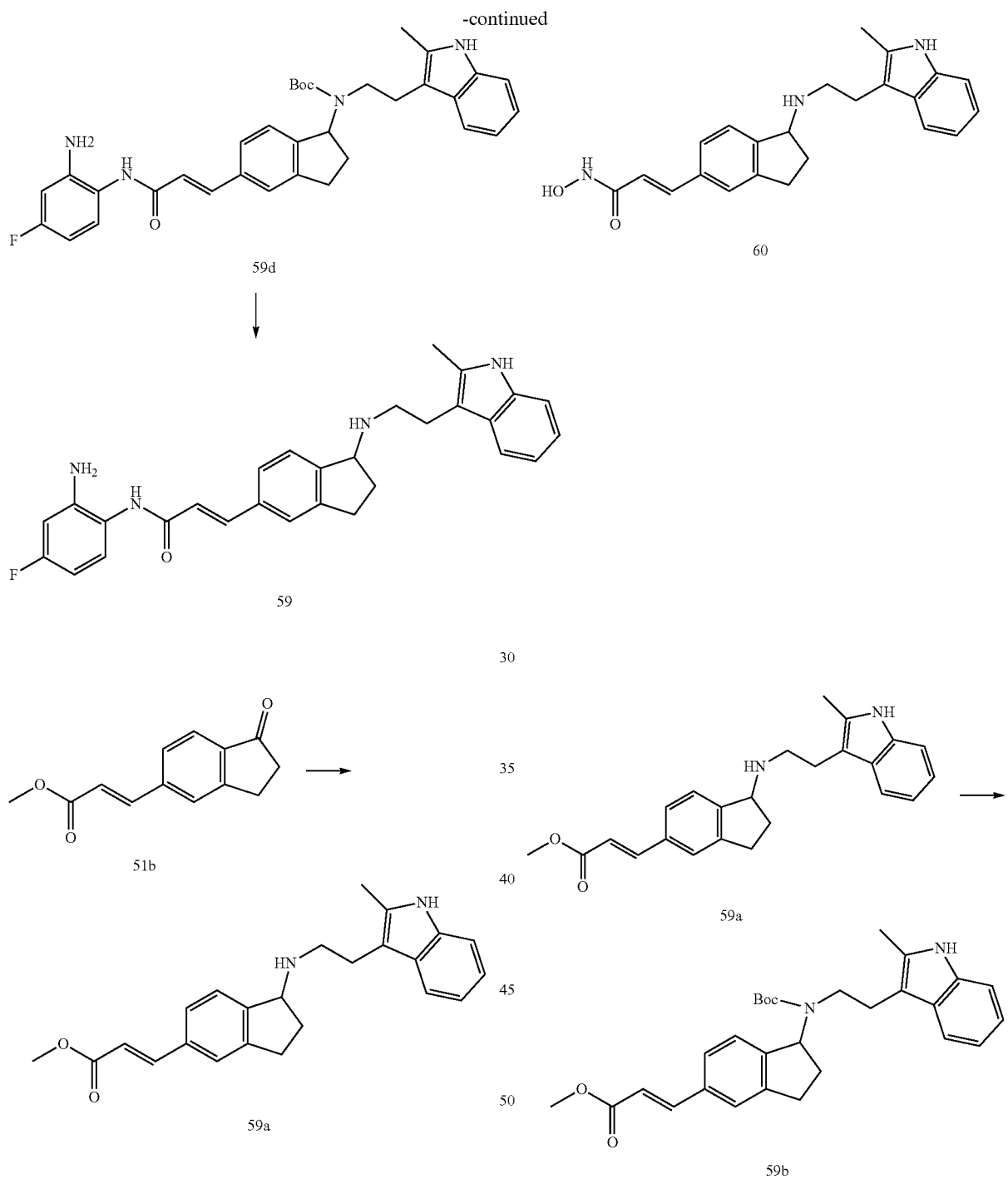

A mixture of Compound 51b (methyl (E)-3-(1-oxo-2,3-dihydro-1H-inden-5-yl)acrylate) (1.0 g, 4.63 mmol), 2-(2-methyl-1H-indol-3-yl)ethan-1-amine (0.89 g, 5.1 mmol) and p-toluenesulfonic acid (26.4 mg, 0.14 mmol) in toluene (30 mL) were stirred at 160° C. for 4 hours. The mixture was diluted with DCM when the temperature at RT, followed by addition of NaB(OAc)$_3$ (980.0 mg, 4.63 mmol) and stirred at RT for overnight.

The mixture was concentrated and purified by silica gel column chromatography (EA only) to provide the product Compound 59a (methyl (E)-3-(1-((2-(2-methyl-1H-indol-3-yl)ethyl)amino)-2,3-dihydro-1H-inden-5-yl)acrylate) (400.0 mg, yield: 23%).

A solution of Compound 59a (methyl (E)-3-(1-((2-(2-methyl-1H-indol-3-yl)ethyl)amino)-2,3-dihydro-1H-inden-5-yl)acrylate) (0.4 g, 1.07 mmol), (Boc)$_2$O (255.4 mg, 1.17 mmol) and DMAP (287.1 mg, 2.35 mmol) in THF (15 mL) was stirred at 50° C. for 2 hours.

The mixture was extracted with EtOAc and NH$_4$Cl (aq.). The organic layer was dried over MgSO$_4$ and concentrated in vacuo and purified by flash chromatography (EtOAc./Hexane=1:2) to provide the black oil product Compound 59b (methyl (E)-3-(1-((tert-butoxycarbonyl)(2-(2-methyl-1H-indol-3-yl)ethyl)amino)-2,3-dihydro-1H-inden-5-yl)acrylate) (190.0 mg, yield 37%).

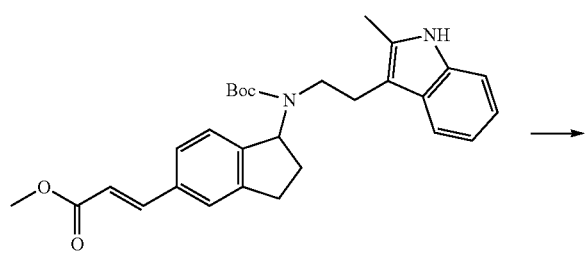

59b

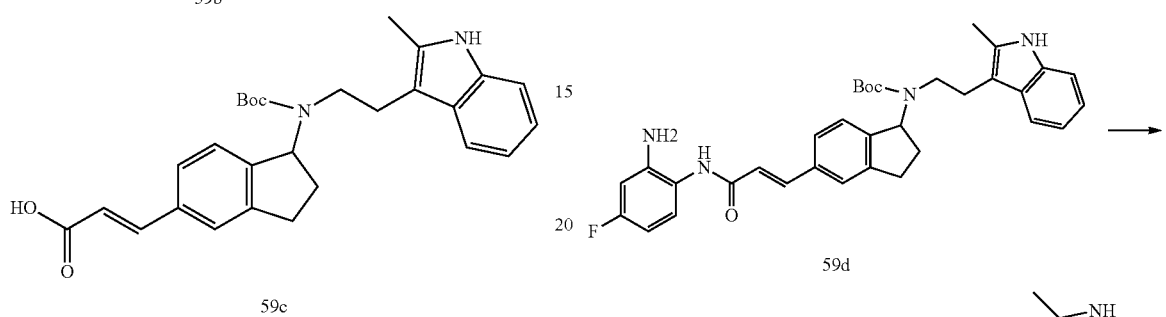

To a solution of Compound 59b (methyl (E)-3-(1-((tert-butoxycarbonyl)(2-(2-methyl-1H-indol-3-yl)ethyl)amino)-2,3-dihydro-1H-inden-5-yl)acrylate) (160.0 mg, 0.34 mmol) in MeOH (5 mL) was added 2N NaOH solution (0.3 mL) at 50° C. and stirred for 3 hours.

The reaction mixture was concentrated to remove organic solvent. The residue was diluted with water and acidified to pH=6 with 2N HCl$_{(aq)}$ and extracted with DCM. The org layer was dried over MgSO$_4$ and concentrated in vacuo to give the product Compound 59c ((E)-3-(1-((tert-butoxycarbonyl)(2-(2-methyl-1H-indol-3-yl)ethyl)amino)-2,3-dihydro-1H-inden-5-yl)acrylic acid) (150.0 mg, yield: 96%).

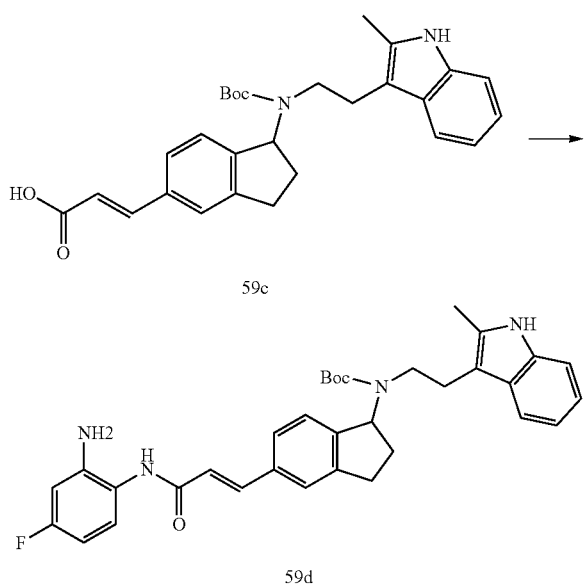

To a stirred solution of 4-Fluoro-1,2-phenylenediamine (29.0 mg, 0.23 mmol) and NMM (0.04 mL, 0.38 mmol) in DCM (5 mL) was added the Compound 59c ((E)-3-(1-((tert-butoxycarbonyl)(2-(2-methyl-1H-indol-3-yl)ethyl)amino)-2,3-dihydro-1H-inden-5-yl)acrylic acid) (88.0 mg, 0.19 mmol) in one portion, followed by the addition of HATU (80.0 mg, 0.21 mmol) in one portion at RT. The resulting mixture was stirred at RT overnight.

The resulting residue was purified by flash chromatography (EtOAc:Hexane=1:2) to provide the product Compound 59d (tert-butyl (E)-(5-(3-((2-amino-4-fluorophenyl)amino)-3-oxoprop-1-en-1-yl)-2,3-dihydro-1H-inden-1-yl)(2-(2-methyl-1H-indol-3-yl)ethyl)carbamate) (50.0 mg, yield 46%).

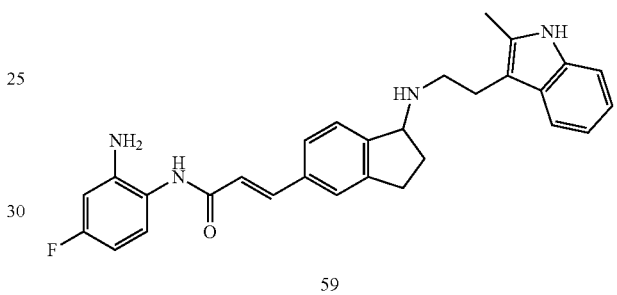

(Tert-butyl (E)-(5-(3-((2-amino-4-fluorophenyl)amino)-3-oxoprop-1-en-1-yl)-2,3-dihydro-1H-inden-1-yl)(2-(2-methyl-1H-indol-3-yl)ethyl)carbamate) (50.0 mg, 0.09 mmol) was added 4N HCl (2.0 mL, in 1,4-Dioxane) at 0° C. The mixture was stirred at RT for 6 hours.

The mixture was concentrated and washed with ether to provide the red product Compound 59 ((E)-N-(2-amino-4-fluorophenyl)-3-(1-((2-(2-methyl-1H-indol-3-yl)ethyl)amino)-2,3-dihydro-1H-inden-5-yl)acrylamide) (21.2 mg, yield 50%).

Compound 59, $^1$H-NMR (500 MHz, d$_6$-DMSO): δ 10.87 (s, 1H), 9.59 (s, 1H), 9.40 (s, 1H), 7.81 (s, 1H), 7.58-7.55 (m, 3H), 7.49-7.48 (m, 1H), 7.36 (s, 1H), 7.26-7.24 (d, 1H), 7.00-6.96 (m, 3H), 6.59 (s, 1H), 6.43 (s, 1H), 4.83 (s, 1H), 3.15-3.08 (m, 5H), 2.93 (s, 1H), 2.45 (s, 1H), 2.36 (s, 3H), 2.26 (s, 1H). ESI-MS m/z calcd for C$_{29}$H$_{29}$FN$_4$O 468.23 (free acid), found 469.1 [M+H]$^+$.

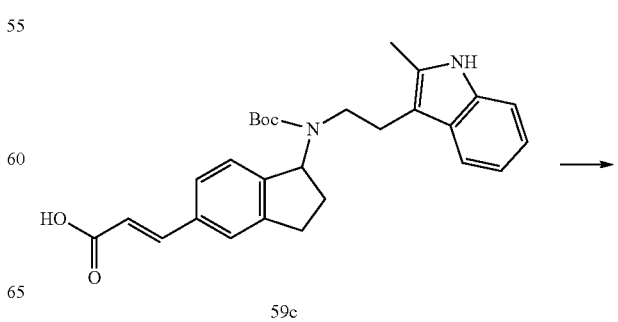

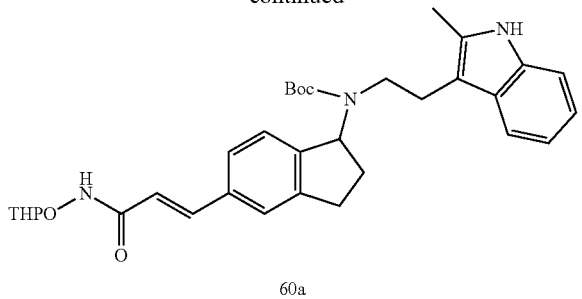

60a

To a stirred solution of O-(Tetrahydro-2H-pyran-2-yl) hydroxylamine (22.3 mg, 0.19 mmol) and DMAP (39.1 mg, 0.32 mmol) in DCM (5 mL) was added the Compound 59c ((E)-3-(1-((tert-butoxy carbonyl)(2-(2-methyl-1H-indol-3-yl)ethyl)amino)-2,3-dihydro-1H-inden-5-yl)acrylic acid) (73.1 mg, 0.16 mmol) in one portion, followed by addition of EDCI (36.4 mg, 0.19 mmol) in one portion at RT and stirred for 12 hours.

The mixture was extracted with $NH_4Cl$(aq.) and brine. The organic layer was dried over $MgSO_4$ and concentrated in vacuo to give the crude material. The resulting residue was purified by silica gel column chromatography (EtOAc: Hex.=1:1) to provide the product Compound 60a (tert-butyl (E)-(2-(2-methyl-1H-indol-3-yl)ethyl)(5-(3-oxo-3-(((tetrahydro-2H-pyran-2-yl)oxy)amino)prop-1-en-1-yl)-2,3-dihydro-1H-inden-1-yl)carbamate) (70.0 mg, yield 78%).

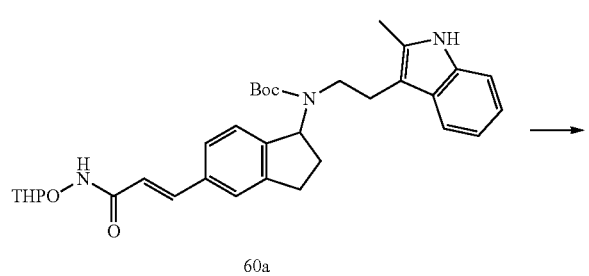

60a

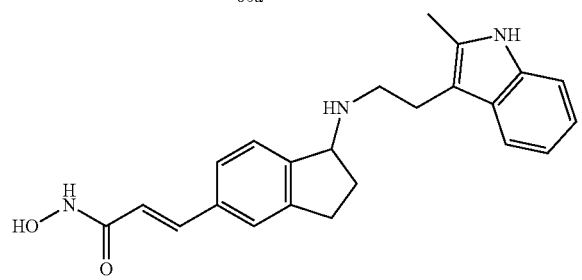

60

Compound 60a (Tert-butyl (E)-(2-(2-methyl-1H-indol-3-yl)ethyl)(5-(3-oxo-3-(((tetrahydro-2H-pyran-2-yl)oxy)amino)prop-1-en-1-yl)-2,3-dihydro-1H-inden-1-yl)carbamate) (70.0 mg, 0.13 mmol) was added 2N HCl (3.0 mL, in diethyl ether) at 0° C. The mixture was stirred at RT for 12 hours.

The mixture was concentrated and washed with DCM to provide the product Compound 60 ((E)-N-hydroxy-3-(1-((2-(2-methyl-1H-indol-3-yl)ethyl)amino)-2,3-dihydro-1H-inden-5-yl)acryl amide) (16.7 mg, yield 34%).

Compound 60, $^1$H-NMR (500 MHz, $d_6$-DMSO): δ 10.87 (s, 1H), 10.68 (s, 1H), 9.70 (s, 1H), 9.47 (s, 1H), 7.80 (s, 1H), 7.61-7.44 (m, 3H), 7.34 (s, 1H), 7.25-7.24 (d, 1H), 7.12-7.10 (m, 1H), 6.99-6.90 (m, 1H), 6.54-6.51 (d, 1H), 4.77 (s, 1H), 3.98 (m, 1H), 3.39-3.33 (m, 1H), 3.12-3.01 (m, 4H), 2.88 (s, 1H), 2.43 (m, 1H), 2.31 (s, 3H). ESI-MS m/z calcd for $C_{23}H_{25}N_3O_2$ 375.19 (free acid), found 376.2 $[M+H]^+$.

Synthesis of Compound 61

Scheme 38

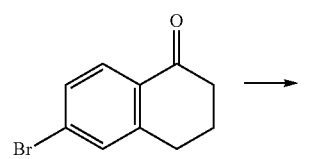

6a

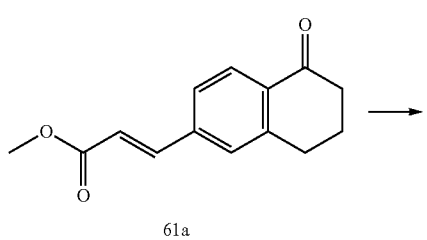

61a

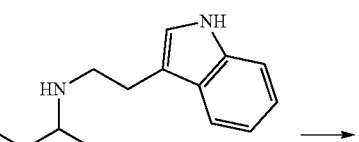

61b

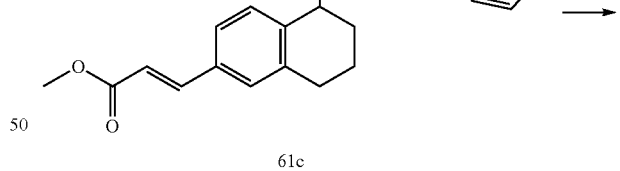

61c

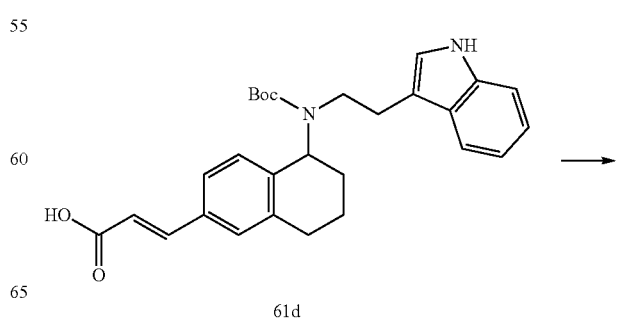

61d

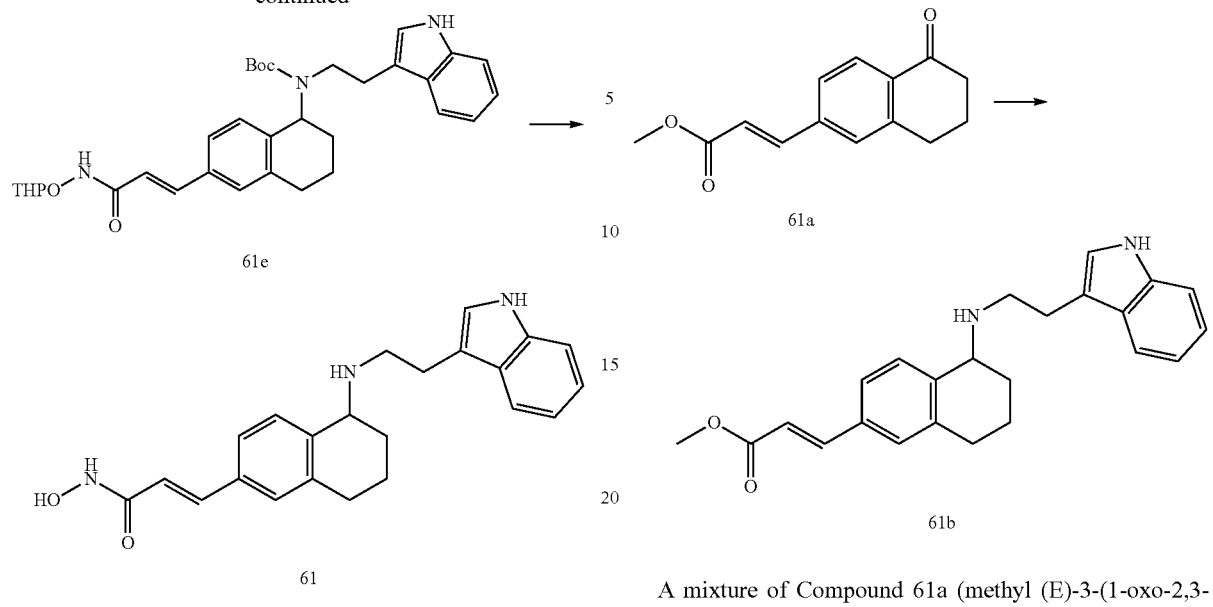

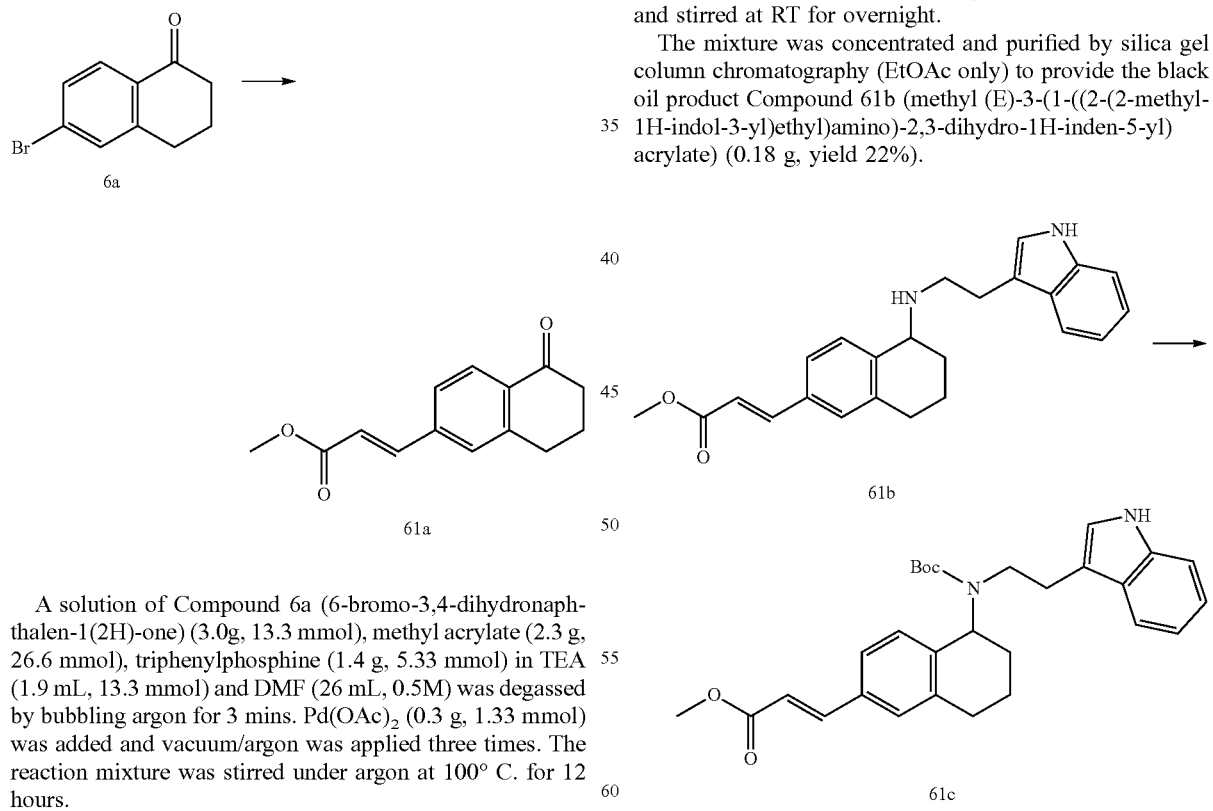

A solution of Compound 6a (6-bromo-3,4-dihydronaphthalen-1(2H)-one) (3.0g, 13.3 mmol), methyl acrylate (2.3 g, 26.6 mmol), triphenylphosphine (1.4 g, 5.33 mmol) in TEA (1.9 mL, 13.3 mmol) and DMF (26 mL, 0.5M) was degassed by bubbling argon for 3 mins. Pd(OAc)₂ (0.3 g, 1.33 mmol) was added and vacuum/argon was applied three times. The reaction mixture was stirred under argon at 100° C. for 12 hours.

The mixture was extracted with EtOAc and NH₄Cl₍aq₎. The organic layer was dried over MgSO₄ and concentrated in vacuo and purified by flash chromatography (EtOAc: Hex=1:5) to provide the product as a yellow solid product Compound 61a (methyl (E)-3-(5-oxo-5,6,7,8-tetrahydronaphthalen-2-yl)acrylate) (2.2 g, yield 72%).

A mixture of Compound 61a (methyl (E)-3-(1-oxo-2,3-dihydro-1H-inden-5-yl)acrylate) (0.5 g, 2.17 mmol), tryptamine (0.38 g, 2.39 mmol) and p-toluenesulfonic acid (12.4 mg, 0.065 mmol) in toluene (15 mL) were stirred at 160° C. for 1 hour, and then stirred at 120° C. for overnight. The mixture was diluted with DCM when the temperature at RT, followed by addition of NaB(OAc)₃ (506.4 mg, 2.39 mmol) and stirred at RT for overnight.

The mixture was concentrated and purified by silica gel column chromatography (EtOAc only) to provide the black oil product Compound 61b (methyl (E)-3-(1-((2-(2-methyl-1H-indol-3-yl)ethyl)amino)-2,3-dihydro-1H-inden-5-yl)acrylate) (0.18 g, yield 22%).

A solution of Compound 61b (methyl (E)-3-(1-((2-(2-methyl-1H-indol-3-yl)ethyl)amino)-2,3-dihydro-1H-inden-5-yl)acrylate) (0.18 g, 0.48 mmol), (Boc)₂O (115.7 mg, 0.53 mmol), and DMAP (129.2 mg, 1.06 mmol) in THF (10 mL) was stirred at 50° C. for 2 hours.

The mixture was extracted with EtOAc and NH₄Cl (aq.) The organic layer was dried over MgSO₄ and concentrated in vacuo and purified by flash chromatography (EtOAc./Hexane=1:1) to provide the black oil product Compound 61c (methyl (E)-3-(5-((2-(1H-indol-3-yl)ethyl)(tert-butoxycarbonyl)amino)-5,6,7,8-tetrahydronaphthalen-2-yl) acrylate) (110.0 mg, yield 48%).

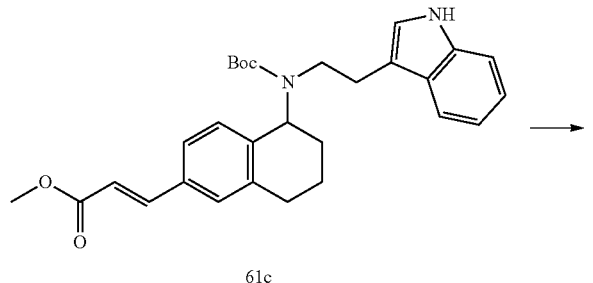

61c

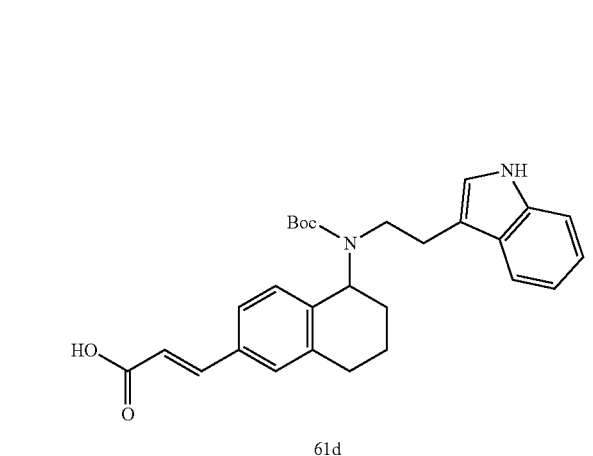

61d

To a solution of Compound 61c (methyl (E)-3-(5-((2-(1H-indol-3-yl)ethyl)(tert-butoxycarbonyl)amino)-5,6,7,8-tetrahydronaphthalen-2-yl) acrylate) (110.0 mg, 0.23 mmol) in MeOH (10 mL) was added 2N NaOH solution (5.0 mL) at RT and stirred for overnight.

The reaction mixture was concentrated to remove organic solvent. The residue was diluted with water and acidified to pH=6 with 2N HCl$_{(aq.)}$. and extracted with DCM. The organic layer was dried over MgSO₄ and concentrated in vacuo to give the product Compound 61d ((E)-3-(5-((2-(1H-indol-3-yl)ethyl)(tert-butoxycarbonyl)amino)-5,6,7,8-tetrahydronaphthalen-2-yl) acrylic acid) (80.0 mg, yield 76%).

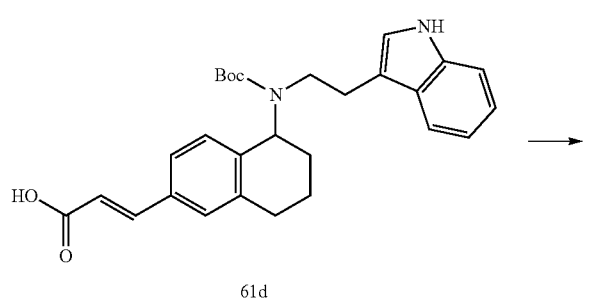

61d

-continued

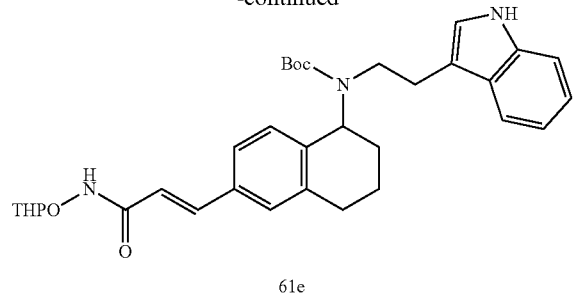

61e

To a stirred solution of O-(Tetrahydro-2H-pyran-2-yl) hydroxylamine (24.64 mg, 0.21 mmol) and DMAP (42.5 mg, 0.35 mmol) in DCM (5 mL) was added the Compound 61d ((E)-3-(5-((2-(1H-indol-3-yl)ethyl)(tert-butoxycarbonyl)amino)-5,6,7,8-tetrahydronaphthalen-2-yl) acrylic acid) (80.0 mg, 0.17 mmol) in one portion, followed by addition of EDCI (40.3 mg, 0.21 mmol) in one portion at RT and stirred for 12 hours.

The mixture was extracted with NH₄Cl(aq.) and brine. The organic layer was dried over MgSO₄ and concentrated in vacuo to give the crude material. The resulting residue was purified by silica gel column chromatography (EtOAc:Hex.=1:3) to provide the product Compound 61e (tert-butyl (E)-(2-(1H-indol-3-yl)ethyl)(6-(3-oxo-3-(((tetrahydro-2H-pyran-2-yl)oxy)amino)prop-1-en-1-yl)-1,2,3,4-tetrahydronaphthalen-1-yl)carbamate) (30.0 mg, yield 32%).

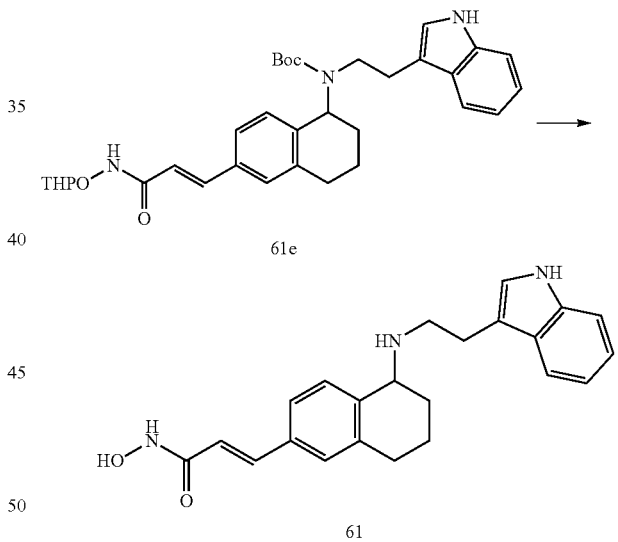

61e

61

Compound 61e (Tert-butyl (E)-(2-(1H-indol-3-yl)ethyl)(6-(3-oxo-3-(((tetrahydro-2H-pyran-2-yl)oxy)amino)prop-1-en-1-yl)-1,2,3,4-tetrahydronaphthalen-1-yl)carbamate). (30.0 mg, 0.17 mmol) was added 2N HCl (3.0 mL, in diethyl ether) at 0° C. The mixture was stirred at RT for 2 hours.

The mixture was concentrated and washed with DCM to provide the product Compound 61 ((E)-3-(5-((2-(1H-indol-3-yl)ethyl)amino)-5,6,7,8-tetrahydronaphthalen-2-yl)-N-hydroxy acrylamide) (6.0 mg, yield 10%).

Compound 61, ¹H-NMR (500 MHz, DMSO): δ 10.96 (s, 1H), 10.78 (s, 1H), 9.02 (s, 1H), 7.61-7.55 (m, 3H), 7.44-7.36 (m, 3H), 7.26 (s, 1H), 7.10-7.01 (d, 2H), 6.51-6.48 (d, 1H), 4.55 (s, 1H), 3.23-3.13 (m, 4H), 2.85-2.80 (d, 2H), 2.14-2.04 (m, 2H), 2.01-1.90 (m, 2H). ESI-MS m/z calcd for C₂₃H₂₅N₃O₂ 375.19 (free acid), found 376.1 [M+H]⁺.

Synthesis of Compounds 62~63
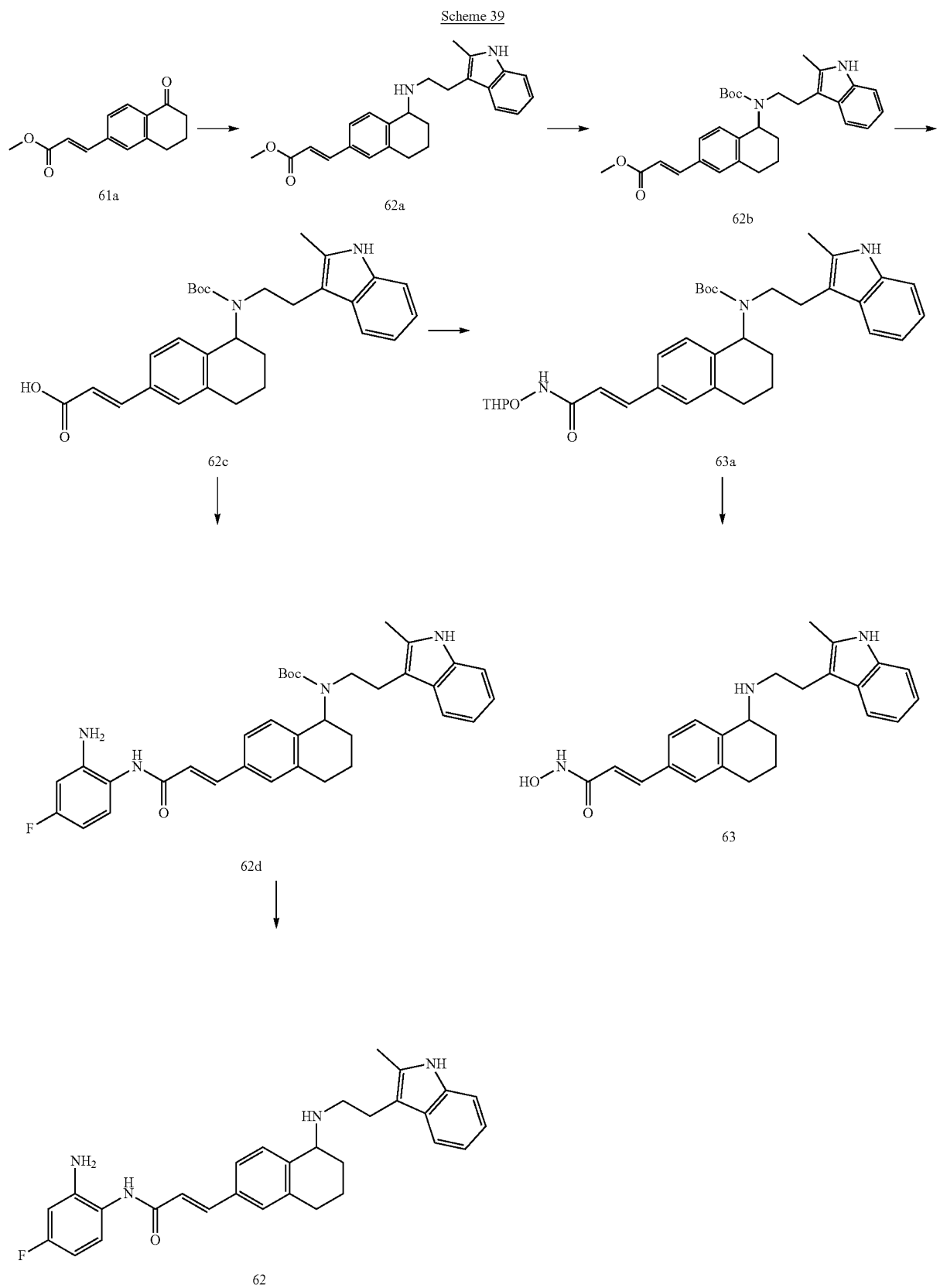

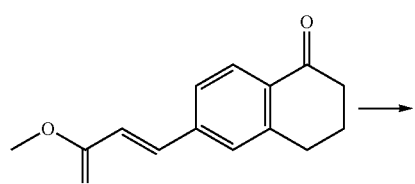

61a

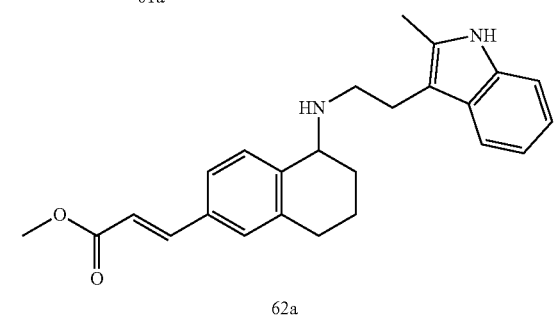

62a

A mixture of Compound 61a (methyl (E)-3-(5-oxo-5,6,7,8-tetrahydronaphthalen-2-yl)acrylate) (1.0 g, 4.34 mmol), 2-(2-methyl-1H-indol-3-yl)ethan-1-amine (0.83 g, 4.8 mmol) and p-Toluenesulfonic acid (24.8 mg, 0.13 mmol) in toluene (30 mL) was stirred at 160° C. for 4 hours. The mixture was diluted with DCM when the temperature at RT, followed by addition of NaB(OAc)$_3$ (0.92 g, 4.34 mmol) and stirred at RT for overnight.

The mixture was concentrated and purified by silica gel column chromatography (EtOAc:Hex.=2:1) to provide the product Compound 62a (methyl (E)-3-(5-((2-(2-methyl-1H-indol-3-yl)ethyl)amino)-5,6,7,8-tetrahydronaphthalen-2-yl)acrylate) (600.0 mg, yield 35%).

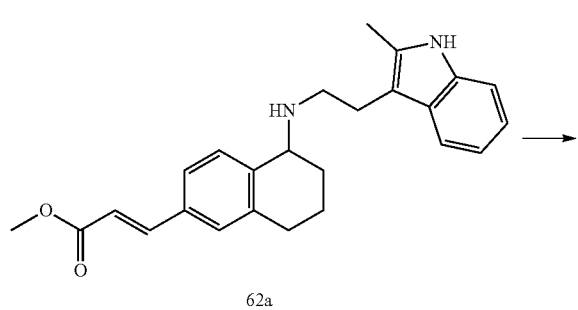

62a

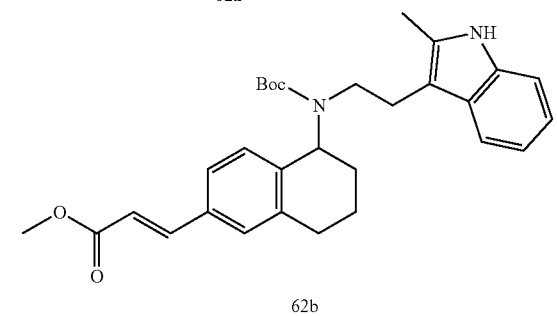

62b

A solution of Compound 62a (methyl (E)-3-(5-((2-(2-methyl-1H-indol-3-yl)ethyl)amino)-5,6,7,8-tetrahydronaphthalen-2-yl)acrylate) (0.4 g, 1.5 mmol), (Boc)$_2$O (403.8 mg, 1.85 mmol) and DMAP (414.0 mg, 3.4 mmol) in THF (15 mL) was stirred at RT for 2 hours.

The mixture was extracted with EtOAc and NaHCO$_3$ (aq.). The organic layer was dried over MgSO$_4$ and concentrated in vacuo and purified by flash chromatography (EtOAc./Hexane=1:1) to provide the product Compound 62b (methyl (E)-3-(5-((tert-butoxycarbonyl)(2-(2-methyl-1H-indol-3-yl)ethyl)amino)-5,6,7,8-tetrahydronaphthalen-2-yl)acrylate) (271.4 mg, yield 37%).

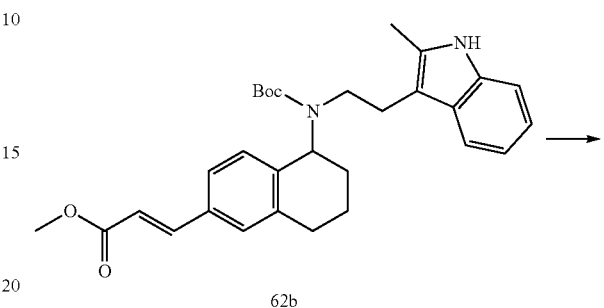

62b

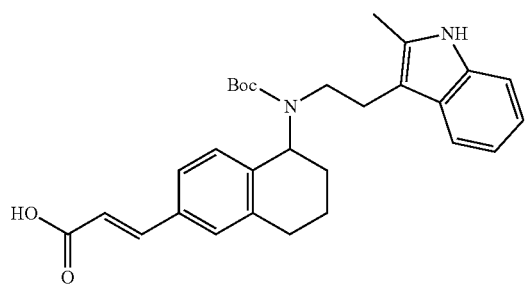

62c

To a solution of Compound 62b (methyl (E)-3-(5-((tert-butoxycarbonyl)(2-(2-methyl-1H-indol-3-yl)ethyl)amino)-5,6,7,8-tetrahydronaphthalen-2-yl)acrylate) (271.0 mg, 0.37 mmol) in MeOH (10 mL) was added 2N NaOH solution (6.0 mL) at RT and stirred for overnight.

The reaction mixture was concentrated to remove the organic solvent. The residue was diluted with water and acidified to pH=6 with 2N HCl$_{(aq)}$ and extracted with DCM. The organic layer was dried over MgSO$_4$ and concentrated in vacuo to give the product Compound 62c ((E)-3-(5-((tert-butoxy carbonyl)(2-(2-methyl-1H-indol-3-yl)ethyl)amino)-5,6,7,8-tetrahydronaphthalen-2-yl)acrylic acid). (220.0 mg, yield 82%).

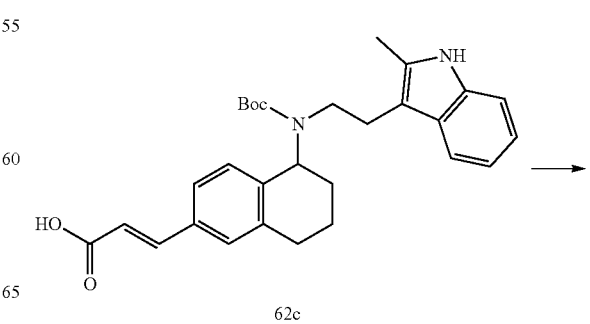

62c

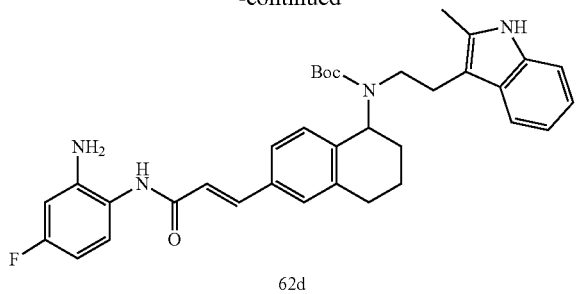

62d

To a stirred solution of 4-Fluoro-1,2-phenylenediamine (30.0 mg, 0.23 mmol) and NMM (0.05 mL, 0.46 mmol) in DCM (5 mL) was added the Compound 62c ((E)-3-(5-((tert-butoxy carbonyl)(2-(2-methyl-1H-indol-3-yl)ethyl)amino)-5,6,7,8-tetrahydronaphthalen-2-yl)acrylic acid) (100.0 mg, 0.21 mmol) in one portion, followed by addition of HATU (87.4 mg, 0.23 mmol) in one portion at RT and stirred for 12 hours.

The mixture was extracted with NH₄Cl(aq.) and brine. The organic layer was dried over MgSO₄ and concentrated in vacuo to give the crude material. The resulting residue was purified by silica gel column chromatography (EtOAc:Hex.=1:1) to provide the product Compound 62d (tert-butyl (E)-(6-(3-((2-amino-4-fluorophenyl)amino)-3-oxoprop-1-en-1-yl)-1,2,3,4-tetrahydronaphthalen-1-yl)(2-(2-methyl-1H-indol-3-yl)ethyl)carbamate) (30.0 mg, yield 25%).

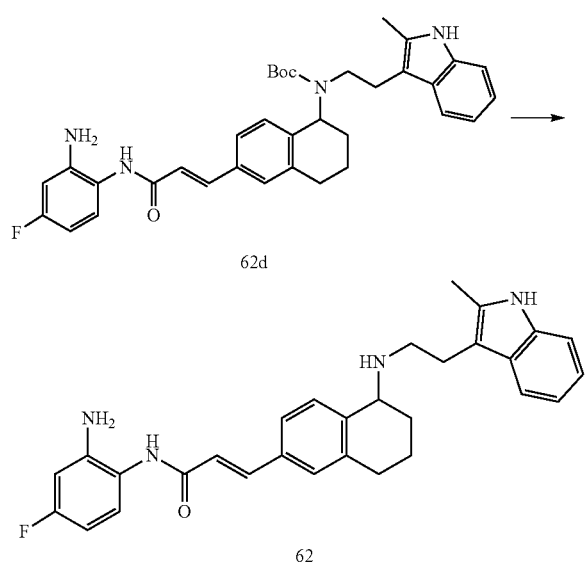

62d

62

Compound 62d (Tert-butyl (E)-(6-(3-((2-amino-4-fluorophenyl)amino)-3-oxoprop-1-en-1-yl)-1,2,3,4-tetrahydronaphthalen-1-yl)(2-(2-methyl-1H-indol-3-yl)ethyl)carbamate). (30.0 mg, 0.05 mmol) was added 2N HCl (3.0 mL, in diethyl ether) at 0° C. The mixture was stirred at RT for overnight.

The mixture was concentrated and washed with DCM to provide the red product Compound 62 ((E)-N-(2-amino-4-fluorophenyl)-3-(5-((2-(2-methyl-1H-indol-3-yl)ethyl)amino)-5,6,7,8-tetrahydronaphthalen-2-yl)acrylamide) (5.0 mg, yield 21%).

Compound 62, ¹H-NMR (500 MHz, d₆-DMSO): δ 10.87 (s, 1H), 9.48 (s, 1H), 9.23 (s, 1H), 9.10 (s, 1H), 8.04-8.03 (d, 1H), 7.70-7.61 (m, 2H), 7.53-7.46 (m, 3H), 7.34-7.31 (t, 1H), 7.28-7.23 (d, 1H), 7.05-6.95 (m, 2H), 6.55-6.53 (d, 1H), 6.39-6.35 (t, 1H), 4.56 (s, 1H), 3.12-3.07 (m, 4H), 2.87-2.80 (m, 2H), 2.15-2.01 (m, 4H), 1.64 (s, 3H). ESI-MS m/z calcd for C₃₀H₃₁FN₄O 482.25 (free acid), found 483.0 [M+H]⁺.

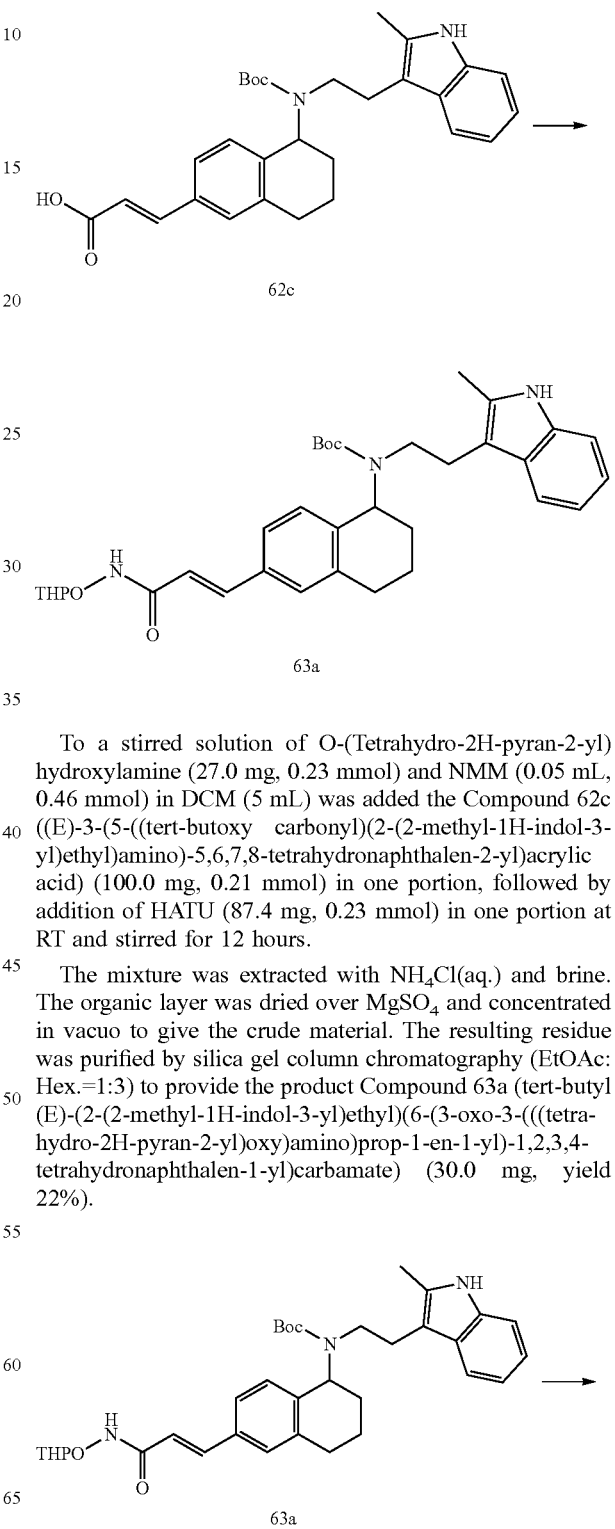

62c

63a

To a stirred solution of O-(Tetrahydro-2H-pyran-2-yl) hydroxylamine (27.0 mg, 0.23 mmol) and NMM (0.05 mL, 0.46 mmol) in DCM (5 mL) was added the Compound 62c ((E)-3-(5-((tert-butoxy carbonyl)(2-(2-methyl-1H-indol-3-yl)ethyl)amino)-5,6,7,8-tetrahydronaphthalen-2-yl)acrylic acid) (100.0 mg, 0.21 mmol) in one portion, followed by addition of HATU (87.4 mg, 0.23 mmol) in one portion at RT and stirred for 12 hours.

The mixture was extracted with NH₄Cl(aq.) and brine. The organic layer was dried over MgSO₄ and concentrated in vacuo to give the crude material. The resulting residue was purified by silica gel column chromatography (EtOAc:Hex.=1:3) to provide the product Compound 63a (tert-butyl (E)-(2-(2-methyl-1H-indol-3-yl)ethyl)(6-(3-oxo-3-(((tetrahydro-2H-pyran-2-yl)oxy)amino)prop-1-en-1-yl)-1,2,3,4-tetrahydronaphthalen-1-yl)carbamate) (30.0 mg, yield 22%).

63a

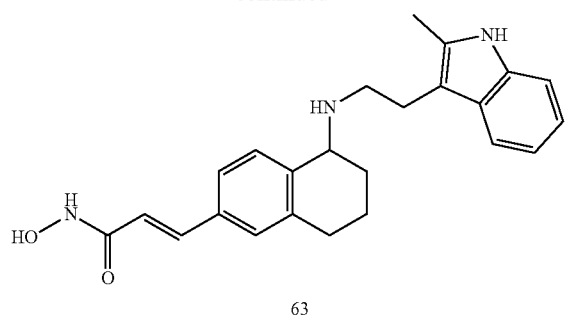

63

Compound 63a (Tert-butyl (E)-(2-(2-methyl-1H-indol-3-yl)ethyl)(6-(3-oxo-3-(((tetrahydro-2H-pyran-2-yl)oxy)amino)prop-1-en-1-yl)-1,2,3,4-tetrahydronaphthalen-1-yl)carbamate) (30.0 mg, 0.05 mmol) was added 2N HCl (3.0 mL, in diethyl ether) at 0° C. The mixture was stirred at RT for 2 hours.

The mixture was concentrated and washed with DCM to provide the red product Compound 63 ((E)-N-hydroxy-3-(5-((2-(2-methyl-1H-indol-3-yl)ethyl)amino)-5,6,7,8-tetrahydronaphthalen-2-yl)acrylamide) (10.0 mg, yield 51%).

Compound 63, $^1$H-NMR (500 MHz, $d_6$-DMSO): δ 10.87 (s, 1H), 10.79 (s, 1H), 9.16 (s, 1H), 7.64-7.63 (m, 1H), 7.46-7.40 (m, 4H), 7.25-7.24 (d, 1H), 7.06-6.93 (dt, 2H), 6.52-6.49 (d, 1H), 4.65 (s, 1H), 3.10-3.05 (m, 4H), 2.90-2.75 (m, 2H), 2.34 (s, 3H), 2.14-2.08 (m, 2H), 2.00-1.91 (m, 2H). ESI-MS m/z calcd for $C_{24}H_{27}N_3O_2$ 389.21 (free acid), found 390.1 [M+H]$^+$.

Synthesis of Compound 64

Scheme 40

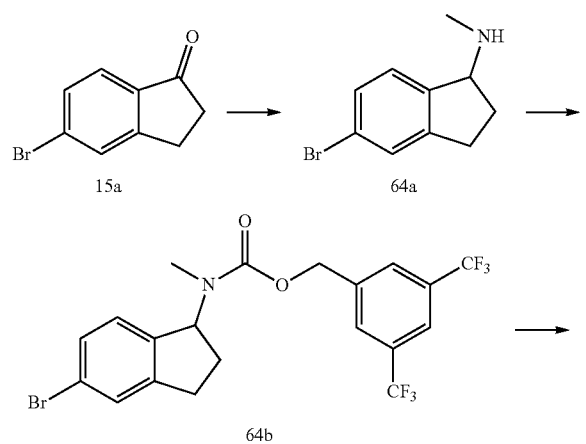

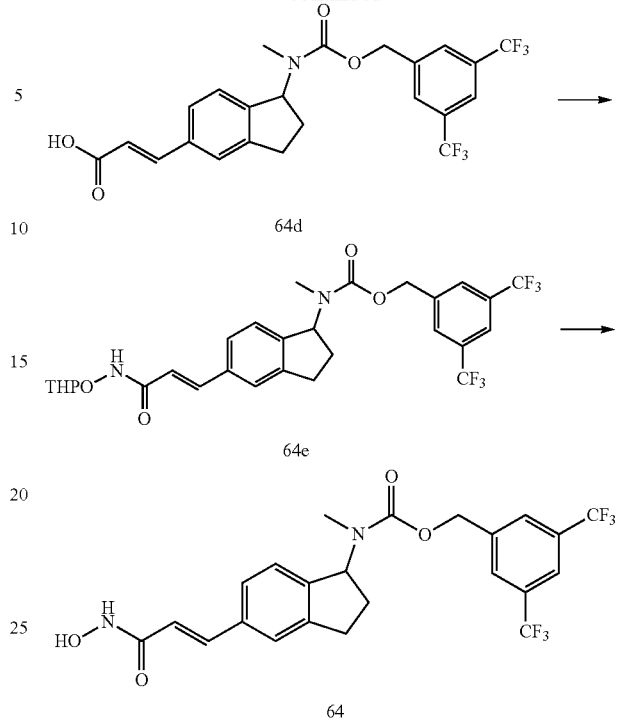

Compound 15a (5-bromo-2,3-dihydro-1H-inden-1-one) (4.3 g, 20.3 mmol) and methylamine (20 mL, 9.8 M in MeOH), in methanol (50 mL) were charged into a round bottom flask and stirred for about 3.5 hours at room temperature to form a solution. Sodium borohydride (1.2 g) was slowly added to the solution at room temperature to form a mixture, and then the mixture is stirred and maintained for completion of the reaction overnight. After that, the solvent and excess methylamine in the mixture was removed under vacuum to produce a residue. Ice-water was added to the residue and then a brown black solid was found, filtered, collected and washed by $NaHCO_3$(aq). Next, the solid was dried under vacuum to afford a product Compound 64a (5-bromo-N-methyl-2,3-dihydro-1H-inden-1-amine) (3.21 g, 14.20 mmol, yield 70%). The product Compound 64a was used in the next step without further purification.

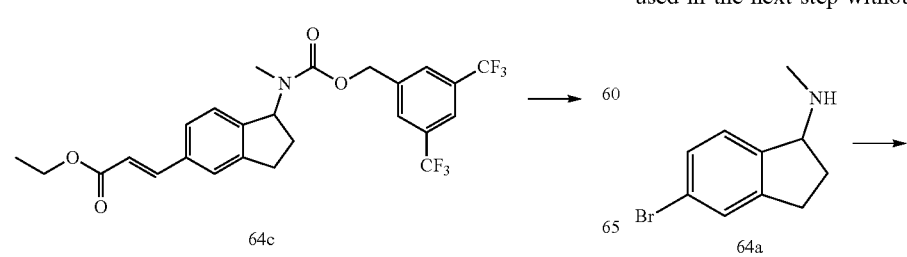

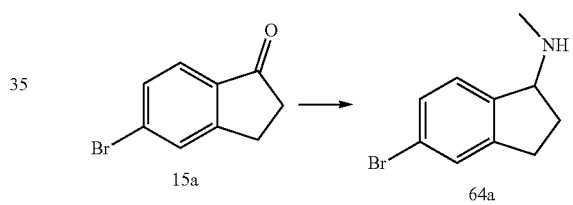

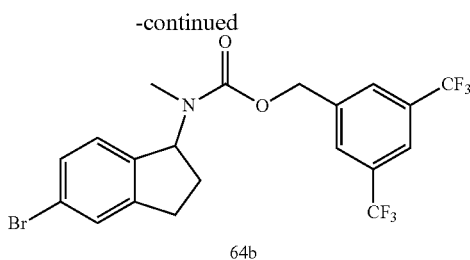

64b

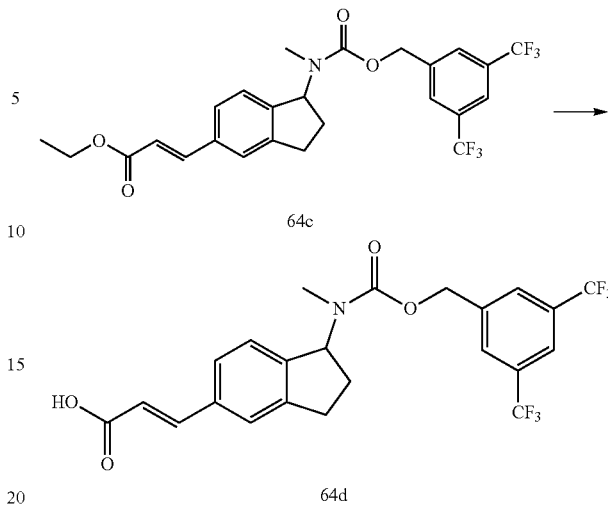

64c

64d

To a solution of 3,5-bis(trifluoromethyl)benzyl alcohol (0.54 g, 2.21 mmol) in DCM (30 mL) was added DIPEA (0.34 g, 2.65 mmol) and triphosgene (0.22 g, 0.74 mmol) at 0° C. The reaction mixture was stirred at the same temperature for 30 min. After the 3,5-bis(trifluoromethyl)benzyl alcohol was consumed, a solution of Compound 64a (0.50 g, 2.21 mmol) and DIPEA (0.34 g, 2.65 mmol) in DCM (10 mL) was added into the reaction mixture. Then the reaction mixture was slowly warmed to RT and stirred for overnight.

After reaction was completed, the solvent was removed under reduced pressure. The residual was diluted with Sat. NH₄Cl and extracted with EtOAc. The combined organic layers were dried over MgSO₄ and concentrated in vacuo. The crude product was purified by silica gel column chromatography using ethyl acetate/hexane=1/4 as elution to yield the desired product Compound 64b (3,5-bis(trifluoromethyl)benzyl(5-bromo-2,3-dihydro-1H-inden-1-yl)(methyl)carbamate) (0.45 g, 0.91 mmol, yield 41%).

To a solution of Compound 64c (ethyl (E)-3-(1-((((3,5-bis(trifluoromethyl)benzyl)oxy)carbonyl)(methyl)amino)-2,3-dihydro-1H-inden-5-yl)acrylate) (0.21 g, 0.41 mmol) in MeOH (10 mL) was added 2N NaOH (0.50 mL, 1.00 mmol) and stirred at RT for overnight.

After reaction was completed, the solvent was removed under reduced pressure. The residual was diluted with ice-cold water and acidified with 1N HCl. The precipitated solid was collected by filtration and washed with water and diethyl ether to afford Compound 64d ((E)-3-(1-((((3,5-bis(trifluoromethyl)benzyl)oxy)carbonyl)(methyl)amino)-2,3-dihydro-1H-inden-5-yl)acrylic acid) (0.20 g, 0.40 mmol, yield 99%). The crude product Compound 64d was used in the next step without further purification.

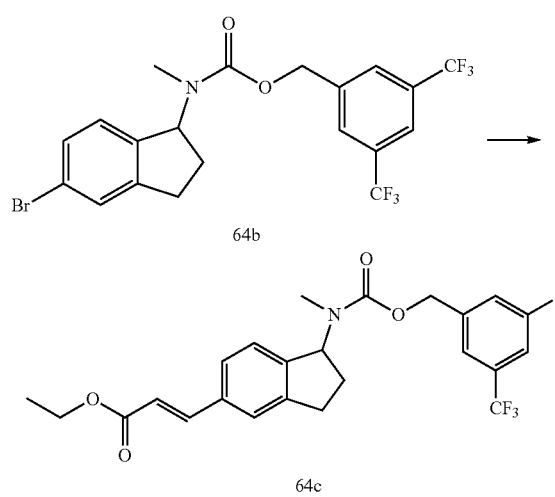

64b

64c

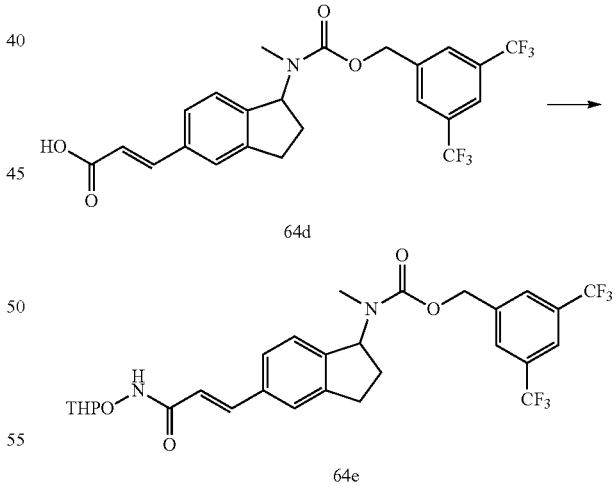

64d

64e

To a solution of Compound 64b (3,5-bis(trifluoromethyl)benzyl (5-bromo-2,3-dihydro-1H-inden-1-yl)(methyl)carbamate) (0.45 g, 0.91 mmol), triphenylphosphine (0.10 g, 0.36 mmol), ethyl acrylate (0.12 g, 1.19 mmol) in DMF/TEA (30 mL, 1:1) was added Pd(OAc)₂ (0.01 g, 0.05 mmol). After addition, the reaction mixture was heated to 100° C. and stirred for overnight.

After reaction was completed, the solvent was removed under reduced pressure. The residual was filtered through celite and washed with EtOAc. After concentration in vacuo, the crude product was purified by silica gel column chromatography using ethyl acetate/hexane=1/4 as elution to yield the desired product Compound 64c (ethyl(E)-3-(1-((((3,5-bis(trifluoromethyl)benzyl)oxy)carbonyl)(methyl)amino)-2,3-dihydro-1H-inden-5-yl)acrylate) (0.21 g, 0.41 mmol, yield 45%).

To a solution of Compound 64d ((E)-3-(1-((((3,5-bis(trifluoromethyl)benzyl)oxy)carbonyl)(methyl)amino)-2,3-dihydro-1H-inden-5-yl)acrylic acid) (0.20 g, 0.40 mmol) and O-(Tetrahydro-2H-pyran-2-yl)hydroxylamine (0.07g, 0.61 mmol) in DCM (10 mL) was added EDCI (0.12 g, 0.61 mmol) at 0° C. After addition, the reaction mixture was slowly warmed to RT and stirred for overnight.

After reaction was completed, the reaction mixture was diluted with EtOAc and washed with Sat. NH₄Cl. The combined organic layers were washed with brine and dried over MgSO$_4$ and concentrated in vacuo. The crude product was purified via flash column chromatography on a silica gel column using 10:1 DCM-MeOH as the eluent to give Compound 64e (3,5-bis(trifluoromethyl)benzyl (E)-methyl (5-(3-oxo-3-(((tetrahydro-2H-pyran-2-yl)oxy)amino)prop-1-en-1-yl)-2,3-dihydro-1H-inden-1-yl)carbamate) (0.15 g, 0.26 mmol, yield 64%).

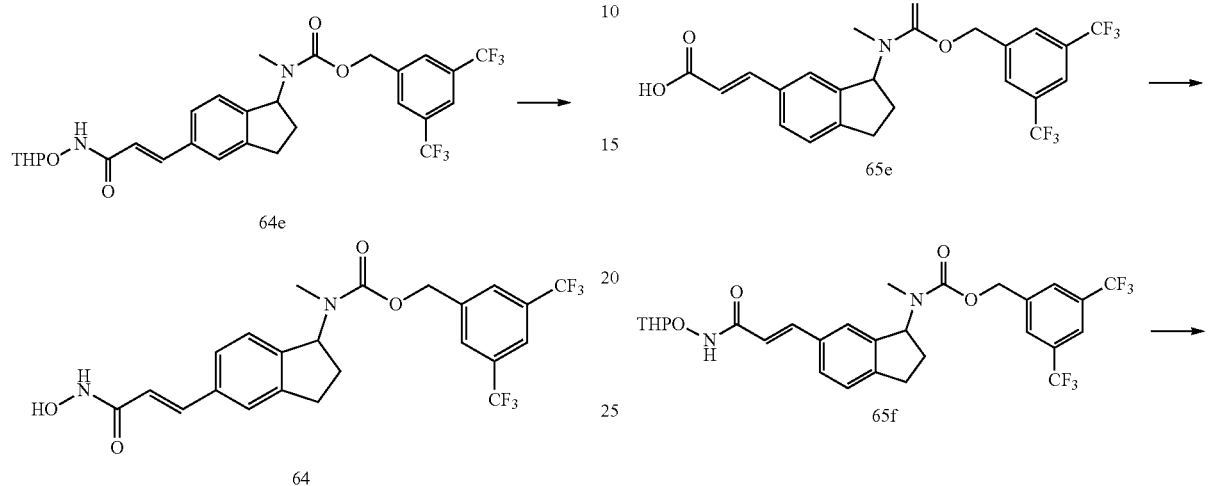

To a solution of Compound 64e (3,5-bis(trifluoromethyl) benzyl (E)-methyl(5-(3-oxo-3-(((tetrahydro-2H-pyran-2-yl) oxy)amino)prop-1-en-1-yl)-2,3-dihydro-1H-inden-1-yl)carbamate) (0.15 g, 0.26 mmol) in MeOH (10 mL) was added 1N HCl (0.5 mL) and stirred for 2 hrs.

After reaction was completed, the solvent was removed under reduced pressure. The precipitated solid was washed with water and ether to get Compound 64 (3,5-bis(trifluoromethyl)benzyl (E)-(5-(3-(hydroxyamino)-3-oxoprop-1-en-1-yl)-2,3-dihydro-1H-inden-1-yl)(methyl)carbamate) (0.03 g, 0.06 mmol, yield 23%).

Compound 64, $^1$H-NMR (500 MHz, CD$_3$OD): δ 8.02-7.94 (m, 3H), 7.57-7.55 (d, 1H), 7.45-7.40 (m, 2H), 7.13-7.12 (d, 1H), 6.46 (s, 1H), 5.81-5.79 (d, 1H), 5.36 (s, 2H), 3.03-2.99 (m, 1H), 2.91-2.86 (m, 1H), 2.70 (s, 3H), 2.45-2.40 (m, 1H), 2.11-2.01 (m, 1H). ESI-MS m/z calcd for C$_{23}$H$_{20}$F$_6$N$_2$O$_4$ 502.13, found 503 [M+H]$^+$.

Synthesis of Compound 65

Scheme 41

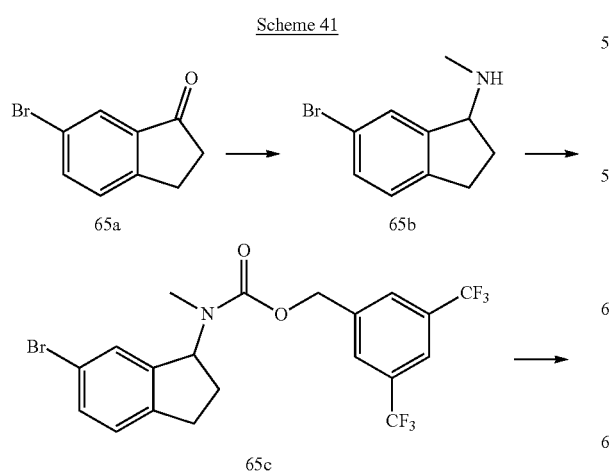

Compound 65a (6-bromoindanole) (4.3 g, 20.3 mmole) and methylamine (20 mL, 9.8 M in MeOH), in methanol (50 mL) were charged into a round bottom flask and stirred for about 3.5 hours at room temperature to form a solution. Sodium borohydride (1.2 g) was slowly added to the solution at room temperature to form a mixture, and then the mixture is stirred and maintained for completion of the reaction overnight. After that, the solvent and excess methylamine in the mixture was removed under vacuum to produce a residue. Ice-water was added to the residue and then a brown black solid was found, filtered, collected and washed by NaHCO$_3$(aq). Next, the solid was dried under vacuum to afford a product Compound 65b (6-bromo-N-methyl-2,3-dihydro-1H-inden-1-amine) (4.04 g, 87% yield). The product Compound 65b was used in the next step without further purification.

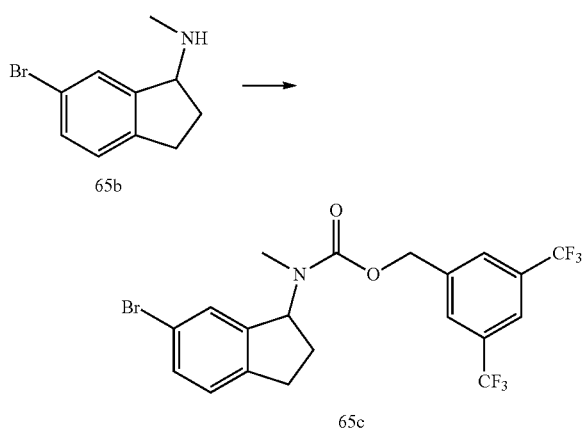

Compound 65c was synthesized by using the same methods for Compound 64b.

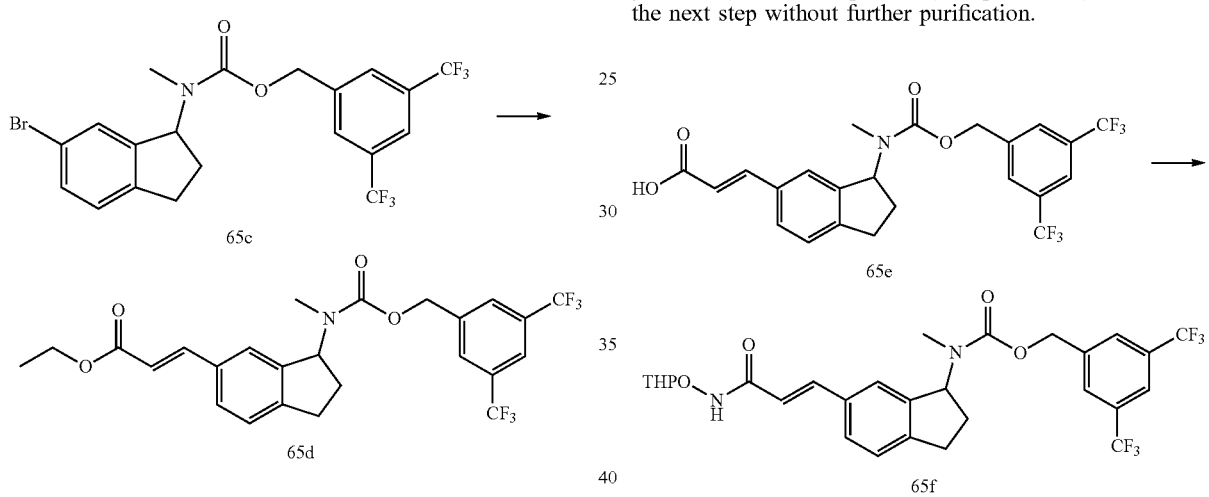

To a solution of Compound 65c ((3,5-bis(trifluoromethyl)benzyl (6-bromo-2,3-dihydro-1H-inden-1-yl)(methyl)carbamate)) (0.93 g, 1.88 mmol) in DMF (10 mL) and triethylamine (5 mL) was added PPh$_3$ (0.12 g, 0.45 mmol), ethyl acrylate (0.94 g, 9.38 mmol) and Pd(OAc)$_2$ (42 mg, 0.19 mmol). The mixture was degassed with Ar for 15 min, then heated to 90° C. for overnight.

After reaction was completed, the solvent was removed under reduced pressure. The residual was filtered through celite and washed with EtOAc. After concentration in vacuo, the crude product was purified via flash column chromatography on a silica gel column using 5:1 hexane-EtOAc as the eluent to yield Compound 65d ((ethyl (E)-3-(3-((((3,5-bis (trifluoromethyl)benzyl)oxy)carbonyl)(methyl)amino)-2,3-dihydro-1H-inden-5-yl)acrylate)) (0.65 g, 1.26 mmol, yield 67%).

To a solution of Compound 65d (0.22 g, 0.42 mmol) in MeOH (10 mL) was added 2N NaOH (1 mL, 2 mmol) and stirred at RT for overnight.

After reaction was completed, the solvent was removed under reduced pressure. The residual was diluted with ice-cold water and acidified with 1N HCl. The precipitated solid was collected by filtration and washed with water and diethyl ether to afford Compound 65e ((E)-3-(3-((((3,5-bis (trifluoromethyl)benzyl)oxy)carbonyl)(methyl)amino)-2,3-dihydro-1H-inden-5-yl)acrylic acid) (0.20 g, 0.41 mmol, yield 98%). The crude product (Compound 65e) was used in the next step without further purification.

To a solution of Compound 65e (0.20 g, 0.41 mmol) and O-(Tetrahydro-2H-pyran-2-yl)hydroxylamine (0.07g, 0.63 mmol) in DCM (10 mL) was added EDCI (0.12 g, 0.63 mmol) at 0° C. After addition, the reaction mixture was slowly warmed to RT and stirred for overnight.

After reaction was completed, the reaction mixture was diluted with EtOAc and washed with Sat. NH$_4$Cl. The combined organic layers were washed with brine and dried over MgSO$_4$ and concentrated in vacuo. The crude product was purified via flash column chromatography on a silica gel column using 10:1 DCM-MeOH as the eluent to give Compound 65f (3,5-bis(trifluoromethyl)benzyl (E)-methyl (6-(3-oxo-3-(((tetrahydro-2H-pyran-2-yl)oxy)amino)prop-1-en-1-yl)-2,3-dihydro-1H-inden-1-yl)carbamate) (0.10 g, 0.18 mmol, yield 43%).

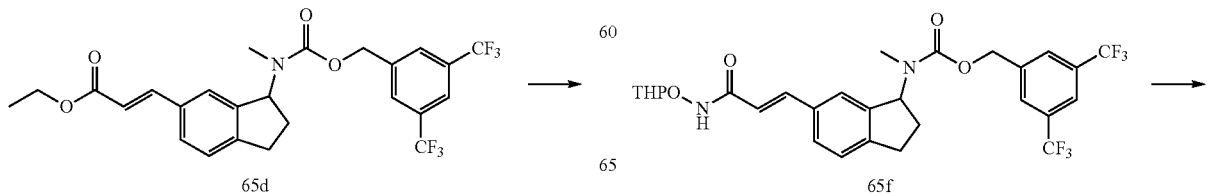

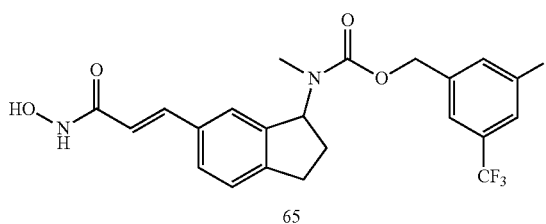
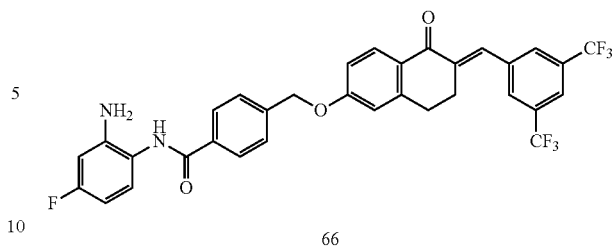

To a solution of Compound 65f (0.10 g, 0.18 mmol) in MeOH (10 mL) was added 1N HCl (0.5 mL) and stirred for 2 hrs.

After reaction was completed, the solvent was removed under reduced pressure. The precipitated solid was washed with water and ether to produce Compound 65 (3,5-bis (trifluoromethyl)benzyl (E)-(6-(3-(hydroxyamino)-3-oxo-prop-1-en-1-yl)-2,3-dihydro-1H-inden-1-yl)(methyl)carbamate) (0.07 g, 0.14 mmol, yield 77%).

Compound 65, $^1$H-NMR (400 MHz, CDCl$_3$): δ 7.86-7.82 (m, 3H), 7.71-7.69 (d, 1H), 7.38-7.31 (m, 3H), 6.28-6.27 (d, 1H), 5.89-5.75 (d, 1H), 5.34-5.32 (d, 2H), 3.01-2.91 (m, 2H), 2.70 (s, 3H), 2.46-2.44 (m, 1H), 2.06-2.02 (m, 1H). ESI-MS m/z calcd for $C_{23}H_{20}F_6N_2O_4$ 502.41, found 503 [M+H]$^+$.

Synthesis of Compound 66

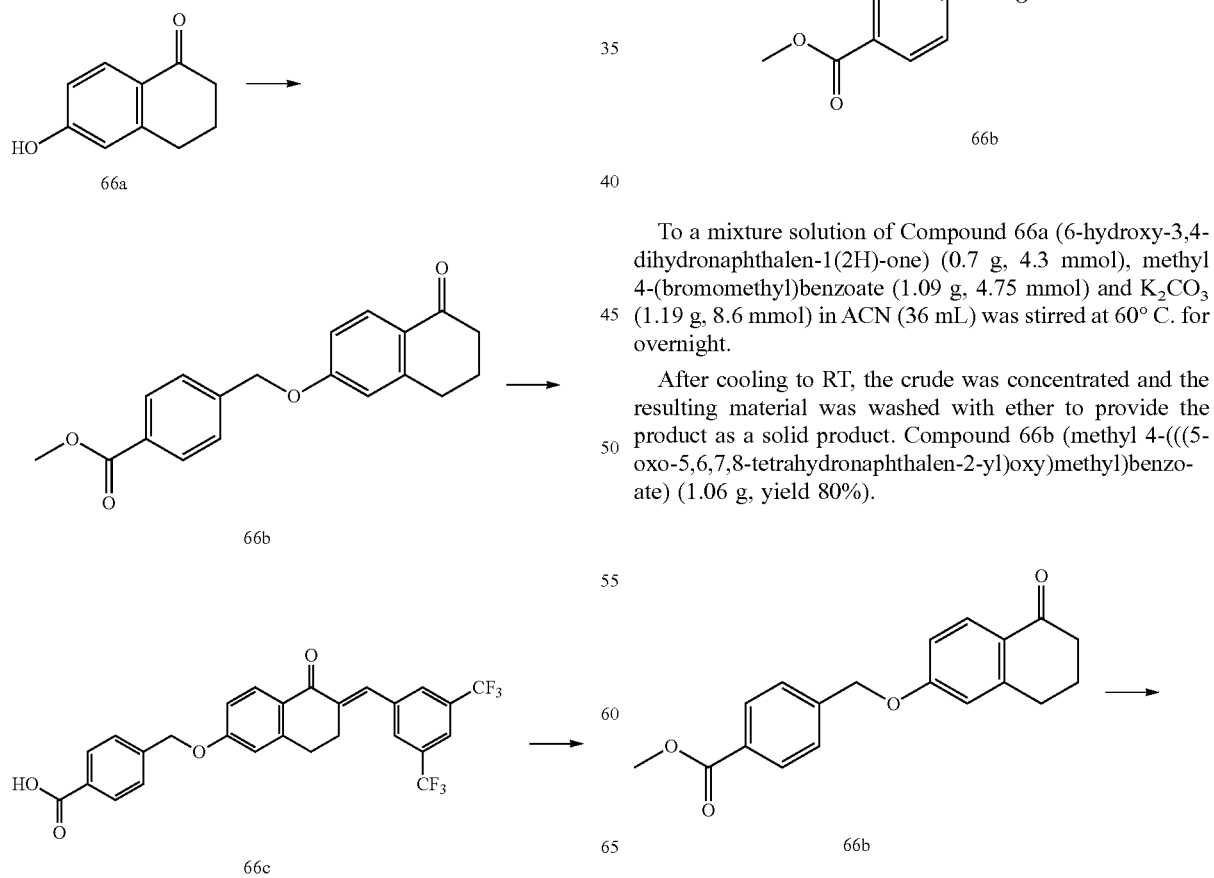

To a mixture solution of Compound 66a (6-hydroxy-3,4-dihydronaphthalen-1(2H)-one) (0.7 g, 4.3 mmol), methyl 4-(bromomethyl)benzoate (1.09 g, 4.75 mmol) and K$_2$CO$_3$ (1.19 g, 8.6 mmol) in ACN (36 mL) was stirred at 60° C. for overnight.

After cooling to RT, the crude was concentrated and the resulting material was washed with ether to provide the product as a solid product. Compound 66b (methyl 4-(((5-oxo-5,6,7,8-tetrahydronaphthalen-2-yl)oxy)methyl)benzoate) (1.06 g, yield 80%).

281

-continued

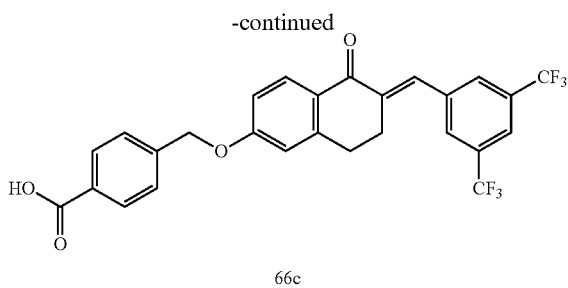

66c

282

-continued

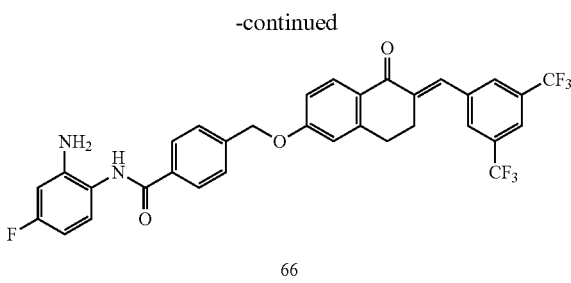

66

To a solution of Compound 66b (methyl 4-(((5-oxo-5,6,7,8-tetrahydronaphthalen-2-yl)oxy)methyl)benzoate) (1.06 g, 3.4 mmol) in a co-solvent of MeOH:H₂O=3:1 (15 mL) was added NaOH (0.26 g, 6.5 mmol) and stirred at 60° C. for 3 hours.

The reaction mixture was concentrated to remove the organic solvent. The residue was diluted with water and acidified to pH 4 with 1N HCl$_{(aq)}$. The resulting precipitate was washed with H₂O and ether. The solid was further dried by pressing it on a filter paper.

Then treated the solid with 1N NaOH solution (1.7 mL) and 3,5-bis(trifluoromethyl)benzaldehyde (98.0 mg, 0.41 mmol) in MeOH (3.4 mL) at RT for 24 hours.

The reaction mixture was concentrated to remove the organic solvent. The residue was diluted with water and acidified to pH=4 with 1N HCl$_{(aq.)}$. The resulting precipitate was filtered, washed with H₂O and MeOH, and dried by pressing it on a filter paper to obtain the white solid product Compound 66c ((E)-4-(((6-(3,5-bis(trifluoromethyl)benzylidene)-5-oxo-5,6,7,8-tetrahydronaphthalen-2-yl)oxy)methyl)benzoic acid) (106.0 mg, yield 60%).

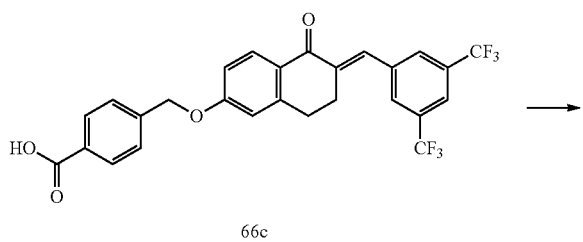

66c

→

To a stirred solution of Compound 66c ((E)-4-(((6-(3,5-bis(trifluoromethyl)-benzylidene)-5-oxo-5,6,7,8-tetrahydronaphthalen-2-yl)oxy)methyl)benzoic acid) (100.0 mg, 0.19 mmol) in DMF (1.9 mL) was added benzene-1,2-diamine (17.0 mg, 0.13 mmol) in one portion, followed by a solution of EDCI (22.0 mg, 0.11 mmol) and HOBt (31.0 mg, 2.30 mmol) in DMF (2.0 mL) was added dropwise to the mixture in one portion at 0° C. The resulting mixture was stirred at RT for overnight.

After which time the mixture concentrated in vacuo to give the crude material. The resulting residue was washed with ether and H₂O to provide the yellow solid product. Compound ((E)-N-(2-aminophenyl)-4-(((6-(3,5-bis(trifluoromethyl)-benzylidene)-5-oxo-5,6,7,8-tetrahydronaphthalen-2-yl)oxy)methyl)benzamide) (58.0 mg, yield 50%).

Compound 66, ¹H-NMR (500 MHz, d₆-DMSO): δ 9.89 (s, 1H), 8.16 (s, 2H), 8.10 (s, 1H), 8.01-7.96 (m, 3H), 7.76 (s, 1H), 7.60-7.58 (d, 2H), 7.16-7.15 (d, 1H), 7.08-7.06 (d, 1H), 7.03 (s, 1H), 6.99-6.96 (t, 1H), 6.79-6.77 (d, 1H), 6.62-6.59 (t, 1H), 5.32 (s, 1H), 4.88 (s, 2H), 3.03 (s, 2H), 2.93 (s, 2H). ESI-MS m/z calcd for $C_{33}H_{24}F_6N_2O_3$ 610.17, found 611.3 [M+H]⁺.

Synthesis of Compounds 67~68

Scheme 43

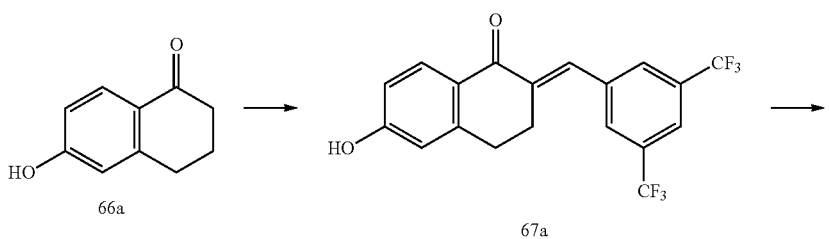

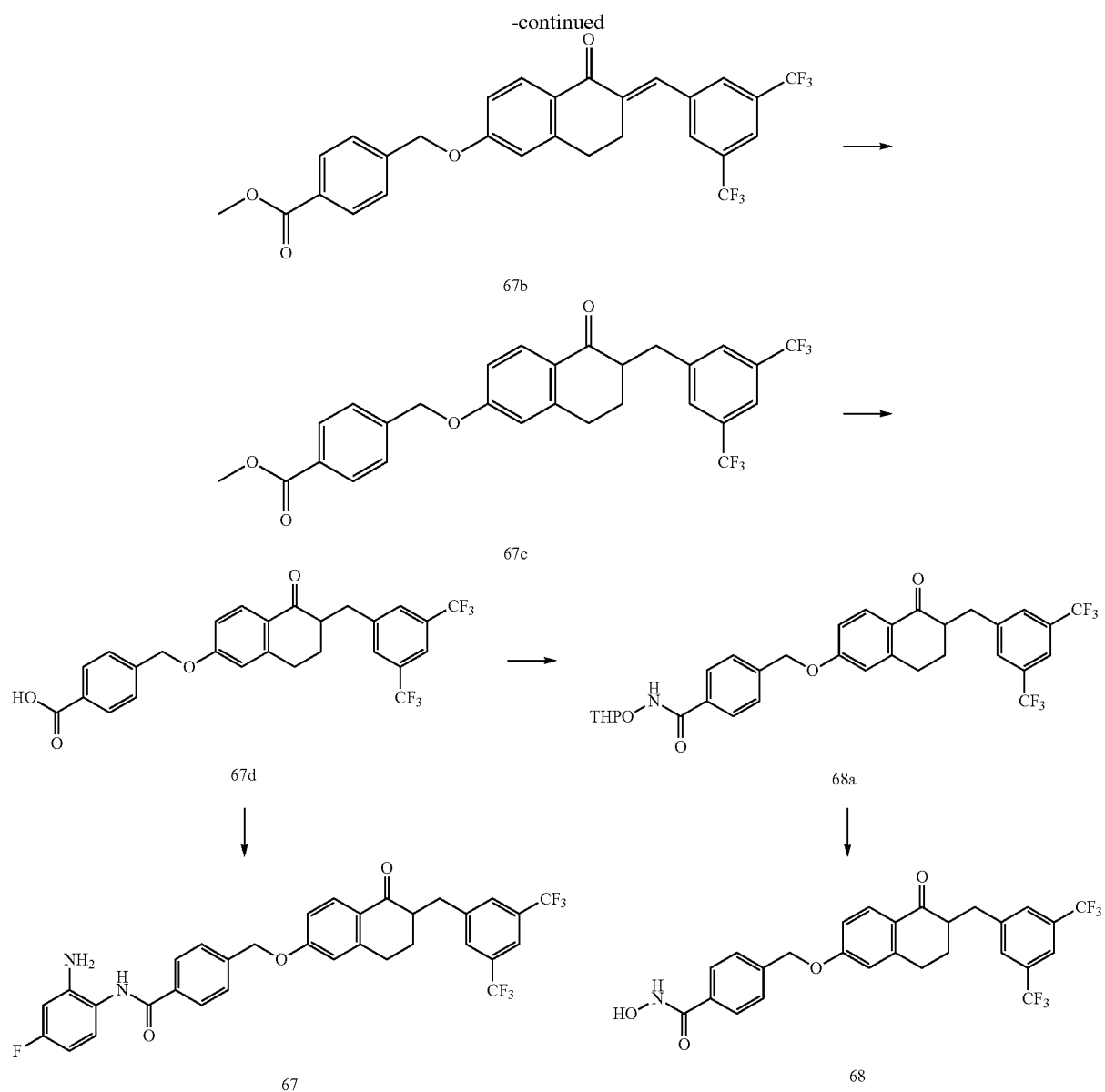

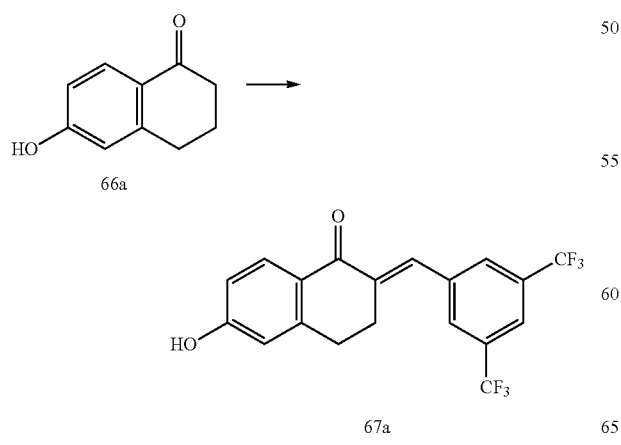

To a solution of Compound 66a (6-Hydroxy-1-tetralone) (1311 mg, 8.00 mmol) in MeOH (60 mL) at RT was added hydrochloric acid (32%; 88 ml), followed 3,5-Bis(trifluoromethyl)benzaldehyde (2195 mg, 9.6 mmol).

The reaction was reflux for 12 hours, then ice-cold water was added and the resulting precipitate was collected by filtration, dried and purified by recrystallization with MeOH to afford the product Compound 67a ((E)-2-(3,5-bis(trifluoromethyl)-benzylidene)-6-hydroxy-3,4-dihydronaphthalen-1(2H)-one) (1556 mg, 49%).

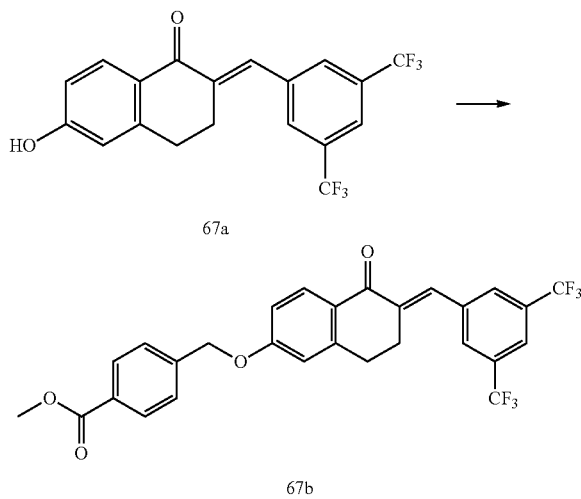

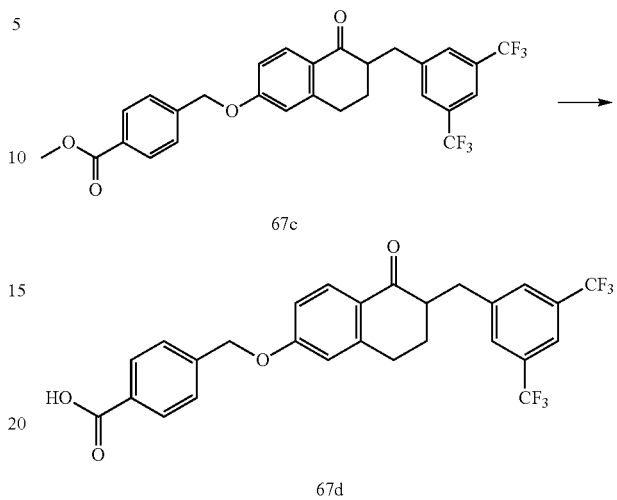

To a solution of Compound 67a ((E)-2-(3,5-bis(trifluoromethyl)-benzylidene)-6-hydroxy-3,4-dihydronaphthalen-1 (2H)-one) (386 mg, 1.00 mmol) in ACN (10 mL) at RT in pressure tube was added methyl 4-(bromomethyl)benzoate (233 mg, 1.00 mmol), Potassium carbonate (139 mg, 1.00 mmol). The tube was sealed and stirred at 95° C. for 90 mins.

After cooling to RT, removed the solvent in vacuo, the crude product was washed with water then recrystallization with ACN to afford the product Compound 67b (methyl (E)-4-(((6-(3,5-bis(trifluoromethyl)benzylidene)-5-oxo-5,6,7,8-tetrahydronaphthalen-2-yl)oxy)methyl)benzoate) (330 mg, 62%).

To a solution of Compound 67b (methyl (E)-4-(((6-(3,5-bis(trifluoro-methyl)benzylidene)-5-oxo-5,6,7,8-tetrahydronaphthalen-2-yl)oxy)methyl)benzoate) (155 mg, 0.29 mmol) in DMSO (6 mL) at rt was added NH$_4$Cl (158 mg, 2.90 mmol), Zinc (99 mg, 1.45 mmol).

The mixture was sealed and stirred at RT for 11 hours, then diluted with EtOAc and washed with water followed brine. The combined organic layer was dried over anhydrous MgSO$_4$. After remove the solvent, the crude product was taken the next step. Compound 67c (methyl 4-(((6-(3,5-bis (trifluoromethyl)benzyl)-5-oxo-5,6,7,8-tetrahydronaphthalen-2-yl)oxy)methyl)benzoate) (145 mg, 93%).

To a solution of Compound 67c (methyl 4-(((6-(3,5-bis (trifluoromethyl)-benzyl)-5-oxo-5,6,7,8-tetrahydronaphthalen-2-yl)oxy)methyl)benzoate) (386 mg, 0.72 mmol) in co-solvent MeOH (60 mL) and DCM (30 mL) was added NaOH aqueous solution (4.0 M, 5 mL) at RT.

The mixture was stirred at RT for 22 hours, then removed the solvent in vacuo followed quench with HCl aqueous solution (1.0 M) to pH=4. The mixture was extracted with EtOAc, then take the organic layer washed with brine. The combined organic layer was dried over anhydrous MgSO$_4$. After remove the solvent, the crude product was taken the next step. Compound 67d (4-(((6-(3,5-bis(trifluoromethyl)-benzyl)-5-oxo-5,6,7,8-tetrahydronaphthalen-2-yl)oxy) methyl)benzoic acid) (265 mg, 70%).

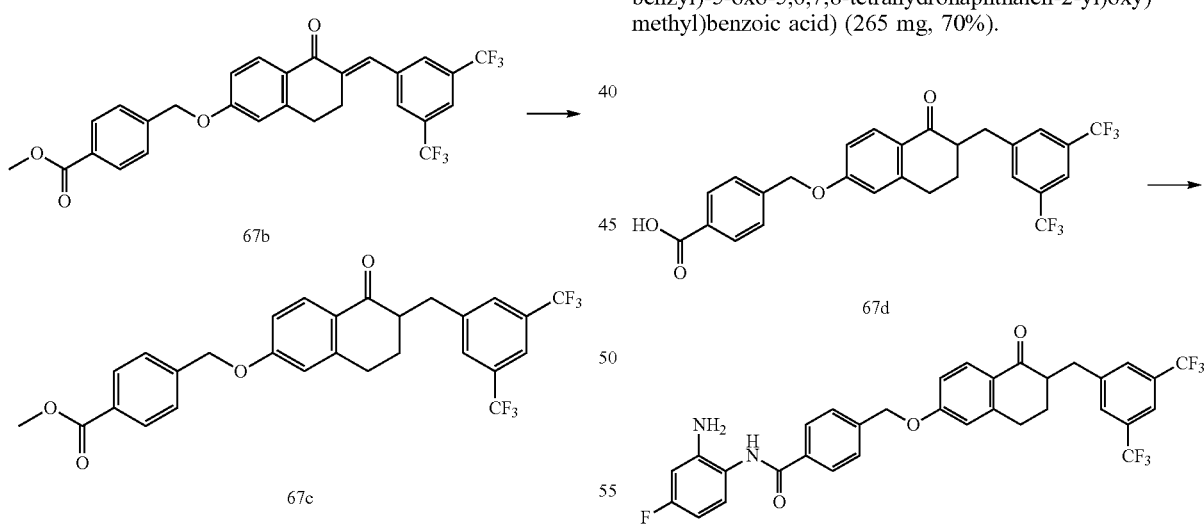

To a solution of Compound 67d (4-(((6-(3,5-bis(trifluoromethyl)benzyl)-5-oxo-5,6,7,8-tetrahydronaphthalen-2-yl) oxy)methyl)benzoic acid) (100 mg, 0.19 mmol) in DMF (30 mL) at 0° C. under nitrogen was added EDC hydrochloride (43 mg, 0.21 mmol), followed DMAP (27 mg, 0.21 mmol) and 4-Fluoro-1,2-phenylenediamine (29 mg, 0.21 mmol). The mixture was allowed to warm to RT and stirred for 12 hours.

After removing the solvent, the crude product was purified by column chromatography (EtOAc:n-hexane=1:2). The crude product was washed with MeOH, n-hexane to afford the product to afford the solid Compound 67 (N-(2-amino-4-fluorophenyl)-4-(((6-(3,5-bis(trifluoromethyl)benzyl)-5-oxo-5,6,7,8-tetrahydronaphthalen-2-yl)oxy)methyl)benzamide) (23 mg, 19%).

Compound 67, ¹H-NMR (500 MHz, d₆-DMSO): δ 9.61 (s, 1H), 7.99 (s, 4H), 7.92 (s, 1H), 7.86-7.85 (d, 1H), 7.57-7.56 (d, 2H), 7.12-7.09 (t, 1H), 7.00-6.99 (d, 1H), 6.95 (s, 1H), 6.55-6.52 (dd, 1H), 6.38-6.34 (m, 1H), 5.28-5.22 (m, 4H), 3.15-2.87 (m, 4H), 1.98-1.95 (m, 1H), 1.75-1.68 (m, 1H). ESI-MS m/z calcd for $C_{33}H_{25}F_7N_2O_3$ 630.17, found 631.0 [M+H]⁺.

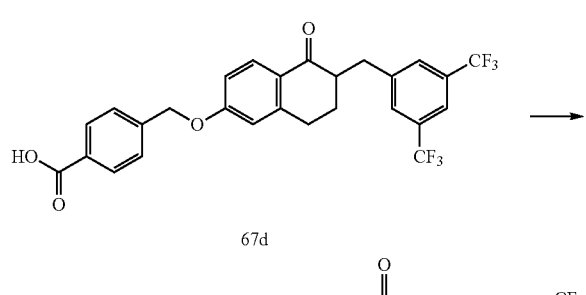

67d

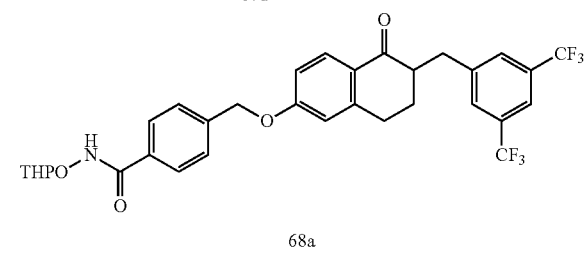

68a

To a solution of Compound 67d (4-(((6-(3,5-bis(trifluoromethyl)benzyl)-5-oxo-5,6,7,8-tetrahydronaphthalen-2-yl)oxy)methyl)benzoic acid) (117 mg, 0.22 mmol) in DMF (30 mL) at 0° C. under nitrogen was added EDC hydrochloride (50 mg, 0.25 mmol), followed DMAP (32 mg, 0.25 mmol) and O-(Tetrahydro-2H-pyran-2-yl)hydroxylamine (33 mg, 0.25 mmol). The mixture was allowed to warm to RT and stirred for 12 hours.

After removing the solvent, the crude product was purified by column chromatography (EtOAc:n-hexane=1:1) to afford the solid Compound 68a (4-(((6-(3,5-bis(trifluoromethyl)benzyl)-5-oxo-5,6,7,8-tetrahydronaphthalen-2-yl)oxy)-methyl)-N-((tetrahydro-2H-pyran-2-yl)oxy)benzamide) (100 mg, 72%).

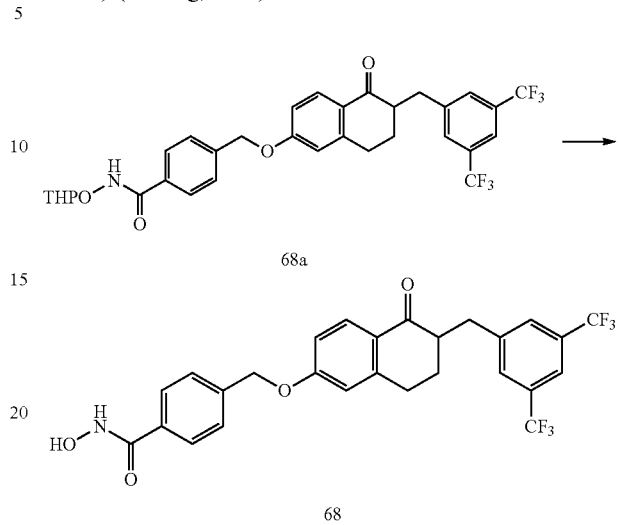

68a

68

To a solution of Compound 68a (4-(((6-(3,5-bis(trifluoromethyl)benzyl)-5-oxo-5,6,7,8-tetrahydronaphthalen-2-yl)oxy)methyl)-N-((tetrahydro-2H-pyran-2-yl)oxy)benzamide) (97 mg, 0.16 mmol) in DCM (9 mL) at RT was added hydrogen chloride solution 2.0 M in diethyl ether (excess, 2 mL).

The reaction was stirred at RT for 12 hours, then remove the solvent and purified by column chromatography (DCM:MeOH=30:1). The crude product was washed with MeOH, n-hexane to afford the product Compound 68 (4-(((6-(3,5-bis(trifluoromethyl)benzyl)-5-oxo-5,6,7,8-tetrahydronaphthalen-2-yl)oxy)methyl)-N-hydroxybenzamide) (19 mg, 23%).

Compound 68, ¹H-NMR (500 MHz, d₆-DMSO): δ 11.24 (s, 1H), 9.07 (s, 1H), 7.99 (s, 2H), 7.91 (s, 1H), 7.86-7.84 (d, 1H), 7.77-7.75 (d, 2H), 7.52-7.50 (d, 2H), 6.98-6.96 (d, 1H), 6.94 (s, 1H), 5.23 (s, 2H), 3.00-2.86 (m, 4H), 1.97-1.94 (m, 1H), 1.72-1.69 (m, 1H). ESI-MS m/z calcd for $C_{27}H_{21}F_6NO_4$ 537.13, found 538.0 [M+H]⁺.

Synthesis of Compounds 69~70

Scheme 44

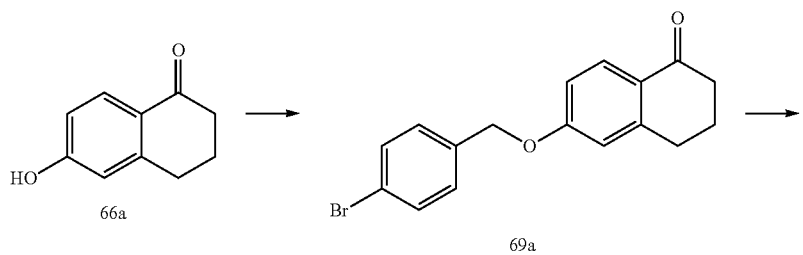

66a

69a

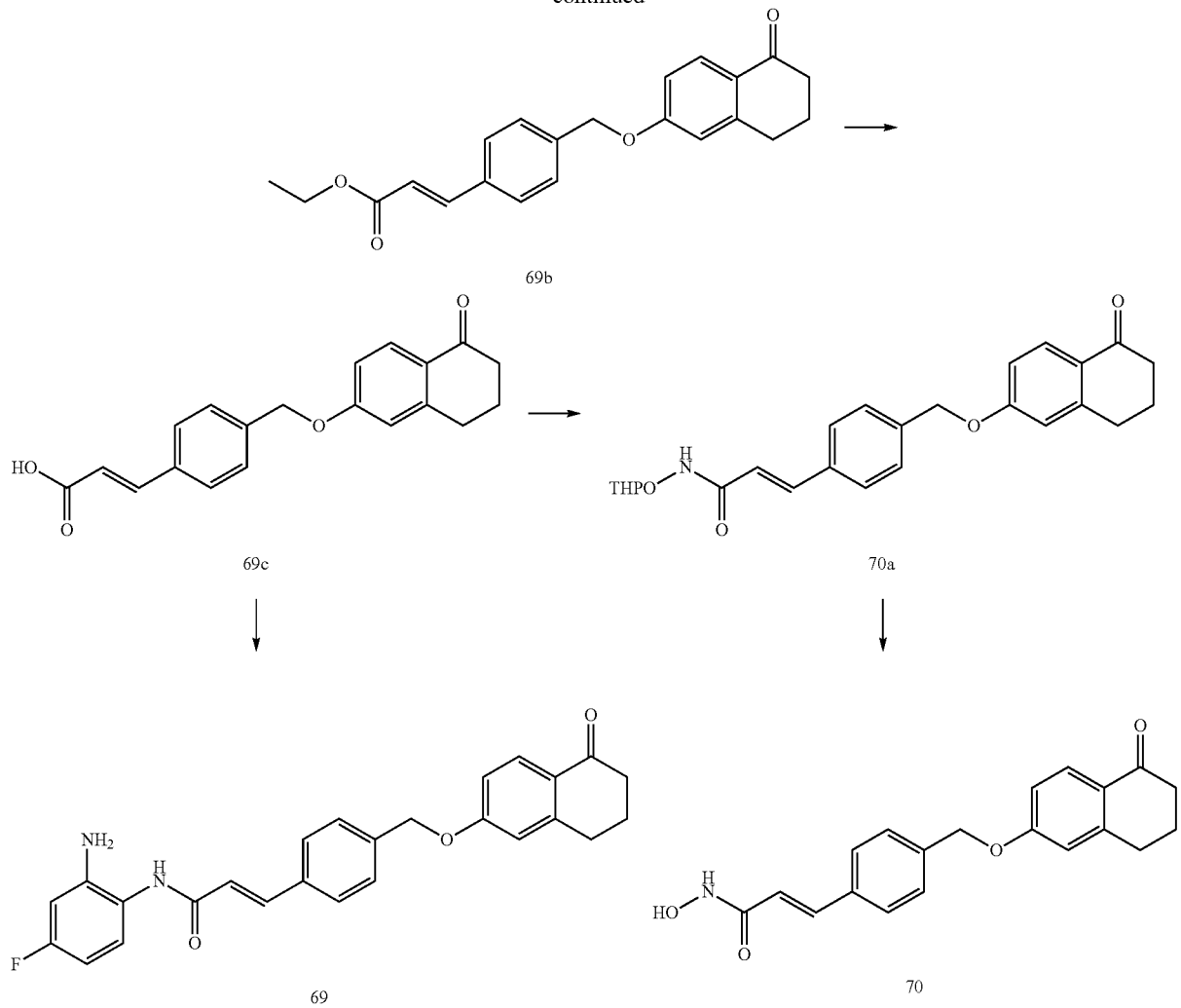

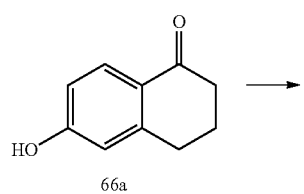

To a solution of Compound 66a (6-Hydroxy-3,4-dihydro-1(2H)-naphthalenone) (1.00 g, 3.54 mmol) and K$_2$CO$_3$ (0.73 g, 5.31 mmol) in ACN (40 mL) was added 1-bromo-4-(bromomethyl)benzene (0.93 g, 3.72 mmol). After addition, the reaction mixture was heated to 50° C. and stirred for overnight.

The reaction was monitored by TLC. After reaction was completed, the solvent was removed under reduced pressure. The residual was diluted with ice-cold water and the precipitated solid was collected by filtration to get the desired product Compound 69a (6-((4-bromobenzyl)oxy)-3,4-dihydronaphthalen-1(2H)-one) (1.00 g, 3.01 mmol, yield 85%).

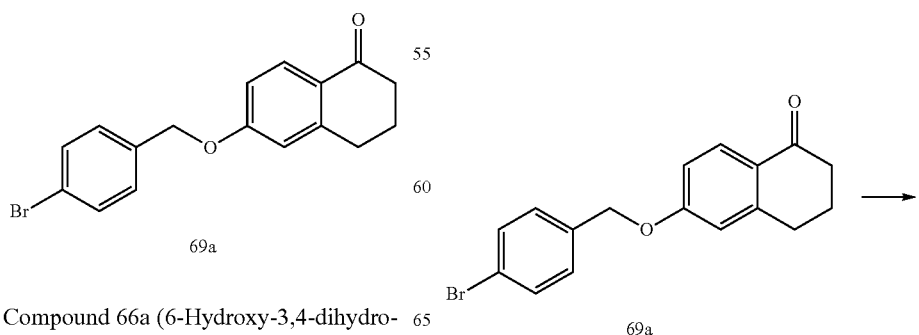

-continued

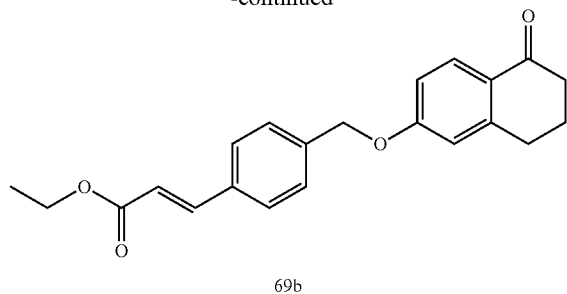
69b

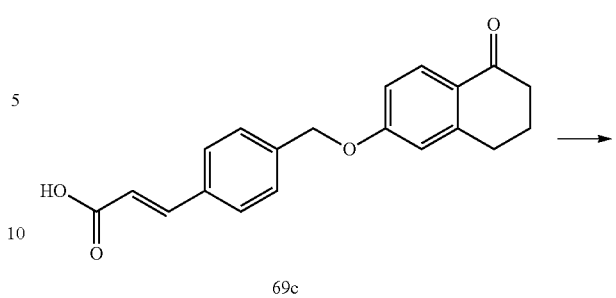
69c

To a solution of Compound 69a (6-((4-bromobenzyl) oxy)-3,4-dihydronaphthalen-1(2H)-one) (0.50 g, 1.51 mmol), triphenylphosphine (0.16 g, 0.60 mmol), ethyl acrylate (0.20 g, 1.96 mmol) in DMF/TEA (30 mL, 1:1) was added Pd(OAc)$_2$ (0.02 g, 0.08 mmol). After addition, the reaction mixture was heated to 100° C. and stirred for overnight.

The reaction was monitored by TLC. After reaction was completed, the reaction mixture was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/4 as elution to yield the desired product Compound 69b (ethyl (E)-3-(4-(((5-oxo-5,6,7,8-tetrahydronaphthalen-2-yl)oxy)methyl) phenyl)acrylate) (0.51 g, 1.45 mmol, yield 96%).

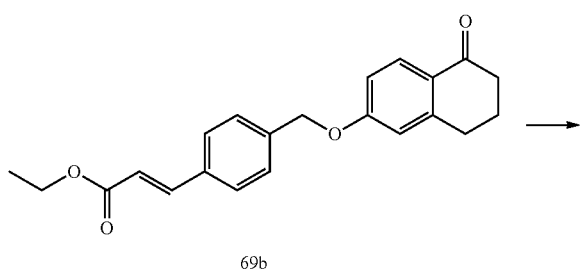
69b

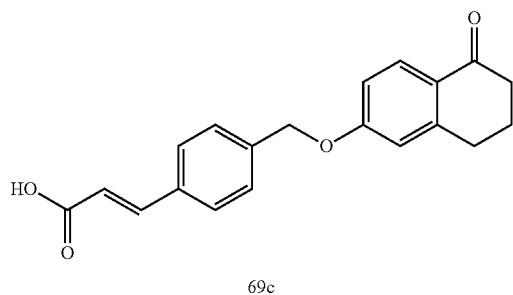
69c

To a solution of Compound 69b (ethyl (E)-3-(4-(((5-oxo-5,6,7,8-tetrahydronaphthalen-2-yl)oxy)methyl)phenyl)acrylate) (0.51 g, 1.45 mmol) in MeOH (50 mL) was added 2N NaOH$_{(aq)}$ (1.5 mL, 3.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 69c ((E)-3-(4-(((5-oxo-5,6,7,8-tetrahydro-naphthalen-2-yl)oxy) methyl)phenyl)acrylic acid) (0.46 g, 1.43 mmol, yield 99%).

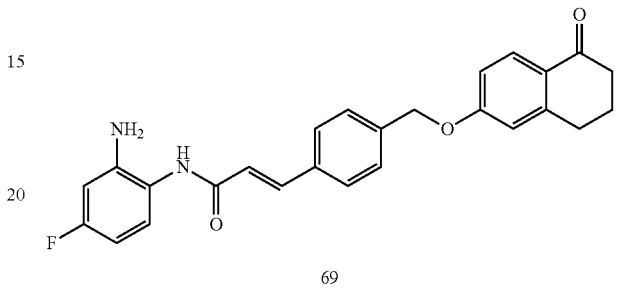
69

To a solution of Compound 69c ((E)-3-(4-(((5-oxo-5,6,7,8-tetrahydro-naphthalen-2-yl)oxy)methyl)phenyl)acrylic acid) (0.07 g, 0.22 mmol), 4-fluoro-1,2-phenylenediamine (0.03 g, 0.26 mmol) and DMAP (0.01 g, 0.11 mmol) in THF (30 mL) was added NMM (0.03 g, 0.33 mmol) and EDCI (0.06 g, 0.33 mmol) at 0 t. After addition, the reaction mixture was warmed to room temperature and stirred for 6 hours.

The reaction was monitored by TLC. After reaction was completed, the solvent was removed under reduced pressure. The residue was diluted with sat. NH$_4$Cl$_{(aq)}$ and extracted with EtOAc. The organic phase was dried with MgSO$_4$ and concentrated under reduced pressure. The crude product was purified by silica gel column chromatography using ethyl acetate/hexane=1/1 as elution to yield the desired product Compound 69 ((E)-N-(2-amino-4-fluorophenyl)-3-(4-(((5-oxo-5,6,7,8-tetra-hydronaphthalen-2-yl)oxy)methyl)phenyl)acrylamide) (0.03 g, 0.07 mmol, yield 31%).

Compound 69, $^1$H-NMR (500 MHz, CD$_3$OD): δ 7.94-7.93 (d, 1H), 7.69-7.64 (m, 3H), 7.52-7.50 (d, 2H), 7.17-7.14 (m, 1H), 6.97-6.95 (dd, 1H), 6.92 (s, 1H), 6.87-6.83 (d, 1H), 6.58-6.56 (dd, 1H), 6.43-6.39 (td, 1H), 5.22 (s, 2H), 2.97-2.95 (t, 2H), 2.61-2.58 (t, 2H), 2.12-2.09 (m, 2H). ESI-MS m/z calcd for C$_{26}$H$_{23}$FN$_2$O$_3$ 430.17, found 431 [M+H]$^+$.

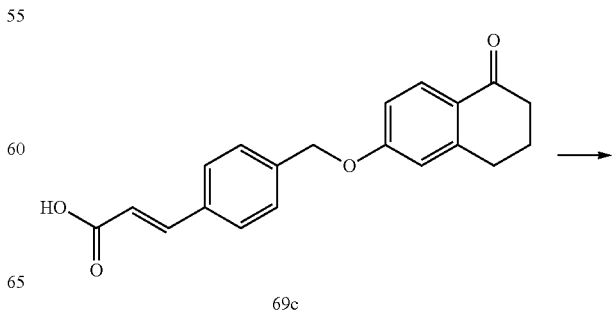
69c

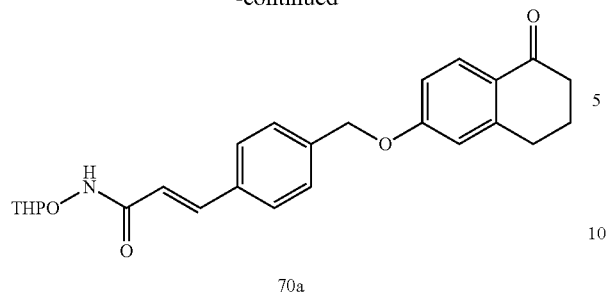

70a

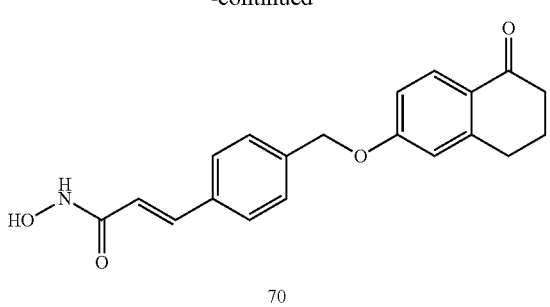

70

To a solution of Compound 69c ((E)-3-(4-(((5-oxo-5,6,7,8-tetrahydro-naphthalen-2-yl)oxy)methyl)phenyl)acrylic acid) (0.12 g, 0.37 mmol), NH$_2$OTHP (0.07 g, 0.56 mmol) and DMAP (0.02 g, 0.19 mmol) in CH$_2$Cl$_2$ (20 mL) was added NMM (0.06 g, 0.56 mmol) and EDCI (0.11 g, 0.56 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=1/1 as elution to yield the desired product Compound 70a ((E)-3-(4-(((5-oxo-5,6,7,8-tetrahydronaphthalen-2-yl)oxy)-methyl)phenyl)-N-((tetrahydro-2H-pyran-2-yl)oxy)acrylamide) (0.09 g, 0.22 mmol, yield 60%).

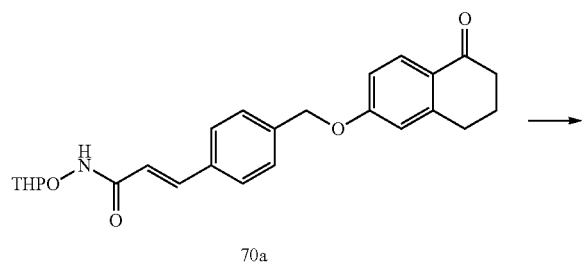

70a

To a solution of Compound 70a ((E)-3-(4-(((5-oxo-5,6,7,8-tetrahydro-naphthalen-2-yl)oxy)-methyl)phenyl)-N-((tetrahydro-2H-pyran-2-yl)oxy)acrylamide) (0.09 g, 0.22 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 70 ((E)-N-hydroxy-3-(4-(((5-oxo-5,6,7,8-tetrahydronaphthalen-2-yl)oxy)-methyl)phenyl)acrylamide) (0.05 g, 0.16 mmol, yield 71%).

Compound 70, $^1$H-NMR (500 MHz, CD$_3$OD): δ 7.94-7.92 (d, 1H), 7.67-7.63 (m, 1H), 7.59-7.57 (m, 2H), 7.49-7.48 (d, 2H), 6.96-6.93 (dd, 1H), 6.91 (s, 1H), 6.50-6.47 (d, 1H), 5.20 (s, 2H), 2.97-2.94 (t, 2H), 2.60-2.58 (t, 2H), 2.11-2.09 (m, 2H). ESI-MS m/z calcd for C$_{20}$H$_{19}$NO$_4$ 337.13, found 338 [M+H]$^+$.

Synthesis of Compounds 71~72

Scheme 45

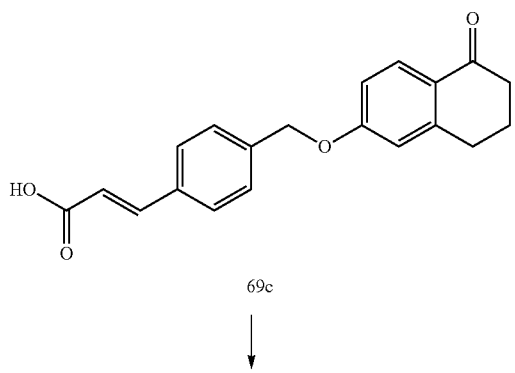

69c

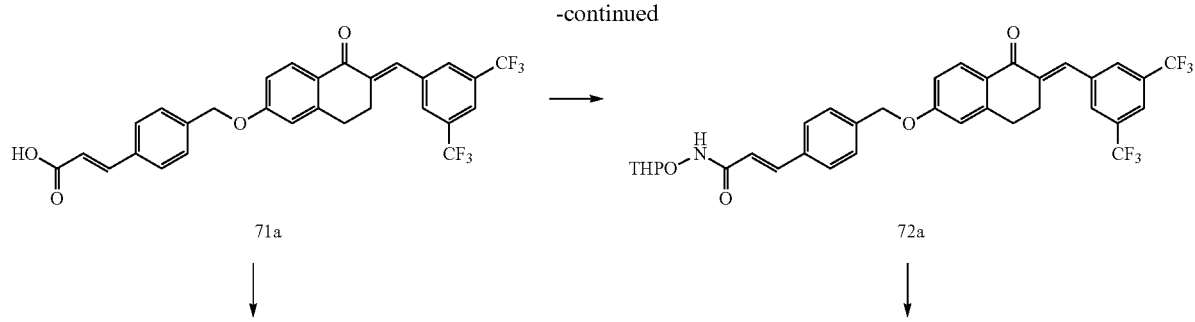

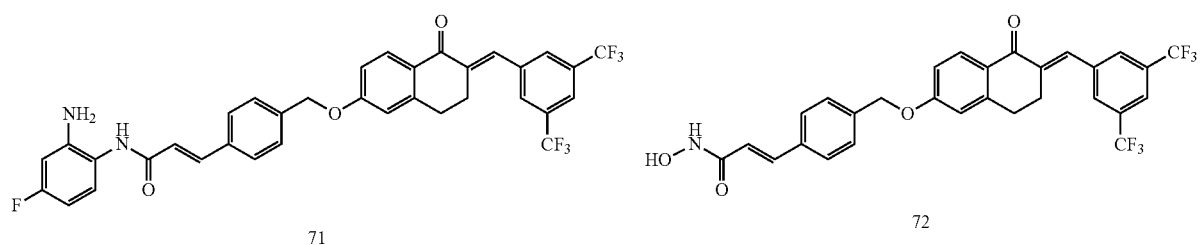

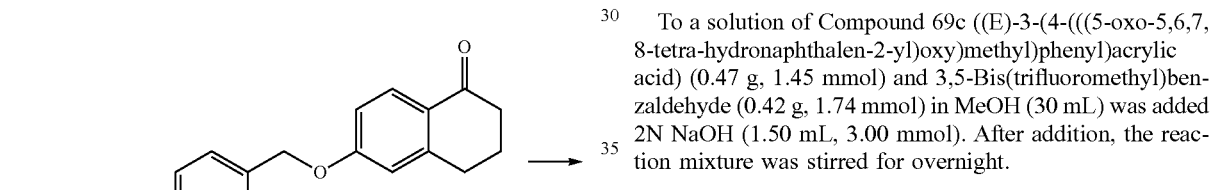

To a solution of Compound 69c ((E)-3-(4-(((5-oxo-5,6,7,8-tetra-hydronaphthalen-2-yl)oxy)methyl)phenyl)acrylic acid) (0.47 g, 1.45 mmol) and 3,5-Bis(trifluoromethyl)benzaldehyde (0.42 g, 1.74 mmol) in MeOH (30 mL) was added 2N NaOH (1.50 mL, 3.00 mmol). After addition, the reaction mixture was stirred for overnight.

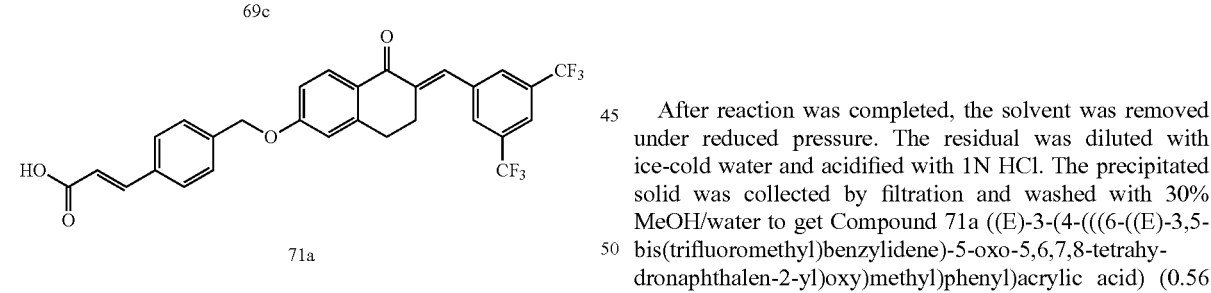

After reaction was completed, the solvent was removed under reduced pressure. The residual was diluted with ice-cold water and acidified with 1N HCl. The precipitated solid was collected by filtration and washed with 30% MeOH/water to get Compound 71a ((E)-3-(4-(((6-((E)-3,5-bis(trifluoromethyl)benzylidene)-5-oxo-5,6,7,8-tetrahydronaphthalen-2-yl)oxy)methyl)phenyl)acrylic acid) (0.56 g, 1.03 mmol, yield 71%).

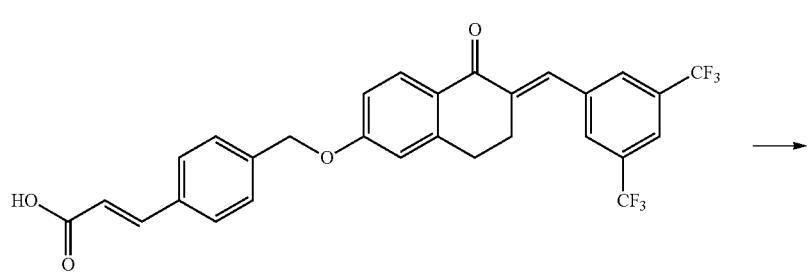

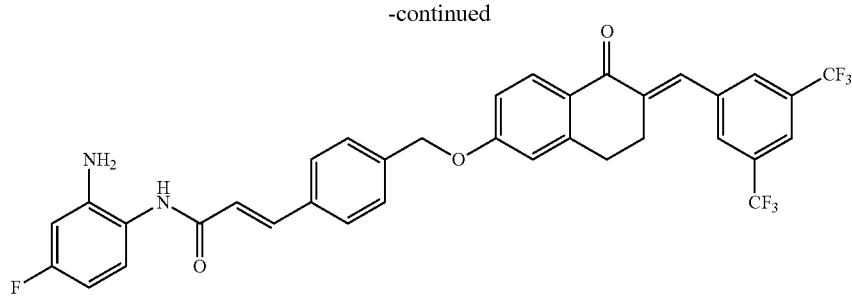

71

To a solution of Compound 71a ((E)-3-(4-(((6-((E)-3,5-bis(trifluoro-methyl)benzylidene)-5-oxo-5,6,7,8-tetrahydronaphthalen-2-yl)oxy)methyl)phenyl)-acrylic acid) (0.20 g, 0.37 mmol), 4-fluoro-1,2-phenylenediamine (0.06 g, 0.44 mmol) and DMAP (0.02 g, 0.19 mmol) in THF (30 mL) was added NMM (0.06 g, 0.55 mmol) and EDCI (0.11 g, 0.55 mmol) at 0° C. After addition, the reaction mixture was warmed to room temperature and stirred for 6 hours.

The reaction was monitored by TLC. After reaction was completed, the solvent was removed under reduced pressure. The residue was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/hexane=1/1 as elution to yield the desired product Compound 71 ((E)-N-(2-amino-4-fluorophenyl)-3-(4 #(6-((E)-3,5-bis(tri-fluoromethyl)benzylidene)-5-oxo-5,6,7,8-tetrahydronaphthalen-2-yl)oxy)methyl)-phenyl)acrylamide) (0.06 g, 0.10 mmol, yield 26%).

Compound 71, $^1$H-NMR (500 MHz, $CDCl_3$): δ 8.15-8.13 (d, 1H), 7.85-7.82 (m, 4H), 7.78-7.75 (d, 1H), 7.60-7.58 (d, 2H), 7.48-7.46 (d, 2H), 7.18 (s, 1H), 6.99-6.97 (d, 1H), 6.81 (s, 1H), 6.62-6.59 (d, 1H), 6.54-6.52 (m, 2H), 5.17 (s, 2H), 4.04 (s, 2H), 3.06-2.96 (m, 4H). ESI-MS m/z calcd for $C_{35}H_{25}F_7N_2O_3$ 654.18, found 655 [M+H]$^+$.

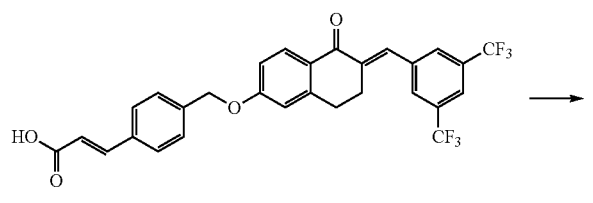

71a

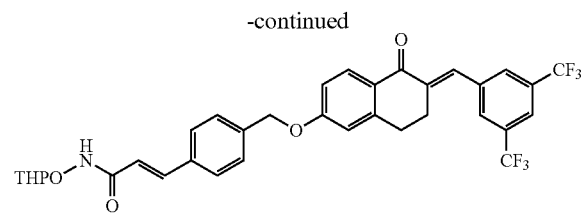

72a

To a solution of Compound 71a ((E)-3-(4-(((6-((E)-3,5-bis(trifluoro-methyl)benzylidene)-5-oxo-5,6,7,8-tetrahydronaphthalen-2-yl)oxy)methyl)phenyl)-acrylic acid) (0.20 g, 0.37 mmol), $NH_2OTHP$ (0.06 g, 0.55 mmol) and DMAP (0.02 g, 0.19 mmol) in $CH_2Cl_2$ (20 mL) was added NMM (0.06 g, 0.55 mmol) and EDCI (0.11 g, 0.55 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with $MgSO_4$ and concentrated under reduced pressure. The crude product was purified by silica gel column chromatography using ethyl acetate/hexane=2/1 as elution to yield the desired product Compound 72a ((E)-3-(4-(((6-((E)-3,5-bis(trifluoromethyl)benzylidene)-5-oxo-5,6,7,8-tetrahydronaphthalen-2-yl)oxy)methyl)phenyl)-N-((tetrahydro-2H-pyran-2-yl)oxy)acrylamide) (0.12 g, 0.19 mmol, yield 50%).

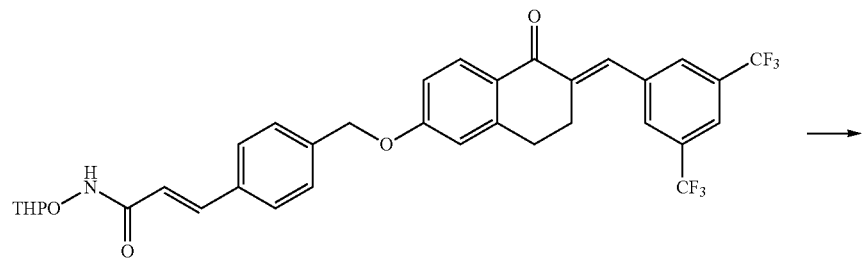

72a

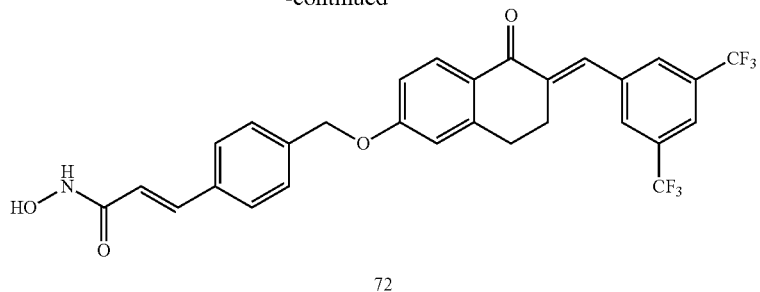

72

To a solution of Compound 72a ((E)-3-(4-(((6-((E)-3,5-bis(trifluoro-methyl)benzylidene)-5-oxo-5,6,7,8-tetrahydronaphthalen-2-yl)oxy)methyl)phenyl)-N-((tetrahydro-2H-pyran-2-yl)oxy)acrylamide) (0.12 g, 0.19 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 72 ((E)-3-(4-(((6-((E)-3,5-bis(trifluoromethyl)benzylidene)-5-oxo-5,6,7,8-tetrahydronaphthalen-2-yl)oxy)methyl)phenyl)-N-hydroxyacrylamide) (0.08 g, 0.14 mmol, yield 74%).

Compound 72, $^1$H-NMR (500 MHz, CDCl$_3$): δ 8.14-8.12 (d, 1H), 7.85-7.82 (m, 4H), 7.74-7.71 (d, 1H), 7.56-7.54 (d, 2H), 7.46-7.44 (d, 2H), 6.98-6.96 (d, 1H), 6.80 (s, 1H), 6.38 (br, 1H), 5.16 (s, 2H), 3.05-2.95 (m, 4H). ESI-MS m/z calcd for C$_{29}$H$_{21}$F$_6$NO$_4$ 561.14, found 562 [M+1-1]$^+$.

Synthesis of Compound 73

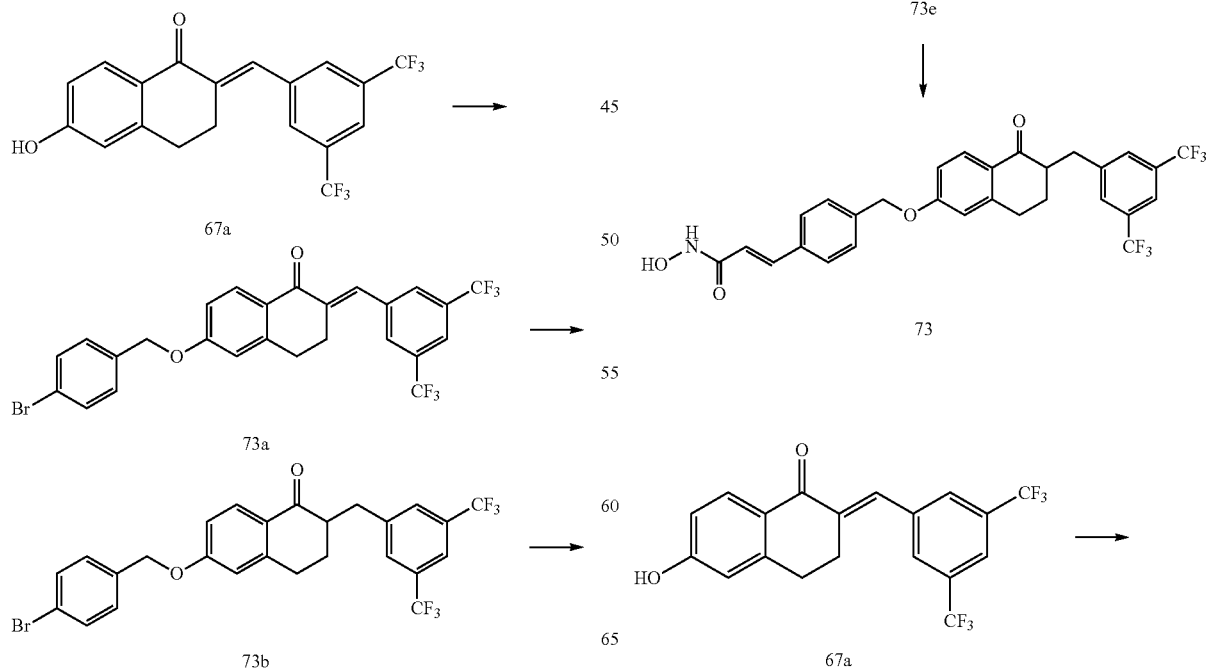

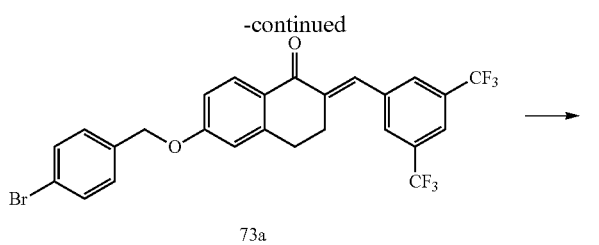

73a

To a solution of Compound 67a ((E)-2-(3,5-bis(trifluoromethyl)-benzylidene)-6-hydroxy-3,4-dihydronaphthalen-1(2H)-one) (386 mg, 1.00 mmol) in ACN (10 mL) at RT in pressure tube was added 4-Bromobenzyl bromide (250 mg, 1.00 mmol), Potassium carbonate (138 mg, 1.00 mmol). The tube was sealed and stirred at 95° C. for 3 hours.

After cooling to RT, removed the solvent in vacuo, the crude product was purified by column chromatography (EtOAc:n-hexane=1:10) to afford the product Compound 73a ((E)-2-(3,5-bis(trifluoromethyl)benzylidene)-64(4-bromobenzyl)oxy)-3,4-dihydronaphthalen-1(2H)-one) (400 mg, 72%).

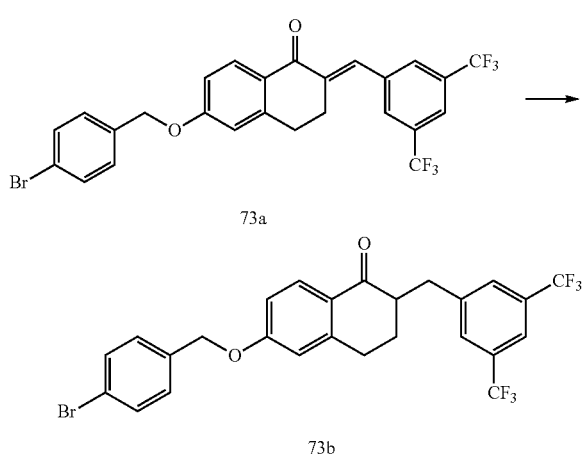

To a solution of Compound 73a ((E)-2-(3,5-bis(trifluoromethyl)-benzylidene)-64(4-bromobenzyl)oxy)-3,4-dihydronaphthalen-1(2H)-one) (400 mg, 0.72 mmol) in DMF (30 mL) at RT was added NH$_4$Cl (386 mg, 7.21 mmol), Zinc (239 mg, 3.60 mmol).

The mixture was sealed and stirred at RT for 12 hours, then diluted with EtOAc and washed with water followed brine. The combined organic layer was dried over anhydrous MgSO$_4$. After remove the solvent, purification by column chromatography (EtOAc:n-hexane=1:10) to afford the product Compound 73b (2-(3,5-bis(trifluoromethyl)benzyl)-6-((4-bromobenzyl)oxy)-3,4-dihydronaphthalen-1(2H)-one) (317 mg, 79%).

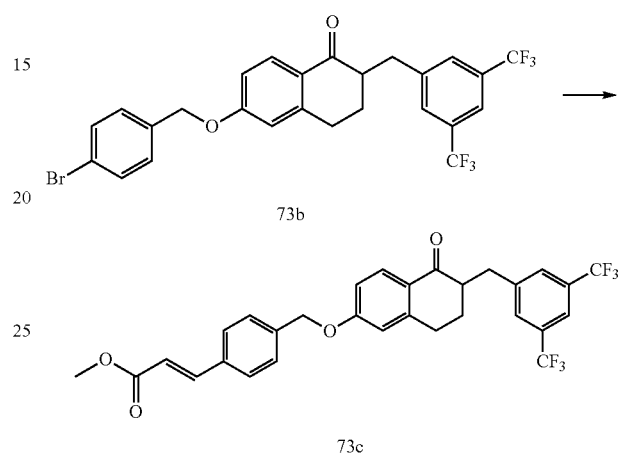

To a solution of Compound 73b (2-(3,5-bis(trifluoromethyl)benzyl)-6-((4-bromobenzyl)oxy)-3,4-dihydronaphthalen-1(2H)-one) (317 mg, 0.57 mmol) in ACN (8 mL) was added methyl acrylate (1.3 mL, 14.2 mmol) at RT in pressure tube, followed Et$_3$N (8 mL), PPh$_3$ (222 mg, 0.85 mmol). The mixture was stirred at RT for 5 mins then degas with nitrogen, followed added Pd(OAc)$_2$ (76 mg, 0.34 mmol) and seal the tube. The reaction was stirred at 100° C. for 21 hours.

After cooling to RT, removed the solvent in vacuo and purified with column chromatography (EtOAc:n-hexane=1:5) to afford the product Compound 73c (methyl (E)-3-(4-(((6-(3,5-bis(trifluoromethyl)benzyl)-5-oxo-5,6,7,8-tetrahydronaphthalen-2-yl)oxy)methyl)phenyl)acrylate) (266 mg, 83%).

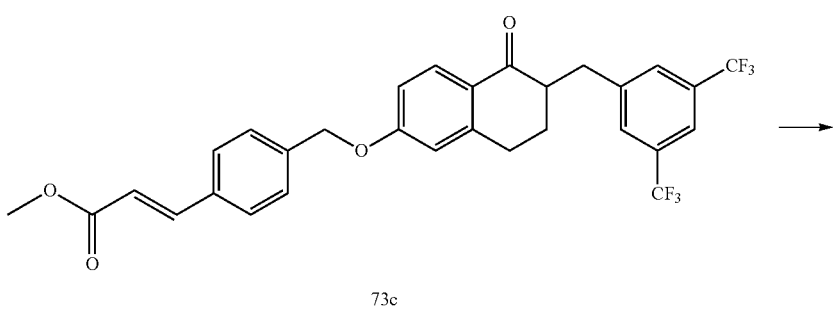

73c

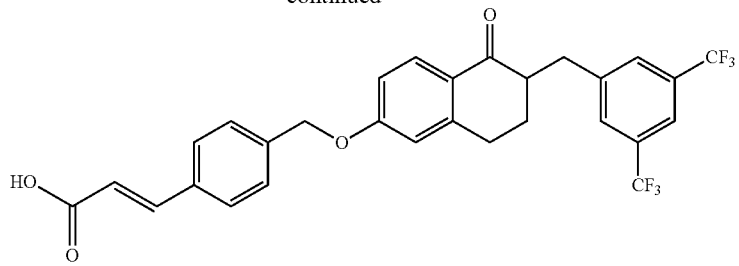

73d

To a solution of Compound 73c (methyl (E)-3-(4-(((6-(3,5-bis(trifluoro-methyl)benzyl)-5-oxo-5,6,7,8-tetrahydronaphthalen-2-yl)oxy)methyl)phenyl)acrylate) (253 mg, 0.45 mmol) in co-solvent MeOH (20 mL) and DCM (40 mL) was added NaOH aqueous solution (4.0 M, 3 mL) at RT.

The mixture was stirred at RT for 12 hours, then removed the solvent in vacuo followed quench with HCl aqueous solution (1.0 M) to pH=4. The mixture was extracted with EtOAc, then take the organic layer washed with brine. The combined organic layer was dried over anhydrous MgSO$_4$. After remove the solvent, purified with column chromatography (EtOAc:n-hexane=1:2) to afford the product. Compound 73d ((E)-3-(4-(((6-(3,5-bis(trifluoromethyl)benzyl)-5-oxo-5,6,7,8-tetra-hydronaphthalen-2-yl)oxy)methyl)phenyl)acrylic acid) (76 mg, 31%).

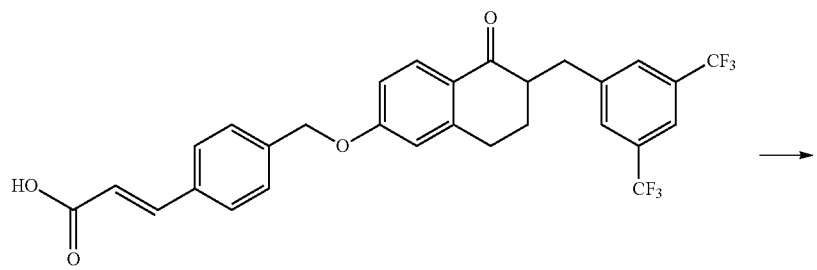

73d

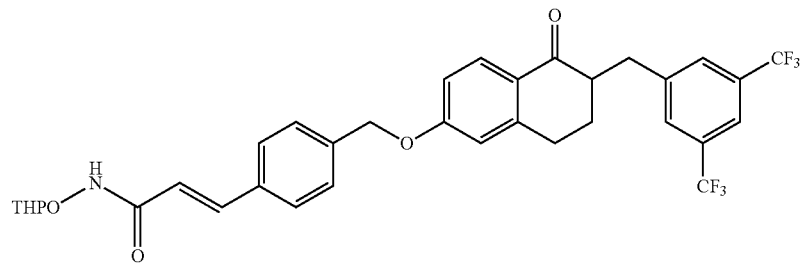

73e

To a solution of Compound 73d ((E)-3-(4-(((6-(3,5-bis(trifluoro-methyl)benzyl)-5-oxo-5,6,7,8-tetra-hydronaphthalen-2-yl)oxy)methyl)phenyl)acrylic acid) (98 mg, 0.18 mmol) in DMF (30 mL) at 0° C. under nitrogen was added EDC hydrochloride (40 mg, 0.21 mmol), followed DMAP (27 mg, 0.21 mmol) and O-(Tetrahydro-2H-pyran-2-yl)hydroxylamine (25 mg, 0.21 mmol). The mixture was allowed to warm to RT and stirred for 20 hours.

After removing the solvent, the crude product was purified by column chromatography (EtOAc:n-hexane=1:1) to afford the solid Compound 73e ((E)-3-(4-(((6-(3,5-bis(trifluoromethyl)benzyl)-5-oxo-5,6,7,8-tetrahydronaphthalen-2-yl)oxy)-methyl)phenyl)-N-((tetrahydro-2H-pyran-2-yl)oxy)acrylamide) (67 mg, 58%).

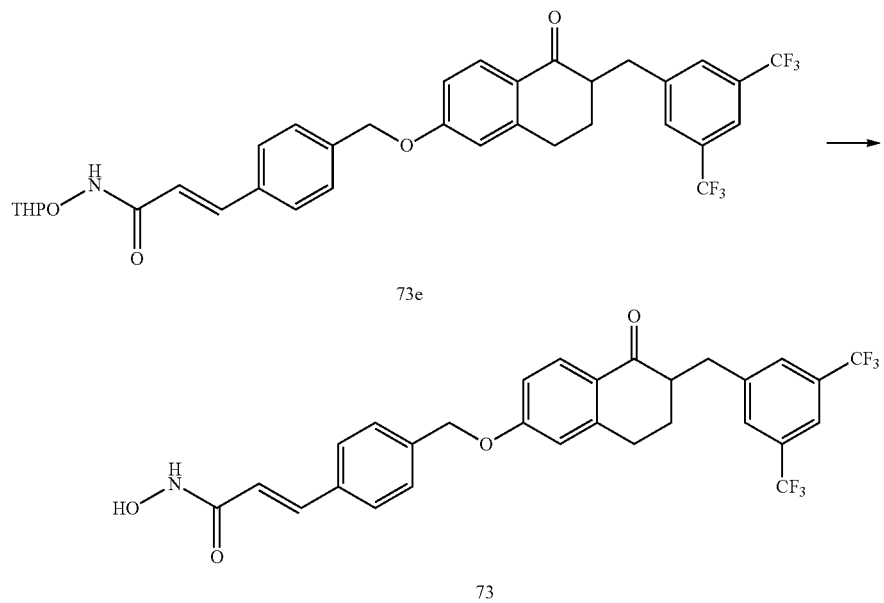

To a solution of Compound 73e ((E)-3-(4-(((6-(3,5-bis(trifluoromethyl)-benzyl)-5-oxo-5,6,7,8-tetrahydronaphtha-len-2-yl)oxy)-m ethyl)phenyl)-N-((tetrahydro-2H-pyran-2-yl)oxy)acrylamide) (29 mg, 0.04 mmol) in DCM (10 mL) at RT was added hydrogen chloride solution 2.0 M in diethyl ether (0.1 mL, 0.20 mmol).

The reaction was stirred at RT for 3 hours, then the solid was filtered out to afford the product Compound 73 ((E)-3-(4-(((6-(3,5-bis(trifluoromethyl)benzyl)-5-oxo-5,6,7,8-tetrahydronaphthalen-2-yl)oxy)methyl)phenyl)-N-hydroxyacrylamide) (15 mg, 60%).

Compound 73, $^1$H-NMR (500 MHz, $d_6$-DMSO): δ 7.99 (s, 2H), 7.91 (s, 1H), 7.86-7.84 (d, 1H), 7.59-7.58 (d, 2H), 7.48-7.44 (d, 3H), 6.98-6.97 (d, 1H), 6.94 (s, 1H), 6.50-6.47 (d, 1H), 5.21 (s, 2H), 3.43-3.40 (m, 1H), 3.00-2.86 (m, 4H), 1.98-1.94 (m, 1H), 1.73-1.70 (m, 1H). ESI-MS m/z calcd for $C_{29}H_{23}F_6NO_2$ 563.15, found 564 [M+H]$^+$.

Synthesis of Compound 74

Scheme 47

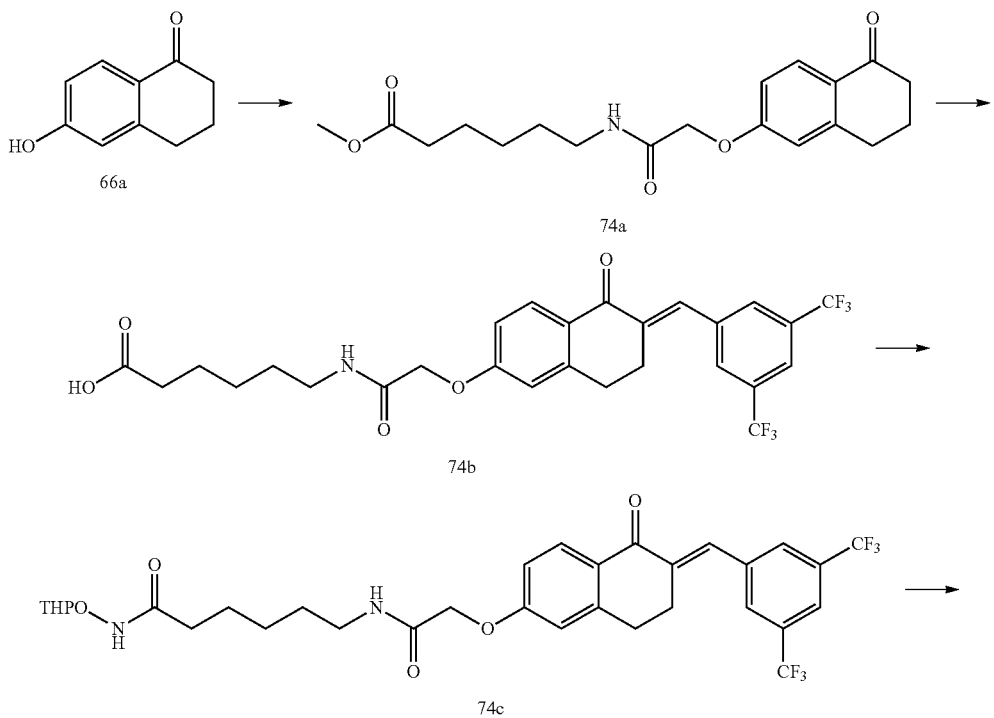

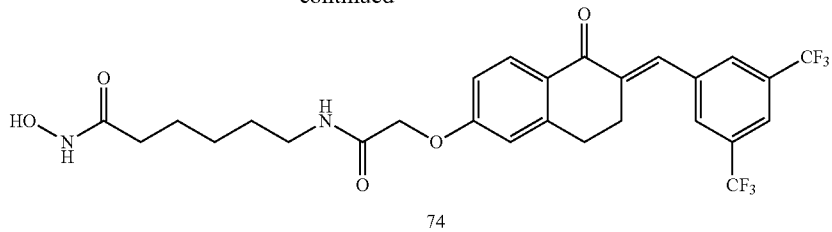

74

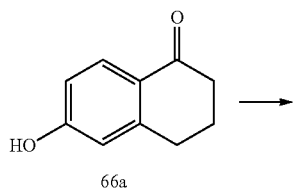

66a

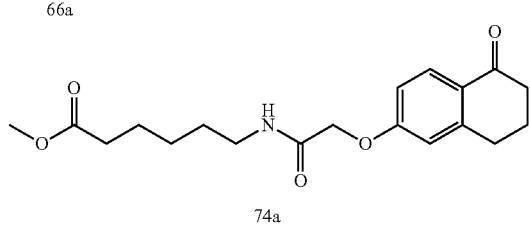

74a

To a solution of Compound 66a (6-Hydroxy-3,4-dihydro-1(2H)-naphthalenone) (0.12 g, 0.74 mmol) and $K_2CO_3$ (0.31 g, 2.22 mmol) in acetone (20 mL) was added methyl 6-(2-chloroacetamido)hexanoate (0.25 g, 1.11 mmol) and KI (catalytic amount). After addition, the reaction mixture was refluxed for overnight.

The reaction was monitored by TLC. After reaction was completed, the solvent was removed under reduced pressure. The residue was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/hexane=2/1 as elution to yield the desired product Compound 74a (methyl 6-(2-((5-oxo-5,6,7,8-tetrahydronaphthalen-2-yl)oxy)-acetamido)hexanoate) (0.24 g, 0.69 mmol, yield 93%).

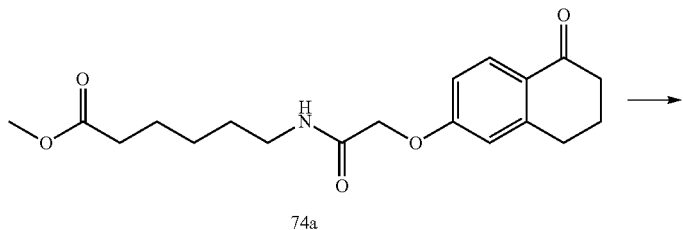

74a

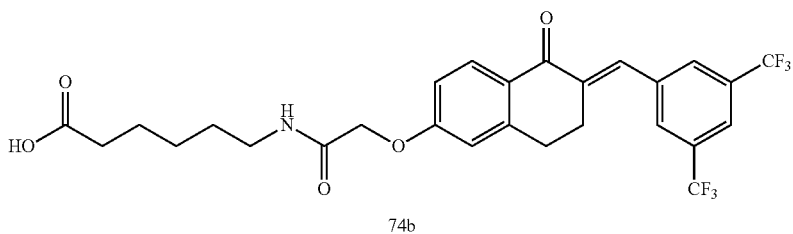

74b

To a solution of Compound 74a (methyl 6-(2-((5-oxo-5,6,7,8-tetrahydronaphthalen-2-yl)oxy)-acetamido)hexanoate) (0.42 g, 1.21 mmol) and 3,5-Bis(trifluoromethyl)benzaldehyde (0.29 g, 1.21 mmol) in MeOH (50 mL) was added 2N NaOH$_{(aq)}$ (1.5 mL, 3.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 74b ((E)-6-(2-((6-(3,5-bis(trifluoromethyl)-benzylidene)-5-oxo-5,6,7,8-tetrahydronaphthalen-2-yl)ox y)acetamido)hexanoic acid) (0.45 g, 0.81 mmol, yield 67%).

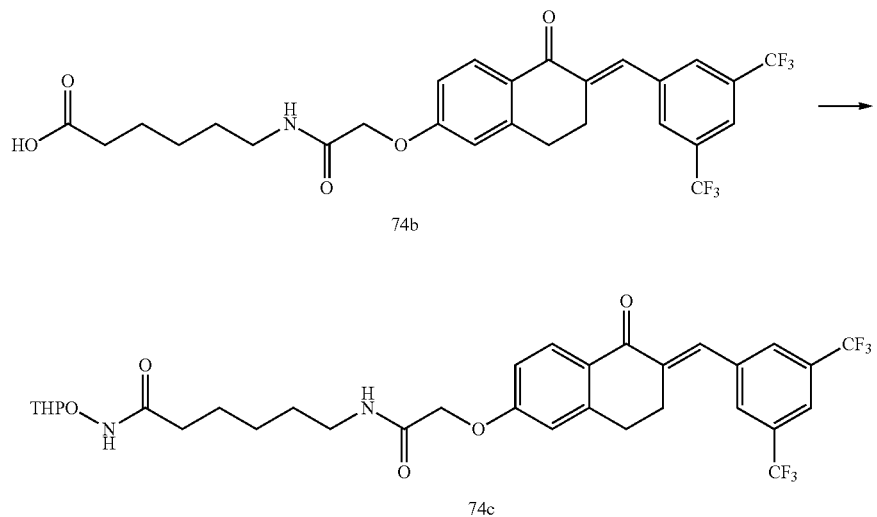

To a solution of Compound 74b ((E)-6-(2-((6-(3,5-bis(trifluoromethyl)-benzylidene)-5-oxo-5,6,7,8-tetrahydronaphthalen-2-yl)ox y)acetamido)hexanoic acid) (0.45 g, 0.81 mmol), NH$_2$OTHP (0.12 g, 1.06 mmol) and DMAP (0.05 g, 0.41 mmol) in CH$_2$Cl$_2$ (50 mL) was added NMM (0.12 g, 1.22 mmol) and EDCI (0.20 g, 1.06 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=2/1 as elution to yield the desired product Compound 74c ((E)-6-(2-((6-(3,5-bis(trifluoromethyl)benzylidene)-5-oxo-5,6,7,8-tetrahydronaphthalen-2-yl)oxy)acetamido)-N-((tetrahydro-2H-pyran-2-yl)oxy)hexanamide) (0.24 g, 0.36 mmol, yield 45%).

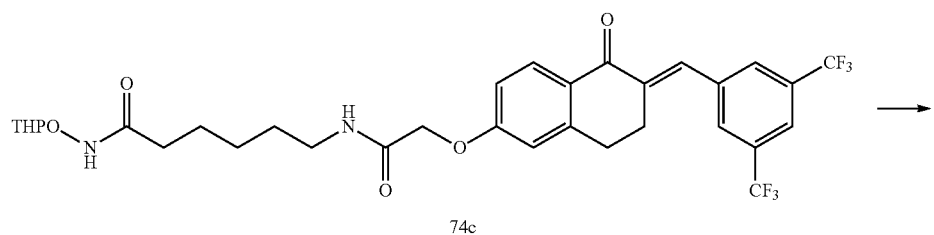

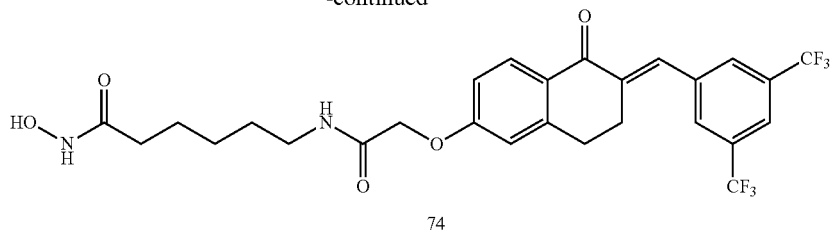

74

To a solution of Compound 74c ((E)-6-(2-((6-(3,5-bis(trifluoromethyl)-benzylidene)-5-oxo-5,6,7,8-tetrahydronaphthalen-2-yl)oxy)acetamido)-N-((tetrahydro-2H-pyran-2-yl)oxy)hexanamide) (0.24 g, 0.36 mmol) in CH$_2$Cl$_2$ (30 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 74 ((E)-6-(2-((6-(3,5-bis(trifluoromethyl)benzylidene)-5-oxo-5,6,7,8-tetra-hydronaphthalen-2-yl)oxy)acetamido)-N-hydroxyhexanamide) (0.02 g, 0.03 mmol, yield 10%).

Compound 74, $^1$H-NMR (500 MHz, CD$_3$OD): δ 8.07-8.06 (d, 1H), 8.02 (s, 2H), 7.97 (s, 1H), 7.82 (s, 1H), 7.05-7.03 (d, 1H), 6.92 (s, 1H), 4.62 (s, 2H), 3.31-3.27 (m, 2H), 3.09-3.00 (m, 4H), 2.09-2.06 (t, 2H), 1.64-1.54 (m, 4H), 1.35-1.33 (m, 2H). ESI-MS m/z calcd for C$_{27}$H$_{26}$F$_6$N$_2$O$_5$ 572.17, found 573 [M+H]$^+$.

Synthesis of Compound 75

Scheme 48

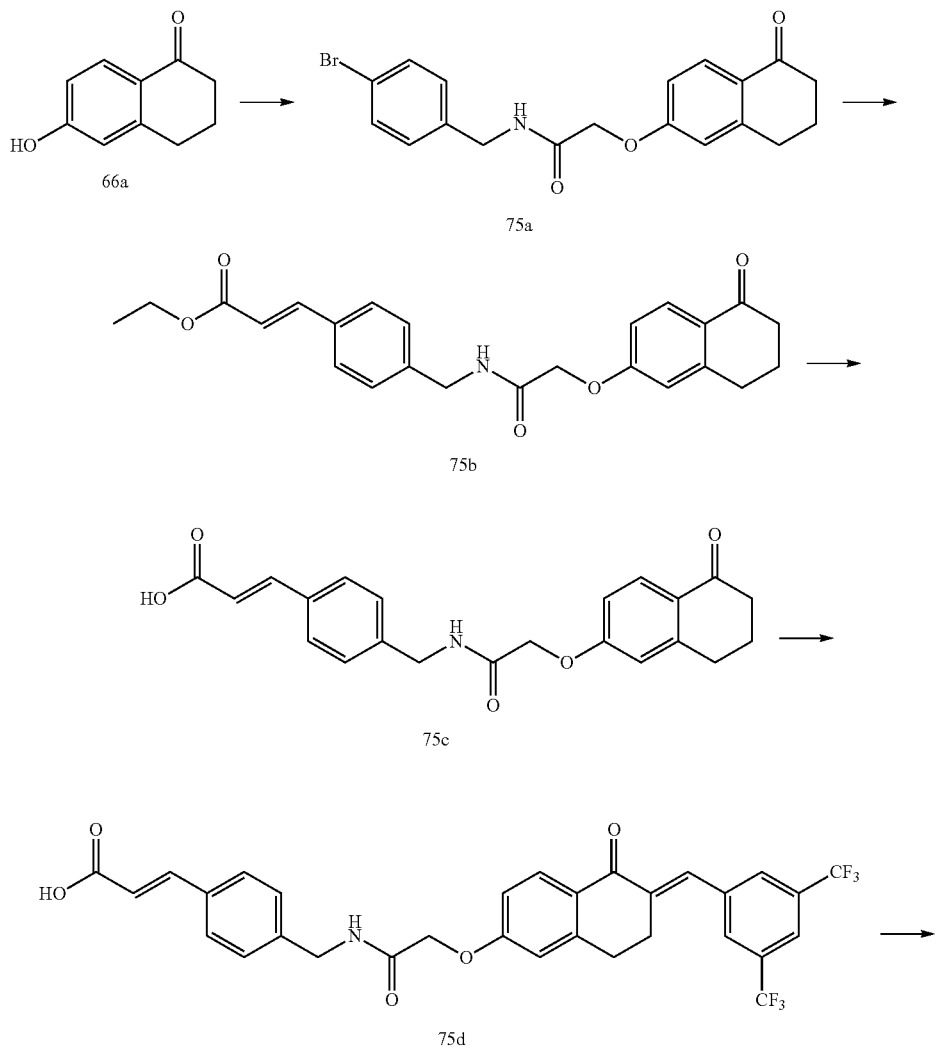

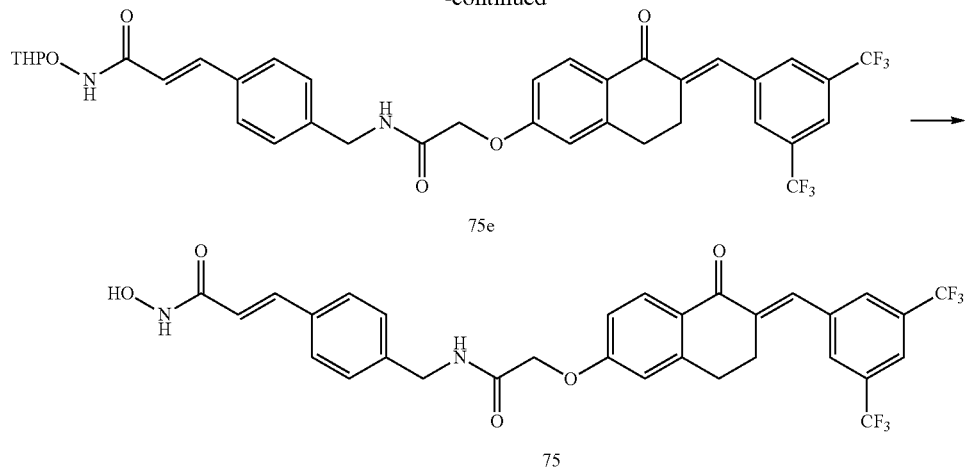

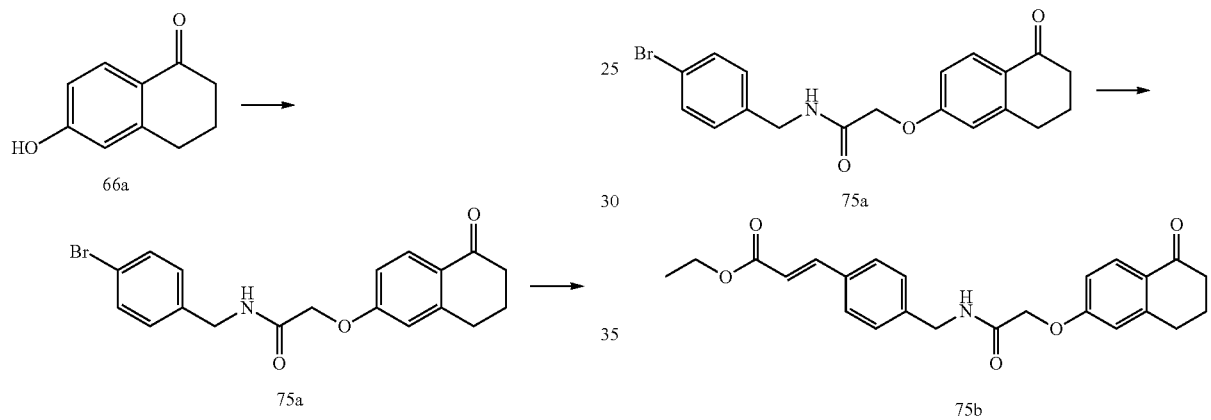

To a solution of Compound 66a (6-Hydroxy-3,4-dihydro-1(2H)-naphthalenone) (0.50 g, 3.08 mmol) and K₂CO₃ (0.85 g, 6.17 mmol) in acetone (50 mL) was added N-(4-bromobenzyl)-2-chloroacetamide (0.81 g, 3.08 mmol) and KI (catalytic amount). After addition, the reaction mixture was refluxed for overnight.

The reaction was monitored by TLC. After reaction was completed, the solvent was removed under reduced pressure. The residue was diluted with sat. NH₄Cl$_{(aq)}$ and extracted with EtOAc. The organic phase was dried with MgSO₄ and concentrated under reduced pressure. The crude product was purified by silica gel column chromatography using ethyl acetate/hexane=1/1 as elution to yield the desired product Compound 75a (N-(4-bromobenzyl)-2-((5-oxo-5,6,7,8-tetrahydronaphthalen-2-yl)oxy)acetamide) (0.97 g, 2.49 mmol, yield 81%).

To a solution of Compound 75a (N-(4-bromobenzyl)-2-((5-oxo-5,6,7,8-tetrahydronaphthalen-2-yl)oxy)acetamide) (0.97 g, 2.49 mmol), triphenylphosphine (0.26 g, 1.00 mmol), ethyl acrylate (0.32 g, 3.24 mmol) in DMF/TEA (50 mL, 1:1) was added Pd(OAc)₂ (0.03 g, 0.12 mmol). After addition, the reaction mixture was heated to 100° C. and stirred for overnight.

The reaction was monitored by TLC. After reaction was completed, the reaction mixture was diluted with sat. NH₄Cl$_{(aq)}$ and extracted with EtOAc. The organic phase was dried with MgSO₄ and concentrated under reduced pressure. The crude product was purified by silica gel column chromatography using ethyl acetate/hexane=1/1 as elution to yield the desired product Compound 75b (ethyl (E)-3-(4-((2-((5-oxo-5,6,7,8-tetrahydronaphthalen-2-yl)oxy)acetamido)methyl)phenyl)acrylate) (0.62 g, 1.51 mmol, yield 61%).

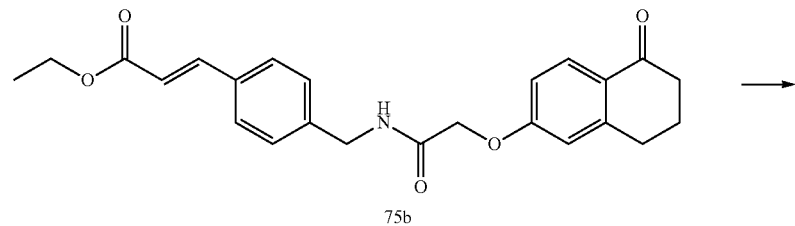

-continued

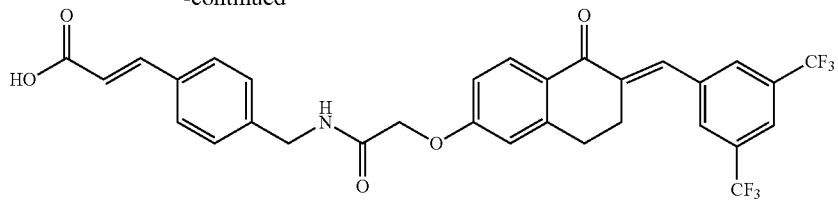

75c

To a solution of Compound 75b (ethyl (E)-3-(4-((2-((5-oxo-5,6,7,8-tetrahydronaphthalen-2-yl)oxy)acetamido)methyl)phenyl)acrylate) (0.62 g, 1.51 mmol) and 3,5-Bis(trifluoromethyl)benzaldehyde (0.40 g, 1.66 mmol) in MeOH (50 mL) was added 2N NaOH$_{(aq)}$ (1.5 mL, 3.00 mmol). After addition, the reaction mixture was stirred for overnight.

The reaction was monitored by TLC. After reaction was completed, the solvent was removed under reduced pressure. The residue was diluted with ice-cold water and acidified with 1N HCl. The precipitated solid was collected by filtration to afford the desired product Compound 75c ((E)-3-(44(24(6-((E)-3,5-bis(trifluoro-methyl)benzylidene)-5-oxo-5,6,7,8-tetrahydronaphthalen-2-yl)oxy)acetamido)-methyl)phenyl)acrylic acid) (0.89 g, 1.47 mmol, yield 97%).

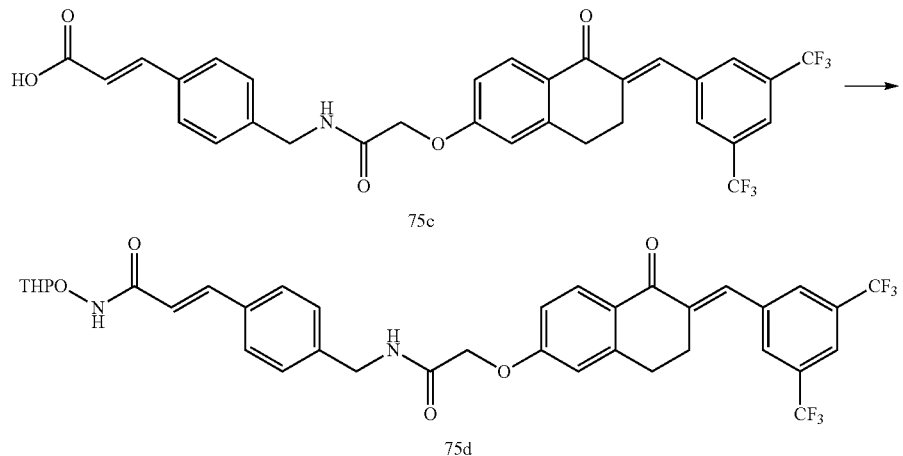

To a solution of Compound 75c ((E)-3-(44(24(6-((E)-3,5-bis(trifluoro-methyl)benzylidene)-5-oxo-5,6,7,8-tetrahydronaphthalen-2-yl)oxy)acetamido)-methyl)phenyl)acrylic acid) (0.89 g, 1.47 mmol), NH$_2$OTHP (0.22 g, 1.91 mmol) and DMAP (0.09 g, 0.74 mmol) in CH$_2$Cl$_2$ (50 mL) was added NMM (0.22 g, 2.21 mmol) and EDCI (0.42 g, 2.21 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=2/1 as elution to yield the desired product Compound 75d ((E)-3-(44(24(6-((E)-3,5-bis(trifluorom-ethyl)benzylidene)-5-oxo-5,6,7,8-tetrahydronaphthalen-2-yl)oxy)acetamido)methyl)phenyl)-N-((tetrahydro-2H-pyran-2-yl)oxy)acrylamide) (0.49 g, 0.69 mmol, yield 47%).

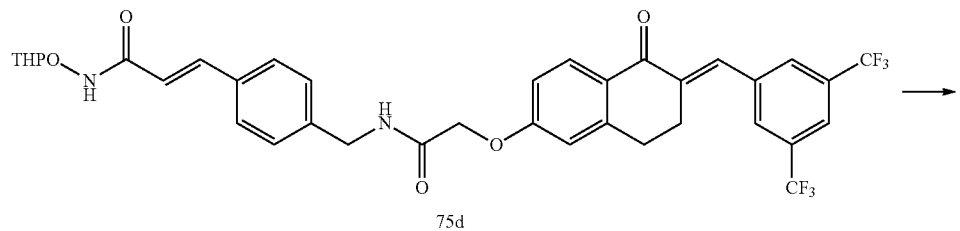

75d

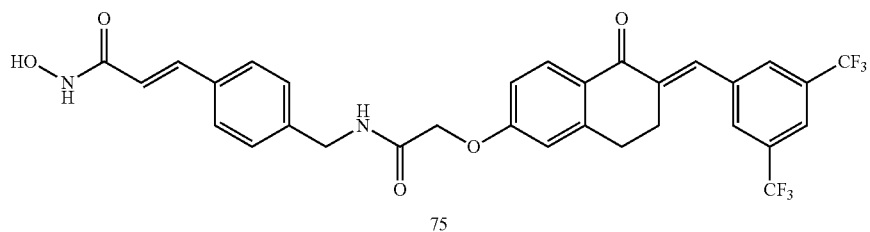

75

To a solution of Compound 75d ((E)-3-(44(24(6-((E)-3,5-bis(trifluoro-methyl)benzylidene)-5-oxo-5,6,7,8-tetrahydronaphthalen-2-yl)oxy)acetamido)-methyl)phenyl)-N-((tetrahydro-2H-pyran-2-yl)oxy)acrylamide) (0.49 g, 0.69 mmol) in CH$_2$Cl$_2$ (50 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 75 ((E)-3-(44(24(6-((E)-3,5-bis(trifluoromethyl) benzylidene)-5-oxo-5,6,7,8-tetrahydronaphthalen-2-yl)oxy) acetamido)methyl)phenyl)-N-hydroxyacrylamide) (0.11 g, 0.18 mmol, yield 26%).

Compound 75, $^1$H-NMR (500 MHz, CD$_3$OD): δ 8.79-8.76 (t, 1H), 8.07-8.05 (d, 1H), 8.02 (s, 2H), 7.97 (s, 1H), 7.82 (s, 1H), 7.56-7.52 (d, 1H), 7.50-7.49 (d, 2H), 7.32-7.30 (d, 2H), 7.04-7.03 (d, 1H), 6.92 (s, 1H), 6.45-6.42 (d, 1H), 4.70 (s, 2H), 4.48 (s, 2H), 3.09-3.06 (t, 2H), 2.98-2.96 (t, 2H). ESI-MS m/z calcd for C$_{31}$H$_{24}$F$_6$N$_2$O$_5$ 618.16, found 619 [M+H]$^+$.

Synthesis of Compounds 76~77

Scheme 49

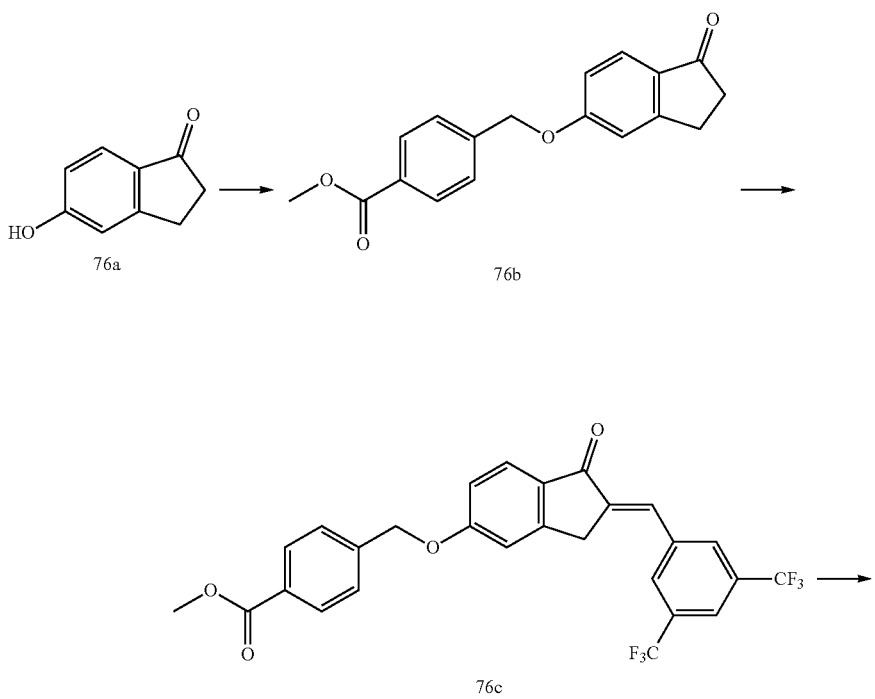

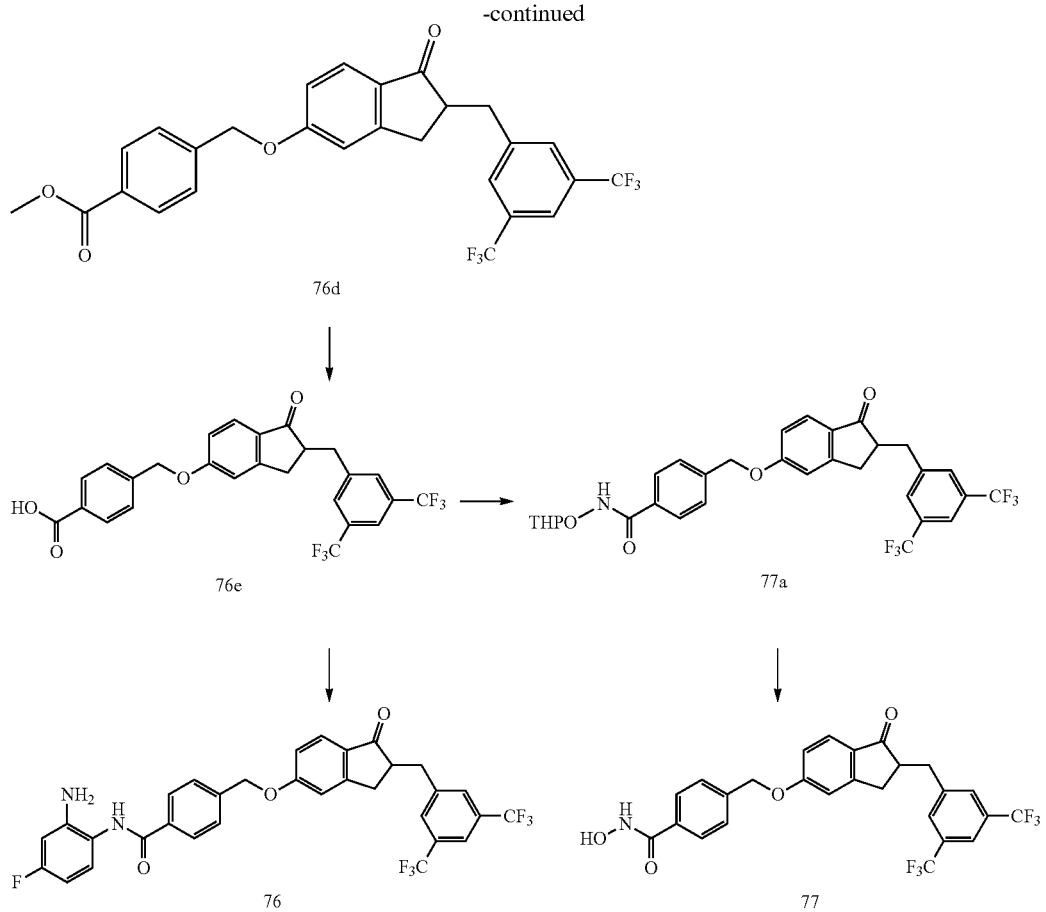

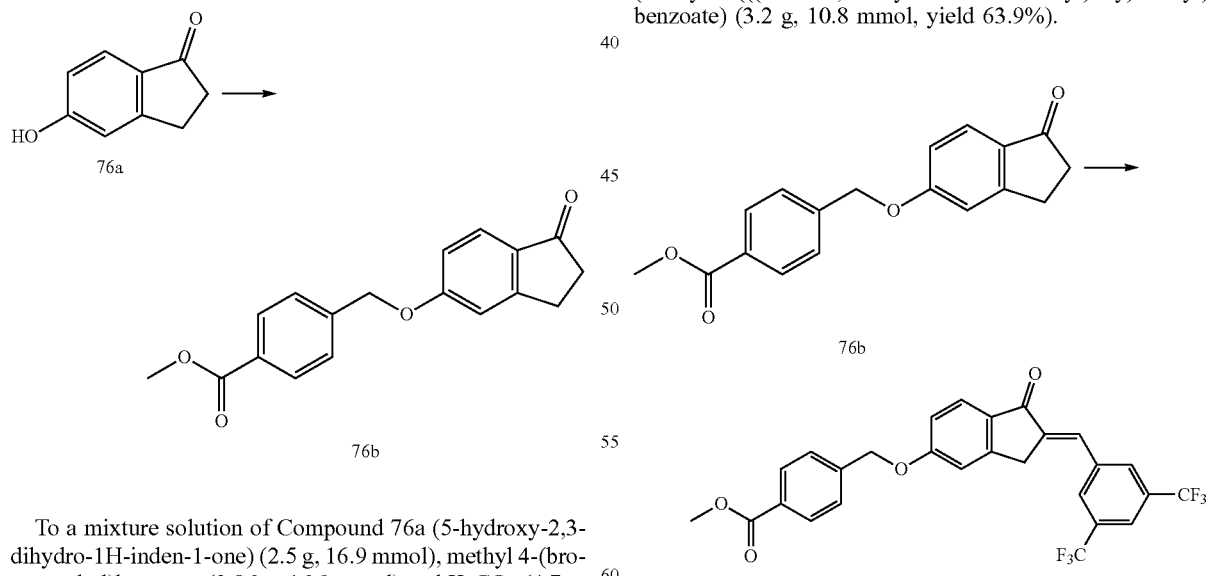

To a mixture solution of Compound 76a (5-hydroxy-2,3-dihydro-1H-inden-1-one) (2.5 g, 16.9 mmol), methyl 4-(bromomethyl)benzoate (3.86 g, 16.9 mmol) and K$_2$CO$_3$ (4.7 g, 33.8 mmol) in ACN (50 mL) was stirred at 50° C. for 16 hours.

After cooling to RT, DCM (50 mL) was added and the mixture was filtered through celite. The filtrate was concentrated and the resulting material was washed with ether to provide the product as a solid product Compound 76b (methyl 4-(((1-oxo-2,3-dihydro-1H-inden-5-yl)oxy)methyl)benzoate) (3.2 g, 10.8 mmol, yield 63.9%).

A 2N NaOH solution (1.5 mL) was added to a mixture of Compound 76b (methyl 4-(((1-oxo-2,3-dihydro-1H-inden-5-yl)oxy)methyl)benzoate) (0.5 g, 1.69 mmol) and 3,5-bis(trifluoromethyl)benzaldehyde (0.45 g, 1.86 mmol) in MeOH (40 mL) at RT and stirred for 16 hours.

The reaction mixture was concentrated to remove the organic solvent. The residue was washed with H₂O and Ether. The white solid was dried in vacuo to provide the product Compound 76c (methyl (E)-4-(((2-(3,5-bis(trifluoromethyl)benzylidene)-1-oxo-2,3-dihydro-1H-inden-5-yl)oxy)methyl)benzoate) (0.72 g, yield 82%).

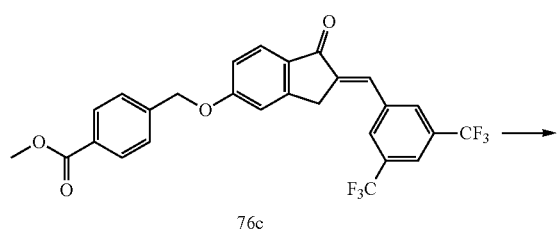
76c

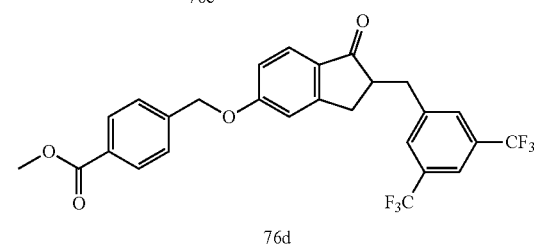
76d

A mixture of Compound 76c (methyl (E)-4-(((2-(3,5-bis(trifluoromethyl)-benzylidene)-1-oxo-2,3-dihydro-1H-inden-5-yl)oxy)methyl)benzoate) (657.0 mg, 1.26 mmol), Zn dust (413.3 mg, 6.3 mmol) and NH₄Cl (675.9 mg, 12.6 mmol) in DMSO (10 mL) were stirred for 0.5 hour.

The mixture was extracted with DCM and brine. The organic layer was dried over MgSO₄ and concentrated in vacuo to give the crude material. The resulting residue was washed with ether to provide the white solid product Compound 76d (methyl 4-(((2-(3,5-bis(trifluoromethyl)benzyl)-1-oxo-2,3-dihydro-1H-inden-5-yl)-oxy)methyl)benzoate) (0.6 g, yield 91%).

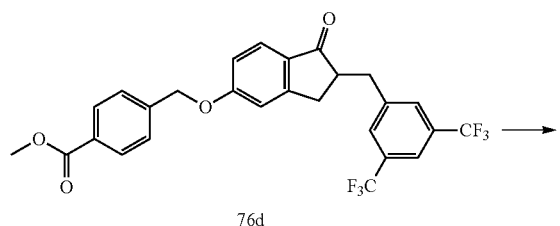
76d

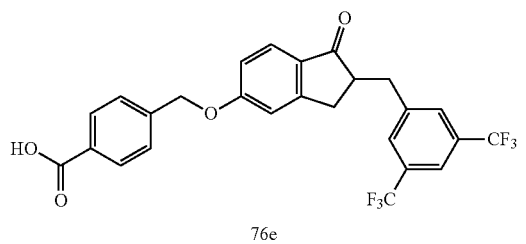
76e

To a solution of Compound 76d (methyl 4-(((2-(3,5-bis(trifluoromethyl)-benzyl)-1-oxo-2,3-dihydro-1H-inden-5-yl)-oxy)methyl)benzoate) (100.0 mg, 0.19 mmol) in MeOH (5 mL) was added 2N NaOH solution (0.5 mL) at RT and stirred for overnight.

The reaction mixture was concentrated to remove the organic solvent. The residue was diluted with water and acidified to pH=6 with 2N HCl$_{(aq)}$ and extracted with DCM. The organic layer was dried over MgSO₄ and concentrated in vacuo to give the product Compound 76e (4-(((2-(3,5-bis(trifluoromethyl)benzyl)-1-oxo-2,3-dihydro-1H-inden-5-yl)oxy)methyl)benzoic acid) (52.1 mg, yield 54%).

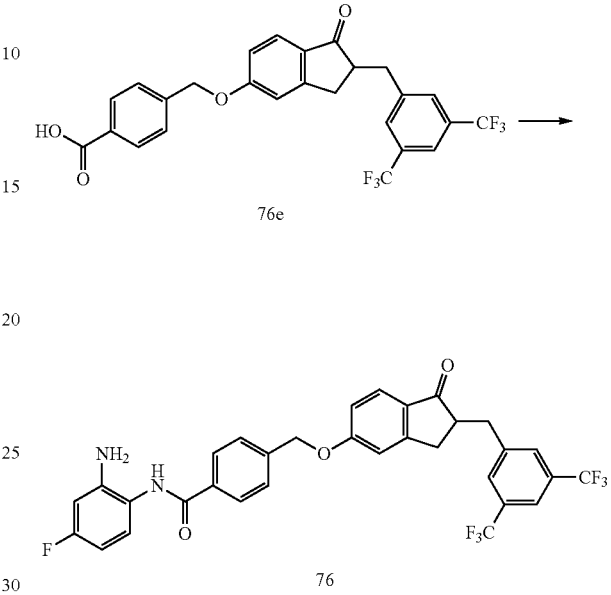
76e

76

To a stirred solution of 4-Fluoro-1,2-phenylenediamine (23.8 mg, 0.19 mmol) and NMM (0.04 mL, 0.32 mmol) in DCM (5 mL) was added Compound 76e (4-(((2-(3,5-bis(trifluoromethyl)benzyl)-1-oxo-2,3-dihydro-1H-inden-5-yl)oxy)methyl)-benzoic acid) (80.0 mg, 0.16 mmol) in one portion, followed by addition of HATU (66.9 mg, 0.18 mmol) in one portion at 0° C. and stirred for 2 hours.

The mixture was extracted with NH₄Cl(aq.) and brine. The organic layer was dried over MgSO₄ and concentrated in vacuo to give the crude material. The resulting residue was washed with ether to provide the product Compound 76 (N-(2-amino-4-fluorophenyl)-4-(((2-(3,5-bis(trifluoromethyl)benzyl)-1-oxo-2,3-dihydro-1H-inden-5-yl)oxy)methyl)benzamide) (15.0 mg, yield 15%).

Compound 76, ¹H-NMR (500 MHz, d₆-DMSO): δ 9.67 (s, 1H), 8.17 (s, 2H), 8.05-8.01 (d, 2H), 7.94 (s, 1H), 7.77-7.72 (s, 1H), 7.63-7.61 (d, 2H), 7.17 (s, 1H), 7.12-7.01 (m, 1H), 6.55-6.52 (d, 1H), 6.37-6.34 (t, 1H), 5.31 (s, 2H), 5.22 (s, 2H), 3.19-3.16 (m, 1H), 3.13-3.06 (m, 2H), 2.94-2.89 (m, 1H), 2.80-2.69 (m, 1H). ESI-MS m/z calcd for C₃₂H₂₃F₇N₂O₃ 616.15, found 617 [M+1-1]⁺.

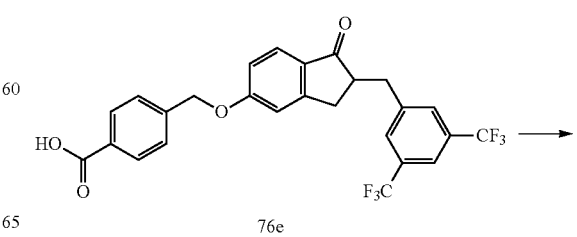
76e

-continued

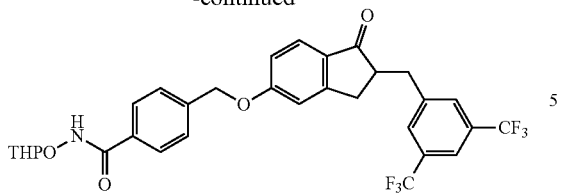

77a

To a stirred solution of 0-(Tetrahydro-2H-pyran-2-yl) hydroxylamine (22.1 mg, 0.19 mmol) and DMAP (28.8 mg, 2.24 mmol) in DCM (6 mL) was added Compound 76e (4-(((2-(3,5-bis(trifluoromethyl)benzyl)-1-oxo-2,3-dihydro-1H-inden-5-yl)oxy)methyl)-benzoic acid) (80.0 mg, 0.16 mmol) in one portion, followed by addition of EDCI (36.4 mg, 0.19 mmol) in one portion at RT. The resulting mixture was stirred at RT for overnight.

After which time it was washed successively with NaHCO$_3$(aq.) and brine. The organic layer was dried over MgSO$_4$ and concentrated in vacuo to give the crude material. The resulting residue was purified by silica gel column chromatography (EtOAc:Hex.=1:1) to provide the product Compound 77a (4-(((2-(3,5-bis(trifluoromethyl)benzyl)-1-oxo-2,3-dihydro-1H-inden-5-yl)oxy)methyl)-N-((tetra hydro-2H-pyran-2-yl)oxy)benzamide) (80.0 mg, yield 82%).

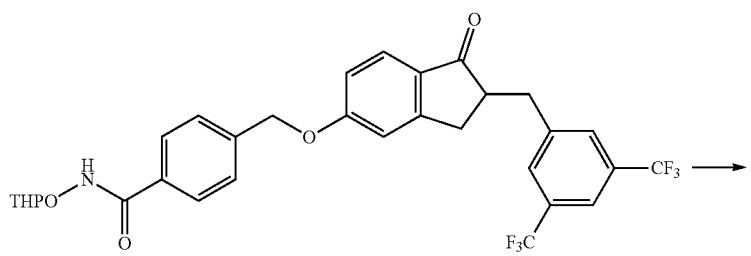

77a

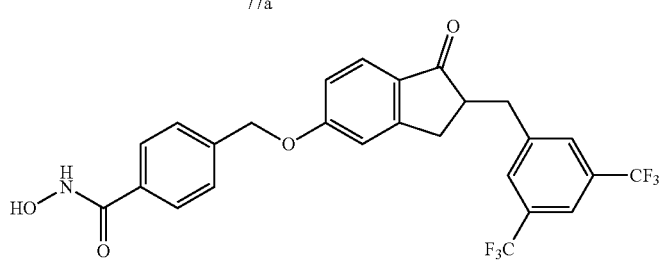

77

A solution of Compound 77a (4-(((2-(3,5-bis(trifluoromethyl)benzyl)-1-oxo-2,3-dihydro-1H-inden-5-yl)oxy) methyl)-N-((tetra hydro-2H-pyran-2-yl)oxy)benzamide) (80.0 mg, 0.13 mmol) in diethyl ether (2 mL) was added 2N HCl (2.0 mL, in diethyl ether) at 0° C. and stirred for 1 hour.

The resulting crude purified by flash chromatography (EtOAc:Hex=2:1) to provide the product Compound 77 (4-(((2-(3,5-bis(trifluoromethyl)benzyl)-1-oxo-2,3-dihydro-1H-inden-5-yl)oxy)methyl)-N-hydroxybenzamide) (11.0 mg, yield 16%).

Compound 77, $^1$H-NMR (500 MHz, d$_6$-DMSO): δ 11.21 (s, 1H), 9.04 (s, 1H), 8.09 (s, 2H), 7.94 (s, 1H), 7.78-7.76 (d, 2H), 7.62-7.60 (d, 1H), 7.52-7.51 (d, 2H), 7.16 (s, 1H), 7.06-7.05 (d, 1H), 5.26 (s, 2H), 3.36-3.33 (m, 1H), 3.19-3.18 (m, 1H), 3.16-3.14 (m, 1H), 2.93-2.91 (m, 1H), 2.80-2.76 (m, 1H). ESI-MS m/z calcd for C$_{26}$H$_{19}$F$_6$NO$_4$ 523.12, found 524 [M+H]$^+$.

Synthesis of Compounds 78~79

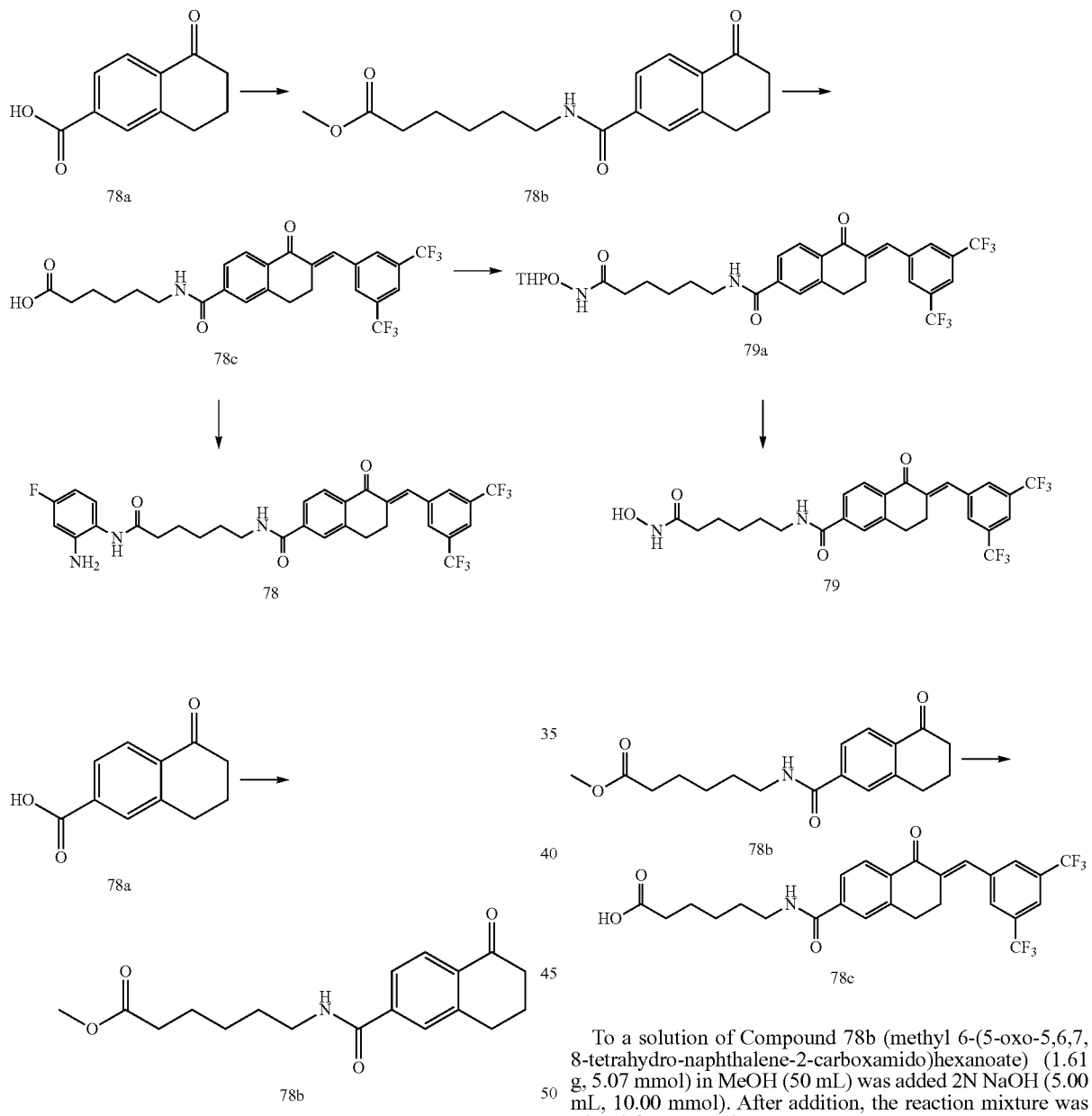

To a solution of Compound 78a (5-Oxo-5,6,7,8-tetrahydro-2-naphthalene-carboxylic acid) (1.00 g, 5.26 mmol), methyl 6-aminohexanoate hydrogen chloride (1.15 g, 6.31 mmol) and DMAP (0.32 g, 2.63 mmol) in DCM (100 mL) was added DIPEA (2.04 g, 15.77 mmol) and EDCI (1.21 g, 6.31 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo to give the desired product Compound 78b (methyl 6-(5-oxo-5,6,7,8-tetrahydro-naphthalene-2-carboxamido)hexanoate) (1.61 g, 5.07 mmol, yield 96%).

To a solution of Compound 78b (methyl 6-(5-oxo-5,6,7,8-tetrahydro-naphthalene-2-carboxamido)hexanoate) (1.61 g, 5.07 mmol) in MeOH (50 mL) was added 2N NaOH (5.00 mL, 10.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 30% MeOH/water to give the intermedia product. It was then treated with 3,5-Bis(trifluoromethyl)-benzaldehyde (1.44 g, 5.93 mmol) in MeOH (50 mL) was added 2N NaOH (5.00 mL, 10.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 30% MeOH/water to get Compound 78c ((E)-6-(6-(3,5-bis(trifluoromethyl)benzylidene)-5-oxo-5,6,7,8-tetrahydro-naphthalene-2-carboxamido)hexanoic acid) (2.44 g, 4.63 mmol, yield 94%).

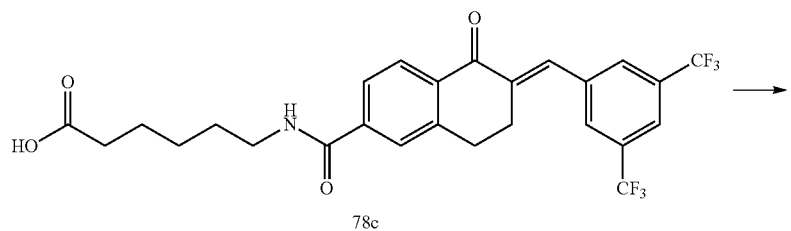

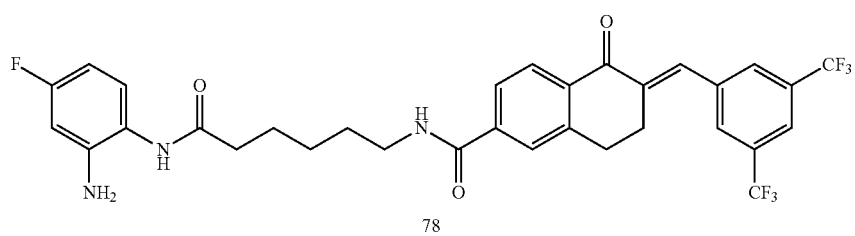

To a solution of Compound 78c ((E)-6-(6-(3,5-bis(trifluoromethyl)-benzylidene)-5-oxo-5,6,7,8-tetrahydro-naphthalene-2-carboxamido)hexanoic acid) (1.48 g, 2.80 mmol), 4-fluoro-1,2-phenylenediamine (0.35 g, 2.80 mmol) and DMAP (0.34 g, 2.80 mmol) in THF (100 mL) was added NMM (0.28 g, 2.80 mmol) and EDCI (0.64 g, 3.36 mmol) at 0° C. After addition, the reaction mixture was warmed to room temperature and stirred for 6 hours.

The reaction was monitored by TLC. After reaction was completed, the solvent was removed under reduced pressure. The residue was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/hexane=2/1 as elution to yield the desired product Compound 78 ((E)-N-(64(2-amino-4-fluorophenyl)amino)-6-oxohexyl)-6-(3,5-bis(trifluoromethyl)-benzylidene)-5-oxo-5,6,7,8-tetrahydronaphthalene-2-carboxamide) (0.05 g, 0.08 mmol, yield 3%).

Compound 78, $^1$H-NMR (500 MHz, $CD_3OD$): δ 8.13-8.11 (d, 1H), 8.05 (s, 2H), 7.99 (s, 1H), 7.88 (s, 1H), 7.80-7.76 (m, 2H), 7.01-6.98 (m, 1H), 6.53-6.51 (m, 1H), 6.35-6.31 (m, 1H), 3.45-3.42 (t, 2H), 3.12-3.03 (m, 4H), 2.45-2.42 (t, 2H), 1.80-1.68 (m, 4H), 1.52-1.50 (m, 2H). ESI-MS m/z calcd for $C_{32}H_{28}F_7N_3O_3$ 635.20, found 636 $[M+H]^+$.

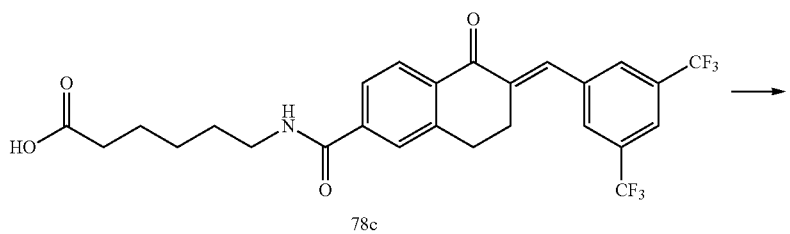

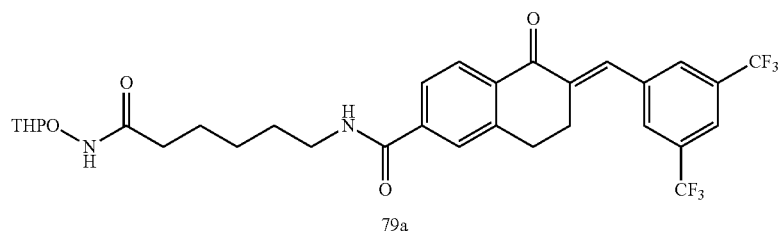

To a solution of Compound 78c ((E)-6-(6-(3,5-bis(trifluoromethyl)-benzylidene)-5-oxo-5,6,7,8-tetrahydro-naphthalene-2-carboxamido)hexanoic acid) (0.45 g, 0.85 mmol), NH₂OTHP (0.15 g, 1.28 mmol) and DMAP (0.05 g, 0.43 mmol) in CH₂Cl₂ (50 mL) was added NMM (0.13 g, 1.28 mmol) and EDCI (0.25 g, 1.28 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO₄ and concentrated under reduced pressure. The crude product was purified by silica gel column chromatography using ethyl acetate/hexane=2/1 as elution to yield the desired product Compound 79a ((E)-6-(3,5-bis(trifluoromethyl)benzylidene)-5-oxo-N-(6-oxo-6-(((tetrahydro-2H-pyran-2-yl)oxy)amino)hexyl)-5,6,7,8-tetrahydronaphthalene-2-carboxamide) (0.17 g, 0.27 mmol, yield 32%).

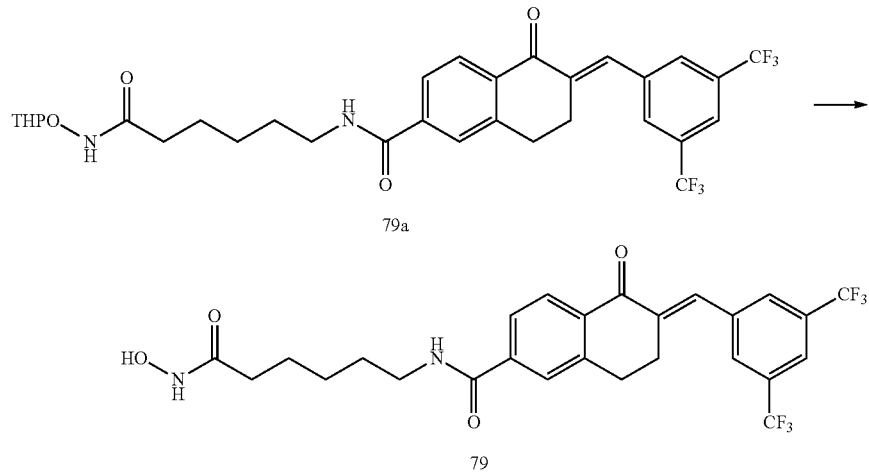

To a solution of Compound 79a ((E)-6-(3,5-bis(trifluoromethyl)benzylidene)-5-oxo-N-(6-oxo-6-(((tetrahydro-2H-pyran-2-yl)-ox y)amino)hexyl)-5,6,7,8-tetrahydronaphthalene-2-carboxamide) (0.17 g, 0.27 mmol) in CH₂Cl₂ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 79 ((E)-6-(3,5-bis(trifluoromethyl)benzylidene)-N-(6-(hydroxyamino)-6-oxohexyl)-5-oxo-5,6,7,8-tetrahydronaphthalene-2-carboxamide) (0.04 g, 0.07 mmol, yield 27%).

Compound 79, ¹H-NMR (500 MHz, CD₃OD): δ 8.14-8.12 (d, 1H), 8.05 (s, 2H), 7.99 (s, 1H), 7.88 (s, 1H), 7.80-7.78 (m, 2H), 3.40-3.38 (t, 2H), 3.13-3.07 (m, 4H), 2.13-2.10 (t, 2H), 1.70-1.62 (m, 4H), 1.45-1.40 (m, 2H). ESI-MS m/z calcd for $C_{26}H_{24}F_6N_2O_4$ 542.16, found 543 [M+1-1]⁺.

Synthesis of Compounds 80~81

Scheme 51

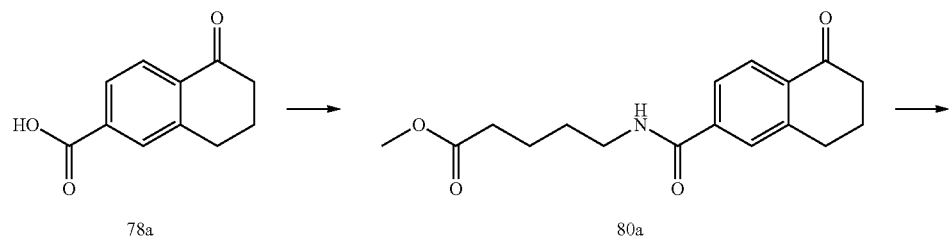

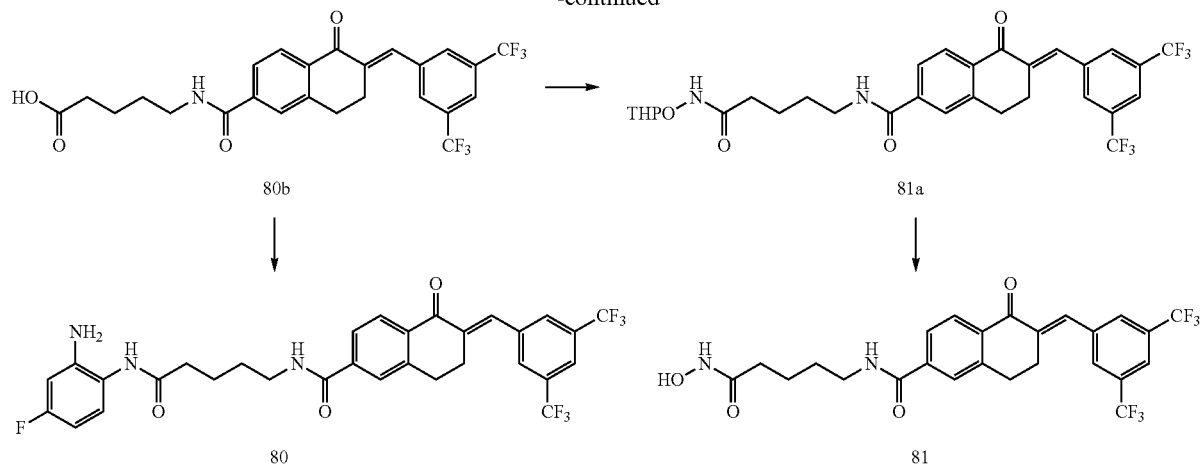

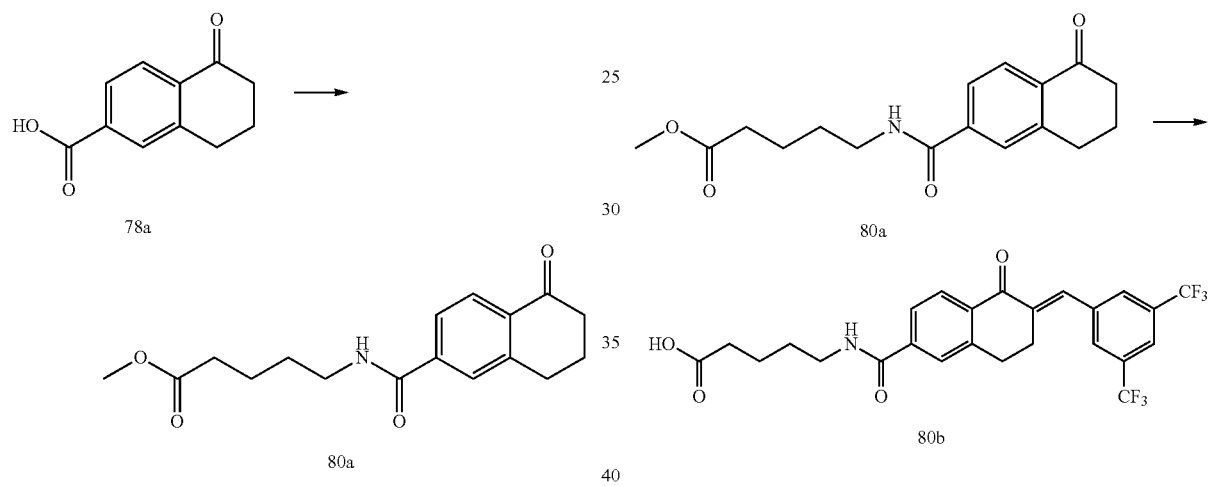

To a solution of Compound 78a (5-Oxo-5,6,7,8-tetrahydro-2-naphthalene-carboxylic acid) (1.00 g, 5.26 mmol), methyl 5-aminopentanoate hydrogen chloride (0.97 g, 5.79 mmol) and DMAP (0.32 g, 2.63 mmol) in DCM (100 mL) was added DIPEA (2.04 g, 15.77 mmol) and EDCI (1.21 g, 6.31 mmol) at 0° C. After addition, the reaction mixture was slowly warmed to RT and stirred for overnight.

After reaction was completed, the solvent was removed under reduced pressure. The residual was diluted with EtOAc and washed with Sat. NH₄Cl. The combined organic layers were washed with brine and dried over MgSO₄ and concentrated in vacuo to give the desired product Compound 80a (methyl 5-(5-oxo-5,6,7,8-tetrahydro-naphthalene-2-carboxamido)pentanoate) (1.37 g, 4.53 mmol, yield 86%).

To a solution of Compound 80a (methyl 5-(5-oxo-5,6,7,8-tetrahydro-naphthalene-2-carboxamido)pentanoate) (1.37 g, 4.53 mmol) and 3,5-Bis-(trifluoromethyl)benzaldehyde (1.27 g, 5.25 mmol) in MeOH (50 mL) was added 2N NaOH (5.00 mL, 10.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 30% MeOH/water to get Compound 80b ((E)-5-(6-(3,5-bis(trifluoromethyl)benzylidene)-5-oxo-5,6,7,8-tetrahydro-naphthalene-2-carboxamido)pentanoic acid) (1.72 g, 3.35 mmol, yield 74%).

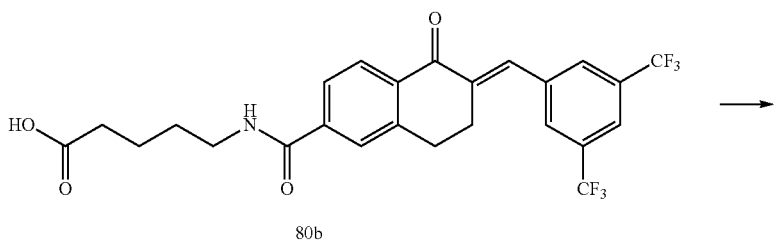

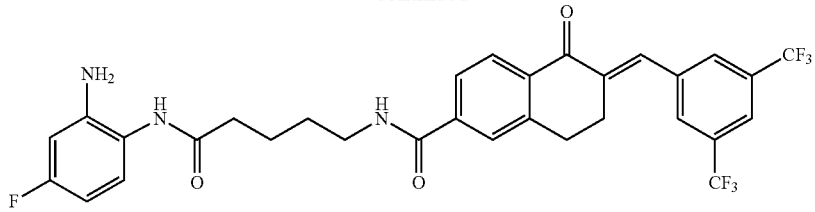

80

To a solution of Compound 80b ((E)-5-(6-(3,5-bis(trifluoromethyl)-benzylidene)-5-oxo-5,6,7,8-tetrahydro-naphthalene-2-carboxamido)pentanoic acid) (0.20 g, 0.39 mmol), 4-fluoro-1,2-phenylenediamine (0.05 g, 0.39 mmol) and DMAP (0.05 g, 0.39 mmol) in THF (30 mL) was added NMM (0.04 g, 0.39 mmol) and EDCI (0.10 g, 0.51 mmol) at 0° C. After addition, the reaction mixture was warmed to room temperature and stirred for 6 hours.

The reaction was monitored by TLC. After reaction was completed, the solvent was removed under reduced pressure. The residue was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/hexane=2/1 as elution to yield the desired product Compound 80 ((E)-N-(54(2-amino-4-fluorophenyl)amino)-5-oxopentyl)-6-(3,5-bis(trifluoromethyl)-benzylidene)-5-oxo-5,6,7,8-tetrahydronaphthalene-2-carboxamide) (0.10 g, 0.16 mmol, yield 42%).

Compound 80, $^1$H-NMR (500 MHz, $CD_3OD$): δ 9.02 (s, 1H), 8.68-8.66 (t, 1H), 8.21 (s, 2H), 8.14 (s, 1H), 8.05-8.04 (d, 1H), 7.85-7.84 (m, 3H), 7.11-7.08 (t, 1H), 6.49-6.46 (dd, 1H), 6.31-6.27 (td, 1H), 5.13 (s, 2H), 3.09-3.01 (m, 4H), 2.36-2.33 (t, 2H), 1.66-1.57 (m, 4H). ESI-MS m/z calcd for $C_{31}H_{26}F_7N_3O_3$ 621.19, found 622 $[M+H]^+$.

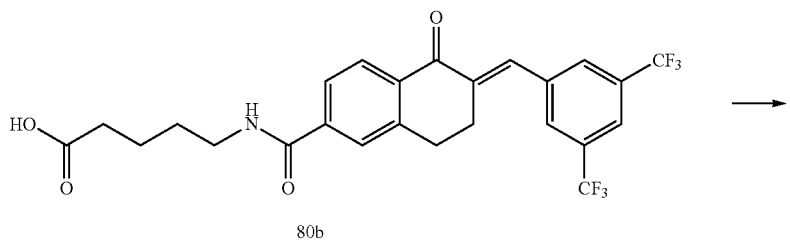

80b

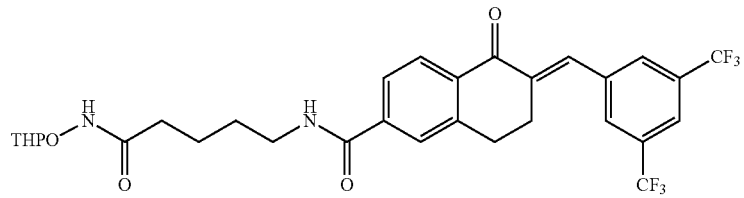

81a

To a solution of Compound 80b ((E)-5-(6-(3,5-bis(trifluoromethyl)-benzylidene)-5-oxo-5,6,7,8-tetrahydro-naphthalene-2-carboxamido)pentanoic acid) (0.20 g, 0.39 mmol), NH$_2$OTHP (0.06 g, 0.51 mmol) and DMAP (0.02 g, 0.20 mmol) in CH$_2$Cl$_2$ (30 mL) was added NMM (0.06 g, 0.59 mmol) and EDCI (0.11 g, 0.59 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/hexane=2/1 as elution to yield the desired product Compound 81a ((E)-6-(3,5-bis(trifluoromethyl)benzylidene)-5-oxo-N-(5-oxo-5-(((tetrahydro-2H-pyran-2-yl)oxy)amino)pentyl)-5,6,7,8-tetrahydronaphthalene-2-carboxamide) (0.11 g, 0.18 mmol, yield 47%).

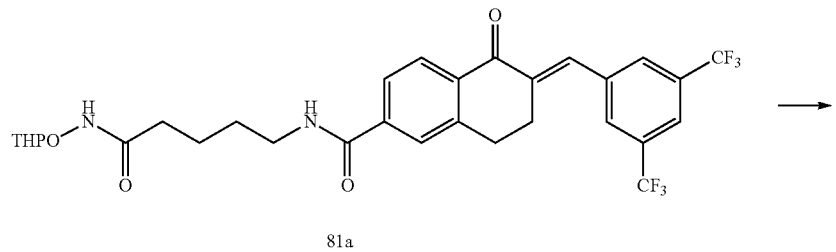

81a

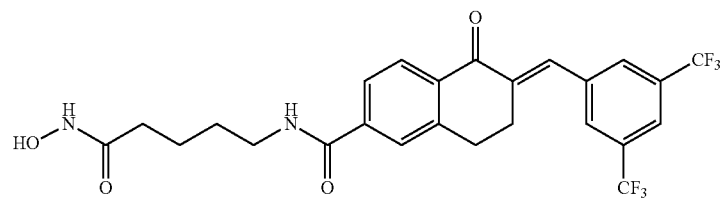

81

To a solution of Compound 81a ((E)-6-(3,5-bis(trifluoromethyl)benzylidene)-5-oxo-N-(5-oxo-5-(((tetrahydro-2H-pyran-2-yl)oxy)amino)pentyl)-5,6,7,8-tetrahydro-naphthalene-2-carboxamide) (0.11 g, 0.18 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 81 ((E)-6-(3,5-bis(trifluoromethyl)benzylidene)-N-(5-(hydroxyamino)-5-oxopentyl)-5-oxo-5,6,7,8-tetrahydronaphthalene-2-carboxamide) (0.01 g, 0.02 mmol, yield 13%).

Compound 81, $^1$H-NMR (500 MHz, CD$_3$OD): δ 8.14-8.12 (d, 1H), 8.05 (s, 2H), 7.99 (s, 1H), 7.88 (s, 1H), 7.80-7.78 (m, 2H), 3.43-3.40 (t, 2H), 3.15-3.12 (t, 2H), 3.08-3.06 (t, 2H), 2.17-2.14 (t, 2H), 1.73-1.64 (m, 4H). ESI-MS m/z calcd for C$_{25}$H$_{22}$F$_6$N$_2$O$_4$ 528.15, found 529 [M+1-1]$^+$.

Synthesis of Compounds 82~83

Scheme 52

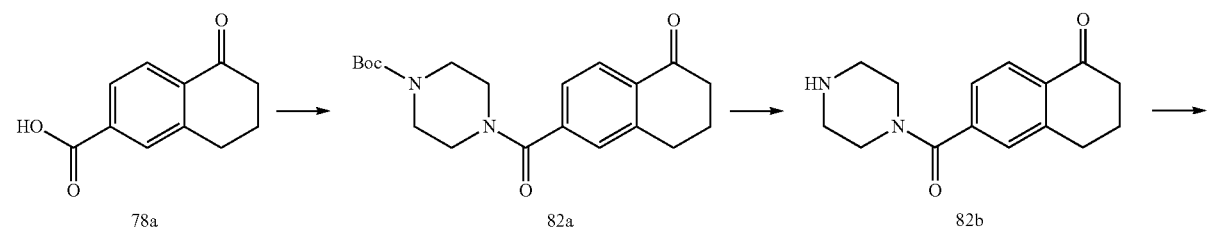

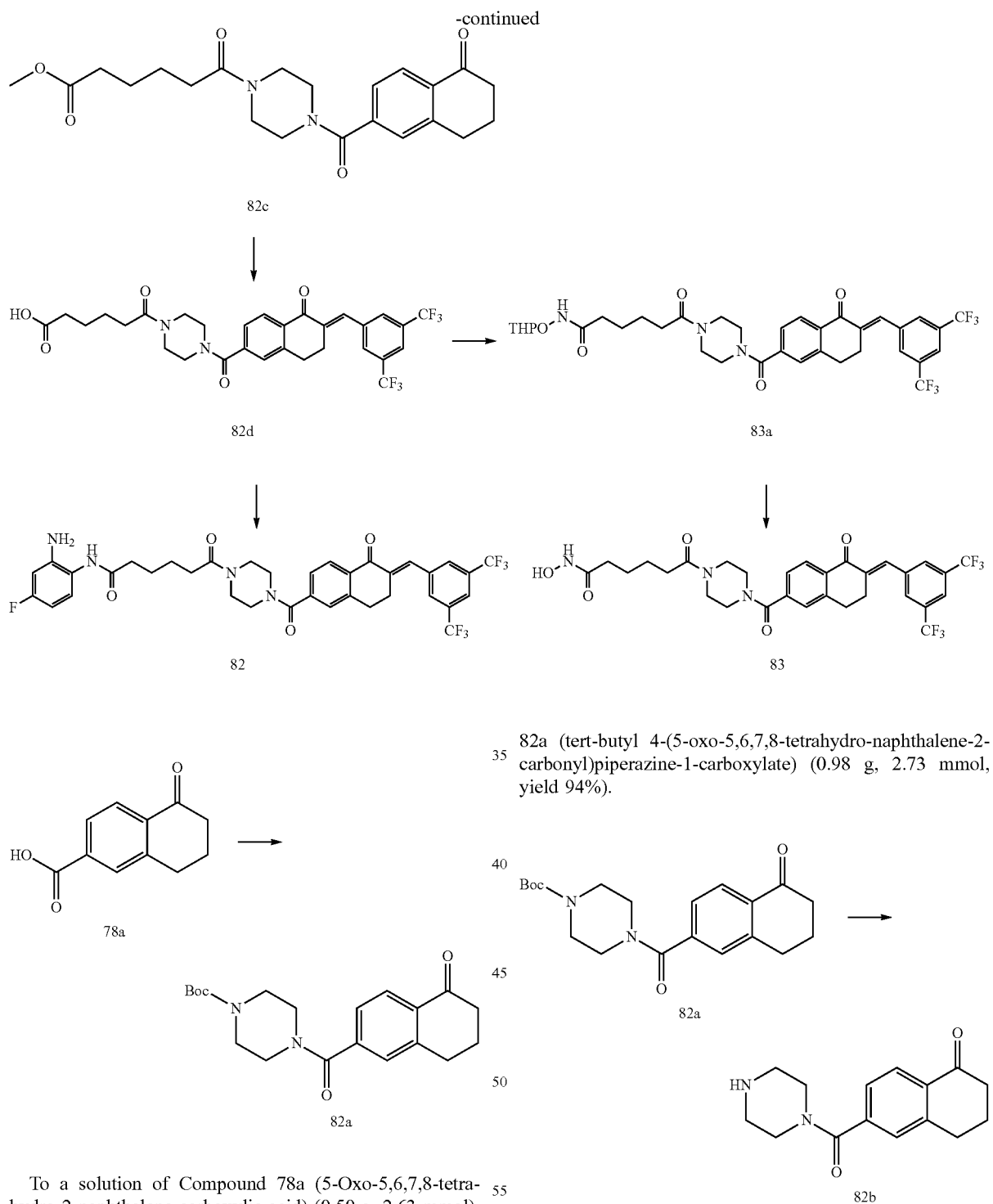

To a solution of Compound 78a (5-Oxo-5,6,7,8-tetrahydro-2-naphthalene-carboxylic acid) (0.50 g, 2.63 mmol), 1-Boc-piperazine (0.54 g, 2.89 mmol) and DMAP (0.16 g, 1.31 mmol) in DCM (50 mL) was added DIPEA (0.51 g, 3.94 mmol) and EDCI (0.66 g, 3.42 mmol) at 0° C. After addition, the reaction mixture was slowly warmed to RT and stirred for overnight.

After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo to give the desired product Compound 82a (tert-butyl 4-(5-oxo-5,6,7,8-tetrahydro-naphthalene-2-carbonyl)piperazine-1-carboxylate) (0.98 g, 2.73 mmol, yield 94%).

To a solution of Compound 82a (tert-butyl 4-(5-oxo-5,6,7,8-tetrahydro-naphthalene-2-carbonyl)piperazine-1-carboxylate) (0.98 g, 2.73 mmol) in CH$_2$Cl$_2$ (20 mL) was added 2N HCl (excess, in diethyl ether). After addition, the reaction mixture was stirred for overnight.

The reaction was monitored by TLC. After reaction was completed, the solvent was removed under reduced pressure to afford the intermediate Compound 82b (6-(piperazine-1-carbonyl)-3,4-dihydronaphthalen-1(2H)-one hydrogen chloride).

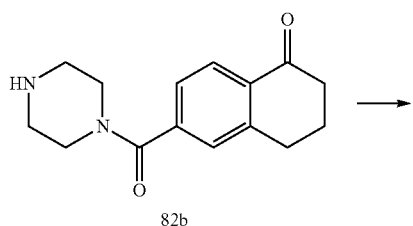

82b

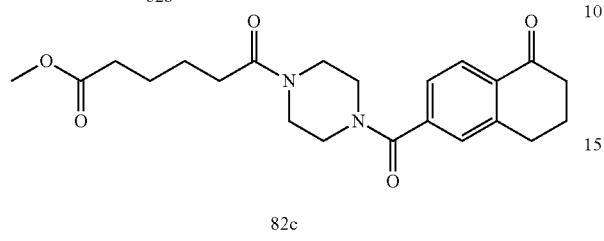

82c

And then, to the solution of Compound 82b (6-(piperazine-1-carbonyl)-3,4-dihydronaphthalen-1(2H)-one hydrogen chloride), 6-methoxy-6-oxohexanoic acid (0.57 g, 3.54 mmol) and DMAP (0.43 g, 3.54 mmol) in CH$_2$Cl$_2$ (30 mL) was added DIPEA (1.06 g, 8.18 mmol) and EDCI (0.78 g, 4.09 mmol) at 0° C. After addition, the reaction mixture was slowly warmed to RT and stirred for overnight.

The reaction was monitored by TLC. After reaction was completed, the solvent was removed under reduced pressure. The residual was diluted with EtOAc and washed with Sat. NH$_4$Cl. The combined organic layers were washed with brine and dried over MgSO$_4$ and concentrated in vacuo to give the desired product Compound 82c (methyl 6-oxo-6-(4-(5-oxo-5,6,7,8-tetrahydronaphthalene-2-carbonyl)piperazin-1-yl)hexanoate) (1.01 g, 2.52 mmol, yield 92%).

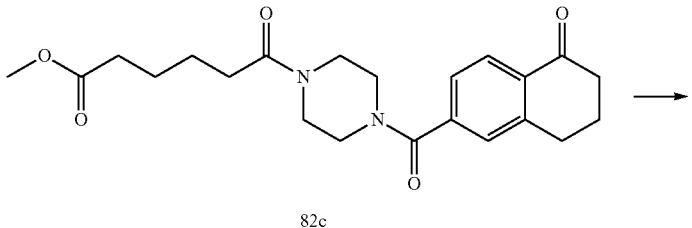

82c

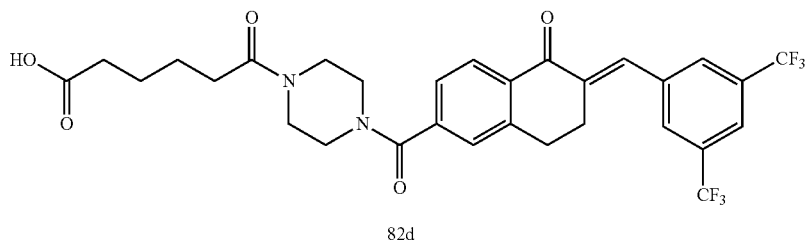

82d

To a solution of Compound 82c (methyl 6-oxo-6-(4-(5-oxo-5,6,7,8-tetrahydronaphthalene-2-carbonyl)piperazin-1-yl)hexanoate) (1.01 g, 2.52 mmol) and 3,5-Bis(trifluoromethyl)benzaldehyde (0.61 g, 2.52 mmol) in MeOH (50 mL) was added 2N NaOH (5.00 mL, 10.00 mmol). After addition, the reaction mixture was stirred for overnight.

After reaction was completed, the solvent was removed under reduced pressure. The residual was diluted with ice-cold water and acidified with 1N HCl. The precipitated solid was collected by filtration and washed with 30% MeOH/water to get Compound 82d ((E)-6-(4-(6-(3,5-bis(trifluoromethyl)benzylidene)-5-oxo-5,6,7,8-tetra-hydronaphthalene-2-carbonyl)piperazin-1-yl)-6-oxohexanoic acid) (0.95 g, 1.56 mmol, yield 62%).

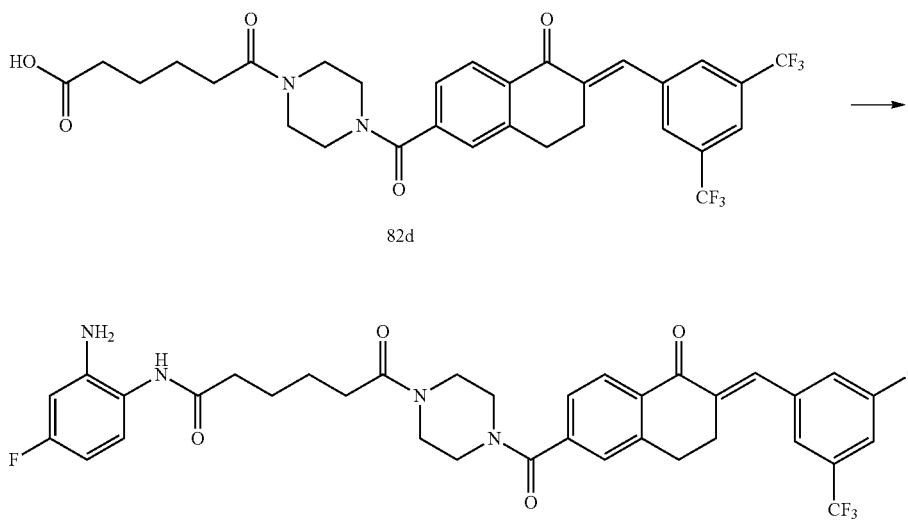

82d

82

To a solution of Compound 82d ((E)-6-(4-(6-(3,5-bis(trifluoromethyl)-benzylidene)-5-oxo-5,6,7,8-tetra-hydronaphthalene-2-carbonyl)-piperazin-1-yl)-6-oxohexanoic acid) (0.23 g, 0.38 mmol), 4-fluoro-1,2-phenylenediamine (0.05 g, 0.38 mmol) and DMAP (0.05 g, 0.38 mmol) in THF (30 mL) was added NMM (0.04 g, 0.38 mmol) and EDCI (0.10 g, 0.49 mmol) at 0° C. After addition, the reaction mixture was warmed to room temperature and stirred for 6 hours.

The reaction was monitored by TLC. After reaction was completed, the solvent was removed under reduced pressure. The residue was diluted with sat. $NH_4Cl_{(aq)}$ and extracted with EtOAc. The organic phase was dried with $MgSO_4$ and concentrated under reduced pressure. The crude product was purified by silica gel column chromatography using ethyl acetate/methanol=10/1 as elution to yield the desired product Compound 82 ((E)-N-(2-amino-4-fluorophenyl)-6-(4-(6-(3,5-bis(trifluoromethyl)benzylidene)-5-oxo-5,6,7,8-tetrahydronaphthalene-2-carbonyl)piperazin-1-yl)-6-oxohexanamide) (0.06 g, 0.08 mmol, yield 21%).

Compound 82, $^1$H-NMR (500 MHz, $CD_3OD$): δ 8.16-8.14 (d, 1H), 8.05 (s, 2H), 7.99 (s, 1H), 7.89 (s, 1H), 7.46-7.44 (d, 1H), 7.42 (s, 1H), 7.05 (m, 1H), 6.54-6.52 (m, 1H), 6.39-6.35 (m, 1H), 3.81-3.45 (m, 8H), 3.15-3.12 (t, 2H), 3.07-3.04 (t, 2H), 2.52-2.44 (m, 4H), 1.81-1.74 (m, 2H), 1.33-1.29 (m, 2H). ESI-MS m/z calcd for $C_{36}H_{33}F_7N_4O_4$ 718.24, found 719 $[M+H]^+$.

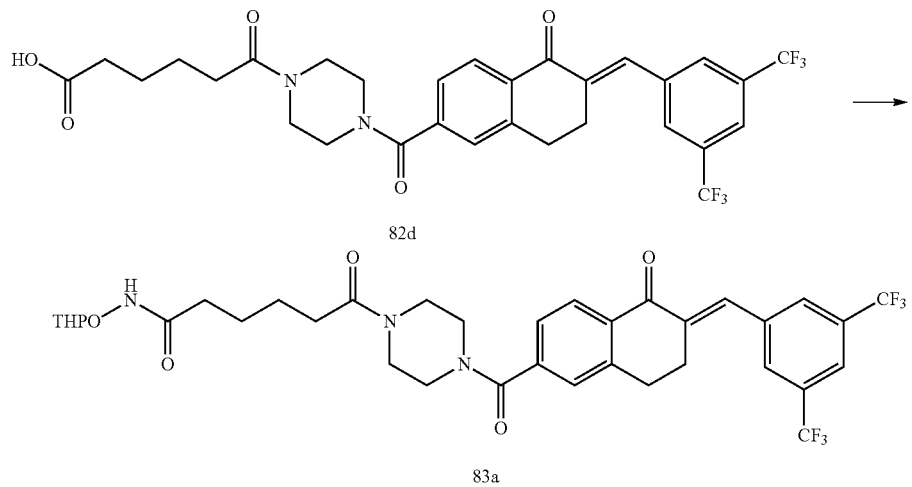

To a solution of Compound 82d ((E)-6-(4-(6-(3,5-bis(trifluoromethyl)-benzylidene)-5-oxo-5,6,7,8-tetra-hydronaphthalene-2-carbonyl)-piperazin-1-yl)-6-oxohexanoic acid) (0.37 g, 0.60 mmol), NH$_2$OTHP (0.09 g, 0.79 mmol) and DMAP (0.04 g, 0.30 mmol) in CH$_2$Cl$_2$ (50 mL) was added NMM (0.09 g, 0.91 mmol) and EDCI (0.17 g, 0.91 mmol) at 0° C. After addition, the reaction mixture was warmed to room temperature and stirred for overnight.

The reaction was monitored by TLC. After reaction was completed, the solvent was removed under reduced pressure. The residue was diluted with ice-cold water and extracted with EtOAc. The organic phase was dried with MgSO$_4$ and concentrated under reduced pressure. The crude product was purified by silica gel column chromatography using ethyl acetate/methanol=10/1 as elution to yield the desired product Compound 83a ((E)-6-(4-(6-(3,5-bis(trifluoromethyl)benzylidene)-5-oxo-5,6,7,8-tetrahydronaphthalene-2-carbonyl)piperazin-1-yl)-6-oxo-N-((tetrahydro-2H-pyran-2-yl)oxy)hexanamide) (0.23 g, 0.32 mmol, yield 53%).

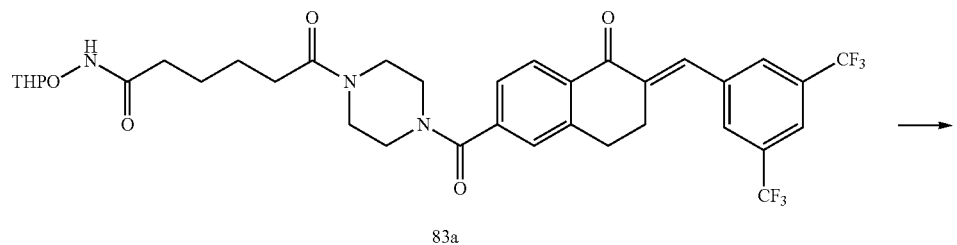

83a

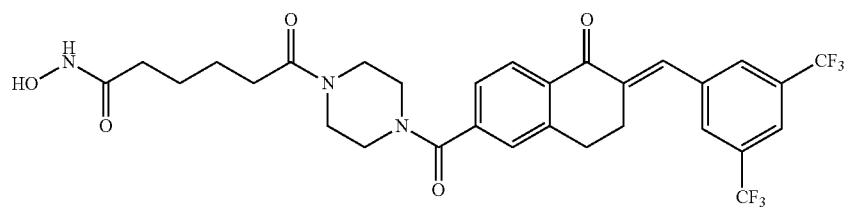

83

To a solution of Compound 83a ((E)-6-(4-(6-(3,5-bis(trifluoromethyl)-benzylidene)-5-oxo-5,6,7,8-tetrahydronaphthalene-2-carbonyl)piperazin-1-yl)-6-oxo-N-((tetrahydro-2H-pyran-2-yl)oxy)hexanamide) (0.23 g, 0.32 mmol) in $CH_2Cl_2$ (20 mL) was added 2N HCl (excess, in diethyl ether). After addition, the reaction mixture was stirred for overnight.

The reaction was monitored by TLC. After reaction was completed, the solvent was removed under reduced pressure. The residue was diluted with diethyl ether, the precipitated solid was collected by filtration to afford the desired product Compound 83 ((E)-6-(4-(6-(3,5-bis(trifluoromethyl)benzylidene)-5-oxo-5,6,7,8-tetrahydro-naphthalene-2-carbonyl)piperazin-1-yl)-N-hydroxy-6-oxohexanamide) (0.09 g, 0.15 mmol, yield 47%).

Compound 83, $^1$H-NMR (500 MHz, $CD_3OD$): δ 8.16-8.15 (d, 1H), 8.05 (s, 2H), 7.99 (s, 1H), 7.89 (s, 1H), 7.47-7.46 (d, 1H), 7.43 (s, 1H), 3.81-3.45 (m, 8H), 3.15-3.13 (t, 2H), 3.07-3.05 (t, 2H), 2.48-2.43 (m, 2H), 2.15-2.12 (m, 2H), 1.65-1.53 (m, 2H), 1.34-1.29 (m, 2H). ESI-MS m/z calcd for $C_{30}H_{29}F_6N_3O_5$ 625.20, found 626 $[M+H]^+$.

Example II: Autotaxin/HDAC Inhibition Assay

To prove that the Compounds 1~83 of the present disclosure have the effect of inhibiting the activity of Autotaxin and HDAC (dual ATX/HDAC inhibitors), the following experiments were performed for evaluation.

Autotaxin Inhibition Screening Assay

ATX (autotaxin) activity was measured by choline release from LPC in presence or absence of test compounds (Compounds 1~83; at concentrations of 4 μM, 20 μM and 50 μM). Twenty (20) ng ATX (10803, Cayman, MI, USA) was incubated with 100 μM 14:0 LPC (855575P, Avanti, AL, USA) in a final volume of 100 μL buffer containing 50 mM Tris pH 8.0, 0.01% Triton X-100, 50 mM $CaCl_2$, 1 unit/ml choline oxidase, 2 unit/ml horseradish peroxidase (HRP), 2 mM homovanilic acid (HVA). The relative amount of released choline was measured by HVA fluorescence in a 96-well plate. Fluorescent intensity was determined at λex/λem=320/450 nm every 60 sec for 90 min with a SpectraMax i3 (Molecular Devices, CA, USA). Data analysis was performed using GraphPad Prism (GraphPad, La Jolla CA, USA).

Inhibition %=[1−(Slope$_{TA}$−Slope$_{Blank}$)/(Slope$_{Vehicle}$−Slope$_{Blank}$)]×100%

HDAC Inhibition Screening Assay

The HDAC1/HDAC2/HDAC3 in vitro activities are detected by Enzo Life Sciences' HDAC1/HDAC2/HDAC3 Fluorimetric Drug Discovery Kit. The assay is based on the FLUOR DE LYS® Substrate and FLUOR DE LYS® Developer combination. The assay procedure has two steps. First, the FLUOR DE LYS® Substrate, which comprises an acetylated lysine side chain, is incubated with HDAC1/HDAC2/HDAC3, respectively. Deacetylation of the substrate sensitizes the substrate so that, in the second step, treatment with the FLUOR DE LYS® Developer produces a fluorophore. The signals of the test compounds (Compounds 1~83; at concentrations of 2 μM, 10 μM and 50 μM) in 96-well plates are detected at 360 nm or 485 nm excitation and 460 nm or 530 nm emission with a Molecular Devices SpectraMax i3 Imaging Cytometer. The HDAC1/HDAC2/HDAC3 activities are expressed in percentage of basal control minus baseline control.

The inhibition rate of the Compounds 1~83 on the activity of autotaxin and HDAC are summarized in Table 1 below.

TABLE 1

| Compound # | HDAC | | | | | | | | | Autotaxin | | |
|---|---|---|---|---|---|---|---|---|---|---|---|---|
| | HDAC1 | | | HDAC2 | | | HDAC3 | | | LPC-CR | | |
| | 2 (μM) | 10 (μM) | 50 (μM) | 2 (μM) | 10 (μM) | 50 (μM) | 2 (μM) | 10 (μM) | 50 (μM) | 4 (μM) | 20 (μM) | 50 (μM) |
| 1 | A | A | A | A | A | A | A | A | A | C | C | C |
| 2 | A | A | A | A | A | A | A | A | A | C | C | C |
| 3 | A | A | A | A | A | A | A | A | A | C | C | C |
| 4 | B | A | A | B | A | A | C | B | A | A | A | A |
| 5 | C | C | C | C | C | C | C | C | C | B | B | B |
| 6 | C | C | C | C | C | C | C | C | C | B | B | B |
| 7 | C | C | B | C | C | B | C | C | B | C | B | B |
| 8 | B | A | A | A | A | A | C | A | A | A | A | A |
| 9 | C | C | C | C | C | C | C | C | C | C | C | C |
| 10 | C | B | A | C | A | A | C | B | A | A | A | A |
| 11 | C | C | C | C | C | C | C | C | C | A | A | A |
| 12 | C | B | A | B | A | A | B | A | A | A | A | A |
| 13 | C | C | C | C | C | C | C | C | C | B | B | B |
| 14 | C | B | A | C | B | A | C | C | A | A | A | A |
| 15 | C | B | A | C | B | A | C | B | A | C | C | C |
| 16 | A | A | A | A | A | A | A | A | A | C | C | C |
| 17 | C | C | C | C | C | C | C | C | C | C | C | C |
| 18 | C | B | A | B | B | A | C | B | A | C | C | C |
| 19 | C | C | C | C | C | C | C | C | C | C | C | C |
| 20 | B | A | A | B | A | A | A | A | A | C | C | C |
| 21 | C | C | C | C | C | C | C | C | C | C | C | C |
| 22 | B | A | A | B | A | A | B | A | A | C | C | C |
| 23 | C | C | C | C | C | C | C | C | C | C | C | C |
| 24 | C | C | B | C | C | B | C | C | C | C | C | C |
| 25 | A | A | A | A | A | A | A | A | A | C | C | C |
| 26 | A | A | A | A | A | A | A | A | A | C | C | C |
| 27 | C | C | C | C | C | C | C | C | C | C | C | C |
| 28 | A | A | A | A | A | A | A | A | A | C | C | C |
| 29 | C | C | C | C | C | B | C | C | C | C | C | C |
| 30 | A | A | A | A | A | A | A | A | A | C | C | B |

TABLE 1-continued

| | HDAC | | | | | | | | | Autotaxin | | |
| --- | --- | --- | --- | --- | --- | --- | --- | --- | --- | --- | --- | --- |
| | HDAC1 | | | HDAC2 | | | HDAC3 | | | LPC-CR | | |
| Compound # | 2 (μM) | 10 (μM) | 50 (μM) | 2 (μM) | 10 (μM) | 50 (μM) | 2 (μM) | 10 (μM) | 50 (μM) | 4 (μM) | 20 (μM) | 50 (μM) |
| 31 | C | B | B | A | A | A | B | A | A | C | C | C |
| 32 | A | A | A | A | A | A | B | A | A | C | C | C |
| 33 | B | A | A | B | A | A | B | A | A | C | C | C |
| 34 | C | A | A | B | A | A | C | B | A | C | C | C |
| 35 | C | C | C | C | C | C | C | C | B | C | C | C |
| 36 | C | A | A | B | A | A | C | B | A | C | C | C |
| 37 | A | A | A | A | A | A | A | A | A | C | C | C |
| 38 | A | A | A | A | A | A | A | A | A | C | C | C |
| 39 | C | C | C | C | C | C | C | B | B | C | C | C |
| 40 | B | A | A | A | A | A | A | A | A | C | C | C |
| 41 | C | C | C | C | C | C | C | C | C | C | C | C |
| 42 | C | B | A | B | B | A | B | A | B | C | C | A |
| 43 | C | C | C | C | C | B | C | B | B | C | C | C |
| 44 | B | A | A | B | A | A | B | A | A | C | C | C |
| 45 | A | A | A | A | A | A | A | A | A | C | C | C |
| 46 | C | B | B | C | B | A | C | C | B | C | C | C |
| 47 | C | C | C | C | B | B | B | B | A | C | C | C |
| 48 | A | A | A | A | A | A | A | A | A | C | C | C |
| 49 | C | C | C | C | C | B | C | C | B | C | C | C |
| 50 | A | A | A | A | A | A | A | A | A | C | C | C |
| 51 | C | B | A | B | A | A | A | A | A | C | C | C |
| 52 | A | A | A | A | A | A | A | A | A | C | C | C |
| 53 | A | A | A | A | A | A | A | A | A | C | C | C |
| 54 | A | A | A | A | A | A | A | A | A | C | C | C |
| 55 | A | A | A | A | A | A | A | A | A | C | C | C |
| 56 | A | A | A | A | A | A | A | A | A | C | C | C |
| 57 | C | B | A | B | A | A | A | A | A | C | C | C |
| 58 | A | A | A | A | A | A | A | A | A | C | C | B |
| 59 | B | A | A | A | A | A | A | A | A | C | C | C |
| 60 | A | A | A | A | A | A | A | A | A | C | C | C |
| 61 | A | A | A | A | A | A | A | A | A | C | C | C |
| 62 | B | A | A | A | A | A | B | A | A | C | C | C |
| 63 | A | A | A | A | A | A | A | A | A | C | C | C |
| 64 | B | A | A | B | A | A | C | B | A | B | B | B |
| 65 | C | B | A | B | A | A | C | B | A | A | A | A |
| 66 | C | C | C | C | C | C | C | C | C | C | C | C |
| 67 | C | C | C | C | C | C | C | C | C | C | C | C |
| 68 | C | C | C | C | C | C | C | C | C | C | C | C |
| 69 | C | C | C | C | C | B | C | C | C | C | C | C |
| 70 | B | A | A | A | A | A | A | A | A | C | B | B |
| 71 | C | C | C | C | C | C | C | C | C | C | C | C |
| 72 | C | C | B | C | C | B | C | C | B | B | B | B |
| 73 | C | C | C | C | C | C | C | C | C | C | C | C |
| 74 | C | A | A | B | A | A | C | A | A | A | A | A |
| 75 | C | C | B | C | C | B | C | C | B | B | B | B |
| 76 | C | C | C | C | C | C | C | C | C | C | C | C |
| 77 | C | C | B | C | B | B | C | C | B | A | A | A |
| 78 | C | C | C | C | C | C | C | C | C | A | A | A |
| 79 | B | A | A | B | A | A | B | A | A | A | A | A |
| 80 | C | C | C | C | C | C | C | C | C | C | C | B |
| 81 | C | C | B | C | C | B | C | B | B | A | A | A |
| 82 | C | C | C | C | C | C | C | C | B | A | A | A |
| 83 | C | C | B | C | C | B | C | C | B | A | A | A |

A = >80% inhibition;
B = 50~80% inhibition;
C = <50% inhibition.

The experimental results revealed that the Compounds 1~83 of the present disclosure have inhibition activities for ATX (autotaxin) and HDAC (histone deacetylase) and are useful as dual inhibitors of HDAC and autotaxin.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A compound selected from the group consisting of the compounds delineated in Table A or a geometric isomer, enantiomer, diastereomer, racemate, pharmaceutically acceptable salt or solvate thereof:

TABLE A
| (No.) | Structure |
|---|---|
| 4 | 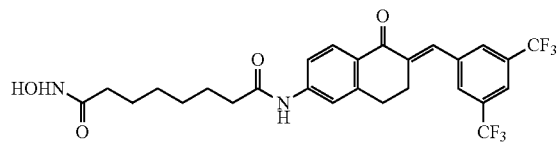 |
| 5 | 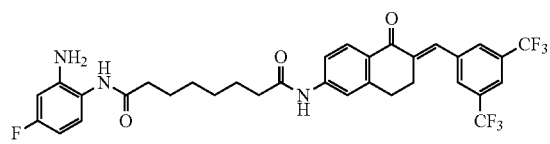 [SMILES: Nc1cc(F)ccc1NC(=O)CCCCCCC(=O)Nc1ccc2c(c1)CC/C(=C\c1cc(C(F)(F)F)cc(C(F)(F)F)c1)C2=O] |
| 6 | 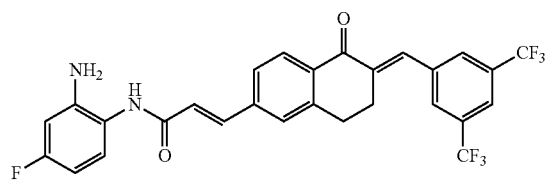 [SMILES: Nc1cc(F)ccc1NC(=O)/C=C/c1ccc2c(c1)CC/C(=C\c1cc(C(F)(F)F)cc(C(F)(F)F)c1)C2=O] |
| 7 | 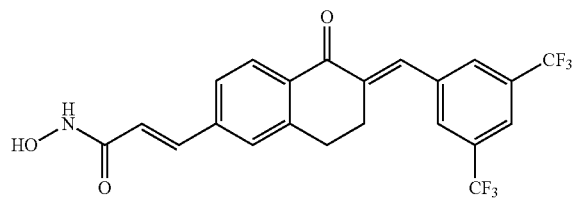 [SMILES: O=C(/C=C/c1ccc2c(c1)CC/C(=C\c1cc(C(F)(F)F)cc(C(F)(F)F)c1)C2=O)NO] |
| 8 | 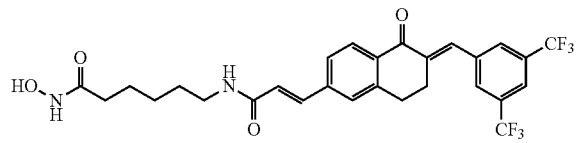 [SMILES: O=C(/C=C/c1ccc2c(c1)CC/C(=C\c1cc(C(F)(F)F)cc(C(F)(F)F)c1)C2=O)NCCCCCC(=O)NO] |
| 9 | 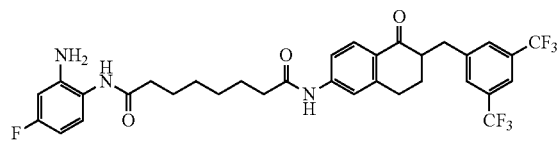 [SMILES: Nc1cc(F)ccc1NC(=O)CCCCCCC(=O)Nc1ccc2c(c1)CCC(Cc1cc(C(F)(F)F)cc(C(F)(F)F)c1)C2=O] |
| 10 | 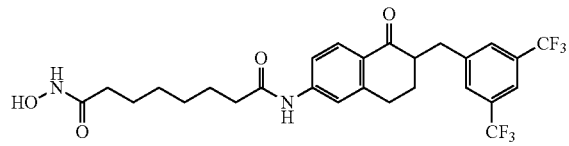 [SMILES: O=C(CCCCCCC(=O)Nc1ccc2c(c1)CCC(Cc1cc(C(F)(F)F)cc(C(F)(F)F)c1)C2=O)NO] |
| 11 | 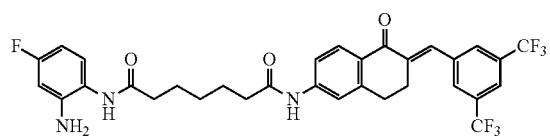 [SMILES: Nc1cc(F)ccc1NC(=O)CCCCCC(=O)Nc1ccc2c(c1)CC/C(=C\c1cc(C(F)(F)F)cc(C(F)(F)F)c1)C2=O] |
| 12 | 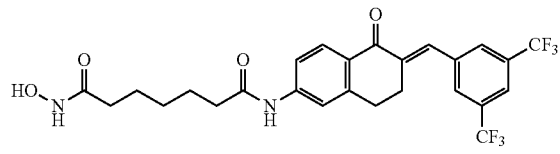 [SMILES: O=C(CCCCCC(=O)Nc1ccc2c(c1)CC/C(=C\c1cc(C(F)(F)F)cc(C(F)(F)F)c1)C2=O)NO] |

TABLE A-continued

| (No.) | Structure |
|---|---|
| 13 | 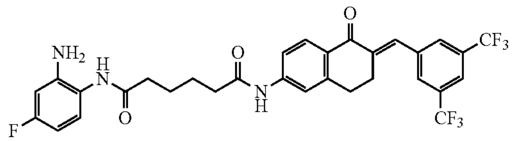 [SMILES: Nc1cc(F)ccc1NC(=O)CCCCC(=O)Nc1ccc2c(c1)CC/C(=C\c1cc(C(F)(F)F)cc(C(F)(F)F)c1)C2=O] |
| 14 | 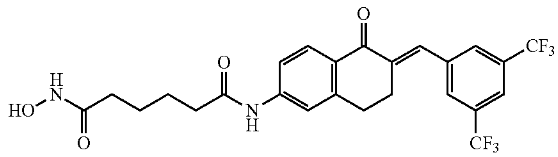 [SMILES: O=C(CCCCC(=O)Nc1ccc2c(c1)CC/C(=C\c1cc(C(F)(F)F)cc(C(F)(F)F)c1)C2=O)NO] |
| 66 | 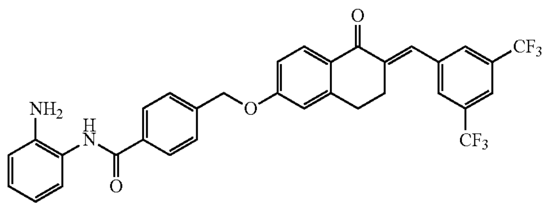 [SMILES: Nc1ccccc1NC(=O)c1ccc(COc2ccc3c(c2)CC/C(=C\c2cc(C(F)(F)F)cc(C(F)(F)F)c2)C3=O)cc1] |
| 67 | 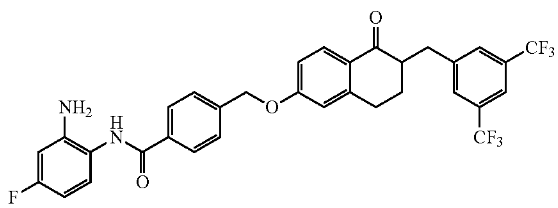 [SMILES: Nc1cc(F)ccc1NC(=O)c1ccc(COc2ccc3c(c2)CCC(Cc2cc(C(F)(F)F)cc(C(F)(F)F)c2)C3=O)cc1] |
| 68 | 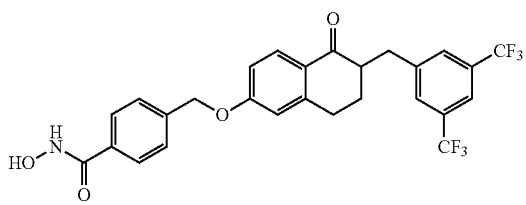 [SMILES: O=C(NO)c1ccc(COc2ccc3c(c2)CCC(Cc2cc(C(F)(F)F)cc(C(F)(F)F)c2)C3=O)cc1] |
| 71 | 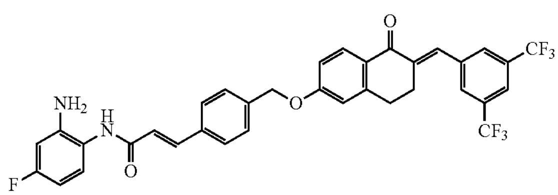 [SMILES: Nc1cc(F)ccc1NC(=O)/C=C/c1ccc(COc2ccc3c(c2)CC/C(=C\c2cc(C(F)(F)F)cc(C(F)(F)F)c2)C3=O)cc1] |
| 72 | 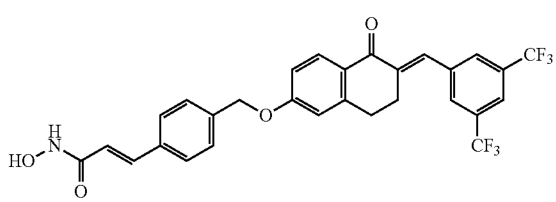 [SMILES: O=C(/C=C/c1ccc(COc2ccc3c(c2)CC/C(=C\c2cc(C(F)(F)F)cc(C(F)(F)F)c2)C3=O)cc1)NO] |
| 73 | 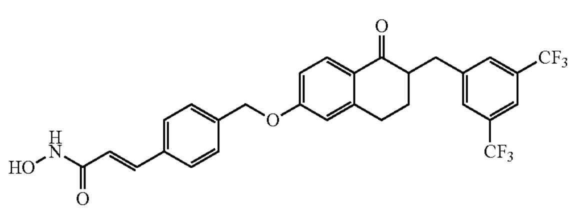 [SMILES: O=C(/C=C/c1ccc(COc2ccc3c(c2)CCC(Cc2cc(C(F)(F)F)cc(C(F)(F)F)c2)C3=O)cc1)NO] |

TABLE A-continued
| (No.) | Structure |
|---|---|
| 74 | 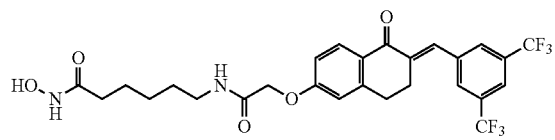 [SMILES: O=C(CCCCCNC(=O)COc1ccc2c(c1)CC/C(=C\c1cc(C(F)(F)F)cc(C(F)(F)F)c1)C2=O)NO] |
| 75 | 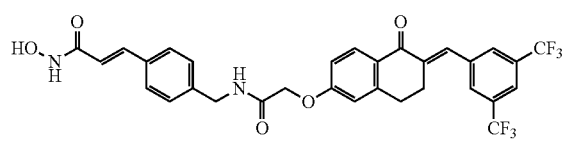 [SMILES: O=C(/C=C/c1ccc(CNC(=O)COc2ccc3c(c2)CC/C(=C\c2cc(C(F)(F)F)cc(C(F)(F)F)c2)C3=O)cc1)NO] |
| 78 | 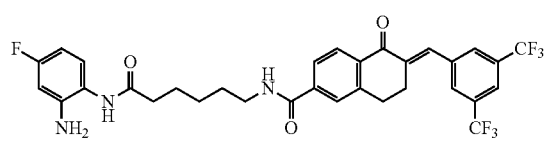 [SMILES: Nc1cc(F)ccc1NC(=O)CCCCCNC(=O)c1ccc2c(c1)CC/C(=C\c1cc(C(F)(F)F)cc(C(F)(F)F)c1)C2=O] |
| 79 | 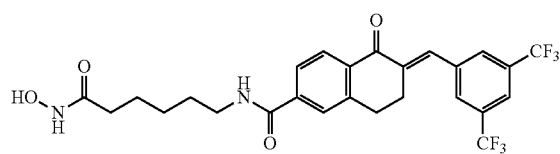 [SMILES: O=C(CCCCCNC(=O)c1ccc2c(c1)CC/C(=C\c1cc(C(F)(F)F)cc(C(F)(F)F)c1)C2=O)NO] |
| 80 | 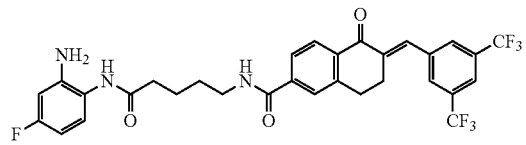 [SMILES: Nc1cc(F)ccc1NC(=O)CCCCNC(=O)c1ccc2c(c1)CC/C(=C\c1cc(C(F)(F)F)cc(C(F)(F)F)c1)C2=O] |
| 81 | 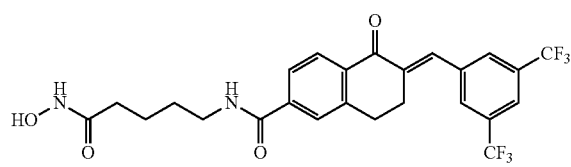 [SMILES: O=C(CCCCNC(=O)c1ccc2c(c1)CC/C(=C\c1cc(C(F)(F)F)cc(C(F)(F)F)c1)C2=O)NO] |
| 82 | 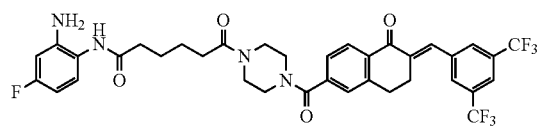 [SMILES: Nc1cc(F)ccc1NC(=O)CCCCC(=O)N1CCN(C(=O)c2ccc3c(c2)CC/C(=C\c2cc(C(F)(F)F)cc(C(F)(F)F)c2)C3=O)CC1] |
| 83 | 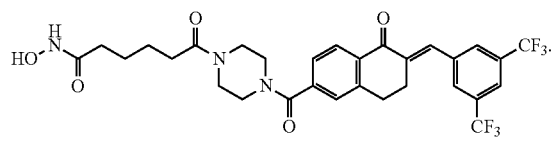 [SMILES: O=C(CCCCC(=O)N1CCN(C(=O)c2ccc3c(c2)CC/C(=C\c2cc(C(F)(F)F)cc(C(F)(F)F)c2)C3=O)CC1)NO] |

2. The compound according to claim 1, wherein the compound is a dual autotaxin/HDAC inhibitor.

3. A pharmaceutical composition comprising a therapeutically effective amount of the compound according to claim 1 and a pharmaceutically acceptable carrier.

4. The compound according to claim 1, wherein the compound is

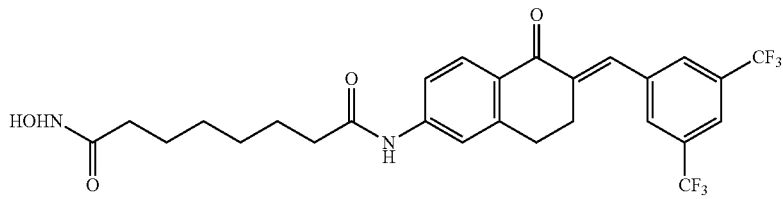

or a geometric isomer, enantiomer, diastereomer, racemate, pharmaceutically acceptable salt or solvate thereof.

5. The compound according to claim 1, wherein the compound is

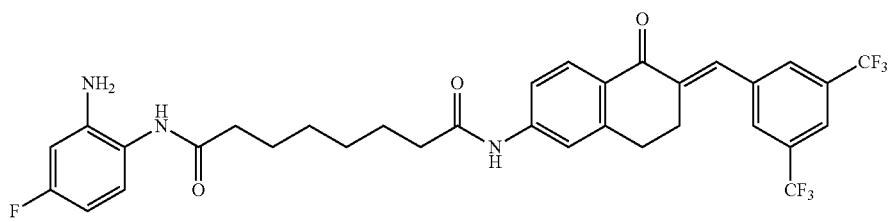 [SMILES: Nc1cc(F)ccc1NC(=O)CCCCCCC(=O)Nc1ccc2c(c1)CC/C(=C\c1cc(C(F)(F)F)cc(C(F)(F)F)c1)C2=O]

or a geometric isomer, enantiomer, diastereomer, racemate, pharmaceutically acceptable salt or solvate thereof.

6. The compound according to claim 1, wherein the compound is

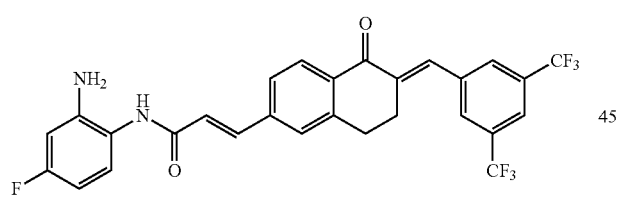

or a geometric isomer, enantiomer, diastereomer, racemate, pharmaceutically acceptable salt or solvate thereof.

7. The compound according to claim 1, wherein the compound is

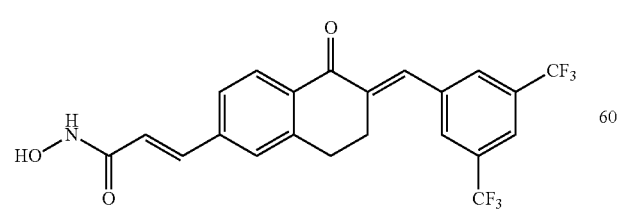

or a geometric isomer, enantiomer, diastereomer, racemate, pharmaceutically acceptable salt or solvate thereof.

8. The compound according to claim 1, wherein the compound is

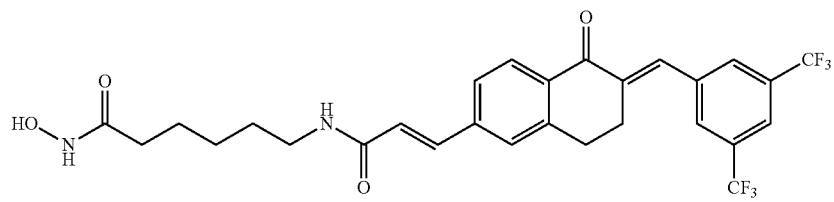 [SMILES: O=C(/C=C/c1ccc2c(c1)CC/C(=C\c1cc(C(F)(F)F)cc(C(F)(F)F)c1)C2=O)NCCCCCC(=O)NO]

or a geometric isomer, enantiomer, diastereomer, racemate, pharmaceutically acceptable salt or solvate thereof.

9. The compound according to claim 1, wherein the compound is

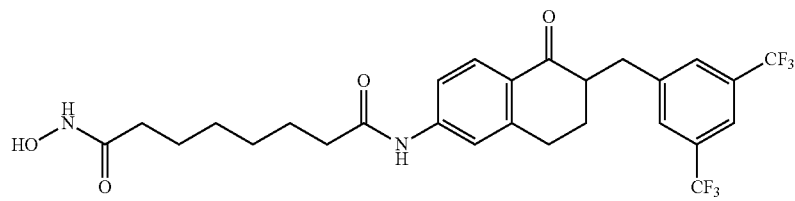 [SMILES: O=C(CCCCCCC(=O)Nc1ccc2c(c1)CCC(Cc1cc(C(F)(F)F)cc(C(F)(F)F)c1)C2=O)NO]

or a geometric isomer, enantiomer, diastereomer, racemate, pharmaceutically acceptable salt or solvate thereof.

10. The compound according to claim 1, wherein the compound is

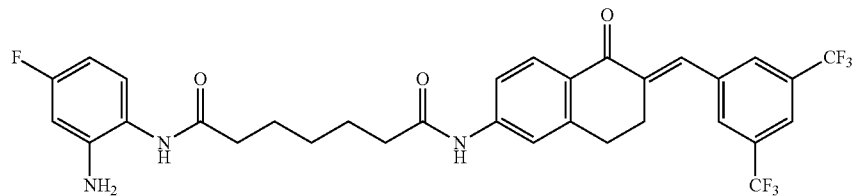 [SMILES: Nc1cc(F)ccc1NC(=O)CCCCCC(=O)Nc1ccc2c(c1)CC/C(=C\c1cc(C(F)(F)F)cc(C(F)(F)F)c1)C2=O]

or a geometric isomer, enantiomer, diastereomer, racemate, pharmaceutically acceptable salt or solvate thereof.

11. The compound according to claim 1, wherein the compound is

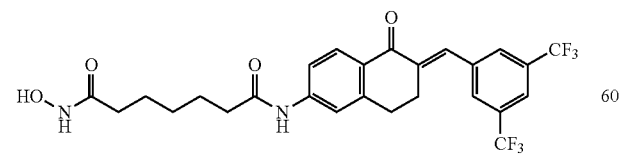

or a geometric isomer, enantiomer, diastereomer, racemate, pharmaceutically acceptable salt or solvate thereof.

12. The compound according to claim 1, wherein the compound is

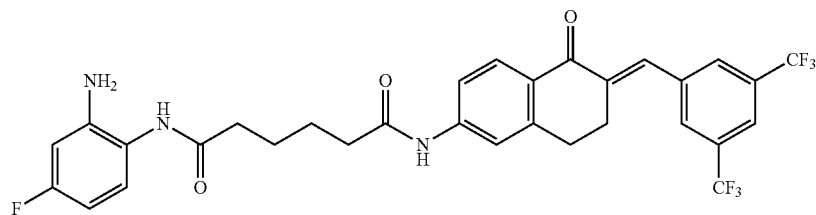 [SMILES: Nc1cc(F)ccc1NC(=O)CCCCC(=O)Nc1ccc2c(c1)CC/C(=C\c1cc(C(F)(F)F)cc(C(F)(F)F)c1)C2=O]

or a geometric isomer, enantiomer, diastereomer, racemate, pharmaceutically acceptable salt or solvate thereof.

13. The compound according to claim 1, wherein the compound is

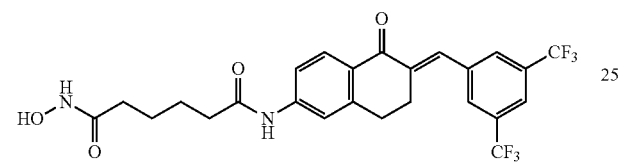

or a geometric isomer, enantiomer, diastereomer, racemate, pharmaceutically acceptable salt or solvate thereof.

14. The compound according to claim 1, wherein the compound is

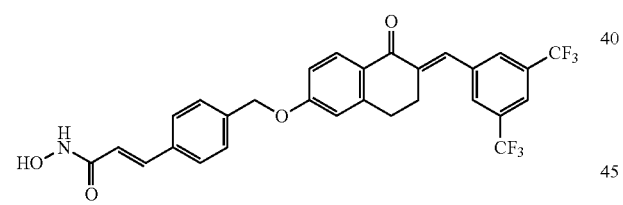

or a geometric isomer, enantiomer, diastereomer, racemate, pharmaceutically acceptable salt or solvate thereof.

15. The compound according to claim 1, wherein the compound is

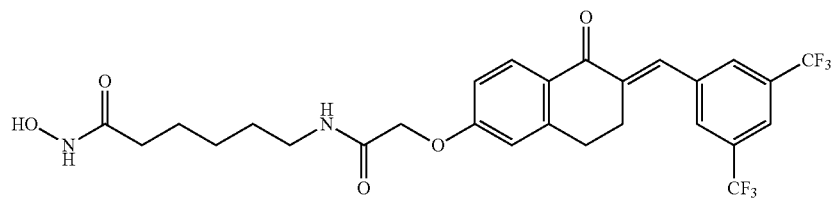 [SMILES: O=C(CCCCCNC(=O)COc1ccc2c(c1)CC/C(=C\c1cc(C(F)(F)F)cc(C(F)(F)F)c1)C2=O)NO]

or a geometric isomer, enantiomer, diastereomer, racemate, pharmaceutically acceptable salt or solvate thereof.

16. The compound according to claim 1, wherein the compound is

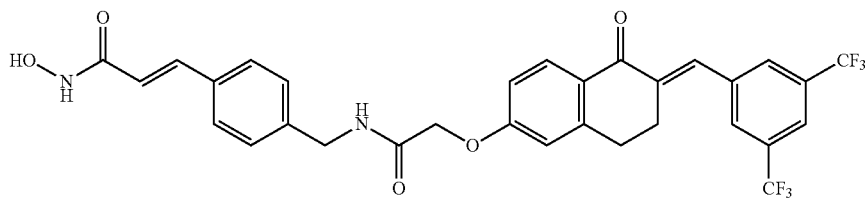 [SMILES: O=C(/C=C/c1ccc(CNC(=O)COc2ccc3c(c2)CC/C(=C\c2cc(C(F)(F)F)cc(C(F)(F)F)c2)C3=O)cc1)NO]

or a geometric isomer, enantiomer, diastereomer, racemate, pharmaceutically acceptable salt or solvate thereof.

17. The compound according to claim 1, wherein the compound is

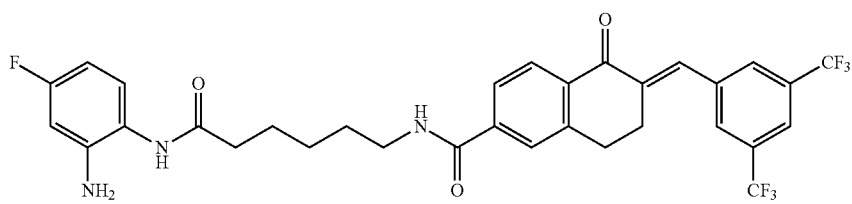 [SMILES: Nc1cc(F)ccc1NC(=O)CCCCCNC(=O)c1ccc2c(c1)CC/C(=C\c1cc(C(F)(F)F)cc(C(F)(F)F)c1)C2=O]

or a geometric isomer, enantiomer, diastereomer, racemate, pharmaceutically acceptable salt or solvate thereof.

18. The compound according to claim 1, wherein the compound

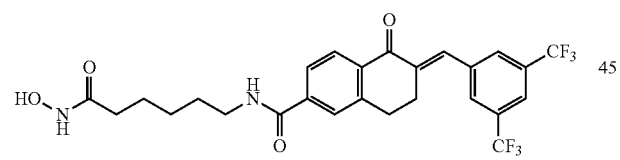

is or a geometric isomer, enantiomer, diastereomer, racemate, pharmaceutically acceptable salt or solvate thereof.

19. The compound according to claim 1, wherein the compound is

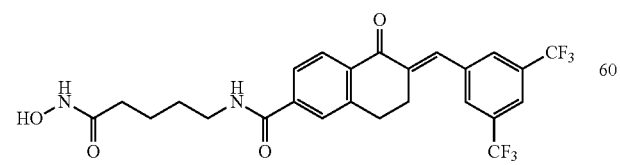

or a geometric isomer, enantiomer, diastereomer, racemate, pharmaceutically acceptable salt or solvate thereof.

20. The compound according to claim 1, wherein the compound is
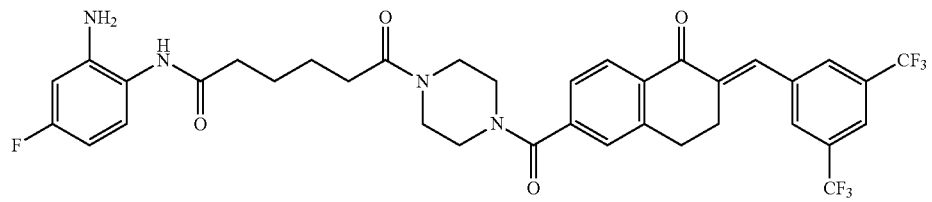 [SMILES: Nc1cc(F)ccc1NC(=O)CCCCC(=O)N1CCN(C(=O)c2ccc3c(c2)CC/C(=C\c2cc(C(F)(F)F)cc(C(F)(F)F)c2)C3=O)CC1]
or a geometric isomer, enantiomer, diastereomer, racemate, pharmaceutically acceptable salt or solvate thereof.
21. The compound according to claim 1, wherein the compound is
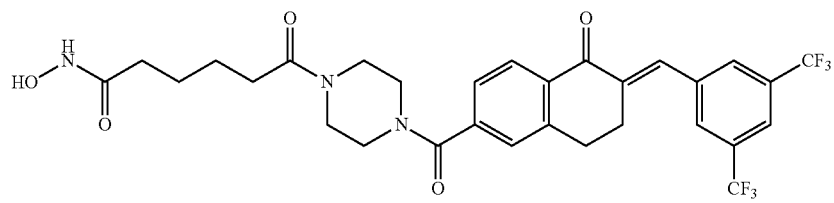 [SMILES: O=C(CCCCC(=O)N1CCN(C(=O)c2ccc3c(c2)CC/C(=C\c2cc(C(F)(F)F)cc(C(F)(F)F)c2)C3=O)CC1)NO]
or a geometric isomer, enantiomer, diastereomer, racemate, pharmaceutically acceptable salt or solvate thereof.
* * * * *